United States Patent [19]
Fässler et al.

[11] Patent Number: 5,753,652
[45] Date of Patent: May 19, 1998

[54] ANTIRETROVIRAL HYDRAZINE DERIVATIVES

[75] Inventors: Alexander Fässler, Oberwil; Guido Bold, Gipf-Oberfrick, both of Switzerland; Marc Lang, Mulhouse, France; Shripad Bhagwat, Lake Bluff, Ill.; Peter Schneider, Bottmingen, Switzerland

[73] Assignee: Novartis Corporation, Summit, N.J.

[21] Appl. No.: 416,420

[22] Filed: Apr. 4, 1995

Related U.S. Application Data

[63] Continuation-in-part of Ser. No. 173,550, Dec. 23, 1993, which is a continuation of Ser. No. 907,497, Jul. 1, 1992, abandoned.

[30] Foreign Application Priority Data

Jul. 3, 1991 [CH] Switzerland .................. 1962/91
Dec. 23, 1992 [CH] Switzerland .................. 3942/92

[51] Int. Cl.$^6$ .............. A61K 31/54; A61K 31/535; C07D 403/04; C07D 403/14
[52] U.S. Cl. ............ 514/227.5; 514/227.8; 514/237.8; 514/614; 514/615; 514/579; 544/59; 544/60; 544/162; 544/168; 544/164; 544/169; 564/1; 564/152; 564/153; 564/154; 564/155; 564/166; 564/162; 564/163; 564/185; 564/190; 564/191; 564/192; 564/193; 564/194; 564/202; 564/217; 564/218; 564/123; 546/152; 546/176; 546/229; 546/336; 548/507
[58] Field of Search ............... 544/58.2, 59, 60, 544/162, 168, 164, 169; 514/227.8, 227.5, 237.8, 614, 615, 579; 564/1, 152, 153, 154, 155, 161, 162, 163, 189–194, 202, 217, 218, 123

[56] References Cited

U.S. PATENT DOCUMENTS

| | | | |
|---|---|---|---|
| 3,669,967 | 6/1972 | Boltze | 514/259 |
| 4,207,338 | 6/1980 | Eckhardt et al. | 424/309 |
| 4,556,654 | 12/1985 | Showalter et al. | 514/259 |
| 5,409,927 | 4/1995 | Bold et al. | 514/237 |

FOREIGN PATENT DOCUMENTS

| | | |
|---|---|---|
| 0382562 | 8/1990 | European Pat. Off. |
| 0402646 | 12/1990 | European Pat. Off. |
| 0491538 | 6/1992 | European Pat. Off. |
| 0521827 | 1/1993 | European Pat. Off. |
| 1355993 | 2/1964 | France |
| 1254461 | 11/1967 | Germany |
| 1257461 | 11/1967 | Germany |
| 292980 | 8/1991 | Germany |
| 4308095 | 9/1994 | Germany |
| 9208698 | 5/1992 | WIPO |
| 9318006 | 9/1993 | WIPO |
| 9419332 | 9/1994 | WIPO |
| 9421604 | 9/1994 | WIPO |
| 9422840 | 10/1994 | WIPO |
| 9502582 | 1/1995 | WIPO |
| 9507269 | 3/1995 | WIPO |

OTHER PUBLICATIONS

Derwent Abstract 94–286706/36 (Corresponding to WO/94/21604.
Derwent Abstract 94–286705/36 (Corresponding to DE 43 08 095).
Derwent Abstract 94.893p—1967; "Hydrazine Derivatives as additives to Photographic Developers".
Streicher et al; Synthese Eines Tzaanalogen Des Antibiotikums Negamycin Chem Ber vol. 108, (1975) 813–819.
Chem Abstr. 82 124,685g (1975).
Ruprecht etal; "Development of Antiviral Treatment Strategies in Murine Models"; AIDS Research and Human Retroviruses 8(6) 1992 pp. 997–1011.
Yarchoan, et al; The Immunology of HIV Infection. Implications for Therapy; AIDS Research and Human Retroviruses 8(6) 1992 pp. 1023–1031.
Harada et al; Infection of HTLV–III/LAV in HTLV–I Carrying Cells MT–2 and MT–4 and Application in a Plague Assay; Science 229, p. 563–566, 1985.
Richards et al.; Sensitive, Soluble Chromogenic Substrates for HIV–I Proteinase; The Journal of Biological Chemistry, 265, p. 7733–7736 (1990).
Billch et al; Synthetic Peptides as Subtrates and Inhibitors of Human Immune Deficiency Virus–I Protease; The Journal of Biological Chemistry; 268, p. 17905–17908 (1988).
Schneider et al; Enzymatic Activity of a Synthetic 99 Residue Protein Corresponding to the Putative HIV–I Protease; Cell, 54, p. 363–368 (1988).
Ciba Geigy Internal Publication Abstract of Roche Protease Inh Mentioning Brit J. Clin. Pharmacol. 34, 155–156 P; Williams et al.
Shaw et al; Brit. J. Clin. Pharmacol., 34, p. 166P–167P (1992).
Murihead et al; Brit J. Clin Pharmacol. 34, 170P–171P (1992).
Srimal et al; Indram J. Exp. Biol. 19(11), p. 1069 (1964).
Evans et al; J. Org. Chem. 50, 4615 (1985).
Chem Abstr. 62:1249 (1965) Corresponding to FR 1,355, 993.
Derwent Abstract 92–016792/03 Corresponding to DD 292, 980 (See P.I. Item "AO").
Wlodawer et al; Science 245, 616 (1989). "Conserved Folding in Retroviral Proteases: Crystal Structure of a Synthetic, HIV–I Prostease".

(List continued on next page.)

*Primary Examiner*—Matthew V. Grumbling
*Attorney, Agent, or Firm*—Gregory D. Ferraro

[57] ABSTRACT

The invention relates to compounds of formula

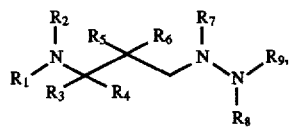

(I)

and salts, pharmaceutical compositions, intermediates and processes of preparation thereof.

18 Claims, No Drawings

OTHER PUBLICATIONS

Sham et al; J. Chem Soc., Chem. Commun. 1993, 1052–3(1993). "Facile Sythesis of Potent HIV–I Protease Inhibitors Containing a Novel Pseude–symmetric Dipeptide Isostere".

Harada et al. Infection of HTLV–III/LAV in HTLV–I–Carrying Cells MT–2 and MT–4 and Application in a Plaque Assay. Science, 229 p. 563–566 (1985).

Basler Zeitung, Wednesday, Jun. 16, 1993, Nr. 137, Tell IV, p. 39.

Richards et al. Sensitive, Soluble Chromogeni Substrates for HIV–I Proteinase, The Journa of Biological Chemistry, 265, p. 7733–7736 (1990).

Billich et al. Synthetic Peptides as Substrat and Inhibitors of Human Immune Deficiency Virus–I Protease, The Journal of Biologoical Chemistry, 268, p. 17905–17908 (1988).

Schneider et al. Enzymatic Activity of a Synthetic 99 Residue Protein Corresponding to the Putative HIV–I Protease, Cell, 54, p. 363–368 (1988).

Ciba–Geigy Internal Publication Abstract of Williams et al. Brit. J. Clin. Pharmacol. 34, 155P–156P; Shaw et al., Brit. J. Clin. Pharmacol., 34, p. 170P–171P (1992).

94,893p—"Hydrazine Derivatives as Additives to Photographic Developers" (1967).

W.Streicher et al "Synthese Eines Azaanalogen Des Antibiotkums Negaylin".

Chem. Ber. vol. 108, (1975) pp. 813–819 and Chem. Abst. 82:124685q (1975) as Translation thereof.

Roberts et al., Science (1990) vol. 248, 358–361.

ANTIRETROVIRAL HYDRAZINE DERIVATIVES

This is a continuation-in-part of application Ser. No. 08/173,550, filed Dec. 23, 1993, which is a continuation-in-part of application Ser. No. 07/907,497, filed Jul. 1, 1992, now abandoned.

The invention relates to a novel class of non-hydrolysable analogues of peptides that are cleavable by aspartate proteases, namely hydrazine derivatives, to processes for the preparation thereof, to pharmaceutical compositions that comprise those peptide analogues, and to the use thereof as medicaments or for the preparation of pharmaceutical compositions for controlling virus-dependent diseases, and to novel intermediates for the preparation of those compounds.

The immune deficiency syndrome AIDS ("Acquired Immunodeficiency Syndrome") is a fatal disease. The disease is becoming increasingly widespread throughout the world primarily within certain risk groups, but it is also spreading beyond those risk groups. The disease already affects millions of people and the control of its causes is one of the most important aims of modern medicine. Hitherto the retroviruses HIV-1 and HIV-2 (HIV representing "Human Immunodeficiency Virus") have been identified as a cause of the disease and they have been characterised by molecular biology. From the point of view of treatment, in addition to previous ways of mitigating the symptoms of AIDS and certain preventive measures, there is particular interest in the search for compositions that interfere with the reproduction of the virus itself but do not damage the intact cells and tissues of the patient.

Compounds that appear especially promising are those which suppress the processing of the protein building blocks of the virus that are biosynthesised in human cells, and thus suppress the correct assembly of those building blocks to form complete, infectious virions.

HIV-1 and HIV-2 each have in their genome a region that codes for a "gag-protease". That "gag-protease" is responsible for the correct proteolytic cleavage of the precursor proteins that are produced from the genome regions coding for the "Group Specific Antigens" (gag). During the cleavage, the structural proteins of the virus core are liberated. The "gag-protease" itself is a component of a precursor protein encoded by the pol-genome region of HIV-1 and HIV-2, which protein also contains the regions for the "reverse transcriptase" and the "integrase" and is thought to be cleaved by autoproteolysis.

The "gag-protease" cleaves the major core protein $p^{24}$ of HIV-1 and HIV-2 preferentially N-terminally of proline residues, for example in the divalent residues Phe-Pro, Leu-Pro or Tyr-Pro. It is a protease having a catalytically active aspartate residue in the active centre, a so-called aspartate protease.

If the action of the "gag-protease" could be suppressed, the proteins necessary for the assembly of the virus core would no longer be available to the virus. This would result in the limitation or even the suppression of the reproduction of the virus. There is therefore a need for inhibitory substances for the "gag-protease" for use as antiviral compositions against AIDS and other retroviral diseases.

A number of "gag-protease" inhibitors containing central groups that are not proteolytically cleavable peptide isosters have already been synthesised. Despite intensive research, however, it has not been possible hitherto for aspartate protease inhibitors suitable for use in humans to be used for the control of AIDS in a majority of infected patients, pharmacodynamic problems being the main determining factor in this regard. In addition, most of the "gag-protease" inhibitors known hitherto have more than two asymmetric carbon atoms in the said central building block, and this necessitates relatively expensive stereospecific syntheses or isomer separation methods. The object of this patent application is, therefore, to provide a novel class of inhibitory substances for viral aspartate proteases having a novel central building block. Furthermore, it should be possible to synthesise that central building block in a sterically simple manner. In addition, the novel central building blocks have amino groups at both ends, so that if suitable substituents are selected, then, for example, structures analogous to retro-inverso-peptides are present.

The compounds according to the invention are compounds of formula

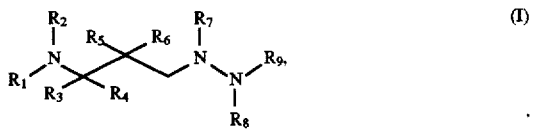

wherein $R_1$ and $R_9$ are each independently of the other hydrogen; acyl; unsubstituted or substituted alkyl, alkenyl or alkynyl; heterocyclyl; sulfo; sulfonyl substituted by unsubstituted or substituted alkyl, aryl, heterocyclyl, alkoxy, which is unsubstituted or substituted, or by aryloxy; sulfamoyl that is unsubstituted or substituted at the nitrogen atom; or phosphoryl substituted by one or two radicals, which may be identical or different, selected from unsubstituted or substituted alkyl, from unsubstituted or substituted cycloalkyl, from aryl, from hydroxy, from unsubstituted or substituted alkoxy, from cycloalkoxy and from aryloxy; with the proviso that not more than one of the radicals $R_1$ and $R_9$ is hydrogen; and $R_2$ and $R_8$ are each independently of the other hydrogen or one of the radicals mentioned above for $R_1$ and $R_9$; or the pairs of substituents $R_1$ and $R_2$, and $R_8$ and $R_9$, each independently of the other, may form together with the nitrogen atom to which they are bonded a heterocyclic ring consisting of the bonding nitrogen atom together with a radical selected from ethylene, trimethylene, tetramethylene and pentamethylene in which a carbon atom may have been replaced by nitrogen, oxygen, sulfur or by sulfur mono- or di-substituted by oxygen and which may be unsaturated, or one of those radicals with an oxo substituent at each of the two carbon atoms linked to the bonding carbon atom and with or without a fused-on benzene or naphthalene ring; $R_3$ and $R_4$ are each independently of the other hydrogen, unsubstituted or substituted alkyl or cycloalkyl; aryl; heterocyclyl; or unsubstituted or substituted alkenyl; or $R_3$ and $R_4$ together form unsubstituted or substituted alkylene, alkylidene or benzo-fused alkylene;

$R_5$ is hydroxy; $R_6$ is hydrogen;

or $R_5$ and $R_6$ together are oxo;

and $R_7$ is unsubstituted or substituted alkyl or cycloalkyl; aryl; heterocyclyl; or unsubstituted or substituted alkenyl;

and salts of the mentioned compounds where salt-forming groups are present.

In the description of this invention, the term "lower" used in the definition of groups or radicals, for example lower alkyl, lower alkoxy, lower alkanoyl etc., means that, unless expressly otherwise defined, the groups or radicals so defined contain up to and including 7, and preferably up to and including 4, carbon atoms.

Unless indicated to the contrary, the radicals $R_1$, $R_2$, $R_3$, $R_4$, $R_7$, $R_8$ and/or $R_9$ may be mono- to poly-substituted, especially mono- to tri-substituted, for example monosubstituted, by identical or different substituents.

The carbon atoms in compounds of formula I substituted by $R_3$ and $R_4$ and by $R_5$ and $R_6$ may, if they are asymmetric, be in the (R)-, (S)- or (R,S)-configuration, as may also any other asymmetric carbon atoms present. Accordingly, the present compounds may be in the form of isomeric mixtures or in the form of pure isomers, especially in the form of diastereoisomeric mixtures, pairs of enantiomers or pure enantiomers. Preferred compounds of formula I are those wherein the carbon atom substituted by $R_3$ or by hydroxy $R_5$ has the (S)-configuration and any other asymmetric carbon atoms that may be present are, independently of one another, in the (R)-, (S)- or (R,S)-configuration.

The general terms and names used in the description of this invention preferably have the following meanings, and within the different levels of meanings of the radicals listed hereinbefore and hereinbelow it is possible to use any combinations or individual radicals instead of the general definitions:

Acyl $R_1$, $R_2$, $R_8$ or $R_9$ has, for example, up to 25, preferably up to 19, carbon atoms and is especially the acyl group of a carboxylic acid, of a semiester of carbonic acid, of an unsubstituted or N-substituted carbamic acid, of an unsubstituted or N-substituted oxalamide or of an unsubstituted or substituted amino acid, it being possible for there to be thiocarbonyl groups instead of carbonyl groups in each of the acyl radicals mentioned. Preferably not more than one of the radicals $R_1$ and $R_2$ and not more than one of the radicals $R_8$ and $R_9$ is acylated.

Preferred acyl groups $R_1$, $R_2$, $R_8$ and $R_9$ of a carboxylic acid are unsubstituted or substituted alkanoyl having up to 19 carbon atoms, for example n-decanoyl, or preferably lower alkanoyl, such as formyl, acetyl, propionyl, butyryl or pivaloyl, or substituted lower alkanoyl, especially in the form of cycloalkyl-lower alkanoyl wherein cycloalkyl has, for example, from 3 to 7 carbon atoms and lower alkanoyl is as defined above, for example cycloalkylcarbonyl, especially having a total of from 4 to 8 carbon atoms, such as cyclopropyl-, cyclobutyl-, cyclopentyl- or cyclohexyl-carbonyl, or 2-cyclohexyl- or 2-cyclopentyl-acetyl, cycloalkenyl-lower alkanoyl where in cycloalkenyl has, for example, from 3 to 7 carbon atoms, such as cycloalkenylcarbonyl, preferably having from 4 to 8 carbon atoms, such as 1-cyclohexenylcarbonyl, 1,4-cyclohexadienylcarbonyl or 1-cyclohexenylacetyl or 1,4-cyclohexadienylacetyl, bicycloalkyl-lower alkanoyl wherein bicycloalkyl contains, for example, from 5 to 10 carbon atoms, for example bicycloalkylcarbonyl, preferably having from 8 to 11 carbon atoms, such as decahydronaphthyl-2-carbonyl, endo- or exo-norbornyl-2-carbonyl, bicyclo[2.2.2]oct-2-ylcarbonyl or bicyclo[3.3.1]non-9-ylcarbonyl, and also bicyclo-hexyl-, -heptyl-, -octyl-, -nonyl- or -decyl-acetyl or -3-propionyl, such as bicyclo[3.1.0]hex-1-, -2- or -3-yl-, bicyclo[4.1.0]hept-1- or -7-yl-, bicyclo[2.2.1]hept-2-yl-, such as endo- or exonorbornyl-, bicyclo[3.2.1]oct-2-yl-, bicyclo[3.3.0]oct-3-yl- or bicyclo[3.3.1]non-9-yl-, and also α- or β-decahydronaphthyl-acetyl or -3-propionyl, bicycloalkenylcarbonyl, preferably having from 8 to 12 carbon atoms, such as 5-norbornen-2-ylcarbonyl or bicyclo[2.2.2]octen-2-ylcarbonyl, tricycloalkyl-lower alkanoyl wherein tricycloalkyl contains, for example, from 8 to 10 carbon atoms, for example tricycloalkylcarbonyl, preferably having from 8 to 11 carbon atoms, such as 1- or 2-adamantylcarbonyl, and also tricyclo[5.2.1.0$^{2,6}$]dec-8-yl- or adamantyl-acetyl, such as 1-adamantyl-acetyl, aryl-lower alkanoyl wherein aryl has from 6 to 14 carbon atoms, such as in phenyl, indenyl, indanyl, naphthyl, anthryl, phenanthryl, acenaphthyl or fluorenyl, and may be unsubstituted or especially mono- to tri-substituted by lower alkyl, for example methyl, ethyl or propyl, halo-lower alkyl, for example trifluoromethyl, phenyl, 1- or 2-naphthyl, hydroxy, lower alkoxy, for example methoxy, carbamoyl-lower alkoxy, N-lower alkylcarbamoyl-lower alkoxy or N,N-di-lower alkylcarbamoyl-lower alkoxy, amino, mono- or di-lower alkylamino, lower alkanoylamino, for example pivaloylamino, halogen, for example fluorine, chlorine or bromine, carboxy, lower alkoxycarbonyl, such as tert-butoxycarbonyl, phenyl-, naphthyl- or fluorenyl-lower alkoxycarbonyl, such as benzyloxycarbonyl, lower alkanoyl, sulfo, lower alkylsulfonyl, for example methylsulfonyl, phosphono, hydroxy-lower alkoxyphosphoryl or di-lower alkoxyphosphoryl, carbamoyl, mono- or di-lower alkylcarbamoyl, sulfamoyl, mono- or di-lower alkylaminosulfonyl, nitro and/or by cyano, wherein phenyl may be present up to three times, for example in diphenyl-, dibenzyl- or triphenyl-lower alkanoyl, such as diphenyl-, dibenzyl- or triphenyl-acetyl, and wherein lower alkanoyl may be unsubstituted or substituted, for example by lower alkyl, for example methyl, heterocyclyl selected from pyrrolyl, furyl, thienyl, imidazolyl, pyrazolyl, oxazolyl, thiazolyl, pyridyl, pyrazinyl, pyrimidinyl, indolyl, quinolyl, isoquinolyl, quinoxalinyl, β-carbolinyl and a benzofused, cyclopenta-, cyclohexa- or cyclohepta-fused derivative of those radicals, which may also be fully or partially saturated, hydroxy, lower alkoxy, lower alkanoyloxy, for example acetoxy, propionyloxy, butyroxy, isobutyroxy or pivaloyloxy, acetoacetoxy, amino- or benzyloxycarbonylamino-lower alkanoyloxy, for example 2-amino- or 2-benzyloxycarbonylamino-2-methylpropionyloxy, aryl-lower alkanoyloxy wherein aryl has from 6 to 10 carbon atoms, for example in benzoyloxy, phenylacetoxy, 1- or 2-naphthoyloxy, lower alkoxycarbonyloxy, for example methoxy-, ethoxy-, n-propoxy-, isopropoxy-, n-butoxy-, isobutoxy-, sec-butoxy-, tert-butoxy-, n-pentyloxy-, isopentyloxy-, neopentyloxy-, tert-pentyloxy-, n-hexyloxy-, isohexyloxy- or n-heptyloxy-carbonyloxy, mono- or di-lower alkylaminocarbonyloxy, for example ethylaminocarbonyloxy or diethylaminocarbonyloxy, aryloxycarbonyloxy wherein aryl has from 6 to 10 carbon atoms, for example phenoxycarbonyloxy or 1- or 2-naphthyloxycarbonyloxy, aryl-lower alkoxycarbonyloxy wherein aryl has from 6 to 14 carbon atoms, especially phenyl-lower alkoxycarbonyloxy, for example benzyloxycarbonyloxy, and also 1- or 2-naphthylmethoxycarbonyloxy or 9-fluorenylmethoxycarbonyloxy, sulfonyloxy, lower alkylsulfonyloxy, for example methyl-, ethyl-, propyl-, isopropyl-, n-butyl-, isobutyl-, sec-butyl-, tert-butyl-, n-pentyl-, isopentyl-, neopentyl-, tert-pentyl-, n-hexyl-, isohexyl- or n-heptyl-sulfonyloxy, phenylsulfonyloxy, 2- or 4-toluenesulfonyloxy, 1- or 2-naphthylsulfonyloxy, carboxy, esterified carboxy selected from lower alkoxycarbonyl, for example methoxy-, ethoxy-, n-propoxy-, isopropoxy-, n-butoxy-, isobutoxy-, sec-butoxy-, tert-butoxy-, n-pentyloxy-, isopentyloxy-, neopentyloxy-, tert-pentyloxy-, n-hexyloxy-, isohexyloxy- or n-heptyloxy-carbonyl, aryloxycarbonyl wherein aryl has from 6 to 10 carbon atoms, for example phenoxycarbonyl or 1- or 2-naphthyloxycarbonyl, aryl-lower alkoxycarbonyl wherein aryl has from 6 to 12 carbon atoms, for example benzyloxycarbonyl, 1- or 2-naphthylmethoxycarbonyl or 2-fluorenylmethoxycarbonyl, lower alkanoyl, lower alkylsulfonyl, for example methyl- or tert-butylsulfonyl, hydroxy-lower alkoxyphosphoryl or di-lower alkoxyphosphoryl, carbamoyl, carbamoyl substituted by one or two radicals selected from lower alkyl, such as methyl, ethyl, propyl, isopropyl, n-butyl, isobutyl, sec-butyl, tert-butyl, n-pentyl, isopentyl, neopentyl, tert-pentyl, n-hexyl, isohexyl or n-heptyl, for example in N-methylcarbamoyl, N-n-butylcarbamoyl or N,N-dimethylcarbamoyl, from carboxy-lower alkyl or lower alkoxycarbonyl-lower alkyl, for example in the form of carboxymethylcarbamoyl (glycinylcarbonyl) or in the form of tert-butoxycarbonylmethylcarbamoyl, from di-lower alkylamino-lower alkyl, for example 2-dimethylaminoethyl, aminocarboxy-lower alkyl, for example 5-amino-5-carboxypentyl, from hydroxy-lower alkyl, for example hydroxymethyl or hydroxyethyl, and from di-lower alkoxy-lower alkyl, for example 2-(2,2-dimethoxyethyl), or carbamoyl substituted by one radical selected from ethylene, trimethylene, tetramethylene and pentamethylene in which a carbon atom may have been replaced by nitrogen, oxygen, sulfur or by sulfur mono- or di-substituted by oxygen and which may be unsaturated, such as piperidin-1-yl-, pyrazin-1-yl-, piperazin-1-yl-, pyrimidin-1-yl-, pyridazin-1-yl-, morpholino-, thiomorpholino- or S,S-dioxothiomorpholino-carbonyl; sulfamoyl, phosphono, benzofuranyl, oxo and/or by cyano and is unbranched or branched, for example selected from benzoyl that is unsubstituted or mono- or poly-substituted by lower alkyl, for example methyl, phenyl, halogen, for example fluorine or chlorine, hydroxy, lower alkoxy, for example methoxy, and/or by nitro, such as 4-chloro-, 4-methoxy- or 4-nitro-benzoyl, naphthylcarbonyl, such as α- or β-naphthylcarbonyl or 1,8-naphthalenedicarbonyl bonded to the amino group via both carbonyl groups, indenylcarbonyl, such as 1-, 2- or 3-indenylcarbonyl, indanylcarbonyl, such as 1- or 2-indanylcarbonyl, phenanthrenylcarbonyl, such as 9-phenanthrenylcarbonyl, phenylacetyl, α-naphthylacetyl, β-naphthylacetyl, lower alkylphenylacetyl, such as 4-methylphenylacetyl, lower alkoxyphenylacetyl, such as 4-methoxyphenylacetyl, 3-phenylpropionyl, 3-(p-hydroxyphenyl)-propionyl, diphenylacetyl, di-(4-methoxyphenyl)-acetyl, triphenylacetyl, 2,2-dibenzylacetyl, anilinophenylacetyl substituted in the phenyl radical by one or two radicals selected from lower alkyl, for example methyl or ethyl, hydroxy, lower alkoxy, for example methoxy, amino, mono- or di-lower alkylamino, for example ethylamino or dimethylamino, halogen, for example fluorine or chlorine, carboxy, sulfo, carbamoyl, sulfamoyl and cyano and/or at the amino group by one or two radicals selected from lower alkyl and benzyl, such as 2-(o,o-dichloroanilino)-phenylacetyl or 2-(o,o-dichloro-N-benzylanilino)-phenylacetyl, 3-α- or 3-β-naphthylpropionyl, 2-benzyl-3-(1-pyrazolyl)-propionyl, 3-phenyl- or 3-α-naphthyl-2-hydroxypropionyl, 3-phenyl- or 3-α-naphthyl-2-lower alkoxypropionyl, such as 3-phenyl- or 3-α-naphthyl-2-neopentyloxypropionyl, 3-phenyl- or 3-α-naphthyl-2-lower alkanoyloxypropionyl, such as 3-phenyl-2-pivaloyloxy- or -2-acetoxy-propionyl, 2-benzyl- or 1- or 2-naphthyl-3-(N-methoxy-N-methylamino)-propionyl, 3-α-naphthyl-2-acetoacetoxypropionyl, 3-α-naphthyl-2-ethylaminocarbonyloxy-propionyl or 3-α-naphthyl-2-(2-amino- or 2-benzyloxycarbonylamino-2-methylpropionyloxy)-propionyl, 3-phenyl- or 3-α-naphthyl-2-carboxymethylpropionyl, 3-phenyl- or 3-α-naphthyl-2-lower alkoxycarbonyl-propionyl, such as 3-α-naphthyl-2-ethoxycarbonyl-propionyl, 3-phenyl- or 3-α-naphthyl-2-benzyloxycarbonyl-methyl-propionyl, 2-(S)benzyl-3-tert-butylsulfonylpropionyl, 3-phenyl-2-phosphono- or -phosphonomethylpropionyl, 3-phenyl-2-dimethoxyphosphoryl- or -dimethoxyphosphorylmethyl-propionyl, 3-phenyl-2-diethoxyphosphoryl- or -diethoxyphosphorylmethyl-propionyl, 3-phenyl-2-ethoxy- or -methoxy-hydroxyphosphorylpropionyl, phenyl-lower alkanoyl wherein the lower alkanoyl radical is substituted by carbamoyl, such as 2(R,S)-carbamoyl-3-phenylpropionyl, 3-phenyl- or 3-α-naphthyl-2-carbamoylpropionyl, 3-phenyl- or 3-α-naphthyl-2-tert-butylcarbamoyl-propionyl, 3-phenyl- or 3-α-naphthyl-2-(2-dimethylaminoethyl)carbamoylpropionyl, 3-α-naphthyl-2-(carboxy- or tert-butoxy-carbonyl)methylcarbamoyl-propionyl, 3-phenyl- or 3-α-naphthyl-2-(3-hydroxy-2-propyl)carbamoyl-propionyl, 3-phenyl- or 3-α-naphthyl-2-(2,2-dimethoxyethyl) carbamoylpropionyl, 3-phenyl- or 3-α-naphthyl-2-(5-amino-5-carboxypentyl)-carbamoylpropionyl, 3-phenyl- or 3-α-naphthyl-2-cyanopropionyl, 3-phenyl- or 3-α-naphthyl-2-cyanomethylpropionyl, 3-phenyl- or 3-α-naphthyl-2-acetonyl-propionyl, 4-hydroxyphenylbutyryl, 4-phenyl- or 4-α-naphthyl-3-carboxybutyryl, 4-phenyl- or 4-(α-naphthyl-3-benzyloxycarbonyl-butyryl, 2-benzyl- or 2-α-naphthylmethyl-4-cyanobutyryl, 2-benzyl-4-(2-benzofuranyl)-4-oxobutyryl, 2-benzyl- or 2-α-naphthylmethyl-5-dimethylamino-pentanoyl, 2-benzyl- or 2-α-naphthylmethyl-4-oxapentanoyl, 2-benzyl- or 2-α-naphthylmethyl-4,4-dimethyl-3-oxo-pentanoyl, 2-benzyl- or 2-α-naphthylmethyl-5-dimethylamino-4-oxo-pentanoyl, and 2-benzyl- or 2-α-naphthylmethyl-5,5-dimethyl-4-oxo-hexanoyl, especially phenyl-lower alkanoyl, such as phenylacetyl, or phenyl-lower alkanoyl wherein the lower alkanoyl radical is substituted by carbamoyl, such as 2(R,S)-carbamoyl-3-phenylpropionyl, phenyl-lower alkenoyl, such as β-phenylacryloyl or β-phenylvinylacetyl, heterocyclyl-lower alkanoyl wherein lower alkanoyl is unsubstituted or substituted as defined above under aryl-lower alkanoyl $R_1$, $R_2$, $R_8$ and $R_9$ and wherein heterocyclyl is preferably a single or double ring system having from 3 to 10 ring atoms, is bonded via a carbon atom or, especially, via a nitrogen atom and contains up to 3 further hetero atoms selected from oxygen, nitrogen, sulfur, selenium, and sulfur linked to 1 or 2 oxygen atoms, the mentioned ring system may also be fused with 1 or 2 phenyl or naphthyl radicals, it being possible for naphthyl also to be fused-on on both sides, or with 1 or 2 cycloalkyl radicals, cycloalkyl preferably having from 5 to 7 ring atoms; and may be unsaturated or partially or fully saturated, for example thienyl-, furyl-, pyranyl-, pyrrolyl-, imidazolyl-, pyrazolyl-, oxazolyl-, isoxazolyl-, thiazolyl-, furazanyl-, tetrazolyl-, pyridyl-, pyrazinyl-, pyrimidinyl-, pyridazinyl-, azepinyl-, indolyl-, benzimidazolyl-, 1H-indazolyl-, quinolyl-, isoquinolyl-, quinoxalinyl-, quinazolinyl-, cinnolyl-, purinyl-, pteridinyl-, naphthyridinyl-, 4H-quinolizinyl-, 3,1-benzofuranyl-, benz[e]indolyl-, 4,1-benzoxazinyl-, 4,1-benzothiazinyl-, carbazolyl-, β-carbolinyl-, phenazinyl-, phenanthridyl-, acridinyl-, phenoxazinyl-, phenothiazinyl-, 1-azaacenaphthenyl-, cyclohexa[b] pyrrolyl-, cyclohepta[b]-pyrrolyl-, cyclohexa[d] pyrazolyl-, cyclohexa[b]pyridyl-, cyclohexa[b] pyrazinyl-, cyclohexa[b]pyrimidinyl-, cyclohexa[b]-1, 4-oxazinyl-, cyclohexa[b]-1,4-thiazinyl-, pyrrolidinyl-, pyrrolinyl-, imidazolidyl-, 2-imidazolinyl-, 2,3-dihydropyridyl-, piperidyl-, piperazinyl-, 2,3,5,6-tetrahydropyrazinyl-, morpholinyl-, thiomorpholinyl-, S,S-dioxo-thiomorpholinyl-, indolinyl-, isoindolinyl-, 4,5,6,7-tetrahydroindolyl-, 1,2,3,4-tetrahydroquinolyl-, 1,2,3,4-tetrahydroisoquinolyl-, chromanyl-, thiochromanyl-, 1,2,3,4-tetrahydro-3,1-benzodiazinyl-, 3,4-dihydro-3H-4,1-benzoxazinyl-, 3,4-dihydro-3H-4, 1-benzothiazinyl-, 2,3,4,5-tetrahydro-1H-5,1-benzazepinyl- or 5,6-dihydrophenanthridinyl-lower alkanoyl, the mentioned heterocyclyl radicals being unsubstituted or substituted by lower alkyl, for example methyl, phenyl, 1- or 2-naphthyl, phenyl-lower alkyl, for example benzyl, hydroxy-lower alkyl, for example hydroxymethyl or 2-hydroxyethyl, lower alkoxy-lower alkyl, for example methoxymethyl or 2-methoxyethyl, phenoxy- or naphthyloxy-lower alkyl, for example 2-phenoxyethyl, 1- or 2-naphthyloxymethyl, phenyl-lower alkoxy- or naphthyl-lower alkoxy-lower alkyl, for example benzyloxy-lower alkyl, lower alkanoyloxy-lower alkyl, for example acetoxymethyl, phenyl- or naphthyl-lower alkanoyloxy-lower alkyl, for example benzoyloxy-, phenylacetoxy- or 1- or 2-naphthoyloxy-methyl, -2-ethyl or -2-(2,2-dimethylethyl), lower alkoxycarbonyloxy-lower alkyl, for example tert-butoxycarbonyloxy-lower alkyl, phenyl-, naphthyl- or fluorenyl-lower alkoxycarbonyloxy-lower alkyl, for example 2-benzyloxycarbonyloxyethyl or 9-fluorenylmethoxycarbonyloxyethyl, amino-lower alkyl, for example aminomethyl, 2-aminoethyl or 2-aminopropyl, carboxy-lower alkyl, for example carboxymethyl or 2-carboxyethyl, hydroxy, lower alkoxy, for example methoxy or ethoxy, phenyl- or naphthyl-lower alkoxy, for example benzyloxy or 1- or 2-naphthyloxy, amino, lower alkylamino, for example methyl-, ethyl- or tert-butyl-amino, di-lower alkylamino, for example dimethyl- or diethyl-amino, carboxy, lower alkoxycarbonyl, for example methoxy-, isopropoxy-, sec-butoxy- or tert-butoxy-carbonyl, phenyl- or naphthyl-lower alkoxycarbonyl, for example benzyloxycarbonyl, halogen, for example fluorine, chlorine, bromine or iodine, especially chlorine or bromine, lower alkanoyl, for example acetyl or pivaloyl, lower alkylsulfonyl, for example methyl- or ethyl-sulfonyl, phosphono, hydroxy-lower alkoxyphosphoryl or dialkoxyphosphoryl, for example dimethoxy- or diethoxy-phosphoryl, carbamoyl, mono- or di-lower alkylcarbamoyl, for example N-methylcarbamoyl, N-n-butylcarbamoyl or N,N-dimethylcarbamoyl, hydroxy- or carboxy-lower alkylcarbamoyl, for example hydroxy- or carboxy-methylcarbamoyl or hydroxy- or carboxy-ethylcarbamoyl, sulfamoyl, nitro, oxo and/or by cyano, with heterocyclyl-lower alkanoyl being selected especially from pyrrolylcarbonyl that is unsubstituted or substituted by lower alkyl or by phenyl, for example 2- or 3-pyrrolylcarbonyl, 4- or 5-methylpyrrolylcarbonyl or 4- or 5-phenylpyrrolyl-2-carbonyl, thienylcarbonyl, such as 2-thienylcarbonyl, furylcarbonyl, such as 2-furylcarbonyl, pyridylcarbonyl, such as 2-, 3- or 4-pyridylcarbonyl, pyrimidin-1-ylcarbonyl, indolylcarbonyl that is unsubstituted or substituted by lower alkyl, such as methyl, phenyl-lower alkyl, such as benzyl, lower alkoxy, such as methoxy, phenyl-lower alkoxy, such as benzyloxy, or by halogen, such as chlorine, such as 2-, 3- or 5-indolylcarbonyl, 1-methyl-, 5-methyl-, 5-methoxy-, 5-benzyloxy-, 5-chloro- or 4,5-dimethyl-indolyl-2-carbonyl, 1-benzylindolyl-2- or -3-carbonyl, 4,5,6,7-tetrahydroindolyl-2-carbonyl, unsubstituted or hydroxy-substituted quinolyl-lower alkanoyl, for example quinolylcarbonyl, such as 2-, 3- or 4-quinolylcarbonyl or 4-hydroxyquinolyl-2-carbonyl, unsubstituted or hydroxy-substituted isoquinolylcarbonyl, such as 1-, 3- or 4-isoquinolylcarbonyl or 1-oxo-1,2-dihydroisoquinolyl-3-carbonyl, 2-quinoxalinylcarbonyl, 2-(3,1-benzofuranyl)-carbonyl, benz[e]indolyl-2-carbonyl, β-carbolinyl-3-carbonyl, cyclohepta[b]pyrrolyl-5-carbonyl, 3-chromanylcarbonyl, 3-thiochromanylcarbonyl, pyrrolidinyl-3-carbonyl, hydroxypyrrolidinylcarbonyl, pyrrolidinyl-3-carbonyl, such as 3- or 4-hydroxypyrrolidinyl-2-carbonyl, oxopyrrolidinylcarbonyl, such as 5-oxopyrrolidinyl-2-carbonyl, piperidylcarbonyl, such as piperidinocarbonyl or 2-, 3- or 4-piperidylcarbonyl, pyrazinylcarbonyl, such as pyrazin-1-ylcarbonyl, piperazinylcarbonyl, such as piperazin-1-ylcarbonyl, morpholinyl-lower alkanoyl, for example morpholinylcarbonyl, such as morpholinocarbonyl, thiomorpholinyl-lower alkanoyl, for example thiomorpholinylcarbonyl, such as thiomorpholinocarbonyl, S,S-dioxothiomorpholinylcarbonyl, such as S,S-dioxothiomorpholinocarbonyl, indolinylcarbonyl, such as 2- or 3-indolinylcarbonyl, 1,2,3,4-tetrahydroquinolylcarbonyl, such as 1,2,3,4-tetrahydroquinolyl-2-, -3- or -4-carbonyl, 1,2,3,4-tetrahydroisoquinolylcarbonyl, such as 1,2,3,4-tetrahydroisoquinolyl-1-, -3- or -4-carbonyl or 1-oxo-1,2,3,4-tetrahydroisoquinolyl-3-carbonyl, tetrazolyl-lower alkanoyl, such as 3-(tetrazol-1-yl)propionyl, and pyridyl-lower alkanoyl, for example pyridylacetyl, such as 2-, 3- or 4-pyridylacetyl, heterocyclyl-lower alkanoyl being selected more especially from morpholinocarbonyl, thiomorpholinocarbonyl, S,S-dioxothiomorpholinocarbonyl, pyridylacetyl, indolylacetyl, benzofuranylacetyl, 4-pyrrolidinylacetyl, 1-imidazolylacetyl, quinolin-2-ylacetyl, indol-2-ylacetyl, 2-morpholino-2-isopropylacetyl and 2-(S,S-dioxothiomorpholino)-2-isopropylacetyl, most especially morpholinocarbonyl, thiomorpholinocarbonyl, quinolin-2-ylcarbonyl, 3-(tetrazol-1-yl)-propionyl or 2- or 3-pyridylacetyl, heterocyclyl-lower alkenoyl wherein heterocyclyl is selected especially from pyrrolyl, furyl, thienyl, imidazolyl, pyrazolyl, oxazolyl, thiazolyl, pyridyl, pyrazinyl, pyrimidinyl, indolyl, quinolyl, isoquinolyl, quinoxalinyl, β-carbolinyl and a benzo-fused, cyclopenta-, cyclohexa- or cyclohepta-fused derivative of those radicals, which may also be fully or partially saturated, for example pyrrolidyl-lower alkenoyl, such as N-pyrrolidylacryloyl, hydroxy-lower alkanoyl, such as 3-hydroxypropionyl or 2-hydroxy-2-methylpentanoyl, hydroxy-lower alkoxy-lower alkanoyl, such as 3-hydroxy-n-propoxycarbonyl, lower alkoxy-lower alkanoyl, for example lower alkoxyacetyl or lower alkoxypropionyl, such as methoxyacetyl, ethoxyacetyl or 3-methoxypropionyl, lower alkoxy-lower alkoxy-lower alkanoyl, such as 2-methoxymethoxy-3-methylpentanoyl, phenoxy-lower alkanoyl or nitrophenoxy-lower alkanoyl, such as phenoxyacetyl or 4-nitrophenoxyacetyl, naphthyloxy-lower alkanoyl, such as α- or β-naphthyloxyacetyl, lower alkanoyloxy-lower alkanoyl wherein lower alkanoyloxy is, for example, acetoxy, propionyloxy, butyroxy, isobutyroxy or pivaloyloxy, such as acetoxyacetyl or 3-acetoxypropionyl, acetoacetoxy-lower alkanoyl, such as 3-acetoacetoxypropionyl amino- or benzyloxycarbonylamino-lower alkanoyloxy-lower alkanoyl, for example 2-amino- or 2-benzyloxycarbonylamino-2-methylpropionyloxy-lower alkanoyl, such as -acetyl or -3-propionyl, aryl-lower alkanoyloxy-lower alkanoyl wherein aryl has from 6 to 10 carbon atoms, such as in benzoyloxy-, phenylacetoxy- or 1- or 2-naphthoyloxy-lower alkanoyl, lower alkoxycarbonyloxy-lower alkanoyl, for example methoxy-, ethoxy-, n-propoxy-, isopropoxy-, n-butoxy-, isobutoxy-, sec-butoxy-, tert-butoxy-, n-pentyloxy-, isopentyloxy-, neopentyloxy-, tert-pentyloxy-, n-hexyloxy-, isohexyloxy- or n-heptyloxycarbonyloxy-lower alkanoyl, such as -acetyl or -3-propionyl, mono- or di-lower alkyl-aminocarbonyloxy-lower alkanoyl, for example ethylaminocarbonyloxy-lower alkanoyl or diethylaminocarbonyloxy-lower alkanoyl, such as -acetyl or -3-propionyl, aryloxycarbonyloxy-lower alkanoyl wherein aryl has from 6 to 10 carbon atoms, for example phenoxycarbonyloxy- or 1- or 2-naphthyloxycarbonyloxy-lower alkanoyl, such as -acetyl or -3-propionyl, aryl-lower alkoxycarbonyloxy-lower alkanoyl wherein aryl has from 6 to 12 carbon atoms, for example phenyl-lower alkoxycarbonyloxy-lower alkanoyl, such as benzyloxycarbonyloxy-acetyl or -3-propionyl, and also 1- or 2-naphthylmethoxycarbonyloxy-lower alkanoyl or 9-fluorenylmethoxycarbonyloxy-lower alkanoyl, such as -acetyl or -3-propionyl, sulfonyloxy-lower alkanoyl, such as -acetyl or -3-propionyl, lower alkylsulfonyloxy-lower alkanoyl, for example methyl-, ethyl-, propyl-, isopropyl-, n-butyl-, isobutyl-, sec-butyl-, tert-butyl-, n-pentyl-, isopentyl-, neopentyl-, tert-pentyl-, n-hexyl-, isohexyl- or n-heptyl-sulfonyloxy-lower alkanoyl, such as -acetyl or -3-propionyl, phenylsulfonyloxy-, 2- or 4-toluenesulfonyloxy- or 1- or 2-naphthylsulfonyloxy-lower alkanoyl, arylmercapto-lower alkanoyl wherein aryl has from 6 to 10 carbon atoms and is preferably phenyl or naphthyl, for example phenylmercapto-lower alkanoyl, such as -acetyl or -3-propionyl, amino-lower alkanoyl wherein the amino group is not in the in α- or β-position, such as 5-aminopentanoyl, lower alkanoylamino-lower alkanoyl wherein the amino group is not in the α- or β-position of the lower alkanoyl radical, such as 5-amino-pentanoyl, lower alkoxycarbonylamino-lower alkanoyl wherein the amino group is not in the α- or β-position of the lower alkanoyl radical, such as 5-(tert-butoxycarbonylamino)-pentanoyl, phenyl-lower alkoxycarbonylamino-lower alkanoyl wherein the amino group is not in the α- or β-position of the lower alkanoyl radical, such as 5-benzyloxycarbonylaminopentanoyl or 6-benzyloxycarbonylaminohexanoyl, amino-lower alkanoyl substituted at the amino nitrogen atom by heterocyclyl-lower alkanoyl as defined above for heterocyclyl-lower alkanoyl $R_1$, $R_2$, $R_8$ or $R_9$, especially by N-morpholino- or N-thiomorpholinocarbonyl, for example N-morpholino- or N-thiomorpholino-carbonylamino-lower alkanoyl, such as N-morpholino- or N-thiomorpholinocarbonylamino-acetyl, halo-lower alkanoyl preferably containing up to 3 halogen atoms, for example α-haloacetyl, such as α-fluoro-, α-chloro-, α-bromo-, α-iodo-, α,α,α-trifluoro- or α,α,α-trichloro-acetyl, or halopropionyl, such as β-chloro- or β-bromo-propionyl, carboxy-lower alkanoyl, for example carboxyacetyl or β-carboxypropionyl, lower alkoxycarbonyl-lower alkanoyl, for example lower alkoxycarbonylacetyl or lower alkoxycarbonylpropionyl, such as methoxycarbonylacetyl, 3-methoxycarbonylpropionyl, ethoxycarbonylacetyl, 3-ethoxycarbonylpropionyl or 3-tert-butoxycarbonylpropionyl, lower alkylcarbonyl-halo-lower alkanoyl, such as 3-ethoxycarbonyl-2-difluoromethylpropionyl, 2-halo-lower alkoxycarbonyl-lower alkanoyl, such as 2-chloro-, 2-bromo-, 2-iodo- or 2,2,2-trichloroethoxycarbonyl-acetyl or -3-propionyl, phenyl- or naphthyl-lower alkoxycarbonyl-lower alkanoyl, for example benzyloxycarbonyl-lower alkanoyl, such as 3-benzyloxycarbonyl-2,2-dimethylpropionyl, heterocyclyl-lower alkoxycarbonyl-lower alkanoyl wherein heterocyclyl is preferably selected from pyrrolyl, furyl, thienyl, imidazolyl, pyrazolyl, oxazolyl, thiazolyl, pyridyl, pyrazinyl, pyrimidinyl, indolyl, quinolyl, isoquinolyl, quinoxalinyl and β-carbolinyl and a benzo-fused, cyclopenta-, cyclohexa- or cyclohepta-fused derivative of those radicals, it also being possible for the mentioned radicals to be fully or partially saturated, such as in 4-pyridylmethoxycarbonyl-acetyl or -3-propionyl or 2-morpholinocarbonyloxy-4-methylpentanoyl, sulfonyl-lower alkanoyl, such as 3-sulfonylpropionyl, lower alkylsulfonyl-lower alkanoyl, such as 2-ethylsulfonyl- or 2-tert-butylsulfonylacetyl, arylsulfonyl-lower alkanoyl wherein aryl preferably has from 6 to 10 carbon atoms, for example phenyl or naphthyl, such as phenylsulfoacetyl, carbamoyl-lower alkanoyl, such as carbamoylacetyl or 3-carbamoylpropionyl, lower alkylcarbamoyl-lower alkanoyl, for example lower alkylcarbamoylacetyl or methylcarbamoyl-lower alkanoyl, such as methylcarbamoylacetyl, di-lower alkylcarbamoyl-lower alkanoyl, for example di-lower alkylcarbamoylacetyl or dimethylcarbamoyl-lower alkanoyl, such as dimethylcarbamoylacetyl, hydroxy-lower alkylcarbamoyl- or di(hydroxy-lower alkyl)carbamoyl-lower alkanoyl, such as hydroxymethylcarbamoyl- or di(hydroxymethyl) carbamoyl-acetyl or -propionyl, N-lower alkoxy-lower alkoxy-lower alkylcarbamoyl-lower alkanoyl, such as 2-isobutyl-3-(2-(2-methoxyethoxy)ethylaminocarbonyl)-propionyl, carboxy-lower alkylcarbamoyl- or di(carboxy-lower alkyl)carbamoyl-lower alkanoyl, such as carboxymethyl- or di(carboxymethyl)carbamoyl-acetyl or -propionyl, carbamoyl-lower alkanoyl substituted at the nitrogen atom by a radical selected from ethylene, trimethylene, tetramethylene and pentamethylene wherein a carbon atom may have been replaced by nitrogen, oxygen, sulfur or by sulfur mono- or di-substituted by oxygen, it also being possible for the radical so formed to be fully or partially unsaturated, for example in the form of piperidino-, pyrazin-1-yl-, piperazin-1-yl-, pyrimidin-1-yl-, pyridazin-1-yl-, morpholino-, thiomorpholino- or S,S-dioxothiomorpholinocarbonyl-lower alkanoyl, such as in morpholinocarbonyl-acetyl, 3-(morpholinocarbonyl)-propionyl or 3-(morpholinocarbonyl)-2-isobutyl-propionyl, N-heterocyclyl-lower alkylcarbamoyl-lower alkanoyl or N-lower alkyl-N-heterocyclyl-lower alkylcarbamoyl-lower alkanoyl wherein heterocyclyl is preferably selected from pyrrolyl, furyl, thienyl, imidazolyl, pyrazolyl, oxazolyl, thiazolyl, pyridyl, pyrazinyl, pyrimidinyl, indolyl, quinolyl, isoquinolyl, quinoxalinyl, β-carbolinyl and a benzo-fused, cyclopenta-, cyclohexa- or cyclohepta-fused derivative of those radicals, which may also be fully or partially saturated, from morpholinyl and thiomorpholinyl, such as N-methyl-2-(N-2-pyridylmethyl)-carbamoylacetyl, 2-(N-morpholino-lower alkylcarbamoyl)-lower alkanoyl, such as 2(R,S)-(N-(2-morpholinoethyl)-carbamoyl-3-methyl-butyryl or 2-(N-(pyridyl-lower alkyl)-carbamoyl)-lower alkanoyl, such as (2(R,S)-(N-(2-pyridylmethyl)-carbamoyl)-3-methyl)-butyryl, sulfamoyl-lower alkanoyl, such as 2-sulfamoylacetyl, N-(phenyl- or naphthyl-lower alkyl)sulfamoyl-lower alkanoyl, such as 3-benzylaminosulfonyl-2-isopropylpropionyl, sulfamoyl-lower alkanoyl substituted at the nitrogen atom by a radical selected from ethylene, trimethylene, tetramethylene and pentamethylene wherein a carbon atom may have been replaced by nitrogen, lower alkyl-substituted, such as methyl-substituted, nitrogen, oxygen, sulfur or by sulfur mono- or di-substituted by oxygen, it also being possible for the radical so formed to be fully or partially unsaturated, for example in the form of piperidino-, pyrazin-1-yl-, piperazin-1-yl-, 4-methylpiperazin-1-yl, pyrimidin-1-yl-, pyridazin-1-yl-, morpholino-, thiomorpholino- or S,S-dioxothiomorpholinosulfonyl-lower alkanoyl, such as 3-(4-methylpiperazinylsulfonyl)-2-isopropylpropionyl or 3-(morpholinosulfonyl)-2-isopropyl-propionyl, oxo-lower alkanoyl, such as acetoacetyl or propionylacetyl, cyano-lower alkanoyl, such as cyanoacetyl, 2- or 3-cyanopropionyl or 2-, 3- or 4-cyanobutyryl, hydroxy-carboxy-lower alkanoyl, such as 2-hydroxy-2-carboxy-acetyl or 2-hydroxy-3-carboxypropionyl, (α-naphthyloxy-carboxy-lower alkanoyl, such as 2-α-naphthyloxy-4-carboxy-butyryl, hydroxy-lower alkoxycarbonyl-lower alkanoyl, for example hydroxy-lower alkoxycarbonyl-acetyl or -propionyl or hydroxy-ethoxy- or hydroxy-methoxy-carbonyl-lower alkanoyl, such as 2-hydroxy-2-ethoxy- or -methoxy-carbonylacetyl or 2-hydroxy-3-ethoxy- or -methoxy-carbonyl-propionyl, α-naphthyloxy-lower alkoxycarbonyl-lower alkanoyl, for example α-naphthyloxy-lower alkoxycarbonyl-acetyl, -propionyl or -butyryl or α-naphthyloxy-ethoxycarbonyl-lower alkanoyl, such as α-naphthyloxy-ethoxycarbonylacetyl, 2-α-naphthyloxy-3-ethoxycarbonylpropionyl or 2-α-naphthyloxy-4-tert-butoxycarbonylbutyryl, α-naphthyloxy-benzyloxycarbonyl-lower alkanoyl, such as 2-α-naphthyloxy-3-benzyloxycarbonyl-propionyl, esterified hydroxy-lower alkoxycarbonyl-lower alkanoyl wherein the hydroxy group is esterified by lower alkanoyl, for example acetyl, propionyl or pivaloyl; by cycloalkyl-lower alkanoyl wherein cycloalkyl has from 3 to 7 carbon atoms and lower alkanoyl is preferably as last defined, for example cyclohexylcarbonyl or 2-cyclohexyl- or 2-cyclopentyl-acetyl; by bicycloalkyl-lower alkanoyl wherein bicycloalkyl has, for example, from 5 to 10, especially from 6 to 9, carbon atoms, such as in bicyclohexyl-, -heptyl-, -octyl-, -nonyl- or -decyl-acetyl or -3-propionyl, for example bicyclo[3.1.0]hex-1-, -2- or -3-yl-, bicyclo[4.1.0]hept-1- or -7-yl-, bicyclo[2.2.1]hept-2-yl-, such as endo- or exo-norbornyl-, bicyclo[3.2.1]oct-2-yl-, bicyclo[3.3.0]oct-3-yl- or bicyclo[3.3.1]non-9-yl-, and also α- or β-decahydronaphthyl-acetyl or -3-propionyl; by tricycloalkyl-lower alkanoyl wherein tricycloalkyl has, for example, from 8 to 10 carbon atoms, for example in tricyclo-[5.2.1.0$^{2,6}$]dec-8-yl- or adamantyl-, such as 1-adamantyl-acetyl; by aryl-lower alkanoyl wherein aryl has from 6 to 14 carbon atoms, for example phenyl, indenyl, indanyl, naphthyl, anthryl, phenanthryl, acenaphthyl or fluorenyl, which may be unsubstituted or mono- to tri-substituted by lower alkyl, such as isopropyl, halo-lower alkyl, such as trifluoromethyl, hydroxy, lower alkoxy, carbamoyl-lower alkoxy, N-lower alkylcarbamoyl-lower alkoxy or N,N-di-lower alkylcarbamoyl-lower alkoxy, amino, mono- or di-lower alkylamino, halogen, such as fluorine, chlorine or bromine, carboxy, lower alkoxycarbonyl, phenyl-, naphthyl- or fluorenyl-lower alkoxycarbonyl, lower alkanoyl, lower alkylsulfonyl, for example methylsulfonyl, phosphono, hydroxy-lower alkoxyphosphoryl or di-lower alkoxyphosphoryl, carbamoyl, mono- or di-lower alkylaminocarbamoyl, sulfamoyl, mono- or di-lower alkylsulfamoyl, nitro and/or by cyano; by lower alkoxycarbonyl, for example tert-butoxycarbonyl; by 2-halo-lower alkoxycarbonyl as defined above; or by phenyl- or fluorenyl-lower alkoxycarbonyl, for example benzyloxycarbonyl or 9-fluorenylmethoxycarbonyl, such as α-acetoxy-α-methoxycarbonyl-acetyl, α-benzoyloxy-, α-(1- or 2-naphthoyloxy)-, α-(phenyl-2-acetoxy)-, α-(1- or 2-naphthyl-2-acetoxy)-, α-(4-methylphenyl-2-acetoxy) -, α-(4-methoxyphenyl-2-acetoxy)- or α-(2-(o,o-dichlorophenyl)-2-acetoxy)-α-methoxycarbonyl-acetyl, dihydroxy-carboxy-lower alkanoyl, such as 2,3-dihydroxy-3-carboxy-propionyl, dihydroxy-lower alkoxycarbonyl-lower alkanoyl, such as 2,3-dihydroxy-3-ethoxy- or -methoxy-carbonyl-propionyl, dihydroxy-lower alkoxycarbonyl-lower alkanoyl esterified by lower alkanoyl, such as acetyl, propionyl or butyryl, lower alkoxycarbonyl, for example tert-butoxycarbonyl, phenyl- or fluorenyl-lower alkoxycarbonyl, such as benzyloxycarbonyl or 9-fluorenylmethoxycarbonyl, lower alkylsulfonyl or by toluenesulfonyl, for example di-lower alkanoyloxy-lower alkoxy-propionyl, such as 2,3-diacetoxy-3-methoxycarbonylpropionyl, α-naphthyloxy-di-lower alkylamino-lower alkanoyl, such as 2-α-naphthyloxy-5-dimethylamino-pentanoyl, α-naphthyloxy-carbamoyl-lower alkanoyl, such as 2-α-naphthyloxy-4-carbamoyl-butyryl, α-naphthyloxy-oxo-lower alkanoyl, such as 2-α-naphthyloxy-4-oxo-pentanoyl, α-naphthyloxy-cyano-lower alkanoyl, such as α-naphthyloxy-cyano-acetyl or 2-α-naphthyloxy-4-cyanobutyryl, lower alkenoyl having from 3 to 7 carbon atoms, preferably having 3 or 4 carbon atoms, lower alkenoyl being unsubstituted or substituted by the same substituents as lower alkanoyl, especially by phenyl, hydroxy, lower alkoxy, such as methoxy, phenyl-lower alkoxy, such as benzyloxy, lower alkanoyloxy, such as acetoxy, lower alkanoylamino, such as acetylamino, lower alkoxycarbonyloxy, such as tert-butoxycarbonyloxy, phenyl- or naphthyl-lower alkoxycarbonyloxy, such as benzyloxycarbonyloxy, carboxy, lower alkoxycarbonyl, such as tert-butoxycarbonyl, phenyl- or naphthyl-lower alkoxycarbonyl, halogen, such as chlorine or bromine, carbamoyl and/or by mono- or di-lower alkyl-carbamoyl, such as in acryloyl, vinylacetyl, crotonoyl or 3- or 4-pentenoyl, 3-phenylacryloyl, 3-phenylvinylacetyl or 5-phenyl-4-acetylaminopenten-2-oyl, cycloalkyl-lower alkenoyl wherein cycloalkyl preferably has from 3 to 7 carbon atoms, for example cyclohexylacryloyl, or lower alkynoyl having from 3 to 7, preferably 3 or 4, carbon atoms, for example propioloyl or 2- or 3-butynoyl.

Preferred acyl groups $R_1$, $R_2$, $R_8$ and $R_9$ of a semiester of carbonic acid are lower alkoxycarbonyl, for example methoxy-, ethoxy-, isopropoxy-, isobutoxy- or tert-lower alkoxy-carbonyl, such as tert-butoxycarbonyl or isobutoxycarbonyl, 2-halo-lower alkoxycarbonyl, such as 2-chloro-, 2-bromo-, 2-iodo- or 2,2,2-trichloroethoxycarbonyl, aryloxycarbonyl wherein aryl has from 6 to 14 carbon atoms and is, for example, phenyl, biphenylyl, 1- or 2-naphthyl, fluorenyl, or phenyl mono- or poly- substituted by lower alkyl, for example methyl or tert-butyl, hydroxy, lower alkoxy, for example methoxy, ethoxy or tert-butoxy, halogen, for example chlorine or bromine, and/or by nitro, such as phenoxycarbonyl, aryl-lower alkoxycarbonyl, for example arylmethoxycarbonyl, wherein aryl has from 6 to 14 carbon atoms and is, for example, phenyl, biphenylyl, 1- or 2-naphthyl, fluorenyl, or phenyl mono- or poly-substituted by lower alkyl, for example methyl or tert-butyl, hydroxy, lower alkoxy, for example methoxy, ethoxy or tert-butoxy, halogen, for example chlorine or bromine, and/or by nitro, for example phenyl-lower alkoxycarbonyl, such as benzyloxycarbonyl, 4-methoxybenzyloxycarbonyl, 4-nitrobenzyloxycarbonyl, diphenyl-lower alkoxycarbonyl, such as diphenylmethoxycarbonyl, di-(4-methoxyphenyl)-methoxycarbonyl, trityloxycarbonyl or fluorenyl-lower alkoxycarbonyl, such as 9-fluorenylmethoxycarbonyl, especially benzyloxycarbonyl, heterocyclyl-lower alkoxycarbonyl wherein heterocyclyl is preferably selected from pyrrolyl, furyl, thienyl, imidazolyl, pyrazolyl, oxazolyl, thiazolyl, pyridyl, pyrazinyl, pyrimidinyl, indolyl, quinolyl, isoquinolyl, quinoxalinyl, β-carbolinyl and a benzo-fused, cyclopenta-, cyclohexa- or cyclohepta-fused derivative of those radicals, which may also be fully or partially saturated, from morpholinyl and from thiomorpholinyl and may be unsubstituted or substituted, especially by lower alkyl, such as methyl, such as 1-methylpyrrolidin-2-yl-methoxycarbonyl, 2-furylmethoxycarbonyl, 2-tetrahydrofuranyl-lower alkoxycarbonyl, such as 2-tetrahydrofuranyl-methoxycarbonyl, 1-methyl-2-piperidylmethoxycarbonyl or 2-morpholino-ethoxycarbonyl, or 2-, 3- or 4-pyridylmethoxycarbonyl, 2-tri-lower alkylsilyl-lower alkoxycarbonyl, such as 2-trimethylsilyloxycarbonyl, or 2-triarylsilyl-lower alkoxycarbonyl wherein aryl is phenyl or 1- or 2-naphthyl, such as triphenylsilylethoxycarbonyl.

Preferred acyl groups $R_1$, $R_2$, $R_8$ and $R_9$ of an unsubstituted or substituted carbamic acid, in addition to suitable radicals already mentioned as preferred acyl groups $R_1$, $R_2$, $R_8$ and $R_9$, are carbamoyl or unsubstituted or substituted N-alkyl- or N,N-dialkylcarbamoyl wherein the alkyl radical has up to 12 carbon atoms, preferably unsubstituted or substituted lower alkyl- or di-lower alkyl-carbamoyl, such as methyl-, ethyl-, propyl-, tert-butyl-, dimethyl-, diethyl- or di-n-propyl-carbamoyl, the substituents being selected from phenyl, for example in benzylcarbamoyl, N-phenyl-lower alkyl-N-lower alkylcarbamoyl, such as N-benzyl-N-methylcarbamoyl, or dibenzylcarbamoyl, heterocyclyl as defined under heterocyclyl-lower alkanoyl $R_1$, $R_2$, $R_8$ and $R_9$, preferably selected from thienyl, furyl, pyranyl, pyrrolyl, imidazolyl, pyrazolyl, oxazolyl, isoxazolyl, thiazolyl, furazanyl, pyridyl, pyrazinyl, pyrimidinyl, pyridazinyl, azepinyl, indolyl, benzimidazolyl, 1H-indazolyl, quinolyl, isoquinolyl, quinoxalinyl, quinazolinyl, cinnolyl, purinyl, pteridinyl, naphthyridinyl, 4H-quinolizinyl, 3,1-benzofuranyl, benz[e]indolyl, 4,1-benzoxazinyl, 4,1-benzothiazinyl, carbazolyl, β-carbolinyl, phenazinyl, phenanthridyl, acridyl, phenoxazinyl, phenothiazinyl, 1-azaacenaphthenyl, cyclohexa[b]pyrrolyl, cyclohepta[b]pyrrolyl, cyclohexa[d]pyrazolyl, cyclohexa[b]pyridyl, cyclohexa[b]pyrazinyl, cyclohexa[b]pyrimidinyl, cyclohexa[b]-1,4-oxazinyl, cyclohexa[b]-1,4-thiazinyl, pyrrolidinyl, pyrrolinyl, imidazolidinyl, 2-imidazolinyl, 2,3-dihydropyridyl, piperidyl, piperazinyl, 2,3,5,6-tetrahydropyrazinyl, morpholinyl, thiomorpholinyl, S,S-dioxothiomorpholinyl, indolinyl, isoindolinyl, 4,5,6,7-tetrahydroindolyl, 1,2,3,4-tetrahydroquinolyl, 1,2,3,4-tetrahydroisoquinolyl, chromanyl, thiochromanyl, 1,2,3,4-tetrahydro-3,1-benzodiazinyl, 3,4-dihydro-3H-4,1-benzoxazinyl, 3,4-dihydro-3H-4,1-benzothiazinyl, 2,3,4,5-tetrahydro-1H-5,1-benzazepinyl and 5,6-dihydrophenanthrid the mentioned radicals being unsubstituted or substituted by lower alkyl, for example methyl, phenyl, 1- or 2-naphthyl, phenyl-lower alkyl, for example benzyl, hydroxy-lower alkyl, for example hydroxymethyl or 2-hydroxyethyl, lower alkoxy-lower alkyl, for example methoxymethyl or 2-methoxyethyl, phenoxy- or naphthyloxy-lower alkyl, for example 2-phenoxyethyl, 1- or 2-naphthyloxymethyl, phenyl-lower alkoxy- or naphthyl-lower alkoxy-lower alkyl, for example benzyloxy-lower alkyl, lower alkanoyloxy-lower alkyl, for example acetoxymethyl, phenyl- or naphthyl-lower alkanoyloxy-lower alkyl, for example benzoyloxy-, phenylacetoxy- or 1- or 2-naphthoyloxy-methyl, -2-ethyl or -2-(2,2-dimethylethyl), lower alkoxycarbonyloxy-lower alkyl, for example tert-butoxycarbonyloxy-lower alkyl, phenyl-, naphthyl- or fluorenyl-lower alkoxycarbonyloxy-lower alkyl, for example 2-benzyloxycarbonyloxyethyl or 9-fluorenylmethoxycarbonyloxyethyl, amino-lower alkyl, for example aminomethyl, 2-aminoethyl or 2-aminopropyl, carboxy-lower alkyl, for example carboxymethyl or 2-carboxyethyl, hydroxy, lower alkoxy, for example methoxy or ethoxy, phenyl- or naphthyl-lower alkoxy, for example benzyloxy or 1- or 2-naphthylmethoxy, amino, lower alkylamino, for example methyl-, ethyl- or tert-butyl-amino, di-lower alkyl-amino, for example dimethyl- or diethyl-amino, carboxy, lower alkoxycarbonyl, for example methoxy-, isopropoxy-, sec-butoxy- or tert-butoxy-carbonyl, phenyl- or naphthyl-lower alkoxycarbonyl, for example benzyloxycarbonyl, halogen, for example fluorine, chlorine, bromine or iodine, especially chlorine or bromine, lower alkanoyl, for example acetyl or pivaloyl, lower alkylsulfonyl, for example methyl- or ethyl-sulfonyl, phosphono, hydroxy-lower alkoxyphosphoryl or dialkoxy-phosphoryl, for example dimethoxy- or diethoxy-phosphoryl, carbamoyl, mono- or di-lower alkylcarbamoyl, for example N-methylcarbamoyl, N-n-butylcarbamoyl or N,N-dimethylcarbamoyl, hydroxy- or carboxy-lower alkylcarbamoyl, for example hydroxy- or carboxy-methylcarbamoyl or hydroxy- or carboxy-ethylcarbamoyl, sulfamoyl, nitro, oxo and/or by cyano, especially pyridyl, such as 2-, 3- or 4-pyridyl, more especially in N-heterocyclyl-lower alkyl-N-lower alkylcarbamoyl, for example N-pyridyl-lower alkyl-N-lower alkylcarbamoyl, such as N-(2-, 3- or 4-pyridylmethyl)-N-methyl-carbamoyl, or in N-heterocyclyl-lower alkylcarbamoyl, for example 2- or 3-pyridyl-lower alkylaminocarbonyl, such as 2- or 3-pyridylmethylaminocarbonyl, hydroxy, for example in hydroxymethyl, 2-hydroxyethyl, 3-hydroxypropyl, 2-hydroxypropyl, N-dihydroxy-lower alkyl, such as 2,3-dihydroxy-n-propyl or 2-hydroxy-2,2-dimethylethyl, lower alkoxy, preferably in lower alkoxy-lower alkyl, for example methoxymethyl or 2-methoxyethyl, lower alkanoyloxy, preferably in lower alkanoyloxy-lower alkyl, for example lower alkanoyloxymethyl or lower alkanoyloxyethyl, such as acetoxymethyl, 2-acetoxyethyl, 3-propionyloxymethyl, 2-propionyloxyethyl, 4-butyroxymethyl or 2-butyroxyethyl, aryloxy or aryloxy and hydroxy wherein aryl has from 6 to 14 carbon atoms, such as phenyl, naphthyl or fluorenyl, preferably in aryloxy-lower alkyl or aryloxyhydroxy-lower alkyl, such as phenoxymethyl, 2-phenoxyethyl, 1- or 2-naphthyloxymethyl or 1- or 2-naphthyloxyethyl, or 2-phenyl-2-hydroxyethyl, aryl being unsubstituted or mono- or di-substituted, for example by lower alkyl, for example methyl, ethyl, propyl, isopropyl, butyl, sec-butyl or tert-butyl, by hydroxy, by lower alkoxy, for example methoxy, ethoxy, propoxy, isopropoxy, butoxy, sec-butoxy or tert-butoxy, by carboxy, by lower alkoxycarbonyl, for example isopropoxycarbonyl, sec-butoxycarbonyl or tert-butoxycarbonyl, or by carbamoyl, lower alkyl- or di-lower alkyl-carbamoyl and/or by mono- or di-(hydroxy- or carboxy-lower alkyl)carbamoyl and it being possible for the mentioned substituents to be present in different ring positions, for example in the form of 4-methylphenoxy, 2,4,5-trimethylphenoxy, 4-hydroxyphenoxy, 4-methoxyphenoxy, 3,5-dimethoxyphenoxy, 2-carboxyphenoxy, 2-tert-butoxycarbonylphenoxy, 2- or 4-carbamoylphenoxy, carbamoyl, carboxy-lower alkylcarbamoyl or hydroxy-lower alkylcarbamoyl, such as in 4-carbamoyl-n-butyl, 7-carbamoyl-n-heptyl, 2-hydroxyethylcarbamoyl-n-butyl or 4-(tris(hydroxymethyl]methyl)-carbamoyl-n-butyl, and also amino, for example in 2-aminoethyl or 3-aminopropyl, lower alkylamino, for example in methyl- or ethyl-aminomethyl, di-lower alkylamino, for example in dimethylaminomethyl, halogen, especially fluorine, chlorine or bromine, for example in 2,2,2-trichloroethyl, sulfo, for example in sulfomethyl or 4-sulfobutylamino, and sulfamoyl, for example in 2-sulfamoylethyl.

Preferred acyl groups $R_1$, $R_2$, $R_8$ and $R_9$ of an unsubstituted or substituted N-substituted oxalamide are oxamoyl or lower alkyloxamoyl, such as methyl- or ethyl-oxamoyl.

Preferred acyl groups $R_1$, $R_2$, $R_8$ and $R_9$ of an unsubstituted or substituted amino acid are formed by the amino acid residues of an α- or β-amino acid, especially a natural α-amino acid having the L-configuration, such as those normally occurring in proteins, or an epimer of such an amino acid, that is to say having the unnatural D-configuration, or a D,L-isomeric mixture thereof, a homologue of such an amino acid, for example wherein the amino acid side chain has been lengthened or shortened by one or two methylene groups, wherein the amino group is in the β-position and/or wherein a methyl group has been replaced by hydrogen, a substituted aromatic amino acid wherein the aromatic radical has from 6 to 14 carbon atoms, for example a substituted phenylalanine or phenylglycine wherein the phenyl may be mono- or poly-substituted by lower alkyl, for example methyl, hydroxy, lower alkoxy, for example methoxy, lower alkanoyloxy, for example acetoxy, amino, lower alkylamino, for example methylamino, di-lower alkylamino, for example dimethylamino, lower alkanoylamino, for example acetylamino or pivaloylamino, lower alkoxycarbonylamino, for example tert-butoxycarbonylamino, arylmethoxycarbonylamino wherein aryl preferably has from 6 to 14 carbon atoms, for example benzyloxycarbonylamino or 9-fluorenylmethoxycarbonylamino, halogen, for example fluorine, chlorine, bromine or iodine, carboxy and/or by nitro, a benzo-fused phenylalanine or phenylglycine, such as α-naphthylalanine, or a hydrogenated phenylalanine or phenylglycine, such as cyclohexylalanine or cyclohexylglycine.

Those amino acids can be substituted at free amino or hydroxy functions, preferably at a free amino function, by one of the radicals mentioned above under acyl $R_1$ as the acyl group of a carboxylic acid, a semiester of carbonic acid, an unsubstituted or N-substituted carbamic acid or an unsubstituted or N-substituted oxalamide or by one of the radicals mentioned below under unsubstituted or substituted alkyl; aryl-lower alkyl; heterocyclyl; heterocyclyl-lower alkyl; sulfo; sulfonyl substituted by alkyl, aryl, aryl-lower alkyl, heterocyclyl-lower alkyl, alkoxy, aryloxy, aryl-lower alkoxy or by heterocyclyl-lower alkoxy; phosphoryl $R_1$, $R_2$, $R_8$ or $R_9$ substituted by one or two identical or different radicals selected from alkyl, cycloalkyl, cycloalkyl-lower alkyl, aryl, aryl-lower alkyl, hydroxy, alkoxy, cycloalkoxy, cycloalkyl-lower alkoxy, aryloxy and aryl-lower alkoxy; and sulfamoyl $R_1$, $R_2$, $R_8$ or $R_9$, which is unsubstituted or substituted at the nitrogen atom; or by one of the radicals mentioned as protecting groups in the section relating to processes.

Especially preferred is the radical, bonded via a carboxy group, of an amino acid selected from glycine (H-Gly-OH), alanine (H-Ala-OH), valine (H-Val-OH), norvaline (α-amino-valeric acid), leucine (H-Leu-OH), isoleucine (H-Ile-OH), norleucine (α-aminohexanoic acid, H-Nle-OH), serine (H-Ser-OH), homoserine (α-amino-γ-hydroxybutyric acid), threonine (H-Thr-OH), methionine (H-Met-OH), cysteine (H-Cys-OH), proline (H-Pro-OH), trans-3- and trans-4-hydroxyproline, phenylalanine (H-Phe-OH), tyrosine (H-Tyr-OH), 4-aminophenylalanine, 4-chlorophenylalanine, 4-carboxyphenylalanine, β-phenylserine (β-hydroxyphenylalanine), phenylglycine, α-naphthylalanine (H-Nal-OH), cyclohexylalanine (H-Cha-OH), cyclohexylglycine, tryptophan (H-Trp-OH), indoline-2-carboxylic acid, 1,2,3,4-tetrahydroisoquinoline-3-carboxylic acid, aspartic acid (H-Asp-OH), asparagine (H-Asn-OH), aminomalonic acid, aminomalonic acid monoamide, glutamic acid (H-Glu-OH), glutamine (H-Gln-OH), histidine (H-His-OH), arginine (H-Arg-OH), lysine (H-Lys-OH), δ-hydroxylysine, ornithine (α,δ-diaminovaleric acid), 3-aminopropanoic acid, α,γ-diaminobutyric acid and α,β-diaminopropionic acid, especially preferably the radical of an aliphatic amino acid selected from valine, alanine, leucine and isoleucine, or an amino acid selected from glycine, glutamic acid and asparagine, it being possible for each of the mentioned amino acids (with the exception of glycine) to be in the D-, L- or (D,L)-form, preferably in the L-form (with the exception of Val which may also be in the (D)- or (D,L)-form), and wherein the α-amino group may be unsubstituted or mono- or di-N-alkylated, for example by lower alkyl, such as methyl or n-propyl, by amino-lower alkyl, such as 3-aminopropyl, by phenyl- or naphthyl-amino-lower alkyl, such as 3-phenylaminopropyl, or by piperazinylcarbonyl-lower alkyl substituted at the nitrogen atom by lower alkyl, such as methyl, such as 4-methylpiperazinylcarbonylmethyl, or may be N-acylated, for example by lower alkanoyl, such as acetyl; by aryl-lower alkanoyl wherein aryl is selected from phenyl, indenyl, indanyl, naphthyl, anthryl, phenanthryl, acenaphthyl and fluorenyl and may be unsubstituted or especially mono- to tri-substituted by lower alkyl, for example methyl, ethyl or propyl, halo-lower alkyl, for example trifluoromethyl, phenyl, 1- or 2-naphthyl, hydroxy, lower alkoxy, for example methoxy, carbamoyl-lower alkoxy, N-lower alkylcarbamoyl-lower alkoxy or N,N-di-lower alkylcarbamoyl-lower alkoxy, amino, mono- or di-lower alkylamino, lower alkanoylamino, for example pivaloylamino, halogen, for example fluorine, chlorine or bromine, carboxy, lower alkoxycarbonyl, such as tert-butoxycarbonyl, phenyl-, naphthyl- or fluorenyl-lower alkoxycarbonyl, such as benzyloxycarbonyl, lower alkanoyl, sulfo, lower alkylsulfonyl, for example methylsulfonyl, phosphono, hydroxy-lower alkoxyphosphoryl or di-lower alkoxyphosphoryl, carbamoyl, mono- or di-lower alkylcarbamoyl, sulfamoyl, mono- or di-lower alkylaminosulfonyl, nitro and/or by cyano, wherein phenyl may be present up to three times, for example in diphenyl-, dibenzyl- or triphenyl-lower alkanoyl, such as diphenyl-, dibenzyl- or triphenyl-acetyl, and wherein lower alkanoyl may be unsubstituted or substituted, for example by lower alkyl, for example methyl, heterocyclyl selected from pyrrolyl, furyl, thienyl, imidazolyl, pyrazolyl, oxazolyl, thiazolyl, pyridyl, pyrazinyl, pyrimidinyl, indolyl, quinolyl, isoquinolyl, quinoxalinyl, β-carbolinyl and a benzo-, cyclopenta-, cyclohexa- or cyclohepta-fused derivative of those radicals, which may also be fully or partially saturated, hydroxy, lower alkoxy, lower alkanoyloxy, for example acetoxy, propionyloxy, butyroxy, isobutyroxy or pivaloyloxy, acetoacetoxy, amino- or benzyloxycarbonylamino-lower alkanoyloxy, for example 2-amino- or 2-benzyloxycarbonylamino-2-methylpropionyloxy, aryl-lower alkanoyloxy wherein aryl has from 6 to 10 carbon atoms, for example in benzoyloxy, phenylacetoxy, 1- or 2-naphthoyloxy, lower alkoxycarbonyloxy, for example methoxy-, ethoxy-, n-propoxy-, isopropoxy-, n-butoxy-, isobutoxy-, sec-butoxy-, tert-butoxy-, n-pentyloxy-, isopentyloxy-, neopentyloxy-, tert-pentyloxy-, n-hexyloxy-, isohexyloxy- or n-heptyloxy-carbonyloxy, mono- or di-lower alkyl-aminocarbonyloxy, for example ethylaminocarbonyloxy or diethylaminocarbonyloxy, aryloxycarbonyloxy wherein aryl has from 6 to 10 carbon atoms, for example phenoxycarbonyloxy or 1- or 2-naphthyloxycarbonyloxy, aryl-lower alkoxycarbonyloxy wherein aryl has from 6 to 14 carbon atoms, especially phenyl-lower alkoxycarbonyloxy, for example benzyloxycarbonyloxy, and also 1- or 2-naphthylmethoxycarbonyloxy or 9-fluorenylmethoxycarbonyloxy, sulfonyloxy, lower alkylsulfonyloxy, for example methyl-, ethyl-, propyl-, isopropyl-, n-butyl-, isobutyl-, sec-butyl-, tert-butyl-, n-pentyl-, isopentyl-, neopentyl-, tert-pentyl-, n-hexyl-, isohexyl- or n-heptyl-sulfonyloxy, or phenylsulfonyloxy, 2- or 4-toluenesulfonyloxy or 1- or 2-naphthylsulfonyloxy, carboxy, esterified carboxy selected from lower alkoxycarbonyl, for example methoxy-, ethoxy-, n-propoxy-, isopropoxy-, n-butoxy-, isobutoxy-, sec-butoxy-, tert-butoxy-, n-pentyloxy-, isopentyloxy-, neopentyloxy-, tert-pentyloxy-, n-hexyloxy-, isohexyloxy- or n-heptyloxy-carbonyl, aryloxycarbonyl wherein aryl has from 6 to 10 carbon atoms, for example phenoxycarbonyl or 1- or 2-naphthyloxycarbonyl, aryl-lower alkoxycarbonyl wherein aryl has from 6 to 12 carbon atoms, for example benzyloxycarbonyl, 1- or 2-naphthylmethoxycarbonyl or 9-fluorenylmethoxycarbonyl, lower alkanoyl, lower alkylsulfonyl, for example methyl- or tert-butyl-sulfonyl, hydroxy-lower alkoxyphosphoryl and di-lower alkoxyphosphoryl, carbamoyl, carbamoyl substituted by one or two radicals selected from lower alkyl, such as methyl, ethyl, propyl, isopropyl, n-butyl, isobutyl, sec-butyl, tert-butyl, n-pentyl, isopentyl, neopentyl, tert-pentyl, n-hexyl, isohexyl or n-heptyl, for example in N-methylcarbamoyl, N-n-butylcarbamoyl or N,N-dimethylcarbamoyl, from carboxy-lower alkyl or lower alkoxycarbonyl-lower alkyl, for example in the form of carboxymethylcar-bamoyl (glycinylcarbonyl) or tert-butoxycarbonylmethylcarbamoyl, from di-lower alkylamino-lower alkyl, for example 2-dimethylaminoethyl, aminocarboxy-lower alkyl, for example 5-amino-5-carboxypentyl, from hydroxy-lower alkyl, for example hydroxymethyl or hydroxyethyl, and from di-lower alkoxy-lower alkyl, for example 2-(2,2-dimethoxyethyl), or carbamoyl substituted by one radical selected from ethylene, trimethylene, tetramethylene and pentamethylene in which a carbon atom may have been replaced by nitrogen, oxygen, sulfur or by sulfur mono- or di-substituted by oxygen and which may be unsaturated, for example in the form of piperidino-, pyrazin-1-yl-, piperazin-1-yl-, pyrimidin-1-yl-, pyridazin-1-yl-, morpholino-, thiomorpholino- or S,S-dioxothiomorpholino-carbonyl; sulfamoyl, phosphono, benzofuranyl, oxo and/or by cyano and is unbranched or branched, preferably by aryl-lower alkanoyl wherein aryl has from 6 to 14 carbon atoms and is unsubstituted or substituted, for example by lower alkanoyl, such as in 2-benzyl-3-pivaloylpropionyl, or by lower alkylsulfonyl, such as in 2-benzyl-3-tert-butylsulfonylpropionyl, with phenyl-lower alkanoyl, for example phenylacetyl, being especially preferred; by heterocyclyl-lower alkanoyl selected from thienyl-, furyl-, pyranyl-, pyrrolyl-, imidazolyl-, pyrazolyl-, oxazolyl-, isoxazolyl-, thiazolyl-, furazanyl-, tetrazolyl-, pyridyl-, pyrazinyl-, pyrimidinyl-, pyridazinyl-, azepinyl-, indolyl-, benzimidazolyl-, 1H-indazolyl-, quinolyl-, isoquinolyl-, quinoxalinyl-, quinazolinyl-, cinnolyl-, purinyl-, pteridinyl-, naphthyridinyl-, 4H-quinolizinyl-, 3,1-benzofuranyl-, benz[e]indolyl-, 4,1-benzoxazinyl-, 4,1-benzothiazinyl-, carbazolyl-, β-carbolinyl-, phenazinyl-, phenanthridyl-, acridyl-, phenoxazinyl-, phenothiazinyl-, 1-azaacenaphthenyl-, cyclohexa[b]pyrrolyl-, cyclohepta[b]pyrrolyl-, cyclohexa[d]pyrazolyl-, cyclohexa[b]pyridyl-, cyclohexa[b]pyrazinyl-, cyclohexa[b]pyrimidinyl-, cyclohexa[b]-1,4-oxazinyl-, cyclohexa[b]-1,4-thiazinyl-, pyrrolidinyl-, pyrrolinyl-, imidazolidinyl-, 2-imidazolinyl-, 2,3-dihydropyridyl-, piperidyl-, piperazinyl-, 2,3,5,6-tetrahydropyrazinyl-, morpholinyl-, thio-morpholinyl-, S,S-dioxothiomorpholinyl-, indolinyl-, isoindolinyl-, 4,5,6,7-tetrahydro-indolyl-, 1,2,3,4-tetrahydroquinolyl-, 1,2,3,4-tetrahydroisoquinolyl-, chromanyl-, thiochromanyl-, 1,2,3,4-tetrahydro-3,1-benzodiazinyl-, 3,4-dihydro-3H-4,1-benzoxazinyl-, 3,4-dihydro-3H-4,1-benzothiazinyl-, 2,3,4,5-tetrahydro-1H-5,1-benzazepinyl- and 5,6-dihydrophenanthridinyl-lower alkanoyl, the mentioned heterocyclyl radicals being unsubstituted or substituted by lower alkyl, for example methyl, phenyl, 1- or 2-naphthyl, phenyl-lower alkyl, for example benzyl, hydroxy-lower alkyl, for example hydroxymethyl or 2-hydroxyethyl, lower alkoxy-lower alkyl, for example methoxymethyl or 2-methoxyethyl, phenoxy- or naphthyloxy-lower alkyl, for example 2-phenoxyethyl, 1- or 2-naphthyloxymethyl, phenyl-lower alkoxy- or naphthyl-lower alkoxy-lower alkyl, for example benzyloxy-lower alkyl, lower alkanoyloxy-lower alkyl, for example acetoxymethyl, phenyl- or naphthyl-lower alkanoyloxy-lower alkyl, for example benzoyloxy-, phenylacetoxy- or 1- or 2-naphthoyloxy-methyl, -2-ethyl or -2-(2,2-dimethylethyl), lower alkoxycarbonyloxy-lower alkyl, for example tert-butoxycarbonyloxy-lower alkyl, phenyl-, naphthyl- or fluorenyl-lower alkoxycarbonyloxy-lower alkyl, for example 2-benzyloxycarbonyloxyethyl or 9-fluorenylmethoxycarbonyloxyethyl, amino-lower alkyl, for example aminomethyl, 2-aminoethyl or 2-aminopropyl, carboxy-lower alkyl, for example carboxymethyl or 2-carboxyethyl, hydroxy, lower alkoxy, for example methoxy or ethoxy, phenyl- or naphthyl-lower alkoxy, for example benzyloxy or 1- or 2-naphthylmethoxy, amino, lower alkylamino, for example methyl-, ethyl- or tert-butyl-amino, di-lower alkylamino, for example dimethyl- or diethyl-amino, carboxy, lower alkoxycarbonyl, for example methoxy-, isopropoxy-, sec-butoxy- or tert-butoxy-carbonyl, phenyl- or naphthyl-lower alkoxycarbonyl, for example benzyloxycarbonyl, halogen, for example fluorine, chlorine, bromine or iodine, especially chlorine or bromine, lower alkanoyl, for example acetyl or pivaloyl, lower alkylsulfonyl, for example methyl- or ethyl-sulfonyl, phosphono, hydroxy-lower alkoxyphosphoryl or dialkoxy-phosphoryl, for example dimethoxy- or diethoxy-phosphoryl, carbamoyl, mono- or di-lower alkylcarbamoyl, for example N-methylcarbamoyl, N-n-butylcarbamoyl or N,N-dimethylcarbamoyl, hydroxy- or carboxy-lower alkylcarbamoyl, for example hydroxy- or carboxy-methylcarbamoyl or hydroxy- or carboxy-ethylcarbamoyl, sulfamoyl, nitro, oxo and/or by cyano, for example pyridylcarbonyl, such as 2-, 3- or 4-pyridylcarbonyl, 3,4-dihydroxypyrrolidinylcarbonyl, N-benzyloxycarbonyl-piperidin-4-ylcarbonyl, 1-methylpiperazin-4-ylcarbonyl, morpholinocarbonyl, thiomorpholinocarbonyl, S,S-dioxothiomorpholinocarbonyl, indol-2-ylcarbonyl, quinol-2-ylcarbonyl, pyridylacetyl, such as 2- or 3-pyridylacetyl, imidazolylacetyl, such as imidazol-1-ylacetyl, morpholinylacetyl, such as morpholinoacetyl, pyridylpropionyl, such as 3-(2- or 3-pyridyl)propionyl, pyrrolidinylpropionyl, such as 3-(4-pyrrolidinyl)propionyl, morpholinylpropionyl, such as 3-morpholinopropionyl, or tetrazolylpropionyl, such as 3-(tetrazol-1-yl)-propionyl; by heterocyclyl-lower alkenoyl wherein heterocyclyl is selected especially from pyrrolyl, furyl, thienyl, imidazolyl, pyrazolyl, oxazolyl, thiazolyl, pyridyl, pyrazinyl, pyrimidinyl, indolyl, quinolyl, isoquinolyl, quinoxalinyl, β-carbolinyl and a benzo-fused, cyclopenta-, cyclohexa- or cyclohepta-fused derivative of those radicals, which may also be fully or partially saturated, for example pyrrolidyl-lower alkenoyl, such as N-pyrrolidyl-acryloyl, halo-lower alkanoyl containing up to 3 halogen atoms, for example α-haloacetyl, such as α-fluoro-, α-chloro-, α-bromo-, α-iodo-, α,α,α-trifluoro- or α,α,α-trichloro-acetyl, or halopropionyl, such as β-chloro- or β-bromo-propionyl; by lower alkoxycarbonyl, such as tert-butoxycarbonyl; by aryl-lower alkoxycarbonyl wherein aryl has from 6 to 14 carbon atoms and is selected, for example, from phenyl, naphthyl and fluorenyl, for example phenyl-lower alkoxycarbonyl, such as benzyloxycarbonyl, or 9-fluorenylmethoxycarbonyl; by heterocyclyl-lower alkoxycarbonyl wherein heterocyclyl is selected especially from pyrrolyl, furyl, thienyl, imidazolyl, pyrazolyl, oxazolyl, thiazolyl, pyridyl, pyrazinyl, pyrimidinyl, indolyl, quinolyl, isoquinolyl, quinoxalinyl, β-carbolinyl and a benzo-fused, cyclopenta-, cyclohexa- or cyclohepta-fused derivative of those radicals, which may also be fully or partially saturated and unsubstituted or substituted especially by lower alkyl, such as methyl, for example 1-methylpyrrolidin-2-yl-methoxycarbonyl, 2-furylmethoxycarbonyl, tetrahydrofuranyl-lower alkoxycarbonyl, such as 2-tetrahydrofuranyl-methoxycarbonyl, 1-methyl-2-piperidyl-methoxycarbonyl or 2-morpholinoethoxycarbonyl; by carboxy-lower alkanoyl, such as 3-carboxypropionyl, 5-carboxypentanoyl or 6-carboxyhexanoyl; by lower alkoxycarbonyl-lower alkanoyl, such as 5-methoxycarbonylpentanoyl or 6-methoxycarbonylhexanoyl; by hydroxy-lower alkoxy-lower alkanoyl, such as 3-hydroxy-n-propoxycarbonyl; by amino-lower alkanoyl wherein the amino group is not in the α- or β-position of the lower alkanoyl radical, such as 5-aminopentanoyl; by phenyl-lower alkoxycarbonylamino-lower alkanoyl wherein the amino group is not in the α- or β-position of the lower alkanoyl radical, such as 5-benzyloxycarbonylaminopentanoyl or 6-benzyloxycarbonylaminohexanoyl;

by amino-lower alkanoyl substituted at the amino nitrogen atom by heterocyclyl-lower alkanoyl, preferably as defined above for heterocyclyl-lower alkanoyl $R_1$, $R_2$, $R_8$ or $R_9$, especially by N-morpholino- or N-thiomorpholino-carbonyl, for example N-morpholino- or N-thiomorpholino-carbonylamino-lower alkanoyl, such as N-morpholino- or N-thiomorpholino-carbonylamino-acetyl;

by carbamoyl; by phenyl-lower alkylaminocarbonyl, such as benzylaminocarbonyl; by N-di-lower alkylamino-lower alkyl-N-lower alkylaminocarbonyl, such as N-(2-dimethylamino)ethyl-N-methylaminocarbonyl; by N-dihydroxy-lower alkyl-N-lower alkylaminocarbonyl, such as N-(2,3-dihydroxy-n-propyl)-N-methylaminocarbonyl; by N-heterocyclyl-lower alkyl-N-lower alkylcarbamoyl wherein heterocyclyl is selected from thienyl, furyl, pyranyl, pyrrolyl, imidazolyl, pyrazolyl, oxazolyl, isoxazolyl, thiazolyl, furazanyl, pyridyl, pyrazinyl, pyrimidinyl, pyridazinyl, azepinyl, indolyl, benzimidazolyl, 1H-indazolyl, quinolyl, isoquinolyl, quinoxalinyl, quinazolinyl, cinnolyl, purinyl, pteridinyl, naphthyridinyl, 4H-quinolizinyl, 3,1-benzofuranyl, benz[e]indolyl, 4,1-benzoxazinyl, 4,1-benzothiazinyl, carbazolyl, β-carbolinyl, phenazinyl, phenanthridyl, acridyl, phenoxazinyl, phenothiazinyl, 1-azaacenaphthenyl, cyclohexa[b]pyrrolyl, cyclohepta[b]pyrrolyl, cyclohexa[d]pyrazolyl, cyclohexa[b]pyridyl, cyclohexa[b]pyrazinyl, cyclohexa[b]pyrimidinyl, cyclohexa[b]-1,4-oxazinyl, cyclohexa[b]-1,4-thiazinyl, pyrrolidinyl, pyrrolinyl, imidazolidinyl, 2-imidazolinyl, 2,3-dihydropyridyl, piperidyl, piperazinyl, 2,3,5,6-tetrahydropyrazinyl, morpholinyl, thiomorpholinyl, S,S-dioxothiomorpholinyl, indolinyl, isoindolinyl, 4,5,6,7-tetrahydroindolyl, 1,2,3,4-tetrahydroquinolyl, 1,2,3,4-tetra-hydroisoquinolyl, chromanyl, thiochromanyl, 1,2,3,4-tetrahydro-3,1-benzodiazinyl, 3,4-dihydro-3H-4,1-benzoxazinyl, 3,4-dihydro-3H-4,1-benzothiazinyl, 2,3,4,5-tetrahydro-1H-5,1-benzazepinyl and 5,6-dihydrophenanthridinyl, the mentioned radicals being unsubstituted or substituted by lower alkyl, for example methyl, phenyl, 1- or 2-naphthyl, phenyl-lower alkyl, for example benzyl, hydroxy-lower alkyl, for example hydroxymethyl or 2-hydroxyethyl, lower alkoxy-lower alkyl, for example methoxymethyl or 2-methoxyethyl, phenoxy- or naphthyloxy-lower alkyl, for example 2-phenoxyethyl, 1- or 2-naphthyloxymethyl, phenyl-lower alkoxy- or naphthyl-lower alkoxy-lower alkyl, for example benzyloxy-lower alkyl, lower alkanoyloxy-lower alkyl, for example acetoxymethyl, phenyl- or naphthyl-lower alkanoyloxy-lower alkyl, for example benzoyloxy-, phenylacetoxy- or 1- or 2-naphthoyloxy-methyl, -2-ethyl or -2-(2,2-dimethylethyl), lower alkoxycarbonyloxy-lower alkyl, for example tert-butoxycarbonyloxy-lower alkyl, phenyl-, naphthyl- or fluorenyl-lower alkoxycarbonyloxy-lower alkyl, for example 2-benzyloxycarbonyloxyethyl or 9-fluorenylmethoxycarbonyloxyethyl, amino-lower alkyl, for example aminomethyl, 2-aminoethyl or 2-aminopropyl, carboxy-lower alkyl, for example carboxymethyl or 2-carboxyethyl, hydroxy, lower alkoxy, for example methoxy or ethoxy, phenyl- or naphthyl-lower alkoxy, for example benzyloxy or 1- or 2-naphthylmethoxy, amino, lower alkylamino, for example methyl-, ethyl- or tert-butyl-amino, di-lower alkyl-amino, for example dimethyl- or diethyl-amino, carboxy, lower alkoxycarbonyl, for example methoxy-, isopropoxy-, sec-butoxy- or tert-butoxy-carbonyl, phenyl- or naphthyl-lower alkoxycarbonyl, for example benzyloxycarbonyl, halogen, for example fluorine, chlorine, bromine or iodine, especially chlorine or bromine, lower alkanoyl, for example acetyl or pivaloyl, lower alkylsulfonyl, for example methyl- or ethyl-sulfonyl, phosphono, hydroxy-lower alkoxyphosphoryl or dialkoxy-phosphoryl, for example dimethoxy- or diethoxy-phosphoryl, carbamoyl, mono- or di-lower alkylcarbamoyl, for example N-methylcarbamoyl, N-n-butylcarbamoyl or N,N-dimethylcarbamoyl, hydroxy- or carboxy-lower alkylcarbamoyl, for example hydroxy- or carboxy-methylcarbamoyl or hydroxy- or carboxy-ethylcarbamoyl, sulfamoyl, nitro, oxo and/or by cyano, especially pyridyl, such as 2-, 3- or 4-pyridyl, for example 2- or 3-pyridyl-lower alkylaminocarbonyl, such as 2- or 3-pyridylmethylaminocarbonyl; by N-2-, N-3- or N-4-pyridyl-lower alkyl-N-lower alkylaminocarbonyl, such as N-2-, N-3- or N-4-pyridylmethyl-N-methylaminocarbonyl;

by heterocyclyl-lower alkylcarbamoyl-lower alkanoyl, such as defined above for heterocyclyl-lower alkylcarbamoyl-lower alkanoyl $R_1$, $R_2$, $R_8$ or $R_9$, for example 2-(N-morpholino-lower alkylcarbamoyl)-lower alkanoyl, such as 2(R,S)-(N-(2-morpholinoethyl)-carbamoyl)-3-methyl-butyryl, or 2-(N-(pyridyl-lower alkyl)-carbamoyl)-lower alkanoyl, such as (2(R,S)-(N-(2-pyridylmethyl)-carbamoyl)-3-methyl)-butyryl;

by sulfonyl; by lower alkylsulfonyl, such as methyl- or ethyl-sulfonyl; by arylsulfonyl wherein aryl has from 6 to 10 carbon atoms and, for example, is selected from phenyl and naphthyl and is unsubstituted or especially substituted by lower alkyl, such as methyl, or by lower alkoxy, such as methoxy, such as p-toluenesulfonyl; by heterocyclylsulfonyl wherein heterocyclyl is preferably selected from pyrrolyl, furyl, thienyl, imidazolyl, pyrazolyl, oxazolyl, thiazolyl, pyridyl, pyrazinyl, pyrimidinyl, indolyl, quinolyl, isoquinolyl, quinoxalinyl, β-carbolinyl and a benzo-fused, cyclopenta-, cyclohexa- or cyclohepta-fused derivative of those radicals, which may also be fully or partially saturated, from morpholinyl and from thiomorpholinyl and may be unsubstituted or substituted, especially by lower alkyl, such as methyl, such as morpholinosulfonyl, thiomorpholinosulfonyl, piperidinosulfonyl, 4-methylpiperazinylsulfonyl or piperazinosulfonyl (heterocyclylsulfonyl not being a substituent in preferred forms); by sulfamoyl or by sulfamoyl substituted by heterocyclyl-lower alkyl, wherein heterocyclyl is as last defined, and/or by lower alkyl, such as N-2-pyridylmethyl-N-methylaminosulfonyl, a carboxy group of the side chain is present in esterified or amidated form, for example in the form of a lower alkyl ester group, such as methoxycarbonyl or tert-butoxycarbonyl, an aryl ester group or an aryl-lower alkyl ester group, aryl being phenyl, 4-nitrophenyl, naphthyl or biphenylyl, for example in the form of a 4-nitrophenoxycarbonyl, benzyloxycarbonyl or 9-fluorenylmethoxycarbonyl group, or in the form of a carbamoyl, a lower alkylcarbamoyl, such as methylcarbamoyl, a di-lower alkylaminocarbamoyl, such as dimethylcarbamoyl, a mono- or di-(hydroxy-lower alkyl)carbamoyl, such as hydroxymethylcarbamoyl or di(hydroxymethyl)carbamoyl, or mono- or di-(carboxy-lower alkyl)carbamoyl group, such as a carboxymethylcarbamoyl or di-(carboxymethyl)carbamoyl group, an amino group of the side chain is present in alkylated form, for example in the form of mono- or di-lower alkylamino, such as n-butylamino or dimethylamino, or in acylated form, for example in the form of lower alkanoylamino, such as acetylamino or pivaloylamino, amino-lower alkanoylamino, such as 3-amino-3,3-dimethylpropionylamino, aryl-lower alkanoylamino wherein aryl has from 6 to 14 carbon atoms, for example phenyl, naphthyl or fluorenyl, and is unsubstituted or substituted by lower alkyl, hydroxy, lower alkoxy, carboxy, carbamoyl or by sulfamoyl, such as 4-hydroxyphenylbutyryl, lower alkoxycarbonylamino, such as tert-butoxycarbonylamino, arylmethoxycarbo-nylamino wherein aryl has from 6 to 14 carbon atoms, such as benzyloxycarbonylamino or 9-fluorenylmethoxycarbonylamino, piperidyl-1-carbonyl, morpholinocarbonyl, thiomorpholinocarbonyl or S,S-dioxothiomorpholinocarbonyl, and/or a hydroxy group of the side chain is present in etherified or esterified form, for example in the form of a lower alkoxy, such as methoxy or tert-butoxy, aryl-lower alkoxy, such as benzyloxy, lower alkanoyloxy, such as acetoxy, or lower alkoxycarbonyloxy group, for example a tert-butoxycarbonyloxy group.

Special preference is given to acyl groups $R_1$, $R_2$, $R_8$ and $R_9$ of an unsubstituted or substituted amino acid selected from phenylalanine, N-(benzyloxycarbonyl)-phenylalanine, N-(2(R,S)-benzyl-3-pivaloyl-propionyl)-phenylalanine, N-(9-fluorenylmethoxycarbonyl)-phenylalanine, tyrosine, N-propyltyrosine, tyrosine-O-methyl ether, N-(3-amino-3,3-dimethylpropionyl)-tyrosine-O-methyl ether, N-(2(S)-benzyl-3-tert-butylsulfonylpropionyl)-tyrosine-O-tert-butyl ether, N-(9-fluorenylmethoxycarbonyl)-tyrosine-O-methyl ether, N-(9-fluorenylmethoxycarbonyl)-tyrosine-O-tert-butyl ether, N-morpholinocarbonyl-glycine, N-(N-(2-, 3- or 4-pyridyl)methyl-N-methylaminocarbonyl)glycine, valine, N-(3-phenylaminopropyl)-valine, N-(4-methylpiperazinylcarbonylmethyl)-valine, N-(trifluoroacetyl)-valine, N-phenylacetyl-valine, N-acetyl-valine, N-(3-phenylpropionyl)-valine, N-(2(R,S)- or -(2S)-benzyl-3-pivaloyl-propionyl)-valine, N-(2-carbamoyl-3-phenyl-propionyl)-valine, N-(2(S)-benzyl-3-tert-butylsulfonylpropionyl)valine, N-(2(R,S)-carbamoyl-3-phenyl-propionyl)-valine, N-(2-, 3- or 4-pyridylcarbonyl)-valine, N-(1-imidazolylacetyl)-valine, N-(2- or 3-pyridylacetyl)-valine, N-(morpholino-acetyl)-valine, N-(3-(2- or 3-pyridyl)-propionyl)-valine, N-(3-(4-pyrrolidinyl)-propionyl)-valine, N-(3-(morpholino)-propionyl)-valine, N-(N-benzyloxycarbonylpiperidin-4-yl-carbonyl)-valine, N-tetrahydrofurylmethoxycarbonyl-valine, N-3-(tetrazol-1-yl)-propionyl-valine, N-(indol-2-ylcarbonyl)-valine, N-(quinoline-2-carbonyl)-valine, N-(1-methylpiperazin-4-ylcarbonyl)-valine, N-(3,4-dihydroxypyrrolidinylcarbonyl)-valine, N-methoxycarbonyl-valine, N-isobutoxycarbonyl-valine, N-tert-butoxycarbonyl-valine, N-benzyloxycarbonyl-valine, N-(2-furylmethoxycarbonyl)-valine, N-(1-methylpyrrolidin-2-yl-methoxycarbonyl)-valine, N-(1-methyl-2-piperidylmethoxycarbonyl)-valine, N-(1-methyl-3-piperidyl-methoxycarbonyl)-valine, N-(2-(morpholino)ethoxycarbonyl)-valine, N-(3-carboxypropionyl)-valine, N-(5-carboxypentanoyl)-valine, N-(6-carboxyhexanoyl)-valine, N-(5-methoxycarbonylpentanoyl)-valine, N-(6-methoxycarbonylhexanoyl)-valine, N-(3-aminopropionyl)-valine, N-(4-aminobutyryl)-valine, N-(5-benzyloxycarbonylaminopentanoyl)-valine, N-(6-benzyloxycarbonylaminohexanoyl)-valine, N-(morpholinocarbonyl)-valine, N-(thiomorpholinocarbonyl)-valine, N-(S,S-dioxothiomorpholinocarbonyl)-valine, N-(N-benzylaminocarbonyl)-valine, N-(N-2-pyridylmethyl-N-methylaminocarbonyl)-valine, N-(N-3-pyridylmethyl-aminocarbonyl)-valine, N-(N-2-pyridylmethyl-aminocarbonyl)-valine, N-morpholino-carbonylamino-acetyl-valine, N-(2-pyrrolidylacryloyl)-valine, N-methylsulfonyl-valine, N-morpholinosulfonyl-valine, N-(p-toluenesulfonyl)-valine, N-(4-methylpiperazinylsulfonyl)-valine, N-(N-(2-pyridylmethyl)-N-methyl-sulfamoyl)-valine, N-(N-2-pyridyl-methyl-N-methyl-aminocarbonyl)-valine, N-(3-aminopropyl)-leucine, N-acetyl-leucine, N-(3-aminopropionyl)-leucine, N-(2(R,S)- or N-(2S)-benzyl-3-pivaloyl-propionyl)-leucine, N-(2(S)-benzyl-3-tert-butylsulfonylpropionyl)-leucine, N-(2-, 3- or 4-pyridylcarbonyl)-leucine, N-(4-thiomorpholinocarbonyl)-leucine, N-(4-(S,S-dioxothiomorpholino)carbonyl)-leucine, N-(4-aminobutyryl)-leucine, N-(3-hydroxy-n-propoxycarbonyl)- leucine, N-(benzyloxycarbonyl)-leucine, N-(N-(2-(dimethylamino)ethyl)-N-methyl-aminocarbonyl)-leucine, N-(N-(2,3-dihydroxy-n-propyl)-N-methyl-aminocarbonyl)-leucine, N-acetyl-isoleucine, N-propionyl-isoleucine, N-(benzyloxycarbonyl)isoleucine, N-(2(R,S)-benzyl-3-pivaloyl-propionyl)-norleucine, N-(2(S)-benzyl-3-tert-butylsulfonylpropionyl)-norleucine, N-(tert-butoxycarbonyl)-norleucine, N-(tert-butoxycarbonyl)-serine, N-(benzyloxycarbonyl)-serine, N-acetyl-serine O-methyl ether, N-(benzyloxycarbonyl)-serine O-methyl ether, N-(2(R,S)-benzyl-3-pivaloyl-propionyl)serine, N-benzyloxycarbonyl-glutamic acid, asparagine, N-benzyloxycarbonyl-asparagine, quinoline-2-carbonyl-asparagine, and N-(morpholinocarbonyl)-asparagine, the amino acid residues preferably being in the (L)- or (D,L)- form, and in the case of valine also in the (D)-form.

Unsubstituted or substituted alkyl $R_1$, $R_2$, $R_8$ or $R_9$ contains an alkyl radical having from 1 to 20, preferably up to 10, carbon atoms, is branched or unbranched, may contain instead of a methylene group a hetero atom selected from thia, aza and selena and is, for example, methyl, ethyl, n-propyl, isopropyl, n-butyl, isobutyl, sec-butyl, tert-butyl, n-pentyl, isopentyl, neopentyl, tert-pentyl, n-hexyl, isohexyl, n-heptyl, n-octyl, n-nonyl or n-decyl. Preference is given to lower alkyl, for example methyl, ethyl, n-propyl, isopropyl, n-butyl, isobutyl, sec-butyl, tert-butyl, n-pentyl, isopentyl, neopentyl, tert-pentyl, n-hexyl, isohexyl or n-heptyl, which is unsubstituted or substituted.

Radicals suitable as substituents in substituted alkyl, preferably substituted lower alkyl, are the radicals mentioned for lower alkanoyl $R_1$, $R_2$, $R_8$ and $R_9$.

Substituted lower alkyl is preferably cycloalkyl-lower alkyl wherein cycloalkyl has from 3 to 7 carbon atoms and lower alkyl is as defined above, for example cycloalkyl-methyl or -ethyl, preferably having a total of from 4 to 13 carbon atoms, for example cyclopropyl-, cyclobutyl-, cyclopentyl- or cyclohexyl-lower alkyl, such as -methyl or -ethyl, cycloalkenyl-lower alkyl, for example cycloalkenylmethyl, wherein cycloalkyl preferably has from 4 to 8 carbon atoms, such as 1-cyclohexenylmethyl, 1,4-cyclohexadienylmethyl or 1-cyclohexenylethyl or 1,4-cyclohexadienylethyl, bicycloalkyl-lower alkyl wherein bicycloalkyl has, for example, from 5 to 10 carbon atoms, for example bicycloalkyl-methyl or -ethyl, preferably having from 8 to 11 carbon atoms, such as decahydronaphthyl-2-methyl, endo- or exo-norbornyl-2-methyl, bicyclo[2.2.2]oct-2-ylmethyl or bicyclo[3.3.1]non-9-ylmethyl, and also bicyclo-hexyl-, -heptyl-, -octyl-, -nonyl- or -decyl-ethyl or -3-propyl, for example bicyclo[3.1.0]hex-1-, -2- or - 3-yl-, bicyclo[4.1.0]hept-1- or -7-yl-, bicyclo[2.2.1]hept-2-yl-, for example endo- or -exo-norbornyl-, bicyclo[3.2.1]oct-2-yl-, bicyclo[3.3.0]oct-3-yl- or bicyclo[3.3.1]non-9-yl-, and also α- or β-decahydronaphthyl-ethyl or -3-propyl, tricycloalkyl-lower alkyl wherein tricycloalkyl contains, for example, from 8 to 10 carbon atoms, for example tricycloalkyl-methyl or -ethyl, preferably having from 8 to 11 carbon atoms, such as 1- or 2-adamantylmethyl, and also tricyclo[5.2.1.0$^{2,6}$]dec-8-yl- or adamantyl-, such as 1-adamantyl-ethyl, aryl-lower alkyl wherein especially aryl has from 6 to 14 carbon atoms, such as in phenyl, indenyl, indanyl, naphthyl, anthryl, phenanthryl, acenaphthyl or fluorenyl, which may be unsubstituted or especially mono- to tri-substituted by lower alkyl, for example methyl, ethyl or isopropyl, halo-lower alkyl, such as trifluoromethyl, phenyl, 1- or 2-naphthyl, hydroxy, lower alkoxy, for example methoxy, carbamoyl-lower alkoxy, N-lower alkylcarbamoyl-lower alkoxy or N,N-di-lower alkylcarbamoyl-lower alkoxy, amino, mono- or di-lower alkylamino, lower alkanoylamino, for example pivaloylamino, halogen, for example fluorine or chlorine, carboxy, lower alkoxycarbonyl, benzyl-, naphthyl- or fluorenyl-lower alkoxycarbonyl, lower alkanoyl, sulfo, lower alkylsulfonyl, phosphono, hydroxy-lower alkoxyphosphoryl or di-lower alkoxyphosphoryl, carbamoyl, mono- or di-lower alkylcarbamoyl, sulfamoyl, mono- or di-lower alkylsulfamoyl, nitro and/or by cyano, wherein phenyl may be present up to three times, such as in diphenyl-, dibenzyl- or triphenyl-lower alkyl, for example diphenyl-, dibenzyl- or triphenyl-2-ethyl, and wherein lower alkyl is unsubstituted or substituted, for example by lower alkyl, such as methyl, heterocyclyl selected from pyrrolyl, furyl, thienyl, imidazolyl, pyrazolyl, oxazolyl, thiazolyl, pyridyl, pyrazinyl, pyrimidinyl, indolyl, quinolyl, isoquinolyl, quinoxalinyl, β-carbolinyl and a benzo-fused, cyclopenta-, cyclohexa- or cyclohepta-fused derivative of those radicals, which may also be fully or partially saturated, hydroxy, lower alkoxy, lower alkanoyloxy, such as acetoxy, propionyloxy, butyroxy, isobutyroxy or pivaloyloxy, acetoacetoxy, amino- or benzyloxycarbonylamino-lower alkanoyloxy, such as 2-amino- or 2-benzyloxycarbonylamino-2-methylpropionyloxy, aryl-lower alkanoyloxy wherein aryl has from 6 to 10 carbon atoms, such as in benzoyloxy, phenylacetoxy, 1- or 2-naphthoyloxy, lower alkoxycarbonyloxy, for example methoxy-, ethoxy-, n-propoxy-, isopropoxy-, n-butoxy-, isobutoxy-, sec-butoxy-, tert-butoxy-, n-pentyloxy-, isopentyloxy-, neopentyloxy, tert-pentyloxy-, n-hexyloxy-, isohexyloxy- or n-heptyloxy-carbonyloxy, mono- or di-lower alkyl-aminocarbonyloxy, such as ethylaminocarbonyloxy or diethylaminocarbonyloxy, aryloxycarbonyloxy wherein aryl has from 6 to 10 carbon atoms, for example phenoxycarbonyloxy or 1- or 2-naphthyloxycarbonyloxy, aryl-lower alkoxycarbonyloxy wherein aryl has from 6 to 12 carbon atoms, for example phenyl-lower alkoxycarbonyloxy, such as benzyloxycarbonyloxy, and also 1- or 2-naphthylmethoxycarbonyloxy or 9-fluorenylmethoxycarbonyloxy, sulfonyloxy, lower alkylsulfonyloxy, for example methyl-, ethyl-, propyl-, isopropyl-, n-butyl-, isobutyl-, sec-butyl-, tert-butyl-, n-pentyl-, isopentyl-, neopentyl-, tert-pentyl-, n-hexyl-, isohexyl- or n-heptyl-sulfonyloxy, phenylsulfonyloxy, 2- or 4-toluenesulfonyloxy, 1- or 2-naphthylsulfonyloxy, amino, mono- or di-lower alkylamino, N-lower alkoxy-N-lower alkylamino, such as N-methoxy-N-methylamino, mono- or di-(phenyl- or -naphthyl-lower alkyl)amino, such as benzylamino, lower alkanoylamino, such as pivaloylamino, carboxy, esterified carboxy selected from lower alkoxycarbonyl, for example methoxy-, ethoxy-, n-propoxy-, isopropoxy-, n-butoxy-, isobutoxy-, sec-butoxy-, tert-butoxy-, n-pentyloxy-, isopentyloxy-, neo-pentyloxy-, tert-pentyloxy-, n-hexyloxy-, isohexyloxy- or n-heptyloxy-carbonyl, aryloxycarbonyl wherein aryl has from 6 to 10 carbon atoms, for example phenoxycarbonyl or 1- or 2-naphthyloxycarbonyl, aryl-lower alkoxycarbonyl wherein aryl has from 6 to 12 carbon atoms, for example benzyloxycarbonyl, 1- or 2-naphthylmethoxycarbonyl or 9-fluorenylmethoxycarbonyl, lower alkanoyl, such as pivaloyl or acetyl, lower alkylsulfonyl, such as tert-butylsulfonyl, hydroxy-lower alkoxyphosphoryl and di-lower alkoxyphosphoryl, carbamoyl, carbamoyl substituted by one or two radicals selected from lower alkyl, for example methyl, ethyl, propyl, isopropyl, n-butyl, isobutyl, sec-butyl, tert-butyl, n-pentyl, isopentyl, neopentyl, tert-pentyl, n-hexyl, isohexyl or n-heptyl, such as in N-methylcarbamoyl, N-n-butylcarbamoyl or N,N-dimethylcarbamoyl, from carboxy-lower alkyl or lower alkoxycarbonyl-lower alkyl, for example in the form of carboxymethylcarbamoyl (glycinylcarbonyl) or tert-butoxycarbonylmethylcarbamoyl, from di-lower alkylamino-lower alkyl, for example 2-dimethylaminoethyl, from aminocarboxy-lower alkyl, such as 5-amino-5-carboxypentyl, from hydroxy-lower alkyl, for example hydroxymethyl or hydroxyethyl, and from di-lower alkoxy-lower alkyl, for example 2-(2,2-dimethoxyethyl), or carbamoyl substituted by one radical selected from ethylene, trimethylene, tetramethylene and pentamethylene in which a carbon atom may have been replaced by nitrogen, oxygen, sulfur or by sulfur mono- or di-substituted by oxygen and which may be unsaturated, for example in the form of piperidino-, pyrazin-1-yl-, piperazin-1-yl-, pyrimidin-1-yl-, pyridazin-1-yl-, morpholino-, thiomorpholino- or S,S-di-oxothiomorpholino-carbonyl; sulfamoyl, phosphono, benzfuranyl, oxo (which is not present at the carbon atom bonded to the amino nitrogen atom linked to $R_1$, $R_2$, $R_8$ or $R_9$) and/or by cyano and is unbranched or branched, is especially selected from phenyl-lower alkyl, such as benzyl that is unsubstituted or mono- or poly-substituted in the benzyl radical by lower alkyl, for example methyl, phenyl, hydroxy, lower alkoxy, for example methoxy, halogen, for example chlorine, nitro, and/or by cyano, such as 4-methoxy-, 4-fluoro-, 4-chloro-, 4-nitro- or 4-cyano-benzyl, naphthylmethyl, such as α- or β-naphthylmethyl, indenylmethyl, for example 1-, 2- or 3-indenylmethyl, indanylmethyl, such as 1- or 2-indanylmethyl, and phenanthrenylmethyl, such as 9-phenanthrenylmethyl, 2-phenylethyl, 2-α-naphthylethyl, 2-β-naphthylethyl, 2-lower alkylphenyl-ethyl, such as 2-(4-methylphenyl)ethyl, 2-lower alkoxyphenylethyl, such as 2-(4-methoxyphenyl)ethyl, 2,2-diphenylethyl, 2,2-di(4-methoxyphenyl)ethyl, 2,2,2-triphenylethyl and 2,2-dibenzylethyl, from phenyl-lower alkyl substituted in the 2- and p-positions by two radicals selected from phenyl-lower alkoxycarbonyl, such as benzyloxycarbonyl, and lower alkanoylamino, such as pivaloylamino, such as 2,p-dibenzyloxycarbonylamino-phenylethyl or 2-pivaloylamino-p-benzyloxycarbonylamino-phenylethyl, 2,p-diamino-phenylethyl, 3-phenylpropyl, 3-(p-hydroxyphenyl)-propyl, 3-α- or 3-β-naphthylpropyl, 2-benzyl-3-(1-pyrazolyl)-propyl, 3-phenyl- or 3-α-naphthyl-2-hydroxy-propyl, 3-phenyl- or 3-α-naphthyl-2-lower alkoxypropyl, such as 3-phenyl- or 3-α-naphthyl-2-neopentyloxy-propyl, 3-phenyl- or 3-(α-naphthyl-2-lower alkanoyloxy-propyl, such as 3-phenyl-2-pivaloyloxy- or -2-acetoxypropyl, 2-benzyl- or 1- or 2-naphthyl-3-(N-methoxyl-N-methylamino)-propyl, 3-phenyl- or 3-α-naphthyl-2-dimethylaminomethyl-propyl, 3-α-naphthyl-2-pivaloyloxy- or -2-acetoxy-propyl, 3-α-naphthyl-2-acetoacetoxy-propyl, 3-α-naphthyl-2-ethylamino-carbonyloxy-propyl or 3-α-naphthyl-2-((2-amino- or 2-benzyloxycarbonylamino)-2-methylpropionyloxy)-propyl, 3-phenyl- or 3-α-naphthyl-2-carboxymethylpropyl, 3-phenyl- or 3-α-naphthyl-2-lower alkoxycarbonyl-propyl, such as 3-α-naphthyl-2-ethoxycarbonyl-propyl, 3-phenyl- or 3-at-naphthyl-2-benzyloxycarbonylmethyl-propyl, 2-(S)-benzyl-3-tert-butylsulfonyl-propyl, 3-phenyl-2-phosphono- or -phosphonomethylpropyl, 3-phenyl-2-dimethoxyphosphoryl- or -dimethoxyphosphorylmethyl-propyl, 3-phenyl-2-diethoxyphosphoryl- or -diethoxyphosphorylmethyl-propyl, 3-phenyl-2-ethoxy- or -methoxyhydroxyphosphoryl-propyl, 3-phenyl- or 3-α-naphthyl-2-carbamoyl-propyl, 3-phenyl- or 3-α-naphthyl-2-tert-butylcarbamoyl-propyl, 3-phenyl- or 3-α-naphthyl-2-(2-dimethylaminoethyl)carbamoyl-propyl, 3-α-naphthyl-2-(carboxy- or tert-butoxycarbonyl)methylcarbamoyl-propyl, 3-phenyl- or 3-α-naphthyl-2-(3-hydroxy-2-propyl)carbamoyl-propyl, 3-phenyl- or 3-α-naphthyl-2-(2,2-dimethoxyethyl)carbamoylpropyl, 3-phenyl- or 3-α-naphthyl-2-(5-amino-5-carboxypentyl)-carbamoylpropyl, 3-phenyl- or 3-α-naphthyl-2-cyano-propyl, 3-phenyl- or 3-α-naphthyl-2-cyanomethyl-propyl, 3-phenyl- or 3-α-naphthyl-2-acetonyl-propyl, 4-hydroxyphenylbutyl, 4-phenyl- or 4-α-naphthyl-3-carboxy-butyl, 4-phenyl- or 4-α-naphthyl-3-benzyloxycarbonyl-butyl, 2-benzyl-4-(2-benzofuranyl)-4-oxobutyl, 2-benzyl- or 2-α-naphthylmethyl-4-cyano-butyl, 2-benzyl- or 2-α-naphthylmethyl-5-dimethylamino-pentyl, 2-benzyl- or 2-α-naphthylmethyl-4-oxo-pentyl, 2-benzyl- or 2-α-naphthylmethyl-4,4-dimethyl-3-oxo-pentyl, 2-benzyl- or 2-α-naphthylmethyl-5-dimethylamino-4-oxo-pentyl or 2-benzyl- or 2-α-naphthylmethyl-5,5-dimethyl-4-oxo-hexyl, preferably phenyl-lower alkyl, such as benzyl, 2-phenylethyl or 3-phenylpropyl, 4-hydroxybenzyl, 1- or 2-naphthylmethyl or 1- or 2-naphthyl-2-ethyl, especially phenyl-lower alkyl as last defined, heterocyclyl-lower alkyl containing especially unsubstituted or substituted heterocyclyl as mentioned under heterocyclyl-lower alkanoyl $R_1$, $R_2$, $R_8$ and $R_9$ and lower alkyl that is unsubstituted or substituted in the same manner as lower alkanoyl in heterocyclyl-lower alkanoyl $R_1$, $R_2$, $R_8$ and $R_9$ (oxo not being present at the carbon atom bonded to the nitrogen atom carrying the radical $R_1$, $R_2$, $R_8$ or $R_9$), for example methyl, 2-ethyl or 3-propyl bonded to unsubstituted or lower alkyl- or phenyl-substituted pyrrolyl, such as 2- or 3-pyrrolyl, 4- or 5-methylpyrrolyl or 4- or 5-phenylpyrrolyl, thienyl, such as 2-thienyl, furyl, such as 2-furyl, pyrazolyl, such as 1-pyrazolyl, tetrazolyl, such as tetrazol-1-yl, pyridyl, such as 2-, 3- or 4-pyridyl, indolyl that is unsubstituted or substituted by lower alkyl, for example methyl, phenyl-lower alkyl, for example benzyl, lower alkoxy, for example methoxy, phenyl-lower alkoxy, for example benzyloxy, or by halogen, for example by chlorine, such as 2-, 3- or 5-indolyl, 1-methyl-, 2-methyl-, 5-methoxy-, 5-benzyloxy-, 5-chloro- or 4,5-dimethyl-indol-2-yl, 1-benzylindol-2-yl or -3-yl, 4,5,6,7-tetrahydroindol-2-yl, cyclohepta[b]pyrrol-5-yl, unsubstituted or hydroxy-substituted quinolyl, such as 2-, 3- or 4-quinolyl or 4-hydroxyquinol-2-yl, unsubstituted or hydroxy-substituted isoquinolyl, such as 1-, 3- or 4-isoquinolyl or 1-oxo-1,2-dihydroisoquinol-3-yl, 2-quinoxalinyl, 3,1-benzfuran-2-yl, benz[e]indol-2-yl, β-carbolin-3-yl, 3-chromanyl, 3-thiochromanyl, 3-pyrrolidinyl, hydroxypyrrolidinyl, such as 3- or 4-hydroxypyrrolidin-2-yl, oxopyrrolidinyl, such as 5-oxopyrrolidin-2-yl, piperidinyl, such as 2-, 3- or 4-piperidinyl, morpholinyl, such as 2- or 3-morpholinyl, thiomorpholinyl, such as 2- or 3-thiomorpholinyl, S,S-dioxothiomorpholinyl, such as S,S-dioxothiomorpholin-2- or -3-yl, indolinyl, such as 2- or 3-indolinyl, 1,2,3,4-tetrahydroquinolyl, such as 1,2,3,4-tetrahydroquinol-2-, -3- or -4-yl, 1,2,3,4-tetrahydroisoquinolyl, such as 1,2,3,4-tetrahydroisoquinol-1-, -2- or -3-yl, or 1-oxo-1,2,3,4-tetrahydroisoquinol-3-yl, or 4-pyrrolidinylmethyl or 1-imidazolylmethyl, hydroxy-lower alkyl, such as 3-hydroxypropyl or 2-hydroxy-3-methylpentyl, lower alkoxy-lower alkyl, for example lower alkoxyethyl or lower alkoxypropyl, such as 2-methoxyethyl, 2-ethoxyethyl or 3-methoxypropyl, lower alkoxy-lower alkoxy-lower alkyl, such as 2-methoxymethoxy-3-methyl-pentyl, phenoxy-lower alkyl or nitrophenoxy-lower alkyl, such as phenoxymethyl, phenoxyethyl or 4-nitrophenoxymethyl, naphthyloxy-lower alkyl, for example α- or β-naphthyloxyethyl, lower alkanoyloxy-lower alkyl, for example lower alkanoyloxyethyl or lower alkanoyloxypropyl, such as acetoxyethyl or 3-acetoxypropyl, acetoacetoxy-lower alkyl, arylmercapto-lower alkyl wherein aryl has from 6 to 10 carbon atoms, for example phenyl or naphthyl, such as phenylmercaptomethyl, amino-lower alkyl, such as 3-aminopropyl or 5-aminopentyl, mono- or di-lower alkylamino-lower alkyl, such as dimethylaminoethyl or 2-dimethyl-amino-2-isopropylethyl, phenyl- or naphthyl-amino-lower alkyl, such as 3-phenylaminopropyl, lower alkanoylamino-lower alkyl, such as 4-acetylaminopentyl, piperazinylcarbonyl-lower alkyl substituted at the nitrogen atom by lower alkyl, such as methyl, such as 4-methylpiperazinylcarbonylmethyl, lower alkoxycarbonylamino-lower alkyl, such as 5-(tert-butoxycarbonylamino)-pentyl or 3-ethoxycarbonylamino-2-isobutyl-propyl, phenyl-lower alkoxycarbonylamino-lower alkyl, such as 5-(benzyloxycarbonylamino)pentyl, aminocarbonylamino-lower alkyl, such as aminocarbonylamino-ethyl, N-phenyl-lower alkyl-N-lower alkylaminocarbonylamino-lower alkyl, for example 2-isobutyl-3-(N-benzyl-N-methylaminocarbonylamino)propyl, halo-lower alkyl, for example 2-haloethyl, such as 2-fluoro-, 2-chloro-, 2-bromo-, 2-iodo-, 2,2,2-trifluoro- or 2,2,2-trichloro-ethyl, trifluoro-lower alkyl, such as trifluoromethyl, or halopropyl, such as 3-chloro- or 3-bromopropyl, carboxy-lower alkyl, for example carboxyethyl or 3-carboxypropyl, lower alkoxycarbonyl-lower alkyl, for example lower alkoxycarbonylethyl or lower alkoxycarbonylpropyl, such as methoxycarbonylethyl, 3-methoxycarbonylpropyl, ethoxycarbonylethyl or 3-ethoxycarbonylpropyl, 2-halo-lower alkoxycarbonyl-lower alkyl, such as 2-chloro-, 2-bromo-, 2-iodo- or 2,2,2-trichloro-ethoxycarbonyl-2-ethyl or -3-propyl, phenyl- or naphthyl-lower alkoxycarbonyl-lower alkyl, for example benzyloxycarbonyl-lower alkyl, such as 3-benzyloxycarbonyl-2,2-dimethylpropyl, heterocyclyl-lower alkoxycarbonyl-lower alkyl wherein heterocyclyl is preferably selected from pyrrolyl, furyl, thienyl, imidazolyl, pyrazolyl, oxazolyl, thiazolyl, pyridyl, pyrazinyl, pyrimidinyl, indolyl, quinolyl, isoquinolyl, quinoxalinyl, β-carbolinyl and a benzo-fused, cyclopenta-, cyclohexa- or cyclohepta-fused derivative of those radicals, it also being possible for the mentioned radicals to be fully or partially saturated, such as in 4-pyridylmethoxycarbonyl-2-ethyl or -3-propyl or 2-morpholinocarbonyloxy-4-methylpentyl, lower alkylsulfonyl-lower alkyl, such as 2-ethylsulfonyl- or 2-tert-butylsulfonyl-methyl, arylsulfonyl-lower alkyl wherein aryl preferably has from 6 to 10 carbon atoms, for example phenyl or naphthyl, such as phenylsulfonylmethyl, carbamoyl-lower alkyl, such as carbamoylethyl or 3-carbamoylpropyl, lower alkylcarbamoyl-lower alkyl, for example lower alkylcarbamoylethyl or methylcarbamoyl-lower alkyl, such as 2-methylcarbamoylethyl, di-lower alkylcarbamoyl-lower alkyl, for example 2-di-lower alkylcarbamoylethyl or dimethylcarbamoyl-lower alkyl, such as 2-dimethylcarbamoylethyl, hydroxy-lower alkylcarbamoyl- or di(hydroxy-lower alkyl)carbamoyl-lower alkyl, such as 2-hydroxymethylcarbamoyl- or di(hydroxymethyl)carbamoyl-2-ethyl or -3-propyl, N-lower alkoxy-lower alkoxy-lower alkylcarbamoyl-lower alkyl, such as 2-isobutyl-3-(2-(2-methoxyethoxy)ethylaminocarbonyl)-propyl, carboxy-lower alkylcarbamoyl- or di(carboxy-lower alkyl)carbamoyl-lower alkyl, such as carboxymethyl- or di(carboxymethyl)carbamoyl-2-ethyl or -3-propyl, carbamoyl-lower alkyl substituted at the nitrogen atom by a radical selected from ethylene, trimethylene, tetramethylene and pentamethylene wherein a carbon atom may have been replaced by nitrogen, oxygen, sulfur or by sulfur mono- or di-substituted by oxygen, it being possible for the radical so formed also to be fully or partially unsaturated, for example in the form of piperidino-, pyrazin-1-yl-, piperazin-1-yl-, pyrimidin-1-yl-, pyridazin-1-yl-, morpholino-, thiomorpholino- or S,S-dioxothiomorpholino-carbonyl-lower alkyl, such as in 2-morpholinocarbonyl-ethyl, 3-(morpholinocarbonyl)-propyl or 3-(morpholinocarbonyl)-2-isobutyl-propyl, N-lower alkyl-N-heterocyclyl-lower alkylcarbamoyl-lower alkyl wherein heterocyclyl is preferably selected from pyrrolyl, furyl, thienyl, imidazolyl, pyrazolyl, oxazolyl, thiazolyl, pyridyl, pyrazinyl, pyrimidinyl, indolyl, quinolyl, isoquinolyl, quinoxalinyl, β-carbolinyl and a benzo-fused, cyclopenta-, cyclohexa- or cyclohepta-fused derivative of those radicals, which may also be fully or partially saturated, such as 2-(N-2-pyridylmethyl)-N-methylcarbamoyl-ethyl, sulfamoyl-lower alkyl, such as 2-sulfamoylethyl, N-(phenyl- or naphthyl-lower alkyl)sulfamoyl-lower alkyl, such as 3-benzylamino-sulfonyl-2-isopropyl-propyl, or sulfamoyl-lower alkyl substituted at the nitrogen atom by a radical selected from ethylene, trimethylene, tetramethylene and pentamethylene wherein a carbon atom may have been replaced by nitrogen, lower alkyl-substituted, such as methyl-substituted, nitrogen, oxygen, sulfur or by sulfur mono- or di-substituted by oxygen, it being possible for the radical so formed also to be fully or partially unsaturated, for example in the form of piperidino-, pyrazin-1-yl-, piperazin-1-yl-, 4-methylpiperazin-1-yl-, pyrimidin-1-yl-, pyridazin-1-yl-, morpholino-, thiomorpholino- or S,S-dioxothiomorpholino-sulfonyl-lower alkyl, such as 3-(4-methylpiperazinylsulfonyl)-2-isopropyl-propyl or 3-(4-morpholinysulfonyl)-2-isopropyl-propyl, oxo-lower alkyl (wherein oxo is not present at the carbon atom bonded to the nitrogen atom carrying the radical $R_1$, $R_2$, $R_8$ or $R_9$), such as 3-oxo-n-butyl or 3-oxo-n-pentyl, cyano-lower alkanoyl, such as cyanomethyl, 2-cyanoethyl, 2- or 3-cyano-n-propyl or 2-, 3- or 4-cyano-n-butyl, hydroxy-carboxy-lower alkyl, such as 2-hydroxy-2-carboxy-ethyl or 2-hydroxy-3-carboxypropyl, α-naphthyloxy-carboxy-lower alkyl, such as 2-α-naphthyloxy-4-carboxy-n-butyl, hydroxy-lower alkoxycarbonyl-lower alkyl, for example 2-hydroxy-2-lower alkoxycarbonyl-ethyl or -propyl or hydroxy-ethoxy- or hydroxy-methoxy-carbonyl-lower alkyl, such as 2-hydroxy-2-ethoxy- or -methoxy-carbonylethyl or 2-hydroxy-3-ethoxy- or -methoxy-carbonylpropyl, α-naphthyloxy-lower alkoxycarbonyl-lower alkyl, for example α-naphthyloxy-lower alkoxycarbonyl-2-ethyl, -2-propyl or -2-butyryl or α-naphthyloxyethoxycarbonyl-lower alkyl, such as α-naphthyloxy-ethoxycarbonyl-2-ethyl, 2-α-naphthyloxy-3-ethoxycarbonylpropyl or 2-α-naphthyloxy-4-tert-butoxycarbonylbutyl, α-naphthyloxy-benzyloxycarbonyl-lower alkyl, such as 2-o-naphthyloxy-3-benzyloxycarbonyl-propyl, esterified hydroxy-lower alkoxycarbonyl-lower alkyl wherein the hydroxy group is esterified by lower alkanoyl, for example acetyl, propionyl or pivaloyl, cycloalkyl-lower alkanoyl wherein cycloalkyl has from 3 to 7 carbon atoms and lower alkanoyl is as last defined, for example cyclohexylcarbonyl or 2-cyclohexyl- or 2-cyclopentyl-acetyl, bicycloalkyl-lower alkanoyl wherein bicycloalkyl has, for example from 5 to 10, especially from 6 to 9, carbon atoms, such as in bicyclo-hexyl-, -heptyl-, -octyl-, -nonyl- or -decyl-acetyl or -3-propionyl, for example bicyclo [3.1.0]hex-1-, -2- or -3-yl-, bicyclo-[4.1.0]hept-1- or -7-yl-, bicyclo[2.2.1]hept-2-yl-, for example endo- or exo-norbornyl-, bicyclo[3.2.1]oct-2-yl-, bicyclo[3.3.0] oct-3-yl- or bicyclo[3.3.1]non-9-yl-, and also α- or β-decahydronaphthyl-acetyl or -3-propionyl, tricycloalkyl-lower alkanoyl wherein tricycloalkyl contains, for example, from 8 to 10 carbon atoms, for example in tricyclo[5.2.1.0$^{2,6}$]dec-8-yl- or adamantyl-, such as 1-adamantyl-acetyl, aryl-lower alkanoyl wherein aryl has from 6 to 14 carbon atoms, for example phenyl, indenyl, indanyl, naphthyl, anthryl, phenanthryl, acenaphthyl or fluorenyl, which may be unsubstituted or mono- to tri-substituted by lower alkyl, hydroxy, lower alkoxy, carbamoyl-lower alkoxy, N-lower alkylcarbamoyl-lower alkoxy or N,N-di-lower alkylcarbamoyl-lower alkoxy, amino, mono- or di-lower alkylamino, halogen, such as fluorine, chlorine or bromine, carboxy, lower alkoxycarbonyl, phenyl-, naphthyl- or fluorenyl-lower alkoxycarbonyl, lower alkanoyl, lower alkylsulfonyl, for example methylsulfonyl, phosphono, hydroxy-lower alkoxy-, phosphoryl or di-lower alkoxyphosphoryl, carbamoyl, sulfamoyl, nitro and/or by cyano, lower alkoxycarbonyl, for example tert-butoxycarbonyl, 2-halo-lower alkoxycarbonyl as defined above, or by phenyl- or fluorenyl-lower alkoxycarbonyl, for example benzyloxycarbonyl or 9-fluorenylmethoxycarbonyl, such as 2-acetoxy-2-methoxycarbonyl-ethyl, 2-benzoyloxy-, 2-(1- or 2-naphthoyloxy)-, 2-(phenyl-2-acetoxy)-, 2-(1- or 2-naphthyl-2-acetoxy)-, 2-(4-methylphenyl-2-acetoxy) -, 2-(4-methoxyphenyl-2-acetoxy)- or 2-(2-(o,o-dichlorophenyl)2-acetoxy)-2-methoxycarbonyl-ethyl or -3-propyl, dihydroxy-carboxy-lower alkyl, such as 2,3-dihydroxy-3-carboxy-propyl, dihydroxy-lower alkoxycarbonyl-lower alkyl, such as 2,3-dihydroxy-3-ethoxy- or -methoxy-carbonyl-propyl, dihydroxy-lower alkoxycarbonyl-lower alkyl esterified by lower alkanoyl, such as acetyl, propionyl or butyryl, lower alkoxycarbonyl, for example tert-butoxycarbonyl, phenyl- or fluorenyl-lower alkoxycarbonyl, such as benzyloxycarbonyl or 9-fluorenylmethoxycarbonyl, lower alkylsulfonyl or by toluenesulfonyl, for example di-lower alkanoyloxy-lower alkoxy-propyl, such as 2,3-diacetoxy-3-methoxycarbonyl-propyl, α-naphthyloxy-di-lower alkylamino-lower alkyl, such as 2-(X-naphthyloxy-5-dimethylaminopentyl, α-naphthyloxy-carbamoyl-lower alkyl, such as 2-α-naphthyloxy-4-carbamoyl-butyl, α-naphthyloxy-oxo-lower alkyl (wherein oxo is not present at the carbon atom bonded to the nitrogen atom carrying the radical $R_1$, $R_2$, $R_8$ or $R_9$), such as 2-α-naphthyloxy-4-oxo-pentyl, or α-naphthyloxy-cyano-lower alkyl, such as 2-α-naphthyloxy-cyano-ethyl or 2-α-naphthyloxy-4-cyanobutyl.

Lower alkyl, such as methyl, ethyl, propyl, isopropyl, n-butyl, isobutyl or tert-butyl, is especially preferred.

Alkenyl $R_1$, $R_2$, $R_8$ or $R_9$ preferably contains from 2 to 10 carbon atoms, is preferably lower alkenyl having from 2 to 7, especially from 2 to 4, carbon atoms and is, for example, vinyl, allyl or 2- or 3-butenyl. Lower alkenyl $R_1$, $R_2$, $R_8$ or $R_9$ may be substituted by the same substituents as may lower alkyl, for example by cycloalkyl, as defined in the case of cycloalkyl-lower alkanoyl $R_1$, $R_2$, $R_8$ or $R_9$, that is unsubstituted or mono- to tri-substituted by lower alkyl, such as isopropyl, halo-lower alkyl, such as trifluoromethyl, hydroxy, lower alkoxy, carbamoyl-lower alkoxy, N-lower alkylcarbamoyl-lower alkoxy or N,N-di-lower alkylcarbamoyl-lower alkoxy, amino, mono- or di-lower alkylamino, halogen, such as fluorine, chlorine or bromine, carboxy, lower alkoxycarbonyl, phenyl-, naphthyl- or fluorenyl-lower alkoxycarbonyl, lower alkanoyl, lower alkylsulfonyl, for example methyl-sulfonyl, phosphono, hydroxy-lower alkoxyphosphoryl or di-lower alkoxyphosphoryl, carbamoyl, mono- or di-lower alkylaminocarbamoyl, sulfamoyl, mono- or di-lower alkylsulfamoyl, nitro and/or by cyano and is bonded, especially at the terminal carbon atom, to lower alkenyl, such as in cyclobutyl-, cyclopentyl-, cyclohexyl- or cycloheptylmethyl-2-vinyl, -2- or -3-allyl or -2-, -3- or -4-but-2-enyl; aryl, as defined under aryl-lower alkanoyl $R_1$, $R_2$, $R_8$ or $R_9$, that is unsubstituted or substituted and is bonded, preferably terminally, to lower alkenyl, such as in styryl, 3-phenylallyl (cinnamyl), 2-(α-naphthyl)-vinyl or 2-(β-naphthyl)-vinyl; unsubstituted or substituted heterocyclyl, as defined under heterocyclyl-lower alkanoyl $R_1$, $R_2$, $R_8$ or $R_9$, preferably selected from pyrrolyl, furyl, thienyl, imidazolyl, pyrazolyl, oxazolyl, thiazolyl, pyridyl, pyrazinyl, pyrimidinyl, indolyl, quinolyl, isoquinolyl, quinoxalinyl, β-carbolinyl and a benzo-, cyclopenta-, cyclohexa- or cyclohepta-fused derivative of those radicals, which may also be fully or partially saturated and are unsubstituted or substituted as indicated above and are bonded via a nitrogen or carbon atom to lower alkenyl, preferably to the terminal carbon atom of the lower alkenyl radical, which is selected, for example, from vinyl, allyl and 2- or 3-butenyl, for example in the form of pyrimidin-1-yl-, piperidino-, pyrazin-1-yl-, piperazin-1-yl-, pyridazin-1-yl-, morpholino-, thiomorpholino- or S,S-dioxothiomorpholino-lower alkenyl, such as in 2-morpholino-vinyl, 3-morpholino-allyl or 4-morpholino-2- or -3-butenyl, pyrrolyl-lower alkenyl that is unsubstituted or substituted by lower alkyl or by phenyl, such as 2- or 3-pyrrolyl-vinyl or -allyl, 4- or 5-methylpyrrolyl-vinyl or -allyl or 4- or 5-phenylpyrrolyl-vinyl or -allyl, thienyl-lower alkenyl, such as 2-thienyl-vinyl or -allyl, furyl-lower alkenyl, such as 2-furyl-vinyl or -allyl, pyridyl-lower alkenyl, such as 2-, 3- or 4-pyridyl-vinyl or -allyl, indolyl-lower alkenyl that is unsubstituted or substituted by lower alkyl, for example methyl, phenyl-lower alkyl, for example benzyl, lower alkoxy, for example methoxy, phenyl-lower alkoxy, for example benzyloxy, or by halogen, for example chlorine, such as 2-, 3- or 5-indolyl-vinyl or -allyl, 1-methyl-, 2-methyl-, 5-methoxy-, 5-benzyloxy-, 5-chloro- or 4,5-dimethyl-indol-2-yl-, 1-benzylindol-2-yl- or -3-yl-vinyl or -allyl, 4,5,6,7-tetrahydroindol-2-yl-methyl, -ethyl or -n-propyl, cyclohepta-[b]pyrrol-5-yl-vinyl or -allyl, unsubstituted or hydroxy-substituted quinolyl-lower alkenyl, for example 2-, 3- or 4-quinolyl- or 4-hydroxyquinol-2-yl-vinyl or -allyl, unsubstituted or hydroxy-substituted isoquinolyl-lower alkenyl, such as 1-, 3- or 4-isoquinolyl- or 1-oxo-1, 2-dihydroisoquinol-3-yl-vinyl or -allyl, 2-quinoxalinyl-vinyl or -allyl, 3,1-benzofuran-2-yl-vinyl or -allyl, benz[e] indol-2-yl-vinyl or -allyl, β-carbolin-3-yl-vinyl or -allyl, 3-chromanyl-vinyl or -allyl, 3-thiochromanyl-vinyl or -allyl, 3-pyrrolidinyl-vinyl or -allyl, hydroxypyrrolidinyl-lower alkenyl, such as 3- or 4-hydroxypyrrolidin-2-yl-vinyl or -allyl, oxopyrrolidinyl-lower alkenyl, such as 5-oxopyrrolidin-2-yl-vinyl or -allyl, piperidinyl-lower alkenyl, such as 2-, 3- or 4-piperidinyl-vinyl- or -allyl, morpholinyl-lower alkenyl, such as 2- or 3-morpholinyl-vinyl or -allyl, thiomorpholinyl-lower alkenyl, such as 2- or 3-thiomorpholinyl-vinyl or -allyl, S,S-dioxothiomorpholinyl-lower alkenyl, such as S,S-dioxothiomorpholin-2- or -3-yl-vinyl or -allyl, indolinyl-lower alkenyl, such as 2- or 3-indolinyl-vinyl or -allyl, 1,2,3,4-tetrahydroquinolyl-lower alkenyl, such as 1,2,3,4-tetrahydroquinol-2-, -3- or -4-yl-vinyl or -allyl, 1,2,3,4-tetrahydroisoquinolyl-lower alkenyl, such as 1,2,3,4-tetrahydroisoquinol-1-, -2- or -3-yl-vinyl or -allyl, or 1-oxo-1,2,3,4-tetrahydroisoquinol-3-yl-vinyl or -allyl; also hydroxy; etherified hydroxy selected from lower alkoxy, such as methoxy or ethoxy, phenoxy or naphthyloxy, phenyl- or naphthyl-lower alkoxy, such as benzyloxy, and heterocyclyl-lower alkoxy wherein heterocyclyl is preferably selected from pyrrolyl, furyl, thienyl, imidazolyl, pyrazolyl, oxazolyl, thiazolyl, pyridyl, pyrazinyl, pyrimidinyl, indolyl, quinolyl, isoquinolyl, quinoxalinyl, β-carbolinyl and a benzo-fused, cyclopenta-, cyclohexa- or cyclohepta-fused derivative of those radicals, which may also be fully or partially saturated, for example 4-pyrrolidinylmethoxy, 1-imidazolylmethoxy, 2-pyridylmethoxy, 3-pyridylmethoxy, quinolin-2-yl-methoxy or indol-2-ylmethoxy; esterified hydroxy selected from lower alkanoyloxy, such as acetoxy, propionyloxy, butyroxy, isobutyroxy or pivaloyloxy, acetoacetoxy, amino- or benzyloxycarbonylamino-lower alkanoyloxy, such as 2-amino- or 2-benzyloxycarbonylamino-2-methylpropionyloxy, aryl-lower alkanoyloxy wherein aryl contains from 6 to 10 carbon atoms, such as in benzoyloxy, phenylacetoxy, 1- or 2-naphthoyloxy, lower alkoxycarbonyloxy, for example methoxy-, ethoxy-, n-propoxy-, isopropoxy-, n-butoxy-, isobutoxy-, sec-butoxy-, tert-butoxy-, n-pentyloxy-, isopentyloxy-, neopentyloxy-, tert-pentyloxy-, n-hexyloxy-, isohexyloxy- or n-heptyloxy-carbonyloxy, mono- or di-lower alkylaminocarbonyloxy, such as ethylaminocarbonyloxy or diethylaminocarbonyloxy, aryloxycarbonyloxy wherein aryl contains from 6 to 10 carbon atoms, for example phenoxy-carbonyloxy or 1- or 2-naphthyloxycarbonyloxy, aryl-lower alkoxycarbonyloxy wherein aryl contains from 6 to 12 carbon atoms, for example phenyl-lower alkoxycarbonyloxy, such as benzyloxycarbonyloxy, and also 1- or 2-naphthylmethoxycarbonyloxy or 9-fluorenylmethoxycarbonyloxy, sulfonyloxy, lower alkylsulfonyloxy, for example methyl-, ethyl-, propyl-, isopropyl-, n-butyl-, isobutyl-, sec-butyl-, tert-butyl-, n-pentyl-, isopentyl-, neopentyl-, tert-pentyl-, n-hexyl-, isohexyl- or n-heptyl-sulfonyloxy, phenylsulfonyloxy, 2- or 4-toluenesulfonyloxy and 1- or 2-naphthylsulfonyloxy; halogen, for example chlorine or bromine; carboxy; esterified carboxy selected from lower alkoxycarbonyl, such as methoxycarbonyl, ethoxycarbonyl and tert-butoxycarbonyl, 2-halo-lower alkoxycarbonyl, for example 2-chloro-, 2-bromo-, 2-iodo- or 2,2,2-trichloro-ethoxycarbonyl, phenyl- or naphthyl-lower alkoxycarbonyl, for example benzyloxycarbonyl, and heterocyclyl-lower alkoxycarbonyl wherein heterocyclyl is preferably selected from pyrrolyl, furyl, thienyl, imidazolyl, pyrazolyl, oxazolyl, thiazolyl, pyridyl, pyrazinyl, pyrimidinyl, indolyl, quinolyl, isoquinolyl, quinoxalinyl, β-carbolinyl and a benzo-fused, cyclopenta-, cyclohexa- or cyclohepta-fused derivative of those radicals, it also being possible for the mentioned radicals to be fully or partially saturated, for example in 4-pyridylmethoxycarbonyl; or amidated carboxy selected from carbamoyl, lower alkylcarbamoyl, such as methylcarbamoyl, di-lower alkylcarbamoyl, such as dimethylcarbamoyl, hydroxy-lower alkylcarbamoyl or di(hydroxy-lower alkyl)carbamoyl, such as hydroxymethylcarbamoyl or di(hydroxymethyl)carbamoyl, N-lower alkoxy-lower alkoxy-lower alkylcarbamoyl, such as 2-(2-methoxyethoxy)ethylaminocarbonyl, carboxy-lower alkylcarbamoyl or di(carboxy-lower alkyl)carbamoyl, for example carboxymethyl- or di(carboxymethyl)-carbamoyl, and from carbamoyl substituted at the nitrogen atom by a radical selected from ethylene, trimethylene, tetramethylene and pentamethylene wherein a carbon atom may have been replaced by nitrogen, oxygen, sulfur or by sulfur mono- or di-substituted by oxygen, it also being possible for the radical so formed to be fully or partially unsaturated, for example in the form of piperidino-, pyrazin-1-yl-, piperazin-1-yl-, pyrimidin-1-yl-, pyridazin-1-yl-, morpholino-, thiomorpholino- or S,S-dioxothiomorpholino-carbonyl, N-lower alkyl-N-heterocyclyl-lower alkylcarbamoyl wherein heterocyclyl is preferably selected from pyrrolyl, furyl, thienyl, imidazolyl, pyrazolyl, oxazolyl, thiazolyl, pyridyl, pyrazinyl, pyrimidinyl, indolyl, quinolyl, isoquinolyl, quinoxalinyl, β-carbolinyl and a benzo-fused, cyclopenta-, cyclohexa- or cyclohepta-fused derivative of those radicals, which may also be fully or partially saturated, for example N-2-pyridylmethyl-N-methylcarbamoyl.

Alkynyl $R_1$, $R_2$, $R_8$ or $R_9$ contains especially from 2 to 10, preferably, as lower alkynyl, from 2 to 7, especially from 2 to 4, carbon atoms, and is, for example, ethynyl, 1-propynyl or 2-propynyl, it being possible for the mentioned radicals to be unsubstituted or substituted by the radicals mentioned for lower alkenyl $R_1$, $R_2$, $R_8$ or $R_9$. Heterocyclyl $R_1$, $R_2$, $R_8$ and $R_9$ is bonded via a carbon atom and contains especially an unsubstituted or substituted heterocyclyl mentioned under heterocyclyl-lower alkanoyl $R_1$, $R_2$, $R_8$ and $R_9$ and is preferably pyrrolyl that is unsubstituted or substituted by lower alkyl or by phenyl, such as 2- or 3-pyrrolyl, 4- or 5-methylpyrrolyl or 4- or 5-phenylpyrrolyl, thienyl, such as 2-thienyl, furyl, such as 2-furyl, pyridyl, such as 2-, 3- or 4-pyridyl, indolyl that is unsubstituted or substituted by lower alkyl, for example methyl, phenyl-lower alkyl, for example benzyl, lower alkoxy, for example methoxy, phenyl-lower alkoxy, for example benzyloxy, or by halogen, for example chlorine, such as 2-, 3- or 5-indolyl, 1-methyl-, 2-methyl-, 5-methoxy-, 5-benzyloxy-, 5-chloro- or 4,5-dimethylindol-2-yl, 1-benzylindol-2-yl or -3-yl, 4,5,6,7-tetrahydroindol-2-yl, unsubstituted or hydroxy-substituted quinolyl, such as 2-, 3- or 4-quinolyl or 4-hydroxyquinol-2-yl, unsubstituted or hydroxy-substituted isoquinolyl, such as 1-, 3- or 4-isoquinolyl or 1-oxo-1,2-dihydroisoquinol-3-yl, 2-quinoxalinyl, 3,1-benzofuran-2-yl, benz[e]indol-2-yl, β-carbolin-3-yl, cyclohepta[b]pyrrol-5-yl, 3-chromanyl, 3-thiochromanyl, 3-pyrrolidinyl, hydroxypyrrolidinyl, such as 3- or 4-hydroxypyrrolidin-2-yl, oxopyrrolidinyl, such as 5-oxopyrrolidin-2-yl, piperidyl, such as 2-, 3- or 4-piperidyl, morpholinyl, such as 2- or 3-morpholinyl, thiomorpholinyl, such as 2- or 3-thiomorpholinyl, S,S-dioxothiomorpholinyl, such as S,S-dioxothiomorpholin-2- or -3-yl, indolinyl, such as 2- or 3-indolinyl, 1,2,3,4-tetrahydroquinolyl, such as 1,2,3,4-tetrahydroquinol-2-, -3- or -4-yl, 1,2,3,4-tetrahydroisoquinolyl, such as 1,2,3,4-tetrahydroisoquinol-1-, -2- or -3-yl, or 1-oxo-1,2,3,4-tetrahydroisoquinol-3-yl.

Alkyl-substituted sulfonyl $R_1$, $R_2$, $R_8$ and $R_9$ preferably contains an unsubstituted or substituted alkyl radical mentioned under alkyl $R_1$, $R_2$, $R_8$ and $R_9$ and is especially lower alkylsulfonyl, such as methylsulfonyl, ethylsulfonyl, n-propylsulfonyl or tert-butylsulfonyl, aryl-lower alkyl-substituted sulfonyl that contains, for example, an unsubstituted or substituted radical mentioned under aryl-lower alkyl $R_1$, $R_2$, $R_8$ and $R_9$ and is selected especially from the radicals benzyl-, 4-chloro-, 4-methoxy- or 4-nitro-benzyl-, naphthylmethyl-, for example α- or β-naphthylmethyl-, 2-phenylethyl-, 2-α-naphthylethyl-, 2-β-naphthylethyl-, 2-(4-methylphenyl)ethyl-, 2-(4-methoxyphenyl)ethyl-, 3-phenylpropyl-, 3-(p-hydroxyphenyl)-propyl-, 2,2-diphenylethyl- and 2,2-di(4-methoxyphenyl)-ethylsulfonyl, or heterocyclyl-lower alkyl-substituted sulfonyl that contains, for example, an unsubstituted or substituted radical mentioned under heterocyclyl-lower alkyl $R_1$, $R_2$, $R_8$ and $R_9$ and is selected especially from radicals such as 2- or 3-pyrrolyl-, 2-thienyl-, 2-furyl-, 1-pyrazolyl-, 2-, 3- or 4-pyridyl-, 2-, 3- or 5-indolyl-, (1-methyl-, 2-methyl-, 5-benzyloxy-, 5-chloro- or 4,5-dimethyl-indol-2-yl)-, (1-benzylindol-2-yl or -3-yl)-, 4,5,6,7-tetrahydroindol-2-yl-, (2-, 3- or 4-quinolyl or 4-hydroxyquinol-2-yl)-, (1-, 3- or 4-isoquinolyl or 1-oxo-1,2-dihydroisoquinol-3-yl)-, 3-pyrrolidinyl-, (3- or 4-hydroxypyrrolidin-2-yl)-, 5-oxopyrrolidin-2-yl-, (2- or 3-morpholinyl)-, (2- or 3-thiomorpholinyl)-, (S,S-dioxothiomorpholin-2- or -3-yl)-, (2- or 3-indolinyl)-, (1,2,3,4-tetrahydroquinol-2-, -3- or -4-yl)- and (1,2,3,4-tetrahydroisoquinol-1-, -2- or -3-yl)-methyl-sulfonyl.

Aryl-substituted sulfonyl $R_1$, $R_2$, $R_8$ and $R_9$ preferably contains an unsubstituted or substituted aryl radical mentioned under aryl-lower alkanoyl $R_1$, $R_2$, $R_8$ and $R_9$ and is especially phenyl- or 1- or 2-naphthyl-sulfonyl that is unsubstituted or mono- or di-substituted by lower alkyl, such as phenylsulfonyl, 2- or 4-toluenesulfonyl or 1- or 2-naphthylsulfonyl.

Heterocyclyl-substituted sulfonyl $R_1$, $R_2$, $R_8$ and $R_9$ preferably contains heterocyclyl that is selected from pyrrolyl, furyl, thienyl, imidazolyl, pyrazolyl, oxazolyl, thiazolyl, pyridyl, pyrazinyl, pyrimidinyl, indolyl, quinolyl, isoquinolyl, quinoxalinyl, β-carbolinyl and a benzo-fused, cyclopenta-, cyclohexa- or cyclohepta-fused derivative of those radicals, which may also be fully or partially saturated, from morpholinyl and from thiomorpholinyl and may be unsubstituted or substituted, especially by lower alkyl, such as methyl, such as morpholinosulfonyl, thiomorpholinosulfonyl, piperidinosulfonyl, 4-methylpiperazinylsulfonyl or piperazinosulfonyl. In especially preferred forms of the invention, heterocyclylsulfonyl as substituent may be absent.

Alkoxy-substituted sulfonyl $R_1$, $R_2$, $R_8$ and $R_9$ preferably contains an unsubstituted or substituted alkyl radical mentioned under alkyl $R_1$, $R_2$, $R_8$ and $R_9$ and is selected especially from lower alkoxy-, such as methoxy-, ethoxy- or tert-butoxysulfonyl, heterocyclyl-lower alkoxysulfonyl that contains, for example, an unsubstituted or substituted heterocyclyl-lower alkyl radical mentioned under heterocyclyl-lower alkyl $R_1$, $R_2$, $R_8$ and $R_9$ and is selected especially from 2- or 3-pyrrolyl-, 2-thienyl-, 2-furyl-, 1-pyrazolyl-, 2-, 3- or 4-pyridyl-, 2-, 3- or 5-indolyl-, (1-methyl-, 2-methyl-, 5-benzyloxy-, 5-chloro- or 4,5-dimethyl-indol-2-yl)-, (1-benzylindol-2-yl or -3-yl)-, 4,5,6,7-tetrahydroindol-2-yl-, (2-, 3- or 4-quinolyl or 4-hydroxyquinol-2-yl)-, (1-, 3- or 4-isoquinolyl or 1-oxo-1,2-dihydroisoquinol-3-yl)-, 3-pyrrolidinyl-, (3- or 4-hydroxypyrrolidin-2-yl)-, 5-oxopyrrolidin-2-yl-, (2- or 3-morpholinyl)-, (2- or 3-thiomorpholinyl)-, (S,S-dioxothiomorpholin-2- or -3-yl)-, (2- or 3-indolinyl)-, (1,2,3,4-tetrahydroquinol-2-, -3- or -4-yl)- and (1,2,3,4-tetrahydroisoquinol-1-, -2- or -3-yl)-methoxysulfonyl or -ethoxysulfonyl, aryl-lower alkoxysulfonyl that contains, for example, an unsubstituted or substituted aryl-lower alkyl radical mentioned under aryl-lower alkyl $R_1$, $R_2$, $R_8$ and $R_9$, such as benzyloxysulfonyl, hydroxy-lower alkoxy-, such as 3-hydroxypropoxy- or 2-hydroxy-3-methylpentyloxysulfonyl, lower alkoxy-lower alkoxy-, for example lower alkoxyethoxy- or lower alkoxypropoxy-, such as methoxyethoxy- or 3-methoxypropoxy-sulfonyl, lower alkoxy-lower alkoxy-lower alkoxy-, such as 2-methoxymethoxy-3-methylpentyloxy-sulfonyl, phenoxy-lower alkoxy- or nitrophenoxy-lower alkoxy-, such as phenoxymethoxy-, phenoxyethoxy- or 4-nitrophenoxymethoxy-sulfonyl, naphthyloxy-lower alkoxy-, such as α- or β-naphthyloxyethoxy-sulfonyl, lower alkanoyloxy-lower alkoxy-, for example lower alkanoyloxyethoxy- or lower alkanoyloxypropoxy-, such as acetoxyethoxy- or 3-acetoxypropoxy-sulfonyl, amino-lower alkoxy-, such as 5-aminopentyloxy-sulfonyl, mono- or di-lower alkylamino-lower alkoxy-, such as dimethylaminoethoxy- or 2-dimethylamino-2-isopropylethoxy-sulfonyl, lower alkanoylamino-lower alkoxy-, such as 4-acetylaminopentyloxy-sulfonyl, lower alkoxycarbonylamino-lower alkoxy-, such as 5-(tert-butoxycarbonylamino)pentyloxy- or 3-ethoxycarbonylamino-2-isobutyl-propoxy-sulfonyl, phenyl-lower alkoxycarbonylamino-lower alkoxy-, such as 5-(benzyloxycarbonylamino)-pentyloxy-sulfonyl, acetoacetoxy-sulfonyl, aminocarbonylamino-lower alkoxy-, such as aminocarbonylamino-ethoxy-sulfonyl, N-phenyl-lower alkyl-N-lower alkyl-aminocarbonylamino-lower alkoxy-, for example 2-isobutyl-3-(N-benzyl-N-methylaminocarbonylamino)propoxy-sulfonyl, halo-lower alkoxy-, for example 2-haloethoxy-, such as (2-chloro-, 2-bromo-, 2-iodo- or 2,2,2-trichloro-ethoxy)-, or halopropoxy-, such as (3-chloro- or 3-bromo-propoxy)sulfonyl, carboxy-lower alkoxy-, such as carboxyethoxy- or 3-carboxypropoxy-sulfonyl, lower alkoxycarbonyl-lower alkoxy-, for example lower alkoxycarbonylethoxy- or lower alkoxycarbonylpropoxy-, such as methoxycarbonylethoxy-, 3-methoxycarbonylpropoxy-, ethoxycarbonylethoxy- or 3-ethoxycarbonylpropoxy-sulfonyl, 2-halo-lower alkoxycarbonyl-lower alkoxy-, such as (2-chloro-, 2-bromo-, 2-iodo- or 2,2,2-trichloro-ethoxycarbonyl-2-ethoxy or 3-propoxy)-sulfonyl, lower alkylsulfonyl-lower alkoxy-, such as (2-ethylsulfonyl- or 2-tert-butylsulfonylmethoxy)-sulfonyl, carbamoyl-lower alkoxy-, such as carbamoylethoxy- or 3-carbamoylpropoxy-sulfonyl, and carbamoyl-lower alkoxysulfonyl substituted at the nitrogen atom by a radical selected from ethylene, trimethylene, tetramethylene and pentamethylene wherein a carbon atom may have been replaced by nitrogen, oxygen, sulfur or by sulfur mono- or di-substituted by oxygen, it also being possible for the radical so formed to be fully or partially unsaturated, for example in the form of (piperidino-, pyrazin-1-yl-, piperazin-1-yl-, pyridazin-1-yl-, pyridazin-1-yl-, morpholino-, thiomorpholino- or S,S-dioxothiomorpholino-carbonyl-lower alkoxy)-, such as in 2-morpholinocarbonyl-ethoxy-, 3-(morpholinocarbonyl)-propoxy- or 3-(morpholinocarbonyl)-2-isobutyl-propoxy-sulfonyl.

Aryloxy-substituted sulfonyl $R_1$, $R_2$, $R_8$ and $R_9$ preferably contains an unsubstituted or substituted aryl radical mentioned under aryl-lower alkanoyl $R_1$, $R_2$, $R_8$ and $R_9$ and is selected especially from benzyloxysulfonyl and 1- or 2-naphthyloxysulfonyl.

Sulfamoyl $R_1$, $R_2$, $R_8$ and $R_9$ substituted at the nitrogen atom may be substituted preferably by the same radicals as may carbamoyl in carbamoyl-lower alkanoyl $R_1$, $R_2$, $R_8$ and $R_9$ and is selected especially from mono- or di-lower alkylsulfamoyl, such as N,N-dimethylsulfamoyl, N-(phenyl- or naphthyl-lower alkyl)sulfamoyl, such as 3-benzylsulfamoyl, and sulfamoyl substituted at the nitrogen atom by a radical selected from ethylene, trimethylene, tetramethylene or pentamethylene wherein a carbon atom may have been replaced by nitrogen, lower alkyl-substituted, such as methyl-substituted, nitrogen, oxygen, sulfur or by sulfur mono- or di-substituted by oxygen, it also being possible for the radical so formed to be fully or partially unsaturated, for example in the form of piperidino-, pyrazin-1-yl-, piperazin-1-yl-, methylpiperazin-1-yl-, pyrimidin-1-yl-, pyridazin-1-yl-, morpholino-, thiomorpholino- or S,S-dioxothiomorpholino-sulfonyl, such as 4-methylpiperazinylsulfonyl or morpholinosulfonyl-2-isopropyl-propyl.

Phosphoryl $R_1$, $R_2$, $R_8$ and $R_9$ substituted by one or two identical or different radicals selected from alkyl, cycloalkyl, cycloalkyl-lower alkyl, aryl, aryl-lower alkyl, hydroxy, alkoxy, cycloalkoxy, cycloalkyl-lower alkoxy, aryloxy and aryl-lower alkoxy preferably contains as unsubstituted or substituted alkyl one or two of the unsubstituted or substituted radicals mentioned under alkyl, especially lower alkyl $R_1$, $R_2$, $R_8$ and $R_9$, for example lower alkyl, such as methyl, ethyl, n-propyl, isopropyl, n-butyl and tert-butyl, cycloalkyl-lower alkyl that is a lower alkyl radical substituted especially terminally by one of the cycloalkyl radicals mentioned under cycloalkyl-lower alkanoyl $R_1$, $R_2$, $R_8$ and $R_9$, such as cyclopropylmethyl, cyclobutylmethyl, cyclopentylmethyl, 2-cyclopentylethyl, 3-cyclopentylpropyl, cyclohexylmethyl, 2-cyclohexylethyl or 3-cyclohexylpropyl, aryl-lower alkyl, as defined under aryl-lower alkyl $R_1$, $R_2$, $R_8$ or $R_9$, especially benzyl, unsubstituted, mono- or poly-substituted preferably by lower alkyl, for example methyl, phenyl, hydroxy, lower alkoxy, for example methoxy, halogen, for example chlorine, and/or by nitro, such as 4-methoxy-, 4-chloro- or 4-nitro-benzyl, naphthylmethyl, such as α- or β-naphthylmethyl, 2-phenylethyl, 2-α-naphthylethyl, 2-β-naphthylethyl, 2-lower alkylphenylethyl, such as 2-(4-methylphenyl)ethyl, 2-lower alkoxyphenylethyl, such as 2-(4-methoxyphenyl)ethyl, 2,2-diphenylethyl, 2,2-di(4- methoxyphenyl)-ethyl, 2,2,2-triphenylethyl, 2,2-dibenzylethyl, 2,p-diamino-phenylethyl, or phenyl-lower alkyl substituted in the 2- and p-positions by two radicals selected from phenyl-lower alkoxycarbonyl, for example benzyloxycarbonyl, and lower alkanoylamino, for example pivaloylamino, such as 2,p-dibenzyloxycarbonylamino-phenylethyl or 2-pivaloylamino-p-benzyloxycarbonylamino-phenylethyl, 3-phenylpropyl, 3-(p-hydroxyphenyl)-propyl, 3-α- or 3-β-naphthylpropyl, 2-benzyl-3-(1-pyrazolyl)-propyl, 3-phenyl- or 3-α-naphthyl-2-hydroxypropyl, 3-phenyl- or 3-α-naphthyl-2-lower alkoxy-propyl, such as 3-phenyl- or 3-α-naphthyl-2-neopentyloxy-propyl, 3-phenyl- or 3-α-naphthyl-2-lower alkanoyloxy-propyl, such as 3-phenyl- or 3-α-naphthyl-2-pivaloyloxy- or -2-acetoxy-propyl, 2-benzyl- or 1- or 2-naphthyl-3-(N-methoxy-N-methylamino)-propyl, 3-phenyl- or 3-α-naphthyl-2-dimethylaminomethyl-propyl, 3-α-naphthyl-2-acetoacetoxy-propyl, 3-α-naphthyl-2-ethylaminocarbonyloxy-propyl or 3-α-naphthyl-2-(2-amino- or 2-benzyloxycarbonylamino-2-methylpropionyloxy)-propyl, 3-phenyl- or 3-α-naphthyl-2-carboxymethyl-propyl, 3-phenyl- or 3-α-naphthyl-2-lower alkoxycarbonyl-propyl, such as 3-α-naphthyl-2-ethoxycarbonylpropyl, 3-phenyl- or 3-α-naphthyl-2-benzyloxycarbonylmethyl-propyl, 2-(S)-benzyl-3-tert-butylsulfonyl-propyl, 3-phenyl-2-phosphono- or -phosphonomethyl-propyl, 3-phenyl-2-dimethoxyphosphoryl- or -dimethoxyphosphorylmethyl-propyl, 3-phenyl-2-diethoxyphosphoryl- or -diethoxyphosphorylmethyl-propyl, 3-phenyl-2-ethoxy- or -methoxy-hydroxyphosphorylpropyl, 3-phenyl- or 3-α-naphthyl-2-carbamoyl-propyl, 3-phenyl- or 3-α-naphthyl-2-tert-butylcarbamoyl-propyl, 3-phenyl- or 3-α-naphthyl-2-(2-dimethylaminoethyl)carbamoyl-propyl, 3-α-naphthyl-2-(carboxy- or tert-butoxycarbonyl) methylcarbamoyl-propyl, 3-phenyl- or 3-α-naphthyl-2-(3-hydroxy-2-propyl)-carbamoyl-propyl, 3-phenyl- or 3-α-naphthyl-2-(2,2-dimethoxyethyl)-carbamoyl-propyl, 3-phenyl- or 3-α-naphthyl-2-(5-amino-5-carboxypentyl)-carbamoyl-propyl, 3-phenyl- or 3-α-naphthyl-2-cyano-propyl, 3-phenyl- or 3-α-naphthyl-2-cyanomethyl-propyl, 3-phenyl- or 3-α-naphthyl-2-acetonyl-propyl, 4-hydroxyphenylbutyl, 4-phenyl- or 4-α-naphthyl-3-carboxybutyl, 4-phenyl- or 4-α-naphthyl-3-benzyloxycarbonyl-butyl, 2-benzyl- or 2-α-naphthylmethyl-4-cyano-butyl, 2-benzyl-4-(2-benzofuranyl)-4-oxobutyl, 2-benzyl- or 2-α-naphthylmethyl-5-dimethylamino-pentyl, 2-benzyl- or 2-α-naphthylmethyl-4-oxo-pentyl, 2-benzyl- or 2-α-naphthylmethyl-4,4-dimethyl-3-oxo-pentyl, 2-benzyl- or 2-α-naphthylmethyl-5-dimethylamino-4-oxo-pentyl, or 2-benzyl- or 2-α-naphthylmethyl-5,5-dimethyl-4-oxo-hexyl, as cycloalkyl one of the radicals mentioned under cycloalkyl-lower alkanoyl $R_1$, $R_2$, $R_8$ and $R_9$, especially cyclopropyl, cyclobutyl, cyclopentyl or cyclohexyl, as aryl one of the unsubstituted or substituted radicals mentioned under aryl-lower alkanoyl $R_1$, $R_2$, $R_8$ and $R_9$, preferably phenyl, unsubstituted, mono- or poly-substituted by lower alkyl, for example methyl, halo-lower alkyl, for example trifluoromethyl, phenyl, hydroxy, lower alkoxy, for example methoxy, halogen, for example fluorine or chlorine, and/or by nitro, such as 4-methyl-, 3-hydroxy-, 4-methoxy-, 4-chloro- or 4-nitro-phenyl, naphthyl, such as α- or β-naphthyl, or anilinophenyl substituted in the phenyl radical by one or two radicals selected from lower alkyl, such as methyl or ethyl, hydroxy, lower alkoxy, such as methoxy, amino, mono- or di-lower alkylamino, such as ethylamino or dimethylamino, halogen, such as fluorine or chlorine, carboxy, sulfo, carbamoyl, sulfamoyl and cyano, and/or at the amino group by one or two radicals selected from lower alkyl and benzyl, such as 2-(o,o-dichloroanilino)-phenyl or 2-(o,o-dichloro-N-benzylanilino)-phenyl, as alkoxy one of the unsubstituted or substituted radicals mentioned in the case of alkoxy-substituted sulfonyl $R_1$, $R_2$, $R_8$ and $R_9$, especially lower alkoxy, such as methoxy, ethoxy or tert-butoxy, cycloalkyl-lower alkoxy with one of the radicals mentioned under phosphoryl $R_1$, $R_2$, $R_8$ and $R_9$ substituted by cycloalkyl-lower alkyl, bonded via oxygen, such as cyclopropylmethoxy, cyclobutylmethoxy, cyclopentylmethoxy, 2-cyclopentylethoxy, 3-cyclopentylpropoxy, cyclohexylmethoxy, 2-cyclohexylethoxy or 3-cyclohexylpropoxy, aryl-lower alkoxy with one of the radicals mentioned under sulfonyl $R_1$, $R_2$, $R_8$ and $R_9$ substituted by aryl-lower alkoxy, bonded via oxygen, especially benzyloxy, hydroxy-lower alkoxy, such as 3-hydroxypropoxy or 2-hydroxy-3-methylpentyloxy, lower alkoxy-lower alkoxy, for example lower alkoxyethoxy or lower alkoxypropoxy, such as methoxyethoxy or 3-methoxypropoxy, lower alkoxy-lower alkoxy-lower alkoxy, such as 2-methoxymethoxy-3-methylpentyloxy, phenoxy-lower alkoxy or nitrophenoxy-lower alkoxy, such as phenoxymethoxy, phenoxyethoxy or 4-nitrophenoxymethoxy, naphthyloxy-lower alkoxy, such as α- or β-naphthyloxyethoxy, lower alkanoyloxy-lower alkoxy, such as lower alkanoyloxyethoxy or lower alkanoyloxypropoxy, such as acetoxyethoxy or 3-acetoxypropoxy, amino-lower alkoxy, such as 5-aminopentyloxy, mono- or di-lower alkylamino-lower alkoxy, such as dimethylaminoethoxy or 2-dimethylamino-2-isopropylethoxy, lower alkanoylamino-lower alkoxy, such as 4-acetylaminopentyloxy, lower alkoxycarbonylamino-lower alkoxy, such as 5-(tert-butoxycarbonylamino)-pentyloxy or 3-ethoxycarbonylamino-2-isobutyl-propoxy, phenyl-lower alkoxycarbonylamino-lower alkoxy, such as 5-(benzyloxycarbonylamino)-pentyloxy, aminocarbonylamino-lower alkoxy, such as aminocarbonylamino-ethoxy, N-phenyl-lower alkyl-N-lower alkyl-aminocarbonylamino-lower alkoxy, such as 2-isobutyl-3-(N-benzyl-N-methylaminocarbonylamino)propoxy, halo-lower alkoxy, for example 2-haloethoxy, such as 2-chloro-, 2-bromo-, 2-iodo- or 2,2,2-trichloro-ethoxy, or halopropoxy, such as 3-chloro- or 3-bromo-propoxy, carboxy-lower alkoxy, such as carboxyethoxy or 3-carboxypropoxy, lower alkoxycarbonyl-lower alkoxy, for example lower alkoxycarbonylethoxy or lower alkoxycarbonylpropoxy, such as methoxycarbonylethoxy, 3-methoxycarbonylpropoxy, ethoxycarbonylethoxy or 3-ethoxycarbonylpropoxy, 2-halo-lower alkoxycarbonyl-lower alkoxy, such as 2-chloro-, 2-bromo-, 2-iodo- or 2,2,2-trichloro-ethoxycarbonyl-2-ethoxy or -3-propoxy, lower alkylsulfonyl-lower alkoxy, such as 2-ethylsulfonyl- or 2-tert-butylsulfonyl-methoxy, carbamoyl-lower alkoxy, such as carbamoylethoxy or 3-carbamoylpropoxy, or carbamoyl-lower alkoxy substituted at the nitrogen atom by a radical selected from ethylene, trimethylene, tetramethylene and pentamethylene wherein a carbon atom may have been replaced by nitrogen, oxygen, sulfur or by sulfur mono- or di-substituted by oxygen, it also being possible for the ring formed to be fully or partially unsaturated, for example in the form of (piperidino-, pyrazin-1-yl-, piperazin-1-yl-, pyrimidin-1-yl-, pyridazin-1-yl-, morpholino-, thiomorpholino- or S,S-dioxothiomorpholino-carbonyl)-lower alkoxy, such as in 2-morpholinocarbonyl-ethoxy, 3-(morpholinocarbonyl)-propoxy or 3-(morpholinocarbonyl)-2-isobutyl-propoxy, as cycloalkoxy one of the cycloalkyl radicals mentioned under cycloalkyl-lower alkanoyl $R_1$, $R_2$, $R_8$ and $R_9$, bonded via oxygen, such as cyclobutoxy, cyclopentyloxy or cyclohexyloxy, or as aryloxy one of the radicals mentioned under aryloxy-substituted sulfonyl $R_1$, $R_2$, $R_8$ and $R_9$, especially benzyloxy or 1- or 2-naphthyloxy, and is especially preferably lower alkylphosphoryl, such as tert-butylphosphoryl, hydroxy-lower alkoxyphosphoryl, such as hydroxy-methoxy-phosphoryl or hydroxyethoxy-phosphoryl, or di-lower alkoxyphosphoryl, such as dimethoxy-phosphoryl or diethoxy-phosphoryl.

The phosphono radicals and the individual definitions of the radicals $R_1$, $R_2$, $R_8$ and $R_9$ mentioned for substituted phosphoryl may also, independently of one another, be omitted from the definition of the radicals $R_1$, $R_2$, $R_8$ and $R_9$ in the compounds of formula I.

Preferably not more than one of the radicals $R_1$ and $R_2$ and of the radicals $R_8$ and $R_9$ is defined by the radicals mentioned under acyl, sulfo, substituted sulfo, phosphono or substituted phosphoryl, while the other radical is selected from the remaining substituents mentioned.

A heterocyclic ring formed by the pairs of substituents RI and $R_2$, and $R_8$ and $R_9$, independently of one another, together with the nitrogen atom to which they are bonded, and comprising the bonding nitrogen atom together with a radical selected from ethylene, trimethylene, tetramethylene and pentamethylene in which a carbon atom may have been replaced by nitrogen, oxygen, sulfur or by sulfur mono- or di-substituted by oxygen and which may be unsaturated, or one of those radicals with an oxo substituent at each of the two carbon atoms linked to the bonding carbon atom and with or without a fused-on benzene or naphthalene ring, is preferably piperidino, pyrazin-1-yl, piperazin-1-yl, pyrimidin-1-yl, pyridazin-1-yl, morpholino, thiomorpholino, S,S-dioxothiomorpholino, succinimido, malimido, oxalimido, maleimido, phthalimido or naphthalene-1,8-dicarbonylimido, preferably only one of the pairs of substituents $R_1$ and $R_2$ or $R_8$ and $R_9$ forming one of the said heterocyclic rings.

Unsubstituted or substituted alkyl $R_3$, $R_4$ or $R_7$ is preferably one of the unsubstituted or substituted radicals mentioned under alkyl $R_1$, $R_2$, $R_8$ and $R_9$ and is selected especially from lower alkyl, for example methyl, ethyl, propyl, isopropyl, n-butyl, isobutyl or tert-butyl, cycloalkyl-lower alkyl that contains, for example, the cycloalkyl radicals mentioned under cycloalkyl-lower alkanoyl $R_1$, $R_2$, $R_8$ or $R_9$, such as cyclopropyl, cyclobutyl, cyclopentyl, cyclohexyl or cycloheptyl, cycloalkyl being unsubstituted or mono- to tri-substituted by lower alkyl, such as isopropyl, halo-lower alkyl, such as trifluoromethyl, hydroxy, lower alkoxy, carbamoyl-lower alkoxy, N-lower alkylcarbamoyl-lower alkoxy or N,N-di-lower alkylcarbamoyl-lower alkoxy, amino, mono- or di-lower alkylamino, halogen, such as fluorine, chlorine or bromine, carboxy, lower alkoxycarbonyl, phenyl-, naphthyl- or fluorenyl-lower alkoxycarbonyl, lower alkanoyl, lower alkylsulfonyl, for example methylsulfonyl, phosphono, hydroxy-lower alkoxy-phosphoryl or di-lower alkoxyphosphoryl, carbamoyl, mono- or di-lower alkylaminocarbamoyl, sulfamoyl, mono- or di-lower alkylsulfamoyl, nitro and/or by cyano and being bonded, preferably terminally, to lower alkyl, especially methyl, ethyl, n-propyl, isopropyl, n-butyl, isobutyl or tert-butyl, such as cyclobutyl-, cyclopentyl-, cyclohexyl- or cycloheptyl-lower alkyl, such as -methyl or -ethyl, especially preferably cyclohexyl-lower alkyl, such as cyclohexylmethyl, bicycloalkyl-lower alkyl wherein bicycloalkyl contains, for example, from 5 to 10, especially from 6 to 9, carbon atoms, for example bicycloalkyl-methyl or -ethyl, preferably having from 8 to 11 carbon atoms, such as decahydronaphthyl-2-methyl, endo- or exo-norbomyl-2-methyl, bicyclo[2.2.2]oct-2-ylmethyl or bicyclo[3.3.1]non-9-ylmethyl, and also bicyclo-hexyl-, -heptyl-, -octyl-, -nonyl- or -decyl-ethyl or -3-propyl, for example bicyclo[3.1.0]hex-1-, -2- or -3-yl-, bicyclo[4.1.0]hept-1- or -7-yl-, bicyclo[2.2.1]hept-2-yl-, for example endo- or exo-norbornyl-, bicyclo[3.2.1]oct-2-yl-, bicyclo[3.3.0]oct-3-yl- or bicyclo[3.3.1]non-9-yl-, and also α- or β-decahydronaphthyl-ethyl or -3-propyl, tricycloalkyl-lower alkyl, wherein tricycloalkyl contains, for example, from 8 to 10 carbon atoms, for example tricycloalkyl-methyl or -ethyl, preferably having from 8 to 11 carbon atoms, such as 1- or 2-adamantylmethyl, and also tricyclo[5.2.1.0$^{2,6}$]dec-8-yl- or adamantyl-, such as 1-adamantyl-ethyl, aryl-lower alkyl, for example as defined under aryl-lower alkyl $R_1$, $R_2$, $R_8$ or $R_9$, that is unsubstituted or substituted as defined there, for example phenyl-lower alkyl, such as benzyl, 2-phenylethyl, 3-phenylpropyl, 4-fluoro-, 4-cyano-, 4-methoxy- or 4-hydroxybenzyl, or 1- or 2-naphthyl-methyl or -2-ethyl, especially phenyl-lower alkyl, as last defined, heterocyclyl-lower alkyl, for example as defined under heterocyclyl-lower alkyl $R_1$, $R_2$, $R_8$ or $R_9$, that is unsubstituted or substituted as defined there and is selected especially from pyrimidin-1-yl-, piperidino-, pyrazin-1-yl-, piperazin-1-yl-, pyridazin-1-yl-, morpholino-, thiomorpholino- or S,S-dioxothiomorpholino-lower alkyl, such as in 2-morpholinoethyl, 3-morpholino-propyl or 3-morpholino-2-isobutyl-propyl, unsubstituted or lower alkyl- or phenyl-substituted pyrrolyl-lower alkyl, such as 2- or 3-pyrrolyl-methyl, -ethyl or -n-propyl, 4- or 5-methylpyrrolyl-methyl, -ethyl or -n-propyl or 4- or 5-phenylpyrrolylmethyl, -ethyl or -n-propyl, thienyl-lower alkyl, such as 2-thienyl-methyl, -ethyl or -n-propyl, 1-imidazolylmethyl, furyl-lower alkyl, such as 2-furyl-methyl, -ethyl or -n-propyl, pyridyl-lower alkyl, such as 2-, 3- or 4-pyridyl-methyl, -ethyl or -n-propyl, indolyl-lower alkyl that is unsubstituted or substituted by lower alkyl, for example methyl, phenyl-lower alkyl, for example benzyl, lower alkoxy, for example methoxy, phenyl-lower alkoxy, for example benzyloxy, or by halogen, for example chlorine, such as 2-, 3- or 5-indolyl-methyl, -ethyl or -n-propyl, 1-methyl-, 2-methyl-, 5-methoxy-, 5-benzyloxy-, 5-chloro- or 4,5-dimethyl-indol-2-yl-, 1-benzylindol-2-yl- or -3-yl-methyl, -ethyl or -n-propyl, 4,5,6,7-tetrahydroindol-2-yl-methyl, -ethyl or -n-propyl, cyclohepta[b]pyrrol-5-yl-methyl, -ethyl or -n-propyl, unsubstituted or hydroxy-substituted quinolyl-lower alkyl, for example 2-, 3- or 4-quinolyl- or 4-hydroxyquinol-2-yl-methyl, -ethyl or -n-propyl, unsubstituted or hydroxy-substituted isoquinolyl-lower alkyl, such as 1-, 3- or 4-isoquinolyl- or 1-oxo-1,2-dihydroisoquinol-3-yl-methyl, -ethyl or -n-propyl, 2-quinoxalinyl-methyl, -ethyl or -n-propyl, 3,1-benzofuran-2-yl-methyl, -ethyl or -n-propyl, benz[e]indol-2-yl-methyl, -ethyl or -n-propyl, β-carbolin-3-yl-methyl, -ethyl or -n-propyl, 3-chromanyl-methyl, -ethyl or -n-propyl, 3-thiochromanyl-methyl, -ethyl or -n-propyl, 3- or 4-pyrrolidinyl-methyl, -ethyl or -n-propyl, hydroxypyrrolidinyl-lower alkyl, such as 3- or 4-hydroxypyrrolidin-2-yl-methyl, -ethyl or -n-propyl, oxopyrrolidinyl-lower alkyl, such as 5-oxopyrrolidin-2-yl-methyl, -ethyl or -n-propyl, piperidinyl-lower alkyl, such as 2-, 3- or 4-piperidinyl-methyl, -ethyl or -n-propyl, morpholinyl-lower alkyl, such as 2- or 3-morpholinyl-methyl, -ethyl or -n-propyl, thiomorpholinyl-lower alkyl, such as 2- or 3-thiomorpholinyl-methyl, -ethyl or -n-propyl, S,S-dioxothiomorpholinyl-lower alkyl, such as S,S-dioxothiomorpholin-2- or -3-yl-methyl, -ethyl or -n-propyl, indolinyl-lower alkyl, such as 2- or 3-indolinyl-methyl, -ethyl or -n-propyl, 1,2,3,4-tetrahydroquinolyl-lower alkyl, such as 1,2,3,4-tetrahydroquinol-2-, -3- or -4-yl-methyl, -ethyl or -n-propyl, 1,2,3,4-tetrahydroisoquinolyl-lower alkyl, such as 1,2,3,4-tetrahydroisoquinol-1-, -2- or -3-yl-methyl, -ethyl or -n-propyl, and 1-oxo-1,2,3,4-tetrahydroisoquinol-3-yl-methyl, -ethyl or -n-propyl, hydroxy-lower alkyl, such as 3-hydroxypropyl or 2-hydroxy-3-methylpentyl, lower alkoxy-lower alkyl, for example lower alkoxyethyl or lower alkoxypropyl, such as 2-methoxyethyl, 2-ethoxyethyl or 3-methoxypropyl, phenoxy-lower alkyl or nitrophenoxy-lower alkyl, such as phenoxymethyl, phenoxyethyl or 4-nitrophenoxymethyl, naphthyloxy-lower alkyl, such as α- or β-naphthyloxyethyl, lower alkanoyloxy-lower alkyl, for example lower alkanoyloxyethyl or lower alkanoyloxypropyl, such as acetoxyethyl or 3-acetoxypropyl, acetoacetoxy-lower alkanoyl, arylmercapto-lower alkyl wherein aryl contains from 6 to 10 carbon atoms, for example phenyl or naphthyl, such as phenylmercaptomethyl, amino-lower alkyl, such as 5-aminopentyl, mono- or di-lower alkylamino-lower alkyl, such as dimethylaminoethyl or 2-dimethylamino-2-isopropylethyl, phenyl- or naphthyl-amino-lower alkyl, such as 3-phenylaminopropyl, lower alkanoylamino-lower alkyl, such as 4-acetylaminopentyl, piperazinylcarbamoyl-lower alkyl substituted at the nitrogen atom by lower alkyl, such as methyl, such as 4-methylpiperazinylcarbonylmethyl, lower alkoxycarbonylamino-lower alkyl, such as 5-(tert-butoxycarbonylamino)-pentyl or 3-ethoxycarbonylamino-2-isobutyl-propyl, phenyl-lower alkoxycarbonylamino-lower alkyl, such as 5-(benzyloxycarbonylamino)pentyl, aminocarbonylamino-lower alkyl, such as 2-aminocarbonylamino-ethyl, N-phenyl-lower alkyl-N-lower alkylaminocarbonylamino-lower alkyl, such as 2-isobutyl-3-(N-benzyl-N-methylaminocarbonylamino)propyl, halo-lower alkyl wherein halogen is selected from fluorine, chlorine, bromine and iodine, for example 2-haloethyl, such as 2-fluoro-, 2-chloro-, 2-bromo-, 2-iodo-, 2,2,2-trifluoro- or 2,2,2-trichloro-ethyl, trifluoro-lower alkyl, such as trifluoromethyl, or halopropyl, such as 3-fluoro-, 3-chloro- or 3-bromopropyl, carboxy-lower alkyl, such as carboxyethyl or 3-carboxypropyl, lower alkoxycarbonyl-lower alkyl, for example lower alkoxycarbonylethyl or lower alkoxycarbonylpropyl, such as methoxycarbonylethyl, 3-methoxycarbonylpropyl, ethoxycarbonylethyl or 3-ethoxycarbonylpropyl, 2-halo-lower alkoxycarbonyl-lower alkyl, such as 2-chloro-, 2-bromo-, 2-iodo- or 2,2,2-trichloro-ethoxycarbonyl-2-ethyl or -3-propyl, phenyl- or naphthyl-lower alkoxycarbonyl-lower alkyl, for example benzyloxycarbonyl-lower alkyl, such as 3-benzyloxycarbonyl-2,2-dimethylpropyl, heterocyclyl-lower alkoxycarbonyl-lower alkyl wherein heterocyclyl is preferably selected from pyrrolyl, furyl, thienyl, imidazolyl, pyrazolyl, oxazolyl, thiazolyl, pyridyl, pyrazinyl, pyrimidinyl, indolyl, quinolyl, isoquinolyl, quinoxalinyl, βcarbolinyl and a benzo-fused, cyclopenta-, cyclohexa- or cyclohepta-fused derivative of those radicals, it also being possible for the mentioned radicals to be fully or partially saturated, such as in 4-pyridylmethyloxycarbonyl-2-ethyl or -3-propyl or 2-morpholinocarbonyloxy-4-methylpentyl, lower alkylsulfonyl-lower alkyl, for example 2-ethylsulfonyl- or 2-tert-butylsulfonymethmethyl, arylsulfonyl-lower alkyl wherein aryl preferably contains from 6 to 10 carbon atoms, for example phenyl or naphthyl, such as phenylsulfomethyl, carbamoyl-lower alkyl, such as carbamoylethyl or 3-carbamoylpropyl, lower alkylcarbamoyl-lower alkyl, for example lower alkylcarbamoylethyl or methylcarbamoyl-lower alkyl, such as 2-methylcarbamoylethyl, di-lower alkylcarbamoyl-lower alkyl, for example 2-di-lower alkylcarbamoylethyl or dimethylcarbamoyl-lower alkyl, such as 2-dimethylcarbamoylethyl, hydroxy-lower alkylcarbamoyl- or di(hydroxy-lower alkyl)carbamoyl-lower alkyl, such as 2-hydroxymethylcarbamoyl- or di(hydroxymethyl)carbamoyl-2-ethyl or -3-propyl, N-lower alkoxy-lower alkoxy-lower alkylcarbamoyl-lower alkyl, such as 2-isobutyl-3-(2-(2-methoxyethoxy)ethylaminocarbonyl)-propyl, carboxy-lower alkylcarbamoyl- or di(carboxy-lower alkyl)carbamoyl-lower alkyl, for example carboxymethyl- or di(carboxymethyl)-carbamoyl-2-ethyl or -3-propyl, carbamoyl-lower alkyl substituted at the nitrogen atom by a radical selected from ethylene, trimethylene, tetramethylene and pentamethylene wherein a carbon atom may have been replaced by nitrogen, oxygen, sulfur or by sulfur mono- or di-substituted by oxygen, it also being possible for the radical so formed to be fully or partially unsaturated, for example in the form of piperidino-, pyrazin-1-yl-, piperazin-1-yl-, pyrimidin-1-yl-, pyridazin-1-yl-, morpholino-, thiomorpholino- or S,S-dioxothiomorpholino-carbonyl-lower alkyl, such as in 2-morpholinocarbonyl-ethyl, 3-(morpholinocarbonyl)-propyl or 3-(morpholinocarbonyl)-2-isobutyl-propyl, N-lower alkyl-N-heterocyclyl-lower alkylcarbamoyl-lower alkyl wherein heterocyclyl is preferably selected from pyrrolyl, furyl, thienyl, imidazolyl, pyrazolyl, oxazolyl, thiazolyl, pyridyl, pyrazinyl, pyrimidinyl, indolyl, quinolyl, isoquinolyl, quinoxalinyl, β-carbolinyl and a benzo-fused, cyclopenta-, cyclohexa- or cyclohepta-fused derivative of those radicals, which may also be fully or partially saturated, such as 2-(N-2-pyridylmethyl)-N-methylcarbamoyl-ethyl, sulfamoyl-lower alkyl, such as 2-sulfamoylethyl, N-(phenyl- or naphthyl-lower alkyl)sulfamoyl-lower alkyl, such as 3-benzylaminosulfonyl-2-isopropyl-propyl, or sulfamoyl-lower alkyl substituted at the nitrogen atom by a radical selected from ethylene, trimethylene, tetramethylene and pentamethylene wherein a carbon atom may have been replaced by nitrogen, nitrogen substituted by lower alkyl, such as methyl, oxygen, sulfur or by sulfur mono- or di-substituted by oxygen, it also being possible for the radical so formed to be fully or partially unsaturated, for example in the form of piperidino-, pyrazin-1-yl-, piperazin-1-yl-, 4-methylpiperazin-1-yl-, pyrimidin-1-yl-, pyridazin-1-yl-, morpholino-, thiomorpholino- or S,S-dioxothiomorpholino-sulfonyl-lower alkyl, for example 3-(4-methylpiperazinylsulfonyl)-2-isopropyl-propyl or 3-(morpholinosulfonyl)-2-isopropyl-propyl, oxo-lower alkyl (wherein oxo is not present at the carbon atom that is bonded to the nitrogen atom carrying the radical $R_7$), such as 3-oxo-n-butyl or 3-oxo-n-pentyl, cyano-lower alkyl, such as cyanomethyl, 2-cyanoethyl, 2- or 3-cyano-n-propyl or 2-, 3- or 4-cyano-n-butyl, hydroxy-carboxy-lower alkyl, such as 2-hydroxy-2-carboxyethyl or 2-hydroxy-3-carboxypropyl, α-naphthyloxy-carboxy-lower alkyl, such as 2-α-naphthyloxy-4-carboxy-n-butyl, hydroxy-lower alkoxycarbonyl-lower alkyl, for example 2-hydroxy-2-lower alkoxycarbonyl-ethyl or -propyl or hydroxy-ethoxy- or hydroxy-methoxy-carbonyl-lower alkyl, such as 2-hydroxy-2-ethoxy- or -methoxy-carbonylethyl or 2-hydroxy-3-ethoxy- or -methoxy-carbonyl-propyl, α-naphthyloxy-lower alkoxycarbonyl-lower alkyl, for example α-naphthyloxy-lower alkoxycarbonyl-2-ethyl, -2-propyl or -2-butyryl or α-naphthyloxyethoxycarbonyl-lower alkyl, such as α-naphthyloxyethoxycarbonyl-2-ethyl, 2-α-naphthyloxy-3-ethoxycarbonylpropyl or 2-α-naphthyloxy-4-tert-butoxycarbonylbutyl, lower alkylcarbonylhalo-lower alkyl, such as 3-ethoxycarbonyl-2-difluoromethyl, α-naphthyloxy-benzyloxycarbonyl-lower alkyl, such as 2-α-naphthyloxy-3-benzyloxycarbonyl-propyl, esterified hydroxy-lower alkoxycarbonyl-lower alkyl wherein the hydroxy group is esterified by lower alkanoyl, for example acetyl, propionyl or pivaloyl, cycloalkyl-lower alkanoyl wherein cycloalkyl contains from 3 to 7 carbon atoms and lower alkanoyl is as last defined, for example cyclohexylcarbonyl or 2-cyclohexyl- or 2-cyclopentyl-acetyl, bicycloalkyl-lower alkanoyl wherein bicycloalkyl contains, for example, from 5 to 10, especially from 6 to 9, carbon atoms, such as in bicyclo-hexyl-, -heptyl-, -octyl-, -nonyl- or -decyl-acetyl or -3-propionyl, for example bicyclo[3.1.0]hex-1-, -2- or -3-yl-, bicyclo-[4.1.0]hept-1- or -7-yl-, bicyclo[2.2.1]hept-2-yl-, for example endo- or exo-norbornyl-, bicyclo[3.2.1]oct-2-yl-, bicyclo[3.3.0]oct-3-yl- or bicyclo[3.3.1]non-9-yl-, and also α- or β-decahydronaphthyl-acetyl or -3-propionyl, tricycloalkyl-lower alkanoyl wherein tricycloalkyl contains, for example, from 8 to 10 carbon atoms, for example in tricyclo[5.2.1.0$^{2,6}$]dec-8-yl- or adamantyl-, such as 1-adamantyl-acetyl, aryl-lower alkanoyl wherein aryl contains from 6 to 14 carbon atoms, for example phenyl, indenyl, indanyl, naphthyl, anthryl, phenanthryl, acenaphthyl or fluorenyl, and may be unsubstituted or mono- to tri-substituted by lower alkyl, hydroxy, lower alkoxy, carbamoyl-lower alkoxy, N-lower alkylcarbamoyl-lower alkoxy or N,N-di-lower alkylcarbamoyl-lower alkoxy, amino, mono- or di-lower alkylamino, halogen, such as fluorine, chlorine or bromine, carboxy, lower alkoxycarbonyl, phenyl-, naphthyl- or fluorenyl-lower alkoxycarbonyl, lower alkanoyl, lower alkylsulfonyl, for example methylsulfonyl, phosphono, hydroxy-lower alkoxyphosphoryl, di-lower alkoxyphosphoryl, carbamoyl, sulfamoyl, nitro and/or by cyano, lower alkoxycarbonyl, for example tert-butoxycarbonyl, 2-halo-lower alkoxycarbonyl, as defined above, or by phenyl- or fluorenyl-lower alkoxycarbonyl, for example benzyloxycarbonyl or 9-fluorenylmethoxycarbonyl, such as 2-acetoxy-2-methoxycarbonyl-ethyl, 2-benzoyloxy-, 2-(1- or 2-naphthoyloxy)-, 2-(phenyl-2-acetoxy)-, 2-(1- or 2-naphthyl-2-acetoxy)-, 2-(4-methylphenyl-2-acetoxy) -, 2-(4-methoxyphenyl-2-acetoxy)- or 2-(2-(o,o-dichlorophenyl)-2-acetoxy)-2-methoxycarbonyl-ethyl or -3-propyl, dihydroxy-carboxy-lower alkyl, such as 2,3-dihydroxy-3-carboxy-propyl, dihydroxy-lower alkoxycarbonyl-lower alkyl, such as 2,3-dihydroxy-3-ethoxy- or -methoxy-carbonyl-propyl, dihydroxy-lower alkoxycarbonyl-lower alkyl esterified by lower alkanoyl, such as acetyl, propionyl or butyryl, lower alkoxycarbonyl, for example tert-butoxycarbonyl, phenyl- or fluorenyl-lower alkoxycarbonyl, such as benzyloxycarbonyl or 9-fluorenylmethoxycarbonyl, lower alkylsulfonyl or by toluenesulfonyl, for example di-lower alkanoyloxy-lower alkoxy-propyl, such as 2,3-diacetoxy-3-methoxycarbonyl-propyl, α-naphthyloxy-di-lower alkylamino-lower alkyl, such as 2-α-naphthyloxy-5-dimethylamino-pentyl, α-naphthyloxy-carbamoyl-lower alkyl, such as 2-α-naphthyloxy-4-carbamoyl-butyl, α-naphthyloxy-oxo-lower alkyl (wherein oxo is not present at the carbon atom that is bonded to the nitrogen atom carrying the radical $R_7$), such as 2-α-naphthyloxy-4-oxo-pentyl, or α-naphthyloxy-cyano-lower alkyl, such as 2-α-naphthyloxy-cyano-ethyl or 2-α-naphthyloxy-4-cyano-butyl.

Lower alkyl that is unsubstituted or mono- or polysubstituted by hydroxy, lower alkoxy, amino, mono- or di-lower alkylamino, fluorine, chlorine or by cyano is preferred, and lower alkyl, such as methyl, ethyl, propyl, isopropyl, n-butyl, isobutyl or tert-butyl, is very especially preferred.

Cycloalkyl $R_3$, $R_4$ or $R_7$ is preferably as defined under cycloalkyl-lower alkanoyl $R_1$, $R_2$, $R_8$ or $R_9$, for example cyclopropyl, cyclobutyl, cyclopentyl, cyclohexyl or cycloheptyl, cycloalkyl being unsubstituted or mono- to tri-substituted by lower alkyl, such as isopropyl, halo-lower alkyl, such as trifluoromethyl, hydroxy, lower alkoxy, carbamoyl-lower alkoxy, N-lower alkylcarbamoyl-lower alkoxy or N,N-di-lower alkylcarbamoyl-lower alkoxy, amino, mono- or di-lower alkylamino, halogen, such as fluorine, chlorine or bromine, carboxy, lower alkoxycarbonyl, phenyl-, naphthyl- or fluorenyl-lower alkoxycarbonyl, lower alkanoyl, lower alkylsulfonyl, for example methylsulfonyl, phosphono, hydroxy-lower alkoxyphosphoryl or di-lower alkoxyphosphoryl, carbamoyl, mono- or di-lower alkylaminocarbamoyl, sulfamoyl, mono- or di-lower alkylsulfamoyl, nitro and/or by cyano, such as cyclobutyl, cyclopentyl, cyclohexyl or cycloheptyl, especially cyclohexyl.

Aryl $R_3$, $R_4$ or $R_7$ is preferably one of the unsubstituted or substituted aryl radicals mentioned under aryl-lower alkanoyl $R_1$, $R_2$, $R_8$ or $R_9$ and is especially phenyl, naphthyl or fluorenyl that is unsubstituted or mono- to tri-substituted by lower alkyl, such as isopropyl, halo-lower alkyl, such as trifluoromethyl, hydroxy, lower alkoxy, carbamoyl-lower alkoxy, N-lower alkylcarbamoyl-lower alkoxy or N,N-di-lower alkylcarbamoyl-lower alkoxy, amino, mono- or di-lower alkylamino, halogen, such as fluorine, chlorine or bromine, carboxy, lower alkoxycarbonyl, phenyl-, naphthyl- or fluorenyl-lower alkoxycarbonyl, lower alkanoyl, lower alkylsulfonyl, for example methylsulfonyl, phosphono, hydroxy-lower alkoxyphosphoryl or di-lower alkoxyphosphoryl, carbamoyl, mono- or di-lower alkylaminocarbamoyl, sulfamoyl, mono- or di-lower alkylsulfamoyl, nitro and/or by cyano, such as phenyl, 4-methoxyphenyl, 4-fluorophenyl, 4-nitrophenyl, 4-cyanophenyl or 1- or 2-naphthyl.

Heterocyclyl $R_3$, $R_4$ or $R_7$ is preferably as defined under heterocyclyl $R_1$, $R_2$, $R_8$ or $R_9$, which is unsubstituted or substituted as defined there, and is selected especially from 2- or 3-pyrrolyl, 4- or 5-methylpyrrolyl or 4- or 5-phenylpyrrolyl, 2-thienyl, 2-furyl, 2-, 3- or 4,5-dimethyl-indol-2-yl, 1-benzylindol-2- or -3-yl, 4,5,6,7-tetrahydroindol-2-yl, cyclohepta[b]pyrrol-5-yl, 2-, 3- or 4-quinolyl or 4-hydroxyquinol-2-yl, 1-, 3- or 4-isoquinolyl, 1-oxo-1,2-dihydroisoquinol-3-yl, 2-quinoxalinyl, 3,1-benzofuran-2-yl, benz[e]indol-2-yl, β-carbolin-3-yl, 3-chromanyl, 3-thiochromanyl, 3-pyrrolidinyl, 3- or 4-hydroxypyrrolidin- 2-yl, such as 5-oxopyrrolidin-2-yl, 2-, 3- or 4-piperidinyl, 2- or 3-morpholinyl, 2- or 3-thiomorpholinyl, S,S-dioxothiomorpholin-2- or -3-yl, 2- or 3-indolinyl, 1,2,3,4-tetrahydroquinol-2-, -3- or -4-yl, 1,2, 3,4-tetrahydroisoquinol-1-, -2- or -3-yl, or 1-oxo-1,2,3,4-tetrahydroisoquinol-3-yl.

Unsubstituted or substituted alkenyl $R_3$, $R_4$ or $R_7$ is preferably as defined under alkenyl $R_1$, $R_2$, $R_8$ or $R_9$, especially lower alkenyl that is unsubstituted or substituted as defined there, for example lower alkenyl, such as vinyl, allyl or 2- or 3-butenyl, cycloalkyl-lower alkenyl wherein cycloalkyl is as defined in the case of cycloalkyl-lower alkanoyl $R_1$, $R_2$, $R_8$ or $R_9$ and is unsubstituted or mono- to tri-substituted by lower alkyl, such as isopropyl, halo-lower alkyl, such as trifluoromethyl, hydroxy, lower alkoxy, carbamoyl-lower alkoxy, N-lower alkylcarbamoyl-lower alkoxy or N,N-di-lower alkylcarbamoyl-lower alkoxy, amino, mono- or di-lower alkylamino, halogen, such as fluorine, chlorine or bromine, carboxy, lower alkoxycarbonyl, phenyl-, naphthyl- or fluorenyl-lower alkoxycarbonyl, lower alkanoyl, lower alkylsulfonyl, for example methylsulfonyl, phosphono, hydroxy-lower alkoxyphosphoryl or di-lower alkoxyphosphoryl, carbamoyl, mono- or di-lower alkylaminocarbamoyl, sulfamoyl, mono- or di-lower alkylsulfamoyl, nitro and/or by cyano and is bonded especially to the terminal carbon atom of lower alkenyl, such as cyclobutyl-, cyclopentyl-, cyclohexyl- or cycloheptyl-methyl-2-vinyl, -2- or -3-allyl or -2-, -3- or -4-but-2-enyl, aryl-lower alkenyl having an unsubstituted or substituted aryl radical defined under aryl $R_3$ or $R_4$ that is bonded, preferably terminally, to lower alkenyl, and having a lower alkenyl radical defined under lower alkenyl $R_1$, $R_2$, $R_8$ or $R_9$, such as styryl, 3-phenylallyl (cinnamyl), 2-(α-naphthyl)-vinyl or 2-(β-naphthyl)-vinyl, or unsubstituted or substituted heterocyclyl-lower alkenyl that contains, for example, an unsubstituted or substituted lower alkenyl radical mentioned under alkenyl $R_1$, $R_2$, $R_8$ or $R_9$, for example vinyl, allyl or 2- or 3-butenyl, that is substituted, preferably at the terminal carbon atom, by an unsubstituted or substituted heterocyclyl radical mentioned under heterocyclyl $R_1$, $R_2$, $R_8$ or $R_9$, for example in the form of pyrimidin-1-yl-, piperidino-, pyrazin-1-yl-, piperazin-1-yl-, pyridazin-1-yl-, morpholino-, thiomorpholino- or S,S-dioxothiomorpholino-lower alkenyl, such as in 2-morpholino-vinyl, 3-morpholinoallyl or 4-morpholino-2- or -3-butenyl, unsubstituted or lower alkyl- or phenyl-substituted pyrrolyl-lower alkenyl, such as 2- or 3-pyrrolyl-vinyl or -allyl, 4- or 5-methylpyrrolylvinyl or -allyl or 4- or 5-phenylpyrrolyl-vinyl or -allyl, thienyl-lower alkenyl, such as 2-thienyl-vinyl or -allyl, furyl-lower alkenyl, such as 2-furyl-vinyl or -allyl, pyridyl-lower alkenyl, such as 2-, 3- or 4-pyridyl-vinyl or -allyl, indolyl-lower alkenyl that is unsubstituted or substituted by lower alkyl, for example methyl, phenyl-lower alkyl, for example benzyl, lower alkoxy, for example methoxy, phenyl-lower alkoxy, for example benzyloxy, or by halogen, for example chlorine, such as 2-, 3- or 5-indolyl-vinyl or -allyl, 1-methyl-, 2-methyl-, 5-methoxy-, 5-benzyloxy-, 5-chloro- or 4,5-dimethyl-indol-2-yl-, 1-benzylindol-2-yl- or -3-yl-vinyl or -allyl, 4,5,6,7-tetrahydroindol-2-yl-methyl, -ethyl or -n-propyl, cyclohepta[b]pyrrol-5-yl-vinyl or -allyl, unsubstituted or hydroxy-substituted quinolyl-lower alkenyl, for example 2-, 3- or 4-quinolyl- or 4-hydroxyquinol-2-yl-vinyl or -allyl, unsubstituted or hydroxy-substituted isoquinolyl-lower alkenyl, such as 1-, 3- or 4-isoquinolyl- or 1-oxo-1,2-dihydroisoquinol-3-yl-vinyl or -allyl, 2-quinoxalinyl-vinyl or -allyl, 3,1-benzofuran-2-yl-vinyl or -allyl, benz[e]indol2-yl-vinyl or -allyl, β-carbolin-3-yl-vinyl or -allyl, 3-chromanyl-vinyl or -allyl, 3-thiochromanyl-vinyl or -allyl, 3-pyrrolidinyl-vinyl or -allyl, hydroxypyrrolidinyl-lower alkenyl, such as 3- or 4-hydroxypyrrolidin-2-yl-vinyl or -allyl, oxopyrrolidinyl-lower alkenyl, such as 5-oxopyrrolidin-2-yl-vinyl or -allyl, piperidinyl-lower alkenyl, such as 2-, 3- or 4-piperidinyl-vinyl or -allyl, morpholinyl-lower alkenyl, such as 2- or 3-morpholinyl-vinyl or -allyl, thiomorpholinyl-lower alkenyl, such as 2- or 3-thiomorpholinyl-vinyl or -allyl, S,S-dioxothiomorpholinyl-lower alkenyl, such as S,S-dioxothiomorpholin-2- or -3-yl-vinyl or -allyl, indolinyl-lower alkenyl, such as 2- or 3-indolinyl-vinyl or -allyl, 1,2,3,4-tetrahydroquinolyl-lower alkenyl, such as 1,2,3,4-tetrahydroquinol-2-, -3- or -4-yl-vinyl or -allyl, 1,2,3,4-tetrahydroisoquinolyl-lower alkenyl, such as 1,2,3,4-tetrahydroisoquinol-1-, -2- or -3-yl-vinyl or -allyl, or 1-oxo-1,2,3,4-tetrahydroisoquinol-3-yl-vinyl or -allyl.

Unsubstituted or substituted alkylene formed by $R_3$ and $R_4$ together contains especially an alkylene radical having up to 20 carbon atoms, it also being possible for the mentioned radicals to contain one or more double bonds, preferably lower alkylene, for example ethylene, trimethylene, tetramethylene, pentamethylene, hexamethylene or heptamethylene, that is unsubstituted or substituted, especially by unsubstituted or substituted aryl, as defined under aryl-lower alkanoyl $R_1$, $R_2$, $R_8$ or $R_9$, preferably by phenyl, indenyl, indanyl, naphthyl, anthryl, phenanthryl, acenaphthyl or fluorenyl, which are unsubstituted or mono- to tri-substituted by radicals such as lower alkyl, for example methyl, ethyl or propyl, halo-lower alkyl, for example trifluoromethyl, phenyl, 1- or 2-naphthyl, hydroxy, lower alkoxy, for example methoxy, carbamoyl-lower alkoxy, N-lower alkylcarbamoyl-lower alkoxy or N,N-di-lower alkylcarbamoyl-lower alkoxy, amino, mono- or di-lower alkylamino, lower alkanoylamino, for example pivaloylamino, halogen, for example fluorine, chlorine or bromine, carboxy, lower alkoxycarbonyl, phenyl-, naphthyl- or fluorenyl-lower alkoxycarbonyl, lower alkanoyl, sulfo, lower alkylsulfonyl, for example methylsulfonyl, phosphono, hydroxy-lower alkoxyphosphoryl or di-lower alkoxyphosphoryl, carbamoyl, mono- or di-lower alkylcarbamoyl, sulfamoyl, mono- or di-lower alkylaminosulfonyl, nitro and/or cyano, and/or is substituted in the same manner as lower alkanoyl in aryl-lower alkanoyl $R_1$, $R_2$, $R_8$ or $R_9$, especially by lower alkyl, for example methyl, hydroxy, lower alkoxy, for example methoxy or ethoxy, lower alkanoyloxy, for example acetoxy or propionyloxy, benzoyloxy, phenylacetoxy or 1- or 2-naphthoyloxy, lower alkoxycarbonyloxy, for example isopropoxycarbonyloxy or tert-butoxycarbonyloxy, phenyl-lower alkoxycarbonyloxy, for example benzyloxycarbonyloxy, 9-fluorenylmethoxycarbonyloxy, sulfonyloxy, lower alkylsulfonyloxy, for example methyl- or ethyl-sulfonyloxy, phenylsulfonyloxy, 2- or 4-toluenesulfonyloxy, amino, mono- or di-lower alkylamino, for example mono- or di-methyl-amino or -ethyl-amino, lower alkanoylamino, for example acetylamino or pivaloylamino, carboxy, lower alkoxycarbonyl, for example isopropoxy- or tert-butoxy-carbonyl, benzyloxycarbonyl, 9-fluorenylmethoxycarbonyl, lower alkanoyl, for example acetyl or propionyl, lower alkylsulfonyl, such as methylsulfonyl or tert-butylsulfonyl, phosphono, carbamoyl, mono- or di-lower alkylcarbamoyl, for example N-methylcarbamoyl or N,N-dimethylcarbamoyl, piperidino, pyrazin-1-yl, pyrimidin-1-yl, pyridazin-1-yl, morpholino, thiomorpholino or S,S-dioxothiomorpholino, sulfamoyl, oxo and/or by cyano, such as ethylene, ethyl-ethylene, trimethylene, propylene or tetramethylene.

Unsubstituted or substituted alkylidene formed by $R_3$ and $R_4$ together contains up to 20 carbon atoms and no double bonds or one or more double bonds in addition to the linking double bond, and is preferably lower alkylidene, for example methylene, ethylidene, propylidene, butylidene or pentylidene, that is unsubstituted or substituted especially by cycloalkyl, such as mentioned under cycloalkyl-lower alkanoyl $R_1$, $R_2$, $R_8$ or $R_9$, for example cyclopropyl, cyclobutyl, cyclopentyl or cyclohexyl, cycloalkenyl, such as mentioned under cycloalkenyl-lower alkanoyl $R_1$, $R_2$, $R_8$ or $R_9$, for example cyclohexen-1-yl or 1,4-cyclohexadienyl, unsubstituted or substituted aryl, such as defined under aryl-lower alkanoyl $R_1$, $R_2$, $R_8$ or $R_9$, preferably by phenyl, indenyl, indanyl, naphthyl, anthryl, phenanthryl, acenaphthyl or fluorenyl, which are unsubstituted or mono- to tri-substituted by radicals such as lower alkyl, for example methyl, ethyl or propyl, halo-lower alkyl, for example trifluoromethyl, phenyl, 1- or 2-naphthyl, hydroxy, lower alkoxy, for example methoxy, carbamoyl-lower alkoxy, N-lower alkylcarbamoyl-lower alkoxy or N,N-di-lower alkylcarbamoyl-lower alkoxy, amino, mono- or di-lower alkylamino, lower alkanoylamino, for example pivaloylamino, halogen, for example fluorine, chlorine or bromine, carboxy, lower alkoxycarbonyl, phenyl-, naphthyl- or fluorenyl-lower alkoxycarbonyl, lower alkanoyl, sulfo, lower alkylsulfonyl, for example methylsulfonyl, phosphono, hydroxy-lower alkoxyphosphoryl or di-lower alkoxyphosphoryl, carbamoyl, mono- or di-lower alkylcarbamoyl, sulfamoyl, mono- or di-lower alkylaminosulfonyl, nitro and/or cyano, and/or is substituted in the same manner as lower alkanoyl in aryl-lower alkanoyl $R_1$, $R_2$, $R_8$ or $R_9$, especially by lower alkyl, for example methyl, hydroxy, lower alkoxy, for example methoxy or ethoxy, lower alkanoyloxy, for example acetoxy or propionyloxy, benzoyloxy, phenylacetoxy or 1- or 2-naphthoyloxy, lower alkoxycarbonyloxy, for example isopropoxycarbonyloxy or tert-butoxycarbonyloxy, phenyl-lower alkoxycarbonyloxy, for example benzyloxycarbonyloxy, 9-fluorenylmethoxycarbonyloxy, sulfonyloxy, lower alkylsulfonyloxy, for example methyl- or ethyl-sulfonyloxy, phenylsulfonyloxy, 2- or 4-toluenesulfonyloxy, amino, mono- or di-lower alkylamino, for example mono- or di-methyl-amino or -ethyl-amino, lower alkanoylamino, for example acetylamino or pivaloylamino, carboxy, lower alkoxycarbonyl, for example isopropoxy- or tert-butoxy-carbonyl, benzyloxycarbonyl, 9-fluorenylmethoxycarbonyl, lower alkanoyl, for example acetyl or propionyl, lower alkylsulfonyl, such as methylsulfonyl or tert-butylsulfonyl, phosphono, carbamoyl, mono- or di-lower alkylcarbamoyl, for example N-methylcarbamoyl or N,N-dimethylcarbamoyl, piperidino, pyrazin-1-yl, pyrimidin-1-yl, pyridazin-1-yl, morpholino, thiomorpholino or S,S-dioxothiomorpholino, sulfamoyl, oxo and/or by cyano, such as ethylidene, propylidene, butylidene, benzylidene or cinnamylidene.

Unsubstituted or substituted benzo-fused alkylene formed by $R_3$ and $R_4$ together contains up to 20 carbon atoms and is preferably lower alkylene, for example ethylene, trimethylene, tetramethylene, pentamethylene, hexamethylene or heptamethylene, onto which a benzene ring has been fused, and is unsubstituted or substituted especially by unsubstituted or substituted aryl, as defined under aryl-lower alkanoyl $R_1$, $R_2$, $R_8$ or $R_9$, preferably by phenyl, indenyl, indanyl, naphthyl, anthryl, phenanthryl, acenaphthyl or fluorenyl, which are unsubstituted or mono- to tri-substituted by radicals such as lower alkyl, for example methyl, ethyl or propyl, halo-lower alkyl, for example trifluoromethyl, phenyl, 1- or 2-naphthyl, hydroxy, lower alkoxy, for example methoxy, carbamoyl-lower alkoxy, N-lower alkylcarbamoyl-lower alkoxy or N,N-di-lower alkylcarbamoyl-lower alkoxy, amino, mono- or di-lower alkylamino, lower alkanoylamino, for example pivaloylamino, halogen, for example fluorine, chlorine or bromine, carboxy, lower alkoxycarbonyl, phenyl-, naphthyl- or fluorenyl-lower alkoxycarbonyl, lower alkanoyl, sulfo, lower alkylsulfonyl, for example methylsulfonyl, phosphono, hydroxy-lower alkoxyphosphoryl or di-lower alkoxyphosphoryl, carbamoyl, mono- or di-lower alkylcarbamoyl, sulfamoyl, mono- or di-lower alkylaminosulfonyl, nitro and/or cyano, and may also be substituted by lower alkyl, for example methyl, hydroxy, lower alkoxy, for example methoxy or ethoxy, lower alkanoyloxy, for example acetoxy or propionyloxy, benzoyloxy, phenylacetoxy or 1- or 2-naphthoyloxy, lower alkoxycarbonyloxy, for example isopropoxycarbonyloxy or tert-butoxycarbonyloxy, phenyl-lower alkoxycarbonyloxy, for example benzyloxycarbonyloxy, 9-fluorenylmethoxycarbonyloxy, sulfonyloxy, lower alkylsulfonyloxy, for example methyl- or ethyl-sulfonyloxy, phenylsulfonyloxy, 2- or 4-toluenesulfonyloxy, amino, mono- or di-lower alkylamino, for example mono- or di-methyl-amino or -ethyl-amino, lower alkanoylamino, for example acetylamino or pivaloylamino, carboxy, lower alkoxycarbonyl, for example isopropoxy- or tert-butoxycarbonyl, benzyloxycarbonyl, 9-fluorenylmethoxycarbonyl, lower alkanoyl, for example acetyl or propionyl, lower alkylsulfonyl, such as methylsulfonyl or tert-butylsulfonyl, phosphono, carbamoyl, mono- or di-lower alkylcarbamoyl, for example N-methylcarbamoyl or N,N-dimethylcarbamoyl, piperidino, pyrazin-1-yl, pyrimidin-1-yl, pyridazin-1-yl, morpholino, thiomorpholino or S,S-dioxothiomorpholino, sulfamoyl, oxo and/or by cyano, such as ortho-phenylene.

When, in the compounds of formula I substituted by the mentioned radicals, nitrogen atoms having free hydrogen and/or hydroxy groups are vicinal with respect to double or triple bonds (as in the case of unsubstituted or substituted alkenyl or alkynyl $R_1$, $R_2$, $R_8$ or $R_9$), the corresponding tautomeric imino and oxo compounds are always also included.

Salts of compounds of formula I are especially acid addition salts, salts with bases or, where several salt-forming groups are present, can also be mixed salts or internal salts.

Salts are especially the pharmaceutically acceptable, non-toxic salts of compounds of formula I.

Such salts are formed, for example, from compounds of formula I having an acid group, for example a carboxy group, a sulfo group, or a phosphoryl group substituted by one or two hydroxy groups, and are, for example, salts thereof with suitable bases, such as non-toxic metal salts derived from metals of groups Ia, Ib, IIa and IIb of the Periodic Table of the Elements, especially suitable alkali metal salts, for example lithium, sodium or potassium salts, or alkaline earth metal salts, for example magnesium or calcium salts, also zinc salts or ammonium salts, as well as salts formed with organic amines, such as unsubstituted or hydroxy-substituted mono-, di- or tri-alkylamines, especially mono-, di- or tri-lower alkylamines, or with quaternary ammonium compounds, for example with N-methyl-N-ethylamine, diethylamine, triethylamine, mono-, bis- or tris-(2-hydroxy-lower alkyl)amines, such as mono-, bis- or tris-(2-hydroxyethyl)amine, 2-hydroxy-tert-butylamine or tris (hydroxymethyl)methylamine, N,N-di-lower alkyl-N-(hydroxy-lower alkyl)amines, such as N,N-dimethyl-N-(2-hydroxyethyl)-amine or tri-(2-hydroxyethyl)-amine, N-methyl-D-glucamine, or quaternary ammonium salts, such as tetrabutylammonium salts. The compounds of formula I having a basic group, for example an amino group, can form acid addition salts, for example with inorganic acids, for example hydrohalic acids, such as hydrochloric acid, sulfuric acid or phosphoric acid, or with organic carboxylic, sulfonic, sulfo or phospho acids or N-substituted sulfamic acids, for example acetic acid, propionic acid, glycolic acid, succinic acid, maleic acid, hydroxymaleic acid, methyl maleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, as well as with amino acids, for example the α-amino acids mentioned hereinbefore, especially glutamic acid and aspartic acid, and with methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, 2- or 3-phosphoglycerate, glucose-6-phosphate, N-cyclohexylsulfamic acid (forming cyclamates) or with other acidic organic compounds, such as ascorbic acid. Compounds of formula I having acid and basic groups can also form internal salts.

For isolation or purification purposes, it is also possible to use pharmaceutically unacceptable salts.

The compounds of the present invention have an inhibiting effect on viral aspartate proteases, especially a gag-protease-inhibiting effect. In the tests described below, at concentrations of $10^{-6}$ to $10^{-9}$ mol/l they inhibit especially the action of the gag-protease of HIV-1 and HIV-2 and are therefore suitable as agents against diseases caused by those viruses or by related retroviruses, for example against AIDS.

The ability of the compounds of formula I to inhibit the proteolytic activity of, for example, HIV-1 protease can be demonstrated, for example, by the method described by J. Hansen et al., The EMBO Journal 7, 1785–1791 (1988). In that method, the inhibition of the action of the gag-protease is measured on a substrate that is a fusion protein of the gag-precursor protein and MS-2, expressed in E. coli. The substrate and its cleavage products are separated by polyacrylamide gel electrophoresis and made visible by immunoblotting using monoclonal antibodies to MS-2.

In a test that is even simpler to carry out and that gives precise quantitative results, there is used as substrate for the gag-protease a synthetic peptide that corresponds to the cleavage site of the gag-precursor protein. That substrate and its cleavage products can be analysed by high-pressure liquid chromatography (HPLC).

For example, there is used as substrate for a recombinant HIV-1 protease (preparation in accordance with Billich, S. et al., J. Biol. Chem. 263(34), 17905–17908 (1990)) a synthetic chromophoric peptide (for example HKARVL[NO$_2$]FEANleS (Bachem, Switzerland) or an icosapeptide such as RRSNQVSQNYPIVQNIQGRR (prepared by peptide synthesis using known methods) that corresponds to one of the cleavage sites of the gag-precursor protein. That substrate and its cleavage products can be analysed by high-pressure liquid chromatography (HPLC).

For that purpose an inhibitor of formula I to be tested is dissolved in dimethyl sulfoxide; the enzyme assay is carried out by adding suitable dilutions of the inhibitor in 20 mM β-morpholinoethanesulfonic acid (MES) buffer, pH 6.0, to the assay mix of 67.2 μM of the above-mentioned chromophoric peptide in 0.3M sodium acetate, 0.1M NaCl, pH 7.4, or 122 µM of the above-mentioned icosapeptide in 20 mM MES buffer, pH 6.0. The size of the batches is 100 µl. The reaction is started by the addition of, in the first case, 2 µl and, in the second case, 10 µl of HIV-1 protease and is stopped in the first case after 15 min by the addition of 100 µl of 0.3M HClO$_4$ and in the second case after incubation for one hour at 37° C. by the addition of 10 µl of 0.3M HClO$_4$. After centrifugation of the sample for 5 min at 10,000×g in 100 µl (batch with chromophoric peptide) or 20 µl (icosapeptide batch) of the resulting supernatant and application to a 125×4.6 mm Nucleosil® C18-5µ HPLC column (Macherey & Nagel, Düren) and elution, the reaction products are quantified by reference to the peak height of the cleavage product at 280 (batch with chromophoric peptide) or at 215 nm (batch with icosapeptide), gradient: 100% eluant 1→50% eluant 1/50% eluant 2 (eluant 1: 75% acetonitrile, 90% H$_2$O, 0.1% trifluoroacetic acid (TFA); eluant 2: 75% acetonitrile, 25% H$_2$O, 0.08% TFA) in the course of 15 min; throughput rate 1 ml/min.

In this test, there are preferably obtained IC$_{50}$ values (IC$_{50}$=the concentration that reduces the activity of HIV-1 protease by 50% compared with a control without an inhibitor) of approximately from $10^{-6}$ to $10^{-9}$M, especially from approximately $10^{-7}$ to approximately $10^{-8}$M, for compounds of formula I.

In a further test it can be shown that the compounds of the present invention protect cells that normally become infected by HIV from such infection or at least slow down such infection. In that test the human T-cell leukaemia cell line MT-2 (Science 229, 563 (1985)), which is extremely sensitive to the cytopathogenic effect of HIV, is incubated with HIV alone or with HIV in the presence of the compounds of the invention and after a few days the viability of the cells thus treated is assessed.

For that purpose the MT-2 cells are kept at 37° C. in humid air with 5% CO$_2$ in RPMI 1640 medium (Gibco, Switzerland; RPMI 1640 comprises an amino acid mixture without L-Gln) supplemented with 10% heat-inactivated foetal calf serum, L-glutamine, hepes (2-[4-(2-hydroxyethyl)-1-piperazino]-ethanesulfonic acid) and standard antibiotics. 50 µl of the particular test compound in culture medium and 100 µl of HIV-1 in culture medium (800 TCID50/ml) (TCID50=Tissue Culture Infectious Dose 50=dose that infects 50% of the MT-2 cells) are added to 4×10$^3$ exponentially growing MT-2 cells in 50 µl of culture medium per well on 96-well microtitre plates. Parallel batches on a further microtitre plate with cells and test compound receive 100 µl of culture medium without virus. After incubation for 4 days, the reverse transcriptase (RT) activity is determined in 10 µl of cell supernatant. The RT activity is determined in 50 mM of tris (α,α,α-tris (hydroxymethyl)methylamine, ultra pure, Merck, Federal Republic of Germany) pH 7.8; 75 mM of KCl, 2 mM of dithiothreitol, 5 mM of MgCl$_2$; 0.05% Nonidet P-40 (detergent; Sigma, Switzerland); 50 µg/ml of polyadenylic acid (Pharmacia, Sweden); 1.6 µg/ml of dT(12–18) (Sigma, Switzerland). The mixture is filtered through a 0.45µ Acrodisc filter (Gellman Science Inc, Ann Arbor) and stored at −20° C. 0.1% (v/v) [alpha-$^{32}$P]dTTP is added to aliquots of that solution in order to achieve a final radioactive activity of 10 µCi/ml. 10 µl of the culture supernatant are transferred to a new 96-well microtitre plate and 30 µl of the mentioned RT cocktail are added thereto. After mixing, the plate is incubated for from 1.5 to 3 hours at 37° C. 5 µl of that reaction mixture are transferred to Whatman DE81 paper (Whatman). The dried filters are washed three times for 5 minutes with 300 mM of NaCl/25 mM of trisodium citrate and once with 95% ethanol and again air-dried. Evaluation is effected in a Matrix Packard 96-well counter (Packard). The ED90 values are calculated and defined as the lowest concentration of the particular test compound that reduces the RT activity by 90% in comparison with cell batches not treated with the test compound. The RT activity is a measure of the reproduction of HIV-1.

In that test, the compounds of the invention exhibit an ED90 of approximately from $10^{-5}$ to $10^{-8}$M, preferably approximately from $5\times10^{-7}$ to $5\times10^{-8}$M.

In the groups of compounds of formula I mentioned below, it may be advantageous, for example in order to replace rather general definitions with more specific definitions, to use definitions of radicals from the above-mentioned general definitions or to insert or omit definitions from the other groups.

Preference is given to a compound of formula I according to claim 1 wherein

R$_1$ and R$_9$ are each independently of the other hydrogen; lower alkanoyl, such as formyl, acetyl, propionyl, butyryl or pivaloyl, especially acetyl; aryl-lower alkanoyl wherein aryl is preferably as defined above under the general definitions of aryl-lower alkanoyl and is unsubstituted or substituted as defined there, i.e. aryl has from 6 to 14 carbon atoms, as in phenyl, indenyl, indanyl, naphthyl, anthryl, phenanthryl, acenaphthyl or fluorenyl, and may be unsubstituted or especially mono- to tri-substituted by lower alkyl, for example methyl, ethyl or propyl, halo-lower alkyl, for example trifluoromethyl, phenyl, 1- or 2-naphthyl, hydroxy, lower alkoxy, for example methoxy, carbamoyl-lower alkoxy, N-lower alkylcarbamoyl-lower alkoxy or N,N-di-lower alkylcarbamoyl-lower alkoxy, amino, mono- or di-lower alkylamino, lower alkanoylamino, for example pivaloylamino, halogen, for example fluorine, chlorine or bromine, carboxy, lower alkoxycarbonyl, such as tert-butoxycarbonyl, phenyl-, naphthyl- or fluorenyl-lower alkoxycarbonyl, such as benzyloxycarbonyl, lower alkanoyl, sulfo, lower alkylsulfonyl, for example methylsulfonyl, phosphono, hydroxy-lower alkoxyphosphoryl or di-lower alkoxyphosphoryl, carbamoyl, mono- or di-lower alkylcarbamoyl, sulfamoyl, mono- or di-lower alkylaminosulfonyl, nitro and/or by cyano, wherein phenyl may be present up to three times, for example in diphenyl-, dibenzyl- or triphenyl-lower alkanoyl, such as diphenyl-, dibenzyl- or triphenyl-acetyl, and wherein lower alkanoyl is unsubstituted or substituted by carbamoyl or by carbamoyl substituted at the nitrogen atom by one or two radicals selected from lower alkyl, carboxy-lower alkyl, lower alkoxycarbonyl-lower alkyl, di-lower alkylamino-lower alkyl, aminocarboxy-lower alkyl, hydroxy-lower alkyl and di-lower alkoxy-lower alkyl, preferably as described under aryl-lower alkanoyl above in the general definitions, for example 4-chloro-, 4-methoxy- or 4-nitro-benzoyl, naphthylcarbonyl, such as α- or β-naphthylcarbonyl, or 1,8-naphthalene-dicarbonyl bonded to the amino group via both carbonyl groups, indenylcarbonyl, such as 1-, 2- or 3-indenylcarbonyl, indanylcarbonyl, such as 1- or 2-indanylcarbonyl, phenanthrenylcarbonyl, such as 9-phenanthrenylcarbonyl, phenyl-lower alkanoyl, such as phenylacetyl or 3-phenylpropionyl, α-naphthylacetyl, β-naphthylacetyl, lower alkylphenylacetyl, such as 4-methylphenylacetyl, lower alkoxyphenylacetyl, such as 4-methoxyphenylacetyl, 3-phenylpropionyl, 3-(p-hydroxyphenyl)propionyl, diphenylacetyl, di(4-methoxyphenyl)acetyl, triphenylacetyl, 2,2-dibenzylacetyl, 3-α- or 3-β-naphthylpropionyl, phenyl-lower alkanoyl wherein the lower alkanoyl radical is substituted by carbamoyl, such as 2(R,S)-carbamoyl-3-phenylpropionyl, 3-phenyl- or 3-α-naphthyl-2-carbamoylpropionyl, 3-phenyl- or 3-α-naphthyl-2-tert-butylcarbamoylpropionyl, 3-phenyl- or 3-α-naphthyl-2-(2-dimethylaminoethyl)carbamoylpropionyl, 3-α-naphthyl-2-(carboxy- or tert-butoxycarbonyl)methylcarbamoylpropionyl, 3-phenyl- or 3-α-naphthyl-2-(3-hydroxy-2-propyl)carbamoylpropionyl, 3-phenyl- or 3-α-naphthyl-2-(2,2-dimethoxyethyl)-carbamoylpropionyl, 3-phenyl- or 3-α-naphthyl-2-(5-amino-5-carboxypentyl)-carbamoylpropionyl, especially phenyl-lower alkanoyl, such as phenylacetyl, or phenyl-lower alkanoyl wherein the lower alkanoyl radical is substituted by carbamoyl, such as 2(R,S)-carbamoyl-3-phenylpropionyl; heterocyclyl-lower alkanoyl that is preferably as defined above for heteroaryl-lower alkanoyl $R_1$, $R_2$, $R_8$ and $R_9$, especially heterocyclyl-lower alkanoyl wherein lower alkanoyl is unsubstituted and wherein heterocyclyl is preferably a single or a double ring system having from 3 to 10 ring atoms, is bonded via a carbon atom or, especially, via a nitrogen atom, contains up to three further hetero atoms selected from oxygen, nitrogen, sulfur, selenium, and sulfur linked to 1 or 2 oxygen atoms, and may be unsaturated or partially or fully saturated, for example thienyl-, furyl-, pyranyl-, pyrrolyl-, imidazolyl-, pyrazolyl-, oxazolyl-, isoxazolyl-, thiazolyl-, furazanyl-, tetrazolyl-, pyridyl-, pyrazinyl-, pyrimidinyl-, pyridazinyl-, azepinyl-, indolyl-, benzimidazolyl-, 1H-indazolyl-, quinolyl-, isoquinolyl-, quinoxalinyl-, quinazolinyl-, cinnolyl-, purinyl-, pteridinyl-, naphthyridinyl-, 4H-quinolizinyl-, 3,1-benzofuranyl-, 4,1-benzoxazinyl-, 4,1-benzothiazinyl-, cyclohexa[b]pyrrolyl-, cyclohepta[b]pyrrolyl-, cyclohexa[d]pyrazolyl-, cyclohexa[b]pyridyl-, cyclohexa[b]pyrazinyl-, cyclohexa[b]pyrimidinyl-, cyclohexa[b]-1,4-oxazinyl-, cyclohexa[b]-1,4-thiazinyl-, pyrrolidinyl-, pyrrolinyl-, imidazolidyl-, 2-imidazolinyl-, 2,3-dihydropyridyl-, piperidyl-, piperazinyl-, 2,3,5,6-tetrahydropyrazinyl-, morpholinyl-, thiomorpholinyl-, S,S-dioxo-thiomorpholinyl-, indolinyl-, isoindolinyl-, 4,5,6,7-tetrahydroindolyl-, 1,2,3,4-tetrahydroquinolyl-, 1,2,3,4-tetrahydroisoquinolyl-, chromanyl-, thiochromanyl-, 1,2,3,4-tetrahydro-3,1-benzodiazinyl-, 3,4-dihydro-3H-4,1-benzoxazinyl- or 3,4-dihydro-3H-4,1-benzothiazinyl-lower alkanoyl, the mentioned heterocyclyl radicals being unsubstituted or substituted by lower alkyl, for example methyl, phenyl, 1- or 2-naphthyl, phenyl-lower alkyl, for example benzyl, hydroxy-lower alkyl, for example hydroxymethyl or 2-hydroxyethyl, lower alkoxy-lower alkyl, for example methoxymethyl or 2-methoxyethyl, phenoxy- or naphthyloxy-lower alkyl, for example 2-phenoxyethyl, 1- or 2-naphthyloxymethyl, phenyl-lower alkoxy- or naphthyl-lower alkoxy-lower alkyl, for example benzyloxy-lower alkyl, lower alkanoyloxy-lower alkyl, for example acetoxymethyl, phenyl- or naphthyl-lower alkanoyloxy-lower alkyl, for example benzoyloxy-, phenylacetoxy- or 1- or 2-naphthoyloxy-methyl, -2-ethyl or -2-(2,2-dimethylethyl), lower alkoxycarbonyloxy-lower alkyl, for example tert-butoxycarbonyloxy-lower alkyl, phenyl-, naphthyl- or fluorenyl-lower alkoxycarbonyloxy-lower alkyl, for example 2-benzyloxycarbonyloxyethyl or 9-fluorenylmethoxycarbonyloxyethyl, amino-lower alkyl, for example aminomethyl, 2-aminoethyl or 2-aminopropyl, carboxy-lower alkyl, for example carboxymethyl or 2-carboxyethyl, hydroxy, lower alkoxy, for example methoxy or ethoxy, phenyl- or naphthyl-lower alkoxy, for example benzyloxy or 1- or 2-naphthyloxy, amino, lower alkylamino, for example methyl-, ethyl- or tert-butyl-amino, di-lower alkylamino, for example dimethyl- or diethyl-amino, carboxy, lower alkoxycarbonyl, for example methoxy-, isopropoxy-, sec-butoxy- or tert-butoxy-carbonyl, phenyl- or naphthyl-lower alkoxycarbonyl, for example benzyloxycarbonyl, halogen, for example fluorine, chlorine, bromine or iodine, especially chlorine or bromine, lower alkanoyl, for example acetyl or pivaloyl, lower alkylsulfonyl, for example methyl- or ethyl-sulfonyl, phosphono, hydroxy-lower alkoxyphosphoryl or dialkoxyphosphoryl, for example dimethoxy- or diethoxy-phosphoryl, carbamoyl, mono- or di-lower alkylcarbamoyl, for example N-methylcarbamoyl, N-n-butylcarbamoyl or N,N-dimethylcarbamoyl, hydroxy- or carboxy-lower alkylcarbamoyl, for example hydroxy- or carboxy-methylcarbamoyl or hydroxy- or carboxyethylcarbamoyl, sulfamoyl, nitro, oxo and/or by cyano, with heterocyclyl-lower alkanoyl being selected especially from pyrrolylcarbonyl that is unsubstituted or substituted by lower alkyl or by phenyl, for example 2- or 3-pyrrolylcarbonyl, 4- or 5-methylpyrrolylcarbonyl or 4- or 5-phenylpyrrolyl-2-carbonyl, thienylcarbonyl, such as 2-thienylcarbonyl, furylcarbonyl, such as 2-furylcarbonyl, pyridylcarbonyl, such as 2-, 3- or 4-pyridylcarbonyl, pyrimidin-1-ylcarbonyl, indolylcarbonyl that is unsubstituted or substituted by lower alkyl, such as methyl, phenyl-lower alkyl, such as benzyl, lower alkoxy, such as methoxy, phenyl-lower alkoxy, such as benzyloxy, or by halogen, such as chlorine, such as 2-, 3- or 5-indolylcarbonyl, 1-methyl-, 5-methyl-, 5-methoxy-, 5-benzyloxy-, 5-chloro- or 4,5-dimethyl-indolyl-2-carbonyl, 1-benzyl-indolyl-2- or -3-carbonyl, 4,5,6,7-tetrahydroindolyl-2-carbonyl, unsubstituted or hydroxy-substituted quinolyl-lower alkanoyl, for example quinolylcarbonyl, such as 2-, 3- or 4-quinolylcarbonyl or 4-hydroxyquinolyl-2-carbonyl, unsubstituted or hydroxy-substituted isoquinolylcarbonyl, such as 1-, 3- or 4-isoquinolylcarbonyl or 1-oxo-1,2-dihydroisoquinolyl- 3-carbonyl, 2-quinoxalinylcarbonyl, 2-(3,1-benzofuranyl)carbonyl, cyclohepta[b]pyrrolyl-5-carbonyl, 3-chromanylcarbonyl, 3-thiochromanylcarbonyl, pyrrolidinyl-3-carbonyl, hydroxypyrrolidinylcarbonyl, such as 3- or 4-hydroxypyrrolidinyl-2-carbonyl, oxopyrrolidinylcarbonyl, such as 5-oxopyrrolidinyl-2-carbonyl, piperidylcarbonyl, such as piperidinocarbonyl or 2-, 3- or 4-piperidylcarbonyl, pyrazinylcarbonyl, such as pyrazin-1-ylcarbonyl, piperazinylcarbonyl, such as piperazin-1-ylcarbonyl, morpholinyl-lower alkanoyl, for example morpholinylcarbonyl, such as morpholinocarbonyl, thiomorpholinyl-lower alkanoyl, for example thiomorpholinylcarbonyl, such as thiomorpholinocarbonyl, S,S-dioxothiomorpholinylcarbonyl, such as S,S- dioxothiomorpholinocarbonyl, indolinylcarbonyl, such as 2- or 3-indolinylcarbonyl, 1,2,3,4-tetrahydroquinolylcarbonyl, such as 1,2,3,4-tetrahydroquinolyl-2-, -3- or -4-carbonyl, 1,2,3,4-tetrahydroisoquinolylcarbonyl, such as 1,2,3,4-tetrahydroisoquinolyl-1-, -3- or -4-carbonyl or 1-oxo-1,2,3,4-tetrahydroisoquinolyl-3-carbonyl, tetrazolyl-lower alkanoyl, such as 3-(tetrazol-1-yl)propionyl, and pyridyl-lower alkanoyl, for example pyridylacetyl, such as 2-, 3- or 4-pyridylacetyl, heterocyclyl-lower alkanoyl being selected more especially from morpholino-lower alkanoyl, such as morpholinocarbonyl, thiomorpholino-lower alkanoyl, such as thiomorpholinocarbonyl, pyridyl-lower alkanoyl, such as 2-, 3-, or 4-pyridylacetyl, quinolinyl-lower alkanoyl, such as quinoline-2-carbonyl, and tetrazolyl-lower alkanoyl, such as 3-tetrazol-1-ylpropionyl; amino-lower alkanoyl substituted at the amino nitrogen atom by heterocyclyl-lower alkanoyl wherein heterocyclyl-lower alkanoyl is as defined above for heterocyclyl-lower alkanoyl $R_1$, $R_2$, $R_8$ or $R_9$, preferably as defined for heterocyclyl-lower alkanoyl $R_1$ and $R_9$, especially amino-lower alkanoyl substituted at the amino nitrogen atom by N-morpholino- or by N-thiomorpholino-carbonyl, more especially N-morpholino- or N-thiomorpholino-carbonylamino-lower alkanoyl, such as N-morpholino- or N-thiomorpholino-carbonylamino-acetyl; halo-lower alkanoyl containing up to three halogen atoms, especially α-haloacetyl, such as α-fluoro-, α-chloro-, α-bromo-, α-iodo-, α,α,α-trifluoro- or α,α,α-trichloro-acetyl, or halopropionyl, such as β-chloro- or β-bromo-propionyl, especially trifluoroacetyl; (N-heterocyclyl-lower alkylcarbamoyl)lower alkanoyl wherein heterocyclyl is preferably selected from pyrrolyl, furyl, thienyl, imidazolyl, pyrazolyl, oxazolyl, thiazolyl, pyridyl, pyrazinyl, pyrimidinyl, indolyl, quinolyl, isoquinolyl, quinoxalinyl, β-carbolinyl and a benzo-fused, cyclopenta-, cyclohexa- or cyclohepta-fused derivative of those radicals, which may also be fully or partially saturated, from morpholinyl and from thiomorpholinyl, especially 2-(N-morpholino-lower alkylcarbamoyl)-lower alkanoyl, such as 2(R,S)-(N-(2-morpholinoethyl)-carbamoyl)-3-methylbutyryl, or 2-(N-(pyridyl-lower alkyl)-carbamoyl)-lower alkanoyl, such as 2(R,S)-(N-(2-pyridylmethyl)-carbamoyl)-3-methylbutyryl; lower alkoxycarbonyl, especially methoxy-, ethoxy-, isopropoxy-, isobutoxy- or tert-lower alkoxy-carbonyl, for example methoxycarbonyl, tert-butoxycarbonyl or isobutoxycarbonyl; aryl-lower alkoxycarbonyl wherein aryl preferably has from 6 to 14 carbon atoms and is, for example, phenyl, biphenylyl, 1- or 2-naphthyl, fluorenyl, or phenyl that is mono- or poly-substituted by lower alkyl, for example methyl or tert-butyl, hydroxy, lower alkoxy, for example methoxy, ethoxy or tert-butoxy, halogen, for example chlorine or bromine, and/or by nitro, for example phenyl-lower alkoxycarbonyl, such as benzyloxycarbonyl, 4-methoxybenzyloxycarbonyl, 4-nitrobenzyloxycarbonyl or fluorenyl-lower alkoxycarbonyl, such as 9-fluorenylmethoxycarbonyl, especially phenyl-lower alkoxycarbonyl, such as benzyloxycarbonyl; heterocyclyl-lower alkoxycarbonyl wherein heterocyclyl is preferably selected from pyrrolyl, furyl, thienyl, imidazolyl, pyrazolyl, oxazolyl, thiazolyl, pyridyl, pyrazinyl, pyrimidinyl, indolyl, quinolyl, isoquinolyl, quinoxalinyl, β-carbolinyl and a benzo-fused, cyclopenta-, cyclohexa- or cyclohepta-fused derivative of those radicals, which may also be fully or partially saturated, and from morpholinyl and from thiomorpholinyl and is unsubstituted or substituted, especially by lower alkyl, such as by methyl, for example 1-methylpyrrolidin-2-ylmethoxycarbonyl, 2-furylmethoxycarbonyl, 2-tetrahydrofuranyl-lower alkoxycarbonyl, such as 2-tetrahydrofurylmethoxycarbonyl, 1-methyl-2-piperidylmethoxycarbonyl or 2-morpholinoethoxycarbonyl, or 2-, 3- or 4-pyridylmethoxycarbonyl, especially tetrahydrofuranyl-lower alkoxycarbonyl, such as 2(R,S)-tetrahydrofuranylmethoxycarbonyl; lower alkylsulfonyl, for example methyl- or ethyl-sulfonyl, such as methylsulfonyl; heterocyclylsulfonyl wherein heterocyclyl is preferably selected from pyrrolyl, furyl, thienyl, imidazolyl, pyrazolyl, oxazolyl, thiazolyl, pyridyl, pyrazinyl, pyrimidinyl, indolyl, quinolyl, isoquinolyl, quinoxalinyl, β-carbolinyl and a benzo-fused, cyclopenta-, cyclohexa- or cyclohepta-fused derivative of those radicals, which may also be fully or partially saturated, from morpholinyl and from thiomorpholinyl and may be unsubstituted or substituted, especially by lower alkyl, such as methyl, such as morpholinosulfonyl, thiomorpholinosulfonyl, piperidinosulfonyl, 4-methylpiperazinylsulfonyl or piperazinosulfonyl; N-heterocyclyl-lower alkyl-N-lower alkylcarbamoyl that is as defined above under unsubstituted or substituted N-alkyl- or N,N-dialkyl-carbamoyl $R_1$, $R_2$, $R_8$ or $R_9$, wherein heterocyclyl is preferably selected from thienyl, furyl, pyranyl, pyrrolyl, imidazolyl, pyrazolyl, oxazolyl, isoxazolyl, thiazolyl, furazanyl, pyridyl, pyrazinyl, pyrimidinyl, pyridazinyl, azepinyl, indolyl, benzimidazolyl, 1H-indazolyl, quinolyl, isoquinolyl, quinoxalinyl, quinazolinyl, cinnolyl, purinyl, pteridinyl, naphthyridinyl, 4H-quinolizinyl, 3,1-benzofuranyl, benz[e]indolyl, 4,1-benzoxazinyl, 4,1-benzothiazinyl, carbazolyl, β-carbolinyl, phenazinyl, phenanthridyl, acridyl, phenoxazinyl, phenothiazinyl, 1-azaacenaphthenyl, cyclohexa[b]pyrrolyl, cyclohepta[b]pyrrolyl, cyclohexa[d]pyrazolyl, cyclohexa[b]pyridyl, cyclohexa[b]pyrazinyl, cyclohexa[b]pyrimidinyl, cyclohexa[b]-1,4-oxazinyl, cyclohexa[b]-1,4-thiazinyl, pyrrolidinyl, pyrrolinyl, imidazolidinyl, 2-imidazolinyl, 2,3-dihydropyridyl, piperidyl, piperazinyl, 2,3,5,6-tetrahydropyrazinyl, morpholinyl, thiomorpholinyl, S,S-dioxothiomorpholinyl, indolinyl, isoindolinyl, 4,5,6,7-tetrahydroindolyl, 1,2,3,4-tetrahydroquinolyl, 1,2,3,4-tetrahydroisoquinolyl, chromanyl, thiochromanyl, 1,2,3,4-tetrahydro-3,1-benzodiazinyl, 3,4-dihydro-3H-4,1-benzoxazinyl, 3,4-dihydro-3H-4,1-benzothiazinyl, 2,3,4,5-tetrahydro-1H-5,1-benzazepinyl and 5,6-dihydrophenanthridinyl, the mentioned radicals being unsubstituted or substituted by lower alkyl, for example methyl, phenyl, 1- or 2-naphthyl, phenyl-lower alkyl, for example benzyl, hydroxy-lower alkyl, for example hydroxymethyl or 2-hydroxyethyl, lower alkoxy-lower alkyl, for example methoxymethyl or 2-methoxyethyl, phenoxy- or naphthyloxy-lower alkyl, for example 2-phenoxyethyl, 1- or 2-naphthyloxymethyl, phenyl-lower alkoxy- or naphthyl-lower alkoxy-lower alkyl, for example benzyloxy-lower alkyl, lower alkanoyloxy-lower alkyl, for example acetoxymethyl, phenyl- or naphthyl-lower alkanoyloxy-lower alkyl, for example benzoyloxy-, phenylacetoxy- or 1- or 2-naphthoyloxy-methyl, -2-ethyl or -2-(2,2-dimethylethyl), lower alkoxycarbonyloxy-lower alkyl, for example tert-butoxycarbonyloxy-lower alkyl, phenyl-, naphthyl- or fluorenyl-lower alkoxycarbonyloxy-lower alkyl, for example 2-benzyloxycarbonyloxyethyl or 9-fluorenylmethoxycarbonyloxyethyl, amino-lower alkyl, for example aminomethyl, 2-aminoethyl or 2-aminopropyl, carboxy-lower alkyl, for example carboxymethyl or 2-carboxyethyl, hydroxy, lower alkoxy, for example methoxy or ethoxy, phenyl- or naphthyl-lower alkoxy, for example benzyloxy or 1- or 2-naphthylmethoxy, amino, lower alkylamino, for example methyl-, ethyl- or tert-butyl-amino, di-lower alkylamino, for example dimethyl- or diethyl-amino, carboxy, lower alkoxycarbonyl, for example methoxy-, isopropoxy-, sec-butoxy- or tert-butoxy-carbonyl, phenyl- or naphthyl-lower alkoxycarbonyl, for example benzyloxycarbonyl, halogen, for example fluorine, chlorine, bromine or iodine, especially chlorine or bromine, lower alkanoyl, for example acetyl or pivaloyl, lower alkylsulfonyl, for example methyl- or ethyl-sulfonyl, phosphono, hydroxy-lower alkoxyphosphoryl or dialkoxyphosphoryl, for example dimethoxy- or diethoxy-phosphoryl, carbamoyl, mono- or di-lower alkylcarbamoyl, for example N-methylcarbamoyl, N-n-butylcarbamoyl or N,N-dimethylcarbamoyl, hydroxy- or carboxy-lower alkylcarbamoyl, for example hydroxy- or carboxy-methylcarbamoyl or hydroxy- or carboxyethylcarbamoyl, sulfamoyl, nitro, oxo and/or by cyano, and is especially pyridyl, such as 2-, 3- or 4-pyridyl, more especially N-pyridyl-lower alkyl-N-lower alkylcarbamoyl, such as N-(2-,3- or ⁴-pyridylmethyl)-N-methylcarbamoyl; or an acyl radical of an amino acid the amino function of which is free or acylated by one of the other radicals mentioned hitherto for R₁ and R₉, the amino acid radicals, each independently of the others, preferably being as defined for unsubstituted or substituted amino acids as acyl $R_1$, $R_2$, $R_8$ and $R_9$, especially the radical of a natural α-amino acid having the L-configuration, such as those normally occurring in proteins, or an epimer of such an amino acid, i.e. having the unnatural D-configuration, or the D,L-isomeric mixture thereof, a homologue of such an amino acid, for example wherein the amino acid side chain has been lengthened or shortened by one or two methylene groups, wherein the amino group is in the β-position and/or wherein a methyl group has been replaced by hydrogen, a substituted aromatic amino acid wherein the aromatic radical has from 6 to 14 carbon atoms, for example a substituted phenylalanine or phenylglycine wherein phenyl may be mono- or poly-substituted by lower alkyl, for example methyl, hydroxy, lower alkoxy, for example methoxy, lower alkanoyloxy, for example acetoxy, amino, lower alkylamino, for example methylamino, di-lower alkylamino, for example dimethylamino, lower alkanoylamino, for example acetylamino or pivaloylamino, lower alkoxycarbonylamino, for example tert-butoxycarbonylamino, arylmethoxycarbonylamino wherein aryl preferably has from 6 to 14 carbon atoms, for example benzyloxycarbonylamino or 9-fluorenylmethoxycarbonylamino, halogen, for example fluorine, chlorine, bromine or iodine, carboxy and/or by nitro, a benzo-fused phenylalanine or phenylglycine, such as α-naphthylalanine, or a hydrogenated phenylalanine or phenylglycine, such as a cyclohexylalanine or cyclohexylglycine, especially the radical, bonded via a carboxy group, of an amino acid selected from glycine (H-Gly-OH), alanine (H-Ala-OH), valine (H-Val-OH), norvaline (α-aminovaleric acid), leucine (H-Leu-OH), isoleucine (H-Ile-OH), norleucine (α-aminohexanoic acid, H-Nle-OH), serine (H-Ser-OH), homoserine (α-amino-γ-hydroxybutyric acid), threonine (H-Thr-OH), methionine (H-Met-OH), cysteine (H-Cys-OH), proline (H-Pro-OH), trans-3- and trans-4-hydroxyproline, phenylalanine (H-Phe-OH), tyrosine (H-Tyr-OH), 4-aminophenylalanine, 4-chlorophenylalanine, 4-carboxyphenylalanine, β-phenylserine (β-hydroxyphenylalanine), phenylglycine, α-naphthylalanine (H-Nal-OH), cyclohexylalanine (H-Cha-OH), cyclohexylglycine, tryptophan (H-Trp-OH), indoline-2-carboxylic acid, 1,2,3,4-tetrahydroisoquinoline-3-carboxylic acid, aspartic acid (H-Asp-OH), asparagine (H-Asn-OH), aminomalonic acid, aminomalonic acid monoamide, glutamic acid (H-Glu-OH), glutamine (H-Gln-OH), histidine (H-His-OH), arginine (H-Arg-OH), lysine (H-Lys-OH), δ-hydroxylysine, ornithine (α,δ-diaminovaleric acid), 3-aminopropanoic acid, α,γ-diaminobutyric acid and α,β-diaminopropionic acid, more especially the radical of an amino acid selected from valine, alanine, leucine, isoleucine, glycine, glutamic acid and asparagine, wherein each of the mentioned amino acids (with the exception of glycine) may be in the D-, L- or (D,L)-form, preferably (with the exception of Val, which may also be in the (D)- or (D,L)-form) in the L-form, the α-amino group is unsubstituted or N-acylated by one of the radicals mentioned above for $R_1$ and $R_9$, especially by lower alkanoyl, phenyl-lower alkanoyl, such as phenylacetyl, phenyl-lower alkanoyl wherein the lower alkanoyl radical is substituted by carbamoyl, such as 2(R,S)-carbamoyl-3-phenylpropionyl, morpholino-lower alkanoyl, such as morpholinocarbonyl, thiomorpholino-lower alkanoyl, such as thiomorpholinocarbonyl, pyridyl-lower alkanoyl, such as 2-, 3- or 4-pyridylacetyl, quinolinyl-lower alkanoyl, such as quinoline-2-carbonyl, tetrazolyl-lower alkanoyl, such as 3-tetrazol-1-ylpropionyl, amino-lower alkanoyl substituted at the amino nitrogen atom by N-morpholino- or N-thiomorpholino-carbonyl, for example N-morpholino- or N-thiomorpholino-carbonylamino-lower alkanoyl, such as N-morpholino- or N-thiomorpholino-carbonylaminoacetyl, halo-lower alkanoyl containing up to three halogen atoms, for example α-haloacetyl, such as α-fluoro-, α-chloro-, α-bromo-α-iodo-, α,α,α-trifluoro- or α,α,α-trichloro-acetyl, or halopropionyl, such as β-chloro- or β-bromo-propionyl, especially trifluoroacetyl, 2-(N-morpholino-lower alkylcarbamoyl)-lower alkanoyl, such as 2(R,S)-(N-(2-morpholinoethyl)-carbamoyl-3-methylbutyryl, 2-(N-(pyridyl-lower alkyl)-carbamoyl)-lower alkanoyl, such as 2(R,S)-(N-(2-pyridylmethyl)-carbamoyl)-lower alkanoyl, lower alkoxycarbonyl, phenyl-lower alkoxycarbonyl, tetrahydrofuranyl-lower alkoxycarbonyl, such as 2(R,S)-tetrahydrofuranylmethoxycarbonyl, lower alkylsulfonyl, morpholinosulfonyl, thiomorpholinosulfonyl, piperidinosulfonyl, 4-methylpiperazinylsulfonyl or piperazinosulfonyl or N-pyridyl-lower alkyl-N-lower alkylcarbamoyl, such as N-(2-, 3- or 4-pyridylmethyl)-N-methylcarbamoyl, special preference being given to N-morpholinocarbonyl-glycine, N-(N-(2-, 3- or 4-pyridyl)methyl-N-methylaminocarbonyl)-glycine, valine, N-(trifluoroacetyl)-valine, N-phenylacetylvaline, N-(2- or 3-pyridyl)-acetyl-valine, N-acetyl-valine, N-(2-carbamoyl-3-phenylpropionyl)-valine, N-(2(R,S)-carbamoyl-3-phenylpropionyl)-valine, N-(2- or 3-pyridylacetyl)-valine, N-2-tetrahydrofurylmethoxycarbonyl-valine, N-(3-(tetrazol-1-yl)propionyl)-valine, N-(quinoline-2-carbonyl)-valine, N-methoxycarbonyl-valine, N-isobutoxycarbonyl-valine, N-tert-butoxycarbonyl-valine, N-benzyloxycarbonyl-valine, N-(morpholinocarbonyl)-valine, N-(thiomorpholinocarbonyl)-valine, N-(S,S-dioxothiomorpholinocarbonyl)-valine, N-(N-2-pyridylmethyl-N-methylaminocarbonyl)-valine, N-morpholinocarbonylaminoacetyl-valine, N-methylsulfonyl-valine, N-acetyl-isoleucine, N-propionyl-isoleucine, N-(benzyloxycarbonyl)-isoleucine, N-benzyloxycarbonylglutamic acid, asparagine, N-benzyloxycarbonyl-asparagine or quinoline-2-carbonylasparagine, the mentioned amino acid radicals preferably being in the (L)- or (D,L)-form, and in the case of valine also in the (D)-form, with the proviso that not more than one of the two radicals $R_1$ and $R_9$ may be hydrogen, $R_2$, $R_4$, $R_6$ and $R_8$ are hydrogen, $R_3$ is lower alkyl, such as isobutyl or n-butyl; cycloalkyl-lower alkyl as defined above for cycloalkyl-lower alkyl $R_3$, $R_4$ and $R_7$, wherein, preferably, cycloalkyl has from 3 to 7 carbon atoms and is unsubstituted or mono- to tri-substituted by lower alkyl, such as isopropyl, halo-lower alkyl, such as trifluoromethyl, hydroxy, lower alkoxy, carbamoyl-lower alkoxy, N-lower alkylcarbamoyl-lower alkoxy or N,N-di-lower alkylcarbamoyl-lower alkoxy, amino, mono- or di-lower alkylamino, halogen, such as fluorine, chlorine or bromine, carboxy, lower alkoxycarbonyl, phenyl-, naphthyl- or fluorenyl-lower alkoxycarbonyl, lower alkanoyl, lower alkylsulfonyl, for example methylsulfonyl, phosphono, hydroxy-lower alkoxyphosphoryl or di-lower alkoxyphosphoryl, carbamoyl, mono- or di-lower alkylaminocarbamoyl, sulfamoyl, mono- or di-lower alkylsulfamoyl, nitro and/or by cyano and is bonded, preferably terminally, to lower alkyl, especially methyl, ethyl, n-propyl, isopropyl, n-butyl, isobutyl or tert-butyl, such as cyclobutyl-, cyclopentyl-, cyclohexyl- or cycloheptyl-lower alkyl, such as -methyl or -ethyl, especially cyclohexyl-lower alkyl, most especially cyclohexylmethyl; or is aryl-lower alkyl that is preferably as defined under aryl-lower alkyl $R_3$, $R_4$ and $R_7$, wherein aryl contains especially from 6 to 14 carbon atoms, such as in phenyl, indenyl, indanyl, naphthyl, anthryl, phenanthryl, acenaphthyl or fluorenyl, and is unsubstituted or substituted, and may be, especially, mono- to tri-substituted by lower alkyl, for example methyl, ethyl or isopropyl, halo-lower alkyl, such as trifluoromethyl, phenyl, 1- or 2-naphthyl, hydroxy, lower alkoxy, for example methoxy, carbamoyl-lower alkoxy, N-lower alkylcarbamoyl-lower alkoxy or N,N-di-lower alkylcarbamoyl-lower alkoxy, amino, mono- or di-lower alkylamino, lower alkanoylamino, for example pivaloylamino, halogen, for example fluorine or chlorine, carboxy, lower alkoxycarbonyl, benzyl-, naphthyl- or fluorenyl-lower alkoxycarbonyl, lower alkanoyl, sulfo, lower alkylsulfonyl, phosphono, hydroxy-lower alkoxyphosphoryl or di-lower alkoxyphosphoryl, carbamoyl, mono- or di-lower alkylcarbamoyl, sulfamoyl, mono- or di-lower alkylsulfamoyl, nitro and/or by cyano, wherein phenyl may be present up to three times, such as in diphenyl-, dibenzyl- or triphenyl-lower alkyl, for example diphenyl-, dibenzyl- or triphenyl-2-ethyl, especially phenyl-lower alkyl that is unsubstituted or substituted by the mentioned substituents, especially benzyl, 2-phenylethyl, 3-phenylpropyl, 4-fluoro-, 4-cyano-, 4-methoxy- or 4-hydroxy-benzyl, $R_5$ is hydroxy, and $R_7$ is unsubstituted or substituted lower alkyl, preferably unsubstituted or substituted as described above for unsubstituted or substituted alkyl $R_3$, $R_4$ or $R_7$, especially lower alkyl, more especially isobutyl or n-butyl, cycloalkyl-lower alkyl, as last described for cycloalkyl-lower alkyl $R_3$, especially cyclohexyl-lower alkyl, such as cyclohexylmethyl, or aryl-lower alkyl, as last described for aryl-lower alkyl $R_3$, especially phenyl-lower alkyl that is unsubstituted or substituted by the mentioned substituents, such as benzyl, 2-phenylethyl, 3-phenylpropyl, 4-fluoro-, 4-cyano-, 4-methoxy- or 4-hydroxy-benzyl, or a salt thereof where a salt-forming group is present.

Of the last-mentioned compounds of formula I, special preference is given to those wherein $R_1$ and $R_9$ are each independently of the other hydrogen; lower alkanoyl; aryl-lower alkanoyl wherein the lower alkanoyl radical is unsubstituted or substituted by carbamoyl or by carbamoyl substituted at the nitrogen atom by one or two radicals selected from lower alkyl, carboxy-lower alkyl, lower alkoxycarbonyl-lower alkyl, di-lower alkylamino-lower alkyl, aminocarboxy-lower alkyl, hydroxy-lower alkyl or by di-lower alkoxy-lower alkyl, and wherein aryl contains from 6 to 14 carbon atoms; heterocyclyl-lower alkanoyl wherein heterocyclyl contains from 3 to 10 ring atoms and up to 4 hetero atoms selected from O, N, S, Se, and S linked to 1 or 2 oxygen atoms (S=O, O=S=O); halo-lower alkanoyl having from 1 to 3 halogen atoms; N-heterocyclyl-lower alkylcarbamoyl-lower alkanoyl; lower alkoxycarbonyl; aryl-lower alkoxycarbonyl wherein aryl contains from 6 to 14 carbon atoms; heterocyclyl-lower alkoxycarbonyl wherein heterocyclyl is selected from pyrrolyl, furyl, thienyl, imidazolyl, pyrazolyl, oxazolyl, thiazolyl, pyridyl, pyrazinyl, pyrimidinyl, indolyl, quinolyl, isoquinolyl, quinoxalinyl, β-carbolinyl and a benzo-fused, cyclopenta-,cyclohexa- or cyclohepta-fused derivative of those radicals, which may also be fully or partially saturated;

lower alkylsulfonyl; N-(heterocyclyl-lower alkyl)-carbamoyl-N-lower alkylcarbamoyl; or the radical, bonded via the carboxy group, of an amino acid selected from glycine, alanine, valine, norvaline, leucine, isoleucine, norleucine, serine, homoserine, threonine, methionine, cysteine, proline, trans-3- and trans-4-hydroxyproline, phenylalanine, tyrosine, 4-aminophenylalanine, 4-chlorophenylalanine, 4-carboxyphenylalanine, β-hydroxyphenylalanine, phenylglycine, α-naphthylalanine, cyclohexylalanine, cyclohexylglycine, tryptophan, aspartic acid, asparagine, aminomalonic acid, aminomalonic acid monoamide, glutamic acid, glutamine, histidine, arginine, lysine, γ-hydroxylysine, ornithine, α,γ-diaminobutyric acid or α,β-diaminopropionic acid, the amino acid radicals being unsubstituted or substituted by one of the mentioned radicals $R_1$ or $R_9$ with the exception of the radical of one of the amino acids itself;

$R_2$, $R_4$, $R_6$ and $R_9$ are hydrogen, $R_3$ is cycloalkyl-lower alkyl wherein cycloalkyl has from 3 to 7 carbon atoms, or is aryl-lower alkyl wherein aryl has from 6 to 14 carbon atoms, $R_5$ is hydroxy, and $R_7$ is lower alkyl, cycloalkyl-lower alkyl wherein cycloalkyl has from 3 to 7 carbon atoms, or is aryl-lower alkyl wherein aryl has from 6 to 14 carbon atoms, and salts of such compounds having salt-forming groups, the general expressions and definitions preferably having the meanings mentioned as preferred in the previous paragraph.

Preference is likewise given to the compounds mentioned in the penultimate section above in which the substituents have all the meanings mentioned with the exception of morpholinosulfonyl, thiomorpholinosulfonyl, piperidinosulfonyl, 4-methylpiperazinylsulfonyl or piperazinosulfonyl as $R_1$ and/or $R_9$.

Preference is given also to the compounds of formula I wherein $R_1$ and $R_9$ are each independently of the other hydrogen, lower alkoxycarbonyl, 2-halo-lower alkoxycarbonyl, aryloxycarbonyl wherein aryl has from 6 to 14 carbon atoms, aryl-lower alkoxycarbonyl wherein aryl has from 6 to 14 carbon atoms, heterocyclyl-lower alkoxycarbonyl wherein heterocyclyl is selected from pyrrolyl, furyl, thienyl, imidazolyl, pyrazolyl, oxazolyl, thiazolyl, pyridyl, pyrazinyl, pyrimidinyl, indolyl, quinolyl, isoquinolyl, quinoxalinyl, β-carbolinyl and a benzo-fused, cyclopenta-, cyclohexa- or cyclohepta-fused derivative of those radicals, which may also be fully or partially saturated, 2-tri-lower alkylsilyl-lower alkoxycarbonyl, 2-triarylsilyl-lower alkoxycarbonyl wherein aryl is phenyl or 1- or 2-naphthyl, the radical, bonded via the carboxy group, of an amino acid selected from glycine, alanine, valine, norvaline, leucine, isoleucine, norleucine, serine, homoserine, threonine, methionine, cysteine, proline, trans-3- and trans-4-hydroxyproline, phenylalanine, tyrosine, 4-aminophenylalanine, 4-chlorophenylalanine, 4-carboxyphenylalanine, β-phenylserine, phenylglycine, α-naphthylalanine, cyclohexylalanine, cyclohexylglycine, tryptophan, indoline-2-carboxylic acid, 1,2,3,4-tetrahydroisoquinoline-3-carboxylic acid, aspartic acid, asparagine, aminomalonic acid, aminomalonic acid monoamide, glutamic acid, glutamine, histidine, arginine, lysine, γ-hydroxylysine, ornithine, α,γ-diaminobutyric acid and α,β-diaminopropionic acid, it being possible for each of those amino acids to be in the D-, L- or (D,L)-form, preferably in the L-form, and wherein the 6θ -amino group may be unsubstituted or mono- or di-N-alkylated by lower alkyl, by amino-lower alkyl, by phenyl- or naphthylamino-lower alkyl, or by piperazinylcarbonyl-lower alkyl substituted at the nitrogen atom by lower alkyl, or may be N-acylated by lower alkanoyl; by aryl-lower alkanoyl wherein aryl is selected from phenyl, indenyl, indanyl, naphthyl, anthryl, phenanthryl, acenaphthyl and fluorenyl and may be unsubstituted or mono- to tri-substituted by lower alkyl, halo-lower alkyl, phenyl, 1- or 2-naphthyl, hydroxy, lower alkoxy, carbamoyl-lower alkoxy, N-lower alkylcarbamoyl-lower alkoxy or N,N-di-lower alkylcarbamoyl-lower alkoxy, amino, mono- or di-lower alkylamino, lower alkanoylamino, halogen, carboxy, lower alkoxycarbonyl, phenyl-, naphthyl- or fluorenyl-lower alkoxycarbonyl, lower alkanoyl, sulfo, lower alkylsulfonyl, phosphono, hydroxy-lower alkoxyphosphoryl or di-lower alkoxyphosphoryl, carbamoyl, mono- or di-lower alkylcarbamoyl, sulfamoyl, mono- or di-lower alkylaminosulfonyl, nitro and/or by cyano, wherein phenyl may be present up to three times, and wherein lower alkanoyl may be unsubstituted or substituted by lower alkyl, heterocyclyl selected from pyrrolyl, furyl, thienyl, imidazolyl, pyrazolyl, oxazolyl, thiazolyl, pyridyl, pyrazinyl, pyrimidinyl, indolyl, quinolyl, isoquinolyl, quinoxalinyl, β-carbolinyl and a benzo-, cyclopenta-, cyclohexa- or cyclohepta-fused derivative of those radicals, which may also be fully or partially saturated, hydroxy, lower alkoxy, lower alkanoyloxy, acetoacetoxy, amino- or benzyloxycarbonylamino-lower alkanoyloxy, aryl-lower alkanoyloxy wherein aryl has from 6 to 10 carbon atoms, lower alkoxycarbonyloxy, mono- or di-lower alkylaminocarbonyloxy, aryloxycarbonyloxy wherein aryl has from 6 to 10 carbon atoms, aryl-lower alkoxycarbonyloxy wherein aryl has from 6 to 14 carbon atoms, sulfonyloxy, lower alkylsulfonyloxy, phenylsulfonyloxy, 2- or 4-toluenesulfonyloxy or 1- or 2-naphthylsulfonyloxy, carboxy, esterified carboxy selected from lower alkoxycarbonyl, aryloxycarbonyl wherein aryl has from 6 to 10 carbon atoms, aryl-lower alkoxycarbonyl wherein aryl has from 6 to 12 carbon atoms, lower alkanoyl, lower alkylsulfonyl, hydroxy-lower alkoxyphosphoryl and di-lower alkoxyphosphoryl, carbamoyl, carbamoyl substituted by one or two radicals selected from lower alkyl, carboxy-lower alkyl, lower alkoxycarbonyl-lower alkyl, di-lower alkylamino-lower alkyl, aminocarboxy-lower alkyl, hydroxy-lower alkyl and di-lower alkoxy-lower alkyl or carbamoyl substituted by one radical selected from ethylene, trimethylene, tetramethylene and pentamethylene, in which a carbon atom may have been replaced by nitrogen, oxygen, sulfur or by sulfur mono- or di-substituted by oxygen and which may be unsaturated, and also sulfamoyl, phosphono, benzofuranyl, oxo and/or by cyano and is branched or unbranched; by heterocyclyl-lower alkanoyl selected from thienyl-, furyl-, pyranyl-, pyrrolyl-, imidazolyl-, pyrazolyl-, oxazolyl-, isoxazolyl-, thiazolyl-, furazanyl, pyridyl-, pyrazinyl-, pyrimidinyl-, pyridazinyl-, azepinyl-, indolyl-, benzimidazolyl-, 1H-indazolyl-, quinolyl-, isoquinolyl-, quinoxalinyl-, quinazolinylcinnolyl-, purinyl-, pteridinyl-, naphthyridinyl-, 4H-quinolizinyl-, 3,1-benzofuranyl-, benz[e]indolyl-, 4,1-benzoxazinyl-, 4,1-benzothiazinyl-, carbazolyl-, β-carbolinyl-, phenazinyl-, phenanthridinyl-, acridyl-, phenoxazinyl-, phenothiazinyl-, 1-azaacenaphthenyl-, cyclohexa[b]pyrrolyl-,cyclohepta[b]pyrrolyl-, cyclohexa[d]pyrazolyl-, cyclohexa[b]pyridyl-, cyclohexa[b]pyrazinyl-, cyclohexa[b]pyrimidinyl-, cyclohexa[b]-1,4-oxazinyl-, cyclohexa[b]-1,4-thiazinyl-, pyrolidinyl-, pyrrolinyl-, imidazolidinyl-, 2-imidazolinyl-, 2,3-dihydropyridyl-, piperidyl-, piperazinyl-, 2,3,5,6-tetrahydropyrazinyl-, morpholinyl-, thiomorpholinyl-, S,S-dioxothiomorpholinyl-, indolinyl-, isoindolinyl-, 4,5,6,7-tetrahydroindolyl-, 1,2,3,4-tetrahydroquinolyl-, 1,2,3,4-tetrahydroisoquinolyl-, chroman-, thiochroman-, 1,2,3,4-tetrahydro-3,1-benzodiazinyl-, 3,4-dihydro-3H-4,1-benzoxazinyl-, 3,4-dihydro-3H-4,1-benzothiazinyl-, 2,3,4,5-tetrahydro-1H-5,1-benzazepinyl- and 5,6-dihydrophenanthridinyl-lower alkanoyl, the mentioned heterocyclyl radicals being unsubstituted or substituted by lower alkyl, phenyl, 1- or 2-naphthyl, phenyl-lower alkyl, hydroxy-lower alkyl, lower alkoxy-lower alkyl, phenoxy- or naphthyloxy-lower alkyl, phenyl-lower alkoxy- or naphthyl-lower alkoxy-lower alkyl, lower alkanoyloxy-lower alkyl, phenyl- or naphthyl-lower alkanoyloxy-lower alkyl, lower alkoxycarbonyloxy-lower alkyl, phenyl-, naphthyl- or fluorenyl-lower alkoxycarbonyloxy-lower alkyl, amino-lower alkyl, carboxy-lower alkyl, hydroxy, lower alkoxy, phenyl- or naphthyl-lower alkoxy, amino, lower alkylamino, di-lower alkylamino, carboxy, lower alkoxycarbonyl, phenyl- or naphthyl-lower alkoxycarbonyl, halogen, lower alkanoyl, lower alkylsulfonyl, phosphono, hydroxy-lower alkoxyphosphoryl, dialkoxyphosphoryl, carbamoyl, mono- or di-lower alkylcarbamoyl, hydroxy- or carboxy-lower alkylcarbamoyl, sulfamoyl, nitro, oxo and/or by cyano; by heterocyclyl-lower alkenoyl wherein heterocyclyl is selected from pyrrolyl, furyl, thienyl, imidazolyl, pyrazolyl, oxazolyl, thiazolyl, pyridyl, pyrazinyl, pyrimidinyl, indolyl, quinolyl, isoquinolyl, quinoxalinyl, β-carbolinyl and a benzo-fused, cyclopenta-, cyclohexa- or cyclohepta-fused derivative of those radicals, which may also be fully or partially saturated; by lower alkoxycarbonyl; by aryl-lower alkoxycarbonyl wherein aryl has from 6 to 14 carbon atoms; by heterocyclyl-lower alkoxycarbonyl wherein heterocyclyl is selected from pyrrolyl, furyl, thienyl, imidazolyl, pyrazolyl, oxazolyl, thiazolyl, pyridyl, pyrazinyl, pyrimidinyl, indolyl, quinolyl, isoquinolyl, quinoxalinyl, β-carbolinyl and a benzo-fused, cyclopenta-, cyclohexa- or cyclohepta-fused derivative of those radicals, which may also be fully or partially saturated and unsubstituted or substituted by lower alkyl; by carboxy-lower alkanoyl; by lower alkoxycarbonyl-lower alkanoyl; by hydroxy-lower alkoxy-lower alkanoyl; by amino-lower alkanoyl; or by benzyloxycarbonylamino-lower alkanoyl wherein the amino group is not bonded in the α- or β-position; by carbamoyl; by phenyl-lower alkylaminocarbonyl; by N-di-lower alkylamino-lower alkyl-N-lower alkylaminocarbonyl; by N-dihydroxy-lower alkyl-N-lower alkylaminocarbonyl; by 2- or 3-pyridyl-lower alkylaminocarbonyl; by N-2-pyridyl-lower alkyl-N-lower alkylaminocarbonyl; by sulfonyl; by lower alkylsulfonyl; by arylsulfonyl wherein aryl has from 6 to 10 carbon atoms and is unsubstituted or substituted by lower alkyl or by lower alkoxy; by heterocyclylsulfonyl wherein heterocyclyl is selected from pyrrolyl, furyl, thienyl, imidazolyl, pyrazolyl, oxazolyl, thiazolyl, pyridyl, pyrazinyl, pyrimidinyl, indolyl, quinolyl, isoquinolyl, quinoxalinyl, β-carbolinyl and a benzo-fused, cyclopenta-, cyclohexa- or cyclohepta-fused derivative of those radicals, which may also be fully or partially saturated; by sulfamoyl; or by sulfamoyl substituted by heterocyclyl-lower alkyl wherein heterocyclyl is as last defined, and/or by lower alkyl;

a carboxy group of the side chain is present in free form or in esterified form as a lower alkyl ester group, as an aryl ester group or as an aryl-lower alkyl ester group, wherein aryl is phenyl, 4-nitrophenyl, naphthyl or biphenylyl, or in amidated form as a carbamoyl, lower alkylcarbamoyl, di-lower alkylaminocarbamoyl, mono- or di-(hydroxy-lower alkyl)-carbamoyl or mono- or di-(carboxy-lower alkyl)-carbamoyl group, an amino group of the side chain is present in free form or in alkylated form as mono- or di-lower alkylamino or in acylated form as lower alkanoylamino, as amino-lower alkanoylamino, as aryl-lower alkanoylamino wherein aryl has from 6 to 14 carbon atoms and is unsubstituted or substituted by lower alkyl, hydroxy, lower alkoxy, carboxy, carbamoyl or by sulfamoyl, as a lower alkoxycarbonylamino group, an arylmethoxycarbonylamino group wherein aryl has from 6 to 14 carbon atoms, as piperidyl-1-carbonyl, morpholinocarbonyl, thiomorpholinocarbonyl or as S,S-dioxothiomorpholinocarbonyl and/or a hydroxy group of the side chain is present in free form or in etherified or esterified form as a lower alkoxy, aryl-lower alkoxy, lower alkanoyloxy or lower alkoxycarbonyloxy group, lower alkylsulfonyl, 2- or 3-pyrrolyl-, 2-thienyl-, 2-furyl-, 1-pyrazolyl-, 2-, 3- or 4-pyridyl-, 2-, 3- or 5-indolyl-, (1-methyl-, 2-methyl-, 5-methoxy-, 5-benzyloxy-, 5-chloro- or 4,5-dimethylindol-2-yl)-, (1-benzylindol-2-yl or -3-yl)-, 4,5,6,7-tetrahydroindol-2-yl-, (2-, 3- or 4-quinolyl or 4-hydroxyquinol-2-yl)-, (1-, 3- or 4-isoquinolyl or 1-oxo-1,2-dihydroisoquinol-3-yl)-, 3-pyrrolidinyl-, (3- or 4-hydroxypyrrolidin-2-yl)-, 5-oxopyrrolidin-2-yl-, (2- or 3-morpholinyl)-, (2- or 3-thiomorpholinyl)-, (S,S-dioxothiomorpholin-2- or -3-yl)-, (2- or 3-indolinyl)-, 1,2,3,4-tetrahydroquinol-2-, -3- or -4-yl)- or (1,2,3,4-tetrahydroisoquinol-1-, -2- or -3-yl)-methylsulfonyl, phenyl- or 1- or 2-naphthyl-sulfonyl that is unsubstituted or mono- or di-substituted by lower alkyl, lower alkoxysulfonyl, or benzyloxysulfonyl or 1- or 2-naphthyloxysulfonyl, with the result that not more than one of the radicals $R_1$ and $R_9$ may be hydrogen, and $R_2$ and $R_8$ are each independently of the other hydrogen or the same radicals as $R_1$ and $R_9$, or the pairs of substituents $R_1$ and $R_9$, and $R_2$ and $R_8$, each independently of the other, together with the bonding nitrogen atom and a radical selected from ethylene, trimethylene, tetramethylene and pentamethylene in which a carbon atom may have been replaced by nitrogen, oxygen, sulfur or by sulfur mono- or di-substituted by oxygen and which may be unsaturated, form a heterocyclic ring, $R_3$ is cycloalkyl-lower alkyl wherein cycloalkyl has from 3 to 7 carbon atoms and is unsubstituted or mono- to tri-substituted by lower alkyl, halo-lower alkyl, hydroxy, lower alkoxy, carbamoyl-lower alkoxy, N-lower alkylcarbamoyl-lower alkoxy or N,N-di-lower alkylcarbamoyl-lower alkoxy, amino, mono- or di-lower alkylamino, halogen, carboxy, lower alkoxycarbonyl, phenyl-, naphthyl- or fluorenyl-lower alkoxycarbonyl, lower alkanoyl, lower alkylsulfonyl, phosphono, hydroxy-lower alkoxyphosphoryl or di-lower alkoxyphosphoryl, carbamoyl, mono- or di-lower alkylaminocarbamoyl, sulfamoyl, mono- or di-lower alkylsulfamoyl, nitro and/or by cyano and is bonded to lower alkyl, or aryl-lower alkyl wherein aryl is selected from phenyl, indenyl, indanyl, naphthyl, anthryl, phenanthryl, acenaphthyl and fluorenyl, which may be unsubstituted or mono- to tri-substituted by lower alkyl, halo-lower alkyl, phenyl, 1- or 2-naphthyl, hydroxy, lower alkoxy, carbamoyl-lower alkoxy, N-lower alkylcarbamoyl-lower alkoxy or N,N-di-lower alkylcarbamoyl-lower alkoxy, amino, mono- or di-lower alkylamino, lower alkanoylamino, halogen, carboxy, lower alkoxycarbonyl, phenyl-, naphthyl- or fluorenyl-lower alkoxycarbonyl, lower alkanoyl, sulfo, lower alkylsulfonyl, phosphono, hydroxy-lower alkoxyphosphoryl or di-lower alkoxyphosphoryl, carbamoyl, mono- or di-lower alkylcarbamoyl, sulfamoyl, mono- or di-lower alkylsulfamoyl, nitro and/or by cyano, wherein phenyl may be present up to three times, and wherein lower alkyl is unsubstituted or substituted by lower alkyl, heterocyclyl selected from pyrrolyl, furyl, thienyl, imidazolyl, pyrazolyl, oxazolyl, thiazolyl, pyridyl, pyrazinyl, pyrimidinyl, indolyl, quinolyl, isoquinolyl, quinoxalinyl, β-carbolinyl and a benzo-fused, cyclopenta-, cyclohexa- or cyclohepta-fused derivative of those radicals, which may also be fully or partially saturated, hydroxy, lower alkoxy, lower alkanoyloxy, acetoacetoxy, amino- or benzyloxycarbonylamino-lower alkanoyloxy, aryl-lower alkanoyloxy wherein aryl has from 6 to 10 carbon atoms, lower alkoxycarbonyloxy, mono- or di-lower alkylaminocarbonyloxy, aryloxycarbonyloxy wherein aryl has from 6 to 10 carbon atoms, aryl-lower alkoxycarbonyloxy wherein aryl has from 6 to 12 carbon atoms, sulfonyloxy, lower alkylsulfonyloxy, phenylsulfonyloxy, 2- or 4-toluenesulfonyloxy or 1- or 2-naphthylsulfonyloxy, amino, mono- or di-lower alkylamino, N-lower alkoxy-N-lower alkylamino, mono- or di-(phenyl- or naphthyl-lower alkyl)-amino, lower alkanoylamino, carboxy, esterified carboxy selected from lower alkoxycarbonyl, aryloxycarbonyl wherein aryl has from 6 to 10 carbon atoms, aryl-lower alkoxycarbonyl wherein aryl has from 6 to 12 carbon atoms, lower alkanoyl, lower alkylsulfonyl, hydroxy-lower alkoxyphosphoryl and di-lower alkoxyphosphoryl, carbamoyl, carbamoyl substituted by one or two radicals selected from lower alkyl, from carboxy-lower alkyl or lower alkoxycarbonyl-lower alkyl, from di-lower alkylamino-lower alkyl, from aminocarboxy-lower alkyl, from hydroxy-lower alkyl and from di-lower alkoxy-lower alkyl, or carbamoyl substituted by one radical selected from ethylene, trimethylene, tetramethylene and pentamethylene in which a carbon atom may have been replaced by nitrogen, oxygen, sulfur or by sulfur mono- or di-substituted by oxygen and which may be unsaturated, and also sulfamoyl, phosphono, benzofuranyl, oxo and/or by cyano and is unbranched or branched, $R_4$ is hydrogen, $R_5$ is hydroxy and $R_6$ is hydrogen, or $R_5$ and $R_6$ together are oxo and $R_7$ is lower alkyl, cycloalkyl-lower alkyl wherein cycloalkyl has from 3 to 7 carbon atoms and is unsubstituted or mono- to tri-substituted by lower alkyl, halo-lower alkyl, hydroxy, lower alkoxy, carbamoyl-lower alkoxy, N-lower alkylcarbamoyl-lower alkoxy or N,N-di-lower alkylcarbamoyl-lower alkoxy, amino, mono- or di-lower alkylamino, halogen, carboxy, lower alkoxycarbonyl, phenyl-, naphthyl- or fluorenyl-lower alkoxycarbonyl, lower alkanoyl, lower alkylsulfonyl, phosphono, hydroxy-lower alkoxyphosphoryl or di-lower alkoxyphosphoryl, carbamoyl, mono- or di-lower alkylaminocarbamoyl, sulfamoyl, mono- or di-lower alkylsulfamoyl, nitro and/or by cyano and is bonded to lower alkyl, bicycloalkyl-lower alkyl wherein bicycloalkyl contains from 5 to 10 carbon atoms, tricycloalkyl-lower alkyl wherein tricycloalkyl contains from 8 to 10 carbon atoms, aryl-lower alkyl wherein aryl is selected from phenyl, indenyl, indanyl, naphthyl, anthryl, phenanthryl, acenaphthyl and fluorenyl, which may be unsubstituted or mono- to tri-substituted by lower alkyl, halo-lower alkyl, phenyl, 1- or 2-naphthyl, hydroxy, lower alkoxy, carbamoyl-lower alkoxy, N-lower alkylcarbamoyl-lower alkoxy, N,N-di-lower alkylcarbamoyl-lower alkoxy, amino, mono- or di-lower alkylamino, lower alkanoylamino, halogen, carboxy, lower alkoxycarbonyl, benzyl-, naphthyl- or fluorenyl-lower alkoxycarbonyl, lower alkanoyl, sulfo, lower alkylsulfonyl, phosphono, hydroxy-lower alkoxyphosphoryl, di-lower alkoxyphosphoryl, carbamoyl, mono- or di-lower alkylcarbamoyl, sulfamoyl, mono- or di-lower alkylsulfamoyl, nitro and/or by cyano, wherein phenyl may be present up to three times, and wherein lower alkyl is unsubstituted or substituted by lower alkyl, heterocyclyl selected from pyrrolyl, furyl, thienyl, imidazolyl, pyrazolyl, oxazolyl, thiazolyl, pyridyl, pyrazinyl, pyrimidinyl, indolyl, quinolyl, isoquinolyl, quinoxalinyl, β-carbolinyl and a benzo-fused, cyclopenta-, cyclohexa- or cyclohepta-fused derivative of those radicals, which may also be fully or partially saturated, hydroxy, lower alkoxy, lower alkanoyloxy, acetoacetoxy, amino- or benzyloxycarbonylamino-lower alkanoyloxy, aryl-lower alkanoyloxy wherein aryl has from 6 to 10 carbon atoms, lower alkoxycarbonyloxy, mono- or di-lower alkylaminocarbonyloxy, aryloxycarbonyloxy wherein aryl has from 6 to 10 carbon atoms, aryl-lower alkoxycarbonyloxy wherein aryl has from 6 to 12 carbon atoms, sulfonyloxy, lower alkylsulfonyloxy, phenylsulfonyloxy, 2- or 4-toluenesulfonyloxy, 1- or 2-naphthylsulfonyloxy, amino, mono- or di-lower alkylamino, N-lower alkoxy-N-lower alkylamino, mono- or di-(phenyl- or naphthyl-lower alkyl)amino, lower alkanoylamino, carboxy, esterified carboxy selected from lower alkoxycarbonyl, aryloxycarbonyl wherein aryl has from 6 to 10 carbon atoms, aryl-lower alkoxycarbonyl wherein aryl has from 6 to 12 carbon atoms, lower alkanoyl, lower alkylsulfonyl, hydroxy-lower alkoxyphosphoryl and di-lower alkoxyphosphoryl, carbamoyl, carbamoyl substituted by one or two radicals selected from lower alkyl, from carboxy-lower alkyl, from lower alkoxycarbonyl-lower alkyl, from di-lower alkylamino-lower alkyl, from aminocarboxy-lower alkyl, from hydroxy-lower alkyl and from di-lower alkoxy-lower alkyl, or carbamoyl substituted by one radical selected from ethylene, trimethylene, tetramethylene and pentamethylene in which a carbon atom may have been replaced by nitrogen, oxygen, sulfur or by sulfur mono- or di-substituted by oxygen and which may be unsaturated, and also sulfamoyl, phosphono, benzofuranyl, oxo (which is not bonded to the carbon atom that is linked to the nitrogen atom bonding the radical $R_7$) and/or by cyano and is unbranched or branched, heterocyclyl-lower alkyl wherein heterocyclyl is preferably selected from pyrrolyl, furyl, thienyl, imidazolyl, pyrazolyl, oxazolyl, thiazolyl, pyridyl, pyrazinyl, pyrimidinyl, indolyl, quinolyl, isoquinolyl, quinoxalinyl, β-carbolinyl and a benzo-fused, cyclopenta-, cyclohexa- or cyclohepta-fused derivative of those radicals, which may also be fully or partially saturated, for example 4-pyrrolidinylmethyl, 1-imidazolylmethyl, 2-pyridylmethyl, 3-pyridylmethyl, quinolin-2-ylmethyl or indol-2-ylmethyl, hydroxy-lower alkyl, lower alkoxy-lower alkyl, phenoxy-lower alkyl or nitrophenoxy-lower alkyl, naphthyloxy-lower alkyl, lower alkanoyloxy-lower alkyl, acetoacetoxy-lower alkyl, arylmercapto-lower alkyl wherein aryl has from 6 to 10 carbon atoms, amino-lower alkyl, mono- or di-lower alkylamino-lower alkyl, phenyl- or naphthyl-amino-lower alkyl, lower alkanoylamino-lower alkyl, piperazinylcarbonyl-lower alkyl substituted at the nitrogen atom by lower alkyl, lower alkoxycarbonylamino-lower alkyl, phenyl-lower alkoxycarbonylamino-lower alkyl, aminocarbonylamino-lower alkyl, N-phenyl-lower alkyl-N-lower alkylaminocarbonylamino-lower alkyl, halo-lower alkyl, carboxy-lower alkyl, lower alkoxycarbonyl-lower alkyl, 2-halo-lower alkoxycarbonyl-lower alkyl, phenyl- or naphthyl-lower alkoxycarbonyl-lower alkyl, heterocyclyl-lower alkoxycarbonyl-lower alkyl wherein heterocyclyl is selected from pyrrolyl, furyl, thienyl, imidazolyl, pyrazolyl, oxazolyl, thiazolyl, pyridyl, pyrazinyl, pyrimidinyl, indolyl, quinolyl, isoquinolyl, quinoxalinyl, β-carbolinyl and a benzo-fused, cyclopenta-, cyclohexa- or cyclohepta-fused derivative of those radicals, it also being possible for the mentioned radicals to be fully or partially saturated, lower alkylsulfonyl-lower alkyl, arylsulfonyl-lower alkyl wherein aryl has from 6 to 10 carbon atoms, carbamoyl-lower alkyl, lower alkylcarbamoyl-lower alkyl, di-lower alkylcarbamoyl-lower alkyl, hydroxy-lower alkylcarbamoyl- or di(hydroxy-lower alkyl)carbamoyl-lower alkyl, N-lower alkoxy-lower alkoxy-lower alkylcarbamoyl-lower alkyl, carboxy-lower alkylcarbamoyl- or di(carboxy-lower alkyl)carbamoyl-lower alkyl, carbamoyl-lower alkyl substituted at the nitrogen atom by one radical selected from ethylene, trimethylene, tetramethylene and pentamethylene wherein a carbon atom may have been replaced by nitrogen, oxygen, sulfur or by sulfur mono- or di-substituted by oxygen, it also being possible for the radical so formed to be fully or partially unsaturated, N-lower alkyl-N-heterocyclyl-lower alkylcarbamoyl-lower alkyl wherein heterocyclyl is selected from pyrrolyl, furyl, thienyl, imidazolyl, pyrazolyl, oxazolyl, thiazolyl, pyridyl, pyrazinyl, pyrimidinyl, indolyl, quinolyl, isoquinolyl, quinoxalinyl, β-carbolinyl and a benzo-fused, cyclopenta-, cyclohexa- or cyclohepta-fused derivative of those radicals, which may also be fully or partially saturated, sulfamoyl-lower alkyl, N-(phenyl- or naphthyl-lower alkyl)sulfamoyl-lower alkyl, sulfamoyl-lower alkyl substituted at the nitrogen atom by one radical selected from ethylene, trimethylene, tetramethylene and pentamethylene wherein a carbon atom may have been replaced by nitrogen, lower alkyl-substituted nitrogen, oxygen, sulfur or by sulfur mono- or di-substituted by oxygen, it also being possible for the radical so formed to be fully or partially unsaturated, oxo-lower alkyl (wherein oxo is not bonded to the carbon atom that is linked to the nitrogen atom that carries $R_7$), cyano-lower alkyl, hydroxy-carboxy-lower alkyl, α-naphthyloxy-carboxy-lower alkyl, hydroxy-lower alkoxycarbonyl-lower alkyl, α-naphthyloxy-lower alkoxycarbonyl-lower alkyl, lower alkylcarboxyhalo-lower alkyl, α-naphthyloxyethoxycarbonyl-lower alkyl, α-naphthyloxy-benzyloxycarbonyl-lower alkyl, esterified hydroxy-lower alkoxycarbonyl-lower alkyl wherein the hydroxy group is esterified by lower alkanoyl, cycloalkyl-lower alkanoyl wherein cycloalkyl has from 3 to 7 carbon atoms, bicycloalkyl-lower alkanoyl wherein bicycloalkyl has from 5 to 10 carbon atoms, tricycloalkyl-lower alkanoyl wherein tricycloalkyl has from 8 to 10 carbon atoms, aryl-lower alkanoyl wherein aryl has from 6 to 14 carbon atoms and may be unsubstituted or mono- to tri-substituted by lower alkyl, hydroxy, lower alkoxy, carbamoyl-lower alkoxy, N-lower alkylcarbamoyl-lower alkoxy or N,N-di-lower alkylcarbamoyl-lower alkoxy, amino, mono- or di-lower alkylamino, halogen, carboxy, lower alkoxycarbonyl, phenyl-, naphthyl- or fluorenyl-lower alkoxycarbonyl, lower alkanoyl, lower alkylsulfonyl, phosphono, hydroxy-lower alkoxyphosphoryl, di-lower alkoxyphosphoryl, carbamoyl, sulfamoyl, nitro and/or by cyano, lower alkoxycarbonyl, 2-halo-lower alkoxycarbonyl or by phenyl- or fluorenyl-lower alkoxycarbonyl, dihydroxy-carboxy-lower alkyl, dihydroxy-lower alkoxycarbonyl-lower alkyl, dihydroxy-lower alkoxycarbonyl-lower alkyl esterified by lower alkanoyl, lower alkoxycarbonyl, phenyl- or fluorenyl-lower alkoxycarbonyl, lower alkylsulfonyl or by toluenesulfonyl, α-naphthyloxy-di-lower alkylamino-lower alkyl, α-naphthyloxy-carbamoyl-lower alkyl, α-naphthyloxy-oxo-lower alkyl (wherein oxo is not bonded to the carbon atom that is linked to the nitrogen atom that carries $R_7$), or α-naphthyloxy-cyano-lower alkyl, and the salts of the mentioned compounds where salt-forming groups are present.

Special preference is given to the compounds of formula I wherein $R_1$ and $R_9$ are each independently of the other hydrogen; lower alkanoyl, such as formyl, acetyl, propionyl, butyryl or pivaloyl, especially acetyl; aryl-lower alkanoyl wherein aryl is phenyl, indenyl, indanyl, naphthyl, anthryl, phenanthryl, acenaphthyl or fluorenyl and may be unsubstituted or especially mono- to tri-substituted by lower alkyl, for example methyl, ethyl or propyl, halo-lower alkyl, for example trifluoromethyl, phenyl, 1- or 2-naphthyl, hydroxy, lower alkoxy, for example methoxy, carbamoyl-lower alkoxy, N-lower alkylcarbamoyl-lower alkoxy, N,N-dilower alkylcarbamoyl-lower alkoxy, amino, mono- or di-lower alkylamino, lower alkanoylamino, for example pivaloylamino, halogen, for example fluorine, chlorine or bromine, carboxy, lower alkoxycarbonyl, such as tert-butoxycarbonyl, phenyl-, naphthyl- or fluorenyl-lower alkoxycarbonyl, such as benzyloxycarbonyl, lower alkanoyl, sulfo, lower alkylsulfonyl, for example methylsulfonyl, phosphono, hydroxy-lower alkoxyphosphoryl, di-lower alkoxyphosphoryl, carbamoyl, mono- or di-lower alkylcarbamoyl, sulfamoyl, mono- or di-lower alkylaminosulfonyl, nitro and/or by cyano, wherein phenyl may be present up to three times, for example in diphenyl-, dibenzyl- or triphenyl-lower alkanoyl, such as diphenyl-, dibenzyl- or triphenyl-acetyl, and wherein lower alkanoyl is unsubstituted or substituted by carbamoyl or by carbamoyl substituted at the nitrogen atom by one or two radicals selected from lower alkyl, carboxy-lower alkyl, lower alkoxycarbonyl-lower alkyl, di-lower alkylamino-lower alkyl, aminocarboxy-lower alkyl, hydroxy-lower alkyl and di-lower alkoxy-lower alkyl, for example by carbamoyl, carbamoyl substituted by one or two radicals selected from methyl, ethyl, propyl, isopropyl, n-butyl, isobutyl, sec-butyl, tert-butyl, n-pentyl, isopentyl, neopentyl, tert-pentyl, n-hexyl, isohexyl and n-heptyl, for example in N-methylcarbamoyl, N-n-butylcarbamoyl or N,N-dimethylcarbamoyl, by carboxymethylcarbamoyl (glycinylcarbonyl), by tert-butoxycarbonylmethylcarbamoyl, by 2-dimethylaminoethyl, by 5-amino-5-carboxypentyl, by hydroxymethyl, by hydroxyethyl or by 2-(2,2-dimethoxyethyl)carbamoyl, for example 4-chloro-, 4-methoxy- or 4-nitro-benzoyl, naphthylcarbonyl, such as α- or β-naphthylcarbonyl, indenylcarbonyl, such as 1-, 2- or 3-indenylcarbonyl, indanylcarbonyl, such as 1- or 2-indanylcarbonyl, phenanthrenylcarbonyl, such as 9-phenanthrenylcarbonyl, phenyl-lower alkanoyl, such as phenylacetyl or 3-phenylpropionyl, phenyl-lower alkanoyl wherein the lower alkanoyl radical is substituted by carbamoyl, such as 2(R,S)-carbamoyl-3-phenylpropionyl, α-naphthylacetyl, β-naphthylacetyl, lower alkylphenylacetyl, such as 4-methylphenylacetyl, lower alkoxyphenylacetyl, such as 4-methoxyphenylacetyl, 3-(p-hydroxyphenyl)-propionyl, diphenylacetyl, di-(4-methoxyphenyl)-acetyl, triphenylacetyl, 2,2-dibenzylacetyl, 3-α- or 3-β-naphthylpropionyl, 3-phenyl- or 3-α-naphthyl-2-carbamoylpropionyl, 3-phenyl- or 3-α-naphthyl-2-tert-butylcarbamoyl-propionyl, 3-phenyl- or 3-α-naphthyl-2-(2-dimethylaminoethyl)carbamoylpropionyl, 3-α-naphthyl-2-(carboxy- or tert-butoxycarbonyl)methylcarbamoyl-propionyl, 3-phenyl- or 3-α-naphthyl-2-(3-hydroxy-2-propyl)carbamoyl-propionyl, 3-phenyl- or 3-α-naphthyl-2-(2,2-dimethoxyethyl)-carbamoylpropionyl, 3-phenyl- or 3-α-naphthyl-2-(5-amino-5-carboxypentyl)-carbamoylpropionyl, especially phenyl-lower alkanoyl, such as phenylacetyl, or phenyl-lower alkanoyl wherein the lower alkanoyl radical is substituted by carbamoyl, such as 2(R,S)-carbamoyl-3-phenyl-propionyl; heterocyclyl-lower alkanoyl wherein lower alkanoyl is unsubstituted and wherein heterocyclyl is selected from thienyl, furyl, pyranyl, pyrrolyl, imidazolyl, pyrazolyl, oxazolyl, isoxazolyl, thiazolyl, furazanyl, tetrazolyl, pyridyl, pyrazinyl, pyrimidinyl, pyridazinyl, azepinyl, indolyl, benzimidazolyl, 1H-indazolyl, quinolyl, isoquinolyl, quinoxalinyl, quinazolinyl, cinnolyl, purinyl, pteridinyl, naphthyridinyl, 4H-quinolizinyl, 3,1-benzofuranyl, 4,1-benzoxazinyl, 4,1-benzothiazinyl, cyclohexa[b]pyrrolyl, cyclohepta[b]pyrrolyl, cyclohexa[d]pyrazolyl, cyclohexa[b]pyridyl, cyclohexa[b]pyrazinyl, cyclohexa[b]pyrimidinyl, cyclohexa[b]-1,4-oxazinyl, cyclohexa[b]-1,4-thiazinyl, pyrrolidinyl, pyrrolinyl, imidazolidyl, 2-imidazolinyl, 2,3-dihydropyridyl, piperidyl, piperazinyl, 2,3,5,6-tetrahydropyrazinyl, morpholinyl, thiomorpholinyl, S,S-dioxo-thiomorpholinyl, indolinyl, isoindolinyl, 4,5,6,7-tetrahydroindolyl, 1,2,3,4-tetrahydroquinolyl, 1,2,3,4-tetrahydroisoquinolyl, chromanyl, thiochromanyl, 1,2,3,4-tetrahydro-3,1-benzodiazinyl, 3,4-dihydro-3H-4,1-benzoxazinyl and 3,4-dihydro-3H-4,1-benzothiazinyl, the mentioned heterocyclyl radicals being unsubstituted or substituted by lower alkyl, for example methyl, phenyl, 1- or 2-naphthyl, phenyl-lower alkyl, for example benzyl, hydroxy-lower alkyl, for example hydroxymethyl or 2-hydroxyethyl, lower alkoxy-lower alkyl, for example methoxymethyl or 2-methoxyethyl, phenoxy- or naphthyloxy-lower alkyl, for example 2-phenoxyethyl, 1- or 2-naphthyloxymethyl, phenyl-lower alkoxy- or naphthyl-lower alkoxy-lower alkyl, for example benzyloxy-lower alkyl, lower alkanoyloxy-lower alkyl, for example acetoxymethyl, phenyl- or naphthyl-lower alkanoyloxy-lower alkyl, for example benzoyloxy-, phenylacetoxy- or 1- or 2-naphthoyloxy-methyl, -2-ethyl or -2-(2,2-dimethylethyl), lower alkoxycarbonyloxy-lower alkyl, for example tert-butoxy-lower alkyl, phenyl-, naphthyl- or fluorenyl-lower alkoxycarbonyloxy-lower alkyl, for example 2-benzyloxycarbonyloxyethyl or 9-fluorenylmethoxycarbonyloxyethyl, amino-lower alkyl, for example aminomethyl, 2-aminoethyl or 2-aminopropyl, carboxy-lower alkyl, for example carboxymethyl or 2-carboxyethyl, hydroxy, lower alkoxy, for example methoxy or ethoxy, phenyl- or naphthyl-lower alkoxy, for example benzyloxy or 1- or 2-naphthyloxy, amino, lower alkylamino, for example methyl-, ethyl- or tert-butyl-amino, di-lower alkylamino, for example dimethyl- or diethyl-amino, carboxy, lower alkoxycarbonyl, for example methoxy-, isopropoxy-, sec-butoxy- or tert-butoxy-carbonyl, phenyl- or naphthyl-lower alkoxycarbonyl, for example benzyloxycarbonyl, halogen, for example fluorine, chlorine, bromine or iodine, especially chlorine or bromine, lower alkanoyl, for example acetyl or pivaloyl, lower alkylsulfonyl, for example methyl- or ethyl-sulfonyl, phosphono, hydroxy-lower alkoxyphosphoryl or dialkoxyphosphoryl, for example dimethoxy- or diethoxy-phosphoryl, carbamoyl, mono- or di-lower alkylcarbamoyl, for example N-methylcarbamoyl, N-n-butylcarbamoyl or N,N-dimethylcarbamoyl, hydroxy- or carboxy-lower alkylcarbamoyl, for example hydroxy- or carboxy-methylcarbamoyl or hydroxy- or carboxy-ethylcarbamoyl, sulfamoyl, nitro, oxo and/or by cyano, heterocyclyl-lower alkanoyl being selected especially from unsubstituted or lower alkyl- or phenyl-substituted pyrrolylcarbonyl, for example 2- or 3-pyrrolylcarbonyl, 4- or 5-methylpyrrolylcarbonyl or 4- or 5-phenylpyrrolyl-2-carbonyl, thienylcarbonyl, such as 2-thienylcarbonyl, furylcarbonyl, such as 2-furylcarbonyl, pyridylcarbonyl, such as 2-, 3- or 4-pyridylcarbonyl, pyrimidin-1-ylcarbonyl, indolylcarbonyl that is unsubstituted or substituted by lower alkyl, such as methyl, phenyl-lower alkyl, such as benzyl, lower alkoxy, such as methoxy, phenyl-lower alkoxy, such as benzyloxy, or by halogen, such as chlorine, such as 2-, 3- or 5-indolylcarbonyl, 1-methyl-, 5-methyl-, 5-methoxy-, 5-benzyloxy-, 5-chloro- or 4,5-dimethyl-indolyl-2-carbonyl, 1-benzylindolyl-2- or -3-carbonyl, 4,5,6,7-tetrahydroindolyl-2-carbonyl, unsubstituted or hydroxy-substituted quinolyl-lower alkanoyl, for example quinolylcarbonyl, such as 2-, 3- or 4-quinolylcarbonyl or 4-hydroxyquinolyl-2-carbonyl, unsubstituted or hydroxy-substituted isoquinolylcarbonyl, such as 1-, 3- or 4-isoquinolylcarbonyl or 1-oxo-1,2-dihydroisoquinolyl-3-carbonyl, 2-quinoxalinylcarbonyl, 2-(3,1-benzofuranyl)-carbonyl, cyclohepta[b]pyrrolyl-5-carbonyl, 3-chromanylcarbonyl, 3-thiochromanylcarbonyl, pyrrolidinyl-3-carbonyl, hydroxypyrrolidinylcarbonyl, such as 3- or 4-hydroxypyrrolidinyl-2-carbonyl, oxopyrrolidinylcarbonyl, such as 5-oxopyrrolidinyl-2-carbonyl, piperidylcarbonyl, such as piperidinocarbonyl or 2-, 3- or 4-piperidylcarbonyl, pyrazinylcarbonyl, such as pyrazin-1-ylcarbonyl, piperazinylcarbonyl, such as piperazin-1-ylcarbonyl, morpholinyl-lower alkanoyl, for example morpholinylcarbonyl, such as morpholinocarbonyl, thiomorpholinyl-lower alkanoyl, for example thiomorpholinylcarbonyl, such as thiomorpholinocarbonyl, S,S-dioxothiomorpholinylcarbonyl, such as S,S-dioxothiomorpholinocarbonyl, indolinylcarbonyl, such as 2- or 3-indolinylcarbonyl, 1,2,3,4-tetrahydroquinolylcarbonyl, such as 1,2,3,4-tetrahydroquinolyl-2-, -3- or -4-carbonyl, 1,2,3,4-tetrahydroisoquinolylcarbonyl, such as 1,2,3,4-tetrahydroisoquinolyl-1-, -3- or -4-carbonyl or 1-oxo-1,2,3,4-tetrahydroisoquinolyl-3-carbonyl, tetrazolyl-lower alkanoyl, such as 3-(tetrazol-1-yl)propionyl, and pyridyl-lower alkanoyl, for example pyridylacetyl, such as 2-, 3- or 4-pyridylacetyl, heterocyclyl-lower alkanoyl being selected more especially from morpholino-lower alkanoyl, such as morpholinocarbonyl, thiomorpholino-lower alkanoyl, such as thiomorpholinocarbonyl, pyridyl-lower alkanoyl, such as 2-, 3- or 4-pyridylacetyl, quinolinyl-lower alkanoyl, such as quinoline-2-carbonyl, and tetrazolyl-lower alkanoyl, such as 3-tetrazol-1-ylpropionyl; amino-lower alkanoyl substituted at the amino nitrogen atom by heterocyclyl-lower alkanoyl wherein heterocyclyl-lower alkanoyl is as defined for heterocyclyl-lower alkanoyl $R_1$ and $R_9$, especially amino-lower alkanoyl substituted at the amino nitrogen atom by N-morpholino- or N-thiomorpholino-carbonyl, especially N-morpholino- or N-thiomorpholino-carbonylamino-lower alkanoyl, such as N-morpholino- or N-thiomorpholino-carbonylamino-acetyl; halo-lower alkanoyl containing up to three halogen atoms, especially α-haloacetyl, such as α-fluoro-, α-chloro-, α-bromo-, α-iodo-, α,α,α-trifluoro- or α,α,α-trichloro-acetyl, or halopropionyl, such as β-chloro- or β-bromo-propionyl, for example trifluoroacetyl; (N-heterocyclyl-lower alkylcarbamoyl)-lower alkanoyl wherein heterocyclyl is selected from pyrrolyl, furyl, thienyl, imidazolyl, pyrazolyl, oxazolyl, thiazolyl, pyridyl, pyrazinyl, pyrimidinyl, indolyl, quinolyl, isoquinolyl, quinoxalinyl, β-carbolinyl and a benzo-fused, cyclopenta-, cyclohexa- or cyclohepta-fused derivative of those radicals, which may also be fully or partially saturated, from morpholine and from thiomorpholine, especially 2-(N-morpholino-lower alkylcarbamoyl)-lower alkanoyl, such as 2(R,S)-(N-(2-morpholinoethyl)-carbamoyl)-3-methyl-butyryl, or 2-(N-(pyridyl-lower alkyl)-carbamoyl)-lower alkanoyl, such as 2(R,S)-(N-(2-pyridylmethyl)-carbamoyl)-3-methyl-butyryl; lower alkoxycarbonyl, especially methoxy-, ethoxy-, isopropoxy-, isobutoxy- or tert-lower alkoxy-carbonyl, for example methoxycarbonyl, tert-butoxycarbonyl or isobutoxycarbonyl; aryl-lower alkoxy-carbonyl wherein aryl is phenyl, biphenylyl, 1- or 2-naphthyl, fluorenyl, or phenyl that is mono- or poly-substituted by lower alkyl, for example methyl or tert-butyl, hydroxy, lower alkoxy, for example methoxy, ethoxy or tert-butoxy, halogen, for example chlorine or bromine, and/or by nitro, for example phenyl-lower alkoxycarbonyl, such as benzyloxycarbonyl, 4-methoxybenzyloxycarbonyl, 4-nitrobenzyloxycarbonyl or fluorenyl-lower alkoxycarbonyl, such as 9-fluorenylmethoxycarbonyl, especially phenyl-lower alkoxycarbonyl, such as benzyloxycarbonyl; heterocyclyl-lower alkoxycarbonyl wherein heterocyclyl is selected from pyrrolyl, furyl, thienyl, imidazolyl, pyrazolyl, oxazolyl, thiazolyl, pyridyl, pyrazinyl, pyrimidinyl, indolyl, quinolyl, isoquinolyl, quinoxalinyl, β-carbolinyl and a benzo-fused, cyclopenta-, cyclohexa- or cyclohepta-fused derivative of those radicals, which may also be fully or partially saturated, and from morpholinyl and thiomorpholinyl and is unsubstituted or substituted by lower alkyl, for example methyl, such as 1-methylpyrrolidin-2-yl-methoxycarbonyl, 2-furylmethoxycarbonyl, 2-tetrahydrofuryl-methoxycarbonyl, 1-methyl-2-piperidyl-methoxycarbonyl or 2-morpholino-ethoxycarbonyl, or 2-, 3- or 4-pyridylmethoxycarbonyl, especially tetrahydrofuranyl-lower alkoxycarbonyl, such as 2(R,S)-tetrahydrofuranylmethoxycarbonyl; lower alkylsulfonyl, for example methyl- or ethyl-sulfonyl, such as methylsulfonyl; morpholinosulfonyl, thiomorpholinosulfonyl, piperidinosulfonyl, 4-methylpiperazinylsulfonyl or piperazinosulfonyl; N-heterocyclyl-lower alkyl-N-lower alkylcarbamoyl wherein heterocyclyl is selected from thienyl, furyl, pyranyl, pyrrolyl, imidazolyl, pyrazolyl, oxazolyl, isoxazolyl, thiazolyl, furazanyl, pyridyl, pyrazinyl, pyrimidinyl, pyridazinyl, azepinyl, indolyl, benzimidazolyl, 1H-indazolyl, quinolyl, isoquinolyl, quinoxalinyl, quinazolinyl, cinnolyl, purinyl, pteridinyl, naphthyridinyl, 4H-quinolizinyl, 3,1-benzofuranyl, benz[e]indolyl, 4,1-benzoxazinyl, 4,1-benzothiazinyl, carbazolyl, β-carbolinyl, phenazinyl, phenanthridyl, acridyl, phenoxazinyl, phenothiazinyl, 1-azaacenaphthenyl, cyclohexa[b]pyrrolyl, cyclohepta[b]pyrrolyl, cyclohexa[d]pyrazolyl, cyclohexa[b]pyridyl, cyclohexa[b]pyrazinyl, cyclohexa[b]pyrimidinyl, cyclohexa[b]-1,4-oxazinyl, cyclohexa[b]-1,4-thiazinyl, pyrrolidinyl, pyrrolinyl, imidazolidinyl, 2-imidazolinyl, 2,3-dihydropyridyl, piperidyl, piperazinyl, 2,3,5,6-tetrahydropyrazinyl, morpholinyl, thiomorpholinyl, S,S-dioxothiomorpholinyl, indolinyl, isoindolinyl, 4,5,6,7-tetrahydroindolyl, 1,2,3,4-tetrahydroquinolyl, 1,2,3,4-tetrahydroisoquinolyl, chromanyl, thiochromanyl, 1,2,3,4-tetrahydro-3,1-benzodiazinyl, 3,4-dihydro-3H-4,1-benzoxazinyl, 3,4-dihydro-3H-4,1-benzothiazinyl, 2,3,4,5-tetrahydro-1H-5,1-benzazepinyl and 5,6-dihydrophenanthridinyl, the mentioned radicals being unsubstituted or substituted by lower alkyl, for example methyl, phenyl, 1- or 2-naphthyl, phenyl-lower alkyl, for example benzyl, hydroxy-lower alkyl, for example hydroxymethyl or 2-hydroxyethyl, lower alkoxy-lower alkyl, for example methoxymethyl or 2-methoxyethyl, phenoxy- or naphthyloxy-lower alkyl, for example 2-phenoxyethyl, 1- or 2-naphthyloxymethyl, phenyl-lower alkoxy- or naphthyl-lower alkoxy-lower alkyl, for example benzyloxy-lower alkyl, lower alkanoyloxy-lower alkyl, for example acetoxymethyl, phenyl- or naphthyl-lower alkanoyloxy-lower alkyl, for example benzoyloxy-, phenylacetoxy- or 1- or 2-naphthoyloxy-methyl, -2-ethyl or -2-(2,2-dimethylethyl), lower alkoxycarbonyloxy-lower alkyl, for example tert-butoxy-lower alkyl, phenyl-, naphthyl- or fluorenyl-lower alkoxycarbonyloxy-lower alkyl, for example 2-benzyloxycarbonyloxyethyl or 9-fluorenylmethoxycarbonyloxyethyl, amino-lower alkyl, for example aminomethyl, 2-aminoethyl or 2-aminopropyl, carboxy-lower alkyl, for example carboxymethyl or 2-carboxyethyl, hydroxy, lower alkoxy, for example methoxy or ethoxy, phenyl- or naphthyl-lower alkoxy, for example benzyloxy or 1- or 2-naphthylmethoxy, amino, lower alkylamino, for example methyl-, ethyl- or tert-butyl-amino, di-lower alkylamino, for example dimethyl- or diethyl-amino, carboxy, lower alkoxycarbonyl, for example methoxy-, isopropoxy-, sec-butoxy- or tert-butoxy-carbonyl, phenyl- or naphthyl-lower alkoxycarbonyl, for example benzyloxycarbonyl, halogen, for example fluorine, chlorine, bromine or iodine, especially chlorine or bromine, lower alkanoyl, for example acetyl or pivaloyl, lower alkylsulfonyl, for example methyl- or ethyl-sulfonyl, phosphono, hydroxy-lower alkoxyphosphoryl or dialkoxyphosphoryl, for example dimethoxy- or diethoxy-phosphoryl, carbamoyl, mono- or di-lower alkylcarbamoyl, for example N-methylcarbamoyl, N-n-butylcarbamoyl or N,N-dimethylcarbamoyl, hydroxy- or carboxy-lower alkylcarbamoyl, for example hydroxy- or carboxy-methylcarbamoyl or hydroxy- or carboxy-ethylcarbamoyl, sulfamoyl, nitro, oxo and/or by cyano, and is especially pyridyl, such as 2-, 3- or 4-pyridyl, especially N-pyridyl-lower alkyl-N-lower alkylcarbamoyl, such as N-(2-, 3- or 4-pyridylmethyl)-N-methylcarbamoyl; or an acyl radical of an amino acid the amino function of which is free or acylated by one of the other radicals mentioned hitherto for $R_1$ and $R_9$, the amino acids being selected from glycine (H-Gly-OH), alanine (H-Ala-OH), valine (H-Val-OH), norvaline (α-aminovaleric acid), leucine (H-Leu-OH), isoleucine (H-Ile-OH), norleucine (α-aminohexanoic acid, H-Nle-OH), serine (H-Ser-OH), homoserine (α-amino-γ-hydroxybutyric acid), threonine (H-Thr-OH), methionine (H-Met-OH), cysteine (H-Cys-OH), proline (H-Pro-OH), trans-3- and trans-4-hydroxyproline, phenylalanine (H-Phe-OH), tyrosine (H-Tyr-OH), 4-aminophenylalanine, 4-chlorophenylalanine, 4-carboxyphenylalanine, β-phenylserine (β-hydroxyphenylalanine), phenylglycine, α-naphthylalanine (H-Nal-OH), cyclohexylalanine (H-Cha-OH), cyclohexylglycine, tryptophan (H-Trp-OH), indoline-2-carboxylic acid, 1,2,3,4-tetrahydroisoquinoline-3-carboxylic acid, aspartic acid (H-Asp-OH), asparagine (H-Asn-OH), aminomalonic acid, aminomalonic acid monoamide, glutamic acid (H-Glu-OH), glutamine (H-Gln-OH), histidine (H-His-OH), arginine (H-Arg-OH), lysine (H-Lys-OH), δ-hydroxylysine, ornithine (α,δ-diaminovaleric acid), 3-aminopropanoic acid, α,γ-diaminobutyric acid and α,β-diaminopropionic acid, more especially the radical of an amino acid selected from valine, alanine, leucine, isoleucine, glycine, glutamic acid and asparagine, it being possible for each of the mentioned amino acids (with the exception of glycine) to be in the D-, L- or (D,L)-form, preferably (with the exception of Val, which may also be in the (D)- or (D,L)-form) in the L-form, and the α-amino group being unsubstituted or N-acylated by one of the radicals mentioned above for $R_1$ and $R_9$, especially by lower alkanoyl, phenyl-lower alkanoyl, such as phenylacetyl, phenyl-lower alkanoyl wherein the lower alkanoyl radical is substituted by carbamoyl, such as 2(R,S)-carbamoyl-3-phenylpropionyl, morpholino-lower alkanoyl, such as morpholinocarbonyl, thiomorpholino-lower alkanoyl, such as thiomorpholinocarbonyl, pyridyl-lower alkanoyl, such as 2-, 3- or 4-pyridylacetyl, quinolinyl-lower alkanoyl, such as quinoline-2-carbonyl, tetrazolyl-lower alkanoyl, such as 3-tetrazol-1-ylpropionyl, amino-lower alkanoyl substituted at the amino nitrogen atom by N-morpholino- or N-thiomorpholino-carbonyl, for example N-morpholino- or N-thiomorpholino-carbonylamino-lower alkanoyl, such as N-morpholino- or N-thiomorpholino-carbonylaminoacetyl, halo-lower alkanoyl containing up to three halogen atoms, for example α-haloacetyl, such as α-fluoro-, α-chloro-, α-bromo-, α-iodo-, α,α,α-trifluoro- or α,α,α-trichloro-acetyl, or halopropionyl, such as β-chloro- or β-bromo-propionyl, especially trifluoroacetyl, 2-(N-morpholino-lower alkylcarbamoyl)-lower alkanoyl, such as 2(R,S)-(N-(2-morpholinoethyl)-carbamoyl)-3-methyl-butyryl, 2-(N-(pyridyl-lower alkyl)-carbamoyl)-lower alkanoyl, such as 2(R,S)-(N-(2-pyridylmethyl)-carbamoyl)-lower alkanoyl, lower alkoxycarbonyl, phenyl-lower alkoxycarbonyl, tetrahydrofuranyl-lower alkoxycarbonyl, such as 2(R,S)-tetrahydrofuranylmethoxycarbonyl, lower alkylsulfonyl or N-pyridyl-lower alkyl-N-lower alkylcarbamoyl, such as N-(2-, 3- or 4-pyridylmethyl)-N-methylcarbamoyl, greatest preference being given to N-morpholinocarbonyl-glycine, N-(N-(2-, 3- or 4-pyridyl)methyl-N-methylaminocarbonyl)-glycine, valine, N-(trifluoroacetyl)-valine, N-phenylacetyl-valine, N-(2- or 3-pyridyl)-acetyl-valine, N-acetyl-valine, N-(2-carbamoyl-3-phenylpropionyl)-valine, N-(2(R,S)-carbamoyl-3-phenylpropionyl)-valine, N-(2- or 3-pyridylacetyl)-valine, N-2-tetrahydrofurylmethoxycarbonyl-valine, N-(3-(tetrazol-1-yl)-propionyl)-valine, N-(quinoline-2-carbonyl)-valine, N-methoxycarbonyl-valine, N-isobutoxycarbonyl-valine, N-tert-butoxycarbonyl-valine, N-benzyloxycarbonyl-valine, N-(morpholinocarbonyl)-valine, N-(thiomorpholinocarbonyl)valine, N-(S,S-dioxothiomorpholinocarbonyl)-valine, N-(N-2-pyridylmethyl-N-methylaminocarbonyl)-valine, N-morpholinocarbonylaminoacetyl-valine, N-methylsulfonyl-valine, morpholinosulfonyl-valine, N-acetyl-isoleucine, N-propionyl-isoleucine, N-(benzyloxycarbonyl)isoleucine, N-benzyloxycarbonyl-glutamic acid, asparagine, N-benzyloxycarbonylasparagine and quinoline-2-carbonyl-asparagine, wherein each of the amino acid radicals is preferably in the (L)- or (D,L)-form, and in the case of valine also in the (D)-form; with the proviso that not more than one of the radicals $R_1$ and $R_9$ is hydrogen, $R_2$, $R_4$, $R_6$ and $R_8$ are hydrogen, $R_3$ is lower alkyl, such as isobutyl or n-butyl; cycloalkyl-lower alkyl wherein cycloalkyl has from 3 to 7 carbon atoms and is unsubstituted or mono- to tri-substituted by lower alkyl, such as isopropyl, halo-lower alkyl, such as trifluoromethyl, hydroxy, lower alkoxy, carbamoyl-lower alkoxy, N-lower alkylcarbamoyl-lower alkoxy or N,N-di-lower alkylcarbamoyl-lower alkoxy, amino, mono- or di-lower alkylamino, halogen, such as fluorine, chlorine or bromine, carboxy, lower alkoxycarbonyl, phenyl-, naphthyl- or fluorenyl-lower alkoxycarbonyl, lower alkanoyl, lower alkylsulfonyl, for example methylsulfonyl, phosphono, hydroxy-lower alkoxyphosphoryl or di-lower alkoxyphosphoryl, carbamoyl, mono- or di-lower alkylaminocarbamoyl, sulfamoyl, mono- or di-lower alkylsulfamoyl, nitro and/or by cyano and is bonded, preferably terminally, to lower alkyl, especially methyl, ethyl, n-propyl, isopropyl, n-butyl, isobutyl or tert-butyl, such as cyclobutyl-, cyclopentyl-, cyclohexyl- or cycloheptyl-lower alkyl, such as -methyl or -ethyl, especially cyclohexyl-lower alkyl, more especially cyclohexylmethyl; or aryl-lower alkyl wherein aryl is phenyl, indenyl, indanyl, naphthyl, anthryl, phenanthryl, acenaphthyl or fluorenyl and is unsubstituted or substituted by lower alkyl, for example methyl, ethyl or isopropyl, halo-lower alkyl, such as trifluoromethyl, phenyl, 1- or 2-naphthyl, hydroxy, lower alkoxy, for example methoxy, carbamoyl-lower alkoxy, N-lower alkylcarbamoyl-lower alkoxy or N,N-di-lower alkylcarbamoyl-lower alkoxy, amino, mono- or di-lower alkylamino, lower alkanoylamino, for example pivaloylamino, halogen, for example fluorine or chlorine, carboxy, lower alkoxycarbonyl, benzyl-, naphthyl- or fluorenyl-lower alkoxycarbonyl, lower alkanoyl, sulfo, lower alkylsulfonyl, phosphono, hydroxy-lower alkoxyphosphoryl or di-lower alkoxyphosphoryl, carbamoyl, mono- or di-lower alkylcarbamoyl, sulfamoyl, mono- or di-lower alkylsulfamoyl, nitro and/or by cyano, wherein phenyl may be present up to three times, such as in diphenyl-, dibenzyl- or triphenyl-lower alkyl, for example diphenyl-, dibenzyl- or triphenyl-2-ethyl, especially phenyl-lower alkyl that is unsubstituted or substituted by the mentioned substituents, especially benzyl, 4-fluoro- or 4-cyano-benzyl, $R_5$ is hydroxy, and $R_7$ is unsubstituted lower alkyl, especially isobutyl or n-butyl; or cycloalkyl-lower alkyl, for example as last described for cycloalkyl-lower alkyl $R_3$, especially cyclohexyl-lower alkyl, more especially cyclohexylmethyl; or aryl-lower alkyl as last described for aryl-lower alkyl $R_3$, especially phenyl-lower alkyl that is unsubstituted or substituted by the mentioned substituents, more especially benzyl, 4-fluoro- or 4-cyano-benzyl, or a salt thereof where at least one salt-forming group is present.

Special preference is given also to the compounds of formula I wherein $R_1$ is lower alkoxycarbonyl, phenyl-lower alkoxycarbonyl, the monovalent radical, bonded via the carboxy group, of an aliphatic amino acid selected from valine, alanine, leucine and isoleucine, or the radical, bonded via the carboxy group, of an aliphatic amino acid as defined above that is acylated at the amino nitrogen atom by one of the radicals phenyl-lower alkanoyl, morpholinyl-lower alkanoyl, thiomorpholinyl-lower alkanoyl, S,S-dioxothiomorpholinyl-lower alkanoyl, pyridyl-lower alkanoyl, lower alkoxycarbonyl and phenyl-lower alkoxycarbonyl, all the mentioned amino acids being in the D-, D,L- or L-form, preferably in the L-form, $R_2$ is hydrogen, $R_3$ is phenyl-lower alkyl, $R_4$ is hydrogen, $R_5$ is hydroxy, $R_6$ is hydrogen, $R_7$ is lower alkyl, cyclohexyl-lower alkyl or phenyl-lower alkyl, $R_8$ is hydrogen and $R_9$ is one of the radicals mentioned for $R_1$ and the asymmetric carbon atoms carrying the radicals $R_3$ and $R_5$ are in the S-configuration, and the pharmacologically acceptable salts of such compounds.

Very special preference is given to the compounds of formula I wherein $R_1$ is tert-butoxycarbonyl, benzyloxycarbonyl, the monovalent radical, bonded via the carboxy group, of the amino acid valine or the radical, bonded via the carboxy group, of alanine acylated at the amino nitrogen atom by one of the radicals phenylacetyl, 3-pyridylacetyl, morpholinocarbonyl, thiomorpholinocarbonyl, tert-butoxycarbonyl and benzyloxycarbonyl, $R_2$ is hydrogen, $R_3$ is benzyl, $R_4$ is hydrogen, $R_5$ is hydroxy, $R_6$ is hydrogen, $R_7$ is isobutyl, cyclohexylmethyl or benzyl, $R_8$ is hydrogen and $R_9$ is one of the radicals mentioned for $R_1$ and the asymmetric carbon atoms carrying the radicals $R_3$ and $R_5$ are in the S-configuration, and the pharmacologically acceptable salts of such compounds.

Great preference is given to the compounds of formula I wherein $R_1$ and $R_9$ are each independently of the other hydrogen, lower alkanoyl, such as acetyl, phenyl-lower alkanoyl, such as phenylacetyl, phenyl-lower alkanoyl wherein the lower alkanoyl radical is substituted by carbamoyl, such as 2(R,S)-carbamoyl-3-phenyl-propionyl, morpholino-lower alkanoyl, such as morpholinocarbonyl, thiomorpholino-lower alkanoyl, such as thiomorpholino-carbonyl, pyridyl-lower alkanoyl, such as 2-, 3- or 4-pyridylacetyl, quinolyl-lower alkanoyl, such as quinoline-2-carbonyl, tetrazolyl-lower alkanoyl, such as 3-tetrazol-1-yl-propionyl, amino-lower alkanoyl substituted at the amino. nitrogen atom by N-morpholino- or N-thiomorpholino-carbonyl, for example N-morpholino- or N-thiomorpholino-carbonylamino-lower alkanoyl, such as N-morpholino- or N-thiomorpholinocarbonylamino-acetyl, halo-lower alkanoyl containing up to three halogen atoms, such as trifluoroacetyl, 2-(N-morpholino-lower alkylcarbamoyl)-lower alkanoyl, such as 2(R,S)-(N-(2-morpholinoethyl)-carbamoyl-3-methyl-butyryl, 2-(N-pyridyl-lower alkylcarbamoyl)-lower alkanoyl, such as 2(R,S)-(N-(2-pyridylmethyl)-carbamoyl)-3-methylbutyryl, lower alkoxycarbonyl, such as methoxy-, isobutoxy- or tert-lower alkoxycarbonyl, phenyl-lower alkoxycarbonyl, such as benzyloxycarbonyl, tetrahydrofuranyl-lower alkoxycarbonyl, such as 2(R,S)-tetrahydrofuranyl-methoxycarbonyl, lower alkylsulfonyl, for example methyl- or ethyl-sulfonyl, morpholinosulfonyl, thiomorpholinosulfonyl, N-pyridyl-lower alkyl-N-lower alkylcarbamoyl, or an acyl radical of an amino acid selected from glycine, alanine, valine, leucine, isoleucine, glutamic acid and asparagine in the (D)-, (L)- or (D,L)-form, wherein the α-amino group is unsubstituted or acylated by one of the other radicals $R_1$ or $R_2$ mentioned hitherto, greatest preference being given to N-morpholinocarbonyl-glycine, N-(N-(2-, 3- or 4-pyridyl)methyl-N-methylaminocarbonyl)-glycine, valine, N-(trifluoroacetyl)-valine, N-phenylacetyl-valine, N-(2- or 3-pyridyl)-acetyl-valine, N-acetyl-valine, N-(2-carbamoyl-3-phenylpropionyl)-valine, N-(2(R,S)-carbamoyl-3-phenyl-propionyl)-valine, N-(2- or 3-pyridylacetyl)-valine, N-2-tetrahydrofurylmethoxycarbonyl-valine, N-(3-(tetrazol-1-yl)propionyl)-valine, N-(quinoline-2-carbonyl)-valine, N-methoxycarbonyl-valine, N-isobutoxycarbonyl-valine, N-tert-butoxycarbonyl-valine, N-benzyloxycarbonyl-valine, N-(morpholinocarbonyl)-valine, N-(thiomorpholinocarbonyl)-valine, N-(S,S-dioxothiomorpholinocarbonyl)-valine, N-(N-2-pyridylmethyl-N-methylaminocarbonyl)-valine, N-morpholinocarbonylaminoacetyl-valine, N-methylsulfonyl-valine, morpholinosulfonyl-valine, N-acetyl-isoleucine, N-propionyl-isoleucine, N-(benzyloxycarbonyl)-isoleucine, N-benzyloxycarbonyl-glutamic acid, asparagine, N-benzyloxycarbonyl-asparagine and quinoline-2-carbonyl-asparagine, wherein the amino acid radicals are each preferably in the (L)- or (D,L)-form, and in the case of valine also in the (D)-form; with the proviso that not more than one of the radicals $R_1$ and $R_9$ is hydrogen, $R_2$, $R_4$, $R_6$ and $R_8$ are hydrogen, $R_3$ is lower alkyl, such as n-butyl or isobutyl, cyclohexyl-lower alkyl, such as cyclohexylmethyl, or phenyl-lower alkyl that is unsubstituted or substituted by halogen, such as fluorine, lower alkoxy, such as methoxy, or by cyano, especially benzyl, 4-fluorobenzyl or 4-cyanobenzyl, $R_5$ is hydroxy, and $R_7$ is lower alkyl; cyclohexyl-lower alkyl; or phenyl-lower alkyl that is unsubstituted or substituted by halogen, such as fluorine, lower alkoxy, such as methoxy, or by cyano; as last defined for $R_3$, or a salt thereof where salt-forming groups are present, still greater preference being given to those compounds in which $R_1$ and/or $R_9$ are not morpholinosulfonyl or thiomorpholinosulfonyl.

Most preferred of all are the compounds mentioned in the Examples and their salts.

The compounds of formula I and salts of such compounds having at least one salt-forming group are obtained by means of processes known per se, for example as follows:

a) a hydrazine derivative of the formula

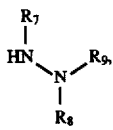
(III)

wherein the radicals are as defined above, is added to an epoxide of the formula

(IV)

wherein the radicals are as defined above, free functional groups, with the exception of those participating in the reaction, being optionally in protected form, and any protecting groups present are removed, or b) for the preparation of compounds of formula I wherein $R_1$ and $R_9$ are acyl; sulfo; sulfonyl substituted by unsubstituted or substituted alkyl, aryl, heterocyclyl, alkoxy, which is unsubstituted or substituted, or by aryloxy; sulfamoyl that is unsubstituted or substituted at the nitrogen atom; or phosphoryl substituted by one or two identical or different radicals selected from substituted or unsubstituted alkyl, unsubstituted or substituted cycloalkyl, aryl, hydroxy, unsubstituted or substituted alkoxy, cycloalkoxy and aryloxy; $R_2$ and $R_8$ are hydrogen, unsubstituted or substituted alkyl, alkenyl or alkynyl, or heterocyclyl, and the remaining radicals are as defined, an amino compound of the formula

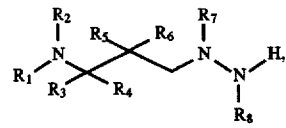
(V)

wherein the radicals are as defined immediately above, is condensed with an acid of the formula $R_9$—OH (VI)

or with a reactive acid derivative thereof, wherein $R_9$ is as defined immediately above, free functional groups, with the exception of those participating in the reaction, being optionally in protected form, and any protecting groups present are removed, or c) for the preparation of compounds of formula I wherein $R_1$ and $R_9$ are acyl; sulfo; sulfonyl substituted by unsubstituted or substituted alkyl, aryl, heterocyclyl, alkoxy, which is unsubstituted or substituted, or by aryloxy; sulfamoyl that is unsubstituted or substituted at the nitrogen atom; or phosphoryl that is substituted by one or two identical or different radicals selected from substituted or unsubstituted alkyl, unsubstituted or substituted cycloalkyl, aryl, hydroxy, unsubstituted or substituted alkoxy, cycloalkoxy and aryloxy; $R_2$ and $R_8$ are hydrogen, unsubstituted or substituted alkyl, alkenyl or alkynyl, or heterocyclyl, and the remaining radicals are as defined, an amino compound of the formula

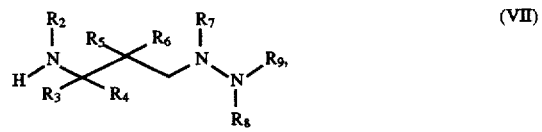
(VII)

wherein the radicals are as defined immediately above, is condensed with an acid of the formula $R_1$—OH (VIII)

or with a reactive acid derivative thereof, wherein $R_1$ is as defined immediately above, free functional groups, with the exception of those participating in the reaction, being optionally in protected form, and any protecting groups present are removed, or d) for the preparation of compounds of formula I wherein $R_1$ and $R_9$ are two identical radicals selected from acyl; sulfo; sulfonyl substituted by unsubstituted or substituted alkyl, aryl, heterocyclyl, alkoxy, which is unsubstituted or substituted, or by aryloxy; sulfamoyl that is unsubstituted or substituted at the nitrogen atom; and phosphoryl that is substituted by one or two identical or different radicals selected from substituted or unsubstituted alkyl, unsubstituted or substituted cycloalkyl, aryl, hydroxy, unsubstituted or substituted alkoxy, cycloalkoxy and aryloxy; $R_2$ and $R_8$ are hydrogen, unsubstituted or substituted alkyl, alkenyl or alkynyl, or heterocyclyl, and the remaining radicals are as defined, a diamino compound of the formula

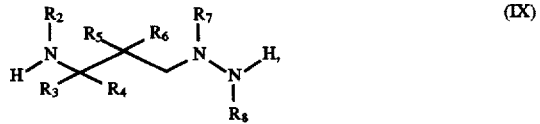
(IX)

wherein the radicals are as defined immediately above, is condensed with an acid suitable for introducing the identical radicals $R_1$ and $R_9$, or with reactive acid derivatives thereof, wherein $R_1$ and $R_9$ are as defined immediately above, free functional groups, with the exception of those participating in the reaction, being optionally in protected form, and any protecting groups present are removed, or e) for the preparation of a compound of formula I wherein in place of the radical $R_7$ there is a radical $R_7''$ which is unsubstituted or substituted alkyl or cycloalkyl, in a compound of the formula I'

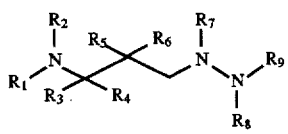

wherein $R_7'$ is hydrogen and the remaining radicals are as defined above, the radical $R_7$ is introduced by substitution with a compound of the formula XII, $$R_7''\text{—}X \tag{XII}$$

wherein X is a leaving group and $R_7''$ is unsubstituted or substituted alkyl or cycloalkyl, free functional groups, with the exception of those participating in the reaction, being optionally in protected form, and any protecting groups present are removed, or f) in a compound of formula I wherein the substituents are as defined above, with the proviso that in the compound of formula I in question at least one functional group is protected by protecting groups, the protecting groups present are removed and, if desired, a compound of formula I obtainable in accordance with any one of processes a) to f) above having at least one salt-forming group is converted into its salt or an obtainable salt is converted into the free compound or into a different salt and/or any isomeric mixtures that are obtainable are separated and/or a compound of formula I according to the invention is converted into a different compound of formula I according to the invention.

The above processes are described in detail below:

Process a) (Addition of an amine to an epoxide):

Depending on the meaning of $R_7$, in the hydrazine derivative of formula III the amino group participating in the reaction preferably has at least one free hydrogen atom; it may, however, itself have been derivatised in order to increase the reactivity of the hydrazine derivative.

The epoxide of formula IV has especially a structure that allows the preferential terminal addition of the hydrazine derivative.

Functional groups in starting materials that are not to participate in the reaction, especially carboxy, amino, hydroxy, mercapto and sulfo groups, can be protected by suitable protecting groups (conventional protecting groups) which are customarily used in the synthesis of peptide compounds, but also in the synthesis of cephalosporins and penicillins as well as nucleic acid derivatives and sugars. Those protecting groups may already be present in the precursors and are intended to protect the relevant functional groups against undesired secondary reactions, such as acylation, etherification, esterification, oxidation, solvolysis, etc.. In certain cases the protecting groups can additionally cause the reactions to proceed selectively, for example stereoselectively. It is a characteristic of protecting groups that they can be removed easily, i.e. without undesired secondary reactions, for example by solvolysis, reduction, photolysis, and also enzymatically, for example also under physiological conditions. Radicals analogous to protecting groups may, however, also be present in the end products. Compounds of formula I having protected functional groups may have a higher degree of metabolic stability or otherwise better pharmacodynamic characteristics than do the corresponding compounds having free functional groups. Hereinbefore and hereinafter, it is protecting groups in the narrower sense that are referred to unless the relevant radicals are present in the end products.

The protection of functional groups by such protecting groups, the protecting groups themselves and the reactions for their removal are described, for example, in standard works such as J. F. W. McOmie, "Protective Groups in Organic Chemistry", Plenum Press, London and New York 1973, in Th. W. Greene, "Protective Groups in Organic Synthesis", Wiley, New York 1981, in "The Peptides"; Volume 3 (E. Gross and J. Meienhofer, eds.), Academic Press, London and New York 1981, in "Methoden der organischen Chemie", Houben-Weyl, 4th edition, Volume 15/I, Georg Thieme Verlag, Stuttgart 1974, in H. -D. Jakubke and H. Jescheit, "Aminosäuren, Peptide, Proteine" ("Amino acids, peptides, proteins"), Verlag Chemie, Weinheim, Deerfield Beach and Basel 1982, and in Jochen Lehmann, "Chemie der Kohlenhydrate: Monosaccharide und Derivate" ("The Chemistry of Carbohydrates: monosaccharides and derivatives"), Georg Thieme Verlag, Stuttgart 1974.

A carboxy group is protected, for example, in the form of an ester group which can be removed selectively under mild conditions. A carboxy group protected in esterified form is esterified especially by a lower alkyl group that is preferably branched in the 1-position of the lower alkyl group or substituted in the 1- or 2-position of the lower alkyl group by suitable substituents.

A protected carboxy group esterified by a lower alkyl group is, for example, methoxycarbonyl or ethoxycarbonyl.

A protected carboxy group esterified by a lower alkyl group that is branched in the 1-position of the lower alkyl group is, for example, tert-lower alkoxycarbonyl, for example tert-butoxycarbonyl.

A protected carboxy group esterified by a lower alkyl group that is substituted in the 1- or 2-position of the lower alkyl group by suitable substituents is, for example, arylmethoxycarbonyl having one or two aryl radicals, wherein aryl is phenyl that is unsubstituted or mono-, di- or trisubstituted, for example, by lower alkyl, for example tert-lower alkyl, such as tert-butyl, lower alkoxy, for example methoxy, hydroxy, halogen, for example chlorine, and/or by nitro, for example benzyloxycarbonyl, benzyloxycarbonyl substituted by the mentioned substituents, for example 4-nitrobenzyloxycarbonyl or 4-methoxybenzyloxycarbonyl, diphenylmethoxycarbonyl or diphenylmethoxycarbonyl substituted by the mentioned substituents, for example di(4-methoxyphenyl)methoxycarbonyl, and also carboxy esterified by a lower alkyl group, the lower alkyl group being substituted in the 1- or 2-position by suitable substituents, such as 1-lower alkoxy-lower alkoxycarbonyl, for example methoxymethoxycarbonyl, 1-methoxyethoxycarbonyl or 1-ethoxyethoxycarbonyl, 1-lower alkylthio-lower alkoxycarbonyl, for example 1-methylthiomethoxycarbonyl or 1-ethylthioethoxycarbonyl, aroylmethoxycarbonyl wherein the aroyl group is benzoyl that is unsubstituted or substituted, for example, by halogen, such as bromine, for example phenacyloxycarbonyl, 2-halo-lower alkoxycarbonyl, for example 2,2,2-trichloroethoxycarbonyl, 2-bromoethoxycarbonyl or 2-iodoethoxycarbonyl, as well as 2-(tri-substituted silyl)-lower alkoxycarbonyl wherein the substituents are each independently of the others an aliphatic, araliphatic, cycloaliphatic or aromatic hydrocarbon radical that is unsubstituted or substituted, for example, by lower alkyl, lower alkoxy, aryl, halogen and/or by nitro, for example lower alkyl, phenyl-lower alkyl, cycloalkyl or phenyl each of which is unsubstituted or substituted as above, for example 2-tri-lower alkylsilyl-lower alkoxycarbonyl, such as 2-tri-lower alkylsilylethoxycarbonyl, for example 2-trimethylsilylethoxycarbonyl or 2-(di-n-butyl-methylsilyl)-ethoxycarbonyl, or 2-triarylsilylethoxycarbonyl, such as triphenylsilylethoxycarbonyl.

A carboxy group can also be protected in the form of an organic silyloxycarbonyl group. An organic silyloxycarbonyl group is, for example, a tri-lower alkylsilyloxycarbonyl group, for example trimethylsilyloxycarbonyl. The silicon atom of the silyloxycarbonyl-group can also be substituted by two lower alkyl groups, for example methyl groups, and the amino group or the carboxy group of a second molecule of formula I. Compounds having such protecting groups can be prepared, for example, using dimethylchlorosilane as silylating agent.

A protected carboxy group is preferably tert-lower alkoxycarbonyl, for example tert-butoxycarbonyl, benzyloxycarbonyl, 4-nitrobenzyloxycarbonyl, 9-fluorenylmethoxycarbonyl or diphenylmethoxycarbonyl.

A protected amino group can be protected by an amino-protecting group, for example in the form of an acylamino, arylmethylamino, etherified mercaptoamino, 2-acyl-lower alk-1-enylamino or silylamino group or in the form of an azido group.

In a corresponding acylamino group, acyl is, for example, the acyl radical of an organic carboxylic acid having, for example, up to 18 carbon atoms, especially an unsubstituted or substituted, for example halo- or aryl-substituted, lower alkanecarboxylic acid or an unsubstituted or substituted, for example halo-, lower alkoxy- or nitro-substituted, benzoic acid, or, preferably, of a carbonic acid semi-ester. Such acyl groups are, for example, lower alkanoyl, such as formyl, acetyl, propionyl or pivaloyl, halo-lower alkanoyl, for example 2-haloacetyl, such as 2-chloro-2-bromo-, 2-iodo-, 2,2,2-trifluoro- or 2,2,2-tri-chloro-acetyl, unsubstituted or substituted, for example halo-, lower alkoxy- or nitro-substituted, benzoyl, such as benzoyl, 4-chlorobenzoyl, 4-methoxybenzoyl or 4-nitro-benzoyl, lower alkoxycarbonyl, preferably lower alkoxycarbonyl that is branched in the 1-position of the lower alkyl radical or suitably substituted in the 1- or 2-position, for example tert-lower alkoxycarbonyl, such as tert-butoxycarbonyl, arylmethoxycarbonyl having one, two or three aryl radicals which are phenyl that is unsubstituted or mono- or poly-substituted, for example, by lower alkyl, especially tert-lower alkyl, such as tert-butyl, lower alkoxy, such as methoxy, hydroxy, halogen, such as chlorine, and/or by nitro, for example benzyloxycarbonyl, 4-nitrobenzyloxycarbonyl, diphenylmethoxycarbonyl, 9-fluorenylmethoxycarbonyl or di(4-methoxyphenyl)methoxycarbonyl, aroylmethoxycarbonyl wherein the aroyl group is preferably benzoyl that is unsubstituted or substituted, for example, by halogen, such as bromine, for example phenacyloxycarbonyl, 2-halo-lower alkoxycarbonyl, for example 2,2,2-trichloroethoxycarbonyl, 2-bromoethoxycarbonyl or 2-iodoethoxycarbonyl, 2-(tri-substituted silyl)-lower alkoxycarbonyl, for example 2-tri-lower alkylsilyl-lower alkoxycarbonyl, such as 2-trimethylsilylethoxycarbonyl or 2-(di-n-butyl-methyl-silyl)-ethoxycarbonyl, or triarylsilyl-lower alkoxycarbonyl, for example 2-triphenylsilylethoxycarbonyl.

In an arylmethylamino group, which is, for example, a mono-, di- or especially tri-arylmethylamino group, the aryl radicals are especially unsubstituted or substituted phenyl radicals. Such groups are, for example, benzyl-, diphenylmethyl- or especially tritylamino.

In an etherified mercaptoamino group the mercapto group is especially in the form of substituted arylthio or aryl-lower alkylthio, wherein aryl is, for example, phenyl that is unsubstituted or substituted, for example, by lower alkyl, such as methyl or tert-butyl, lower alkoxy, such as methoxy, halogen, such as chlorine, and/or by nitro, for example 4-nitrophenylthio.

In a 2-acyl-lower alk-1-enyl radical that can be used as an amino-protecting group, acyl is, for example, the corresponding radical of a lower alkanecarboxylic acid, of a benzoic acid that is unsubstituted or substituted, for example, by lower alkyl, such as methyl or tert-butyl, lower alkoxy, such as methoxy, halogen, such as chlorine, and/or by nitro, or especially of a carbonic acid semi-ester, such as a carbonic acid lower alkyl semi-ester. Corresponding protecting groups are especially 1-lower alkanoyl-lower alk-1-en-2-yl, for example 1-lower alkanoylprop-1-en-2-yl, such as 1-acetylprop-1-en-2-yl, or lower alkoxycarbonyl-lower alk-1-en-2-yl, for example lower alkoxycarbonyl-prop-1-en-2-yl, such as 1-ethoxycarbonylprop-1-en-2-yl.

A silylamino group is, for example, a tri-lower alkylsilylamino group, for example trimethylsilylamino or tert-butyl-dimethylsilylamino. The silicon atom of the silylamino group can also be substituted by only two lower alkyl groups, for example methyl groups, and the amino group or carboxy group of a second molecule of formula I. Compounds having such protecting groups can be prepared, for example, using the corresponding chlorosilanes, such as dimethylchlorosilane, as silylating agents.

An amino group can also be protected by conversion into the protonated form; suitable corresponding anions are especially those of strong inorganic acids, such as sulfuric acid, phosphoric acid or hydrohalic acids, for example the chlorine or bromine anion, or of organic sulfonic acids, such as p-toluenesulfonic acid.

Preferred amino-protecting groups are lower alkoxycarbonyl, phenyl-lower alkoxycarbonyl, fluorenyl-lower alkoxycarbonyl, 2-lower alkanoyl-lower alk-1-en-2-yl and lower alkoxycarbonyl-lower alk-1-en-2-yl.

A hydroxy group can be protected, for example, by an acyl group, for example lower alkanoyl substituted by halogen, such as chlorine, such as 2,2-dichloroacetyl, or especially by an acyl radical of a carbonic acid semi-ester mentioned for protected amino groups. A preferred hydroxy-protecting group is, for example, 2,2,2-trichloroethoxycarbonyl, 4-nitrobenzyloxycarbonyl, diphenylmethoxycarbonyl or trityl. A hydroxy group can also be protected by tri-lower alkylsilyl, for example trimethylsilyl, triisopropylsilyl or tertbutyl-dimethylsilyl, a readily removable etherifying group, for example an alkyl group, such as tert-lower alkyl, for example tert-butyl, an oxa- or a thia-aliphatic or -cycloaliphatic, especially 2-oxa- or 2-thia-aliphatic or -cycloaliphatic, hydrocarbon radical, for example 1-lower alkoxy-lower alkyl or 1-lower alkylthio-lower alkyl, such as methoxymethyl, 1-methoxyethyl, 1-ethoxyethyl, methylthiomethyl, 1-methylthioethyl or 1-ethylthioethyl, or 2-oxa- or 2-thia-cycloalkyl having from 5 to 7 ring atoms, such as 2-tetra-hydrofuryl or 2-tetrahydropyranyl, or a corresponding thia analogue, as well as by 1-phenyl-lower alkyl, such as benzyl, diphenylmethyl or trityl, wherein the phenyl radicals can be substituted, for example, by halogen, for example chlorine, lower alkoxy, for example methoxy, and/or by nitro.

Two hydroxy groups, especially adjacent hydroxy groups, occurring in a molecule, or a hydroxy group and an amino group that are adjacent to one another, can be protected, for example, by bivalent protecting groups, such as a methylene group that is preferably substituted, for example, by one or two lower alkyl radicals or by oxo, for example unsubstituted or substituted alkylidene, for example lower alkylidene, such as isopropylidene, cycloalkylidene, such as cyclohexylidene, a carbonyl group or benzylidene.

A mercapto group, for example in cysteine, can be protected especially by S-alkylation with unsubstituted or substituted alkyl radicals, by silylation, by thioacetal formation, by S-acylation or by the formation of asymmetric disulfide groupings. Preferred mercapto-protecting groups are, for example, benzyl that is unsubstituted or substituted in the phenyl radical, for example by methoxy or by nitro, such as 4-methoxybenzyl, diphenylmethyl that is unsubstituted or substituted in the phenyl radical, for example by methoxy, such as di-(4-methoxyphenyl)-methyl, triphenylmethyl, pyridyldiphenylmethyl, trimethylsilyl, benzylthiomethyl, tetrahydropyranyl, acylaminomethyl, such as acetamidomethyl, isobutyrylacetamidomethyl or 2-chloroacetamidomethyl, benzoyl, benzyloxycarbonyl or alkyl-, especially lower alkyl-aminocarbonyl, such as ethylaminocarbonyl, as well as lower alkylthio, such as S-ethylthio or S-tert-butylthio, or S-sulfo.

A sulfo group can be protected, for example, by lower alkyl, for example methyl or ethyl, by phenyl or in the form of a sulfonamide, for example in the form of an imidazolide.

In the context of this Application, a protecting group, for example a carboxy-protecting group, is to be understood as being expressly also a polymeric carrier that is bonded in a readily removable manner to the functional group, for example the carboxy group, to be protected, for example a carrier suitable for the Merrifield synthesis. An example of such a suitable polymeric carrier is a polystyrene resin, weakly cross-linked by copolymerisation with divinylbenzene, that carries bridge members suitable for reversible bonding.

The addition of the compounds of formula III to the epoxides of formula IV is preferably effected under the reaction conditions customary for the addition of nucleophiles to epoxides.

The addition is effected especially in aqueous solution and/or in the presence of polar solvents, such as alcohols, for example methanol, ethanol or ethylene glycol, ethers, such as dioxane, amides, such as dimethylformamide, or phenols, such as phenol, and also under anhydrous conditions, in apolar solvents, such as benzene and toluene, or in benzene/water emulsions, where appropriate in the presence of acid or basic catalysts, for example hydroxide solutions, such as sodium hydroxide solution, or in the presence of solid phase catalysts doped with the hydrazine, such as aluminium oxide, in ethers, for example diethyl ether, in general at temperatures of approximately from 0° C. to the boiling temperature of the reaction mixture in question, preferably from 20° to 130° C., where appropriate under reflux, under increased pressure, for example in a bomb tube, it being possible also to exceed the boiling temperature, and/or under inert gas, such as nitrogen or argon, it being possible for each of the two compounds of formula III and IV to be present in excess, for example in a molar ratio of from 1:1 to 1:100, preferably in a molar ratio of from 1:1 to 1:10, especially in a ratio of from 1:1 to 1:3.

The freeing of protected groups is effected as appropriate by the methods described under Process f) (Removal of protecting groups).
Process b) (Formation of an amide bond)

In starting materials of formulae V and VI, functional groups, with the exception of the groups that are intended to participate in the reaction or that do not react under the reaction conditions, are protected each independently of the others by one of the protecting groups mentioned under Process a).

The compounds of formula VI contain a free carboxy, sulfo or phosphoryl group or reactive acid derivatives thereof, for example the derived activated esters or reactive anhydrides, and also reactive cyclic amides. The reactive acid derivatives can also be formed in situ.

Activated esters of compounds of formula VI having a terminal carboxy group are especially esters unsaturated at the linking carbon atom of the esterifying radical, for example of the vinyl ester type, such as vinyl esters (obtainable, for example, by transesterification of a corresponding ester with vinyl acetate; activated vinyl ester method), carbamoyl esters (obtainable, for example, by treatment of the corresponding acid with an isoxazolium reagent; 1,2-oxazolium or Woodward method), or 1-lower alkoxyvinyl esters (obtainable, for example, by treatment of the corresponding acid with a lower alkoxyacetylene; ethoxyacetylene method), or esters of the amidino type, such as N,N'-disubstituted amidino esters (obtainable, for example, by treatment of the corresponding acid with a suitable N,N'-disubstituted carbodiimide, for example N,N'-dicyclohexylcarbodiimide; carbodiimide method), or N,N-disubstituted amidino esters (obtainable, for example, by treatment of the corresponding acid with an N,N-disubstituted cyanamide; cyanamide method), suitable aryl esters, especially phenyl esters suitably substituted by electron-attracting substituents (obtainable, for example, by treatment of the corresponding acid with a suitably substituted phenol, for example 4-nitrophenol, 4-methylsulfonylphenol, 2,4,5-trichlorophenol, 2,3,4,5,6-pentachlorophenol or 4-phenyldiazophenol, in the presence of a condensation agent, such as N,N'-dicyclohexylcarbodiimide; activated aryl esters method), cyanomethyl esters (obtainable, for example, by treatment of the corresponding acid with chloroacetonitrile in the presence of a base; cyanomethyl esters method), thioesters, especially unsubstituted or substituted, for example nitrosubstituted, phenylthio esters (obtainable, for example, by treatment of the corresponding acid with unsubstituted or substituted, for example nitro-substituted, thiophenols, inter alia by the anhydride or carbodiimide method; activated thiol esters method), or especially amino or amido esters (obtainable, for example, by treatment of the corresponding acid with an N-hydroxyamino or N-hydroxyamido compound, for example N-hydroxysuccinimide, N-hydroxypiperidine, N-hydroxyphthalimide, N-hydroxy-5-norbornene-2,3-di-carboxylic acid imide, 1-hydroxybenzotriazole or 3-hydroxy-3,4-dihydro-1,2,3-benzotriazin-4-one, for example by the anhydride or carbodiimide method; activated N-hydroxy esters method). Internal esters, for example γ-lactones, can also be used.

Anhydrides of acids may be symmetric or preferably mixed anhydrides of those acids, for example anhydrides with inorganic acids, such as acid halides, especially acid chlorides (obtainable, for example, by treatment of the corresponding acid with thionyl chloride, phosphorus pentachloride, phosgene or oxalyl chloride; acid chloride method), azides (obtainable, for example, from a corresponding acid ester via the corresponding hydrazide by treatment thereof with nitrous acid; azide method), anhydrides with carbonic acid semi-esters, for example carbonic acid lower alkyl semi-esters (obtainable, for example, by treatment of the corresponding acid with chloroformic acid lower alkyl esters or with a 1-lower alkoxycarbonyl-2-lower alkoxy-1,2-dihydroquinoline; mixed O-alkylcarbonic acid anhydrides method), or anhydrides with dihalogenated, especially dichlorinated, phosphoric acid (obtainable, for example, by treatment of the corresponding acid with phosphorus oxychloride; phosphorus oxychloride method), anhydrides with other phosphoric acid derivatives (for example those obtainable with phenyl-N-phenylphosphoramidochloridate or by reaction of alkylphosphoric acid amides in the presence of sulfonic acid anhydrides and/or racemisation-reducing additives, such as N-hydroxybenzotriazole, or in the presence of cyanophosphonic acid diethyl ester) or with phosphorous acid derivatives, or anhydrides with organic acids, such as mixed anhydrides with organic acids, such as mixed anhydrides with organic carboxylic acids (obtainable, for example, by treatment of the corresponding acid with an unsubstituted or substituted lower alkane- or phenyl-lower alkane-carboxylic acid halide, for example phenylacetic acid chloride, pivalic acid chloride or trifluoroacetic acid chloride; mixed carboxylic acid anhydrides method) or with organic sulfonic acids (obtainable, for example, by treatment of a salt, such as an alkali metal salt, of the corresponding acid with a suitable organic sulfonic acid halide, such as lower alkane- or aryl-, for example methane- or p-toluene-sulfonic acid chloride; mixed sulfonic acid anhydrides method) and symmetric anhydrides (obtainable, for example, by condensation of the corresponding acid in the presence of a carbodiimide or 1-diethylaminopropyne; symmetric anhydrides method).

Suitable cyclic amides are especially amides having five-membered diazacycles of aromatic character, such as amides with imidazoles, for example imidazole (obtainable, for example, by treatment of the corresponding acid with N,N'-carbonyldiimidazole; imidazole method), or pyrazole, for example 3,5-dimethylpyrazole (obtainable, for example, via the acid hydrazide by treatment with acetylacetone; pyrazolide method).

As mentioned, derivatives of carboxylic acids that are used as acylating agents can also be formed in situ. For example, N,N'-disubstituted amidino esters can be formed in situ by reacting a mixture of the starting material of formula V and the acid used as acylating agent, in the presence of a suitable N,N'-disubstituted carbodiimide, for example N,N'-cyclohexylcarbodiimide. In addition, amino or amido esters of the acids used as acylating agents can be formed in the presence of the starting material of formula V to be acylated, by reacting a mixture of the corresponding acid and amino starting materials in the presence of an N,N'-disubstituted carbodiimide, for example N,N'-dicyclohexylcarbodiimide, and of an N-hydroxyamine or N-hydroxyamide, for example N-hydroxysuccinimide, where appropriate in the presence of a suitable base, for example 4-dimethylamino-pyridine. Moreover, activation in situ can be achieved by reaction with N,N,N',N'-tetraalkyluronium compounds, such as O-benzotriazol-1-yl-N,N,N',N'-tetramethyluronium hexafluorophosphate, O-(1,2-dihydro-2-oxo-1-pyridyl)-N,N,N',N'-tetramethyluronium tetrafluoroborate or O-(3,4-dihydro-4-oxo-1,2,3-benzotriazolin-3-yl)-N,N,N',N'-tetramethyluronium tetrafluoroborate. Finally, phosphoric acid anhydrides of the carboxylic acids of formula VI or VII can be prepared in situ by reacting an alkylphosphoric acid amide, such as hexamethylphosphoric acid triamide, in the presence of a sulfonic acid anhydride, such as 4-toluenesulfonic acid anhydride, with a salt, such as a tetrafluoroborate, for example sodium tetrafluoroborate, or with another derivative of hexamethylphosphoric acid triamide, such as benzotriazol-1-yloxy-tris(dimethylamino) phosphonium hexafluoride, preferably in the presence of a racemisation-reducing additive, such as N-hydroxybenzotriazole.

In an analogous manner, many of the reaction types listed above for carboxylic acids of formula VI can also be carried out for compounds of formula III having a terminal sulfonyl or phosphoryl group in the condensation with compounds of formula V to form sulfonamides.

For example, it is possible to use activated sulfonic acid esters, for example the corresponding aryl esters, especially those substituted by nitro groups, such as phenyl esters, it being possible for the amine component of formula V also to be used in the form of an alkali metal amide, for example an alkali metal arylamide, such as sodium aniline amide, or an alkali metal salt of nitrogen-containing heterocycles, for example potassium pyrrolide.

In addition, reactive anhydrides, such as the corresponding symmetric acid anhydrides (which can be prepared, for example, by reaction of the alkylsulfonic acid silver salts with alkylsulfonyl chlorides) or, preferably, the corresponding asymmetric acid anhydrides, for example anhydrides with inorganic acids, such as sulfonyl halides, especially sulfonyl chlorides (obtainable, for example, by reaction of the corresponding sulfonic acids with inorganic acid chlorides, for example thionyl chloride, phosphorus pentachloride), with organic carboxylic acids (obtainable, for example, by treatment of a sulfonic acid halide with the salt of a carboxylic acid, such as an alkali metal salt, analogously to the above-mentioned mixed sulfonic acid anhydrides method), or azides (obtainable, for example, from a corresponding sulfonic acid chloride and sodium azide or via the corresponding hydrazide and treatment thereof with nitrous acid analogously to the above-mentioned azide method).

The phosphoryl radicals $R_9$ having the above-mentioned substituents can be fused to compounds of formula V by analogous processes, such as by means of activated phosphorus derivatives, for example correspondingly substituted phosphoryl halides having one or more halogen atoms, such as phosphorus oxychloride, in the absence or the presence of bases, such as sterically hindered amines, in aqueous or non-aqueous solvents, any excess halogen atoms subsequently being replaced by suitable substituents by hydrolysis or by reaction with the corresponding alcohols.

The phosphoryl radicals substituted by hydroxy, alkoxy, cycloalkoxy, cycloalkyl-lower alkoxy, aryloxy or by aryl-lower alkoxy can be reacted with the compounds of formula V, for example by reaction of the correspondingly substituted phosphites, for example diaryloxyphosphite or dialkoxyphosphite, or the correspondingly substituted mono- or di-halo-, such as mono- or di-chloro-phosphates, in the presence of a base, such as 2,6-dimethylpyridine, triethylamine or imidazole, in aqueous or anhydrous solvents, such as alcohols, for example ethanol, corresponding esters or dichloromethane or tetrachloromethane, where appropriate under a protective gas, such as argon, at temperatures of from $-50°$ to $100°$ C., preferably from $-10°$ to $50°$ C., especially under the conditions described in European Patent Application EP-A 0 376 040 published on 04.07.90.

The corresponding phosphoryl radicals substituted symmetrically or, preferably, asymmetrically by the mentioned radicals bonded via oxy can be obtained by reaction of phosphorus trihalides, such as phosphorus trichloride, with the corresponding amines of formula V and in the presence of organic amines, such as triethylamine, the corresponding dichlorophosphoryl compounds being formed, reaction of those compounds with the first corresponding alcohol or with water which are preferably used in stoichiometric amounts, in the presence of a tertiary amine, and where appropriate subsequent reaction of the second halogen atom with a further alcohol or water in the presence of a tertiary amine, to obtain the corresponding disubstituted phosphite compounds which are then oxidised, for example with halogens, such as iodine, peroxides, such as hydrogen peroxide, peracids, such as m-chloroperbenzoic acid, or with molecular oxygen.

The amino group of compounds of formula V that participates in the reaction preferably carries at least one reactive hydrogen atom, especially when the carboxy, sulfonyl or phosphoryl group with which it reacts is present in reactive form; it may, however, itself have been derivatised, for example by reaction with a phosphite, such as diethylchlorophosphite, 1,2-phenylenechlorophosphite, ethyl dichlorophosphite, ethylenechlorophosphite or tetraethylpyrophosphite. A derivative of such a compound having an amino group is, for example, also a carbamic acid halide or an isocyanate, the amino group that participates in the reaction being substituted by halocarbonyl, for example chlorocarbonyl, or being modified in the form of an isocyanate group; in the latter case only compounds of formula I that carry a hydrogen atom at the nitrogen atom of the amide group formed by the reaction are obtainable.

If the compound of formula V is mono-substituted at the amino group by lower alkyl or by aryl-lower alkyl, then a corresponding urea compound also constitutes a reactive derivative. For example, on heating equimolar amounts of that urea compound and the compound of formula VI or VIII having a free carboxy group, corresponding compounds of formula I are obtained.

Condensation for the preparation of an amide bond can be carried out in a manner known per se, for example as described in standard works such as "Houben-Weyl, Methoden der organischen Chemie", 4th edition, Volume 15/II (1974), Volume IX (1955) Volume E 11 (1985), Georg Thieme Verlag, Stuttgart, "The Peptides" (E. Gross and J. Meienhofer, eds.), Volumes 1 and 2, Academic Press, London and New York, 1979/1980, or M. Bodansky, "Principles of Peptide Synthesis", Springer-Verlag, Berlin 1984.

The condensation of a free carboxylic acid with the corresponding amine can be carried out preferably in the presence of one of the customary condensation agents, or using carboxylic acid anhydrides or carboxylic acid halides, such as chlorides, or activated carboxylic acid esters, such as p-nitrophenyl esters. Customary condensation agents are, for example, carbodiimides, for example diethyl-, dipropyl-, N-ethyl-N'-(3-dimethylaminopropyl)-carbodiimide or especially dicyclohexylcarbodiimide, also suitable carbonyl compounds, for example carbonylimidazole, 1,2-oxazolium compounds, for example 2-ethyl-5-phenyl-1,2-oxazolium 3'-sulfonate and 2-tert-butyl-5-methylisoxazolium perchlorate, or a suitable acylamino compound, for example 2-ethoxy-1-ethoxycarbonyl-1,2-dihydroquinoline, N,N,N', N'-tetraalkyluronium compounds, such as O-benzotriazol-1-yl-N,N,N',N'-tetramethyluronium hexafluorophosphate, also activated phosphoric acid derivatives, for example diphenylphosphoryl azide, diethylphosphoryl cyanide, phenyl-N-phenylphosphoroamidochloridate, bis(2-oxo-3-oxazolidinyl)phosphinic acid chloride or 1-benzotriazolyloxy-tris(dimethylamino)phosphonium hexafluorophosphate.

If desired, an organic base is added, preferably a tertiary amine, for example a tri-lower alkylamine having bulky radicals, for example ethyl diisopropylamine or triethylamine, and/or a heterocyclic base, for example 4-dimethylaminopyridine or preferably N-methylmorpholine or pyridine.

The condensation of activated esters, reactive anhydrides or reactive cyclic amides with the corresponding amines is customarily carried out in the presence of an organic base, for example simple tri-lower alkylamines, for example triethylamine or tributylamine, or one of the above-mentioned organic bases. If desired, a condensation agent is additionally used, for example as described for free carboxylic acids.

The condensation of acid anhydrides with amines can be effected, for example, in the presence of inorganic carbonates, for example ammonium or alkali metal carbonates or hydrogen carbonates, such as sodium or potassium carbonate or hydrogen carbonate (if desired together with a sulfate).

Carboxylic acid chlorides, for example the chlorocarbonic acid derivatives derived from the acid of formula VI, or sulfonic acid chlorides are condensed with the corresponding amines preferably in the presence of an organic amine, for example the above-mentioned tri-lower alkylamines or heterocyclic bases, where appropriate in the presence of a hydrogen sulfate.

The condensation is preferably carried out in an inert, aprotic, preferably anhydrous, solvent or solvent mixture, for example in a carboxylic acid amide, for example formamide or dimethylformamide, a halogenated hydrocarbon, for example methylene chloride, carbon tetrachloride or chlorobenzene, a ketone, for example acetone, a cyclic ether, for example tetrahydrofuran, an ester, for example ethyl acetate, or a nitrile, for example acetonitrile, or in a mixture thereof, as appropriate at reduced or elevated temperature, for example in a temperature range of from approximately −40° C. to approximately +100° C., preferably from approximately −10° C. to approximately +50° C., and in the case where arylsulfonyl esters are used also at approximately from +100° C. to +200° C., and where appropriate under an inert gas atmosphere, for example a nitrogen or argon atmosphere.

Aqueous, for example alcoholic, solvents, for example ethanol, or aromatic solvents, for example benzene or toluene, may also be used. When alkali metal hydroxides are present as bases, acetone can also be added where appropriate.

The condensation can also be carried out in accordance with the technique known as solid phase synthesis which originates from R. Merrifield and is described, for example, in Angew. Chem. 97, 801–812 (1985), Naturwissenschaften 71, 252–258 (1984) or in R. A. Houghten, Proc. Natl. Acad. Sci. USA 82, 5131–5135 (1985).

Depending on the starting compounds used, the radicals $R_1$ and $R_9$ in the obtainable compounds of formula I can be identical or different from one another.

The freeing of protected groups is effected where appropriate by the methods described under Process f) (Removal of protecting groups).

Process c) (Formation of an amide bond)

In starting materials of formulae VII and VIII, functional groups, with the exception of the groups that are intended to participate in the reaction or that do not react under the reaction conditions, are protected each independently of the others by one of the protecting groups mentioned under Process a).

The process is totally analogous to the process mentioned under Process b) except that instead of compounds of formula V those of formula VII are used, and instead of compounds of formula VI those of formula VIII are used, and, in the case of the acylation $R_1$ instead of $R_9$ bonds to compounds of formula VII instead of the compounds of formula V.

Depending on the starting materials used, the radicals $R_1$ and $R_9$ in the obtainable compounds of formula I can be identical or different from one another.

The freeing of protected groups is effected where appropriate by the methods described under Process f) (Removal of protecting groups).

Process d) (Formation of an amide bond)

In starting materials of formula IX and in the acid suitable for introducing the identical radicals $R_1$ and $R_9$, or the reactive derivatives thereof, functional groups that are not intended to participate in the reaction or that do not react under the reaction conditions are protected each independently of the others by one of the protecting groups mentioned under Process a).

The acid suitable for introducing the identical radicals $R_1$ and $R_9$ is preferably an acid of formula VI or VIII.

Preferred as starting materials of formula IX that may be protected by protecting groups are those of formula II which are described below in the section relating to starting materials.

The process is totally analogous to the process mentioned under Process b), except that instead of compounds of formula V those of formula IX are used, and instead of compounds of formula VI those of formula VI or VIII are used.

The freeing of protected groups is effected where appropriate by the methods described under Process f) (Removal of protecting groups).

Process e) (Alkylation of a secondary nitrogen atom)

In starting materials of formula I' and in the compound of formula XII suitable for introducing the radical $R_7$", or the reactive derivatives thereof, functional groups that are not intended to participate in the reaction or that do not react under the reaction conditions are protected each independently of the others by one of the protecting groups mentioned under Process a).

A leaving group X is especially a nucleofugal leaving group selected from hydroxy esterified by a strong inorganic or organic acid, such as hydroxy esterified by a mineral acid, for example a hydrohalic acid, such as hydrochloric acid, hydrobromic acid or hydriodic acid, or by a strong organic sulfonic acid, such as a lower alkanesulfonic acid that is unsubstituted or substituted, for example by halogen, such as fluorine, or an aromatic sulfonic acid, for example a benzenesulfonic acid that is unsubstituted or substituted by lower alkyl, such as methyl, halogen, such as bromine, and/or by nitro, for example a methanesulfonic acid, p-bromotoluenesulfonic acid or p-toluenesulfonic acid, or hydroxy esterified by hydrazoic acid.

The substitution can take place under the conditions of a first-order or second-order nucleophilic substitution.

For example, the compound of formula XII wherein X is a leaving group having a high polarisability of the electron shell, for example iodine, can be reacted in a polar aprotic solvent, for example acetone, acetonitrile, nitromethane, dimethyl sulfoxide or dimethylformamide. The reaction may also be carried out in water to which, where appropriate, an organic solvent, for example ethanol, tetrahydrofuran or acetone, has been added as solubiliser. The substitution reaction is carried out as appropriate at reduced or elevated temperature, for example in a temperature range of from approximately −40° to approximately 100° C., preferably from approximately −10° to approximately 50° C., and where appropriate under an inert gas, for example under a nitrogen or argon atmosphere.

The freeing of protected groups is effected where appropriate by the methods described under Process f) (Removal of protecting groups).

Process f) (Removal of protecting groups)

The removal of protecting groups that are not constituents of the desired end product of formula I, for example the carboxy-, amino-, hydroxy-, mercapto- and/or sulfo- protecting groups, is effected in a manner known per se, for example by means of solvolysis, especially hydrolysis, alcoholysis or acidolysis, or by means of reduction, especially hydrogenolysis or chemical reduction, as well as by photolysis, as appropriate stepwise or simultaneously, it being possible also to use enzymatic methods. The removal of the protecting groups is described, for example, in the standard works mentioned above in the section relating to "Protecting groups".

For example, protected carboxy, for example tert-lower alkoxycarbonyl, lower alkoxycarbonyl substituted in the 2-position by a trisubstituted silyl group or in the 1-position by lower alkoxy or lower alkylthio, or unsubstituted or substituted diphenylmethoxycarbonyl can be converted into free carboxy by treatment with a suitable acid, such as formic acid, hydrogen chloride or trifluoroacetic acid, where appropriate with the addition of a nucleophilic compound, such as phenol or anisole. Carboxy can also be freed from lower alkoxycarbonyl by means of bases, such as hydroxides, for example alkali metal hydroxides, such as sodium hydroxide or potassium hydroxide. Unsubstituted or substituted benzyloxycarbonyl can be freed, for example, by means of hydrogenolysis, i.e. by treatment with hydrogen in the presence of a metal hydrogenation catalyst, such as a palladium catalyst. In addition, suitably substituted benzyloxycarbonyl, such as 4-nitro-benzyloxycarbonyl, can also be converted into free carboxy by reduction, for example by treatment with an alkali metal dithionate, such as sodium dithionate, or with a reducing metal, for example zinc, or a reducing metal salt, such as a chromium(II) salt, for example chromium(II) chloride, customarily in the presence of a hydrogen-yielding agent that, together with the metal, is capable of producing nascent hydrogen, such as an acid, especially a suitable carboxylic acid, such as an unsubstituted or substituted, for example hydroxy-substituted, lower alkanecarboxylic acid, for example acetic acid, formic acid, glycolic acid, diphenylglycolic acid, lactic acid, mandelic acid, 4-chloromandelic acid or tartaric acid, or in the presence of an alcohol or thiol, water preferably being added. By treatment with a reducing metal or metal salt, as described above, 2-halo-lower alkoxycarbonyl (where appropriate after conversion of a 2-bromo-lower alkoxycarbonyl group into a corresponding 2-iodo-lower alkoxycarbonyl group) or aroylmethoxycarbonyl can also be converted into free carboxy. Aroylmethoxycarbonyl can also be cleaved by treatment with a nucleophilic, preferably salt-forming, reagent, such as sodium thiophenolate or sodium iodide. 2-(tri-substituted silyl)-lower alkoxycarbonyl, such as 2-tri-lower alkylsilyl-lower alkoxycarbonyl, can also be converted into free carboxy by treatment with a salt of hydrofluoric acid that yields the fluoride anion, such as an alkali metal fluoride, for example sodium or potassium fluoride, where appropriate in the presence of a macrocyclic polyether ("Crown ether"), or with a fluoride of an organic quaternary base, such as tetra-lower alkylammonium fluoride or tri-lower alkylaryl-lower alkylammonium fluoride, for example tetraethylammonium fluoride or tetrabutylammonium fluoride, in the presence of an aprotic, polar solvent, such as dimethyl sulfoxide or N,N-dimethylacetamide. Carboxy protected in the form of organic silyloxycarbonyl, such as tri-lower alkylsilyloxycarbonyl, for example trimethylsilyloxycarbonyl, can be freed in customary manner by solvolysis, for example by treatment with water, an alcohol or an acid, or, furthermore, a fluoride, as described above. Esterified carboxy can also be freed enzymatically, for example by means of esterases or suitable peptidases, for example esterified arginine or lysine, such as lysine methyl ester, using trypsin.

A protected amino group is freed in a manner known per se and, according to the nature of the protecting groups, in various ways, preferably by solvolysis or reduction. Lower alkoxycarbonylamino, such as tert-butoxycarbonylamino, can be cleaved in the presence of acids, for example mineral acids, for example a hydrogen halide, such as hydrogen chloride or hydrogen bromide, or sulfuric or phosphoric acids, preferably hydrogen chloride, or strong organic acids, such as trihaloacetic acid, for example trifluoroacetic acid, or formic acid, in polar solvents, such as water, or ethers, preferably cyclic ethers, such as dioxane. 2-halo-lower alkoxycarbonylamino (where appropriate after conversion of a 2-bromo-lower alkoxycarbonylamino group into a 2-iodo-lower alkoxycarbonylamino group), or dissolved directly in a liquid organic carboxylic acid, such as formic acid and aroylmethoxycarbonylamino or 4-nitrobenzyloxycarbonylamino can be cleaved, for example, by treatment with a suitable reducing agent, such as zinc in the presence of a suitable carboxylic acid, such as aqueous acetic acid. Aroylmethoxycarbonylamino can also be cleaved by treatment with a nucleophilic, preferably salt-forming, reagent, such as sodium thiophenolate, and 4-nitrobenzyloxycarbonylamino also by treatment with an alkali metal dithionate, for example sodium dithionate. Unsubstituted or substituted diphenylmethoxycarbonylamino, tert-lower alkoxycarbonylamino or 2-(tri-substituted silyl)-lower alkoxycarbonylamino, such as 2-tri-lower alkylsilyl-lower alkoxycarbonylamino, can be freed by treatment with a suitable acid, for example formic acid or trifluoroacetic acid; unsubstituted or substituted benzyloxycarbonylamino can be freed, for example, by means of hydrogenolysis, i.e. by treatment with hydrogen in the presence of a suitable hydrogenation catalyst, such as a platinum or palladium catalyst; unsubstituted or substituted triarylmethylamino or formylamino can be freed, for example, by treatment with an acid, such as a mineral acid, for example hydrochloric acid, or an organic acid, for example formic, acetic or trifluoroacetic acid, where appropriate in the presence of water; and an amino group protected in the form of silylamino can be freed, for example, by means of hydrolysis or alcoholysis. An amino group protected by 2-haloacetyl, for example 2-chloroacetyl, can be freed by treatment with thiourea in the presence of a base, or with a thiolate salt, such as an alkali metal thiolate of thiourea, and subsequent solvolysis, such as alcoholysis or hydrolysis, of the resulting substitution product; and amino is freed from trifluoroacetylamino, for example, by hydrogenolysis with bases, such as alkali metal hydroxides or carbonates, such as $Na_2CO_3$ or $K_2CO_3$, in polar solvents, for example alcohols, such as methanol, at temperatures of from 0° to 100° C., especially at from 40° to 80° C. An amino group protected by 2-(tri-substituted silyl)-lower alkoxycarbonyl, such as 2-tri-lower alkylsilyl-lower alkoxycarbonyl, can also be converted into the free amino group by treatment with a salt of hydrofluoric acid that yields fluoride anions as indicated above in connection with the freeing of a correspondingly protected carboxy group. Likewise, silyl bonded directly to a hetero atom, such as nitrogen, such as trimethylsilyl, can be removed using fluoride ions.

Amino protected in the form of an azido group is converted into free amino, for example, by reduction, for example by catalytic hydrogenation with hydrogen in the presence of a hydrogenation catalyst, such as platinum oxide, palladium or Raney nickel, by reduction using mercapto compounds, such as dithiothreitol or mercaptoethanol, or by treatment with zinc in the presence of an acid, such as acetic acid. The catalytic hydrogenation is preferably carried out in an inert solvent, such as a halogenated hydrocarbon, for example methylene chloride, or in water or in a mixture of water and an organic solvent, such as an alcohol or dioxane, at approximately from 20° C. to 25° C., or with cooling or heating.

A hydroxy or mercapto group protected by a suitable acyl group, a tri-lower alkylsilyl group or by unsubstituted or substituted 1-phenyl-lower alkyl is freed analogously to a correspondingly protected amino group. A hydroxy or mercapto group protected by 2,2-dichloroacetyl is freed, for example, by basic hydrolysis, and a hydroxy or mercapto group protected by tert-lower alkyl or by a 2-oxa- or 2-thia-aliphatic or -cycloaliphatic hydrocarbon radical is freed by acidolysis, for example by treatment with a mineral acid or a strong carboxylic acid, for example trifluoroacetic acid. Mercapto protected by pyridyldiphenylmethyl can be freed, for example, using mercury(II) salts at pH 2-6 or by zinc/acetic acid or by electrolytic reduction; acetamidomethyl and isobutyrylamidomethyl can be freed, for example, by reaction with mercury(II) salts at pH 2-6; 2-chloroacetamidomethyl can be freed, for example, using 1-piperidinothiocarboxamide; and S-ethylthio, S-tert-butylthio and S-sulfo can be freed, for example, by thiolysis with thiophenol, thioglycolic acid, sodium thiophenolate or 1,4-dithiothreitol. Two hydroxy groups or an adjacent amino and hydroxy group which are protected together by means of a bivalent protecting group, preferably, for example, by a methylene group mono- or di-substituted by lower alkyl, such as lower alkylidene, for example isopropylidene, cycloalkylidene, for example cyclohexylidene, or benzylidene, can be freed by acid solvolysis, especially in the presence of a mineral acid or a strong organic acid. A tri-lower alkylsilyl group is likewise removed by acidolysis, for example by a mineral acid, preferably hydrofluoric acid, or a strong carboxylic acid. 2-halo-lower alkoxycarbonyl is removed using the above-mentioned reducing agents, for example a reducing metal, such as zinc, reducing metal salts, such as chromium(II) salts, or by sulfur compounds, for example sodium dithionate or preferably sodium sulfide and carbon disulfide.

A sulfo group protected in the form of a sulfonic acid ester or a sulfonamide is freed, for example, by acid hydrolysis, for example in the presence of a mineral acid, or preferably by basic hydrolysis, for example with alkali metal hydroxide or alkali metal carbonate, for example sodium carbonate.

When several protected functional groups are present, if desired the protecting groups can be so selected that more than one such group can be removed simultaneously, for example by acidolysis, such as by treatment with trifluoroacetic acid, or with hydrogen and a hydrogenation catalyst, such as a palladium-on-carbon catalyst. Conversely, the groups can also be so selected that they cannot all be removed simultaneously, but rather in a desired sequence, the corresponding intermediates being obtained.

Additional Process Steps

In the additional process steps, which are optional, functional groups of the starting compounds that are not to take part in the reaction may be in unprotected or protected form, for example may be protected by one or more of the protecting groups mentioned above under Process a). The protecting groups may be retained in the end products or some or all of them may be removed according to one of the methods mentioned under Process f).

Salts of compounds of formula I having at least one salt-forming group may be prepared in a manner known per se. For example salts of compounds of formula I having acid groups may be formed, for example, by treating the compounds with metal compounds, such as alkali metal salts of suitable organic carboxylic acids, e.g. the sodium salt of 2-ethyl-hexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of formula I are obtained in customary manner, e.g. by treating the compounds with an acid or a suitable anion exchange reagent. Internal salts of compounds of formula I comprising acid and basic salt-forming groups, e.g. a free carboxy group and a free amino group, may be formed, e.g. by the neutralisation of salts, such as acid addition salts, to the isoelectric point, e.g. with weak bases, or by treatment with ion exchangers.

Salts can be converted in customary manner into the free compounds; metal and ammonium salts can be converted, for example, by treatment with suitable acids, and acid addition salts, for example, by treatment with a suitable basic agent.

Stereoisomeric mixtures, that is mixtures of diastereoisomers and/or enantiomers, such as, for example, racemic mixtures, can be separated in a manner known per se by suitable separating processes into the corresponding isomers. For example mixtures of diastereoisomers can be separated into the individual diastereoisomers by fractional crystallisation, chromatography, solvent partition etc. Racemates can be separated from one another, after conversion of the optical antipodes into diastereoisomers for example by reaction with optically active compounds, e.g. optically active acids or bases, by chromatography on column materials covered with optically active compounds or by enzymatic methods, e.g. by selective reaction of only one of the two enantiomers. This separation can be carried out either at the stage of one of the starting products or with the compounds of formula I themselves.

The configuration at individual chirality centres in a compound of formula I can be selectively reversed. For example the configuration of asymmetric carbon atoms that carry nucleophilic substituents, such as amino or hydroxy, can be reversed by second-order nucleophilic substitution, optionally after conversion of the bonded nucleophilic substituent into a suitable nucleofugal leaving group and reaction with a reagent that introduces the original substituent, or the configuration at carbon atoms having hydroxy groups, such as the $R_5$-carrying carbon atom of formula I, can be reversed by oxidation and reduction of compounds of formula I as described below.

The radicals hydroxy $R_5$ and hydrogen $R_6$ in a compound of formula I can be oxidised to an oxo group, the oxidising agents used preferably being those that selectively convert the hydroxy group into a keto group, for example chromic acid or a derivative thereof, such as pyridinium chromate or tert-butyl chromate, dichromate/sulfuric acid, sulfur trioxide in the presence of heterocyclic bases, such as pyridine/$SO_3$, also nitric acid, pyrolusite or selenium dioxide, or dimethyl sulfoxide in the presence of oxalyl chloride, in water, aqueous or organic solvents, such as halogenated solvents, e.g. methylene chloride, carboxylic acid amides, such as dimethylformamide, or di-lower alkyl sulfoxides, such as dimethyl sulfoxide, in the presence or absence of basic amines, e.g. tri-lower alkylamines, such as triethylamine, at temperatures of from −50° to 100° C., preferably from −10° to 50° C., for example as described in European Patent Application EP-A-0 236 734.

Conversely, in compounds of formula I obtained in that manner in which $R_5$ and $R_6$ together form an oxo group, the oxo group can be reduced to a hydroxy group. Suitable reducing agents for reducing the oxo group in a compound of formula I are those that under the reaction conditions of the process reduce an isolated keto group selectively or more quickly than amide groups present in compounds of formula I.

There may be mentioned, especially, suitable borohydrides, such as alkali metal borohydrides, especially sodium borohydride, lithium borohydride or sodium cyanoborohydride, also zinc borohydride, or suitable aluminium hydrides, such as alkali metal lower alkoxyaluminium hydrides having voluminous radicals, e.g. lithium tri-tert-butoxyaluminium hydride.

The reduction can also be carried out with hydrogen in the presence of suitable heavy metal catalysts, e.g. Raney nickel or platinum or palladium catalysts, e.g. platinum/- or palladium/activated carbon, or according to Meerwein-Ponndorf-Verley with the aid of aluminium alkanolates, preferably aluminium-2-propanolate or ethanolate.

The reduction can preferably be carried out with stoichiometric amounts or an expediently measured excess of the reducing agent in an inert solvent at temperatures of from −80° C. to the boiling point of the solvent, e.g. from −20° C. to +100° C., if necessary under a protective gas, e.g. nitrogen or argon. An excess of the reducing agent is necessary especially when it reacts also with the solvent, e.g. the protons of a protic solvent.

When sodium borohydride is used, polar protic solvents are suitable, e.g. methanol, ethanol or isopropanol; when the other reducing agents are used, polar aprotic solvents are suitable, e.g. tetrahydrofuran.

In a compound of formula I in which $R_1$, $R_2$, $R_8$ and $R_9$ contain no aryl radicals or aryl radicals that are not very reactive, an aryl radical present in $R_7$, $R_3$ and/or $R_4$, especially a phenyl radical, can be hydrogenated for example by catalytic hydrogenation, especially in the presence of heavy metal oxides, such as rhodium/platinum mixed oxides, e.g. with the Nishimura catalyst, preferably in a polar solvent, such as an alcohol, e.g. methanol or ethanol, at temperatures of from 0° to 80° C., especially from 10° to 40° C., and at a hydrogen pressure of from 1 to 10 atm, preferably at approximately normal pressure.

In an obtainable compound of formula I an amino or carboxamide group may be substituted, a carboxy group that is free or in reactive form may be esterified or amidated, or an esterified or amidated carboxy group may be converted into a free carboxy group.

The substitution of a carboxamide group or of another primary or secondary amino group, e.g. in order to introduce radicals such as unsubstituted or substituted alkyl, alkenyl or alkynyl, aryl-lower alkyl, or heterocyclyl or heterocyclyl-lower alkyl bonded by carbon $R_1$, $R_2$, $R_8$ or $R_9$ into compounds of formula I in which one or more of the mentioned radicals are hydrogen, is effected e.g. by alkylation.

Suitable agents for alkylating a carboxamide group in a compound of formula I are e.g. diazo compounds, e.g. diazomethane. Diazomethane can be decomposed in an inert solvent, the free methylene formed reacting with the carboxamide group in the compound of formula I. The decomposition of diazomethane is carried out preferably by catalysis, e.g. in the presence of a noble metal in finely divided form, e.g. copper, or of a noble metal salt, e.g. copper(I) chloride or copper(II) sulfate.

Alkylating agents are also mentioned in German Offenlegungsschrift 2 331 133, e.g. alkyl halides, sulfonic acid esters, Meerwein salts or 1-substituted 3-aryltriazenes, which can be reacted under the conditions mentioned therein with a compound of formula I having a carboxamide group.

Further alkylating agents are selected from compounds of formulae $$R_1-X \quad (X),$$

$$R_2-X \quad (XI),$$

$$R_8-X \quad (XIII)$$

and $$R_9-X \quad (XIV),$$

wherein X is a leaving group and the remaining radicals are as defined, with the exception of acyl, sulfo unsubstituted or substituted as above, phosphono, and phosphoryl substituted as above. A leaving group is especially a nucleofugal leaving group selected from hydroxy esterified by a strong inorganic or organic acid, such as hydroxy esterified by a mineral acid, e.g. a hydrohalic acid, such as hydrochloric, hydrobromic or hydriodic acid, or by a strong organic sulfonic acid, such as an unsubstituted or substituted, for example halo-substituted, such as fluoro-substituted, lower alkanesulfonic acid, or an aromatic sulfonic acid, e.g. a benzenesulfonic acid that is unsubstituted or substituted by lower alkyl, such as methyl, by halogen, such as bromine, and/or by nitro, e.g. a methanesulfonic, trimethanesulfonic or p-toluenesulfonic acid, and hydroxy esterified by hydrazoic acid.

The reaction can be carried out under the conditions of a first-order or second-order nucleophilic substitution.

For example, one of the compounds of formulae X to XIV wherein X is a leaving group with high polarisability of the electron shell, e.g. iodine, can be reacted in a polar aprotic solvent, e.g. acetone, acetonitrile, nitromethane, dimethyl sulfoxide or dimethylformamide. The reaction may also be carried out in water to which, where appropriate, an organic solvent, e.g. ethanol, tetrahydrofuran or acetone, has been added as solubiliser. The substitution reaction is carried out if desired at reduced or elevated temperature, e.g. in a temperature range of from approximately –40° to approximately 100° C., preferably from approximately –10° to approximately 50° C., and if desired under an inert gas, e.g. under a nitrogen or argon atmosphere.

For the esterification or amidation of a carboxy group in a compound of formula I, if desired the free acid can be used or the free acid can be converted into one of the above-mentioned reactive derivatives and reacted with an alcohol, with ammonia, or with a primary or secondary amine, or, in the case of esterification, the free acid or a reactive salt, e.g. the caesium salt, can be reacted with a reactive derivative of an alcohol. For example the caesium salt of a carboxylic acid can be reacted with a halide or sulfonic acid ester corresponding to the alcohol. The esterification of the carboxy group can also be carried out with other customary alkylating agents, e.g. with diazomethane, alkyl halides, sulfonic acid esters, Meerwein salts or 1-substituted 3-aryltriazenes, etc.

One of the methods described above for the removal of the carboxy-protecting groups or, if desired, an alkaline hydrolysis in accordance with customary reaction conditions, such as those specified in Organikum, 17th edition, VEB Deutscher Verlag der Wissenschaften, Berlin 1988, can be used to convert an esterified or amidated carboxy group into the free carboxy group.

An esterified carboxy group in a compound of formula I can be converted by aminolysis with ammonia or with a primary or secondary amine into an unsubstituted or substituted carboxamide group. The aminolysis can be carried out according to customary reaction conditions, such as those specified for such reactions in Organikum, 15th edition, VEB Deutscher Verlag der Wissenschaften, Berlin (East) 1976.

A free amino group present in a compound of formula I can be acylated, for example to introduce one of the radicals acyl, sulfo, substituted sulfonyl, phosphono or substituted phosphoryl mentioned for $R_1$, $R_2$, $R_8$ or $R_9$. The acylation is carried out according to one of the methods mentioned above under Process b), c) or d) for condensation or according to one of the methods mentioned for protecting groups or, for example, according to one of the processes mentioned in Organikum, 17th edition, VEB Deutscher Verlag der Wissenschaften, Berlin (East) 1988.

In an obtainable compound of formula I wherein the substituents are as defined and at least one free hydroxy group is present and the remaining functional groups are in protected form, the free hydroxy group can be acylated or etherified.

The acylation can be carried out with acylating reagents according to one of the methods mentioned under Processes b) to d), according to one of the methods mentioned for protecting groups, or according to one of the processes mentioned in Organikum, 17th edition, VEB Deutscher Verlag der Wissenschaften, Berlin (East) 1988.

The etherification can be carried out with the above-mentioned alkylating agents and under the same reaction conditions, e.g. with diazomethane, alkyl halides, sulfonic acid esters, Meerwein salts, 1-substituted 3-aryltriazenes, etc.

In an obtainable compound of formula I a sulfinyl or sulfonyl group can be produced from a thio group, and the corresponding sulfoxide or sulfone from a sulfide, by oxidation.

The oxidation to the sulfonyl group or to the sulfone can be carried out with most of the customary oxidising agents. The oxidising agents used are especially preferably those that oxidise the thio group or the sulfide sulfur selectively in the presence of other functional groups of the compound of formula I in question, e.g. amino or hydroxy groups; examples of such oxidising agents are aromatic or aliphatic peroxycarboxylic acids, e.g. peroxybenzoic acid, monoperphthalic acid, m-chloroperbenzoic acid, peracetic acid, performic acid or trifluoroperacetic acid. The oxidation with peroxycarboxylic acids is carried out in the customary solvents suitable therefor, for example chlorinated hydrocarbons, e.g. methylene chloride or chloroform, ethers, such as diethyl ether, esters, such as ethyl acetate or the like, at temperatures of from –78° C. to room temperature, e.g. from –20° C. to +10° C., preferably about 0° C. The peroxycarboxylic acid can also be formed in situ, e.g. with hydrogen peroxide in acetic acid or formic acid that may or may not contain acetic anhydride, e.g. with 30% or 90% hydrogen peroxide in acetic acid/acetic anhydride. Also suitable are other peroxo compounds, for example potassium peroxomonosulfate in lower alkanol/water mixtures, e.g. methanol/water or ethanol/water, or in aqueous acetic acid at temperatures of from –70° C. to +30° C., e.g. from –20° C. to room temperature, and also sodium metaperiodate in methanol or methanol/water mixtures at temperatures of from 0° C. to 50° C., e.g. approximately room temperature. If stoichiometric amounts of the mentioned oxidising agents are used it is also possible for the corresponding sulfinic acids or sulfoxides to be obtained. There are suitable for that purpose, for example, sodium metaperiodate in methanol or methanol/water mixtures at temperatures of from −15° C. to room temperature, e.g. approximately 0° C., m-chloroperbenzoic acid in methylene chloride, chloroform or ethyl acetate at temperatures of from −78° C. to 10° C., preferably from −30° C. to 0° C., also tert-butylhypochlorite in lower alkanols, e.g. methanol, or hydrogen peroxide in acetone or acetic acid at temperatures of approximately 0° C., or the above-mentioned potassium peroxomonosulfate at low temperatures.

If desired, the corresponding thio compound or the corresponding sulfide can be obtained by reducing a sulfonyl group or a sulfone radical in an obtainable compound of formula I, for example with diisobutylaluminium hydride in ether or tetrahydrofuran.

In an obtainable compound of formula I having a sulfinyl group, that group can be reduced to a thio group. Selective reducing agents that leave other functional groups of the compound of formula I, e.g. the amide function, unchanged are preferred. Examples of such selective reducing agents are dichloroborane, which is preferably used in tetrahydrofuran or dimethoxyethane at temperatures of from −30° C. to +10° C., triphenylphosphine in boiling carbon tetrachloride, trichlorosilane or hexachlorodisilane, iron pentacarbonyl, also sodium hydrogen sulfite in aqueous/ alcoholic solvents, e.g. water/methanol, water/ethanol or also water/tetrahydrofuran, at temperatures of from −10° C. to +50° C., also sodium borohydride in the presence of cobalt(II) chloride or also hydrogen in the presence of catalytic amounts of palladium, e.g. palladium/carbon in boiling ethanol.

Protecting groups present in a compound of formula I or suitable radicals $R_1$, $R_2$, $R_8$ or $R_9$, i.e. those representing acyl, sulfo, substituted sulfo, phosphono or substituted phosphoryl, can be removed according to one of the processes mentioned under Process f), especially by hydrolysis, for example in the presence of bases, such as alkali or alkaline earth metal hydroxides, e.g. sodium hydroxide, or acids, such as organic acids or mineral acids, e.g. hydrogen halide, such as hydrogen chloride. The hydrolysis is carried out under customary conditions, for example in aqueous solution or in anhydrous solvents, especially in ethers, such as dioxane, at temperatures of from −50° C. to the reflux temperature of the corresponding reaction mixtures, e.g. from 0° C. to 50° C., preferably in the presence of a protective gas, such as argon or nitrogen.

All of the process steps specified above can be carried out under reaction conditions that are known per se, preferably those specifically mentioned, in the absence or customarily in the presence of solvents or diluents, preferably those that are inert towards and dissolve the reagents used, in the absence or presence of catalysts, condensation agents or neutralising agents, e.g. ion exchangers, such as cation exchangers, e.g. in the $H^+$ form, depending on the nature of the reaction and/or the reactants at reduced, normal or elevated temperature, e.g. in a temperature range of from approximately −100° C. to approximately 190° C., preferably from approximately −80° C. to approximately 150° C., e.g. at from −80° to −60° C., at room temperature, at from −20° to 40° C. or at the boiling point of the solvent used, under atmospheric pressure or in a closed vessel, if desired under pressure, and/or under an inert atmosphere, e.g. under an argon or nitrogen atmosphere.

In the case of all starting compounds and intermediates where there are salt-forming groups, salts may be present. Salts may also be present during the reaction of such compounds, provided they do not interfere in the reaction.

At all stages of the reaction, isomeric mixtures that are obtained can be separated into the individual isomers, e.g. diastereoisomers or enantiomers, or into any mixtures of isomers, e.g. racemates or diastereoisomeric mixtures, for example analogously to the methods described under "Additional Process Steps".

In certain cases, for example in the case of hydrogenation, it is possible to achieve stereo-selective reactions, so that e.g. simplified production of individual isomers is possible.

The solvents from which those suitable for the reaction in question can be selected include, for example, water, esters, such as lower alkyl lower alkanoates, e.g. diethyl acetate, ethers, such as aliphatic ethers, e.g. diethyl ether, or cyclic ethers, e.g. tetrahydrofuran, liquid aromatic hydrocarbons, such as benzene or toluene, alcohols, such as methanol, ethanol or 1- or 2-propanol, nitriles, such as acetonitrile, halogenated hydrocarbons, such as methylene chloride, acid amides, such as dimethylformamide, bases, such as heterocyclic nitrogen bases, e.g. pyridine, carboxylic acid anhydrides, such as lower alkanoic acid anhydrides, e.g. acetic anhydride, cyclic, linear or branched hydrocarbons, such as cyclohexane, hexane or isopentane, or mixtures of those solvents, e.g. aqueous solutions, provided nothing else is specified in the description of the process. Such solvent mixtures can also be us ed in working up, for example by chromatography or partitioning.

The invention relates also to those embodiments of the process in which a compound obtainable at any stage as intermediate is used as starting material and the remaining steps are carried out, or the process is discontinued at any stage, or a starting material is formed under the reaction conditions or is used in the form of a reactive derivative or salt, or in which a compound obtainable according to the process of the invention is produced under the process conditions and further processed in situ. The starting materials used are preferably those that result in the compounds referred to above as preferred, especially those referred to as especially preferred, more especially preferred and/or preferred above all.

Pharmaceutical Compositions

The invention relates also to pharmaceutical compositions comprising compounds of formula I.

The pharmacologically acceptable compounds of the present invention may be used, e.g., for the preparation of pharmaceutical compositions that comprise an effective amount of the active ingredient together or in admixture with a significant amount of inorganic or organic, solid or liquid, pharmaceutically acceptable carriers.

The invention relates also to a pharmaceutical composition that is suitable for administration to warm-blooded animals, especially humans, for the treatment or prevention of a disease that responds to inhibition of a retroviral protease, especially a retroviral aspartate protease, such as HIV-I- or HIV-II-gag protease, e.g. a retroviral disease such as AIDS, comprising an amount of a compound of formula I effective for the inhibition of retroviral protease, or a pharmaceutically acceptable salt thereof, together with at least one pharmaceutically acceptable carrier.

The pharmaceutical compositions according to the invention are those for enteral, such as nasal, rectal or oral, or parenteral, such as intramuscular or intravenous, administration to warm-blooded animals (humans or animals), that comprise an effective dose of the pharmacological active ingredient, alone or together with a significant amount of a pharmaceutically acceptable carrier. The dose of the active ingredient depends on the species of warm-blooded animal, the body weight, the age and the individual condition, individual pharmacokinetic data, the disease to be treated and the method of administration.

The invention relates also to a method of treating diseases caused by viruses, especially by retroviruses, for example AIDS, which comprises administering a therapeutically effective amount of a compound of formula I according to the invention, especially to a warm-blooded animal, for example a human, who on account of one of the mentioned diseases, especially AIDS, requires such treatment. The dose to be administered to warm-blooded animals, for example humans of approximately 70 kg body weight, is from approximately 3 mg to approximately 3 g, preferably from approximately 10 mg to approximately 1.5 g, for example from approximately 300 mg to 1000 mg per person per day, divided preferably into 1 to 3 single doses which may, for example, be of the same size. Usually, children receive half of the adult dose.

The pharmaceutical compositions comprise from approximately 1% to approximately 95%, preferably from approximately 20% to approximately 90% active ingredient. Pharmaceutical compositions according to the invention may be, for example, in unit dose form, such as in the form of ampoules, vials, suppositories, dragées, tablets or capsules.

The pharmaceutical compositions of the present invention are prepared in a manner known per se, for example by means of conventional dissolving, lyophilising, mixing, granulating or confectioning processes.

Solutions of the active ingredient, and also suspensions, and especially isotonic aqueous solutions or suspensions, are preferably used, it being possible, for example in the case of lyophilised compositions that comprise the active ingredient alone or together with a carrier, e.g. mannitol, for such solutions or suspensions to be produced prior to use. The pharmaceutical compositions may be sterilised and/or may comprise excipients, e.g. preservatives, stabilisers, wetting and/or emulsifying agents, solubilisers, salts for regulating the osmotic pressure and/or buffers, and are prepared in a manner known per se, e.g. by means of conventional dissolving or lyophilising processes. The said solutions or suspensions may comprise viscosity-increasing substances, such as sodium carboxymethylcellulose, carboxymethylcellulose, dextran, polyvinylpyrrolidone or gelatin.

Suspensions in oil comprise as the oil component the synthetic or semi-synthetic vegetable oils customary for injection purposes. There may be mentioned as such especially liquid fatty acid esters that contain as the acid component a long-chained fatty acid having from 8 to 22, especially from 12 to 22, carbon atoms, e.g. lauric acid, tridecylic acid, myristic acid, pentadecylic acid, palmitic acid, margaric acid, stearic acid, arachidic acid, behenic acid or corresponding unsaturated acids, e.g. oleic acid, elaidic acid, erucic acid, brasidic acid or linoleic acid, if desired with the addition of antioxidants, e.g. vitamin E, β-carotene or 3,5-di-tert-butyl-4-hydroxytoluene. The alcohol component of those fatty acid esters has a maximum of 6 carbon atoms and is a mono- or poly-hydric, e.g. a mono-, di- or tri-hydric, alcohol, e.g. methanol, ethanol, propanol, butanol or pentanol or the isomers thereof, but especially glycol and glycerol. The following examples of fatty acid esters are therefore to be mentioned: ethyl oleate, isopropyl myristate, isopropyl palmitate, "Labrafil M 2375" (polyoxyethylene glycerol trioleate, Gattefossé, Paris), "Miglyol 812" (triglyceride of saturated fatty acids with a chain length of $C_8$ to $C_{12}$, Hüls AG, Germany), but especially vegetable oils, such as cottonseed oil, almond oil, olive oil, castor oil, sesame oil, soybean oil and more especially groundnut oil.

The injection compositions are prepared in customary manner under sterile conditions; the same applies also to introducing the compositions into ampoules or vials and sealing the containers.

Pharmaceutical compositions for oral administration can be obtained by combining the active ingredient with solid carriers, if desired granulating a resulting mixture, and processing the mixture, if desired or necessary, after the addition of appropriate excipients, into tablets, dragée cores or capsules. It is also possible for them to be incorporated into plastics carriers that permit the release or diffusion of the active ingredients in measured amounts.

Suitable carriers are especially fillers, such as sugars, e.g. lactose, saccharose, mannitol or sorbitol, cellulose preparations and/or calcium phosphates, e.g. tricalcium phosphate or calcium hydrogen phosphate, and binders, such as starch pastes using e.g. corn, wheat, rice or potato starch, gelatin, tragacanth, methylcellulose, hydroxypropylmethylcellulose, sodium carboxymethylcellulose and/or polyvinylpyrrolidone, and/or, if desired, disintegrators, such as the above-mentioned starches, also carboxymethyl starch, crosslinked polyvinylpyrrolidone, agar, alginic acid or a salt thereof, such as sodium alginate. Excipients are especially flow conditioners and lubricants, e.g. silicic acid, talc, stearic acid or salts thereof, such as magnesium or calcium stearate, and/or polyethylene glycol. Dragée cores are provided with suitable, optionally enteric, coatings, there being used, inter alia, concentrated sugar solutions which may comprise gum arabic, talc, polyvinylpyrrolidone, polyethylene glycol and/or titanium dioxide, or coating solutions in suitable organic solvents, or, for the preparation of enteric coatings, solutions of suitable cellulose preparations, such as ethylcellulose phthalate or hydroxypropylmethylcellulose phthalate. Capsules are dry-filled capsules made of gelatin and soft sealed capsules made of gelatin and a plasticiser, such as glycerol or sorbitol. The dry-filled capsules may comprise the active ingredient in the form of granules, e.g. with fillers, such as lactose, binders, such as starches, and/or glidants, such as talc or magnesium stearate, and if desired with stabilisers. In soft capsules the active ingredient is preferably dissolved or suspended in suitable oily excipients, such as fatty oils, paraffin oil or liquid polyethylene glycols, it being possible also for stabilisers and/or antibacterial agents to be added. Dyes or pigments may be added to the tablets or dragée coatings or the capsule casings, e.g. for identification purposes or to indicate different doses of active ingredient.

Starting materials

The present invention relates also to novel starting materials and/or intermediates and to processes for their preparation. Preferably the starting materials and reaction conditions are so selected that the compounds listed above as preferred are obtained.

In the preparation of all starting materials free functional groups that are not to participate in the reaction in question may be in unprotected or protected form, for example they may be protected by the protecting groups mentioned above under Process a). Those protecting groups may be removed at appropriate times by the reactions described under Process f).

The starting materials of Process a) are known or, if novel, can be prepared according to processes known per se, e.g. compounds of formula III can be prepared from hydrazine or suitable derivatives thereof and compounds of formula IV can be prepared from suitable amino acids or analogues thereof, for example those having one or two of the mentioned side chains $R_3$ and $R_4$.

The compounds of formula III can be obtained, for example, from compounds of formula $H_2N-NH-R_{11}$ (XV)

wherein $R_{11}$ is hydrogen or an amino-protecting group, as described above under Process b), especially tert-lower alkoxycarbonyl, such as tert-butoxycarbonyl, aryl-lower alkoxycarbonyl, such as benzyloxycarbonyl or 9-fluorenylmethoxycarbonyl, or one of the above-mentioned acylamino-protecting groups by, in order to prepare a compound of formula I wherein in place of $R_7$ there is a radical $R_7''$ which is unsubstituted or substituted alkyl or cycloalkyl, alkylating with a compound of formula XII to introduce $R_7''$, as described above under Process e), or introducing the radical $R_7$ by reaction of suitable carbonyl compounds with the free amino group of the compound of formula VIII or an acylated derivative thereof and subsequent reduction of the resulting hydrazone to form hydrazine derivatives of formula $R_7-NH-NH-R_{11}$ (XVI), wherein the radicals in all of the mentioned compounds are as defined hereinbefore and functional groups in participating reagents that are not to take part in the reaction are, if desired, protected, where appropriate removing the protecting group $R_{11}$, if it does not correspond to one of the radicals $R_8$ or $R_9$ in compounds of formula I, and/or removing other protecting groups, and reacting the radicals $R_8$ and $R_9$ other than hydrogen, by condensation under the conditions mentioned in Process b), with acids of formula VI or of formula $R_8-OH$ (XVII), wherein $R_8$ is as defined, or by alkylation with a compound of formula XIII or XIV, as defined above, or both, in accordance with the conditions indicated above in the additional process steps.

The carbonyl compounds suitable for the introduction of $R_7$ that are used for the preparation of compounds of formula XVI are aldehydes or ketones of which the reactive carbonyl group is a component of one of the mentioned radicals $R_7$ after the reaction with compounds of formula XV and the subsequent reduction, preferably aldehydes that are suitable for the introduction of lower alkyl, cyclohexyl-lower alkyl or phenyl-lower alkyl.

The reaction of the carbonyl compounds with the compounds of formula XVI to form the corresponding hydrazones is carried out under the conditions customary for the reaction of carbonyl compounds with amines, preferably in polar organic solvents, e.g. ethers, such as tetrahydrofuran or diethyl ether, alcohols, such as methanol or ethanol, carboxylic acid amides, such as dimethylformamide, or esters, such as ethyl acetate, or in aqueous solution, preferably in methanol, and also in the presence or absence of acid catalysts, e.g. carboxylic acids, such as formic acid or acetic acid, or sulfonic acids, such as p-toluenesulfonic acid, at temperatures of from 0° C. to the reflux temperature of the reaction mixture, preferably at temperatures of from 20° C. to the reflux temperature of the reaction mixture.

The reduction of the resulting hydrazones is carried out preferably by hydrogenation in the presence of a suitable catalyst. Suitable catalysts used for the hydrogenation include metals, such as nickel, iron, cobalt or ruthenium, and noble metals and their oxides, such as palladium or rhodium and their oxides, where appropriate applied e.g. to a suitable support, such as barium sulfate, aluminium oxide or activated carbon, or in the form of skeleton catalysts, such as Raney nickel. Customary solvents for the catalytic hydrogenation are, for example, water, alcohols, such as methanol or ethanol, esters, such as ethyl acetate, ethers, such as dioxane, chlorinated hydrocarbons, such as dichloromethane, carboxylic acid amides, such as dimethylformamide, or carboxylic acids, such as glacial acetic acid, or mixtures of those solvents. The hydrogenation is carried out at temperatures of from 10° to 250° C., preferably from room temperature to 100° C., and at hydrogen pressures of from 1 to 200 bar, preferably from 1 to 10 bar, in the customary apparatus. Especially preferred for the preparation of compounds of formula XV are reaction conditions analogous to those described in J. Chem. Soc. Perkin I, 1712 (1975).

The compounds of formula IV can be obtained, for example, by the reduction of amino acids of formula

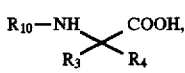
(XVIII)

wherein $R_{10}$ is hydrogen or one of the amino-protecting groups mentioned under Process a), especially tert-lower alkoxycarbonyl, such as tert-butoxycarbonyl, aryl-lower alkoxycarbonyl, such as benzyloxycarbonyl or 9-fluorenylmethoxycarbonyl, or one of the acylamino-protecting groups mentioned under that process, and $R_3$ and $R_4$ are as defined for compounds of formula I, preferably of amino acids of formula

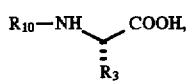
(XVIII A)

wherein the radicals are as defined, to aldehydes of formula

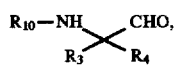
(XIX)

wherein the radicals are as defined, preferably to the aldehydes of formula

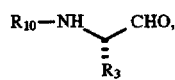
(XIX A)

wherein the radicals are as defined (which are obtainable, for example, from compounds of formula XVIII A), by reaction of those aldehydes with an ylide compound, preferably a sulfur-ylide compound, to form an epoxide of formula

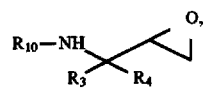
(XX)

wherein the radicals are as defined, preferably to compounds of formula

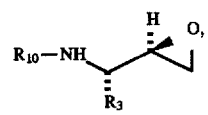
(XX A)

(obtainable, for example, from compounds of formula XIX A), wherein the radicals are as defined, where appropriate removal of the protecting group $R_{11}$, provided that does not correspond to one of the radicals $R_8$ or $R_9$ in compounds of formula I, and acylation of the amino group of the resulting compound with an acid of formula VIII or formula $R_2-OH$ (XXI), wherein the radicals are as defined, under the conditions described for Process b), and/or alkylation of the amino group of the resulting compound with reagents having nucleofugal leaving groups of formula X or XI, wherein the radicals are as defined, under the conditions described for additional process steps.

The reduction of amino acids of formula XVIII or XVIII A to the corresponding aldehydes XIX and XIX A is carried out, for example, by reduction to the corresponding alcohols and subsequent oxidation to the said aldehydes.

The reduction to the alcohols is carried out, for example, by hydrogenation of the acid halides or other activated carboxylic acid derivatives mentioned under Process b) under the conditions mentioned for the hydrogenation of hydrazones obtained from compounds of formula XVI, or with complex hydrides, such as sodium borohydride. The subsequent oxidation of the resulting alcohols is possible, for example, under the conditions for the oxidation of compounds of formula I in which $R_5$ is hydroxy and $R_6$ is hydrogen to compounds of formula I in which $R_5$ and $R_6$ together are oxo, as described in the additional process steps, or by oxidation of the hydroxy group with a sulfoxide, such as dimethyl sulfoxide, in the presence of a reagent that activates the hydroxy group, such as a carboxylic acid chloride, e.g. oxalyl chloride, in an inert solvent, e.g. a halogenated hydrocarbon, such as dichloromethane, and/or an acyclic or cyclic ether, such as tetrahydrofuran, at from $-80°$ to $0°$ C., e.g. from $-78°$ to $-50°$ C.

Direct reduction of the amino acids to the aldehydes is also possible, for example by hydrogenation in the presence of a partially contaminated palladium catalyst or by reduction of the corresponding amino acid ester, e.g. the lower alkyl ester, such as ethyl ester, with complex hydrides, e.g. borohydrides, such as sodium borohydride, or preferably aluminium hydrides, e.g. lithium aluminium hydride, lithium tri-(tert-butoxy)aluminium hydride or especially diisobutylaluminium hydride, in apolar solvents, e.g. in hydrocarbons or aromatic solvents, such as toluene, at from $-100°$ to $0°$ C., preferably from $-70°$ to $-30°$ C., and subsequent reaction to form the corresponding semicarbazones, e.g. with the corresponding acid salts of semicarbazones, such as semicarbazide hydrochloride, in aqueous solvent systems, such as alcohol/water, e.g. ethanol/water, at temperatures of from $-20°$ to $60°$ C., preferably from $10°$ to $30°$ C., and reaction of the resulting semicarbazone with a reactive aldehyde, e.g. formaldehyde, in an inert solvent, for example a polar organic solvent, e.g. a carboxylic acid amide, such as dimethylformamide, at temperatures of from $-30°$ to $60°$ C., preferably from $0°$ to $30°$ C., and then with an acid, for example a strong mineral acid, such as hydrogen halide, in aqueous solution, if desired in the presence of the previously used solvent, at temperatures of from $-40°$ to $50°$ C., preferably from $-10°$ to $30°$ C. The corresponding esters are obtained by reaction of the amino acids with the corresponding carboxylic acids, for example ethanol, analogously to the conditions used in the condensation in Process b), for example by reaction with inorganic acid halides, such as thionyl chloride, in organic solvent mixtures, such as mixtures of aromatic and alcoholic solvents, e.g. toluene and ethanol, at temperatures of from $-50°$ to $50°$ C., preferably from $-10°$ to $20°$ C.

The preparation of compounds of formulae XIX and XIX A is carried out especially preferably under conditions analogous to the reaction conditions mentioned in J. Org. Chem. 47, 3016 (1982) or J. Org. Chem. 43, 3624 (1978).

A sulfur-ylide suitable for the reaction of compounds of formula XIX or XIX A to form the epoxides of formula XX or XX A is, for example, a dialkylsulfonium methylide, e.g. dimethylsulfonium methylide, an alkyl- or phenyl-dialkylaminosulfoxonium methylide, e.g. methyl- or phenyl-dimethylaminosulfoxonium methylide, or a dialkylsulfoxonium methylide, e.g. dimethyl- or diethyl-sulfoxonium methylide.

The relevant sulfur-ylide compound is expediently prepared in situ from the corresponding sulfonium or sulfoxonium salt and a base, e.g. sodium hydride, in a dipolar aprotic solvent, e.g. dimethyl sulfoxide, or an ether, e.g. tetrahydrofuran or 1,2-dimethoxyethane, and then reacted with compounds of formula XIX or XIX A. The reaction is normally carried out at room temperature, with cooling e.g. to $-20°$ C., or with gentle heating e.g. up to $40°$ C. The simultaneously formed sulfide, sulfinamide or sulfoxide is removed during the subsequent aqueous working-up.

The reaction with a sulfur-ylide is carried out especially preferably analogously to the conditions mentioned in J. Org. Chem. 50, 4615 (1985).

The compound of formula XX (preferably XX A) can also be obtained from a compound of formula XIX (preferably XIX A), as defined above, by reaction thereof with a tri-lower alkyl-silylmethyl-Grignard compound, e.g. prepared from the corresponding halo-methylsilane, such as chloromethyl-trimethylsilane, in an inert solvent, e.g. an ether, such as dioxane or diethyl ether, at temperatures of from $0°$ to $50°$ C., e.g. from room temperature to approximately $40°$ C., subsequent removal of the silyl radical and formation of a double bond, e.g. by means of treatment with a Lewis acid, such as $BF_3$, an amino-protecting group $R_{10}$ present preferably also being removed, in an inert solvent, e.g. an ether, such as diethyl ether, or a halogenated hydrocarbon, such as dichloromethane, or a mixture thereof, at temperatures of from $-50°$ C. to the reflux temperature, especially from $0°$ to $30°$ C., if necessary, acylation once more to introduce an amino-protecting group as $R_{10}$, as defined above, and oxidation of the resulting double bond to the oxirane, preferably with a percarboxylic acid, e.g. m-chloroperbenzoic acid, in an inert solvent, e.g. a halogenated hydrocarbon, such as dichloromethane, at temperatures of from $-20°$ C. to the reflux temperature of the mixture, e.g. at from $10°$ to $30°$ C.

The starting materials of Processes b), c) and d) are known or; if novel, can be prepared according to processes known per se, e.g. the compound of formula V can be prepared from suitable hydrazine derivatives of formula III wherein $R_9$ is hydrogen and the remaining radicals are as defined for compounds of formula V, and suitable epoxides of formula IV wherein the radicals are as defined for compounds of formula V (Process b), the compound of formula VII can be prepared from suitable hydrazine derivatives of formula III wherein the radicals are as defined for compounds of formula VII, and suitable epoxides of formula IV wherein $R_1$ is hydrogen and the remaining radicals are as defined for compounds of formula VII (Process c), and the compound of formula IX can be prepared from suitable hydrazine derivatives of formula III wherein $R_9$ is hydrogen and the remaining radicals are as defined for compounds of formula IX (Process d) and suitable epoxides of formula IV wherein $R_1$ is hydrogen and the remaining radicals are as defined for compounds of formula IX (Process d), analogously to Process a), where appropriate with the use and removal of protecting groups.

The compounds of formula I' wherein the substituents are as defined above can be prepared, for example, from compounds of formula III'

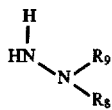 (III)

wherein the radicals are as defined for compounds of formula I, in the manner described in Process b), by reaction with a compound of formula IV, wherein any functional groups present that are not to take part in the reaction are in protected form as described in that Process and can be freed after the reaction.

There are preferred for Process d) the starting materials of formula

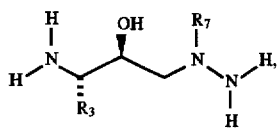 (II)

wherein $R_3$ is unsubstituted or substituted alkyl or cycloalkyl; aryl; heterocyclyl; or unsubstituted or substituted alkenyl; and $R_7$ is unsubstituted or substituted alkyl or cycloalkyl; aryl; heterocyclyl; or unsubstituted or substituted alkenyl, and the salts of the said compounds where salt-forming groups are present, which are intermediates according to the invention.

They may be protected especially at one or both amino groups and, in the case where two amino-protecting groups are present, these may be identical or different from one another.

There may be used as amino-protecting groups, for example, the amino-protecting groups mentioned above in Process a). The radicals $R_3$ and $R_7$ mentioned for compounds of formula II are as defined above for compounds of formula I in the definition of the radicals $R_3$ and $R_7$.

Especially preferred are compounds of formula II wherein $R_3$ is cyclohexyl-lower alkyl, phenyl-lower alkyl or p-fluorophenyl-lower alkyl and $R_7$ is lower alkyl, cyclohexyl-lower alkyl, phenyl-lower alkyl, p-cyanophenyl-lower alkyl or p-fluorophenyl-lower alkyl, and the salts of the said compounds where salt-forming groups are present.

Especially preferred in particular are compounds of formula II wherein $R_3$ is phenyl-lower akyl and $R_7$ is lower alkyl, cyclohexyl-lower alkyl or phenyl-lower alkyl, and the salts of the said compounds where salt-forming groups are present.

More especially preferred are compounds of formula II wherein $R_3$ is cyclohexylmethyl, benzyl or p-fluorobenzyl and $R_7$ is n-butyl, isobutyl, cyclohexylmethyl, benzyl, p-fluorobenzyl or p-cyanobenzyl, and the salts of the said compounds where salt-forming groups are present.

More especially preferred in particular are compounds of formula II wherein $R_3$ is benzyl and $R_7$ is isobutyl, cyclohexylmethyl or benzyl, and the salts of the said compounds where salt-forming groups are present.

Preferred above all are the compounds of formula II mentioned in the Examples.

The compounds of formula II wherein the substituents are as defined, or their salts where salt-forming groups are present, are prepared, for example, by adding a hydrazine derivative of formula

 (XVI), wherein $R_{10}$ is an amino-protecting group, to an epoxide of formula

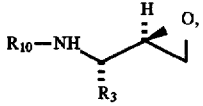 (XX A)

wherein $R_{11}$ is an amino-protecting group, and if desired, converting a compound of formula II having at least one salt-forming group obtainable according to the preceding Process a) into its salt or converting an obtainable salt into the free compound or into a different salt and/or separating any isomeric mixtures that are obtainable and/or removing any protecting groups present in a compound of formula II and/or converting a compound of formula II according to the invention into a different compound of formula II according to the invention.

The preparation and conversion of salts, the separation of isomeric mixtures, the removal of protecting groups and the conversion of compounds of formula II are carried out analogously to the processes described hereinbefore for compounds of formula I.

Especially preferred is the preparation of starting materials of formula II, wherein the substituents are as defined, by the removal of protecting groups from compounds of formula II wherein one or both amino groups are protected by amino-protecting groups, especially under the conditions for the hydrolysis of compounds of formula I, as described in the additional process steps.

The methods for the addition of compounds of formula XVI to those of formula XX A are described above under Process a) in the preparation of compounds of formula I.

The preparation of the protected compounds of formula I is carried out, for example, according to any one of the processes mentioned so far, especially from compounds of formulae III and IV, wherein functional groups in those compounds are if desired protected by protecting groups, as described in Process a).

The acids of formulae VI, VIII, XVII and XXI and the compounds having nucleofugal groups of formulae X, XI, XII, XIII, XIV and XV are known or, if novel, can be prepared according to processes known per se.

The invention in addition relates to novel antiretroviral compounds with Acyl-protected central group, to processes for the preparation of those compounds, to novel intermediates for the preparation of those compounds, especially those having antiretroviral activity, to pharmaceutical compositions comprising those compounds, to those compounds for use in a therapeutic method of treating the human or animal body and to the use of those compounds for the therapeutic treatment of the human or animal body or for the preparation of pharmaceutical compositions.

The principal aim at present is to make available such compounds having the best possible pharmacokinetic properties.

A requirement for therapeutic effectiveness in vivo is the achievement of good bioavailability, for example good absorptive capacity and/or a high blood level, also in the case of enteral, such as oral, administration, in order thus to obtain sufficiently high concentrations in the infected cells.

The object of the present invention is to provide compounds having excellent antiretroviral activity, especially very good bioavailability.

The acylated compounds according to the invention are compounds of formula

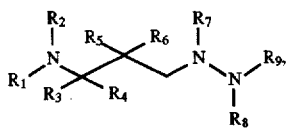

(I-A)

wherein $R_1$ and $R_9$ are each independently of the other hydrogen; acyl; unsubstituted or substituted alkyl; sulfo; or sulfonyl substituted by unsubstituted or substituted alkyl, aryl or by heterocyclyl, with the proviso that not more than one of the radicals $R_1$ and $R_9$ is hydrogen; and $R_2$ and $R_8$ are each independently of the other hydrogen or unsubstituted or substituted alkyl;

$R_3$ and $R_4$ are each independently of the other hydrogen, unsubstituted or substituted alkyl, unsubstituted or substituted cycloalkyl or aryl;

$R_5$ is acyloxy;

$R_6$ is hydrogen; and $R_7$ is unsubstituted or substituted alkyl, unsubstituted or substituted cycloalkyl or aryl; and salts of the mentioned compounds where salt-forming groups are present, with the exception of the compound wherein $R_1$ and $R_9$ are each acetyl, $R_2$, $R_3$, $R_4$, $R_6$ and $R_8$ are each hydrogen, $R_5$ is acetoxy and $R_7$ is 2,2-[N-ethoxycarbonylmethyl)-N-methyl]hydrazin-1-ylcarbonylmethyl.

In the description of compounds of formula I-A the term "lower" used in the definition of groups or radicals, for example lower alkyl, lower alkoxy, lower alkanoyl etc., means that, unless expressly otherwise defined, the groups or radicals so defined contain up to and including a maximum of 7, and preferably up to and including 4, carbon atoms. In the case of lower alkenyl or lower alkynyl, from 2 to 7, preferably from 3 to 7, and especially 3 or 4, carbon atoms are present.

Unless indicated to the contrary, where substituted the radicals $R_1$, $R_2$, $R_3$, $R_4$, $R_7$, $R_8$ and/or $R_9$ are mono- or poly-substituted, especially mono- to tri-substituted, for example mono-substituted, by identical or different substituents.

If a radical that is defined by referring back to another substituent is defined "independently" of the radical used for the definition, it means that if both radicals are present in a compound they need not be identical, although they can, however, be identical.

The carbon atoms in compounds of formula I-A substituted by $R_3$ and $R_4$ and by $R_5$ and $R_6$ may, if they are asymmetric, be in the (R)-, (S)- or (R,S)-configuration, as may also any other asymmetric carbon atoms present. Accordingly, the present compounds may be in the form of isomeric mixtures or in the form of pure isomers, especially in the form of diastereoisomeric mixtures, pairs of enantiomers or pure enantiomers. Preferred compounds of formula I-A are those wherein the carbon atoms substituted by $R_3$ and by $R_5$ have the (S)-configuration and any other asymmetric carbon atoms that may be present are, independently of one another, in the (R)-, (S)- or (R,S)-configuration.

Unless otherwise indicated, the general terms and names used in the description of the present invention preferably have the following meanings:

Acyl $R_1$ or $R_9$ has, for example, up to 25, preferably up to 19, carbon atoms and is especially the acyl group of a carboxylic acid, of a semiester of carbonic acid, of an unsubstituted or N-substituted carbamic acid or of an unsubstituted or substituted amino acid.

Preferred acyl groups $R_1$ or $R_9$ of a carboxylic acid are unsubstituted or substituted alkanoyl, alkenoyl or alkynoyl having up to 19 carbon atoms, for example n-decanoyl, or preferably lower alkanoyl, such as formyl, acetyl, propionyl, butyryl or pivaloyl; or also or especially 3,3-dimethylbutyryl; or substituted lower alkanoyl wherein preferably up to four, especially (except in the case of halogen which may be present up to three times as a substituent) up to two, substituents may be present, especially one substituent (except in the case of halogen which may be present up to three times as a substituent), the substituents being selected especially from cycloalkyl-lower alkanoyl wherein cycloalkyl has, for example, from 3 to 7 carbon atoms and lower alkanoyl is as defined above, for example cycloalkylcarbonyl, for example having a total of from 4 to 8 carbon atoms, such as cyclopropyl-, cyclobutyl-, cyclopentyl- or cyclohexyl-carbonyl, or 2-cyclohexyl- or 2-cyclopentyl-acetyl, cycloalkenyl-lower alkanoyl wherein cycloalkenyl has, for example, from 3 to 7 carbon atoms, such as cycloalkenylcarbonyl, for example having from 4 to 8 carbon atoms, such as 1-cyclohexenylcarbonyl, 1,4-cyclohexadienylcarbonyl or 1-cyclohexenylacetyl or 1,4-cyclohexadienylacetyl, bicycloalkyl-lower alkanoyl wherein bicycloalkyl contains, for example, from 5 to 10 carbon atoms, for example bicycloalkylcarbonyl, preferably having from 8 to 11 carbon atoms, such as decahydronaphthyl-2-carbonyl, bicyclohexyl-, bicycloheptyl-, bicyclooctyl-, bicyclononyl- or bicyclodecyl-acetyl or -3-propionyl, bicycloalkenylcarbonyl, preferably having from 8 to 12 carbon atoms, especially in bicycloalkenylcarbonyl, such as 5-norbornen-2-ylcarbonyl or bicyclo[2.2.2]octen-2-yl-carbonyl, tricycloalkyl-lower alkanoyl wherein tricycloalkyl contains, for example, from 8 to 10 carbon atoms, for example tricycloalkylcarbonyl, preferably having from 8 to 11 carbon atoms, such as 1- or 2-adamantylcarbonyl, aryl-lower alkanoyl wherein aryl has from 6 to 14 ring carbon atoms, such as in phenyl, indenyl, indanyl, naphthyl, anthryl, phenanthryl, acenaphthyl or fluorenyl, and may be unsubstituted or mono- to tri-substituted especially by lower alkyl, for example methyl, ethyl or propyl, halo-lower alkyl, for example trifluoromethyl, phenyl, 1- or 2-naphthyl, hydroxy, lower alkoxy, for example methoxy, carbamoyl-lower alkoxy, N-lower alkylcarbamoyl-lower alkoxy or N,N-di-lower alkylcarbamoyl-lower alkoxy, amino, mono- or di-lower alkylamino, lower alkanoylamino, for example pivaloylamino, halogen, for example fluorine, chlorine or bromine, carboxy, lower alkoxycarbonyl, such as tert-butoxycarbonyl, phenyl-, naphthyl- or fluorenyl-lower alkoxycarbonyl, such as benzyloxycarbonyl, lower alkanoyl, sulfo, lower alkylsulfonyl, for example methylsulfonyl, phosphono, hydroxy-lower alkoxyphosphoryl or di-lower alkoxyphosphoryl, carbamoyl, mono- or di-lower alkylcarbamoyl, sulfamoyl, mono- or di-lower alkylaminosulfonyl, nitro and/or by cyano, wherein phenyl may be present up to three times, for example in diphenyl-, dibenzyl- or triphenyl-lower alkanoyl, such as diphenyl-, dibenzyl- or tri-phenyl-acetyl, and wherein lower alkanoyl may be unsubstituted or substituted, for example by carboxy; lower alkoxycarbonyl, for example methoxy-, ethoxy-, n-propoxy-, isopropoxy-, n-butoxy-, isobutoxy-, sec-butoxy-, tert-butoxy-, n-pentyloxy-, isopentyloxy-, neopentyloxy-, tert-pentyloxy-, n-hexyloxy-, isohexyloxy- or n-heptyloxy-carbonyl; aryl-lower alkoxycarbonyl wherein aryl has from 6 to 12 carbon atoms, for example benzyloxycarbonyl; carbamoyl, carbamoyl substituted at the nitrogen atom by one or two radicals selected from lower alkyl, such as methyl, ethyl, propyl, isopropyl, n-butyl, isobutyl, sec-butyl and tert-butyl, for example in N-methylcarbamoyl, N-n-butyl-carbamoyl or N,N-dimethylcarbamoyl, from carboxy-lower alkyl or lower alkoxycarbonyl-lower alkyl, for example in the form of carboxymethylcarbamoyl (glycinylcarbonyl) or in the form of tert-butoxycarbonylmethylcarbamoyl, from di-lower alkylamino-lower alkyl, for example 2-dimethylaminoethyl, from hydroxy-lower alkyl, for example hydroxymethyl or hydroxyethyl, and from di-lower alkoxy-lower alkyl, for example 2-(2, 2-dimethoxyethyl); and/or by cyano and is unbranched or branched, selected especially from phenyl-lower alkanoyl, such as benzoyl, phenylacetyl or 3-phenylpropionyl, which may be unsubstituted or mono- or poly-substituted at the phenyl ring, for example by lower alkyl, for example methyl, phenyl, halogen, for example fluorine or chlorine, hydroxy, lower alkoxy, for example methoxy, and/or by nitro, such as 4-chloro-, 4-methoxy- or 4-nitro-benzoyl, naphthylcarbonyl, such as α- or β-naphthylcarbonyl or 1,8-naphthalenedicarbonyl bonded to the amino group via both carbonyl groups, indenylcarbonyl, such as 1-, 2- or 3-indenylcarbonyl, indanylcarbonyl, such as 1- or 2-indanylcarbonyl, phenanthrenylcarbonyl, such as 9-phenanthrenylcarbonyl, α-naphthylacetyl, β-naphthylacetyl, lower alkylphenylacetyl, such as 4-methylphenylacetyl, lower alkoxyphenylacetyl, such as 4-methoxyphenylacetyl, 3-(p-hydroxyphenyl)-propionyl, diphenylacetyl, di(4-methoxyphenyl)acetyl, triphenylacetyl, 2,2-dibenzylacetyl, 3-α- or 3-β-naphthylpropionyl, phenyl-lower alkanoyl wherein the lower alkanoyl radical is substituted by carbamoyl, for example 2-carbamoyl-3-phenylpropionyl, such as 2-(R,S) carbamoyl-3-phenylpropionyl, 3-α-naphthyl-2-carbamoylpropionyl, 3-phenyl- or 3-α-naphthyl-2-tert-butylcarbamoyl-propionyl, 3-phenyl- or 3-α-naphthyl-2-(2-dimethylaminoethyl) carbamoylpropionyl, 3-α-naphthyl-2-(carboxy- or tert-butoxy-carbonyl-)methylcarbamoyl-propionyl, 3-phenyl- or 3-α-naphthyl-2-(3-hydroxy-2-propyl) carbamoyl-propionyl, 3-phenyl- or 3-α-naphthyl-2-(2,2-dimethoxyethyl)carbamoylpropionyl and 3-phenyl- or 3-α-naphthyl-2-(5-amino-5-carboxypentyl)-carbamoylpropionyl, especially phenyl-lower alkanoyl, such as phenylacetyl, or phenyl-lower alkanoyl wherein the lower alkanoyl radical is substituted by carbamoyl, such as 2-(R,S) carbamoyl-3-phenylpropionyl, heterocyclyl-lower alkanoyl wherein lower alkanoyl is unsubstituted or substituted as defined above under aryl-lower alkanoyl $R_1$ or $R_9$ and wherein heterocyclyl is preferably a single or double ring system having from 3 to 10 ring atoms, is bonded via a carbon atom or, especially, via a nitrogen atom and contains up to 3 further hetero atoms selected from oxygen, nitrogen, sulfur, and sulfur linked to 1 or 2 oxygen atoms; the mentioned ring system may also be fused with 1 or 2 phenyl or naphthyl radicals, it being possible for naphthyl also to be fused-on by two sides, or with 1 or 2 cycloalkyl radicals, cycloalkyl preferably having from 5 to 7 ring atoms; and which may be unsaturated or partially or fully saturated, for example thienyl, furyl, pyrrolyl, imidazolyl, pyrazolyl, oxazolyl, thiazolyl, tetrazolyl, pyridyl, pyrazinyl, pyrimidinyl, pyridazinyl, indolyl, benzimidazolyl, quinolyl, isoquinolyl, 3,1-benzofuranyl, cyclohexa[b]pyrrolyl, cyclohexa[b] pyridyl, cyclohexa[b]pyrazinyl, cyclohexa[b] pyrimidinyl, pyrrolidinyl, pyrrolinyl, imidazolidyl, piperidyl, piperazinyl, morpholinyl, thiomorpholinyl, S,S-dioxo-thiomorpholinyl, indolinyl, isoindolinyl, 4,5,6,7-tetrahydroindolyl, 1,2,3,4-tetrahydroquinolyl or 1,2,3,4-tetrahydroisoquinolyl, with heterocyclyl, for example one of the last-mentioned radicals, being unsubstituted or substituted by lower alkyl, for example methyl, phenyl, 1- or 2-naphthyl, phenyl-lower alkyl, for example benzyl, hydroxy-lower alkyl, for example hydroxymethyl or 2-hydroxyethyl, lower alkoxy-lower alkyl, for example methoxymethyl or 2-methoxyethyl, lower alkanoyloxy-lower alkyl, for example acetoxymethyl, phenyl- or naphthyl-lower alkanoyloxy-lower alkyl, for example benzoyloxy-, phenylacetoxy- or 1- or 2-naphthoyloxy-methyl, -2-ethyl or -2-(2,2-dimethylethyl), lower alkoxycarbonyloxy-lower alkyl, for example tert-butoxycarbonyloxy-lower alkyl, phenyl-lower alkoxycarbonyloxy-lower alkyl, for example 2-benzyloxycarbonyloxyethyl, amino-lower alkyl, for example aminomethyl, hydroxy, lower alkoxy, for example methoxy or ethoxy, amino, lower alkylamino, for example methyl-, ethyl- or tert-butyl-amino, di-lower alkylamino, for example dimethyl- or diethyl-amino, carboxy, lower alkoxycarbonyl, for example methoxy-, isopropoxy-, sec-butoxy- or tert-butoxy-carbonyl, phenyl- or naphthyl-lower alkoxycarbonyl, for example benzyloxycarbonyl, halogen, for example fluorine, chlorine, bromine or iodine, especially chlorine or bromine, lower alkanoyl, for example acetyl or pivaloyl, carbamoyl, mono- or di-lower alkylcarbamoyl, for example N-methylcarbamoyl, N-n-butylcarbamoyl or N,N-dimethylcarbamoyl, hydroxy- or carboxy-lower alkylcarbamoyl, for example hydroxy- or carboxy-methylcarbamoyl or hydroxy- or carboxyethylcarbamoyl, nitro, oxo and/ or by cyano; especially in heterocyclyl-lower alkanoyl wherein lower alkanoyl is unsubstituted or substituted independently by one of the substituents defined above under aryl-lower alkanoyl $R_1$ or $R_9$; with heterocyclyl-lower alkanoyl being selected especially from pyrrolylcarbonyl, for example 2- or 3-pyrrolylcarbonyl, thienylcarbonyl, such as 2-thienylcarbonyl, furylcarbonyl, such as 2-furylcarbonyl, indolylcarbonyl, such as 2-, 3- or 5-indolylcarbonyl, 4,5,6,7-tetrahydroindolyl-2-carbonyl, quinolyl-lower alkanoyl, for example quinolylcarbonyl, such as 2-, 3- or 4-quinolylcarbonyl, isoquinolylcarbonyl, such as 1-, 3- or 4-isoquinolylcarbonyl, piperidylcarbonyl, such as piperidinocarbonyl or 2-, 3- or 4-piperidylcarbonyl, piperazinylcarbonyl, such as piperazin-1-ylcarbonyl, morpholinyl-lower alkanoyl, for example morpholino-lower alkanoyl, such as morpholinocarbonyl, thiomorpholinyl-lower alkanoyl, for example thiomorpholino-lower alkanoyl, such as thiomorpholinocarbonyl, S,S-dioxothiomorpholinylcarbonyl, such as S,S-dioxothiomorpholinocarbonyl, 1,2,3,4-tetrahydroquinolylcarbonyl, such as 1,2,3,4-tetrahydroquinolyl-2-, -3- or -4-carbonyl, 1,2,3,4-tetrahydroisoquinolylcarbonyl, such as 1,2,3,4-tetrahydroisoquinolyl-1-, -3- or -4-carbonyl, tetrazolyl-lower alkanoyl, such as 3-(tetrazol-1-yl)-propionyl, and pyridyl-lower alkanoyl, for example pyridylcarbonyl, such as 2-, 3- or 4-pyridylcarbonyl, or pyridylacetyl, such as 2-, 3- or 4-pyridylacetyl; and heterocyclyl-lower alkanoyl being selected most especially from morpholinocarbonyl, thiomorpholinocarbonyl, quinolin-2-ylcarbonyl, 3-(tetrazol-1-yl)-propionyl, 2-pyridylcarbonyl and 2- or 3-pyridylacetyl, hydroxy-lower alkanoyl, such as 3-hydroxypropionyl or 2-hydroxy-3-methylpentanoyl, hydroxy-lower alkoxy-lower alkanoyl, such as 3-hydroxy-n-propoxycarbonyl, lower alkoxy-lower alkanoyl, for example lower alkoxy-acetyl or lower alkoxypropionyl, such as methoxyacetyl, ethoxyacetyl or 3-methoxypropionyl, lower alkoxy-lower alkoxy-lower alkanoyl, such as 2-methoxymethoxy-3-methylpentanoyl or also or especially 2-(methoxy)ethoxyacetyl, lower alkanoyloxy-lower alkanoyl wherein lower alkanoyloxy is, for example, acetoxy, propionyloxy, butyryloxy, isobutyryloxy or pivaloyloxy, such as acetoxyacetyl or 3-acetoxypropionyl, amino-lower alkanoyl wherein the amino group is not in the α- or β-position, such as 5-aminopentanoyl, lower alkanoylamino-lower alkanoyl wherein the amino group is not in the α- or β-position of the lower alkanoyl radical, such as 5-pivaloylamino-pentanoyl, lower alkoxycarbonylamino-lower alkanoyl wherein the amino group is not in the α- or β-position of the lower alkanoyl radical, such as 5-(tert-butoxycarbonylamino)-pentanoyl, phenyl-lower alkoxycarbonylamino that is not the in α- or β-position relative to the bonding carboxy group of the acyl radical, especially in phenyl-lower alkoxycarbonylamino-lower alkanoyl wherein the amino group is not in the α- or β-position of the lower alkanoyl radical, such as 5-benzyloxycarbonylaminopentanoyl or 6-benzyloxycarbonylaminohexanoyl, amino-lower alkanoyl substituted at the amino nitrogen atom by heterocyclyl-lower alkanoyl as defined above for heterocylyl-lower alkanoyl $R_1$ or $R_9$, especially by N-morpholino- or N-thiomorpholino-carbonyl, especially by N-morpholino- or N-thiomorpholino-carbonylamino-lower alkanoyl, such as N-morpholino- or N-thiomorpholinocarbonylamino-acetyl, halo-lower alkanoyl containing up to 3 halogen atoms, for example α-haloacetyl, such as α-fluoro-, α-chloro-, α-bromo-, α-iodo-, α,α,α-trifluoro- or α,α,α-trichloro-acetyl, or halopropionyl, such as β-chloro- or β-bromo-propionyl, carboxy-lower alkanoyl, for example carboxyacetyl or β-carboxypropionyl, lower alkoxycarbonyl-lower alkanoyl, for example lower alkoxycarbonylacetyl or lower alkoxycarbonylpropionyl, such as methoxycarbonylacetyl, 3-methoxycarbonylpropionyl, ethoxycarbonylacetyl, 3-ethoxycarbonylpropionyl or 3-tert-butoxycarbonylpropionyl, sulfonyl-lower alkanoyl, such as 3-sulfonylpropionyl, carbamoyl-lower alkanoyl, such as carbamoylacetyl or 3-carbamoylpropionyl, alkylcarbamoyl, especially in lower alkylcarbamoyl-lower alkanoyl, for example lower alkylcarbamoyl-acetyl or methylcarbamoyl-lower alkanoyl, such as methylcarbamoylacetyl, di-lower alkylcarbamoyl-lower alkanoyl, for example di-lower alkylcarbamoylacetyl or dimethylcarbamoyl-lower alkanoyl, such as dimethylcarbamoylacetyl, carbamoyl-lower alkanoyl substituted at the nitrogen atom by a radical selected from ethylene, trimethylene, tetramethylene and pentamethylene wherein a carbon atom may have been replaced by nitrogen, oxygen, sulfur or by sulfur mono- or di-substituted by oxygen, especially in correspondingly N-substituted carbamoyl-lower alkanoyl, it also being possible for the radical so formed to be fully or partially unsaturated, for example in the form of piperidino-, pyrazin-1-yl-, piperazin-1-yl-, pyrimidin-1-yl-, pyridazin-1-yl-, morpholino-, thiomorpholino- or S,S-dioxothiomorpholino-carbonyl-lower alkanoyl, such as in morpholinocarbonyl-acetyl, 3-(morpholinocarbonyl)-propionyl or 3-(morpholinocarbonyl)-2-isobutyl-propionyl, N-heterocyclyl-lower alkylcarbamoyl-lower alkanoyl or N-lower alkyl-N-heterocyclyl-lower alkylcarbamoyl-lower alkanoyl wherein heterocyclyl is preferably selected from pyrrolyl, furyl, thienyl, imidazolyl, pyrazolyl, oxazolyl, thiazolyl, pyridyl, pyrazinyl, pyrimidinyl, indolyl, quinolyl and isoquinolyl, which may also be fully or partially saturated, from morpholinyl and thiomorpholinyl, such as N-methyl-2-(N-2-pyridylmethyl)-carbamoylacetyl, 2-(N-morpholino-lower alkylcarbamoyl)-lower alkanoyl, such as 2(R,S)-(N-(2-morpholinoethyl)-carbamoyl)-3-methyl-butyryl, or 2-(N-(pyridyl-lower alkyl)-carbamoyl)-lower alkanoyl, such as (2(R,S)-(N-(2-pyridylmethyl)-carbamoyl)-3-methyl)-butyryl, oxo-lower alkanoyl, such as acetoacetyl or propionylacetyl, and cyano-lower alkanoyl, such as cyanoacetyl, 2- or 3-cyanopropionyl or 2-, 3- or 4-cyanobutyryl;

lower alkenoyl having from 3 to 7 carbon atoms, preferably having 3 or 4 carbon atoms, such as acryloyl, vinylacetyl, crotonoyl or 3- or 4-pentenoyl, or lower alkynoyl having from 3 to 7, preferably 3 or 4, carbon atoms, for example propioloyl or 2- or 3-butynoyl.

Preferred acyl groups $R_1$ or $R_9$ of a semiester of carbonic acid are lower alkoxycarbonyl, for example methoxy-, ethoxy-, n-propoxy-, isopropoxy-, isobutoxy- or tert-lower alkoxy-carbonyl, or also or especially n-propoxycarbonyl, such as tert-butoxycarbonyl or isobutoxycarbonyl, 2-halo-lower alkoxycarbonyl, such as 2-chloro-, 2-bromo-, 2-iodo- or 2,2,2-trichloroethoxycarbonyl, aryl-lower alkoxycarbonyl, for example arylmethoxycarbonyl, wherein aryl has from 6 to 14 carbon atoms and is, for example, phenyl, biphenylyl, 1- or 2-naphthyl, fluorenyl, or phenyl mono- or polysubstituted by lower alkyl, for example methyl or tert-butyl, hydroxy, lower alkoxy, for example methoxy, ethoxy or tert-butoxy, halogen, for example chlorine or bromine, and/or by nitro, for example phenyl-lower alkoxycarbonyl, such as benzyloxycarbonyl or 4-methoxybenzyloxycarbonyl, heterocyclyl-lower alkoxycarbonyl wherein heterocyclyl is preferably selected from pyrrolyl, furyl, thienyl, imidazolyl, pyrazolyl, oxazolyl, thiazolyl, pyridyl, pyrazinyl, pyrimidinyl, indolyl, quinolyl and isoquinolyl, which may also be fully or partially saturated, from morpholinyl and from thiomorpholinyl and may be unsubstituted or substituted, especially by lower alkyl, such as methyl, such as furylmethoxycarbonyl, tetrahydrofuryl-lower alkoxycarbonyl, such as 2-tetrahydrofuryl-methoxycarbonyl, 2-morpholino-ethoxycarbonyl, or 2-, 3- or 4-pyridylmethoxycarbonyl, lower alkenyloxycarbonyl wherein preferably the lower alkenyl radical is bonded to the bonding oxygen atom via a saturated carbon atom, such as allyloxycarbonyl, lower alkoxy-lower alkoxycarbonyl, such as 2-methoxyethoxycarbonyl, or (lower alkoxy-lower alkoxy)-lower alkoxycarbonyl, such as 2-(2-methoxyethoxy)ethoxycarbonyl.

Preferred acyl groups $R_1$ or $R_9$ of an unsubstituted or substituted carbamic acid, are carbamoyl or unsubstituted or substituted N-alkyl- or N,N-dialkylcarbamoyl wherein the alkyl radical has up to 12 carbon atoms, preferably unsubstituted or substituted lower alkyl- or di-lower alkyl-carbamoyl, such as methyl-, ethyl-, propyl-, tert-butyl-, dimethyl-, diethyl- or di-n-propyl-carbamoyl, the substituents being selected from phenyl, for example in benzylcarbamoyl, N-phenyl-lower alkyl-N-lower alkylcarbamoyl, such as N-benzyl-N-methylcarbamoyl, or dibenzylcarbamoyl, heterocyclyl that is independently as defined as a substituent of lower alkanoyl $R_1$ and $R_9$, preferably pyridyl, such as 2-, 3- or 4-pyridyl, more especially in N-heterocyclyl-lower alkyl-N-lower alkylcarbamoyl, for example N-pyridyl-lower alkyl-N-lower alkylcarbamoyl, such as N-(2-, 3- or 4-pyridylmethyl)-N-methyl-carbamoyl, or in N-heterocyclyl-lower alkylcarbamoyl, for example 2- or 3-pyridyl-lower alkylaminocarbonyl, such as 2- or 3-pyridylmethylaminocarbonyl, hydroxy, for example in hydroxymethyl, 2-hydroxyethyl,3-hydroxypropyl, 2-hydroxypropyl, and lower alkoxy, preferably in lower alkoxy-lower alkyl, for example methoxymethyl or 2-methoxyethyl; or also or especially N-lower alkyl-N-morpholino-lower alkylaminocarbonyl, such as N-methyl-N-(2-morpholinoethyl)aminocarbonyl, or N-morpholino-lower alkylaminocarbonyl, such as N-(2-morpholinoethyl)aminocarbonyl.

Preferred acyl groups $R_1$ or $R_9$ of an unsubstituted or substituted amino acid are formed by the amino acid residues, bonded via the carbonyl of their carboxy group, of an α- or β-amino acid, especially a natural α-amino acid having the L-configuration, such as those normally occurring in proteins, or an epimer of such an amino acid, that is to say having the unnatural D-configuration, or a D,L-isomeric mixture thereof, a homologue of such an amino acid, for example wherein the amino acid side chain has been lengthened or shortened by one or two methylene groups, wherein the amino group is in the β-position and/or wherein a methyl group has been replaced by hydrogen, a substituted aromatic amino acid wherein the aromatic radical has from 6 to 14 carbon atoms, for example a substituted phenylalanine or phenylglycine wherein the phenyl may be mono- or poly-substituted by lower alkyl, for example methyl, hydroxy, lower alkoxy, for example methoxy, lower alkanoyloxy, for example acetoxy, amino, lower alkylamino, for example methylamino, di-lower alkylamino, for example dimethylamino, lower alkanoylamino, for example acetylamino or pivaloylamino, lower alkoxycarbonylamino, for example tert-butoxycarbonylamino, arylmethoxycarbonylamino wherein aryl preferably has from 6 to 14 carbon atoms, for example benzyloxycarbonylamino or 9-fluorenylmethoxycarbonylamino, halogen, for example fluorine, chlorine, bromine or iodine, carboxy and/or by nitro, a benzo-fused phenylalanine or phenylglycine, such as α-naphthylalanine, or a hydrogenated phenylalanine or phenylglycine, such as cyclohexylalanine or cyclohexylglycine.

Those amino acids can be substituted at free amino or hydroxy functions, preferably at a free amino function, by one of the radicals mentioned above under acyl $R_1$ or $R_9$ as the acyl group of a carboxylic acid, a semiester of carbonic acid or an unsubstituted or N-substituted carbamic acid or by one of the radicals mentioned below under unsubstituted or substituted alkyl $R_1$, $R_2$, $R_8$ or $R_9$.

Especially preferred is the radical, bonded via its carbonyl group, of an amino acid selected from glycine (H-Gly-OH), alanine (H-Ala-OH), valine (H-Val-OH), norvaline (α-aminovaleric acid), leucine (H-Leu-OH), isoleucine (H-Ile-OH), norleucine (α-aminohexanoic acid, H-Nle-OH), serine (H-Ser-OH), homoserine (α-amino-γ-hydroxybutyric acid), threonine (H-Thr-OH), methionine (H-Met-OH), cysteine (H-Cys-OH), proline (H-Pro-OH), trans-3- and trans-4-hydroxyproline, phenylalanine (H-Phe-OH), tyrosine (H-Tyr-OH), 4-aminophenylalanine, 4-chlorophenylalanine, 4-carboxyphenylalanine, β-phenylserine (β-hydroxyphenylalanine), phenylglycine, α-naphthylalanine (H-Nal-OH), cyclohexylalanine (H-Cha-OH), cyclohexylglycine, tryptophan (H-Trp-OH), indoline-2-carboxylic acid, 1,2,3,4-tetrahydroisoquinoline-3-carboxylic acid, aspartic acid (H-Asp-OH), asparagine (H-Asn-OH), aminomalonic acid, aminomalonic acid monoamide, glutamic acid (H-Glu-OH), glutamine (H-Gln-OH), histidine (H-His-OH), arginine (H-Arg-OH), lysine (H-Lys-OH), δ-hydroxylysine, ornithine (α,δ-diaminovaleric acid), 3-aminopropanoic acid, α,γ-diaminobutyric acid and α,β-diaminopropionic acid, especially preferably the radical of an aliphatic amino acid selected from valine, alanine, leucine and isoleucine, or an amino acid selected from glycine, glutamic acid and asparagine, it being possible for each of the mentioned amino acids (with the exception of glycine) to be in the D-, L- or (D,L)-form, preferably in the L-form (with the exception of Val which may also be in the (D)- or (D,L)-form), wherein the α-amino group may be unsubstituted or mono- or di-N-alkylated, for example by lower alkyl, such as methyl or n-propyl, or by amino-lower alkyl, such as 3-aminopropyl, or may be N-acylated by one of the acyl radicals mentioned above under acyl $R_1$ as a radical of a carboxylic acid, of a semiester of carbonic acid or of an unsubstituted or N-substituted carbamic acid, preferably by lower alkanoyl, such as acetyl; by aryl-lower alkanoyl wherein aryl is selected from phenyl, indenyl, indanyl, naphthyl, anthryl, phenanthryl, acenaphthyl and fluorenyl and may be unsubstituted or mono- to tri-substituted especially by lower alkyl, for example methyl, ethyl or propyl, halo-lower alkyl, for example trifluoromethyl, phenyl, 1- or 2-naphthyl, hydroxy, lower alkoxy, for example methoxy, carbamoyl-lower alkoxy, N-lower alkylcarbamoyl-lower alkoxy or N,N-di-lower alkylcarbamoyl-lower alkoxy, amino, mono- or di-lower alkylamino, lower alkanoylamino, for example pivaloylamino, halogen, for example fluorine, chlorine or bromine, carboxy, lower alkoxycarbonyl, such as tert-butoxycarbonyl, phenyl-, naphthyl- or fluorenyl-lower alkoxycarbonyl, such as benzyloxycarbonyl, lower alkanoyl, sulfo, lower alkylsulfonyl, for example methylsulfonyl, phosphono, hydroxy-lower alkoxyphosphoryl or di-lower alkoxyphosphoryl, carbamoyl, mono- or di-lower alkylcarbamoyl, sulfamoyl, mono- or di-lower alkylaminosulfonyl, nitro and/or by cyano, and wherein lower alkanoyl may be unsubstituted or substituted especially by carboxy, lower alkoxycarbonyl, for example methoxy-, ethoxy-, n-propoxy-, isopropoxy-, n-butoxy-, isobutoxy-, sec-butoxy-, tert-butoxy-, n-pentyloxy-, isopentyloxy-, neopentyloxy-, tert-pentyloxy-, n-hexyloxy-, isohexyloxy- or n-heptyloxy-carbonyl, aryl-lower alkoxycarbonyl wherein aryl has from 6 to 12 carbon atoms, for example benzyloxycarbonyl, carbamoyl, carbamoyl substituted by one or two radicals selected from lower alkyl, such as methyl, ethyl, propyl, isopropyl, n-butyl, isobutyl, sec-butyl, tert-butyl, n-pentyl, isopentyl, neopentyl, tert-pentyl, n-hexyl, isohexyl or n-heptyl, for example in N-methylcarbamoyl, N-n-butylcarbamoyl or N,N-dimethylcarbamoyl, from carboxy-lower alkyl or lower alkoxycarbonyl-lower alkyl, for example in the form of carboxymethylcarbamoyl (glycinylcarbonyl) or tert-butoxycarbonylmethylcarbamoyl, from di-lower alkylamino-lower alkyl, for example 2-dimethylaminoethyl, from hydroxy-lower alkyl, for example hydroxymethyl or hydroxyethyl, and from di-lower alkoxy-lower alkyl, for example 2-(2,2-dimethoxyethyl), and/or by cyano and is unbranched or branched, with phenyl-lower alkanoyl, such as phenylacetyl, or phenyl-lower alkanoyl wherein the lower alkanoyl radical is substituted by carbamoyl, such as 2-carbamoyl-3-phenyl-propionyl, being especially preferred; by heterocyclyl-lower alkanoyl wherein heterocyclyl is independently as defined as a substituent of lower alkanoyl $R_1$ and is especially morpholino, thiomorpholino, pyridyl, quinolyl or tetrazolyl, more especially pyridylcarbonyl, such as 2-, 3- or 4-pyridylcarbonyl, morpholinocarbonyl, thiomorpholinocarbonyl, S,S-dioxothiomorpholinocarbonyl, indol-2-ylcarbonyl, quinolin-2-ylcarbonyl, pyridylacetyl, such as 2- or 3-pyridylacetyl, imidazolylacetyl, such as imidazol-1-ylacetyl, morpholinylacetyl, such as morpholinoacetyl, pyridylpropionyl, such as 3-(2- or 3-pyridyl)propionyl, pyrrolidinylpropionyl, such as 3-(4-pyrrolidinyl) propionyl, morpholinylpropionyl, such as 3-morpholinopropionyl, or tetrazolylpropionyl, such as 3-(tetrazol-1-yl)-propionyl; by halo-lower alkanoyl containing up to 3 halogen atoms, for example α-haloacetyl, such as α-fluoro-, α-chloro-, α-bromo-, α-iodo-, ααα-trifluoro- or α,α,α-trichloro-acetyl, or halopropionyl, such as β-chloro- or β-bromo-propionyl; by lower alkoxy-lower alkoxy-lower alkanoyl; by lower alkoxycarbonyl, such as tert-butoxycarbonyl; by aryl-lower alkoxycarbonyl wherein aryl has from 6 to 14 carbon atoms and is selected, for example, from phenyl, naphthyl and fluorenyl, for example phenyl-lower alkoxycarbonyl, such as benzyloxycarbonyl, or 9-fluorenylmethoxycarbonyl; by heterocyclyl-lower alkoxycarbonyl wherein heterocyclyl is selected especially from pyrrolyl, furyl, thienyl, imidazolyl, pyrazolyl, oxazolyl, thiazolyl, pyridyl, pyrazinyl, pyrimidinyl, indolyl, quinolyl and isoquinolyl, which may also be fully or partially saturated and unsubstituted or substituted especially by lower alkyl, such as methyl, for example 2-furylmethoxycarbonyl, tetrahydrofuryl-lower alkoxycarbonyl, such as 2-tetrahydrofuryl-methoxycarbonyl, or 2-morpholino-ethoxycarbonyl; by lower alkenyloxycarbonyl (preferably with a saturated carbon atom at the bonding oxygen atom), such as allyloxycarbonyl; by lower alkoxy-lower alkoxycarbonyl, such as 2-methoxyethoxycarbonyl; by (lower alkoxy-lower alkoxy)-lower alkoxycarbonyl, such as 2-(2-methoxyethoxy)ethoxycarbonyl; by carboxy-lower alkanoyl, such as 3-carboxypropionyl; by lower alkoxycarbonyl-lower alkanoyl; by amino-lower alkanoyl substituted at the amino nitrogen atom by heterocyclyl-lower alkanoyl wherein heterocyclyl is preferably independently as defined above as a substituent of lower alkanoyl $R_1$ or $R_9$, especially by N-morpholino- or N-thiomorpholino-carbonyl, for example N-morpholino- or N-thiomorpholino-carbonylamino-lower alkanoyl, such as N-morpholino- or N-thiomorpholino-carbonylamino-acetyl; by carbamoyl; by phenyl-lower alkylaminocarbonyl, such as benzylaminocarbonyl; by N-heterocyclyl-lower alkyl-N-lower alkylcarbamoyl or N-heterocyclyl-lower alkylcarbamoyl wherein heterocyclyl is independently as defined above as a substituent of lower alkanoyl $R_1$ or $R_9$, especially as pyridyl, such as 2-, 3- or 4-pyridyl, especially 2- or 3-pyridyl-lower alkylaminocarbonyl, such as 2- or 3-pyridylmethylaminocarbonyl; or by N-2-, N-3- or N-4-pyridyl-lower alkyl-N-lower alkylaminocarbonyl, such as N-2-, N-3- or N-4-pyridylmethyl-N-methylaminocarbonyl; by heterocyclyl-lower alkylcarbamoyl-lower alkanoyl wherein heterocyclyl is independently as defined in the definition thereof as a substituent of lower alkyl $R_1$, $R_2$, $R_8$ or $R_9$, for example 2-(N-morpholino-lower alkylcarbamoyl)-lower alkanoyl, such as 2(R,S)-(N-(2-morpholinoethyl)-carbamoyl)-3-methyl-butyryl, or 2-(N-(pyridyl-lower alkyl)carbamoyl)-lower alkanoyl, such as (2(R,S)-(N-(2-pyridylmethyl)-carbamoyl)-3-methyl)butyryl; by sulfonyl; by lower alkanesulfonyl, such as methane- or ethane-sulfonyl; by arylsulfonyl (aryl-$SO_2$) wherein aryl has from 6 to 10 carbon atoms and, for example, is selected from phenyl and naphthyl and is unsubstituted or especially substituted by lower alkyl, such as methyl, or by lower alkoxy, such as methoxy, such as p-toluenesulfonyl; or by heterocyclylsulfonyl (heterocyclyl-$SO_2$—) wherein heterocyclyl is preferably selected from pyrrolyl, furyl, thienyl, imidazolyl, pyrazolyl, oxazolyl, thiazolyl, pyridyl, pyrazinyl, pyrimidinyl, indolyl, quinolyl and isoquinolyl, which may also be fully or partially saturated, from morpholinyl and from thiomorpholinyl and may be unsubstituted or substituted especially by lower alkyl, such as methyl, such as morpholinosulfonyl, thiomorpholinosulfonyl, piperidinosulfonyl or piperazinosulfonyl (heterocyclylsulfonyl not being a substituent in preferred forms);
or is acylated also or especially by lower alkylaminocarbonyl, such as tert-butylaminocarbonyl, N,N-di-lower alkylaminocarbonyl, such as N,N-dimethylaminocarbonyl, lower alkoxy-lower alkylaminocarbonyl, such as N-(2-methoxyethyl) aminocarbonyl, N-lower alkyl-N-morpholino-lower alkylaminocarbonyl, such as N-methyl-N-(2-morpholinoethyl)aminocarbonyl, or N-morpholino-lower alkylaminocarbonyl; and/or a hydroxy group of the side chain is present in etherified or esterified form, for example in the form of lower alkoxy, such as methoxy or tert-butoxy, aryl-lower alkoxy, such as benzyloxy, lower alkanoyloxy, such as acetoxy, or lower alkoxycarbonyloxy, for example tert-butoxycarbonyloxy.

Special preference is given to acyl groups $R_1$ or $R_9$, bonded via the carbonyl group of their carboxy function, of an unsubstituted or substituted amino acid selected from phenylalanine, N-(benzyloxycarbonyl)-phenylalanine, tyrosine, tyrosine-O-methyl ether, N-morpholinocarbonyl-glycine, N-(N-(2-, 3- or 4-pyridyl)methyl-N-methylaminocarbonyl)glycine, valine, N-(trifluoroacetyl)-valine, N-phenylacetyl-valine, N-acetyl-vale, N-(3-phenylpropionyl)-valine, N-(2-carbamoyl-3-phenyl-propionyl)-valine, such as N-(2(R,S)carbamoyl-3-phenyl-propionyl)-valine, N-(2- or 3-pyridylacetyl)-valine, N-tetrahydrofurylmethoxycarbonyl-valine, N-(2-methoxy) ethoxycarbonylvaline, N-3-(tetrazol-1-yl)propionyl-valine, N-(indol-2-ylcarbonyl)-valine, N-(quinolin-2-ylcarbonyl)-valine, N-methoxycarbonyl-valine, N-ethoxycarbonyl-valine, N-isobutoxycarbonyl-valine, N-tert-butoxycarbonyl-valine, N-benzyloxycarbonyl-valine, N-(2-furylmethoxycarbonyl)-valine, N-allyloxycarbonyl-valine, N-(morpholinocarbonyl)-valine, N-(thiomorpholinocarbonyl)-valine, N-(S,S-dioxothiomorpholinocarbonyl)-valine, N-(N-2-pyridylmethyl-N-methylaminocarbonyl)-valine, N-(N-3-pyridylmethyl-aminocarbonyl)-valine, N-(N-2-pyridylmethyl-aminocarbonyl)-valine, N-morpholino-carbonylaminoacetyl-valine, N-methanesulfonyl-valine, N-morpholinosulfonyl-valine, N-acetyl-leucine, N-(4-thiomorpholinocarbonyl)-leucine, N-(4-(S,S-dioxothiomorpholino)carbonyl)-leucine, N-(benzyloxycarbonyl)-leucine, N-acetyl-isoleucine, N-propionyl-isoleucine, N-(benzyloxycarbonyl)-isoleucine, N-(tert-butoxycarbonyl)-norleucine, N-benzyloxycarbonyl-glutamic acid, asparagine, glutamine, N-benzyloxycarbonyl-asparagine, quinolin-2-ylcarbonyl-asparagine and N-(morpholinocarbonyl)-asparagine; or also or especially the corresponding radicals of N-(3,3-dimethylbutyryl)-valine, N-(n-propoxycarbonyl)-valine, N-(2-(2-methoxyethoxy)ethoxycarbonyl)-valine, N-(2-methoxyethoxyacetyl)-valine, N-(N,N-dimethylaminocarbonyl)-valine, N-(N-(2-methoxyethyl)amino)-valine, N-(benzylaminocarbonyl)-valine, N-(2-morpholinoethylaminocarbonyl)-valine or N-(N-methyl-N-(2-morpholinoethyl)aminocarbonyl)-valine; the amino acid residues preferably being in the (L)- or (D,L)-form, and in the case of valine also in the (D)-form.

It should be mentioned that on all levels of definitions those compounds of formula I-A are to be regarded as especially preferred wherein $R_9$ corresponds to the acyl moiety of an α-amino acid that is bonded via the carbonyl group of its carboxy function and that is acylated on its α-amino nitrogen by an acyl group of a carboxylic acid, a semiester of carbonic acid or an unsubstituted or N-substituted carbamic acid, as defined above for $R_1$ or $R_9$.

Unsubstituted or substituted alkyl $R_1$, $R_2$, $R_8$ or $R_9$ is an alkyl radical having from 1 to 20, preferably up to 10, carbon atoms, is branched or unbranched, and is, for example, methyl, ethyl, n-propyl, isopropyl, n-butyl, isobutyl, sec-butyl, tert-butyl, n-pentyl, isopentyl, neopentyl, tert-pentyl, n-hexyl, isohexyl, n-heptyl, n-octyl, n-nonyl or n-decyl. Preference is given to lower alkyl, for example methyl, ethyl, n-propyl, isopropyl, n-butyl, isobutyl, sec-butyl, tert-butyl, n-pentyl, isopentyl, neopentyl, tert-pentyl, n-heptyl, isohexyl or n-heptyl, which is unsubstituted or substituted.

Radicals suitable as substituents in substituted alkyl $R_1$, $R_2$, $R_8$ or $R_9$, preferably substituted lower alkyl, are the radicals mentioned for lower alkanoyl $R_1$ and $R_9$.

Preference is given especially to unsubstituted lower alkyl, such as methyl, ethyl, propyl, isopropyl, n-butyl, isobutyl or tert-butyl.

Alkyl-substituted sulfonyl $R_1$ or $R_9$ (alkyl-$SO_2$—) preferably contains an unsubstituted or substituted alkyl radical mentioned under alkyl $R_1$, $R_2$, $R_8$ and $R_9$ and is especially
lower alkanesulfonyl, such as methanesulfonyl, ethanesulfonyl, n-propanesulfonyl or S-tert-butylsulfonyl, or
aryl-lower alkyl-substituted sulfonyl (aryl-lower alkyl-$SO_2$—) that contains, for example, an unsubstituted or substituted aryl radical as defined for aryl-substituted lower alkyl $R_1$, $R_2$, $R_8$ and $R_9$ and is selected especially from phenylmethane-, 4-chloro-phenylmethane-, 4-methoxy-phenylmethane- or 4-nitro-phenylmethane-, naphthylmethane-, for example α- or β-naphthylmethane-, 2-phenylethane-, 2-α-naphthylethane-, 2-β-naphthylethane-, 2-(4-methylphenyl)ethane-, 2-(4-methoxyphenyl)ethane-, 3-phenylpropane-, 3-(p-hydroxyphenyl)-propane-, 2,2-diphenylethane- and 2,2-di(4-methoxyphenyl) ethanesulfonyl.

Aryl-substituted sulfonyl $R_1$ or $R_9$ (aryl-$SO_2$—) preferably contains an unsubstituted or substituted aryl radical mentioned in the definition of aryl as a substituent of lower alkanoyl $R_1$ or $R_9$ and is especially benzene- or 1- or 2-naphthalene-sulfonyl that is unsubstituted or mono- or di-substituted by lower alkyl, such as benzenesulfonyl, 2- or 4-toluenesulfonyl or 1- or 2-naphthalenesulfonyl.

Heterocyclyl-substituted sulfonyl $R_1$ or $R_9$ (heterocyclyl-$SO_2$—) preferably contains heterocyclyl that is selected from pyrrolyl, furyl, thienyl, imidazolyl, pyrazolyl, oxazolyl, thiazolyl, pyridyl, pyrazinyl, pyrimidinyl, indolyl, quinolyl and isoquinolyl, which may also be fully or partially saturated, from morpholinyl and from thiomorpholinyl and may be unsubstituted or substituted, especially by lower alkyl, such as methyl, such as morpholinosulfonyl, thiomorpholinosulfonyl, piperidinosulfonyl or piperazinosulfonyl. In especially preferred forms of the invention, heterocyclylsulfonyl as substituent may be absent.

Acyloxy $R_5$ has, for example, up to 25, preferably up to 19, carbon atoms and is especially the acyloxy group, bonded via its carbonyl to the bonding oxygen atom, of a carboxylic acid or of an unsubstituted or substituted amino acid, also an aminocarbonyloxy group, an N-substituted aminocarbonyloxy group or an acyl radical of a semiester of carbonic acid linked via its carbonyl group to the bonding oxygen atom.

A preferred acyloxy group $R_5$ of a carboxylic acid is, for example, unsubstituted $C_1$–$C_{20}$alkanoyloxy, for example n-decanoyloxy or palmitoyloxy, $C_3$–$C_{20}$alkenoyloxy or $C_3$–$C_{20}$alkynoyloxy, or substituted $C_1$–$C_{20}$alkanoyloxy, $C_3$–$C_{20}$alkenoyloxy or $C_3$–$C_{20}$alkynoyloxy, especially lower alkanoyloxy, octanoyloxy, nonanoyloxy, decanoyloxy, undecanoyloxy, dodecanoyloxy or also or especially palmitoyloxy; $C_3$–$C_7$alkenoyloxy; or $C_3$–$C_7$alkynoyloxy; or substituted lower alkanoyloxy wherein the substituents are selected, for example, from one or more radicals, preferably from up to three radicals, especially from one radical selected from the group consisting of hydroxy, lower alkoxy, phenoxy, naphthyloxy, lower alkanoyloxy, phenyl-lower alkanoyloxy, such as benzoyloxy or phenylacetoxy, halogen, such as fluorine, chlorine, bromine or iodine, especially fluorine or chlorine, carboxy, lower alkoxycarbonyl, phenyl-lower alkoxycarbonyl, such as benzyloxycarbonyl, carbamoyl, lower alkylcarbamoyl, hydroxy-lower alkylcarbamoyl, di-lower alkylcarbamoyl, bis(hydroxy-lower alkyl)carbamoyl, cyano, oxo, $C_3$–$C_8$cycloalkyl, such as cyclopropyl, cyclobutyl, cyclopentyl or cyclohexyl, $C_6$–$C_{12}$bicycloalkyl, such as decahydronaphth-2-yl, $C_9$–$C_{14}$tricycloalkyl, such as 1- or 2-adamantyl, $C_4$–$C_8$cycloalkenyl, such as 1-cyclohexenyl or 1,4-cyclohexadienyl, heterocyclyl which is preferably a saturated, partially saturated or unsaturated single ring containing from 3 to 7, preferably from 5 to 7, ring atoms and up to four hetero atoms selected from nitrogen, sulfur and oxygen, preferably 1 or 2 of the mentioned hetero atoms, the ring either being present as such or being once or twice, preferably once, benzofused, cyclopenta-, cyclohexa- or cyclohepta-fused, and which may be unsubstituted or substituted especially by lower alkyl, lower alkanoyl, hydroxy, lower alkoxy, phenyl-lower alkoxy, such as benzyloxy, hydroxy-lower alkyl, such as hydroxymethyl, halogen, cyano and/or by trifluoromethyl, for example pyrrolyl, 2,5-dihydropyrrolyl, furyl, thienyl, tetrahydrofuryl, cyclohepta[b]pyrrolyl, pyrrolidinyl, imidazolyl, imidazolidinyl, pyrazolinyl, pyrazolidinyl, triazolyl, such as 1,2,3-, 1,2,4- or 1,3,4-triazolyl, tetrazolyl, such as 1- or 2-tetrazolyl, tetrahydro-oxazolyl, tetrahydroisoxazolyl, tetrahydro-thiazolyl, tetrahydro-isothiazolyl, indolyl, isoindolyl, quinolyl, isoquinolyl, benzimidazolyl, benzofuranyl, pyridyl, pyrimidinyl, piperidinyl, piperazin-1-yl, morpholino, thiomorpholino, S,S-dioxothiomorpholino, 1,2-dihydro- or 1,2,3,4-tetrahydroquinolyl, or 1,2-dihydro- or 1,2,3,4-tetrahydro-isoquinolyl, the mentioned radicals being unsubstituted or substituted as above, especially by lower alkyl, for example in 4-lower alkyl-piperazin-1-yl, such as 4-methyl- or 4-ethyl-piperazin-1-yl, by lower alkanoyl, for example in 4-lower alkanoyl-piperazin-1-yl, such as 4-acetylpiperazin-1-yl, or by hydroxy-lower alkyl, for example in 5-hydroxymethylfuran-2-yl-carbonyl; and aryl, preferably $C_6$–$C_{14}$aryl, for example phenyl, naphthyl, such as 1- or 2-naphthyl, or fluorenyl, such as fluoren-9-yl, aryl being unsubstituted or mono- or poly-substituted, preferably mono-substituted, for example, by lower alkyl, for example methyl, halo-lower alkyl, such as trifluoromethyl or chloro- or bromo-methyl, halogen, for example fluorine or chlorine, hydroxy, lower alkoxy, such as methoxy, lower alkanoyloxy, carboxy, lower alkoxycarbonyl, phenyl-lower alkoxycarbonyl, carbamoyl, mono- or di-lower alkylcarbamoyl, mono- or di-hydroxy-lower alkylcarbamoyl, such as heterocyclyl-lower alkyl wherein heterocyclyl is as defined above as a substituent of lower alkanoyloxy $R_5$, especially heterocyclylmethyl wherein heterocyclyl is bonded via a ring nitrogen atom, for example piperidinomethyl, piperazin-1-ylmethyl, 4-lower alkyl-piperazin-1-ylmethyl, such as 4-methyl- or 4-ethyl-piperazin-1-ylmethyl, 4-lower alkanoyl-piperazin-1-ylmethyl, such as 4-acetyl-piperazin-1-ylmethyl, morpholinomethyl or thiomorpholinomethyl, cyano and/or by nitro, and especially phenyl substituted in the p-position by one of the mentioned radicals;

for example lower alkanoyloxy, such as formyloxy, acetoxy, propionyloxy, pivaloyloxy or heptanoyloxy, such as n-heptanoyloxy, hydroxy-lower alkanoyloxy, for example β-hydroxypropionyloxy, lower alkoxy-lower alkanoyloxy, for example lower alkoxyacetoxy or lower alkoxypropionyloxy, such as methoxyacetoxy or β-methoxypropionyloxy, lower alkanoyloxy-lower alkanoyloxy, for example lower alkanoyloxyacetoxy or lower alkanoyloxypropionyloxy, such as acetoxyacetoxy or β-acetoxypropionyloxy, halo-lower alkanoyloxy, for example α-haloacetoxy, such as α-chloro-, α-bromo-, α-iodo-, α,α,α-trifluoro- or α,α,α-trichloro-acetoxy, or halopropionyloxy, such as β-chloro- or β-bromo-propionyloxy, carboxy-lower alkanoyloxy, for example carboxyacetoxy or 3-carboxypropionyloxy, lower alkoxycarbonyl-lower alkanoyloxy, for example lower alkoxycarbonylacetoxy or lower alkoxycarbonylpropionyloxy, such as methoxycarbonylacetoxy, β-methoxycarbonylpropionyloxy, ethoxycarbonylacetoxy, β-ethoxycarbonylpropionyloxy, tert-butoxycarbonylacetoxy or β-tert-butoxycarbonylpropionyloxy, carbamoyl-lower alkanoyloxy, for example carbamoylacetoxy or β-carbamoylpropionyloxy, lower alkylcarbamoyl-lower alkanoyloxy, di-lower alkylcarbamoyl-lower alkanoyloxy, hydroxy-carboxy-lower alkanoyloxy, hydroxy-lower alkoxycarbonyl-lower alkanoyloxy, dihydroxy-carboxy-lower alkanoyloxy, dihydroxy-lower alkoxycarbonyl-lower alkanoyloxy, heterocyclyl-lower alkanoyloxy, for example pyrrolylcarbonyloxy, such as 2- or 3-pyrrolylcarbonyloxy, furylcarbonyloxy, for example 2-furylcarbonyloxy, 5-hydroxymethyl-furan-2-ylcarbonyloxy, thienylcarbonyloxy, for example 2-thienylcarbonyloxy, imidazolylcarbonyloxy, such as 4-imidazolylcarbonyloxy, imidazolylacetoxy, such as 4-imidazolylacetoxy, imidazolylpropionyloxy, such as 3-(4-imidazolyl)propionyloxy, pyridylcarbonyloxy, for example 2-, 3- or 4-pyridylcarbonyloxy, indolylcarbonyloxy, for example 2-, 3- or 5-indolylcarbonyloxy, 1-methyl-, 5-methyl-, 5-methoxy-, 5-benzyloxy-, 5-chloro- or 4,5-dimethyl-indolyl-2-carbonyloxy, quinolylcarbonyloxy, such as quinolin-2-ylcarbonyloxy, pyrrolidinylcarboxy, such as pyrrolidinyl-3-carbonyloxy, piperidinylcarbonyloxy, for example 2-, 3- or 4-piperidinylcarbonyloxy, morpholinocarbonyloxy, thiomorpholinocarbonyloxy, morpholinoacetoxy, thiomorpholinoacetoxy, or 4-lower alkyl-1-piperazinoacetoxy, such as 4-methylpiperazinoacetoxy, lower alkenoyloxy, for example acryloyloxy, vinylacetoxy, crotonoyloxy or 3- or 4-pentenoyloxy, lower alkynoyloxy, for example propioloyloxy or 2- or 3-butynoyloxy, $C_3$–$C_8$cycloalkylcarbonyloxy or $C_3$–$C_8$cycloalkylacetoxy, for example cyclopropyl-, cyclobutyl-, cyclopentyl- or cyclohexyl-carbonyloxy, cyclopropylacetoxy, cyclopentylacetoxy or cyclohexylacetoxy, phenyl-lower alkanoyloxy, for example benzoyloxy, phenylacetoxy or 3-phenylpropionyloxy, wherein phenyl is unsubstituted or mono- or poly-substituted by lower alkyl, for example methyl, halo-lower alkyl, such as chloro- or bromo-methyl, halogen, for example fluorine or chlorine, hydroxy, lower alkoxy, for example methoxy, piperidinomethyl, piperazin-1-ylmethyl, 4-lower alkyl-piperazin-1-ylmethyl, such as 4-methyl- or 4-ethyl-piperazin-1-ylmethyl, 4-lower alkanoyl-piperazin-1-ylmethyl, such as 4-acetyl-piperazin-1-ylmethyl, morpholino-lower alkyl, such as morpholinomethyl, thiomorpholinomethyl, cyano and/or by nitro, for example 4-chloromethyl-, 4-bromo-methyl-, 4-fluoro-, 4-chloro-, 4-methoxy-, 4-morpholinomethyl-, 4-thiomorpholino-methyl-, 4-cyano- or 4-nitro-benzoyloxy, or lower alkylphenylacetoxy, such as 4-methylphenylacetoxy.

A preferred acyloxy $R_5$ of an acyl radical, linked via its carbonyl group to the bonding oxygen atom, of a semiester of carbonic acid is, for example, unsubstituted or substituted alkoxycarbonyloxy, especially unsubstituted or substituted lower alkoxycarbonyloxy, for example methoxy-, ethoxy- or tert-lower alkoxy-carbonyloxy, such as tert-butoxycarbonyloxy, 2-halo-lower alkoxycarbonyloxy, for example 2-chloro-, 2-bromo-, 2-iodo- or 2,2,2-trichloro-ethoxycarbonyloxy; aryl-lower alkoxycarbonyloxy, for example arylmethoxycarbonyloxy, wherein aryl preferably has from 6 to 14 carbon atoms, is unsubstituted or mono- or poly-substituted, preferably mono-substituted, for example, by lower alkyl, for example methyl, halo-lower alkyl, such as trifluoromethyl or chloro- or bromo-methyl, halogen, for example fluorine or chlorine, hydroxy, lower alkoxy, such as methoxy, lower alkanoyloxy, carboxy, lower alkoxycarbonyl, phenyl-lower alkoxycarbonyl, carbamoyl, mono- or di-lower alkylcarbamoyl, mono- or di-hydroxy-lower alkylcarbamoyl, heterocyclyl-lower alkyl wherein heterocyclyl is as defined above as a substituent of lower alkanoyloxy $R_5$, especially heterocyclylmethyl wherein heterocyclyl is bonded via a ring nitrogen atom, for example piperidinomethyl, piperazin-1-ylmethyl, 4-lower alkyl-piperazin-1-ylmethyl, such as 4-methyl- or 4-ethyl-piperazin-1-ylmethyl, 4-lower alkanoyl-piperazin-1-ylmethyl, such as 4-acetyl-piperazin-1-ylmethyl, morpholinomethyl or thiomorpholinomethyl, cyano and/or by nitro, and is especially phenyl, 1- or 2-naphthyl, fluorenyl, or phenyl mono- or poly-substituted by lower alkyl, for example methyl or tert-butyl, lower alkoxy, for example methoxy, ethoxy or tert-butoxy, hydroxy, halogen, for example fluorine, chlorine or bromine, and/or by nitro, for example phenyl-lower alkoxycarbonyloxy, such as benzyloxycarbonyloxy, 4-methoxybenzyloxycarbonyloxy, 4-nitrobenzyloxycarbonyloxy, diphenyl-lower alkoxycarbonyloxy, such as diphenylmethoxycarbonyloxy, di(4-methoxyphenyl)methoxycarbonyloxy, trityloxycarbonyloxy or fluorenyl-lower alkoxycarbonyloxy, such as 9-fluorenylmethoxycarbonyloxy; or heterocyclyl-lower alkoxycarbonyloxy wherein heterocyclyl is as defined above as a substituent of lower alkanoyloxy $R_5$, for example furan-2-ylmethoxycarbonyloxy or pyridin-2-, -3- or -4-ylmethoxycarbonyl. The definitions falling under the definition of acyloxy groups $R_5$ of a semiester of carbonic acid may in preferred forms be omitted from all the definitions of compounds of formula I-A mentioned hereinbefore and hereinafter.

A preferred N-substituted aminocarbonyloxy group as acyloxy $R_5$ carries at the nitrogen atom one or two substituents selected independently of one another from unsubstituted or substituted lower alkyl (the substituents being selected from those mentioned above for substituted lower alkanoyloxy $R_5$ and being present in the number theredefined, preferably substituents selected from hydroxy, lower alkoxy, lower alkanoyloxy, phenyl-lower alkanoyloxy, such as benzoyloxy or phenylacetoxy, halogen, such as fluorine, chlorine, bromine or iodine, especially fluorine or chlorine, carboxy, lower alkoxycarbonyl, phenyl-lower alkoxycarbonyl, such as benzyloxycarbonyl, cyano, oxo and phenyl or naphthyl, which are unsubstituted or mono- or poly-substituted, preferably mono-substituted, for example, by lower alkyl, for example methyl, halo-lower alkyl, such as trifluoromethyl or chloro- or bromo-methyl, halogen, for example fluorine or chlorine, hydroxy, lower alkoxy, such as methoxy, lower alkanoyloxy, carboxy, lower alkoxycarbonyl, phenyl-lower alkoxycarbonyl, cyano and/or by nitro, especially phenyl substituted in the p-position by one of the mentioned radicals), especially unsubstituted lower alkyl, such as methyl or ethyl, and aryl which preferably has from 6 to 14 carbon atoms and is unsubstituted or mono- or poly-substituted, preferably mono-substituted, for example, by lower alkyl, for example methyl, halo-lower alkyl, such as chloro- or bromo-methyl, halogen, for example fluorine or chlorine, hydroxy, lower alkoxy, such as methoxy, lower alkanoyloxy, carboxy, lower alkoxycarbonyl, phenyl-lower alkoxycarbonyl, halo-lower alkyl, such as trifluoromethyl, cyano and/or by nitro, the nitrogen atom of the carbamoyl group carrying not more than one aryl radical;

an acyloxy group $R_5$ of an N-substituted carbamic acid is especially mono- or di-lower alkylaminocarbonyloxy, such as N-methyl-, N-ethyl-, N,N-dimethyl- or N,N-diethylaminocarbonyloxy, or phenyl-lower alkylaminocarbonyloxy wherein phenyl is unsubstituted or substituted by lower alkyl, for example methyl, halo-lower alkyl, such as chloro- or bromo-methyl or trifluoromethyl, halogen, for example fluorine or chlorine, hydroxy, lower alkoxy, such as methoxy, carboxy and/or by cyano, preferably by up to three of those substituents selected independently of one another, especially by one of those substituents, for example in the p-position, such as in N-benzyl-, N-(4-fluorobenzyl)-, N-(4-chlorobenzyl)-, N-(4-trifluoromethylbenzyl)- or N-(4-cyanobenzyl)-aminocarbonyloxy; especially preferred is aminocarbonyloxy substituted by only one radical at the nitrogen atom, for example N-lower alkylaminocarbonyloxy, such as N-methyl- or N-ethyl-aminocarbonyloxy, or phenyl-lower alkylaminocarbonyloxy wherein phenyl is unsubstituted or substituted by lower alkyl, such as methyl, halo-lower alkyl, such as chloro- or bromo-methyl or trifluoromethyl, halogen, such as fluorine or chlorine, hydroxy, lower alkoxy, such as methoxy, carboxy and/or by cyano, preferably by up to three of those substituents selected independently of one another, especially by one of those substituents, for example in the p-position, such as in N-benzyl-, N-(4-fluorobenzyl)-, N-(4-chlorobenzyl)-, N-(4-trifluoromethylbenzyl)- or N-(4-cyanobenzyl)-aminocarbonyloxy. The definitions falling under the definition of acyloxy groups $R_5$ of an N-substituted carbamic acid, and the radical aminocarbonyloxy $R_5$ may in preferred forms be omitted from all the definitions of compounds of formula I-A mentioned hereinbefore and hereinafter.

An unsubstituted or substituted amino acid in acyloxy $R_5$ bonded via its carbonyl to the bonding oxygen atom is preferably formed by the amino acid residues (aminoacyloxy), bonded via the carbonyl of their carboxy group and an oxygen atom, of an α-, β-, γ- or δ-amino acid, especially of a natural α-amino acid having the L-configuration, such as those normally occurring in proteins, or an epimer of such an amino acid, that is to say having the unnatural D-configuration, or a D,L-isomeric mixture thereof, a homologue of such an amino acid, for example wherein the amino acid side chain has been lengthened or shortened by one or two methylene groups, wherein the amino group is in the β-, γ- or δ-position and/or wherein a methyl group has been replaced by hydrogen, a substituted aromatic amino acid wherein the aromatic radical has from 6 to 14 carbon atoms, for example a substituted phenylalanine or phenylglycine wherein the phenyl may be mono- or poly-substituted by lower alkyl, for example methyl, hydroxy, lower alkoxy, for example methoxy, lower alkanoyloxy, for example acetoxy, amino, lower alkylamino, for example methylamino, di-lower alkylamino, for example dimethylamino, lower alkanoylamino, for example acetylamino or pivaloylamino, lower alkoxycarbonylamino, for example tert-butoxycarbonylamino, arylmethoxycarbonylamino wherein aryl preferably has from 6 to 14 carbon atoms, for example benzyloxycarbonylamino or 9-fluorenylmethoxycarbonylamino, halogen, for example fluorine, chlorine, bromine or iodine, carboxy and/or by nitro, a benzo-fused phenylalanine or phenylglycine, such as α-naphthylalanine, or a hydrogenated phenylalanine or phenylglycine, such as cyclohexylalanine or cyclohexylglycine.

Those amino acid residues may be substituted at free amino or hydroxy functions, as described above for amino acid residues $R_1$ or $R_9$.

Especially preferred is the residue, bonded via the carbonyl of its carboxy group and an oxygen atom, of an amino acid selected from glycine (H-Gly-OH), alanine (H-Ala-OH), 2-aminobutyric acid, 3-aminobutyric acid, 4-aminobutyric acid, 3-aminopentanoic acid, 4-aminopentanoic acid, 5-aminopentanoic acid, 3-aminohexanoic acid, 4-aminohexanoic acid or 5-aminohexanoic acid, valine (H-Val-OH), norvaline (α-aminovaleric acid), leucine (H-Leu-OH), isoleucine (H-Ile-OH), norleucine (α-aminohexanoic acid, H-Nle-OH), serine (H-Ser-OH), homoserine (α-amino-γ-hydroxybutyric acid), threonine (H-Thr-OH), methionine (H-Met-OH), cysteine (H-Cys-OH), proline (H-Pro-OH), trans-3- and trans-4-hydroxyproline, phenylalanine (H-Phe-OH), tyrosine (H-Tyr-OH), 4-aminophenylalanine, 4-chlorophenylalanine, 4-carboxyphenylalanine, β-phenylserine (β-hydroxyphenylalanine), phenylglycine, α-naphthylalanine (H-Nal-OH), cyclohexylalanine (H-Cha-OH), cyclohexylglycine, tryptophan (H-Trp-OH), indoline-2-carboxylic acid, 1,2,3,4-tetrahydroisoquinoline-3-carboxylic acid, aspartic acid (H-Asp-OH), asparagine (H-Asn-OH), aminomalonic acid, aminomalonic acid monoamide, glutamic acid (H-Glu-OH), glutamine (H-Gln-OH), histidine (H-His-OH), arginine (H-Arg-OH), lysine (H-Lys-OH), δ-hydroxylysine, ornithine (α,δ-diaminovaleric acid), 3-aminopropanoic acid, α,γ-diaminobutyric acid and α,δ-diaminopropionic acid, especially the residue of an aliphatic amino acid selected from alanine, valine, norvaline, leucine, 3-aminopropionic acid, 2-aminobutyric acid, 3-aminobutyric acid, 4-aminobutyric acid, 3-aminopentanoic acid, 4-aminopentanoic acid, 5-aminopentanoic acid, 3-aminohexanoic acid, 4-aminohexanoic acid or 5-aminohexanoic acid and isoleucine or an amino acid selected from glycine, asparagine, glutamine, methionine, lysine, histidine, proline and phenylalanine, it being possible for each of the mentioned amino acids to be in the D-, L- or (D,L)-form, preferably in the L-form (except in cases where there is no asymmetric carbon atom, for example in the case of glycine), and an amino group is unsubstituted or is mono- or di-N-alkylated, for example by lower alkyl, such as methyl, n-propyl or n-butyl, by pyridyl-lower alkyl, such as 2-, 3- or 4-pyridylmethyl, and/or by phenyl-lower alkyl, such as benzyl, and/or is N-acylated, for example by unsubstituted or substituted lower alkanoyl, as defined above for lower alkanoyloxy $R_5$, especially by acetyl, propionyl or pivaloyl, by aryl-lower alkanoyl, for example phenyl-lower alkanoyl, such as benzoyl or phenylacetyl, by lower alkoxycarbonyl, such as tert-butoxycarbonyl, or by aryl-lower alkoxycarbonyl, for example phenyl-lower alkoxycarbonyl, such as benzyloxycarbonyl.

Of the last-mentioned residues, preference is given to acyloxy groups $R_5$ of an unsubstituted or substituted amino acid selected from aminoacetoxy (glycyloxy), N-lower alkylaminoacetoxy, N,N-di-lower alkylaminoacetoxy, N-lower alkyl-N-phenyl-lower alkylaminoacetoxy, N-lower alkyl-N-lower alkoxycarbonylaminoacetoxy and N-phenyl-lower alkoxycarbonyl-N-lower alkylaminoacetoxy, for example N-methylaminoacetoxy, N,N-dimethylaminoacetoxy, N-methyl-N-(n-butyl)aminoacetoxy, N-methyl-N-benzylaminoacetoxy, N-methyl-N-[(2-, 3- or 4-)pyridylmethyl]-aminoacetoxy, such as N-methyl-N-3-pyridylmethylaminoacetoxy, N-methyl-N-tert-butoxycarbonylaminoacetoxy, N-benzyloxycarbonyl-N-lower alkylaminoacetoxy, prolyloxy, histidyloxy, glutamyloxy and asparagyloxy, the amino acid residues preferably being in the (L)- or the (D)- or (D,L)-form (except in cases where there is no asymmetric carbon atom, for example in the case of Gly).

Unsubstituted or substituted alkyl $R_3$, $R_4$ or $R_7$ is preferably one of the radicals mentioned under alkyl $R_1$, $R_2$, $R_8$ and $R_9$ and is unsubstituted or substituted, especially by the substituents mentioned for lower alkanoyl $R_1$ or $R_9$, especially one of those substituents, and is selected especially from lower alkyl, for example methyl, ethyl, propyl, isopropyl, n-butyl, isobutyl or tert-butyl, cycloalkyl-lower alkyl wherein cycloalkyl has, for example, from 3 to 7 carbon atoms, such as cyclopropyl, cyclobutyl, cyclopentyl, cyclohexyl or cycloheptyl, cycloalkyl being unsubstituted or mono- to tri-substituted by lower alkyl, such as isopropyl, halo-lower alkyl, such as trifluoromethyl, hydroxy, lower alkoxy, amino, mono- or di-lower alkylamino, halogen, such as fluorine, chlorine or bromine, nitro and/or by cyano and being bonded, preferably terminally, to lower alkyl, especially methyl, ethyl, n-propyl, isopropyl, n-butyl, isobutyl or tert-butyl, for example cyclobutyl-, cyclopentyl-, cyclohexyl- or cycloheptyl-lower alkyl, such as -methyl or -ethyl, preferably cyclohexyl-lower alkyl, such as cyclohexylmethyl, and aryl-lower alkyl wherein aryl is, for example, independently as defined for aryl as a substituent of lower alkanoyl $R_1$ or $R_9$, which is unsubstituted or substituted as there-defined, especially phenyl-lower alkyl, such as benzyl, 2-phenylethyl, 3-phenylpropyl, 4-fluorobenzyl, 4-cyanobenzyl, 4-trifluorobenzyl, 4-hydroxybenzyl or 4-methoxybenzyl, or: 4-lower alkoxybenzyl (especially having more total alkoxy carbon atoms than in 4-methoxybenzyl), such as 4-isobutoxybenzyl, 3,4-di-lower alkoxybenzyl, such as 3,4-dimethoxybenzyl, phenyl-lower alkoxybenzyl, such as 4-benzyloxybenzyl, 4-(3,4-di-lower alkoxybenzyloxy) benzyl, lower alkoxy-lower alkoxybenzyl, such as 4-(2-methoxyethoxy)benzyl, lower alkylenedioxyphenylmethyl, such as 3,4-methylenedioxyphenylmethyl, or biphenylylmethyl, such as 4-biphenylylmethyl, especially phenyl-lower alkyl, most especially as last defined; or (also or especially)

thienylmethyl or tetrahydropyranylmethyl, such as 2-thienylmethyl or 4-(2,3,5,6-tetra-hydro) pyranylmethyl.

Cycloalkyl $R_3$, $R_4$ or $R_7$ is preferably as defined in the definition thereof as a substituent of lower alkanoyl $R_1$ or $R_9$, and is, for example, cyclopropyl, cyclobutyl, cyclopentyl, cyclohexyl or cycloheptyl, cycloalkyl being unsubstituted or mono- to tri-substituted by lower alkyl, such as isopropyl, halo-lower alkyl, such as trifluoromethyl, hydroxy, lower alkoxy, amino, mono- or di-lower alkylamino, halogen, such as fluorine, chlorine or bromine, nitro and/or by cyano, such as cyclobutyl, cyclopentyl, cyclohexyl or cycloheptyl, especially cyclohexyl.

Aryl $R_3$, $R_4$ or $R_7$ is preferably independently as defined in the definition thereof as a substituent of lower alkanoyl $R_1$ or $R_9$ and, as in that definition, is unsubstituted or substituted, and is especially phenyl that is unsubstituted or mono- to tri-substituted by lower alkyl, such as isopropyl, halo-lower alkyl, such as trifluoromethyl, hydroxy, lower alkoxy, halogen, such as fluorine, chlorine or bromine, nitro and/or by cyano, such as phenyl, 4-methoxyphenyl, 4-fluorophenyl, 4-trifluoromethylphenyl or 4-cyanophenyl.

When, in the compounds of formula I-A, nitrogen atoms having free hydrogen and/or hydroxy groups are vicinal with respect to double or triple bonds, the corresponding tautomeric imino and oxo compounds are always also included.

Salts of compounds of formula I-A are especially acid addition salts, salts with bases or, where several salt-forming groups are present, can also be mixed salts or internal salts.

Salts are especially the pharmaceutically acceptable, non-toxic salts of compounds of formula I-A, the salts being selected from the salts, as defined above, of compounds of formula I (formula I-A being substituted for formula I).

For isolation or purification purposes, it is also possible to use pharmaceutically unacceptable salts.

The compounds of formula I-A have valuable pharmacological properties. They have antiretroviral activity, especially against AIDS, for example against HIV-1 and HIV-2. They serve as metabolic precursors for compounds of formula I-A

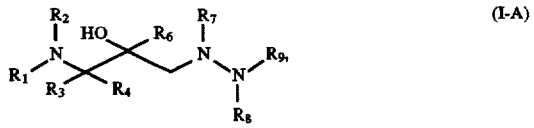

(I-A)

wherein the radicals are as defined for compounds of formula I-A (analogues of the compounds of formula I having hydroxy instead of $R_5$), which are suitable as inhibitors of retroviral aspartate proteases, especially as inhibitors of the gag-protease of HIV-1 or HIV-2 (and possibly the asparto-proteases of other retroviruses that cause symptoms analogous to AIDS), and therefore for the treatment of retroviral diseases, such as AIDS or its precursors. In that treatment, the compounds of formula I (having hydroxy instead of $R_5$ in formula I) are released in the body of the animal to be treated, especially a warm-blooded animal, including a human, from the compounds of formula I-A.

The compounds of formula I-A preferably have advantageous pharmacodynamic properties in relation to the compounds of formula I, which can be demonstrated, for example, as follows:

The compounds of formula I-A to be investigated and, as control, the comparison compound of formula I are each dissolved in dimethyl sulfoxide (DMSO) in a concentration of 240 mg/ml. The resulting solutions are diluted with 20% (w/v) hydroxypropyl-β-cyclodextrin (HPβCD) to obtain a concentration of the test compound of 12 mg/ml. That solution is administered to mice in a dose of 120 mg/kg by means of artificial special feeding. 60, 90 and 120 min after administration the animals are sacrificed and blood is removed. Three or four animals are examined per time point. The blood is heparinised and prepared for analysis as follows: an internal standard is added to the heparinised blood in a final concentration of 4 μM. The blood is centrifuged. 0.25 ml of plasma is drawn off and deproteinised with an equal volume of acetonitrile. After centrifugation the supernatant is concentrated by drying in vacuo and the residue is suspended in 20 μl of 3M NaCl solution and 100 μl of 0.05M phthalate buffer having a pH of 3.0. The suspension is extracted first with 1 ml, then with 0.2 ml of diisopropyl ether. The diisopropyl ether solution is concentrated to dryness by evaporation and the residue is dissolved in 50% (v/v) aqueous acetonitrile. The solution is analysed by reversed-phase HPLC.

The analysis by reversed-phase HPLC is carried out using a 125×4.6 mm Nucleosil® $C_{18}$-column (reversed-phase material supplied by Macherey-Nagel, Düren, Federal Republic of Germany, based on silica gel derivatised with hydrocarbon radicals having 18 carbon atoms) equilibrated with a mobile phase of 50% acetonitrile in water/0.1% trifluoroacetic acid. The flow rate is 1 ml/min. Detection is effected at 215 nm. Standards for the compounds in blood are worked up analogously to the blood samples and used to establish standard curves on the basis of which the in vivo concentrations are determined.

The following results are obtainable from a comparison of the compounds of formula I-A with those of formula I (active component, having hydroxy instead of acyloxy $R_5$): the concentration of the active component of formula I in the blood of mice after oral administration of a compound of formula I, for example of a compound of formula I-A wherein $R_1$ is acetyl, may, at most time points, especially at all the above-mentioned time points, be significantly higher, for example more than three times higher, especially more than ten times higher and more especially from approximately 20 to approximately 150 times higher, than when a compound of formula I is administered in non-esterified form. Alternatively, or in addition, thereto the absorption of a compound of formula I-A, for example of a compound of formula I-A wherein $R_1$ is acetyl, may be significantly higher, for example more than four times higher, than the absorption of a compound of formula II. It is also possible over a prolonged period to maintain a higher blood level with a compound of formula I-A than with a compound of formula I.

The obtainable blood concentration of a compound of formula I at the mentioned time points is preferably significantly higher than the ED90 determined for the corresponding compound of formula I in the cell test (see below).

The compounds of formula I-A, and the compounds of formula I, can also be used as standards in comparisons of different test systems on different species of animals, which represents a further, commercial use. By comparing blood levels in different species of animals, for example, it is possible to compare different animal models.

The compounds of formula I that can be released under physiological conditions from the compounds of formula I-A of the present invention or that serve as starting materials in the preparation of compounds of formula I-A, or the salts thereof, have an inhibiting action on viral aspartate proteases, especially a gag-protease-inhibiting action. In the tests described below, at concentrations of $10^{-6}$ to $10^{-9}$ mol/l they inhibit especially the action of the gag-protease of HIV-1 and HIV-2 and are therefore suitable as agents against diseases caused by those retroviruses or by related retroviruses, for example against AIDS or the precursors of AIDS.

The blood levels of those compounds of formula I can be determined analogously to the methods mentioned above for compounds of formula I-A.

The ability of the compounds of formula I to inhibit the proteolytic activity of, for example, HIV-1 protease can be demonstrated, for example, by the method described above (especially according to Richards et al., J. Biol. Chem. 265 (14), 7733–7736 (1990) with the icosapeptide RRSNQVSQNYPIVQNIQGRR, and the ability of compounds of formula I to protect cells from infection by HIV can be demonstrated by the test with MT-2 cells described above, with results as given above.

In the groups of compounds of formula I-A mentioned below, it may be advantageous, for example in order to replace rather general definitions with more specific definitions, to use definitions of radicals from the above-mentioned general definitions.

Preference is given to a compound of formula I-A wherein $R_1$ and $R_9$ are each independently of the other hydrogen; lower alkanoyl, such as formyl, acetyl, propionyl, butyryl or pivaloyl, or also or especially 3,3-dimethylbutyryl; especially acetyl; aryl-lower alkanoyl wherein aryl has from 6 to 14 carbon atoms, preferably as in phenyl, indenyl, indanyl, naphthyl, anthryl, phenanthryl, acenaphthyl or fluorenyl, and may be unsubstituted or mono- to tri-substituted especially by lower alkyl, for example methyl, ethyl or propyl, halo-lower alkyl, for example trifluoromethyl, phenyl, 1- or 2-naphthyl, hydroxy, lower alkoxy, for example methoxy, carbamoyl-lower alkoxy, N-lower alkylcarbamoyl-lower alkoxy or N,N-di-lower alkylcarbamoyl-lower alkoxy, amino, mono- or di-lower alkylamino, lower alkanoylamino, for example pivaloylamino, halogen, for example fluorine, chlorine or bromine, carboxy, lower alkoxycarbonyl, such as tert-butoxycarbonyl, phenyl-, naphthyl- or fluorenyl-lower alkoxycarbonyl, such as benzyloxycarbonyl, lower alkanoyl, sulfo, lower alkylsulfonyl, for example methylsulfonyl, phosphono, hydroxy-lower alkoxyphosphoryl or di-lower alkoxyphosphoryl, carbamoyl, mono- or di-lower alkylcarbamoyl, sulfamoyl, mono- or di-lower alkylaminosulfonyl, nitro and/or by cyano, and wherein lower alkanoyl is unsubstituted or substituted by carbamoyl or by carbamoyl substituted at the nitrogen atom by one or two radicals selected from lower alkyl, carboxy-lower alkyl, lower alkoxycarbonyl-lower alkyl, di-lower alkylamino-lower alkyl, hydroxy-lower alkyl and di-lower alkoxy-lower alkyl, preferably as described under aryl-lower alkanoyl above in the general definitions, for example 4-chloro-, 4-methoxy- or 4-nitro-benzoyl, naphthylcarbonyl, such as α- or β-naphthylcarbonyl, or 1,8-naphthalenedicarbonyl bonded to the amino group via both carbonyl groups, phenyl-lower alkanoyl, such as phenylacetyl or 3-phenylpropionyl, lower alkylphenylacetyl, such as 4-methylphenylacetyl, lower alkoxyphenylacetyl, such as 4-methoxyphenylacetyl, 3-(p-hydroxyphenyl)-propionyl, diphenylacetyl, di(4-methoxyphenyl)acetyl, triphenylacetyl, 2,2-dibenzylacetyl, 3-α- or 3-β-naphthylpropionyl, phenyl-lower alkanoyl wherein the lower alkanoyl radical is substituted by carbamoyl, such as 2-carbamoyl-3-phenylpropionyl, for example 2(R,S)-carbamoyl-3-phenylpropionyl, 3-phenyl- or 3-α-naphthyl-2-carbamoylpropionyl, 3-phenyl- or 3-α-naphthyl2-tert-butylcarbamoylpropionyl, 3-phenyl- or 3-α-naphthyl-2-(2-dimethylaminoethyl)carbamoylpropionyl, especially phenyl-lower alkanoyl, such as phenylacetyl, or phenyl-lower alkanoyl wherein the lower alkanoyl radical is substituted by carbamoyl, such as 2-carbamoyl-3-phenylpropionyl, for example 2(R,S)-carbamoyl-3-phenylpropionyl; heterocyclyl-lower alkanoyl wherein heterocyclyl is thienyl, furyl, pyrrolyl, imidazolyl, pyrazolyl, oxazolyl, thiazolyl, tetrazolyl, pyridyl, pyrazinyl, pyrimidinyl, pyridazinyl, indolyl, benzimidazolyl, quinolyl, isoquinolyl, 3,1-benzofuranyl, cyclohexa[b]pyrrolyl, cyclohexa[b]pyridyl, cyclohexa[b]pyrazinyl, cyclohexa[b]pyrimidinyl, pyrrolidinyl, pyrrolinyl, imidazolidyl, piperidyl, piperazinyl, morpholinyl, thiomorpholinyl, S,S-dioxothiomorpholinyl, indolinyl, isoindolinyl, 4,5,6,7-tetrahydroindolyl, 1,2,3,4-tetrahydroquinolyl or 1,2,3,4-tetrahydroisoquinolyl, which is bonded via a ring carbon atom or a ring nitrogen atom, in the case of saturated heterocyclic compounds preferably via a ring nitrogen atom, especially indolylcarbonyl, such as 2-, 3- or 5-indolylcarbonyl, quinolyl-lower alkanoyl, for example quinolylcarbonyl, such as 2-, 3- or 4-quinolylcarbonyl, piperidylcarbonyl, such as piperidinocarbonyl or 2-, 3- or 4-piperidylcarbonyl, piperazinylcarbonyl, such as piperazin-1-ylcarbonyl, morpholinyl-lower alkanoyl, for example morpholino-lower alkanoyl, for example morpholinocarbonyl, such as morpholinocarbonyl, thiomorpholinyl-lower alkanoyl, for example thiomorpholino-lower alkanoyl, such as thiomorpholinocarbonyl, such as thiomorpholinocarbonyl, S,S-dioxothiomorpholinylcarbonyl, such as S,S-dioxothiomorpholinocarbonyl, tetrazolyl-lower alkanoyl, such as 3-(tetrazol-1-yl)-propionyl, and pyridyl-lower alkanoyl, for example pyridylcarbonyl, such as 2-, 3- or 4-pyridylcarbonyl, or pyridylacetyl, such as 2-, 3- or 4-pyridylacetyl, with heterocyclyl-lower alkanoyl being selected especially from morpholino-lower alkanoyl, such as morpholinocarbonyl, thiomorpholino-lower alkanoyl, such as thiomorpholinocarbonyl, pyridyl-lower alkanoyl, such as 2-, 3- or 4-pyridylacetyl, and tetrazolyl-lower alkanoyl, such as 3-tetrazol-1-ylpropionyl; (lower alkoxy-lower alkoxy)-lower alkanoyl; amino-lower alkanoyl substituted at the amino nitrogen atom by heterocyclyl-lower alkanoyl wherein heterocyclyl-lower alkanoyl is independently as defined above for heterocyclyl-lower alkanoyl $R_1$ or $R_9$, especially amino-lower alkanoyl substituted at the amino nitrogen atom by N-morpholino-carbonyl or by N-thiomorpholinocarbonyl, more especially N-morpholino- or N-thiomorpholino-carbonylamino-lower alkanoyl, such as N-morpholino- or N-thiomorpholino-carbonylamino-acetyl; halo-lower alkanoyl containing up to three halogen atoms, especially α-haloacetyl, such as α-fluoro-, α-chloro-, α-bromo-, α-iodo-, α,α,α-trifluoro- or α,α,αtrichloro-acetyl, or halopropionyl, such as β-chloro- or β-bromo-propionyl, especially trifluoroacetyl; (N-heterocyclyl-lower alkylcarbamoyl)-lower alkanoyl wherein heterocyclyl is preferably selected from pyrrolyl, furyl, thienyl, imidazolyl, pyrazolyl, oxazolyl, thiazolyl, pyridyl, pyrazinyl, pyrimidinyl, indolyl, quinolyl and isoquinolyl, which may also be fully or partially saturated, from morpholinyl and from thiomorpholinyl, especially 2-(N-morpholino-lower alkylcarbamoyl)-lower alkanoyl, such as 2(R,S)-(N-(2-morpholinoethyl)-carbamoyl)-3-methylbutyryl, or 2-(N-(pyridyl-lower alkyl)-carbamoyl)-lower alkanoyl, such as 2(R,S)(N-(2-pyridylmethyl)-carbamoyl)-3-methylbutyryl; lower alkoxycarbonyl, especially methoxy-, ethoxy-, isopropoxy-, isobutoxy- or tert-lower alkoxy-carbonyl, for example methoxycarbonyl, tert-butoxycarbonyl or isobutoxycarbonyl; aryl-lower alkoxycarbonyl wherein aryl is phenyl, biphenylyl, 1- or 2-naphthyl, fluorenyl, or phenyl that is mono- or poly-substituted, preferably up to tri-substituted, especially mono-substituted, by lower alkyl, for example methyl or tert-butyl, hydroxy, lower alkoxy, for example methoxy, ethoxy or tert-butoxy, halogen, for example chlorine or bromine, and/or by nitro, for example phenyl-lower alkoxycarbonyl, such as benzyloxycarbonyl or 4-methoxybenzyloxycarbonyl, especially phenyl-lower alkoxycarbonyl, such as benzyloxycarbonyl; heterocyclyl-lower alkoxycarbonyl wherein heterocyclyl is selected from pyrrolyl, furyl, thienyl, imidazolyl, pyrazolyl, oxazolyl, thiazolyl, pyridyl, pyrazinyl, pyrimidinyl, indolyl, quinolyl and isoquinolyl, which may also be fully or partially saturated, and from morpholinyl and from thiomorpholinyl and is unsubstituted or substituted by lower alkyl, such as by methyl, for example 2-furylmethoxycarbonyl, or tetrahydrofuryl-lower alkoxycarbonyl, such as 2-tetrahydrofurylmethoxycarbonyl, especially tetrahydrofuryl-lower alkoxycarbonyl, such as 2(R,S)-tetrahydrofurylmethoxycarbonyl; lower alkenyloxycarbonyl wherein the lower alkenyl radical is bonded to the oxygen atom via a saturated carbon atom, for example allyloxycarbonyl; lower alkoxy-lower alkoxycarbonyl, such as 2-methoxyethoxycarbonyl; (lower alkoxy-lower alkoxy)-lower alkoxycarbonyl, such as 2-(2-methoxyethoxy)ethoxycarbonyl; lower alkanesulfonyl, for example methane- or ethane-sulfonyl, especially methanesulfonyl; heterocyclylsulfonyl (heterocyclyl-SO$_2$—) wherein heterocyclyl is selected from pyrrolyl, furyl, thienyl, imidazolyl, pyrazolyl, oxazolyl, thiazolyl, pyridyl, pyrazinyl, pyrimidinyl, indolyl, quinolyl and isoquinolyl, which may also be fully or partially saturated, from morpholinyl and from thiomorpholinyl and may be unsubstituted or substituted by lower alkyl, such as methyl, such as morpholinosulfonyl, thiomorpholinosulfonyl, piperidinosulfonyl or piperazinosulfonyl; carbamoyl; N-heterocyclyl-lower alkyl-N-lower alkylcarbamoyl wherein heterocyclyl is independently one of the radicals mentioned above in the definition of heterocyclyl-lower alkanoyl $R_1$ or $R_9$, especially pyridyl, such as 2-, 3- or 4-pyridyl, preferably N-pyridyl-lower alkyl-N-lower alkylcarbamoyl, such as N-(2-, 3- or 4-pyridylmethyl)-N-methylcarbamoyl; or also or especially N-lower alkyl-N-(morpholino-lower alkyl)-aminocarbonyl, such as N-methyl-N-(2-morpholinoethyl)-aminocarbonyl; or an acyl radical of an amino acid the amino function of which is free or acylated by one of the other radicals mentioned hitherto for $R_1$ and $R_9$ with the exception of one of the mentioned aminoacyl radicals, the amino acid residues being selected from the residues, bonded via the carbonyl of their 1-carboxy group, of the amino acids glycine, alanine, valine, norvaline, leucine, isoleucine, norleucine, serine, homoserine, threonine, methionine, cysteine, proline, trans-3- and trans-4-hydroxyproline, phenylalanine, tyrosine, 4-aminophenylalanine, 4-chlorophenylalanine, 4-carboxyphenylalanine, β-phenylserine, phenylglycine, α-naphthylalanine, cyclohexylalanine, cyclohexylglycine, tryptophan, indoline-2-carboxylic acid, 1,2,3,4-tetrahydroisoquinoline-3-carboxylic acid, aspartic acid, asparagine, aminomalonic acid, aminomalonic acid monoamide, glutamic acid, glutamine, histidine, arginine, lysine, δ-hydroxylysine, ornithine, 3-aminopropanoic acid, α,γ-diaminobutyric acid and α,β-diaminopropionic acid, more especially the residues of an amino acid selected from valine, alanine, leucine, isoleucine, glycine, glutamic acid and asparagine, it being possible for each of the mentioned amino acids to be in the D-, L- or (D,L)-form, preferably in the L-form (with the exception of Val, which may also be in the (D)- or (D,L)-form); and the α-amino group being unsubstituted or N-acylated by one of the radicals mentioned above for $R_1$ and $R_9$, especially by lower alkanoyl, phenyl-lower alkanoyl, such as phenylacetyl, phenyl-lower alkanoyl wherein the lower alkanoyl radical is substituted by carbamoyl, such as 2(R,S)-carbamoyl-3-phenyl-propionyl, morpholino-lower alkanoyl, such as morpholinocarbonyl, thiomorpholino-lower alkanoyl, such as thiomorpholino-carbonyl, pyridyl-lower alkanoyl, such as 2-, 3- or 4-pyridylacetyl, quinolinyl-lower alkanoyl, such as quinolin-2-ylcarbonyl, tetrazolyl-lower alkanoyl, such as 3-tetrazol-1-ylpropionyl, lower alkoxy-lower alkoxy-lower alkanoyl, amino-lower alkanoyl substituted at the amino nitrogen atom by N-morpholino- or N-thiomorpholinocarbonyl, for example N-morpholino- or N-thiomorpholino-carbonylamino-lower alkanoyl, such as N-morpholino- or N-thiomorpholino-carbonylaminoacetyl, halo-lower alkanoyl containing up to three halogen atoms, for example α-haloacetyl, such as α-fluoro-, α-chloro-, α-bromo-, α-iodo-, α,α,α-trifluoro- or α,α,α-trichloro-acetyl, or halopropionyl, such as β-chloro- or β-bromo-propionyl, especially trifluoroacetyl, 2-(N-morpholino-lower alkylcarbamoyl)-lower alkanoyl, such as 2(R,S)-(N-(2-morpholinoethyl)-carbamoyl-3-methyl-butyryl, 2-(N-(pyridyl-lower alkyl)-carbamoyl)-lower alkanoyl, such as 2(R,S)-(N-(2-pyridylmethyl)-carbamoyl)-lower alkanoyl, lower alkoxycarbonyl, phenyl-lower alkoxycarbonyl, tetrahydrofuryl-lower alkoxycarbonyl, such as 2(R,S)-tetrahydrofurylmethoxycarbonyl, lower alkenyloxycarbonyl wherein the lower alkenyl radical is bonded via a saturated carbon atom to the bonding oxygen atom, lower alkoxy-lower alkoxycarbonyl, (lower alkoxy-lower alkoxy)-lower alkoxycarbonyl, lower alkanesulfonyl, morpholinosulfonyl, thiomorpholinosulfonyl, piperidinosulfonyl, 4-methylpiperazinylsulfonyl or piperazinosulfonyl or N-pyridyl-lower alkyl-N-lower alkyl-carbamoyl, such as N-(2-, 3- or 4-pyridylmethyl)-N-methyl-carbamoyl; or also or especially N-(phenyl-lower alkyl)-aminocarbonyl, such as N-benzylaminocarbonyl, N-lower alkylaminocarbonyl, such as tert-butylaminocarbonyl, N,N-di-lower alkylaminocarbonyl, such as N,N-dimethylaminocarbonyl, N-(lower alkoxy-lower alkyl)-aminocarbonyl, such as N-($^2$-methoxyethoxy)-aminocarbonyl or N-(morpholino-lower alkyl) aminocarbonyl, such as N-($^2$-morpholinoethyl)-aminocarbonyl, or an acyl radical of an amino acid, as defined above, wherein the α-amino group is acylated by one of those radicals, with the proviso that not more than one of the two radicals $R_1$ and $R_9$ may be hydrogen, $R_2$, $R_4$, $R_6$ and $R_8$ are hydrogen, $R_3$ is lower alkyl, such as isobutyl or n-butyl; $C_3$–$C_7$cycloalkyl-lower alkyl wherein $C_3$–$C_7$cycloalkyl is unsubstituted or mono- to tri-substituted by lower alkyl, such as isopropyl, halo-lower alkyl, such as trifluoromethyl, hydroxy, lower alkoxy, amino, mono- or di-lower alkylamino, halogen, such as fluorine, chlorine or bromine, nitro and/or by cyano and is bonded, preferably terminally, to lower alkyl, especially methyl, ethyl, n-propyl, isopropyl, n-butyl, isobutyl or tert-butyl, such as cyclobutyl-, cyclopentyl-, cyclohexyl- or cycloheptyl-lower alkyl, such as -methyl or -ethyl, especially cyclohexyl-lower alkyl, most especially cyclohexylmethyl; or is aryl-lower alkyl wherein aryl is independently as defined in aryl-lower alkanoyl $R_1$ or $R_9$, or is also or especially phenyl-lower alkoxybenzyl, 4-(3,4-di-lower alkoxybenzyloxy)benzyl, lower alkoxy-lower alkoxybenzyl or lower alkylenedioxyphenylmethyl, and is especially phenyl that may be unsubstituted or mono- to tri-substituted by lower alkyl, for example methyl, ethyl or isopropyl, halo-lower alkyl, such as trifluoromethyl, phenyl, 1- or 2-naphthyl, hydroxy, lower alkoxy, for example methoxy, or also or especially isobutoxy, carbamoyl-lower alkoxy, N-lower alkylcarbamoyl-lower alkoxy or N,N-di-lower alkylcarbamoyl-lower alkoxy, amino, mono- or di-lower alkylamino, lower alkanoylamino, for example pivaloylamino, halogen, for example fluorine or chlorine, carboxy, lower alkoxycarbonyl, benzyl-, naphthyl- or fluorenyl-lower alkoxycarbonyl, lower alkanoyl, sulfo, lower alkylsulfonyl, phosphono, hydroxy-lower alkoxyphosphoryl or di-lower alkoxyphosphoryl, carbamoyl, mono- or di-lower alkylcarbamoyl, sulfamoyl, mono- or di-lower alkylsulfamoyl, nitro and/or by cyano, especially phenyl-lower alkyl that is unsubstituted or substituted by the mentioned substituents, especially benzyl, 2-phenylethyl, 3-phenylpropyl, 4-fluoro-, 4-trifluoromethyl-, 4-cyano-, 4-methoxy- or 4-hydroxy-benzyl, or also or especially: 4-lower alkoxybenzyl (especially having more total alkoxy carbon atoms than in 4-methoxybenzyl), such as 4-isobutoxybenzyl, 3,4-di-lower alkoxybenzyl, such as 3,4-dimethoxybenzyl, phenyl-lower alkoxybenzyl, such as 4-benzyloxybenzyl, 4-(3,4-di-lower alkoxybenzyloxy)benzyl, lower alkoxy-lower alkoxybenzyl, such as 4-(2-methoxyethoxy)benzyl, lower alkylenedioxyphenylmethyl, such as 3,4-methylenedioxyphenylmethyl, or biphenylylmethyl, such as 4-biphenylylmethyl, more especially phenyl-lower alkyl, especially as last defined, or also or especially thienylmethyl or tetrahydropyranylmethyl, such as 2-thienylmethyl or 4-(2,3,5,6-tetrahydro) pyranylmethyl, $R_5$ is lower alkanoyloxy, octanoyloxy, nonanoyloxy, decanoyloxy, undecanoyloxy, dodecanoyloxy, hydroxy-lower alkanoyloxy, lower alkoxy-lower alkanoyloxy, lower alkanoyloxy-lower alkanoyloxy, halo-lower alkanoyloxy, for example α-haloacetoxy, such as α-chloro-, α-bromo-, α-iodo-, α,α,α-trifluoro- or α,α,α-trichloro-acetoxy, carboxy-lower alkanoyloxy, lower alkoxycarbonyl-lower alkanoyloxy, carbamoyl-lower alkanoyloxy, lower alkylcarbamoyl-lower alkanoyloxy, di-lower alkylcarbamoyl-lower alkanoyloxy, hydroxy-carboxy-lower alkanoyloxy, hydroxy-lower alkoxycarbonyl-lower alkanoyloxy, dihydroxy-carboxy-lower alkanoyloxy, dihydroxy-lower alkoxycarbonyl-lower alkanoyloxy, pyrrolylcarbonyloxy, such as 2- or 3-pyrrolylcarbonyloxy, furyl-lower alkanoyloxy, for example furylcarbonyloxy, such as 2-furylcarbonyloxy, thienylcarbonyloxy, for example 2-thienylcarbonyloxy, imidazolyl-lower alkanoyloxy, for example imidazolylcarbonyloxy, such as 4-imidazolylcarbonyloxy, imidazolylacetoxy, such as 4-imidazolylacetoxy, imidazolylpropionyloxy, such as 3-(4-imidazolylpropionyloxy, pyridyl-lower alkanoyloxy, such as pyridylcarbonyloxy, for example 2-, 3- or 4-pyridylcarbonyloxy, indolylcarbonyloxy, for example 2-, 3- or 5-indolylcarbonyloxy, quinolyl-lower alkanoyloxy, such as quinolinylcarbonyloxy, such as quinolin-2-ylcarbonyloxy, pyrrolidinylcarboxy, such as pyrrolidinyl-3-carbonyloxy, piperidinylcarbonyloxy, for example 2-, 3- or 4-piperidinylcarbonyloxy, morpholinocarbonyloxy, thiomorpholinocarbonyloxy, morpholinoacetoxy, thiomorpholinoacetoxy or 4-lower alkyl-1-piperazinoacetoxy, such as 4-methyl-piperazinoacetoxy, lower alkenoyloxy (wherein the lower alkenoyl radical is preferably bonded to the bonding oxygen atom via a saturated carbon atom), for example acryloyloxy, vinylacetoxy, crotonoyloxy or 3- or 4-pentenoyloxy, lower alkynoyloxy, for example propioloyloxy or 2- or 3-butynoyloxy, $C_3$–$C_8$cycloalkylcarbonyloxy, $C_3$–$C_8$cycloalkylacetoxy, phenyl-lower alkanoyloxy, for example benzoyloxy, phenylacetoxy or 3-phenylpropionyloxy, which may be unsubstituted, mono- or poly-substituted in the phenyl radical by lower alkyl, for example methyl, halo-lower alkyl, such as chloro- or bromo-methyl, halogen, for example fluorine or chlorine, hydroxy, lower alkoxy, for example methoxy, piperidinomethyl, piperazin-1-ylmethyl, 4-lower alkyl-piperazin-1-ylmethyl, such as 4-methyl- or 4-ethyl-piperazin-1-ylmethyl, 4-lower alkanoyl-piperazin-1-ylmethyl, such as 4-acetyl-piperazin-1-ylmethyl, morpholino-lower alkyl, such as morpholinomethyl, thiomorpholinomethyl, cyano and/or by nitro, especially mono-substituted by one of the mentioned substituents, or is the residue, bonded via a carbonyloxy group containing the carbonyl from the carboxy group of the amino acid in question, of an amino acid selected from glycine, alanine, 2-aminobutyric acid, 3-aminobutyric acid, 4-aminobutyric acid, 3-aminopentanoic acid, 4-aminopentanoic acid, 5-aminopentanoic acid, 3-aminohexanoic acid, 4-aminohexanoic acid, 5-aminohexanoic acid, valine, norvaline, leucine, isoleucine, norleucine, serine, homoserine, threonine, methionine, cysteine, proline, phenylalanine, tyrosine, cyclohexylalanine, tryptophan, aspartic acid, asparagine, glutamic acid, glutamine, histidine, arginine, lysine, ornithine, 3-aminopropanoic acid, α,γ-diaminobutyric acid and α,β-diaminopropionic acid; especially the radical, bonded via carbonyloxy, of an aliphatic amino acid selected from alanine, valine, norvaline, leucine, 3-aminopropionic acid, 2-aminobutyric acid, 3-aminobutyric acid, 4-aminobutyric acid, 3-aminopentanoic acid, 4-aminopentanoic acid, 5-aminopentanoic acid, 3-aminohexanoic acid, 4-aminohexanoic acid, 5-aminohexanoic acid and isoleucine or an amino acid selected from glycine, asparagine, glutamine, methionine, lysine, histidine, proline and phenylalanine, it being possible for each of the mentioned amino acids to be in the D-, L- or (D,L)-form, preferably in the L-form (except in cases where there is no asymmetric carbon atom, for example in the case of glycine); and wherein an amino group is unsubstituted or is mono-or di-N-alkylated by lower alkyl, such as methyl, n-propyl or n-butyl, by pyridyl-lower alkyl, such as 2-, 3- or 4-pyridylmethyl, and/or by phenyl-lower alkyl, such as benzyl, and/or is N-acylated by lower alkanoyl, especially acetyl, propionyl or pivaloyl, by phenyl-lower alkanoyl, such as benzoyl or phenylacetyl, by lower alkoxycarbonyl, such as tert-butoxycarbonyl, or by phenyl-lower alkoxycarbonyl, such as benzyloxycarbonyl; or is also or especially palmitoyloxy;

and $R_7$ is independently of $R_3$ one of the radicals theredefined, especially lower alkyl, more especially isobutyl or n-butyl, $C_3$–$C_7$cycloalkyl-lower alkyl, especially cyclohexyl-lower alkyl, such as cyclohexylmethyl, or aryl-lower alkyl, as described for aryl-lower alkyl $R_3$, especially phenyl-lower alkyl that is unsubstituted or substituted by the mentioned substituents, such as benzyl, 2-phenylethyl, 3-phenylpropyl, 4-fluoro-, 4-trifluoromethyl-, 4-cyano-, 4-methoxy- or 4-hydroxy-benzyl, or also or especially 4-lower alkoxybenzyl (especially having more total alkoxy carbon atoms than 4-methoxybenzyl), such as 4-isobutoxybenzyl, 3,4-di-lower alkoxybenzyl, such as 3,4-dimethoxybenzyl, phenyl-lower alkoxybenzyl, such as 4-benzyloxybenzyl, 4-(3,4-di-lower alkoxybenzyloxy) benzyl, lower alkoxy-lower alkoxybenzyl, such as 4-(2-methoxyethoxy)benzyl, lower alkylenedioxyphenylmethyl, such as 3,4-methylenedioxyphenylmethyl, or biphenylylmethyl, such as 4-biphenylylmethyl, especially phenyl-lower alkyl, especially as last defined, or also or especially thienylmethyl or tetrahydropyranylmethyl, such as 2-thienylmethyl or 4-(2,3,5,6-tetrahydro) pyranylmethyl, or a salt thereof where at least one salt-forming group is present.

Great preference is given to a compound of formula I-A wherein $R_1$ and $R_9$ are each independently of the other hydrogen, lower alkanoyl, such as acetyl or propionyl, phenyl-lower alkanoyl, such as phenylacetyl, phenyl-lower alkanoyl wherein the lower alkanoyl radical is substituted by carbamoyl, such as 2-carbamoyl-3-phenyl-propionyl, morpholino-lower alkanoyl, such as morpholinocarbonyl, thiomorpholino-lower alkanoyl, such as thiomorpholino-carbonyl, pyridyl-lower alkanoyl, such as 2-, 3- or 4-pyridylacetyl, quinolyl-lower alkanoyl, such as quinolin-2-ylcarbonyl, tetrazolyl-lower alkanoyl, such as 3-tetrazol-1-yl-propionyl, amino-lower alkanoyl substituted at the amino nitrogen atom by N-morpholino- or N-thiomorpholino-carbonyl, for example N-morpholino- or N-thiomorpholino-carbonylamino-lower alkanoyl, such as N-morpholino- or N-thiomorpholinocarbonylamino-acetyl, halo-lower alkanoyl containing up to three halogen atoms, such as trifluoroacetyl, 2-(N-morpholino-lower alkylcarbamoyl)-lower alkanoyl, such as 2(R,S)(N-(2-morpholinoethyl)-carbamoyl)-3-methyl-butyryl, 2-(N-pyridyl-lower alkylcarbamoyl)-lower alkanoyl, such as 2(R, S)-(N-(2-pyridylmethyl)-carbamoyl)-3-methylbutyryl, lower alkoxycarbonyl, such as methoxy-, ethoxy-, isobutoxy- or tert-lower alkoxy-carbonyl, phenyl-lower alkoxycarbonyl, such as benzyloxycarbonyl, tetrahydrofuryl-lower alkoxycarbonyl, such as 2-tetrahydrofuryl-methoxycarbonyl, lower alkenyloxycarbonyl (preferably having lower alkenyl bonded via a saturated carbon atom to the bonding oxygen atom), such as allyloxycarbonyl, lower alkoxy-lower alkoxycarbonyl, such as 2-methoxyethoxycarbonyl, (lower alkoxy-lower alkoxy)-lower alkoxycarbonyl, such as 2-(2-methoxyethoxy)-ethoxycarbonyl, lower alkanesulfonyl, for example methane- or ethane-sulfonyl, morpholinosulfonyl, thiomorpholinosulfonyl, N-pyridyl-lower alkyl-N-lower alkylcarbamoyl, such as N-(2-pyridylmethyl)-N-methylaminocarbonyl, or an acyl radical, bonded via the carbonyl of its carboxy group, of an amino acid selected from glycine, alanine, valine, leucine, isoleucine, glutamic acid and asparagine in the (D)-, (L)- or (D,L)-form (with the exception of glycine), wherein the α-amino group is unsubstituted or acylated by one of the other radicals $R_1$ or $R_9$ mentioned hitherto, with the exception of an acyl radical of an amino acid, greatest preference being given to the acyl radicals of N-morpholinocarbonyl-glycine, N-(N-(2-, 3-or 4-pyridyl)methyl-N-methylaminocarbonyl)-glycine, valine, N-(trifluoroacetyl)-valine, N-phenylacetyl-valine, N-acetyl-valine, N-(2-carbamoyl-3-phenyl-propionyl)-valine, N-(2-, 3- or 4-pyridylacetyl)-valine, N-2-tetrahydrofuryl-[2H]-methoxycarbonyl-valine, N-(2-methoxy)ethoxycarbonyl-valine, N-(2-methoxyethoxy)ethoxycarbonyl-valine, N-(3-(tetrazol-1-yl)-propionyl)-valine, N-(quinolin-2-ylcarbonyl)-valine, N-methoxycarbonyl-valine, N-isobutoxycarbonyl-valine, N-tert-butoxycarbonyl-valine, N-benzyloxycarbonyl-valine, N-(morpholinocarbonyl)-valine, N-(N-(morpholinocarbonyl)aminoacetyl)-valine, N-(thiomorpholinocarbonyl)-valine, N-(N-2-pyridylmethyl-N-methylaminocarbonyl)-valine, N-morpholinocarbonylaminoacetyl-valine, N-methylsulfonylvaline, morpholinosulfonyl-valine, N-acetyl-isoleucine, N-propionyl-isoleucine, N-(benzyloxycarbonyl)-isoleucine, glutamic acid, N-benzyloxycarbonyl-glutamic acid, asparagine, N-benzyloxycarbonyl-asparagine and/or quinolin-2-ylcarbonyl-asparagine, wherein the amino acid residues are each preferably in the (L)- or (D,L)-form, and in the case of valine also in the (D)-form; with the proviso that not more than one of the radicals $R_1$ and $R_9$ is hydrogen, $R_2$, $R_4$, $R_6$ and $R_8$ are hydrogen, $R_3$ is lower alkyl, such as n-butyl or isobutyl, cyclohexyl-lower alkyl, such as cyclohexylmethyl, or phenyl-lower alkyl that is unsubstituted or substituted by halogen, such as fluorine, lower alkoxy, such as methoxy, or by cyano, especially benzyl, 4-fluorobenzyl or 4-cyanobenzyl, $R_5$ is lower alkanoyloxy, such as acetoxy, propionyloxy, butyryloxy, pentanoyloxy or pivaloyloxy, octanoyloxy, decanoyloxy, dodecanoyloxy, carboxy-lower alkanoyloxy, such as 3-carboxypropionyloxy, furyl-lower alkanoyloxy, such as 2-furylcarbonyloxy, imidazolyl-lower alkanoyloxy, such as 4-imidazolylcarbonyloxy, 4-imidazolylacetoxy or 3-(4-imidazolyl)-propionyloxy, pyridyl-lower alkanoyloxy, such as 2-, 3- or 4-pyridylcarboxy, 2-pyridylacetoxy or 3-(2-pyridyl)propionyloxy, quinolyl-lower alkanoyloxy, such as quinolin-2-ylcarbonyloxy, aminoacetoxy (glycyloxy), N-lower alkylaminoacetoxy, such as N-methylaminoacetoxy, N,N-di-lower alkylaminoacetoxy, such as N,N-dimethylaminoacetoxy, N-lower alkyl-N-phenyl-lower alkoxycarbonylaminoacetoxy, such as N-benzyloxycarbonyl-N-methyl-aminoacetoxy, phenyl-lower alkanoyloxy, such as benzoyloxy, 4-morpholino-lower alkylbenzoyloxy, such as 4-morpholinomethylbenzoyloxy, 4-halomethylbenzoyloxy, histidyloxy or prolyloxy and $R_7$ is as last defined for $R_3$, especially lower alkyl, such as isobutyl or n-butyl; cyclohexyl-lower alkyl; or phenyl-lower alkyl that is unsubstituted or substituted by halogen, such as fluorine, lower alkoxy, such as methoxy, or by cyano; as last defined for $R_3$, or a salt thereof where at least one salt-forming group is present, still greater preference being given to those compounds in which $R_1$ and/or $R_9$ are not morpholinosulfonyl or thiomorpholinosulfonyl.

Especially preferred is a compound of formula I-A wherein $R_1$ is lower alkoxycarbonyl, halo-lower alkoxycarbonyl, phenyl-lower alkoxycarbonyl, the monovalent residue, bonded via carbonyl, of an aliphatic amino acid selected from valine, alanine, leucine and isoleucine or the residue, bonded via carbonyl, of an aliphatic amino acid as defined above acylated at the amino nitrogen atom by one of the radicals phenyl-lower alkanoyl, morpholinyl-lower alkanoyl, thiomorpholinyl-lower alkanoyl, pyridyl-lower alkanoyl, lower alkoxycarbonyl and phenyl-lower alkoxycarbonyl, all the mentioned amino acids being in the D-, D,L- or L-form, preferably in the L-form, $R_2$ is hydrogen, $R_3$ is phenyl-lower alkyl, 4-fluorophenyl-lower alkyl or cyclohexyl-lower alkyl, $R_4$ is hydrogen, $R_5$ is lower alkanoyloxy, octanoyloxy, decanoyloxy, dodecanoyloxy, carboxy-lower alkanoyloxy, furyl-lower alkanoyloxy, imidazolyl-lower alkanoyloxy, pyridyl-lower alkanoyloxy, quinolyl-lower alkanoyloxy, aminoacetoxy (glycyloxy), N-lower alkylaminoacetoxy, N,N-di-lower alkylaminoacetoxy, N-lower alkyl-N-phenyl-lower alkoxycarbonylaminoacetoxy, phenyl-lower alkanoyloxy, 4-morpholinomethylbenzoyloxy, 4-halomethylbenzoyloxy, histidyloxy or prolyloxy (=pyrrolidin-2-ylcarbonyloxy), $R_6$ is hydrogen, $R_7$ is lower alkyl, cyclohexyl-lower alkyl, phenyl-lower alkyl, 4-cyanophenyl-lower alkyl or 4-fluorophenyl-lower alkyl, $R_8$ is hydrogen and $R_9$ is one of the radicals mentioned for $R_1$, and the asymmetric carbon atoms carrying the radicals $R_3$ and $R_5$ are in the S-configuration, and pharmaceutically acceptable salts thereof.

Great preference is given to a compound of formula I-A wherein $R_1$ and $R_9$ are N-methoxycarbonylvalyl, $R_2$, $R_4$, $R_6$ and $R_8$ are hydrogen, $R_3$ is benzyl or cyclohexylmethyl, $R_5$ is lower alkanoyloxy, especially acetoxy, or pyridylcarbonyloxy, especially 2-pyridylcarbonyloxy, and $R_7$ is cyclohexylmethyl or benzyl, and pharmaceutically acceptable salts thereof, especially an isomer of that compound wherein the carbon atom carrying $R_3$ and the carbon atom carrying $R_5$ are in the (S)-configuration.

Great preference is given also to a compound of formula I-A wherein $R_1$ and $R_9$ are each independently of the other N-lower alkoxycarbonyl-valyl, $R_2$ is hydrogen, $R_3$ is phenylmethyl or cyclohexylmethyl, $R_4$ is hydrogen, $R_5$ is palmitoyloxy, lower alkoxy-lower alkanoyloxy or pyridylcarbonyloxy, $R_6$ is hydrogen, $R_7$ is phenylmethyl or cyclohexylmethyl and $R_8$ is hydrogen, or a pharmaceutically acceptable salt thereof.

Of those compounds, special preference is given to

1-[2(S)-palmitoyloxy-3(S)-(N-(methoxy-carbonyl)-(L)-valyl)amino-4-phenyl-butyl]-1-[cyclohexylmethyl]-2-[N-methoxy-carbonyl-(L)-valyl]hydrazine of formula I-A, or a pharmaceutically acceptable salt thereof; or 1[-2(S)-(methoxy-acetoxy)-3(S)-(N-(methoxy-carbonyl)-(L)-valyl)amino-4-phenylbutyl]-1-[cyclohexylmethyl]-2-[N-methoxy-carbonyl-(L)-valyl]hydrazine of formula I-A, or a pharmaceutically acceptable salt thereof; or 1-[2(S)-(2-pyridyl-carbonyl)oxy-3(S)-(tert-butoxy-carbonyl)amino-4-phenyl-butyl]-1-[cyclohexylmethyl] -2-[tert-butoxy-carbonyl]hydrazine of formula I-A, or a pharmaceutically acceptable salt thereof.

Especially preferred are, finally, also compounds of formula I-A wherein $R_1$ is quinolin2-yl-carbonyl-(L)-asparaginyl, $R_2$ is hydrogen, $R_3$ is phenylmethyl, 4-lower alkoxyphenylmethyl or 4-benzyloxyphenylmethyl, $R_4$ is hydrogen, $R_5$ is lower alkanoyloxy, such as butyryloxy, octanoyloxy, decanoyloxy, dodecanoyloxy, palmitoyloxy, lower alkoxy-lower alkanoyloxy, such as methoxyacetoxy, carboxy-lower alkanoyloxy, furyl-lower alkanoyloxy, imidazolyl-lower alkanoyloxy, pyridyl-lower alkanoyloxy, such as especially pyridinylcarbonyloxy, for example 2- or 3-pyridinylcarbonyloxy, quinolyl-lower alkanoyloxy, aminoacetoxy (glycyloxy), N-lower alkylaminoacetoxy, N,N-di-lower alkylaminoacetoxy, N-lower alkyl-N-phenyl-lower alkoxycarbonylaminoacetoxy, phenyl-lower alkanoyloxy, 4-morpholinomethylbenzoyloxy, 4-halomethylbenzoyloxy, histidyloxy or prolyloxy (=pyrrolidin-2-ylcarbonyloxy), $R_6$ is hydrogen, $R_7$ is phenylmethyl, 4-lower alkoxyphenylmethyl or cyclohexylmethyl, $R_8$ is hydrogen and $R_9$ is lower alkoxycarbonyl-(L)-valyl, lower alkoxy-lower alkoxy-lower alkoxycarbonyl-(L)-valyl, phenyl-lower alkoxycarbonyl-(L)-valyl, lower alkanoyl-(L)-valyl, benzylaminocarbonyl or $C_3$–$C_7$alkenyloxycarbonyl, or (less preferably) lower alkoxycarbonyl, or pharmaceutically acceptable salts thereof, especially a compound selected from 1-[2(S)-(2-pyridylcarbonyl)oxy-3(S)-(N-quinoline-2-carbonyl)-(L)-asparaginyl)amino4-phenylbutyl-1-[phenylmethyl]-2-[N-(methoxycarbonyl)-(L)-valyl] hydrazine, 1-[2(S)-butyryloxy-3(S)-(N-quinoline-2-carbonyl)-(L)-asparaginyl)amino-4-phenylbutyl-1-[phenylmethyl]-2-[N-(methoxycarbonyl)-(L)-valyl]hydrazine, 1-[2(S)-(2-pyridylcarbonyl)oxy-3(S)-(N-quinoline-2-carbonyl)-(L)-asparaginyl)amino 4-phenylbutyl-1-[4-methoxyphenylmethyl]-2-[N-(benzyloxycarbonyl)-(L)-valyl]hydrazine, and 1-[2(S)-(methoxy-acetyl)oxy-3(S)-(N-quinoline-2-carbonyl)-(L)-asparaginyl)amino-4-phenylbutyl-1-[4-methoxyphenylmethyl]-2-[N-(benzyloxycarbonyl)-(L)-valyl]hydrazine; or a pharmaceutically acceptable salt thereof.

Very special preference is given to compounds of formula I-A selected from

1-[2(S)-propionyloxy-3(S)-(N-(methoxycarbonyl)-(L)-valyl)amino-4-phenyl-butyl]-1-[cyclohexylmethyl]-2-[N-(methoxycarbonyl)-(L)-valyl]hydrazine;

1-[2(S)-butyryloxy-3(S)-(N-(methoxycarbonyl)-(L)-valyl) amino-4-phenyl-butyl]-1-[cyclohexylmethyl]-2-[N-(methoxycarbonyl)-(L)-valyl]hydrazine;

1-[2(S)-pentanoyloxy-3(S)-(N-(methoxycarbonyl)-(L)-valyl)amino-4-phenyl-butyl]-1-[cyclohexylmethyl]-2-[N-(methoxycarbonyl)-(L)-valyl]hydrazine;

1-[2(S)-octanoyloxy-3(S)-(N-(methoxycarbonyl)-(L)-valyl) amino-4-phenyl-butyl]-1-[cyclohexylmethyl]-2-[N-(methoxycarbonyl)-(L)-valyl]hydrazine;

1-[2(S)-decanoyloxy-3(S)-(N-(methoxycarbonyl)-(L)-valyl)amino-4-phenyl-butyl]-1-[cyclohexylmethyl]-2-[N-(methoxycarbonyl)-(L)-valyl]hydrazine;

1-[2(S)-dodecanoyloxy-3(S)-(N-(methoxycarbonyl)-(L)-valyl)amino-4-phenyl-butyl]-1-[cyclohexylmethyl]-2-[N-(methoxycarbonyl)-(L)-valyl]hydrazine;

1-[2(S)-pivaloyloxy-3(S)-(N-(methoxycarbonyl)-(L)-valyl) amino-4-phenyl-butyl]-1-[cyclohexylmethyl]-2-[N-(methoxycarbonyl)-(L)-valyl]hydrazine;

1-[2(S)-(2-furylcarbonyl)oxy-3(S)-(N-(methoxycarbonyl)-(L)-valyl)amino-4-phenylbutyl]-1-[cyclohexylmethyl]-2-[N-(methoxycarbonyl)-(L)-valyl]hydrazine;

1-[2(S)-(4-imidazolylcarbonyl)oxy-3(S)-(N-(methoxycarbonyl)-(L)-valyl)amino-4-phenyl-butyl]-1-[cyclohexylmethyl]-2-[N-(methoxycarbonyl)-(L)-valyl]hydrazine;

1-[2(S)-(4-imidazolylacetyl)oxy-3(S)-(N-(methoxycarbonyl)-(L)-valyl)amino-4-phenylbutyl]-1-[cyclohexylmethyl]-2-[N-(methoxycarbonyl)-(L)-valyl]hydrazine;

1-[2(S)-(3-(4-imidazolyl)-propionyl)oxy-3(S)-(N-(methoxycarbonyl)-(L)-valyl)amino-4-phenyl-butyl]-1-[cyclohexylmethyl]-2-[N-(methoxycarbonyl)-(L)-valyl]hydrazine;

1-[2(S)-benzoyloxy-3(S)-(N-(methoxycarbonyl)-(L)-valyl) amino-4-phenyl-butyl]-1-[cyclohexylmethyl]-2-[N-(methoxycarbonyl)-(L)-valyl]hydrazine;

1-[2(S)-(2-pyridylacetyl)oxy-3(S)-(N-(methoxycarbonyl)-(L)-valyl)amino-4-phenylbutyl]-1-[cyclohexylmethyl]-2-[N-(methoxycarbonyl)-(L)-valyl]hydrazine;

1-[2(S)-(3-(pyridin-2-yl)-propionyl)oxy-3(S)-(N-(methoxycarbonyl)-(L)-valyl)amino-4-phenylbutyl)]-1-[cyclohexylmethyl]-2-[N-(methoxycarbonyl)-(L)-valyl] hydrazine;

1-[2(S)-(quinolin-2-ylcarbonyl)oxy-3(S)-(N-(methoxycarbonyl)-(L)-valyl)amino-4-phenyl-butyl]-1-[cyclohexylmethyl]-2-[N-(methoxycarbonyl)-(L)-valyl] hydrazine;

1-[2(S)-(aminoacetyl)oxy-3(S)-(N-(methoxycarbonyl)-(L)-valyl)amino-4-phenyl-butyl]-1-[cyclohexylmethyl]-2-[N-(methoxycarbonyl)-(L)-valyl]hydrazine;

1-[2(S)-(N-methylaminoacetyl)oxy-3(S)-(N-(methoxycarbonyl)-(L)-valyl)amino-4-phenyl-butyl]-1-[cyclohexylmethyl]-2-[N-(methoxycarbonyl)-(L)-valyl] hydrazine;

1-[2(S)-(N,N-dimethylaminoacetyl)oxy-3(S)-(N-(methoxycarbonyl)-(L)-valyl)amino-4-phenyl-butyl]-1-[cyclohexylmethyl]-2-[N-(methoxycarbonyl)-(L)-valyl] hydrazine;

1-[2(S)-(N-benzyloxycarbonyl-N-methyl-aminoacetyl)oxy-3(S)-(N-(methoxycarbonyl)(L)-valyl)amino-4-phenyl-butyl]-1-[cyclohexylmethyl]-2-[N-(methoxycarbonyl)(L)-valyl]hydrazine;

1-[2(S)-prolyloxy-3(S)-(N-(methoxycarbonyl)-(L)-valyl) amino-4-phenyl-butyl]-1-[cyclohexylmethyl]-2-[N-(methoxycarbonyl)-(L)-valyl]hydrazine;

1-[2(S)-(4-morpholinomethylbenzoyl)oxy-3(S)-(N-(methoxycarbonyl)-(L)-valyl)amino-4-phenyl-butyl]-1-[cyclohexylmethyl]-2-[N-(methoxycarbonyl)-(L)-valyl] hydrazine;

1-[2(S)-(4-chloromethylbenzoyl)oxy-3(S)-(N-(methoxycarbonyl)-(L)-valyl)amino-4-phenyl-butyl]-1-[cyclohexylmethyl]-2-[N-(methoxycarbonyl)-(L)-valyl] hydrazine; and 1-[2(S)-(3-carboxypropionyl)oxy-3(S)-(N-(methoxycarbonyl)-(L)-valyl)amino-4-phenylbutyl]-1-[cyclohexylmethyl]-2-[N-(methoxycarbonyl)-(L)-valyl] hydrazine, or pharmaceutically acceptable salts thereof.

Most preferred of all are the compounds mentioned in the Examples and their salts.

The compounds of formula I-A and salts of such compounds having at least one salt-forming group are obtained by means of processes known per se, for example as follows:

i) a hydroxy compound of formula I

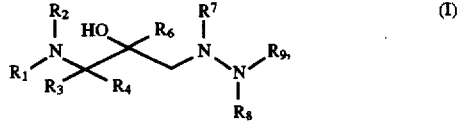

wherein the radicals are as defined for compounds of formula I-A, is acylated with a carboxylic acid of formula XXII

R$_5$—H or with a reactive acid derivative thereof, wherein R$_5$ is as defined for compounds of formula I-A, free functional groups in the starting materials of formulae I and XXII that are not to participate in the reaction being if necessary in protected form, and any protecting groups present are removed, or ii) for the preparation of compounds of formula I-A wherein (in correspondence with the meaning of definitions for compounds of formula I-A) R$_9$ is acyl, sulfo, or sulfonyl substituted by unsubstituted or substituted alkyl, aryl or heterocyclyl, and the remaining radicals are as defined, an amino compound of formula

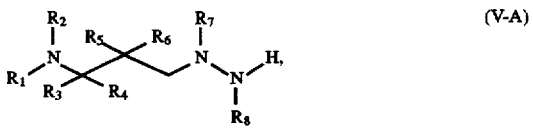

wherein the radicals are as defined immediately above, is condensed with an acid of formula

R$_9$'—OH    (VI-A), or with a reactive acid derivative thereof, wherein R$_9$' is as defined for R$_9$ (in correspondence with the meaning of definitions for compounds of formula I-A) with the exception of hydrogen and unsubstituted or substituted alkyl, free functional groups, with the exception of those participating in the reaction, being if necessary in protected form, and any protecting groups present are removed, or iii) for the preparation of compounds of formula I-A wherein (in correspondence with the meaning of definitions for compounds of formula I-A) $R_1$ is acyl, sulfo, or sulfonyl substituted by unsubstituted or substituted alkyl, aryl or heterocyclyl, and the remaining radicals are as defined, an amino compound of formula

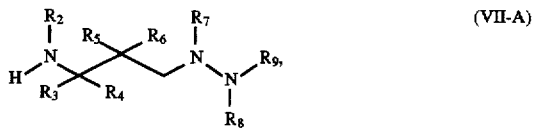

wherein the radicals are as defined immediately above, is condensed with an acid of formula $$R_1'\text{—OH} \qquad \text{(VIII),}$$

or with a reactive acid derivative thereof, wherein (in correspondence with the meaning of definitions for compounds of formula I-A) $R_1'$ is as defined for $R_1$ with the exception of hydrogen and unsubstituted or substituted alkyl, free functional groups, with the exception of those participating in the reaction, being if necessary in protected form, and any protecting groups present are removed, or iv) for the preparation of compounds of formula I-A wherein (in correspondence with the meaning of definitions for compounds of formula I-A) $R_1$ and $R_9$ are two identical radicals selected from acyl, sulfo, and sulfonyl substituted by unsubstituted or substituted alkyl, aryl or heterocyclyl, and the remaining radicals are as defined, a diamino compound of formula

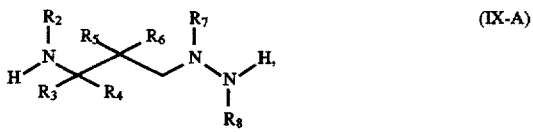

wherein the radicals are as defined immediately above, is condensed with an acid suitable for introducing the identical radicals $R_1$ and $R_9$, or with a reactive acid derivative thereof, wherein $R_1$ and $R_9$ are as defined immediately above, free functional groups, with the exception of those participating in the reaction, being if necessary in protected form, and any protecting groups present are removed, or v) for the preparation of a compound of formula I-A wherein in place of $R_7$ there is a radical $R_7''$ which (in correspondence with the meaning of definitions for compounds of formula I-A) is unsubstituted or substituted alkyl or cycloalkyl, in a compound of formula I-A'

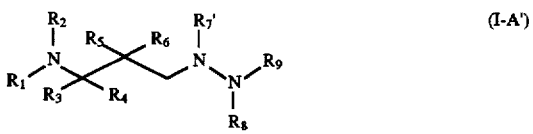

wherein $R_7'$ is hydrogen and the remaining radicals are as defined (in correspondence with the meaning of definitions for compounds of formula I-A), the radical $R_7''$ is introduced by substitution with a compound of formula XII $$R_7''\text{—X} \qquad \text{(XII),}$$

wherein X is a leaving group and $R_7''$ (in correspondence with the meaning of definitions for compounds of formula I-A) is unsubstituted or substituted alkyl or cycloalkyl, free functional groups, with the exception of those participating in the reaction, being optionally in protected form, and any protecting groups present are removed, or vi) in a compound of formula I-A wherein the substituents are as defined above with the proviso that in the compound of formula I-A in question at least one functional group is protected by protecting groups, the protecting groups present are removed, and, if desired, a compound of formula I-A obtainable in accordance with any one of processes i) to vi) above having at least one salt-forming group is converted into its salt or an obtainable salt is converted into the free compound or into a different salt and/or any isomeric mixtures that are obtainable are separated and/or a compound of formula I-A according to the invention is converted into a different compound of formula I-A according to the invention.

The said processes are described in detail below; unless otherwise indicated, the radicals $R_1$, $R_2$, $R_3$, $R_4$, $R_5$, $R_6$, $R_7$, $R_8$ and $R_9$ are as defined for compounds of formula I-A:

Process i) (Acylation of a hydroxy group)

The acylation of the hydroxy group is effected, for example, in a manner known per se using an acid of formula XXII wherein $R_5$ is as defined with the exception of aminocarbonyloxy and the radical of an N-substituted carbamic acid bonded via its aminocarbonyloxy group, or using a reactive derivative thereof. A suitable reactive derivative is, for example, a carboxylic acid of formula XXIIa $$R_5'\text{—}Z_1 \qquad \text{(XXIIa),}$$

wherein $R_5'$ is one of the acyl radicals occurring in acyloxy, as defined above, and wherein $Z_1$ is reactively activated hydroxy (the compound of formula XXIIa thus contains, instead of a hydroxy function bonded to the carbonyl group, reactively activated hydroxy, preferably as defined below). The free carboxylic acid of formula XXII can be activated, for example, by strong acids, such as a hydrohalic, sulfuric, sulfonic or carboxylic acid, or by acidic ion exchangers, for example hydrochloric, hydrobromic or hydriodic acid, sulfuric acid, an unsubstituted or substituted, for example halo-substituted, alkanecarboxylic acid, or by an acid of formula XXII, preferably using an excess of the acid of formula XXII, if necessary with the bonding of resulting water of reaction by water-binding agents, with removal of the water of reaction by azeotropic distillation or with extractive esterification, by acid anhydrides, especially inorganic acid anhydrides, or more especially organic acid anhydrides, for example carboxylic acid anhydrides, such as lower alkanecarboxylic acid anhydrides (with the exception of formic acid anhydride), for example acetic anhydride, or by suitable activating or coupling reagents of the type listed below, especially also in situ. $R_5'$—$Z_1$ may especially also be a carboxylic acid azide ($Z_1$=azido; obtainable, for example, by reaction of a corresponding acid ester via the corresponding hydrazide and treatment thereof with nitrous acid); a carboxylic acid halide ($Z_1$=halogen, especially chlorine or bromine), especially an acid chloride or bromide, obtainable, for example, by reaction with organic acid halides, especially with oxalyl dihalides, such as oxalyl dichloride, or with inorganic acid halides, for example with acid halides of phosphorus or sulfur, such as phosphorus trichloride, phosphorus tribromide, phosphorus pentachloride, phosphorus pentabromide, phosphorus oxychloride, phosphorus oxybromide, thionyl chloride or thionyl bromide, or especially under mild conditions with tetra-lower alkyl-α-halo-enamines, for example tetramethyl-α-halo-enamines, especially 1-chloro-N,N,2-trimethyl-1- propenamine (preferably by reaction in inert solvents, especially chlorinated hydrocarbons, such as methylene chloride or chloroform, or ethers, such as diethyl ether, dioxane or tetrahydrofuran, at preferred temperatures of from −78° to 50° C., especially from −60° to 30° C., for example from −10° C. to room temperature (cf. Devos, A., et al., J. C. S. Chem. Commun. 1979, 1180–1181, and Haveaux, B., et al., Org. Synth. 59, 26 (1980)), it being possible for the resulting acid halide, for example the acid chloride of formula XXIIa wherein $Z_1$ is chlorine, also to be used further in situ, for example by reaction with the compound of formula I in the presence of tertiary nitrogen bases, such as pyridine and/or dimethylaminopyridine (DMAP, which is preferably added in catalytic amounts), at preferred temperatures of from −20° to 50° C., especially from 0° C. to room temperature); an activated ester wherein $Z_1$ is the radical of an alcohol having electron-attracting substituents, especially cyanomethoxy or aryloxy wherein aryl is preferably phenyl or naphthyl that is mono- or poly-substituted by halogen, nitro and/or by cyano, for example nitrophenoxy, such as 4-nitrophenoxy or 2,4-dinitrophenoxy, or poly-halophenoxy, such as pentachlorophenoxy; or a symmetrical or, preferably, asymmetrical acid anhydride which can be obtained, for example, by the action of a salt, for example an alkali metal salt, of an acid of formula XXII or its reaction partner, preferably a lower alkanecarboxylic acid, such as acetic acid, such as the sodium or potassium salt, on a complementary acid halide, especially, in the case of the reaction of a salt of a carboxylic acid of formula XXII, a carboxylic acid halide, for example chloride, such as acetyl chloride, and, in the case of the reaction of a carboxylic acid halide of formula XXIIa wherein Z, is halogen, for example chlorine or bromine, with a salt of a lower alkanecarboxylic acid, especially sodium or potassium acetate. There may be used as activating and coupling reagents for activating carboxylic acids of formula XXII in situ especially carbodiimides, for example N,N'-di-$C_1$–$C_4$alkyl- or N,N'-di-$C_5$–$C_7$cycloalkylcarbodiimide, such as diisopropylcarbodiimide or N,N'-dicyclohexylcarbodiimide, advantageously with the addition of an activating catalyst, such as N-hydroxysuccinimide or unsubstituted or substituted, for example halo-, $C_1$–$C_7$alkyl- or $C_1$–$C_7$alkoxy-substituted, N-hydroxy-benzotriazole or N-hydroxy-5-norbornene-2,3-dicarboxamide, $C_1$–$C_4$alkylhaloformate, for example isobutyl chloroformate, suitable carbonyl compounds, for example N,N-carbonyldiimidazole, suitable 1,2-oxazolium compounds, for example 2-ethyl-5-phenyl-1,2-oxazolium 3'-sulfonate or 2-tert-butyl-5-methyl-isoxazolium perchlorate, suitable acylamino compounds, for example 2-ethoxy-1-ethoxycarbonyl-1,2-dihydroquinoline, or suitable phosphoryl cyanamides or azides, for example diethylphosphoryl cyanamide or diphenylphosphoryl azide, also triphenylphosphine disulfide or 1-$C_1$–$C_4$alkyl-2-halopyridinium halides, for example 1-methyl-2-chloropyridinium iodide.

If in the compound of formula XXII two free carboxy groups are present, for example in carboxy-lower alkanoic acids, such as 3-carboxypropanoic acid, there may also be present as activated acid derivative an internal anhydride, for example a succinic anhydride. $Z_1$ is preferably halogen, such as chlorine or bromine, and acyloxy, for example lower alkanoyloxy, such as acetoxy.

For the specific case of the introduction of an acyl radical of a semiester of carbonic acid linked via its carbonyl group to the bonding oxygen atom there are suitable especially the compounds of formula XXIIa wherein $Z_1$ is halogen, such as chlorine, which can be prepared, for example, by reaction of the complementary alcohols, for example unsubstituted or substituted alkyl alcohols, aryl-lower alkyl alcohols or heterocyclyl-lower alkyl alcohols, as defined in the definition of unsubstituted or substituted alkoxycarbonyloxy, aryl-lower alkoxycarbonyloxy or heterocyclyl-lower alkoxycarbonyloxy $R_5$, with phosgene or with analogues thereof that contain other halogen atoms, especially bromine, instead of chlorine, preferably in the presence of tertiary nitrogen bases, such as pyridine or triethylamine, and in inert solvents, for example chlorinated hydrocarbons, such as methylene chloride or chloroform, ethers, such as diethyl ether, tetrahydrofuran or dioxane, or carboxylic acid amides, such as dimethylformamide. Also suitable are corresponding N-carbonyl azolides of formula XXIIa ($Z_1$=an N-containing heterocycle, such as 1-imidazolido) which are obtained, for example, by reaction with the corresponding N,N'-carbonyl diazolides, such as N,N'-carbonyl diimidazole, under conditions such as those just described for phosgene and analogues with other halogen atoms. The reaction of compounds of formula I with corresponding compounds of formula XXIIa then likewise takes place under those conditions (cf. Staab, H. A., Angew. Chemie 7,4 407 (1962)).

For the specific case of the introduction of aminocarbonyloxy $R_5$ or of an N-substituted aminocarbonyloxy group $R_5$ there is suitable as activated acid derivative especially the corresponding isocyanate of formula XXIIb

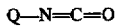

Q—N=C=O                                    (XXIIb)

wherein Q is an amino-protecting group, for example trihaloacetyl, such as trifluoro- or trichloro-acetyl, or one of the unsubstituted or substituted lower alkyl radicals or aryl radicals mentioned above in the definition of aminocarbonyloxy $R_5$ wherein the amino group carries 1 or 2 substituents, it being possible, when Q is an amino-protecting group, to obtain after the reaction with the compound of formula I the corresponding compound of formula I-A wherein $R_5$ is free aminocarbonyloxy by removal of the protecting group Q as described below for the freeing of amino protected by acyl, especially by acid hydrolysis, or, when Q is one of the mentioned substituted or unsubstituted lower alkyl radicals or aryl radicals, a corresponding compound of formula I-A having aminocarbonyloxy $R_5$ mono-substituted at the nitrogen atom. Both aminocarbonyloxy and N-mono-substituted aminocarbonyloxy $R_5$ can be converted into N-disubstituted aminocarbonyloxy by alkylation with a further unsubstituted or substituted lower alkyl radical using suitable starting materials and conditions analogous to those described below in the "Additional Process Steps".

The reactions can be carried out under reaction conditions known per se, at customary temperatures, in the presence or, especially when lower alkanoyl anhydrides are used to activate the carboxylic acid of formula XXII, in the absence of inert solvents or diluents, for example in acid amides, for example carboxylic acid amides, such as dimethylformamide, dimethylacetamide or 1,3-dimethyl-3, 4,5,6-tetrahydro-2(1H)-pyrimidinone (DMPU), or amides of inorganic acids, such as hexamethylphosphoric acid triamide, ethers, for example cyclic ethers, such as tetrahydrofuran or dioxane, or acyclic ethers, such as diethyl ether or ethylene glycol dimethyl ether, halogenated hydrocarbons, such as halo-lower alkanes, for example methylene chloride or chloroform, ketones, such as acetone, nitriles, such as acetonitrile, acid anhydrides, such as acetic anhydride, esters, such as ethyl acetate, bisalkane sulfines, such as dimethyl sulfoxide, nitrogen heterocycles, such as pyridine, or mixtures of those solvents, especially in anhydrous solvents or solvent mixtures, it being possible to select for the above-mentioned reactions the particular solvents that are suitable in each case, there being used, as appropriate and expedient, salts of the compounds used, especially metal salts of carboxylic acids that are used, such as the alkali metal or alkaline earth metal salts, for example sodium or potassium salts, in the absence or the presence of catalysts, such as dimethylaminopyridine, condensation agents or neutralising agents, such as tertiary nitrogen bases, for example pyridine, triethylamine, N-methylmorpholine, dimethylaminopyridine or ethyl diisopropylamine, and, depending on the nature of the reaction and/or the reactants, under atmospheric pressure or in a closed vessel, under normal pressure or under elevated pressure, for example at the pressure produced in the reaction mixture under the reaction conditions in a closed tube, and/or in an inert atmosphere, for example under an argon or nitrogen atmosphere. Preference is given to reaction conditions that are mentioned specifically in any particular case or, especially, that are analogous to those mentioned in the Examples. The course of the reaction is advantageously monitored using customary methods of analysis, especially using thin-layer chromatography. It is possible to select from those reaction conditions those that are suitable for each of the reactions described in this text, reaction conditions that are specifically mentioned being especially preferred.

The reaction according to the invention is preferably carried out under mild conditions, especially at temperatures of from $-10°$ C. to $60°$ C., for example from $0°$ C. to room temperature or at slightly elevated temperatures up to about $50°$ C., for example approximately from $0°$ C. to room temperature. Both in the case of the reaction with a carboxylic acid halide of formula XXIIa wherein $Z_1$ is halogen, such as chlorine or bromine, and in the case of the reaction with an anhydride, especially a symmetrical anhydride $(Z_1\!=\!O\!-\!R_5')$, the corresponding compound of formula XXIIa (halide and $R_5'\!-\!O\!-\!R_5'$, respectively) is used especially in an approximately equimolar amount in relation to the compound of formula I or in excess, for example from 0.95 to 10 times the molar amount.

Preferred as compounds of formula I for Process a) are the starting compounds of formula

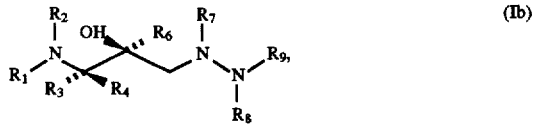

wherein the radicals are as defined for compounds of formula I-A, and the salts of the mentioned compounds where salt-forming groups are present.

Functional groups in starting materials the reaction of which is to be avoided, especially carboxy, amino, hydroxy, mercapto and sulfo groups, can be protected by suitable protecting groups (conventional protecting groups) which are customarily used in the synthesis of peptide compounds, and also in the synthesis of cephalosporins and penicillins as well as nucleic acid derivatives and sugars. Those protecting groups may already be present in the precursors and are intended to protect the functional groups in question against undesired secondary reactions, such as acylation, etherification, esterification, oxidation, solvolysis, etc. In certain cases the protecting groups can additionally cause the reactions to proceed selectively, for example stereoselectively. It is characteristic of protecting groups that they can be removed easily, i.e. without undesired secondary reactions taking place, for example by solvolysis, reduction, photolysis, and also enzymatically, for example also under physiological conditions, and, especially, that they are not present in the end products.

The protection of functional groups by such protecting groups, the protecting groups themselves and the reactions for their removal are described above in the description of the manufacture of compounds of formula I under process a) and process b).

Process ii) (Condensation to form an amide bond)

In starting materials of formulae V-A and VI-A, functional groups, with the exception of the groups that are intended to participate in the reaction or that do not react under the reaction conditions, are protected each independently of the others by one of the protecting groups mentioned above under Process a) for the preparation of compounds of formula I.

The reaction conditions are analogous to those mentioned under process b) for the synthesis of compounds of formula I, if instead of the compounds of formulae V and VI mentioned there the compounds of formulae V-A and VI-A are employed.

For the specific case of the introduction of a radical of a semiester of carbonic acid $R_9$ there are suitable especially the compounds of formula VI-A', $$R_x\!-\!O\!-\!(C\!=\!O)\!-\!Z_2 \text{(VI-A')}$$

wherein $R_x$ is especially lower alkyl, halo-lower alkyl, aryl-lower alkyl, heterocyclyl-lower alkyl, lower alkenyl, lower alkoxy-lower alkyl or (lower alkoxy-lower alkoxy) lower alkyl, as in the definition of acyl groups $R_9$ of a semiester of carbonic acid, and wherein $Z_2$ is halogen, such as chlorine, which can be prepared, for example, by reaction of the complementary alcohols, such as lower alkyl alcohols, halo-lower alkyl alcohols, aryl-lower alkyl alcohols, heterocyclyl-lower alkyl alcohols, lower alkenyl alcohols, lower alkoxy-lower alkyl alcohols or (lower alkoxy-lower alkoxy)-lower alkyl alcohols, with phosgene or with analogues thereof that contain other halogen atoms, especially bromine, instead of chlorine, preferably in the presence of tertiary nitrogen bases, such as pyridine or triethylamine, and in inert solvents, for example chlorinated hydrocarbons, such as methylene chloride or chloroform, ethers, such as diethyl ether, tetrahydrofuran or dioxane, or carboxylic acid amides, such as dimethylformamide. Also suitable are corresponding N-carbonyl azolides of formula VI-A' ($Z_2$=an N-containing heterocycle, such as 1-imidazolido) which are obtained, for example, by reaction with the corresponding N,N'-carbonyl diazolides, such as N,N'-carbonyl diimidazole, under conditions such as those just described for phosgene and analogues with other halogen atoms. The reaction of compounds of formula V-A with corresponding compounds of formula VI-A' then likewise takes place under those conditions (cf. Staab, H. A., Angew. Chemie 74, 407 (1962)).

For the specific case of the introduction of a radical $R_9$ of an unsubstituted or N-substituted carbamic acid, such as carbamoyl or unsubstituted or substituted N-alkylcarbamoyl, there is suitable as activated acid derivative especially the corresponding isocyanate of formula VI-A"

$$W\!-\!N\!=\!C\!=\!O \quad \text{(VI-A")}$$

wherein W is an amino-protecting group, for example trihaloacetyl, such as trifluoro- or trichloro-acetyl, or one of the unsubstituted or substituted alkyl radicals mentioned above in the definition of acyl groups $R_9$ of a substituted carbamic acid, it being possible, when W is an aminoprotecting group, to obtain after the reaction with the compound of formula V-A the corresponding compound of formula I-A wherein $R_9$ is carbamoyl by removal of the protecting group W as described under process f) for the preparation of compounds of formula I for the freeing of protected amino, especially by acid hydrolysis, or, when W is one of the mentioned substituted or unsubstituted lower alkyl radicals, a corresponding compound of formula I-A having aminocarbonyl $R_9$ mono-substituted at the nitrogen atom. Both aminocarbonyl and N-mono-substituted aminocarbonyl $R_9$ can be converted into N-disubstituted aminocarbonyl by alkylation with a further unsubstituted or substituted lower alkyl radical using suitable starting materials under conditions analogous to those described below in the "Additional Process Steps".

The reactions with the compounds of formulae VI-A' and VI-A" are effected under reaction conditions analogous to those mentioned for the reaction of compounds of formula XXIIa and XXIIb with those of formula I under Process i).

Depending on the starting compounds used, the radicals $R_1$ and $R_9$ in the obtainable compounds of formula I-A can be identical or different from one another.

The freeing of protected groups is effected where appropriate by the methods described for the preparation of compounds of formula I under Process f) (Removal of protecting groups).

Process iii) (Formation of an amide bond)

In starting materials of formulae VII-A and VIII-A, functional groups, with the exception of the groups that are intended to participate in the reaction or that do not react under the reaction conditions, are protected each independently of the others by one of the protecting groups mentioned under Process a) for the synthesis of compounds of formula I.

The process is totally analogous to the process mentioned under Process ii) except that instead of compounds of formula V-A those of formula VII-A are used, and instead of compounds of formula VI-A those of formula VIII-A are used.

Depending on the starting compounds used, the radicals $R_1$ and $R_9$ in the obtainable compounds of formula I-A can be identical or different from one another.

In the reactions in Process i), and also in iii) and iv), in some cases the acyl radical in acyloxy $R_5$ may migrate to the nitrogen atom to which $R_9$ is to be linked; analogous secondary reactions are possible in Processes c) and d).

The freeing of protected groups is effected where appropriate by the methods described for the preparation of compounds of formula I under Process f) (Removal of protecting groups).

Process iv) (Formation of an amide bond)

In starting materials of formula IX-A and in the acid suitable for introducing the identical radicals $R_1'$ and $R_9'$, or the reactive derivatives thereof, functional groups that are not intended to participate in the reaction or that do not react under the reaction conditions are protected each independently of the others by one of the protecting groups mentioned for the preparation of compounds of formula I under Process a).

The acid suitable for introducing the identical radicals $R_1'$ and $R_9'$ is preferably an acid of formula VI-A or VIII-A, or it is present in the form of a reactive derivative of such an acid, as described above.

Preferred as starting compounds of formula IX-A that may be protected by protecting groups are those which are described as being preferred in the section relating to starting compounds.

The conditions for the process are analogous to those mentioned under Process ii), except that instead of compounds of formula V-A those of formula IX-A are used, and instead of compounds of formula VI-A those of formula VI-A or VIII-A are used.

The freeing of protected groups is effected where appropriate by the methods described for the preparation of compounds of formula I under Process f) (Removal of protecting groups).

Process v) (Alkylation of a secondary nitrogen atom)

In starting materials of formula I-A' and in the compound of formula XII-A suitable for introducing the radical $R_7"$, or the reactive derivatives thereof, functional groups that are not intended to participate in the reaction or that do not react under the reaction conditions are protected each independently of the others by one of the protecting groups mentioned for the synthesis of compounds of formula I under Process a).

A leaving group X is especially a nucleofugal leaving group selected from hydroxy esterified by a strong inorganic or organic acid, such as hydroxy esterified by a mineral acid, for example a hydrohalic acid, such as hydrochloric acid, hydrobromic acid or hydriodic acid, or by a strong organic sulfonic acid, such as a lower alkanesulfonic acid that is unsubstituted or substituted, for example by halogen, such as fluorine, or an aromatic sulfonic acid, for example a benzenesulfonic acid that is unsubstituted or substituted by lower alkyl, such as methyl, halogen, such as bromine, and/or by nitro, for example a methanesulfonic acid, p-bromotoluenesulfonic acid or p-toluenesulfonic acid, and hydroxy esterified by hydrazoic acid.

The substitution can take place under the conditions of a first-order or second-order nucleophilic substitution.

For example, a compound of formula XII-A, especially a compound of formula XII-A wherein X is a leaving group having a high polarisability of the electron shell, for example iodine, can be used in a polar aprotic solvent, for example acetone, acetonitrile, nitromethane, dimethyl sulfoxide or dimethylformamide. The reaction may alternatively be carried out in water to which, where appropriate, an organic solvent, for example ethanol, tetrahydrofuran or acetone, has been added as solubiliser. The substitution reaction is carried out at room temperature or at reduced or elevated temperature, for example in a temperature range of from approximately $-40°$ to approximately $100°$ C., preferably from approximately $-10°$ to approximately $50°$ C., and where appropriate under an inert gas, for example under a nitrogen or argon atmosphere.

The freeing of protected groups is effected where appropriate by the methods described for the preparation of compounds of formula I under Process f) (Removal of protecting groups).

Process vi) (Removal of protecting groups)

The removal of protecting groups that are not constituents of the desired end product of formula I-A, for example the carboxy-, amino-, hydroxy-, mercapto- and/or sulfoprotecting groups, is effected in a manner known per se, for example by means of solvolysis, especially hydrolysis, alcoholysis or acidolysis, or by means of reduction, especially hydrogenolysis or chemical reduction, as well as by photolysis, as appropriate stepwise or simultaneously, it being possible also to use enzymatic methods. The removal of the protecting groups is described, for example, in the standard works mentioned for the synthesis of compounds of formula I under Process a) in the section relating to protecting groups; cleavage is effected analogously to the removal of protecting groups described for compounds of formula I in process f).

Additional Process Steps

In the additional process steps, which are optional, functional groups of the starting compounds that are not to take part in the reaction may be in unprotected or protected form, for example may be protected by one or more of the protecting groups mentioned above for the preparation of compounds of formula I under Process a). The protecting groups may be retained in the end products or some or all of them may be removed according to one of the methods mentioned for the preparation of compounds of formula I under Process f).

Additional process steps can be carried out as described for the preparation of compounds of formula I, if instead of a compound of formula I a compound of formula I-A is employed. An exception is the lack of the possibility for a direct conversion of compounds of formula I-A into different ones by means of a direct oxidation of $R_5$=hydroxy and $R_6$=hydrogen to $R_5$+$R_6$=oxo.

In addition, the following conversions are possible:

In a compound of formula I-A, a $C_3$–$C_7$alkenyl radical or $C_3$–$C_7$alkynyl radical present in $R_1$ and/or $R_9$, especially an allyl radical, for example in allyloxycarbonyl, can be hydrogenated, for example by catalytic hydrogenation in the presence of metal, such as platinum or especially palladium, catalysts, which are free or, preferably, on a carrier, such as carbon or silica gel, especially in the presence of palladium on activated carbon, preferably in a polar solvent, such as a lower alkanol, for example methanol or ethanol, at temperatures of from 0° to 80° C., especially from 0° to 40° C., and under a hydrogen pressure of a maximum of 10 atm, preferably under approximately normal pressure.

Starting materials for the preparation of compounds of formula I-A:

The present invention relates also to novel starting materials and/or intermediates and to processes for their preparation. The starting materials used and the reaction conditions selected are preferably those that result in the compounds described as being preferred. Attention is drawn to the fact that in the case of starting compounds of formula V-A, VII-A and IX-A, the acyl radical of acyloxy $R_5$ may migrate to a nitrogen atom; Processes ii), iii) and iv) above should therefore be regarded as being subject to that reservation. Processes i), v) and vi) and their starting compounds are preferred, especially Processes i) and vi).

In the preparation of all starting materials free functional groups that are not to participate in the reaction in question may be in unprotected or protected form, for example they may be protected by the protecting groups mentioned above for the preparation of compounds of formula I under Process a). Those protecting groups may be freed at appropriate times by the reaction described for the preparation of compounds of formula I under Process f). The protecting groups are introduced, for example, as in the description of Process a) for the preparation of compounds of formula I.

The hydroxy compounds of formula I used as starting materials, and other starting compounds, are obtained analogously to the processes a) to f) described above for the synthesis of compounds of formula I, using starting materials with the substituents as defined for compounds of formula I-A. Preferably, instead of compounds of formula IV there are used those of formula IV-A

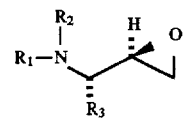

(IV-A)

wherein each of the radicals is as defined above, free functional groups, with the exception of those participating in the reaction, being if necessary in protected form. When the compound of formula IV-A is used, the preferred starting materials of formula Ib are obtained, as mentioned under Process i). The starting materials of formulae IV-A are known or, if novel, can be prepared according to processes known per se, for example from suitable amino acids or analogues thereof, for example those having one of the mentioned side chains $R_3$.

The compounds of formula III (with substituents as defined for formula I-A) can be obtained, for example, from corresponding compounds of formulae XV, XVI and XVII, as described above.

The corresponding carbonyl compounds suitable for the introduction of $R_7$ that are used for the preparation of compounds of formula XVI are known aldehydes or ketones that can be prepared by processes known per se or are commercially available, the reactive carbonyl group of which is, after reaction with compounds of formula XV and subsequent reduction, a component of one of the mentioned radicals $R_7$, preferably lower alkane aldehydes, cyclohexyl-lower alkane aldehydes or phenyl-lower alkane aldehydes.

The compounds of formula IV (with substituent definitions corresponding to those for formula I-A) can be obtained, for example, from the corresponding compounds of formula XVIII, as described above.

The reduction of amino acids of formula XVIII or XVIII A to the corresponding aldehydes XIX and XIX A is carried out, for example, by reduction to the corresponding alcohols and subsequent oxidation to the mentioned aldehydes.

The reduction to the alcohols is carried out, for example, by hydrogenation of the amino acid halides or other activated carboxylic acid derivatives (for example with activated hydroxy analogously to compounds of formula XXIIa, as defined under Process i)) under the conditions mentioned for the hydrogenation of hydrazones obtained from compounds of formula XVI, or with complex hydrides, such as sodium borohydride. The subsequent oxidation of the resulting alcohols is preferably carried out using oxidising agents that allow the aldehydes of formula XIX or XIX A to be obtained selectively (i.e. without further oxidation of the aldehydes to the carboxylic acids), for example using potassium ferrate ($K_2FeO_4$) in aqueous solvents or manganese dioxide in organic solvents, or organic chromic acid derivatives, such as pyridinium dichromate or tert-butyl chromate, in inert organic solvents, for example chlorinated hydrocarbons, such as methylene chloride or chloroform, in the presence or absence of basic amines, for example tri-lower alkylamines, such as triethylamine, at temperatures of from –50° to 100° C., preferably at from –10° to 50° C., for example as described in European Patent Application EP-A-0 236 734, or especially by oxidation of the hydroxy group with a sulfoxide, such as dimethyl sulfoxide, in the presence of a reagent that activates the hydroxy group, for example a carboxylic acid chloride, such as oxalyl chloride, in an inert solvent, for example a chlorinated hydrocarbon, such as dichloromethane, and/or an acyclic or cyclic ether, such as tetrahydrofuran, at from –80° to 0° C., for example from –78° to –50° C.

The preferred starting material of formula Ib in Process i), or a salt thereof, is prepared, for example, by adding a hydrazine derivative of the above-defined formula XVI (with substituent definitions corresponding to those for compounds of formula I) to an epoxide of the above-defined formula IV-A, and if desired converting a compound of formula Ib obtainable in accordance with the above process having at least one salt-forming group into its salt or converting an obtainable salt into the free compound or into a different salt and/or where appropriate separating obtainable isomeric mixtures and/or removing protecting groups present in a compound of formula Ib and/or converting a compound of formula Ib according to the invention into a different compound of formula Ib according to the invention.

The preparation and conversion of salts, the separation of isomeric mixtures, the removal of protecting groups and the conversion of compounds of formula Ib are effected analogously to the processes described above for compounds of formula I.

The starting materials of Processes i), iii) and iv) can be prepared in accordance with processes known per se; for example, analogously to Process i), if necessary with the use and removal of protecting groups, compounds of formula V-A can be prepared from corresponding hydrazine derivatives of formula III wherein $R_9$ is hydrogen and the remaining radicals are as defined for compounds of formula V-A, and epoxides of formula IV wherein the radicals are as defined for compounds of formula V-A, with subsequent acylation of the resulting compound of formula V-A'

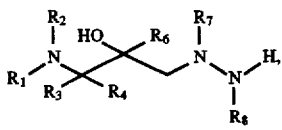

(V-A')

especially of formula V-A"

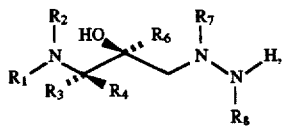

(V-A")

wherein the radicals are as defined for compounds of formula I-A and wherein instead of the radical $R_5$ present in a compound of formula V-A there is a free hydroxy group, with a carboxylic acid of formula XXII or an activated carboxylic acid derivative thereof, as described under Process i) (yields starting material of formula V-A for Process ii)); compounds of formula VII-A can be prepared from hydrazine derivatives of formula III wherein the radicals are as defined for compounds of formula VII-A, and corresponding epoxides of formula IV wherein $R_1$ is hydrogen and the remaining radicals are as defined for compounds of formula VII-A, with subsequent acylation of the resulting compound of formula VII-A'

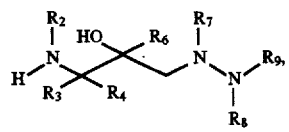

(VII-A')

especially of formula VII-A"

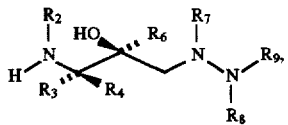

(VII-A")

wherein the radicals are as defined for compounds of formula I-A and instead of the radical $R_5$ present in a compound of formula VII-A there is a free hydroxy group, with a carboxylic acid of formula XXII or an activated carboxylic acid derivative thereof, as described under Process i) (yields starting material of formula VII-A for Process iii)); and compounds of formula IX-A can be prepared from hydrazine derivatives of formula III wherein $R_9$ is hydrogen and the remaining radicals are as defined for compounds of formula IX-A, and epoxides of formula IV wherein $R_1$ is hydrogen and the remaining radicals are as defined for compounds of formula IX-A, with subsequent acylation of the resulting compound of formula IX-A'

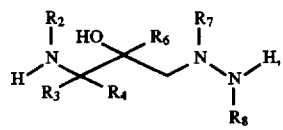

(IX-A')

especially of formula IX-A"

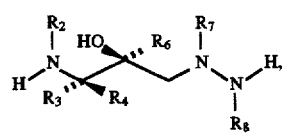

(IX-A")

wherein the radicals are as defined for compounds of formula I-A and wherein instead of the radical $R_5$ present in a compound of formula IX-A there is a free hydroxy group, with a carboxylic acid of formula XXII or an activated carboxylic acid derivative thereof, as described under Process i) (yields starting material of formula IX-A for Process iv)). In the mentioned preparation processes for the preparation of the preferred compounds of formula V-A (via V-A"), VII-A (via VII-A") and IX-A (via IX-A") wherein the carbon atoms carrying $R_3$ and $R_5$ are both in the (S)-configuration, preference is given to the use of the epoxides of formula IV-A.

Compounds of formula I-A' wherein the substituents are as defined above, can be prepared, for example, from a compound of formula III-A

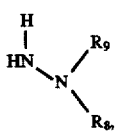

(III-A)

wherein the radicals are as defined for compounds of formula I-A, by reaction with a compound of formula IV, especially IV-A (which results in the preferred compounds of formula I-A' wherein the carbon atoms carrying $R_3$ and $R_5$ are both in the (S)-configuration), as described for the reaction of compounds of formula III with those of formula IV or IV-A, and subsequent acylation of the resulting compound of formula I-A"

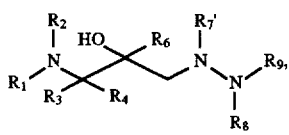

(I-A'')

especially of formula I-A''',

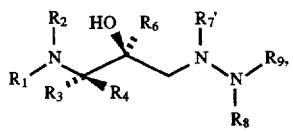

(I-A''')

wherein the radicals are as defined for compounds of formula I-A', with a compound of formula XXII or an activated carboxylic acid derivative thereof (preparation of the radical acyloxy $R_5$) under reaction conditions analogous to those described under Process i) (in that case there is to be used instead of the compound of formula I an analogous compound containing $R_7$ instead of $R_7'$; as in that case, any functional groups present that are not intended to participate in the reaction are where necessary in protected form and can be freed after the reaction.

Of the starting compounds of formula I or Ib, the compound of formula $R_4$ is hydrogen, $R_6$ is hydrogen, $R_7$ is phenylmethyl, 4-lower alkoxyphenylmethyl or cyclohexylmethyl, $R_8$ is hydrogen and $R_9$ is lower alkoxycarbonyl-(L)-valyl, lower alkoxy-lower alkoxy-lower alkoxycarbonyl(L)-valyl, phenyl-lower alkoxycarbonyl-(L)-valyl, lower alkanoyl-(L)-valyl, benzylaminocarbonyl or $C_3$-$C_7$alkenyloxycarbonyl, or also lower alkoxycarbonyl, or pharmaceutically acceptable salts thereof, more especially to one of those compounds of formula I selected from the compounds having the names:

1-[2(S)-hydroxy-3(S)-(N-(quinoline-2-carbonyl)-(L)-asparaginyl)amino-4-phenyl-butyl]-1-[cyclohexylmethyl]-2-[N-(benzyloxycarbonyl)-(L)-valyl]hydrazine (especially preferred), 1-[2(S)-hydroxy-3(S)-(N-(quinoline-2-carbonyl)-(L)-asparaginyl)amino-4-phenyl-butyl]-1-[cyclohexylmethyl]-2-[tert-butoxycarbonyl]hydrazine, 1-[2(S)-hydroxy3(S)-(N-(quinoline-2-carbonyl)-(L)-asparaginyl)amino-4-phenyl-butyl]-1-[cyclohexylmethyl]-2-[N-methoxy-carbonyl-(L)-valyl]hydrazine (especially preferred), (II''')

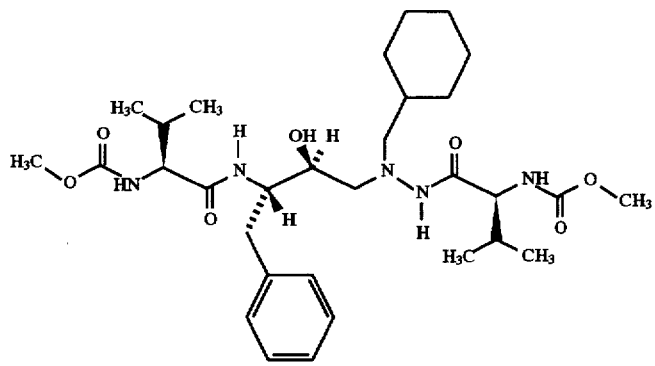

is especially preferred. On the one hand, that compound is a preferred intermediate in Process i), but on the other it is itself a preferred compound according to the invention, since it has good pharmacological activity, especially on the basis of its unexpectedly good activity in the cell test described above, which indicates that it will be highly effective in vivo.

Further compounds of formula I according to the invention which have advantageous pharmacological properties (especially those described for compounds of formula I and/or, more preferentially, of formula I-A) and to which the present Application therefore preferably relates are given below (the present invention also relates to the corresponding processes for the preparation of those compounds, to pharmaceutical compositions comprising those compounds, to those compounds for use in a therapeutic method for the treatment of the human or animal body and to the use of those compounds in the therapeutic treatment of the human or animal body or in the preparation of pharmaceutical compositions, in each case analogously to the corresponding aspects of the invention relating to compounds of formula I; the same applies to compounds of formula Ic):

Preference is given to compounds of formula I wherein $R_1$ is quinolin-2-yl-carbonyl-(L)-asparaginyl, $R_2$ is hydrogen, $R_3$ is phenylmethyl, 4-lower alkoxyphenylmethyl or 4-benzyloxyphenylmethyl, 1-[2(S)-hydroxy-3(S)-(N-(quinoline-2-carbonyl)-(L)-asparaginyl)amino-4-phenyl-butyl]-1-[cyclohexylmethyl]-2-[3,3-dimethylbutyryl]hydrazine, 1-[2(S)-hydroxy-3(S)-(N-(quinoline-2-carbonyl)-(L)-asparaginyl)amino-4-phenyl-butyl]-1-[cyclohexylmethyl]-2-[tert-butylamino-carbonyl]hydrazine, 1-[2(S)-hydroxy-3(S)-(N-(quinoline-2-carbonyl)-(L)-asparaginyl)amino-4-phenyl-butyl]-1-[cyclohexylmethyl]-2-[benzylamino-carbonyl]hydrazine, 1-[2(S)-hydroxy-3(S)-(N-(quinoline-2-carbonyl)-(L)-asparaginyl)amino-4-phenyl-butyl]-1-[benzyl]-2-[N-methoxy-carbonyl)-(L)-valyl]hydrazine, 1-2(S)-hydroxy-3(S)-(N-(quinoline-2-carbonyl)-(L)-asparaginyl)amino-4-phenyl-butyl]-1-[benzyl]-2-[N-ethoxy-carbonyl)-(L)-valyl]hydrazine (especially preferred), 1-[2(S)-hydroxy-3(S)-(N-(quinoline-2-carbonyl)-(L)-asparaginyl)amino-4-phenyl-butyl]-1-[benzyl]-2-[N-benzyloxy-carbonyl)-(L)-valyl]hydrazine, 1-[2(S)-hydroxy-3(S)-(N-(quinoline-2-carbonyl)-(L)-asparaginyl)amino-4-phenyl-butyl]-1-[benzyl]-2-[N-allyloxy-carbonyl)-(L)-valyl]hydrazine, 1-[2(S)-hydroxy-3(S)-(N-(quinoline-$^2$-carbonyl)-(L)-asparaginyl)amino-4-phenyl-butyl]-1-[4-methoxyphenylmethyl]-2-[N-methoxy-carbonyl)-(L)- valyl]hydrazine (especially preferred), 1-[2(S)-hydroxy-3 (S)-(N-(quinoline-2-carbonyl)-(L)-asparaginyl)amino-4-phenyl-butyl]-1-[4-methoxyphenylmethyl]-2-[N-benzyloxy-carbonyl)-(L)-valyl]hydrazine (especially preferred), 1-[2(S)-hydroxy-3(S)-(N-(quinoline-2-carbonyl)-(L)-asparaginyl)amino-4-phenyl-butyl]-1-[4-methoxyphenylmethyl]-2-[N-allyloxy-carbonyl)-(L)-valyl]hydrazine (especially preferred), 1-[2(S)-hydroxy-3(S)-(N-(quinoline-2-carbonyl)-(L)-asparaginyl)amino-4-(4-methoxyphenyl)-butyl]-1-[benzyl]-2-[N-methoxy-carbonyl)-(L)-valyl]hydrazine, 1-[2(S)-hydroxy-3(S)-(N-(quinoline-2-carbonyl)-(L)-asparaginyl)amino-4-(4-methoxyphenyl)-butyl]-1-[benzyl]-2-[N-benzyloxy-carbonyl)-(L)-valyl]hydrazine, 1-[2(S)-hydroxy-3(S)-(N-(quinoline-2-carbonyl)-(L)-asparaginyl)amino-4-(4-benzyloxyphenyl)-butyl]-1-[benzyl]-2-[N-methoxy-carbonyl)-(L)-valyl]hydrazine, 1-[2(S)-hydroxy-3(S)-(N-(quinoline-2-carbonyl)-(L)-asparaginyl)amino-4-(4-benzyloxyphenyl)-butyl]-1-[benzyl]-2-[N-allyloxy-carbonyl)-(L)-valyl]hydrazine, 1-[2(S)-hydroxy-3(S)-(N-(quinoline-2-carbonyl)-(L)-asparaginyl)amino-4-phenyl-butyl]-1-[4-methoxyphenylmethyl]-2-[N-methoxy-carbonyl)-(L)-valyl]hydrazine, 1-[2(S)-hydroxy-3(S)-(N-(quinoline-2-carbonyl)-(L)-asparaginyl)amino-4-phenyl-butyl]-1-[4-methoxyphenylmethyl]-2-[N-allyloxy-carbonyl)-(L)-valyl]hydrazine, 1-[2(S)-hydroxy-3(S)-(N-(quinoline-2-carbonyl)-(L)-asparaginyl)amino-4-phenyl-butyl]-1-[4-benzyloxyphenylmethyl]-2-[N-methoxy-carbonyl)-(L)-valyl]hydrazine, 1-[2(S)-hydroxy-3(S)-(N-(quinoline-2-carbonyl)-(L)-asparaginyl)amino-4-phenyl-butyl]-1-[2(S)-hydroxy-3(S)-(N-quinoline-2-carbonyl)-(L)-asparaginyl)amino-4-phenylbutyl-1-[phenylmethyl]-2-[N-(2-(2-methoxyethoxy)ethoxycarbonyl)-(L)-valyl]hydrazine (especially preferred), 1-[2(S)-hydroxy-3(S)-(N-quinoline-2-carbonyl)-(L)-asparaginyl)amino-4-phenylbutyl-1-[4-methoxyphenylmethyl]-2-[tert-butoxy-carbonyl]hydrazine, and 1-[2(S)-hydroxy-3(S)-(N-quinoline-2-carbonyl)-(L)-asparaginyl)amino-4-phenylbutyl- 1-[4-methoxyphenylmethyl]-2-[N-(ethoxycarbonyl)-(L)-valyl]hydrazine, or a pharmaceutically acceptable salt of each of those compounds.

Preference is given also to compounds of formula I wherein $R_1$ is lower alkenyloxycarbonyl-(L)-valyl, the radicals $R_2$, $R_4$, $R_6$ and $R_8$ are each hydrogen, $R_3$ is phenylmethyl, $R_7$ is cyclohexylmethyl and $R_9$ is N-lower alkenyloxycarbonyl-(L)-valyl, or pharmaceutically acceptable salts thereof, especially a compound having the name 1-[2(S)-hydroxy-3(S)-(N-allyloxycarbonyl-(L)-valyl)amino-4-phenylbutyl]-1-[cyclohexylmethyl]-2-[N-allyloxycarbonyl-(L)-valyl]hydrazine, or a pharmaceutically acceptable salt thereof.

Preference is given also to compounds of formula I wherein $R_1$ is lower alkoxy-lower alkoxy-lower alkoxycarbonyl-(L)-valyl, the radicals $R_2$, $R_4$, $R_6$ and $R_8$ are each hydrogen, $R_3$ is phenylmethyl, $R_7$ is cyclohexylmethyl and $R_9$ is lower alkoxy-lower alkoxy-lower alkoxycarbonyl-(L)-valyl, or pharmaceutically acceptable salts thereof, especially a compound having the name 1-[2(S)-hydroxy-3(S)-(N-(2-(2-methoxyethoxy)ethoxy)carbonyl-(L)-valyl)amino-4-phenylbutyl]-1-[cyclohexylmethyl]-2-[N-(2-(2-methoxyethoxy)ethoxy)carbonyl-(L)-valyl]hydrazine (especially preferred), or a pharmaceutically acceptable salt thereof.

Preference is given also to compounds of formula I wherein $R_1$ is lower alkoxy-lower alkoxy-lower alkanoyl-(L)-valyl, the radicals $R_2$, $R_4$, $R_6$ and $R_8$ are each hydrogen, $R_3$ is phenylmethyl, $R_7$ is cyclohexylmethyl and $R_9$ is lower alkoxy-lower alkoxy-lower alkanoyl-(L)-valyl, or pharmaceutically acceptable salts thereof, especially a compound having the name 1-[2(S)-hydroxy-3(S)-(N-(2-methoxyethoxy)acetyl-(L)-valyl)amino-4-phenylbutyl]-1-[cyclohexylmethyl]-2-[N-(2-methoxyethoxy)acetyl-(L)-valyl]hydrazine, or a pharmaceutically acceptable salt thereof.

Preference is given also to compounds of formula I wherein $R_1$ and $R_9$ are each independently of the other acetyl-(L)-valyl, methoxycarbonyl-(L)-valyl, ethoxycarbonyl-(L)-valyl, dimethylaminocarbonyl-(L)-valyl, (2-methoxyethyl)aminocarbonyl-(L)-valyl, N-(2-morpholin-4-yl-ethyl)aminocarbonyl-(L)-valyl or N-(2-morpholin-4-yl-ethyl)-N-methyl-aminocarbonyl-(L)-valyl, the radicals $R_2$, $R_4$, $R_6$ and $R_8$ are each hydrogen, $R_3$ is phenylmethyl, and $R_7$ is thien-2-ylmethyl or 2,3,5,6-tetrahydropyran-4-ylmethyl, or pharmaceutically acceptable. salts thereof, especially a single compound or several compounds selected from: 1-[2(S)-hydroxy-3(S)-(N-acetyl-(L)-valyl)amino-4-phenylbutyl]-1-[thien-2-ylmethyl]-2-[N-acetyl-(L)-valyl]hydrazine;

1-[2(S)-hydroxy-3(S)-(N-methoxycarbonyl-(L)-valyl) amino-4-phenylbutyl]-1-[thien-2-yl-methyl]-2-[N-methoxycarbonyl-(L)-valyl]hydrazine;

1-[2(S)-hydroxy-3(S)-(N-ethoxycarbonyl-(L)-valyl)amino-4-phenylbutyl]-1-[thien-2-yl-methyl]-2-[N-ethoxycarbonyl-(L)-valyl]hydrazine;

1-[2(S)-hydroxy-3(S)-(N-(N,N-dimethylaminocarbonyl)-(L)-valyl)amino-4-phenylbutyl]-1-[thien-2-ylmethyl]-2-[N-(N,N-dimethylaminocarbonyl)-(L)-valyl]hydrazine;

1-[2(S)-hydroxy-3(S)-(N-(N-(2-methoxyethyl) aminocarbonyl)-(L)-valyl)amino-4-phenyl-butyl]-1-[thien-2-ylmethyl]-2-[N-(N-(2-methoxyethyl) aminocarbonyl)-(L)-valyl]hydrazine;

1-[2(S)- hydroxy-3(S)-(N-(N-(2-(morpholin-4-yl)ethyl) aminocarbonyl)-(L)-valyl)amino-4-phenylbutyl]-1-[thien-2-ylmethyl]-2-[N-(N-(2-(morpholin-4-yl)ethyl) aminocarbonyl)-(L)-valyl]hydrazine;

1-[2(S)-hydroxy-3(S)-(N-(N-(2-(morpholin-4-yl)ethyl)-N-methyl-aminocarbonyl)-(L)-valyl)amino-4-phenylbutyl]-1-[thien-2-ylmethyl]-2-[N-(N-(2-(morpholin-4-yl)ethyl)-N-methylaminocarbonyl)-(L)-valyl]hydrazine;

1-[2(S)-hydroxy-3(S)-(N-acetyl-(L)-valyl)amino-4-phenylbutyl]-1-[2,3,5,6-tetrahydropyran4-ylmethyl]-2-[N-acetyl-(L)-valyl]hydrazine;

1-[2(S)-hydroxy-3(S)-(N-methoxycarbonyl-(L)-valyl) amino-4-phenylbutyl]-1-[2,3,5,6-tetrahydropyran-4-ylmethyl]-2-[N-methoxycarbonyl-(L)-valyl]hydrazine;

1-[2(S)-hydroxy-3(S)-(N-ethoxycarbonyl-(L)-valyl)amino-4-phenylbutyl]-1-[2,3,5,6-tetrahydropyran-4-ylmethyl]-2-[N-ethoxycarbonyl-(L)-valyl]hydrazine;

1-[2(S)-hydroxy-3(S)-(N-(N,N-dimethylaminocarbonyl)-(L)-valyl)amino-4-phenylbutyl]-1-[2,3,5,6-tetrahydropyran-4-ylmethyl]-2-[N-(N,N-dimethylaminocarbonyl)-(L)-valyl]hydrazine;

1-[2(S)-hydroxy-3(S)-(N-(N-(2-methoxyethyl) aminocarbonyl)-(L)-valyl)amino-4-phenylbutyl]-1-[2,3, 5,6-tetrahydropyran-4-ylmethyl]-2-[N-(N-(2-methoxyethyl)aminocarbonyl)-(L)-valyl]hydrazine;

1-[2(S)-hydroxy-3(S)-(N-(N-(2-(morpholin-4-yl)ethyl) aminocarbonyl)-(L)-valyl)amino-4-phenylbutyl]-1-[2,3, 5,6-tetrahydropyran-4-ylmethyl]-2-[N-(N-(2-(morpholin-4-yl)ethyl)aminocarbonyl)-(L)-valyl]hydrazine and 1-[2(S)-hydroxy-3(S)-(N-(N-(2-(morpholin-4-yl)ethyl)-
N-methyl-aminocarbonyl)-(L)-valyl)amino-4-
phenylbutyl]-1-[2,3,5,6-tetrahydropyran-4-ylmethyl]-2-
[N-(N-(2-(morpholin-4-yl)ethyl)-N-
methylaminocarbonyl)-(L)-valyl]hydrazine,
or a pharmaceutically acceptable salt thereof.

Preference is given also to compounds of formula I wherein $R_1$ and $R_9$ are each independently of the other acetyl-(L)-valyl, methoxycarbonyl-(L)-valyl, ethoxycarbonyl-(L)-valyl, dimethylaminocarbonyl-(L)-valyl, (2-methoxyethyl)aminocarbonyl-(L)-valyl, N-(2-morpholin-4-yl-ethyl)aminocarbonyl-(L)-valyl or N-(2-morpholin-4-yl-ethyl)-N-methyl-aminocarbonyl-(L)-valyl, the radicals $R_2$, $R_4$, $R_6$ and $R_8$ are each hydrogen, $R_3$ is phenylmethyl, and $R_7$ is 4-hydroxyphenylmethyl, 4-methoxyphenylmethyl, 4-isobutoxyphenylmethyl, 4-benzyloxyphenylmethyl, 3,4-dimethoxyphenylmethyl, methylene-4,5-dioxyphenylmethyl, 4-(2-methoxyethoxy)phenylmethyl or 4-biphenylylmethyl, or pharmaceutically acceptable salts thereof, especially a single compound or several compounds selected from the compounds having the names:

1-[2(S)-hydroxy-3(S)-(N-acetyl-(L)-valyl)amino-4-phenylbutyl]-1-[4-hydroxyphenylmethyl]-2-[N-acetyl-(L)-valyl]hydrazine;

1-[2(S)-hydroxy-3(S)-(N-methoxycarbonyl-(L)-valyl)amino-4-phenylbutyl]-1-[4-hydroxyphenylmethyl]-2-[N-methoxycarbonyl-(L)-valyl]hydrazine (especially preferred);

1-[2(S)-hydroxy-3(S)-(N-ethoxycarbonyl-(L)-valyl)amino-4-phenylbutyl]-1-[4-hydroxyphenylmethyl]-2-[N-ethoxycarbonyl-(L)-valyl]hydrazine;

1-[2(S)-hydroxy-3(S)-(N-(N,N-dimethylaminocarbonyl)-(L)-valyl)amino-4-phenylbutyl]-1-[4-hydroxyphenylmethyl]-2-[N-(N,N-dimethylaminocarbonyl)-(L)-valyl]hydrazine;

1-[2(S)-hydroxy-3(S)-(N-(N-(2-methoxyethyl)aminocarbonyl)-(L)-valyl)amino-4-phenylbutyl]-1-[4-hydroxyphenylmethyl]-2-[N-(N-(2-methoxyethyl)aminocarbonyl)-(L)-valyl]hydrazine;

1-[2(S)-hydroxy-3(S)-(N-(N-(2-(morpholin-4-yl)ethyl)aminocarbonyl)-(L)-valyl)amino-4-phenylbutyl]-1-[4-hydroxyphenylmethyl]-2-[N-(N-(2-(morpholin-4-yl)ethyl)aminocarbonyl)-(L)-valyl]hydrazine;

1-[2(S)-hydroxy-3(S)-(N-(N-(2-(morpholin-4-yl)ethyl)-N-methyl-aminocarbonyl)-(L)-valyl)amino-4-phenylbutyl]-1-[4-hydroxyphenylmethyl]-2-[N-(N-(2-(morpholin-4-yl)ethyl)-N-methylaminocarbonyl)-(L)-valyl]hydrazine;

1-[2(S)-hydroxy-3(S)-(N-acetyl-(L)-valyl)amino-4-phenylbutyl]-1-[4-methoxyphenylmethyl]-2-[N-acetyl-(L)-valyl]hydrazine (especially preferred);

1-[2(S)-hydroxy-3(S)-(N-methoxycarbonyl-(L)-valyl)amino-4-phenylbutyl]-1-[4-methoxyphenylmethyl]-2-[N-methoxycarbonyl-(L)-valyl]hydrazine (especially preferred);

1-[2(S)-hydroxy-3(S)-(N-ethoxycarbonyl-(L)-valyl)amino-4-phenylbutyl]-1-[4-methoxyphenylmethyl]-2-[N-ethoxycarbonyl-(L)-valyl]hydrazine (especially preferred);

1-[2(S)-hydroxy-3(S)-(N-(N,N-dimethylaminocarbonyl)-(L)-valyl)amino-4-phenylbutyl]-1-[4-methoxyphenylmethyl]-2-[N-(N,N-dimethylaminocarbonyl)-(L)-valyl]hydrazine (especially preferred);

1-[2(S)-hydroxy-3(S)-(N-(N-(2-methoxyethyl)aminocarbonyl)-(L)-valyl)amino-4-phenylbutyl]-1-[4-methoxyphenylmethyl]-2-[N-(N-(2-methoxyethyl)aminocarbonyl)-(L)-valyl]hydrazine;

1-[2(S)-hydroxy-3(S)-(N-(N-(2-(morpholin-4-yl)ethyl)aminocarbonyl)-(L)-valyl)amino-4-phenylbutyl]-1-[4-methoxyphenylmethyl]-2-[N-(N-(2-(morpholin-4-yl)ethyl)aminocarbonyl)-(L)-valyl]hydrazine;

1-[2(S)-hydroxy-3(S)-(N-(N-(2-(morpholin-4-yl)ethyl)-N-methyl-aminocarbonyl)-(L)-valyl)amino-4-phenylbutyl]-1-[4-methoxyphenylmethyl]-2-[N-(N-(2-(morpholin-4-yl)ethyl)-N-methylaminocarbonyl)-(L)-valyl]hydrazine;

1-[2(S)-hydroxy-3(S)-(N-acetyl-(L)-valyl)amino-4-phenylbutyl]-1-[4-benzyloxyphenylmethyl]-2-[N-acetyl-(L)-valyl]hydrazine;

1-[2(S)-hydroxy-3(S)-(N-methoxycarbonyl-(L)-valyl)amino-4-phenylbutyl]-1-[4-benzyloxyphenylmethyl]-2-[N-methoxycarbonyl-(L)-valyl]hydrazine;

1-[2(S)-hydroxy-3(S)-(N-ethoxycarbonyl-(L)-valyl)amino-4-phenylbutyl]-1-[4-benzyloxyphenylmethyl]-2-[N-ethoxycarbonyl-(L)-valyl]hydrazine;

1-[2(S)-hydroxy-3(S)-(N-(N,N-dimethylaminocarbonyl)-(L)-valyl)amino-4-phenylbutyl]-1-[4-benzyloxyphenylmethyl]-2-[N-(N,N-dimethylaminocarbonyl)-(L)-valyl]hydrazine;

1-[2(S)-hydroxy-3(S)-(N-(N-(2-methoxyethyl)aminocarbonyl)-(L)-valyl)amino-4-phenylbutyl]-1-[4-benzyloxyphenylmethyl]-2-[N-(N-(2-methoxyethyl)aminocarbonyl)(L)-valyl]hydrazine;

1-[2(S)-hydroxy-3(S)-(N-(N-(2-(morpholin-4-yl)ethyl)aminocarbonyl)-(L)-valyl)amino-4-phenylbutyl]-1-[4-benzyloxyphenylmethyl]-2-[N-(N-(2-(morpholin-4-yl)ethyl)aminocarbonyl)-(L)-valyl]hydrazine;

1-[2(S)-hydroxy-3(S)-(N-(N-(2-(morpholin-4-yl)ethyl)-N-methyl-aminocarbonyl)-(L)-valyl)amino-4-phenylbutyl]-1-[4-benzyloxyphenylmethyl]-2-[N-(N-(2-(morpholin-4-yl)ethyl)-N-methylaminocarbonyl)-(L)-valyl]hydrazine;

1-[2(S)-hydroxy-3(S)-(N-acetyl-(L)-valyl)amino-4-phenylbutyl]-1-[4-(3,4-dimethoxybenzyl)oxyphenylmethyl]-2-[N-acetyl-(L)-valyl]hydrazine;

1-[2(S)-hydroxy-3(S)-(N-methoxycarbonyl-(L)-valyl)amino-4-phenylbutyl]-1-[4-(3,4-dimethoxybenzyl)oxyphenylmethyl]-2-[N-methoxycarbonyl-(L)-valyl]hydrazine;

1-[2(S)-hydroxy-3(S)-(N-ethoxycarbonyl-(L)-valyl)amino-4-phenylbutyl]-1-[4-(3,4-dimethoxybenzyl)oxyphenylmethyl]-2-[N-ethoxycarbonyl-(L)-valyl]hydrazine;

1-[2(S)-hydroxy-3(S)-(N-(N,N-dimethylaminocarbonyl)-(L)-valyl)amino-4-phenylbutyl]-1-[4-(3,4-dimethoxybenzyl)oxyphenylmethyl]-2-[N-(N,N-dimethylaminocarbonyl)(L)-valyl]hydrazine;

1-[2(S)-hydroxy-3(S)-(N-(N-(2-methoxyethyl)aminocarbonyl)-(L)-valyl)amino-4-phenylbutyl]-1-[4-(3,4-dimethoxybenzyl)oxyphenylmethyl]-2-[N-(N-(2-methoxyethyl)aminocarbonyl)-(L)-valyl]hydrazine;

1-[2(S)-hydroxy-3(S)-(N-(N-(2-(morpholin-4-yl)ethyl)aminocarbonyl)-(L)-valyl)amino-4-phenylbutyl]-1-[4-(3,4-dimethoxybenzyl)oxyphenylmethyl]-2-[N-(N-(2-(morpholin-4-yl)ethyl)aminocarbonyl)-(L)-valyl]hydrazine;

1-[2(S)-hydroxy-3(S)-(N-(N-(2-(morpholin-4-yl)ethyl)-N-methyl-aminocarbonyl)-(L)-valyl)amino-4-phenylbutyl]-1-[4-(3,4-dimethoxybenzyl)oxyphenylmethyl]-2-[N-(N-(2-(morpholin-4-yl)ethyl)-N-methylaminocarbonyl)-(L)-valyl]hydrazine;

1-[2(S)-hydroxy-3(S)-(N-acetyl-(L)-valyl)amino-4-phenylbutyl]-1-[4-isobutoxyphenylmethyl]-2-[N-acetyl-(L)-valyl]hydrazine;

1-[2(S)-hydroxy-3(S)-(N-methoxycarbonyl-(L)-valyl) amino-4-phenylbutyl]-1-[4-isobutoxyphenylmethyl]-2-[N-methoxycarbonyl-(L)-valyl]hydrazine;

1-[2(S)-hydroxy-3(S)-(N-ethoxycarbonyl-(L)-valyl)amino-4-phenylbutyl]-1-[4-isobutoxyphenylmethyl]-2-[N-ethoxycarbonyl-(L)-valyl]hydrazine;

1-[2(S)-hydroxy-3(S)-(N-(N,N-dimethylaminocarbonyl)-(L)-valyl)amino-4-phenylbutyl]-1-[4-isobutoxyphenylmethyl]-2-[N-(N,N-dimethylaminocarbonyl)-(L)-valyl]hydrazine;

1-[2(S)-hydroxy-3(S)-(N-(N-(2-methoxyethyl) aminocarbonyl)-(L)-valyl)amino-4-phenylbutyl]-1-[4-isobutoxyphenylmethyl]-2-[N-(N-(2-methoxyethyl) aminocarbonyl)-(L)-valyl]-hydrazine;

1-[2(S)-hydroxy-3(S)-(N-(N-(2-(morpholin-4-yl)ethyl) aminocarbonyl)-(L)-valyl)amino-4-phenylbutyl]-1-[4-isobutoxyphenylmethyl]-2-[N-(N-(2-(morpholin-4-yl) ethyl)aminocarbonyl)-(L)-valyl]hydrazine;

1-[2(S)-hydroxy-3(S)-(N-(N-(2-(morpholin-4-yl)ethyl)-N-methyl-aminocarbonyl)-(L)-valyl)amino-4-phenylbutyl]-1-[4-isobutoxyphenylmethyl]-2-[N-(N-(2-(morpholin-4-yl)ethyl)-N-methylaminocarbonyl)-(L)-valyl]hydrazine;

1-[2(S)-hydroxy-3(S)-(N-acetyl-(L)-valyl)amino-4-phenylbutyl]-1-[4-(2-methoxyethoxy)phenylmethyl]-2-[N-acetyl-(L)-valyl]hydrazine;

1-[2(S)-hydroxy-3(S)-(N-methoxycarbonyl-(L)-valyl) amino-4-phenylbutyl]-1-[4-(2-methoxyethoxy) phenylmethyl]-2-[N-methoxycarbonyl-(L)-valyl] hydrazine;

1-[2(S)-hydroxy-3(S)-(N-ethoxycarbonyl-(L)-valyl)amino-4-phenylbutyl]-1-[4-(2-methoxyethoxy)phenylmethyl]-2-[N-ethoxycarbonyl-(L)-valyl]hydrazine;

1-[2(S)-hydroxy-3(S)-(N-(N,N-dimethylaminocarbonyl)-(L)-valyl)amino-4-phenylbutyl]-1-[4-(2-methoxyethoxy)phenylmethyl]-2-[N-(N,N-dimethylaminocarbonyl)-(L)-valyl]hydrazine;

1-[2(S)-hydroxy-3(S)-(N-(N-(2-methoxyethyl) aminocarbonyl)-(L)-valyl)amino-4-phenylbutyl]-1-[4-(2-methoxyethoxy)phenylmethyl]-2-[N-(N-(2-methoxyethyl)aminocarbonyl)-(L)-valyl]hydrazine;

1-[2(S)-hydroxy-3(S)-(N-(N-(2-(morpholin-4-yl)ethyl) aminocarbonyl)-(L)-valyl)amino-4-phenylbutyl]-1-[4-(2-methoxyethoxy)phenylmethyl]-2-[N-(N-(2-(morpholin-4-yl)ethyl)aminocarbonyl)-(L)-valyl]hydrazine;

1-[2(S)-hydroxy-3(S)-(N-(N-(2-(morpholin-4-yl)ethyl)-N-methyl-aminocarbonyl)-(L)-valyl)amino-4-phenylbutyl]-1-[4-(2-methoxyethoxy)phenylmethyl]-2-[N-(N-(2-(morpholin-4-yl)ethyl)-N-methylaminocarbonyl)-(L)-valyl]hydrazine;

1-[2(S)-hydroxy-3(S)-(N-acetyl-(L)-valyl)amino-4-phenylbutyl]-1-[methylene-3,4-dioxyphenylmethyl]-2-[N-acetyl-(L)-valyl]hydrazine;

1-[2(S)-hydroxy-3(S)-(N-methoxycarbonyl-(L)-valyl) amino-4-phenylbutyl]-1-[methylene-3,4-dioxyphenylmethyl]-2-[N-methoxycarbonyl-(L)-valyl] hydrazine;

1-[2(S)-hydroxy-3(S)-(N-ethoxycarbonyl-(L)-valyl)amino-4-phenylbutyl]-1-[methylene-3,4-dioxyphenylmethyl]-2-[N-ethoxycarbonyl-(L)-valyl]hydrazine;

1-[2(S)-hydroxy-3(S)-(N-(N,N-dimethylaminocarbonyl)-(L)-valyl)amino-4-phenylbutyl]-1-[methylene-3,4-dioxyphenylmethyl]-2-[N-(N,N-dimethylaminocarbonyl)-(L)-valyl]hydrazine;

1-[2(S)-hydroxy-3(S)-(N-(N-(2-methoxyethyl) aminocarbonyl)-(L)-valyl)amino-4-phenylbutyl]-1-[methylene-3,4-dioxyphenylmethyl]-2-[N-(N-(2-methoxyethyl)aminocarbonyl)-(L)-valyl]hydrazine;

1-[2(S)-hydroxy-3(S)-(N-(N-(2-(morpholin-4-yl)ethyl) aminocarbonyl)-(L)-valyl)amino-4-phenylbutyl]-1-[methylene-3,4-dioxyphenylmethyl]-2-[N-(N-(2-(morpholin-4-yl)ethyl)aminocarbonyl)-(L)-valyl] hydrazine;

1-[2(S)-hydroxy-3(S)-(N-(N-(2-(morpholin-4-yl)ethyl)-N-methyl-aminocarbonyl)-(L)-valyl)amino-4-phenylbutyl]-1-[methylene-3,4-dioxyphenylmethyl]-2-[N-(N-(2-(morpholin-4-yl)ethyl)-N-methylaminocarbonyl)-(L)-valyl]hydrazine;

1-[2(S)-hydroxy-3(S)-(N-acetyl-(L)-valyl)amino-4-phenylbutyl]-1-[3,4-dimethoxyphenylmethyl]-2-[N-acetyl-(L)-valyl]hydrazine;

1-[2(S)-hydroxy-3(S)-(N-methoxycarbonyl-(L)-valyl) amino-4-phenylbutyl]-1-[3,4-dimethoxyphenylmethyl]-2-[N-methoxycarbonyl-(L)-valyl]hydrazine;

1-[2(S)-hydroxy-3(S)-(N-ethoxycarbonyl-(L)-valyl)amino-4-phenylbutyl]-1-[3,4-dimethoxyphenylmethyl]-2-[N-ethoxycarbonyl-(L)-valyl]hydrazine;

1-[2(S)-hydroxy-3(S)-(N-(N,N-dimethylaminocarbonyl)-(L)-valyl)amino-4-phenylbutyl]-1-[3,4-dimethoxyphenylmethyl]-2-[N-(N,N-dimethylaminocarbonyl)-(L)-valyl]hydrazine;

1-[2(S)-hydroxy-3 (S)-(N-(N-(2-methoxyethyl) aminocarbonyl)-(L)-valyl)amino-4-phenylbutyl]-1-[3,4-dimethoxyphenylmethyl]-2-[N-(N-(2-methoxyethyl) aminocarbonyl)-(L)-valyl]hydrazine:

1-[2(S)-hydroxy-3(S)-(N-(N-(2-(morpholin-4-yl)ethyl) aminocarbonyl)-(L)-valyl)amino-4-phenylbutyl]-1-[3,4-dimethoxyphenylmethyl]-2-[N-(N-(2-(morpholin-4-yl) ethyl)aminocarbonyl)-(L)-valyl]hydrazine;

1-[2(S)-hydroxy-3(S)-(N-(N-(2-(morpholin-4-yl)ethyl)-N-methyl-aminocarbonyl)-(L)-valyl)amino-4-phenylbutyl]-1-[3,4-dimethoxyphenylmethyl]-2-[N-(N-(2-(morpholin-4-yl)ethyl)-N-methylaminocarbonyl)-(L)-valyl] hydrazine;

1-[2(S)-hydroxy-3(S)-(N-acetyl-(L)-valyl)amino-4-phenylbutyl]-1-[4-biphenylylmethyl]-2-[N-acetyl-(L)-valyl]hydrazine;

1-[2(S)-hydroxy-3(S)-(N-methoxycarbonyl-(L)-valyl) amino-4-phenylbutyl]-1-[4-biphenylmethyl]-2-N-methoxycarbonyl-(L)-valyl]hydrazine;

1-[2(S)-hydroxy-3(S)-(N-ethoxycarbonyl-(L)-valyl)amino-4-phenylbutyl]-1-[4-biphenylylmethyl]-2-[N-ethoxycarbonyl-(L)-valyl]hydrazine;

1-[2(S)-hydroxy-3(S)-(N-(N,N-dimethylaminocarbonyl)-(L)-valyl)amino-4-phenylbutyl]-1-[4-biphenylylmethyl]-2-[N-(N,N-dimethylaminocarbonyl)-(L)-valyl]hydrazine;

1-[2(S)-hydroxy-3(S)-(N-(N-(2-methoxyethyl) aminocarbonyl)-(L)-valyl)amino-4-phenylbutyl]-1-[4-biphenylylmethyl]-2-[N-(N-(2-methoxyethyl) aminocarbonyl)-(L)-valyl]hydrazine;

1-[2(S)-hydroxy-3(S)-(N-(N-(2-(morpholin-4-yl)ethyl) aminocarbonyl)-(L)-valyl)amino-4-phenylbutyl]-1-[4-biphenylylmethyl]-2-[N-(N-(2-(morpholin-4-yl)ethyl) aminocarbonyl)-(L)-valyl]hydrazine and 1-[2(S)-hydroxy-3(S)-(N-(N-(2-(morpholin-4-yl)ethyl)-N-methyl-aminocarbonyl)-(L)-valyl)amino-4-phenylbutyl]-1-[4-biphenylylmethyl]-2-[N-(N-(2-(morpholin-4-yl) ethyl)N-methylaminocarbonyl)-(L)-valyl]hydrazine, or pharmaceutically acceptable salts thereof.

Preference is given also to compounds of formula I wherein $R_1$ and $R_9$ are each methoxycarbonyl-(L)-valyl, the radicals $R_2$, $R_4$, $R_6$ and $R_8$ are each hydrogen, $R_3$ is phenylmethyl, and $R_7$ is 4-lower alkoxyphenylmethyl or 4-benzyloxyphenylmethyl, or pharmaceutically acceptable salts thereof.

Preference is given finally to the following compounds of formula I:

1-[2(S)-hydroxy-3(S)-(N-ethoxycarbonyl-(L)-valyl)amino-4-phenylbutyl]-1-[cyclohexylmethyl]-2-[N-ethoxycarbonyl-(L)-valyl]hydrazine, 1-[2(S)-hydroxy-3(S)-(N-trifluoroacetyl-(L)-valyl)amino-4-phenylbutyl]-1-[cyclohexylmethyl]-2-[N-trifluoroacetyl-(L)-valyl]hydrazine, 1-[2(S)-hydroxy-3(S)-(N-(methoxy-carbonyl)-(L)-valyl)amino-4-cyclohexyl-butyl]-1-[cyclohexylmethyl]-2-[N-methoxy-carbonyl-(L)-valyl]hydrazine, 1-[2(S)-hydroxy-3(S)-(N-(n-propoxy-carbonyl)-(L)-valyl)amino-4-phenyl-butyl]-1-[cyclohexylmethyl]-2-[N-(n-propyl)oxy-carbonyl-(L)-valyl]hydrazine, 1-[2(R)-hydroxy-3(S)-(N-(methoxy-carbonyl)-(L)-valyl)amino-4-phenyl-butyl]-1-[cyclohexylmethyl]-2-[N-methoxy-carbonyl-(L)-valyl]hydrazine, 1-[2(R)-hydroxy-3(R)-(N-(methoxy-carbonyl)-(L)-valyl)amino-4-phenyl-butyl]-1-[cyclohexylmethyl]-2-[N-methoxy-carbonyl-(L)-valyl]hydrazine, 1-[2(S)-hydroxy-3(S)-(benzyloxy-carbonyl-amino)-4-phenyl-butyl]-1-[phenylmethyl]-2-[N-methoxy-carbonyl-(L)-valyl]hydrazine, 1-[2(S)-hydroxy-3(S)-(N-(methoxy-carbonyl)-(L)-valyl)amino-4-cyclohexyl-butyl]-1-[phenylmethyl]-2-[N-methoxy-carbonyl)-(L)-valyl]hydrazine, 1-[2(S)-hydroxy-3(S)-(N-methoxycarbonyl-(L)-valyl)amino-4-cyclohexyl-butyl]-1-[4-methoxyphenylmethyl]-2-[N-methoxy-carbonyl)-(L)-valyl]hydrazine, 1-[2(S)-hydroxy-3(S)-(N-methoxycarbonyl-(L)-valyl)amino-4-cyclohexyl-butyl]-1-[4-isobutoxyphenylmethyl]-2-[N-methoxy-carbonyl)-(L)-valyl]hydrazine, 1-[2(S)-hydroxy-3(S)-(N-methoxycarbonyl-(L)-valyl)amino-4-cyclohexyl-butyl]-1-[4-ethoxyphenylmethyl]-2-[N-methoxy-carbonyl)-(L)-valyl]hydrazine, 1-[2(S)-hydroxy-3(S)-(N-methoxycarbonyl-(L)-valyl)amino-4-cyclohexyl-butyl]-1-[4-benzyloxyphenylmethyl]-2-[N-methoxy-carbonyl)-(L)-valyl]hydrazine, and/or 1-[2(S)-hydroxy-3(S)-(N-methoxycarbonyl-(L)-valyl)amino-4-phenyl-butyl]-1-[cyclohexylmethyl]-2-[2-pyridylcarbonyl]hydrazine, or a pharmaceutically acceptable salt thereof in each case.

The preparation of compounds of formula Ib, especially the preparation according to the invention of the compound of formula Ic, is effected, for example, analogously to the preparation of compounds of formula I, as described above.

If desired, a compound of formula Ib, especially Ic, can be converted into its salt, or an obtainable salt can be converted into the free compound or into a different salt, and/or isomeric mixtures that may be obtainable can be separated and/or a compound of formula Ib, especially Ic, according to the invention can be converted into a different compound of formula Ib, especially Ic, according to the invention. The conditions correspond to those described above for additional process steps carried out using compounds of formula I or I-A.

The compounds of formula Ic are prepared according to the invention preferably from compounds of formula IX-A" wherein $R_2$, $R_4$, $R_6$ and $R_8$ are hydrogen, $R_3$ is benzyl and $R_7$ is cyclohexylmethyl, and from N-methoxycarbonyl-(L)-valine or a reactive acid derivative thereof (corresponding to the compounds of formulae VI-A and VIII-A wherein $R_9'$ and $R_1'$ are N-methoxycarbonyl-(L)-valyl), analogously to Process i), as described above.

The acids of formulae XXII, VI-A, VIII-A and XXIIa, the acid derivatives thereof, for example of formulae VI-A', VI-A" and XXIIb, are commercially available, known or, if they are novel, can be prepared in accordance with processes known per se, for example analogously to the processes mentioned in the Examples, using suitable starting materials. The same applies to all further starting materials.

There may be mentioned by way of example the preparation of an aryl-lower alkanoic acid (a compound of formula XXII) substituted by heterocyclylmethyl, wherein heterocyclyl is bonded via a ring nitrogen atom, which is preferably effected by reacting an aryl-lower alkanoyl radical substituted by halomethyl, such as chloro- or bromomethyl, such as chloromethylbenzoyl or bromomethylbenzoyl, with a corresponding heterocyclic nitrogen base, such as piperidine, piperazine, 1-lower alkylpiperazine, 1-lower alkanoylpiperazine or especially morpholine or thiomorpholine, with nucleophilic substitution of the halogen atom.

Amino acid derivatives of formula XXII, VI-A or VIII-A wherein the α-amino group is alkylated by a radical selected from phenyl-lower alkyl and heterocyclyl-lower alkyl can be prepared, for example, by reductive amination of the amino acid (protected, if necessary, at further groups that are not intended to participate in the reaction) having a primary or secondary α-amino group, with a phenyl-lower alkyl ketone or aldehyde, such as benzaldehyde, or heterocyclyl-lower alkyl ketone or aldehyde, for example heterocyclyl aldehyde, for example furan aldehyde, such as furan-2-aldehyde, or pyridine aldehyde, such as pyridine-3-aldehyde, for example with catalytic hydrogenation, for example in the presence of a heavy metal catalyst, such as Raney nickel, under normal pressure or under pressures of from 1 to 100 bar, preferably at approximately 100 bar, or with reduction by means of complex boron hydrides, such as sodium cyanoborohydride.

The isocyanates of formulae XXIIb and VI-A" can be prepared, for example, from the corresponding amine precursors by conversion of the amino group into the isocyanato group, for example by reaction with phosgene with heating, for example under reflux conditions, or by the dropwise addition of the primary, secondary or tertiary amine, in liquid form or dissolved in a solvent, to an excess of phosgene in a suitable solvent (toluene, xylene, ligroin, chlorobenzene, α-chloronaphthalene, etc.) with cooling (for example at from −50° to 0° C.), there being formed as intermediate a mixture of carbamoyl chloride and amine hydrochloride which is then phosgenated further at elevated temperature (for example at from 50° C. to the reflux temperature) until complete dissolution is obtained, HCl being eliminated.

The following applies generally to all the processes mentioned hereinbefore and hereinafter:

As a result of the close relationship between the compounds of formula I and I-A and their salts and starting materials (starting compounds and intermediates) in free form and in the form of their salts, hereinbefore and hereinafter any reference to the free compounds and their salts should be understood as including the corresponding salts and free compounds, respectively, where appropriate and expedient.

All the process steps listed above can be carried out under reaction conditions known per se, preferably those specifically mentioned, in the absence or, customarily, the presence of solvents or diluents, preferably those that are inert towards the reagents used and are solvents therefor, in the absence or presence of catalysts, condensation agents or neutralising agents, for example ion exchangers, such as cation exchangers, for example in the $H^+$ form, and, depending on the nature of the reaction and/or of the reactants, at reduced, normal or elevated temperature, for example in a temperature range from approximately −100° C. to approximately 190° C., preferably from approximately −80° C. to approximately 150° C., for example from −80° to −60° C., at room temperature, from −20° to 40° C. or at the reflux temperature, under atmospheric pressure or in a closed vessel, if necessary under pressure, and/or in an inert atmosphere, for example under an argon or nitrogen atmosphere.

Isomeric mixtures occurring at any stage of the reaction may be separated into the individual isomers, for example diastereoisomers or enantiomers, or into any desired mixtures of isomers, for example racemates or diastereoisomeric mixtures, for example analogously to the methods described under the "Additional Process Steps".

In certain cases, for example in the case of hydrogenation, it is possible to achieve stereo-selective reactions, which, for example, enable individual isomers to be obtained more easily.

The solvents from which those suitable for a particular reaction can be selected include, for example, water, esters, such as lower alkyl-lower alkanoates, for example ethyl acetate, ethers, such as aliphatic ethers, for example diethyl ether, or cyclic ethers, for example tetrahydrofuran, liquid aromatic hydrocarbons, such as benzene or toluene, alcohols, such as methanol, ethanol or 1- or 2-propanol, nitrites, such as acetonitrile, halogenated hydrocarbons, such as methylene chloride, acid amides, such as dimethylformamide, bases, such as heterocyclic nitrogen bases, for example pyridine, carboxylic acid anhydrides, such as lower alkanoic acid anhydrides, for example acetic anhydride, cyclic, linear or branched hydrocarbons, such as cyclohexane, hexane or isopentane, or mixtures of those solvents, for example aqueous solutions, unless the description of the process indicates otherwise. Such solvent mixtures can also be used in the working-up, for example by chromatography or partitioning.

The compounds, including their salts, can also be obtained in the form of hydrates, or their crystals may, for example, include the solvent used for crystallisation.

The invention relates also to those forms of the process in which a compound obtainable as intermediate at any stage of the process is used as starting material and the remaining process steps are carried out, or in which a starting material is formed under the reaction conditions or is used in the form of a derivative, for example in protected form or in the form of a salt, or a compound obtainable by the process according to the invention is produced under the process conditions and further processed in situ. In the process of the present invention it is preferable to use those starting materials that lead to the compounds (of formula I or Ib) described in the introduction as being especially valuable. Special preference is given to reaction conditions analogous to those mentioned in the Examples.

Where necessary, protected starting compounds can be used at any stage of the process and the protecting groups removed at suitable stages of the reaction.

Protecting groups, their introduction and their removal are as described (for the preparation of compounds of formula I) under Processes a) and f).

Pharmaceutical Compositions

The invention relates also to pharmaceutical compositions comprising compounds of formula I-A or (especially those compounds that are described as being preferred) of formula Ib.

For the pharmaceutical preparations, their preparation and their use, the corresponding passage given under the same heading for compounds of formula I is applicable, if instead of compounds of the formula I those of formula I-A or Ib are employed.

The invention relates also to a method of treating diseases caused by viruses, especially by retroviruses, for example AIDS, which comprises administering a therapeutically effective amount of a compound of formula I-A or formula Ib according to the invention, especially to a warm-blooded animal, for example a human, who on account of one of the mentioned diseases, especially AIDS, requires such treatment. The dose to be administered to warm-blooded animals, for example humans of approximately 70 kg body weight, is from approximately 3 mg to approximately 3 g, preferably from approximately 10 mg to approximately 1.5 g, for example approximately from 100 mg to 1000 mg per person per day, divided preferably into 1 to 3 single doses which may, for example, be of the same size. Usually, children receive half of the adult dose.

The following Examples serve to illustrate the invention but do not limit the scope thereof in any way.

Temperatures are given in degrees Celsius (°C.). Where no temperature is specified, the reaction takes place at room temperature. The $R_f$ values, which indicate the ratio of the seepage propagation of the substance in question to the seepage propagation of the eluant front, are determined on thin layer silica gel plates by thin layer chromatography (TLC) in the following solvent systems:

| A | chloroform/methanol/water/acetic acid | 75:27:5:0.5 |
|---|---|---|
| B | chloroform/methanol/water/acetic acid | 90:10:1:0.5 |
| C | chloroform/methanol/water/acetic acid | 85:13:1.5:0.5 |
| D | chloroform/methanol | 95:5 |
| E | chloroform/methanol | 95:5 |
| F | hexane/ethyl acetate | 2:1 |
| G | methylene chloride/diethyl ether/methanol | 20:20:1 |
| H | methylene chloride/diethyl ether | 1:1 |
| I | toluene/ethyl acetate | 2:1 |
| K | chloroform/methanol | 5:1 |
| J | methylene chloride/diethyl ether | 5:1 |
| L | hexane/ethyl acetate | 4:1 |
| M | hexane/ethyl acetate | 5:1 |
| N | hexane/ethyl acetate | 1:1 |
| O | ethyl acetate | — |
| P | methylene chloride/ethanol/NH$_3$aq. | 90:10:1 |
| Q | methylene chloride/diethyl ether | 10:1 |
| R | hexane/ethyl acetate | 3:1 |
| S | methylene chloride/diethyl ether | 20:1 |
| T: | chloroform/methanol | 30:1 |
| U: | chloroform/methanol | 15:1 |
| V: | methylene chloride/diethyl ether/hexane | 1:1:3 |
| W: | methylene chloride/diethyl ether | 20:1 |
| X: | methylene chloride/methanol | 40:1 |
| Y: | toluene/ethyl acetate | 4:1 |
| Z: | methylene chloride/methanol | 30:1 |
| A': | methylene chloride/methanol | 15:1 |
| B': | methylene chloride/methanol | 10:1 |
| C': | hexane/ethyl acetate | 1:3 |
| D': | ethyl acetate/ethanol | 100:3 |
| E': | ethyl acetate/ethanol | 20:1 |
| F': | ethyl acetate/ethanol | 10:1 |
| G': | methylene chloride/methanol | 9:1 |
| H': | ethyl acetate/hexane | 3:2 |
| I': | methylene chloride/methanol | 12:1 |
| J': | methylene chloride/methanol | 19:1 |
| K' | methylene chloride/diethyl ether/methanol | 10:10:1 |

The abbreviation "$R_f(A)$", for example, indicates that the $R_f$ value was determined in solvent system A. The ratio of solvents to one another is always given in parts by volume.

HPLC gradients

I 20%→100% a)in b)for 35min

II 0%→40% a)in b)for 30min

III 20%→60% a)in b)for 60min

IV 10%→50% a) in b) for 60 min

V 20%→100% a)in b)for 20min

Eluant a): acetonitrile +0.05% TFA; eluant b): water+ 0.05% TFA. Column (250×4.6 mm) filled with "Reversed-Phase" material $C_{18}$-Nucleosil® (5 μm average particle size, silica gel covalently derivatised with octadecylsilanes, Macherey & Nagel, Duren, FRG). Detection by UV-absorption at 215 nm. The retention times ($t_{Ret}$) are given in minutes. Flow rate 1 ml/min.

The same abbreviations are used to identify the eluant systems in flash chromatography and medium-pressure chromatography.

The other short forms and abbreviations used have the following meanings:

abs. absolute (indicates that the solvent is anhydrous)

atm physical atmospheres (unit of pressure)-1 atm corresponds to 1.013 bar

Boc tert-butoxycarbonyl

BOP benzotriazol-1-yloxy-tris(dimethylamino) phosphonium hexafluorophosphate brine saturated sodium chloride solution DCC dicyclohexylcarbodiimide DIPE diisopropyl ether DMAP dimethylaminopyridine DMF dimethylformamide DMSO dimethyl sulfoxide EDC N-ethyl-N'-(3-dimethylamino propyl)-carbodiimide hydrochloride ether diethyl ether h hour(s)

HBTU O-benzotriazol-1-yl-N,N,N'N'-tetramethyluronium hexafluorophosphate

HOBt 1-hydroxybenzotriazole

HV high vacuum min minute(s)

MS mass spectroscopy

NMM N-methylmorpholine

RE rotary evaporator

RT room temperature

TFA trifluoroacetic acid

THF tetrahydrofuran

Z benzyloxycarbonyl

Mass spectroscopic data are obtained either by conventional MS or according to the "Fast-Atom-Bombardment" (FAB-MS) method. The mass data refer in the former case to the unprotonated molecule ion $(M)^+$ or to the protonated molecule ion $(M+H)^+$.

The values for proton nuclear resonance spectroscopy ($^1$H-NMR) are given in ppm (parts per million) based on tetramethylsilane as the internal standard. s=singlet, d=doublet, t=triplet, q=quartet, m=multiplet, dd=double doublet, br=broad.

The values for IR spectra are given in $cm^{-1}$, and the solvent in question is in round brackets. Where given, s indicates a strong, m a medium and w a weak intensity of the band in question.

The residue referred to as -[Phe$^{NN}$Phe] is the divalent residue of 3(S)-amino-4-phenyl-1-(N-benzylhydrazino)-butan-2(S)-ol and has the formula

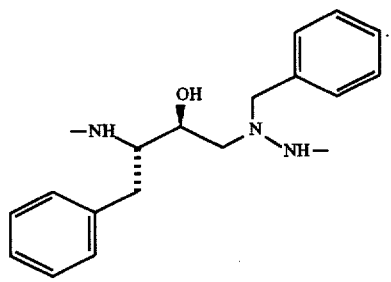

The residue referred to as -[Phe$^{NN}$Cha] is the divalent residue of 3(S)-amino-4-phenyl-1-(N-cyclohexylmethylhydrazino)-butan-2(S)-ol and has the formula

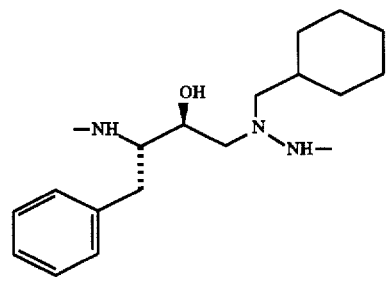

The residue referred to as -[Phe$^{NN}$Leu] is the divalent residue of 3(S)-amino-4-phenyl-1-(N-isobutylhydrazino)-butan-2(S)-ol and has the formula

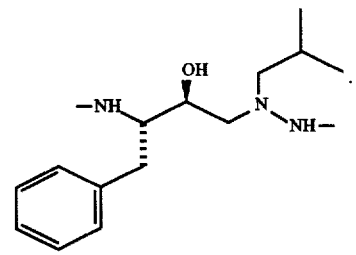

The residue referred to as -[Phe$^{NN}$Nle] is the residue of 3(S)-amino-4-phenyl-1-(N-n-butylhydrazino)-butan-2(S)-ol and has the formula

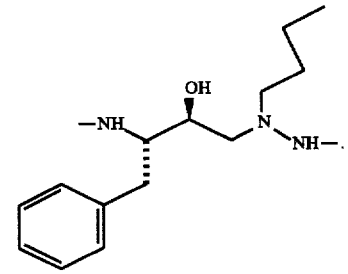

The residue referred to as -[Phe$^{NN}$(p-F)Phe] is the divalent residue of 3(S)-amino-4-phenyl-1-(N-(p-fluorophenylmethyl)-hydrazino)-butan-2(S)-ol and has the formula

167

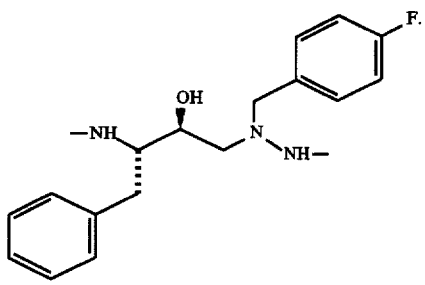

The residue referred to as -[(p-F)Phe^NN(p-F)Phe] is the divalent residue of 3(S)-amino-4-(p-fluorophenyl)-1-(N-(p-fluorophenylmethyl)-hydrazino)-butan-2(S)-ol and has the formula

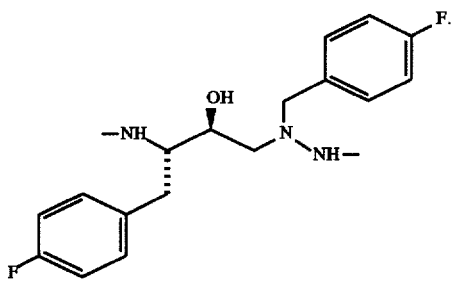

The residue referred to as -[Phe^NN(p-CN)Phe] is the divalent residue of 3(S)-amino-4-phenyl-1-(N-(p-cyanophenylmethyl)-hydrazino)-butan-2(S)-ol and has the formula

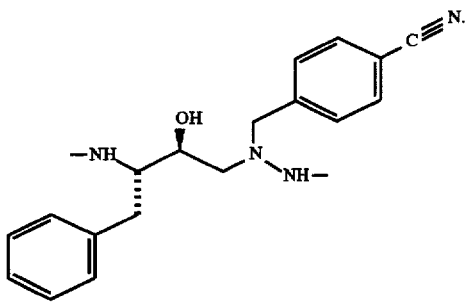

The residue referred to as -[Cha^NN Leu] is the divalent residue of 3(S)-amino-4-cyclohexyl-1-(N-isobutyl-hydrazino)-butan-2(S)-ol and has the formula

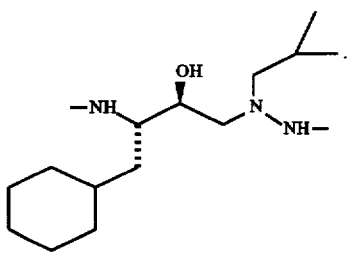

The divalent radical of 1-[2(S)-acetoxy-3(S)-amino-4-phenylbutyl]-[1-cyclohexylmethyl]hydrazine has the formula

168

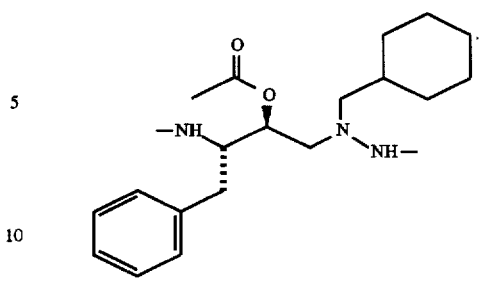

The abbreviations customarily used in peptide chemistry are used to name divalent residues of natural α-amino acids. However, contrary to customary peptide nomenclature in which the amino terminus is on the left-hand side and the carboxy terminus is on the right-hand side, amino acids that are on the right-hand side of the residues -[Phe^NN Phe], -[Phe^NN Cha], -[Phe^NN Leu], -[Phe^NN Nle], -[Phe^NN(p-F)Phe], -[(p-F)Phe^NN(p-F)Phe], -[Phe^NN(p-CN)Phe] or -[Cha^NN Leu] in the compound names, have the linking carboxy group on the left, which is indicated by an arrow (←) symbolising the reversal of the direction of linkage. The configuration at the α-carbon atom, if it is known, is indicated by the prefix (L)- or (D)-. Tyrosine residues etherified at the phenolic hydroxy group by the radical R are designated by Tyr(OR). Nle denotes the residue of norleucine.

EXAMPLE 1

Boc-[Phe^NN Phe]-Boc

A solution of 300 mg (1.14 mmol) of (2R)-[1'(S)-Boc-amino-2'-phenylethyl]oxirane (J. Org. Chem. 50, 4615 (1985)) and 253 mg (1.14 mmol) of tert-butyl-3-benzyl-carbazate (J. Chem. Soc., Perkin I, 1712 (1975)) in 4 ml of methanol is heated under reflux for 12 hours. After cooling the reaction mixture to 0° a large portion of the title compound precipitates. The mother liquor is concentrated by evaporation and the residue is dissolved in a small amount of methylene chloride. After the dropwise addition of hexane a further amount of the title compound is obtained in the form of a white precipitate. FAB-MS: (M+H)⁺=486, t_Ref(I)=26.8 min, R_f(E)=0.70.

EXAMPLE 2

Z-(L)-Val-[Phe^NN Phe]←((L)-Val-Z)

191 mg (0.76 mmol) of Z-(L)-valine, 336 mg (0.76 mmol) of BOP and 103 mg (0.76 mmol) of HOBt are dissolved in 5 ml of a 0.3M solution of NMM in DMF, and after 10 minutes 100 mg (0.25 mmol) of H-[Phe^NN Phe]-H.3HCl are added and the mixture is stirred for 2 hours at RT under a nitrogen atmosphere. The reaction mixture is concentrated by evaporation, and the residue is dissolved in methylene chloride and washed twice with saturated sodium hydrogen carbonate solution. The organic phases are filtered through cotton wadding and concentrated by evaporation and the residue is purified by means of chromatography on silica gel with methylene chloride/ether (1:1). Lyophilisation of the product-containing fractions from dioxane yields the title compound in the form of a white solid. FAB-MS: (M+H)⁺ =752, t_Ref(I)=27.8 min, R_f(E)=0.45.

The starting material is prepared as follows:

a) H-[Phe^NN Phe]-H.3HCl

A solution of 280 mg (0.58 mmol) of Boc-[Phe^NN Phe]-Boc from Example 1 in 10 ml of 4N hydrogen chloride in dioxane is stirred for 2 hours at RT under a nitrogen atmosphere and then lyophilised. Lyophilisation once more from dioxane/tert-butanol yields the title compound in the form of a flocculent solid. FAB-MS: (M+H)⁺=286, $t_{Ref}$(II) =23.1 min, $R_f$(C)=0.17.

EXAMPLE 3

Boc-(L)-Val-[Phe$^{NN}$Phe]←((L)-Val-Boc)

The title compound is obtained in a manner analogous to that described in Example 2 from 50 mg (0.13 mmol) of H-[Phe$^{NN}$Phe]-H.3HCl, 83 mg (0.83 mmol) of Boc-(L)-valine, 168 mg (0.38 mmol) of BOP, 51 mg (0.38 mmol) of HOBt and 2.5 ml of 0.3M NMM in DMF after chromatographic purification on silica gel with chloroform/methanol (95:5) and lyophilisation from dioxane. FAB-MS: (M+H)⁺ =684, $t_{Ref}$(I)=27.4 min, $R_f$(E)=0.38.

EXAMPLE 4

Boc-[Phe$^{NN}$Cha]-Boc

The title compound is obtained analogously to Example 1, from 231 mg (0.88 mmol) of (2R,3S)-1-[3-Boc-amino-2-phenylethyl]oxirane and 200 mg (0.88 mmol) of tert-butyl-3-cyclohexylmethyl-carbazate, in the form of a white precipitate from hexane. FAB-MS: (M+H)⁺=492, $t_{Ref}$(I)=30.4 min, $R_f$(E)=0.78.

The starting material is prepared as follows:
a) tert-Butyl-3-cyclohexylmethyl-carbazate 10.2 g (45.1 mmol) of cyclohexylcarbaldehyde-tert-butoxycarbonylhydrazone, dissolved in 400 ml of methanol, are hydrogenated in the presence of 5.1 g of 5% platinum on carbon at RT and 4 atm hydrogen pressure. When the reaction is complete, the catalyst is removed by filtration and the filtrate is concentrated by evaporation. The residue is dissolved in methylene chloride and washed with water. Concentration by evaporation of the organic phase yields the title compound in the form of a colourless resin. ¹H-NMR (200 MHz, CDCl₃): 6.1 (s, br, 1H), 3.9 (s, br, 1H), 2.65 (d, 2H), 1.8–0.75 (m, 11H), 1.45 (s, 9H), $t_{Ref}$(I)=32.0 min, $R_f$(E)=0.75.

b) Cyclohexylcarbaldehyde-tert-butoxycarbonylhydrazone

A solution of 10.8 g (81.2 mmol) of tert-butylcarbazate and 10.1 g (90 mmol) of cyclohexylcarbaldehyde in 400 ml of ethanol is heated under reflux for 2 hours. Half of the solvent is then removed by distillation and the title compound is precipitated by the addition of water. It is directly further used in a).

EXAMPLE 5

H-(L)-Val-[Phe$^{NN}$Phe]←((L)-Val)-H.3HCl

A solution of 40 mg (0.06 mmol) of Boc-(L)-Val-[Phe$^{NN}$Phe]←((L)-Val)-Boc from Example 3 in 4 ml of 4N hydrogen chloride in dioxane is stirred at RT for 1 h. The mixture is then diluted with dioxane and, after lyophilisation, the title compound is obtained in the form of the hydrochloride. FAB-MS: (M+H)⁺=484, $t_{Ref}$(II)=25.8 min, $R_f$(A)=0.45.

EXAMPLE 6

N-Thiomorpholinocarbonyl-(L)-Val-[Phe$^{NN}$Phe]←(N-thiomorpholinocarbonyl-(L)-Val)

35 μl (0.25 mmol) of triethylamine and 16 mg (0.1 mmol) of (4-thiomorpholinylcarbonyl)chloride are added in succession at RT to a solution of 20 mg (0.03 mmol) of H-(L)-Val-[Phe$^{NN}$Phe]←((L)-Val)-H.3HCl from Example 5 in 0.5 ml of DMF, and the mixture is stirred for 1 h at RT. The reaction mixture is diluted with chloroform and washed with saturated sodium hydrogen carbonate solution. The organic phase is filtered through cotton wadding and concentrated by evaporation, and the residue is chromatographed on silica gel with a gradient of chloroform/methanol (15:1→8:1). The product fractions are concentrated by evaporation and precipitated with methylene chloride/DIPE. Lyophilisation from dioxane yields the title compound in the form of a flocculent solid. FAB-MS: (M+H)⁺=742, $t_{Ref}$(I)=21.6 min, $R_f$(D)=0.54.

The starting material is prepared as follows:
a) (4-Thiomorpholinylcarbonyl)chloride A solution of 10 g (97 mmol) of thiomorpholine in 200 ml of toluene is added dropwise at 0° to a solution of 85 ml (165 mmol) of 20% phosgene in toluene and the white suspension is stirred for 1 h at RT. Excess phosgene is driven off by introducing nitrogen, the suspension is filtered, and the filtrate is concentrated by evaporation. The title compound is obtained in the form of a yellow oil. IR (CH₂Cl₂, cm⁻¹): 1735, 1450, 1440, 1405, 1370, 1290, 1180.

EXAMPLE 7

N-Morpholinocarbonyl-(L)-Val-[Phe$^{NN}$Phe]←(N-morpholinocarbonyl-(L)-Val)

210 μl (1.52 mmol) of triethylamine are added to a solution of 100 mg (0.25 mmol) of H-[Phe$^{NN}$Phe]-H.3HCl from Example 2a), 163 mg (0.76 mmol) of N-morpholinocarbonyl-(L)-valine and 288 mg (0.76 mmol) of HBTU in 2 ml of DMF and the mixture is stirred for 16 h at RT under a nitrogen atmosphere. The reaction mixture is fully concentrated by evaporation, and the residue is dissolved in methylene chloride and washed with saturated sodium hydrogen carbonate solution. The organic phase is filtered through cotton wadding, concentrated by evaporation and chromatographed on silica gel with methylene chloride/methanol (15:1). The title compound is precipitated from methylene chloride/hexane and, after lyophilisation from dioxane/tert-butanol, is obtained in the form of a flocculent solid. FAB-MS: (M+H)⁺=710, $t_{Ref}$(I)=16.3 min, $R_f$(E)=0.16.

The starting material is prepared as follows:
a) N-Morpholinocarbonyl-(L)-valine 2.7 g (8.4 mmol) of N-morpholinocarbonyl-(L)-valine-benzyl ester are dissolved in 75 ml of ethyl acetate and the solution is hydrogenated for 3 h in the presence of 500 mg of 10% palladium on carbon at 1 atm hydrogen pressure and RT. The catalyst is filtered off and, after concentrating the solvent by evaporation, the title compound is obtained in the form of a colourless oil. ¹H-NMR (300 MHz, CD₃OD): 4.15 (m, 1H), 3.65 (m, 4H), 3.40 (m, 4H), 2.12 (m, 1H), 0.95 (2d, 6H).

b) N-Morpholinocarbonyl-(L)-valine-benzyl ester 0.8 ml (8.1 mmol) of (morpholinocarbonyl)chloride (preparation: J. Med. Chem. 31, 2277 (1988)) and 4.1 ml (24.1 mmol) of N-ethyldiisopropylamine are added to a solution of 4 g (10.5 mmol) of (L)-valine-benzyl ester 4-toluenesulfonate in 56 ml of methylene chloride and the mixture is stirred at RT for 24 h. The reaction mixture is diluted with ethyl acetate and washed in succession with 1N hydrochloric acid, water, saturated sodium hydrogen carbonate solution and brine. The organic phase is dried over sodium sulfate and concentrated by evaporation. Chromatography on silica gel with ethyl acetate yields N-morpholinocarbonyl-(L)-valine-benzyl ester in the form of a colourless oil. The ester is directly further used in a).

EXAMPLE 8

Phenylacetyl-(L)-Val-[Phe$^{NN}$Phe]←(N-phenylacetyl-(L)-Val)

The title compound is obtained analogously to Example 7 from 100 mg (0.25 mmol) of H-[Phe$^{NN}$Phe]-H.3HCl from Example 2a), 143 mg (0.61 mmol) of phenylacetyl-(L)-valine (preparation: Mem. Tokyo Univ. Agric. 20, 51 (1978) ), 230 mg (0.61 mmol) of HBTU and 200 µl (1.42 mmol) of triethylamine after chromatographic purification with methylene chloride/ether/methanol (20:20:1) and lyophilisation from dioxane/tert-butanol. FAB-MS: (M+H)$^+$=720, $t_{Ref}$(I)= 23.7 min, R$_f$(G)=0.21.

EXAMPLE 9

N-(3-Pyridylacetyl)(L)-Val-[Phe$^{NN}$Phe]←(N-(3pridylacetyl)-(L)-Val)

The title compound is obtained analogously to Example 7 in the form of a white solid from 100 mg (0.25 mmol) of H-[Phe$^{NN}$Phe]-H.3HCl from Example 2a, 576 mg (1.52 mmol) of HBTU, 358 mg (1.52 mmol) of N-(3-pyridylacetyl)-(L)-valine and 316 µl (2.3 mmol) of triethylamine after chromatographic purification with chloroform/methanol (5:1) and lyophilisation from dioxane/tert-butanol. FAB-MS: (M+H)$^+$=722, $t_{Ref}$(II)=27.9 min, R$_f$(A)=0.71.

The starting material is prepared as follows:

a) N-(3-Pyridylacetyl)-(L)-valine 3.4 g of N-(3-pyridylacetyl)-(L)-valine-tert-butyl ester are dissolved in 20 ml of trifluoroacetic acid/methylene chloride (1:1) and the solution is stirred at RT for 16 h. The reaction solution is fully concentrated by evaporation and the residue is digested with DIPE. The title compound is obtained in the form of a white amorphous solid. $^1$H-NMR (200 MHz, CD$_3$OD): 8.9–8.6 (m, broad, 1H), 8.5 (m, 1H), 7.95 (m, 1H), 4.33 (m, 1H), 3.93 (s, 2H), 2.2 (m, 1H), 0.98 (2d, 6H).

b) N-(3-Pyridylacetyl)-(L)-valine-tert-butyl ester 4.2 ml of triethylamine are added dropwise at 0° to a solution of 3.36 g (16 mmol) of (L)-valine-tert-butyl ester.HCl, 2 g (14.5 mmol) of 3-pyridylacetic acid and 2.17 ml (14.3 mmol) of cyanophosphonic acid diethyl ester in 20 ml of DMF. The reaction mixture is stirred for 48 h at RT, and then diluted with methylene chloride and washed with 10% citric acid as well as saturated sodium hydrogen carbonate solution. The organic phase is filtered through cotton wadding and, after removal of the solvent by evaporation, yields N-(3-pyridylacetyl)-(L)-valine-tert-butyl ester, which is directly further used in a).

EXAMPLE 10

Boc-(L)-Val-[Phe$^{NN}$Cha]←((L)-Val)-Boc

The title compound is obtained analogously to Example 7 in the form of a flocculent solid starting from 500 mg (1.25 mmol) of H-[Phe$^{NN}$Cha]-H.3HCl, 1.08 g (4.98 mmol) of Boc-(L)-valine, 1.89 g (4.98 mmol) of HBTU and 1.39 ml (9.96 mmol) of triethylamine after chromatographic purification on silica gel with methylene chloride/ether (1:1) and lyophilisation from dioxane. FAB-MS: (M+H)$^+$=690, $t_{Ref}$(I)=29.3 min, R$_f$(H)=0.48.

The starting material is prepared as follows:

a) H-[Phe$^{NN}$Cha]-H.3HCl 1.10 g (2.2 mmol) of Boc-[Phe$^{NN}$Cha]-Boc from Example 4 are dissolved in 20 ml of 4N hydrogen chloride in dioxane and the solution is stirred at RT for 3 h. Lyophilisation of the reaction solution yields the title compound in the form of the hydrochloride. FAB-MS: (M+H)$^+$=292, $t_{Ref}$(II)=27.3 min.

EXAMPLE 11

Z-(L)-Val-[Phe$^{NN}$Cha]←((L)-Val)-Z

The title compound is obtained analogously to Example 2 from 50 mg (0.12 mmol) of H-[Phe$^{NN}$Cha]-H.3HCl from Example 10a, 94 mg (0.37 mmol) of Z-(L)-valine, 165 mg (0.37 mmol) of BOP, 51 mg (0.37 mmol) of HOBt and 2.5 ml of 0.3M NMM in DMF after chromatographic purification on silica gel with methylene chloride/ether (1:1) and lyophilisation from dioxane. FAB-MS: (M+H)$^+$=758, $t_{Ref}$(I)=29.1 min, R$_f$(H)=0.55.

EXAMPLE 12

Boc-[Phe$^{NN}$Leu]-Boc

The title compound is obtained analogously to Example 1, starting from 1.0 g (3.8 mmol) of (2R)-[1'(S)-Boc-amino-2'-phenylethyl]oxirane and 715 mg (3.8 mmol) of tert-butyl-3-isobutyl-carbazate (preparation: J. Chem. Soc., Perkin I, 1712 (1975)), in the form of a precipitate from hexane. FAB-MS: (M+H)$^+$=452, $t_{Ref}$(I)=27.2 min, R$_f$(I)=0.55.

EXAMPLE 13

Z-(L)-Val-[Phe$^{NN}$Leu]←((L)-Val)-Z

The title compound is obtained analogously to Example 2 starting from 60 mg (0.17 mmol) of H-[Phe$^{NN}$Leu]-H.3HCl, 125 mg (0.50 mmol) of Z-(L)-valine, 221 mg (0.50 mmol) of BOP, 67 mg (0.50 mmol) of HOBt and 3.3 ml of 0.3M NMM in DMF after chromatographic purification on silica gel with methylene chloride/ether (1:1) and lyophilisation from dioxane. FAB-MS: (M+H)$^+$=718, $t_{Ref}$(I)=26.8 min, R$_f$(H)=0.38.

The starting material is prepared as follows:

a) H-[Phe$^{NN}$Leu]-H.3HCl

The title compound is obtained analogously to Example 10a), in the form of a lyophilisate, from 1.21 g (2.48 mmol) of Boc-[Phe$^{NN}$Leu]-Boc from Example 12. FAB-MS: (M+H)$^+$=252, $t_{Ref}$(II)=20.9 min, R$_f$(K)=0.23.

EXAMPLE 14

H-(L)-Val-[Phe$^{NN}$Cha]←((L)-Val)-H.3HCl

The title compound is obtained analogously to Example 10a), from 632 mg (0.91 mmol) of Boc-(L)-Val-[Phe$^{NN}$Cha]←((L)-Val)-Boc from Example 10, in the form of the hydrochloride after lyophilisation. FAB-MS: (M+H)$^+$=490, $t_{Ref}$(II)=29.4 min, R$_f$(K)=0.23.

EXAMPLE 15

N-(3-Pyridylacetyl)-(L)-Val-[Phe$^{NN}$Leu]←(N-(3-pyridylacetyl)-(L)-Val)

The title compound is obtained analogously to Example 9 from 90 mg (0.25 mmol) of H-[Phe$^{NN}$Leu]-H.3HCl from Example 13a), 358 mg (1.52 mmol) of N-(3-pyridylacetyl)-(L)-valine, 576 mg (1.52 mmol) of HBTU and 316 µl (2.5 mmol) of triethylamine after chromatographic purification with methylene chloride/methanol (15:1) and lyophilisation from dioxane/tert-butanol/water. FAB-MS: (M+H)$^+$+688, $t_{Ref}$(IV)=15.5 min, R$_f$(D)=0.37.

EXAMPLE 16

N-Trifluoroacetyl-[Phe$^{NN}$(p-F)Phe]-Boc

A solution of 4.0 g (15.4 mmol) of 2(R)-[1'(S)-(trifluoroacetylamino)-2'-phenylethyl]oxirane and 3.89 g (16.2 mmol) of tert-butyl-3-(p-fluorophenyl-methyl)-carbazate in 35 ml of methanol are heated at 80° C. for approximately 20 h in a bomb tube. The reaction mixture is concentrated by evaporation, the residue is dissolved in a small amount of dichloromethane, and the title compound is precipitated therefrom using hexane (refrigerator). Column chromatography (SiO$_2$, methylene chloride/ether 95:7) yields further product. TLC R$_f$(J)=0.57; t$_{Ret}$(I)=24.3 min; FAB-MS (M+H)$^+$=500.

The starting materials are prepared as follows:

a) N-3(S)-(Boc-amino)-2(R,S)-hydroxy-4-phenyl-1-trimethylsilyl-butane

Under a nitrogen atmosphere, 24.7 g (1.02 mol) of magnesium are placed in 100 ml of abs. ether and over a period of 35 minutes a small amount of iodine and, at the same time, 132.5 ml (0.95 mol) of chloromethyltrimethylsilane and 300 ml of ether are added, the temperature being maintained at 38° C. by means of an ice bath. The reaction mixture obtained is then stirred for 1.5 h at RT. After the mixture has been cooled to −60° C., a suspension of 48.6 g (0.195 mol) of N-Boc-phenylalaninal (preparation: D. J. Kempf, J. Org. Chem. 51, 3921 (1986)) in 1.1 l of ether is added over a period of 40 min. Over a period of 90 min the reaction mixture is warmed to RT and stirred for a further 90 min at that temperature. The mixture is then poured onto 2 l of ice-water and 1.5 l of 10% aqueous citric acid. The separated aqueous phase is extracted twice with 500 ml of ether. All ether extracts are washed with 500 ml of 10% citric acid and twice with brine. After drying over sodium sulfate the residue is concentrated in vacuo and the resulting title compound is further used without additional purification. TLC R$_f$(L)=0.6; FAB-MS (M+H)$^+$=338.

b) 1-Phenyl-3-buten-2(S)-amine 35.6 ml (0.28 mol) of an approximately 48% solution of boron trifluoride in ether are added at 5° C., over a period of 10 min, to a solution of 18.8 g (0.055 mol) of 3(S)-(Boc-amino)-2(R,S)-hydroxy-4-phenyl-1-trimethylsilyl-butane in 420 ml of methylene chloride. The reaction mixture is then stirred at RT for 16 h, cooled to 10°0 C. and, over a period of 20 min, 276 ml of a 4N sodium hydroxide solution are added. The aqueous phase is removed and extracted twice with 400 ml of methylene chloride each time. The combined organic extracts are washed with brine and dried over sodium sulfate. The title product is further used without additional purification. TLC R$_f$(C)=0.15; IR (methylene chloride) (cm$^{-1}$): 3370, 3020, 2920, 1640, 1605.

c) N-Trifluoroacetyl-1-phenyl-3-buten-2(S)-amine 17.0 ml (121 mmol) of trifluoroacetic acid anhydride are added dropwise, at 0° C., to 11.9 g (81 mmol) of 1-phenyl-3-buten-2(S)-amine dissolved in 210 ml of methylene chloride and 70 ml of pyridine. The mixture is stirred for 0.5 h at 0° C. and then extracted twice with dilute HCl, water and brine. The aqueous phases are washed a further twice with methylene chloride, dried with sodium sulfate and concentrated by evaporation: TLC R$_f$(M)=0.4.

d) 2(R)-[1'(S)-(Trifluoroacetylamino)-2'-phenylethyl]-oxirane 54.28 g (314 mmol) of m-chloroperbenzoic acid are added to a solution of 14.5 g (60 mmol) of N-trifluoroacetyl-1-phenyl-3-buten-2(S)-amine in 600 ml of chloroform and the mixture is stirred for 24 h at RT to complete the reaction. The reaction mixture is washed twice with 10% sodium sulfite solution, twice with saturated sodium carbonate solution, water and brine. The aqueous phases are extracted a further twice with methylene chloride and the combined organic phases are dried with sodium sulfate and concentrated by evaporation to yield the title compound, which is used in the next step without being further purified: TLC R$_f$(N)=0.6.

e) p-Fluorophenylcarbaldehyde-tert-butoxycarbonylhydrazone 32 g (242 mmol) of tert-butylcarbazate and 30 g (242 mmol) of p-fluorobenzaldehyde in 300 ml of ethanol are reacted analogously to Example 4b) for 3 h at 80° C. to form the title compound, which crystallises on cooling and diluting with water: TLC R$_f$(N)=0.48; t$_{Ret}$(I)=19.4 min.

f) tert-Butyl-3-(p-fluorophenyl-methyl)-carbazate 55 g (231 mmol) of p-fluorophenylcarbaldehyde-tert-butoxycarbonylhydrazone in 500 ml of THF are hydrogenated with 5.5 g of palladium (5%) on carbon analogously to Example 4a) to yield the title compound: $^1$H-NMR (200 MHz, CD$_3$OD): 7.35 (dd, 8 and 6 Hz, 2H), 7.05 (t, 8 Hz, 2H), 3.9 (s, 2H), 1.45 (s, 9H).

EXAMPLE 17

N-Morpholinocarbonyl-(L)-Val-[Phe$^{NN}$(p-F)Phe]-Boc

A mixture of 185 mg (0.80 mmol) of N-morpholinocarbonyl-(L)-valine (for preparation see Example 7a)), 270 mg (0.67 mmol) of H-[Phe$^{NN}$(p-F)Phe]-Boc, 311 mg (0.70 mmol) of BOP and 95 mg (0.70 mmol) of HOBT is dissolved at RT in 6.8 ml of 0.3M NMM/DMF and stirred for 5 h at RT. The reaction mixture is concentrated by evaporation under HV and the residue is partitioned between 4 portions of methylene chloride and 2 portions of 1M sodium carbonate solution, water and brine. The combined organic phases are dried over sodium sulfate, concentrated by evaporation and purified by column chromatography (SiO$_2$, ethyl acetate): TLC R$_f$(O)=0.38; t$_{Ret}$(I)= 21.8 min; FAB-MS (M+H)$^+$=616.

The starting material is prepared as follows:

a) H-[Phe$^{NN}$(p-F)Phe]-Boc

At 70° C., 15 ml of a 1M aqueous solution of potassium carbonate are added dropwise to a solution of 0.3 g (0.6 mmol) of N-trifluoroacetyl-[Phe$^{NN}$(p-F)Phe]-Boc (for preparation see Example 16) in 50 ml of methanol under a nitrogen atmosphere and the mixture is stirred for 25 h at that temperature. The reaction mixture is concentrated by evaporation under HV, methylene chloride is added to the residue and the mixture is washed twice with water and brine. The aqueous phases are extracted twice with methylene chloride and the organic phases are dried with sodium sulfate and concentrated by evaporation. The crude product is used in the next step without being further purified: t$_{Ret}$(I)=16.2 min.

EXAMPLE 18

N-Morpholinocarbonyl-(L)-Val-[Phe$^{NN}$(p-F)Phe]←((L)-Val)-Z 129 mg (0.34 mmol) of HBTU are added to a solution of 86 mg (0.34 mmol) of Z-(L)-Val and 160 mg (0.31 mmol) of N-morpholinocarbonyl-(L)-Val-[Phe$^{NN}$(p-F)Phe]-H in 2.7 ml of 0.25M NMM/CH$_3$CN (0.25M NMM in CH$_3$CN). After 4 h at RT the mixture is concentrated by evaporation and the residue is partitioned between 3 portions of methylene chloride and 2 portions of saturated sodium hydrogen carbonate solution and brine. The organic phases are dried with sodium sulfate and concentrated by evaporation to yield the title compound which is obtained in pure form after digestion from methylene chloride/ether 1:1: TLC R$_f$(P)= 0.4; t$_{Ret}$(I)=22.4 min; FAB-MS (M+H)$^+$=749.

The starting material is prepared as follows:

a) N-Morpholinocarbonyl-(L)-Val-[Phe$^{NN}$(p-F)Phe]-H 210 mg (0.34 mmol) of N-morpholinocarbonyl-(L)-Val-[Phe$^{NN}$(p-F)Phe]-Boc (Example 17) are dissolved in 105 ml of formic acid and the solution is stirred for 4 h at RT and then concentrated by evaporation. The residue is taken up in methylene chloride and the solution is washed with saturated sodium hydrogen carbonate solution and brine. Extraction of the aqueous phases with 2 portions of methylene chloride, drying the organic phases with sodium sulfate and concentrating by evaporation yields the title compound, which is used in the next step without being further purified: $t_{Ref}$(I) =12.9.

EXAMPLE 19

N-Morpholinocarbonyl-(L)-Val-[Phe$^{NN}$(p-F)Phe]←(L)-Val)-H 160 mg (0.21 mmol) of N-morpholinocarbonyl-(L)-Val-[Phe$^{NN}$(p-F)Phe]←((L)-Val)-Z (Example 18) in 6 ml of ethanol are hydrogenated with 40 mg of palladium (10%) on carbon at normal pressure. Filtration through Celite® (siliceous earth, filter aid from Fluka, Buchs, Switzerland), concentration by evaporation and lyophilisation from dioxane yield the title compound: $t_{Ref}$(hydrochloride, I)=13.4 min; FAB-MS (M+H)$^+$=615.

EXAMPLE 20

N-Morpholinocarbonyl-(L)-Val-[Phe$^{NN}$(p-F)Phe]←(L)-Val)-(N-morpholinocarbonyl-Gly)

54 mg (0.143 mmol) of HBTU are added to a solution of 26.9 mg (0.143 mmol) of N-morpholinocarbonyl-glycine and 80 mg (0.130 mmol) of N-morpholinocarbonyl-(L)-Val-[Phe$^{NN}$(p-F)Phe]←((L)-Val)-H in 1.1 ml of 0.25M NMM/CH$_3$CN and the mixture is stirred for 16 h at RT. The mixture is concentrated by evaporation and the residue is partitioned between 3 portions of ethyl acetate and water and 2 portions of saturated sodium hydrogen carbonate solution, water and brine. The organic phases are dried with sodium sulfate and concentrated by evaporation to yield the title compound which, after dissolving in a small amount of DMF and precipitating with DIPE is obtained in pure form: $t_{Ref}$(I)= 15.1 min; FAB-MS (M+H)$^+$=785.

The starting material is prepared as follows:
a) N-Morpholinocarbonyl-glycine-benzyl ester Analogously to Example 7b), 7.69 g (22.8 mmol) of glycine-benzyl ester 4-toluenesulfonate and 2.8 g (19 mmol) of (morpholinocarbonyl)chloride in 118 ml of methylene chloride and 9 ml (53 mmol) of N-ethyldiisopropylamine are reacted for 18 h. The title compound is obtained in pure form after extraction with methylene chloride and digestion with hexane: $t_{Ref}$(I)=11.6 min.
b) N-Morpholinocarbonyl-glycine Analogously to Example 7a), 4.8 g (18.3 mmol) of N-morpholinocarbonyl-glycine-benzyl ester in 100 ml of ethyl acetate are hydrogenated with 1 g of palladium (10%) on carbon to yield the title compound: $^1$H-NMR (300 MHz, CDCl$_3$): 3.88 (s, 2H), 3.64 (s, 4H), 3.50 (s, 2H), 3.35 (s, 4H).

EXAMPLE 21

Z-(L)-Val-[Phe$^{NN}$(p-F)Phe]-Boc 463 mg (1.22 mmol) of HBTU are added to a solution of 335 mg (1.33 mmol) of Z-(L)-Val and 448 mg (1.11 mmol) of H-[Phe$^{NN}$(p-F)Phe]-Boc (for preparation see Example 17a)) in 9.4 ml of 0.25M NMM/CH$_3$CN (0.25M NMM in CH$_3$CN). After stirring for 16 h at RT, the mixture is concentrated by evaporation and the residue is partitioned between 3 portions of methylene chloride and 2 portions of saturated sodium hydrogen carbonate solution and brine. The organic phases are dried with sodium sulfate and concentrated by evaporation to yield the title compound, which is purified by column chromatography (SiO$_2$, hexane/ethyl acetate 4:1→1:1): $t_{Ref}$(I)=26.6 min; FAB-MS (M+H)$^+$=637.

EXAMPLE 22

Z-(L)-Val-[Phe$^{NN}$(p-F)Phe]←((L)-Val)-Boc

Analogously to Example 18, 165 mg (0.76 mmol) of Boc-(L)-Val and 371 mg (0.69 mmol) of Z-(L)-Val-[Phe$^{NN}$(p-F)Phe]-H in 6 ml of 0.25M NMM/CH$_3$CN are reacted with 289 mg (0.76 mmol) of HBTU to yield the title compound, which can be crystallised directly from the reaction solution and filtered off: $t_{Ref}$(I)=27.2 min; FAB-MS (M+H)$^+$=736.

The starting material is prepared as follows:
a) Z-(L)-Val-[Phe$^{NN}$(p-F)Phe]-H Analogously to Example 18a), 440 mg (0.69 mmol) of Z-(L)-Val-[Phe$^{NN}$(p-F)Phe]-Boc are deprotected with 212 ml of formic acid to yield the title compound: $t_{Ref}$(I)=17.8 min.

EXAMPLE 23

Z-(L)-Val-[Phe$^{NN}$(p-F)Phe]←((L)-Val)-H

Analogously to Example 18a), 250 mg (0.34 mmol) of Z-(L)-Val-[Phe$^{NN}$(p-F)Phe]←((L)-Val)-Boc (Example 22) are deprotected with 50 ml of formic acid to yield the title compound: $t_{Ref}$(I)=18.0 min; FAB-MS (M+H)$^+$=636.

EXAMPLE 24

Z-(L)-Val-[Phe$^{NN}$(p-F)Phe]←((L)-Val)←(N-morpholinocarbonyl-Gly)

Analogously to Example 20, 32 mg (0.17 mmol) of N-morpholinocarbonyl-glycine (Example 20b)) and 99 mg (0.16 mmol) of Z-(L)-Val-[Phe$^{NN}$(p-F)Phe]←((L)-Val)-H in 1.3 ml of 0.25M NMM/CH$_3$CN are reacted with 65 mg (0.17 mmol) of HBTU to yield the title compound, which crystallises directly from the reaction solution: $t_{Ref}$(I)=21.1 min; FAB-MS (M+H)$^+$=806.

EXAMPLE 25

Z-(L)-Asn-[Phe$^{NN}$(p-F)Phe]-Boc 3.0 g (7.8 mmol) of Z-(L)-asparagine-p-nitrophenyl ester (Bachem, Bubendorf/Switzerland) are added to a solution of 2.09 g (5.2 mmol) of H-[Phe$^{NN}$(p-F)Phe]-Boc (for preparation see Example 17a)) in 68 ml of DMF and 2.7 ml (16 mmol) of N-ethyl-diisopropylamine. The mixture is stirred for 16 h at RT and concentrated by evaporation under HV, and the residue is taken up in a large amount of methylene chloride (poorly soluble) and washed with 2 portions of 5% potassium carbonate solution. The aqueous phases are extracted twice more with a large amount of methylene chloride, and the combined organic phases are dried with sodium sulfate and concentrated by evaporation. The title compound is obtained by dissolving the crude product in a small amount of methanol and precipitating by the addition of toluene at −20° C.: $t_{Ref}$(I)=21.2 min.

EXAMPLE 26

H-(L)-Asn-[Phe$^{NN}$(p-F)Phe]-Boc

Analogously to Example 19, 0.40 g (0.61 mmol) of Z-(L)-Asn-[Phe$^{NN}$(p-F)Phe]-Boc are hydrogenated in 20 ml of methanol to yield the title compound: $t_{Ref}$(I)=14.9 min.

EXAMPLE 27

Quinoline-2-carbonyl-(L)-Asn-[Phe$^{NN}$(p-F)Phe]-Boc

Analogously to Example 17, 134 mg (0.78 mmol) of quinoline-2-carboxylic acid (Fluka, Buchs/Switzerland) in 4 ml of 0.3M NMM/DMF are reacted with 344 mg (0.78 mmol) of BOP, 105 mg (0.78 mmol) of HOBT and 268 mg (0.52 mmol) of H-(L)-Asn-[Phe$^{NN}$(p-F)Phe]-Boc. Since, according to HPLC, there is still some H-(L)-Asn-[Phe$^{NN}$(p-F)Phe]-Boc present after stirring for 16 h at RT, a further 299 mg of BOP, 70 mg of HOBT, 89 mg of quinaldic acid and 113 μl of NMM are added. After a further 16 h the mixture is concentrated by evaporation and the residue is partitioned between 3 portions of methylene chloride and 2 portions of saturated sodium hydrogen carbonate solution and brine. The combined organic phases are dried with sodium sulfate and concentrated by evaporation. The crude product is dissolved in a small amount of DMF, precipitated with DIPE and cooled to −20° C. to yield the title compound: $t_{Ref}(I)$=22.8 min; FAB-MS (M+H)$^+$=673.

EXAMPLE 28

Z-(L)-Asn-[Phe$^{NN}$(p-F)Phe]←((L)-Val)-Z 88 mg (0.35 mmol) of Z-(L)-Val in 3.8 ml of 0.3M NMM/DMF are activated with 153 mg (0.35 mmol) of BOP and 47 mg (0.35 mmol) of HOBT and, after 15 min, 144 mg (0.23 mmol) of Z-(L)-Asn-[Phe$^{NN}$(p-F)Phe]-H.2HCl are added. The reaction mixture is stirred for 14 h at RT and then concentrated by evaporation, the residue is dissolved in 2 ml of methanol and partitioned between 3 portions of methylene chloride and 2 portions of 1M sodium carbonate solution, and the organic phases are dried with sodium sulfate and concentrated by evaporation. Repeated dissolution of the crude product in a small amount of DMF and precipitation with DIPE yield the title compound: $t_{Ref}(I)$=22.2 min; FAB-MS (M+H)$^+$=785.

The starting material is prepared as follows:

a) Z-(L)-Asn-[Phe$^{NN}$(p-F)Phe]-H.2HCl

Under a nitrogen atmosphere, 2 ml of 4N HCl/dioxane (Fluka, Buchs/Switzerland) are added to a solution of 150 mg (0.23 mmol) of Z-(L)-Asn-[Phe$^{NN}$(p-F)Phe]-Boc (Example 25) in 1 ml of dioxane. The reaction mixture is stirred for 1.5 h at RT and then lyophilised, and the lyophilisate is directly further reacted.

EXAMPLE 29

Trifluoroacetyl-[Phe$^{NN}$(p-F)Phe]←((L)-Val)-Z

Analogously to Example 17, 239 mg (0.95 mmol) of Z-(L)-Val in 10.5 ml of 0.3M NMM/DMF are reacted for 15 h with 421 mg (0.95 mmol) of BOP, 129 mg (0.95 mmol) of HOBT and 0.3 g (0.63 mmol) of N-trifluoroacetyl-[Phe$^{NN}$(p-F)Phe]-H. Column chromatography (SiO$_2$, methylene chloride/ether 10:1) and precipitation from DMF solution with DIPE yield the title compound: TLC R$_f$(Q)0.15; $t_{Ref}$(I) =25.9 min; FAB-MS (M+H)$^+$=633.

The starting material is prepared as follows:

a) N-Trifluoroacetyl-[Phe$^{NN}$(p-F)Phe]-H

At 0° C., 5 ml of trifluoroacetic acid are added to 0.20 g (0.40 mmol) of N-trifluoroacetyl-[Phe$^{NN}$(p-F)Phe]-Boc (for preparation see Example 16) in 5 ml of methylene chloride. The reaction mixture is stirred for 4 h at 0° C. and for 2 h at RT and then concentrated by evaporation. Lyophilisation of the residue from dioxane yields the title compound, which is further reacted without being purified: $t_{Ref}(I)$=14.7 min.

EXAMPLE 30

Z-(L)-Asn-[Phe$^{NN}$Phe]-Boc

Analogously to Example 25, 167 mg (0.34 mmol) of H-[Phe$^{NN}$Phe]-Boc in 3.6 ml of DMF and 0.18 ml (1 mmol) of N-ethyl-diisopropylamine are reacted with 0.20 g (0.52 mmol) of Z-(L)-asparagine-p-nitrophenyl ester to yield the title compound, which is obtained in pure form by column chromatography (SiO$_2$, ethyl acetate): TLC R$_f$(O)=0.19; $t_{Ref}(I)$=20.9 min.

The starting material is prepared as follows:

a) N-Trifluoroacetyl-[Phe$^{NN}$Phe]-Boc

Analogously to Example 16, 1.82 g (7.0 mmol) of 2(R)-[1'(S)-(trifluoroacetylamino)-2'-phenylethyl]-oxirane (Example 16d)) and 1.58 g (7.1 mmol) of tert-butyl-3-benzylcarbazate (J. Chem., Perkin I, 1712 (1975)) in 15 ml of methanol are reacted in a bomb tube to yield the title compound, which is isolated by column chromatography (SiO$_2$, methylene chloride/ether 50:1): TLC R$_f$(J)=0.38; $t_{Ref}(I)$=24.5 min.

b) H-[Phe$^{NN}$Phe]-Boc

Analogously to Example 17a), 258 mg (0.53 mmol) of N-trifluoroacetyl-[Phe$^{NN}$Phe]-Boc in 60 ml of methanol are reacted with 10.7 ml of 1M potassium carbonate solution to yield the title compound.

EXAMPLE 31

Z-(L)-Val-[(p-F)Phe$^{NN}$(p-F)Phe]-Boc

Analogously to Example 21, 18 mg (0.070 mmol) of Z-(L)-Val and 27 mg (0.064 mmol) of H-[(p-F)Phe$^{NN}$(p-F)Phe]-Boc in 0.6 ml of 0.25M NMM/CH$_3$CN are reacted with 26.6 mg (0.070 mmol) of HBTU to yield the title compound, which is purified by dissolving in a small amount of methylene chloride and precipitating with DIPE: FAB-MS (M+H)$^+$=655.

The starting material is prepared as follows:

a) N-Boc-(p-fluorophenylalanine)

In 0.4 l of dioxane/water 1:1 20 g (109 mmol) of p-fluorophenylalanine (Fluka, Buchs, Switzerland) are reacted with 35.5 g (163 mmol) of Boc-anhydride and 150 g (1.09 mol) of potassium carbonate. After 4 h, the reaction mixture is acidified with citric acid solution and extracted with 3 portions of ethyl acetate. The organic phases are washed with 10% citric acid, water and brine, dried with sodium sulfate and concentrated by evaporation. Dissolution of the residue in a small amount of methylene chloride and crystallisation by the addition of hexane yields the title compound: $t_{Ref}(I)$=16.9 min.

b) N-Boc-(p-fluorophenylalaninol)

At from −5° C. to −10° C. 9.66 ml (69 mmol) of triethylamine are added to a solution of 17.9 g (63 mmol) of N-Boc-(p-fluorophenylalanine) in 73 ml of abs. THF, and a solution of 9.05 ml (69 mmol) of chloroformic acid isobutyl ester in 44 ml of abs. THF is added dropwise thereto. After stirring for 0.5 h at RT, the resulting precipitate is filtered off with suction. The filtrate is added dropwise, with cooling, to 4.77 g (126 mmol) of sodium borohydride in 28 ml of water. The mixture is stirred for 4 h at RT and acidified with 10% citric acid, the THF is partially removed by evaporation using a RE and the residue is partitioned between 3 portions of ethyl acetate and 2 portions of 2N sodium hydroxide solution, water, saturated sodium hydrogen carbonate solution and brine. The organic phases are dried with sodium sulfate, concentrated by evaporation, dissolved in a small amount of methylene chloride and crystallised by the addition of hexane to yield the title compound: TLC $R_f(N)=0.36$; $t_{Ret}(I)=16.8$ min; $^1$H-NMR (200 MHz, CD$_3$OD): 7.24 (dd, 8 and 5 Hz, 2H), 6.98 (t, 8 Hz, 2H), 3.73 (m, 1H), 3.47 (d, 5 Hz, 2H), 2.88 (dd, 13 and 6 Hz, 1H), 2.62 (dd, 13 and 8 Hz, 1H), 1.36 (s, 9H).

c) N-Boc-(p-fluorophenylalaninal)

Under a nitrogen atmosphere, 4.44 ml (62.4 mmol) of DMSO dissolved in 76 ml of methylene chloride are added dropwise to a solution, cooled to −60° C., of 4.0 ml (46.8 mmol) of oxalyl chloride in 44 ml of methylene chloride. After stirring for 15 minutes, resulting in a clear reaction solution, 8.4 g (31.2 mmol) of N-Boc-(p-fluorophenylalaninol) in the form of a solution in 185 ml of methylene chloride/THF 1:1 are added (→precipitation) and the mixture is then stirred for 25 min. 17.3 ml (124.8 mmol) of triethylamine dissolved in 38 ml of methylene chloride are then added. After the mixture has been stirred for 30 min, 278 ml of a 20% potassium hydrogen sulfate solution are added dropwise, followed by 220 ml of hexane. The mixture is left to warm to RT, and the aqueous phase is removed and extracted with 2 portions of ether. The organic phases are washed with saturated sodium hydrogen carbonate solution, water and brine, dried with sodium sulfate and concentrated by evaporation to yield the title compound, which is used in the next step without being further purified: $^1$H-NMR (200 MHz, CDCl$_3$): 9.63 (s, 1H), 6.9–7.2 (2m, 4H), 5.04 (m, 1H), 4.42 (m, 1H), 3.10 (m, 2H), 1.43 (s, 9H).

d) N-3(S)-(Boc-amino)-2(R,S)-hydroxy-4-(p-fluorophenyl)-1-trimethylsilyl-butane

Analogously to Example 16a), 1.63 g (67 mmol) of magnesium in 33 ml of abs. ether are reacted with 8.3 ml (60 mmol) of chloromethyltrimethylsilane to form the Grignard compound which, after reaction with 13 mmol of N-Boc-(p-fluorophenylalaninal), extraction and column chromatography (SiO$_2$, hexane/ethyl acetate 5:1→4:1), yields the title compound in the form of a diastereoisomeric mixture: TLC $R_f(L)=0.32$; $t_{Ret}(I)=24.9$ min (22%)/25.5 min (78%); FAB-MS (M+H)$^+$=356.

e) 1-(p-Fluorophenyl)-3-buten-2(S)-amine p Analogously to Example 16b), 1.1 g (3.1 mmol) of N-3(S)-(Boc-amino)-2 (R,S)-hydroxy-4-(p-fluorophenyl)-1-trimethylsilyl-butane in 22 ml of methylene chloride are reacted with 1.9 ml (15.5 mmol) of an approximately 48% solution of boron trifluoride in ether to yield the title compound: $^1$H-NMR (300 MHz, CDCl$_3$): 7.2–7.10 and 7.05–6.9 (2m, each 2 H), 5.9–5.8 (m, 1H), 5.2–5.0 (m, 2H), 3.57 (m, 1H), 2.79 (dd, 12 and 6H), 2.62 (dd, 12 and 8 Hz, 1H), 1.7 (sb, 2H).

f) N-Trifluoroacetyl-1-(p-fluorophenyl)-3-buten-2(S)-amine

Analogously to Example 16c), 364 mg (2.2 mmol) of 1-(p-fluorophenyl)-3-buten-2(S)amine in 1.8 ml of methylene chloride and 5.4 ml of pyridine are reacted with 460 µl (3.3 mmol) of trifluoroacetic acid anhydride to yield the title compound, which after digestion with hexane is obtained in pure form: TLC $R_f(F)=0.58$; MS (M)$^+$=261.

g) 2(R)-[1'(S)-(Trifluoroacetylamino)-2'-(p-fluorophenyl)ethyl]-oxirane

Analogously to Example 16d), 359 mg (1.37 mmol) of N-trifluoroacetyl-1-(p-fluorophenyl)-3-buten-2(S)-amine in 9 ml of chloroform are oxidised with 1.18 g (6.87 mmol) of m-chloroperbenzoic acid to yield the title compound: TLC $R_f(R)=0.45$.

h) N-Trifluoroacetyl-[(p-F)Phe$^{NN}$(p-F)Phe]-Boc

Analogously to Example 16.415 mg (1.49 mmol) of 2(R)-[1'(S)-(trifluoroacetylamino)-2'-(p-fluorophenyl)ethyl]-oxirane and 377 mg (1.57 mmol) of tert-butyl-3-(p-fluorophenyl-methyl)-carbazate in 9 ml of methanol are reacted to yield the title compound: TLC $R_f(S)=0.53$; FAB-MS (M+H)$^+$=518; $^1$H-NMR (300 MHz, CD$_3$OD): 7.4–7.3 and 7.3–7.2 (2m, each 2H), 7.05–6.9 (m, 4H), 4.23 (m, 1H), 3.90–3.65 (m, 3H), 3.03–2.78 and 2.74–2.60 (2m, each 2H), 1.30 (s, 9H).

i) H-[(p-F)Phe$^{NN}$(p-F)Phe]-Boc

Analogously to Example 17a), 285 mg (0.55 mmol) of N-trifluoroacetyl-[(p-F)Phe$^{NN}$(p-F)Phe]-Boc in 45 ml of methanol are reacted with 14 ml of 1M potassium carbonate solution to yield the title compound: $t_{Ret}(I)=16.4$ min.

EXAMPLE 32

Z-(L)-Val-[(p-F)Phe$^{NN}$(p-F)Phe]-H

Analogously to Example 18a), 215 mg (0.33 mmol) of Z-(L)-Val-[(p-F)Phe$^{NN}$(p-F)Phe]-Boc are deprotected with 100 ml of formic acid to yield the title compound: FAB-MS (M+H)$^+$=555.

EXAMPLE 33

Z-(L)-Val-[(p-F)Phe$^{NN}$(p-F)Phe]←(N-(N-(2-pyridylmethyl)-N-methylaminocarbonyl)-(L)-Val)

Analogously to Example 18, 23.6 mg (0.089 mmol) of N-(N-(2-pyridylmethyl)-N-methylaminocarbonyl)-(L)-valine (for preparation see EP 402646 A1, 19th Dec. 1990) and 45 mg (0.081 mmol) of Z-(L)-Val-[(p-F)Phe$^{NN}$(p-F) Phe]-H are reacted with 33.8 mg (0.089 mmol) of HBTU in 0.76 ml of 0.25M NMM/CH$_3$CN to yield the title compound which is recrystallised with DMF/DIPE: TLC $R_f(O)=0.39$; FAB-MS (M+H)$^+$=802.

EXAMPLE 34

Z-(L)-Val-[(p-F)Phe$^{NN}$(p-F)Phe]←(N-(2(R,S)-carbamoyl-3-phenyl-propionyl)(L)-Val)

Analogously to Example 18, 26.0 mg (0.089 mmol) of N-(2(R,S)-carbamoyl-3-phenyl-propionyl)-(L)-valine (preparation: Synth., Struct., Funct., Proc. Am. Pept. Symp., 7$^{th}$, 85, (1981)) and 45 mg (0.081 mmol) of Z-(L)-Val-[(p-F)Phe$^{NN}$(p-F)Phe]-H (Example 32) are reacted with 33.8 mg (0.089 mmol) of HBTU in 0.76 ml of 0.25M NMM/CH$_3$CN to yield the title compound which is recrystallised with DMF/DIPE: $R_f(P)=0.64$; FAB-MS (M+H)$^+$=829.

EXAMPLE 35

Acetyl-Val-[Phe$^{NN}$Phe]←(N-acetyl-Val)

Analogously to Example 7, the title compound is obtained from 100 mg (0.25 mmol) of H-[Phe$^{NN}$Phe]-H.3HCl from Example 2a), 121 mg (0.76 mmol) of N-acetyl-(L)-valine, 288 mg (0.76 mmol) of HBTU and 0.211 ml (1.52 mmol) of triethylamine in DMF after lyophilisation from dioxane. FAB-MS: (M+H)$^+$=568, $t_{Ret}(I)=15.0$ min., $R_f(B)=0.46$.

EXAMPLE 36

Z-(D)-Val-[Phe$^{NN}$Phe]←((D)-Val)-Z

Analogously to Example 2, the title compound is obtained from 50 mg (0.123 mmol) of H-[Phe$^{NN}$Phe]-H.3HCl from Example 2a), 95 mg (0.38 mmol) of Z-(D)-valine, 168 mg (0.38 mmol) of BOP, 51 mg (0.38 mmol) of HOBt and 2.53 ml of 0.3M NMM in DMF after lyophilisation from dioxane. FAB-MS: (M+H)$^+$=752, $t_{Ret}(I)=26.4$ min, $R_f(H)=0.21$.

EXAMPLE 37

Quinoline-2-carbonyl-Val-[Phe$^{NN}$Phe]→(N-quinoline-2-carbonyl-Val)

145 mg (0.53 mmol) of N-(quinoline-2-carbonyl)-(L)-valine, 235 mg (0.53 mmol) of BOP and 72 mg (0.53 mmol)

of HOBt are dissolved in 3.5 ml of a 0.3M solution of NMM in DMF, after 10 min 70 mg (0.18 mmol) of H-[Phe$^{NN}$Phe]-H.HCl (Example 2a)) are added, and the mixture is stirred for 5 h at RT under a nitrogen atmosphere. The reaction mixture is concentrated by evaporation and the residue is dissolved in methylene chloride and washed twice with saturated sodium hydrogen carbonate solution, once with 10% citric acid and once again with saturated sodium hydrogen carbonate solution. The organic phases are filtered through cotton wadding and concentrated by evaporation, and the residue is precipitated twice from methylene chloride/methanol by the addition of DIPE. Lyophilisation from dioxane yields the title compound in the form of a white solid (mixture of two diastereoisomers differentiable by HPLC). FAB-MS: (M+H)$^+$=794, $t_{Ref}$(A)=29.1 and 29.3 min, $R_f$(B)=0.81.

a) N-(Quinoline-2-carbonyl)-(L)-valine 3.28 g (15.9 mmol) of N,N-dicyclohexylcarbodiimide and 2.0 ml (14.5 mmol) of triethylamine are added to a solution of 2.5 g (14.5 mmol) of (L)-valyl-tert-butyl ester and 2.5 g (14.5 mmol) of quinoline-2-carboxylic acid in 100 ml of methylene chlorides (10:1) and the mixture is stirred for 18 h at RT. The reaction mixture is cooled to −18° and filtered off from the urea. The filtrate is concentrated by evaporation, and the residue is dissolved in methylene chloride and washed once with saturated sodium hydrogen carbonate solution and once with water. The organic phases are filtered through cotton wadding, concentrated by evaporation and, after chromatographic purification on silica gel with hexane/ethyl acetate (2:1), yield N-(quinoline-2-carbonyl)-(L)-valyl-tert-butyl ester. 2.59 g (12.2 mmol) thereof are left at RT in methylene chloride/TFA (1:1) for 4.5 h. After concentration by evaporation the residue is purified by chromatography on silica gel with hexane/ethyl acetate (2:1). The product-containing fractions are concentrated by evaporation, dissolved in methylene chloride again, and converted into the hydrochloride of the title compound by washing with 1N sodium hydroxide solution and 1N hydrochloric acid. $^1$H-NMR (200 MHz, CD$_3$OD): 1.05 and 1.07 (2 d, J=6 Hz, 6H), 2.40 (m, 1H), 4.65 (m, 1H), 7.70 (m, 1H), 7.85 (m, 1H), 8.00 (dxd, 1H), 8.20 (m, 2H), 8.48 (d, 1H).

EXAMPLE 38

Acetyl-(L)-Val-[Phe$^{NN}$Cha]←-(N-acetyl-(L)-Val)

Analogously to Example 37, the title compound is obtained from 160 mg (0.40 mmol) of H-[Phe$^{NN}$Cha]-H.3HCl from Example 10a), 190 mg (1.19 mmol) of N-acetyl-(L)-valine, 525 mg (1.19 mmol) of BOP, 160 mg (1.19 mmol) of HOBt and 7.9 ml of 0.3M NMM in DMF after precipitation from chloroform/methanol with DIPE and lyophilisation from dioxane. FAB-MS: (M+H)$^+$=574, $t_{Ref}$(I)=18.1 min, $R_f$(B)=0.30.

EXAMPLE 39

N-(3-Pyridylacetyl)-(L)-Val-[Phe$^{NN}$Cha]←(N-(3-pyridylacetyl)-(L)-Val).3HCl

Analogously to Example 7, the title compound is obtained from 100 mg (0.25 mmol) of H-[Phe$^{NN}$Cha]-H.3HCl from Example 10a), 358 mg (1.52 mmol) of N-(3-pyridylacetyl)-(L)-valine from Example 9a), 576 mg (1.52 mmol) of HBTU and 0.316 ml (2.28 mmol) of triethylamine in DMF after chromatographic purification on silica gel with methylene chloride/methanol (15:1) and lyophilisation of the product-containing fractions from dioxane. FAB-MS: (M+H)$^+$=728, $t_{Ref}$(I)=11.3 min, $R_f$(U)=0.21.

EXAMPLE 40

Acetyl-Ile-[Phe$^{NN}$Cha]←(N-acetyl-Ile)

Analogously to Example 37, the title compound is obtained from 160 mg (0.40 mmol) of H-[Phe$^{NN}$Cha]-H.3HCl from Example 10a), 206 mg (1.19 mmol) of N-acetyl-(L)-isoleucine, 525 mg (1.19 mmol) of BOP, 160 mg (1.19 mmol) of HOBt and 7.9 ml of 0.3M NMM in DMF after precipitation from methylene chloride/methanol by the addition of DIPE and lyophilisation from dioxane/tert-butanol (mixture of 2 diastereoisomers differentiable by HPLC). FAB-MS: (M+H)$^+$=602, $t_{Ref}$(I)=20.4 and 20.7 min, $R_f$(D)=0.33.

EXAMPLE 41

Thiomorpholinocarbonyl-(L)-Val-[Phe$^{NN}$Cha]←(N-thiomorpholinocarbonyl-(L)-Val)

Analogously to Example 6, the title compound is obtained starting from 70 mg (0.12 mmol) of H-(L-Val)-[Phe$^{NN}$Cha]←(N-(L)-Val)-H.3HCl from Example 14, 58 mg (0.35 mmol) of (4-thiomorpholinylcarbonyl)chloride from Example 6a) and 0.127 ml of triethylamine in 2 ml of DMF after chromatographic purification on silica gel with methylene chloride/methanol (95:5) and lyophilisation of the product-containing fractions from dioxane. FAB-MS: (M+H)$^+$=748, $t_{Ref}$(I)=24.0 min, $R_f$(B)=0.70.

EXAMPLE 42

Z-(L)-Glu-[Phe$^{NN}$(p-F)Phe]←((L)-Glu)-Z

A solution of 130 mg (0.14 mmol) of Z-(L)-Glu(O-tert-butyl)-[Phe$^{NN}$(p-F)Phe]←((L)-Glu(O-tert-butyl))-Z [(Glu (O-tert-butyl) here denotes the radical of glutamic acid esterified at the γ-carboxy group by a tert-butyl radical] in 8 ml of methylene chloride/TFA (1:1) is stirred for 3 h at RT. The solvent is evaporated off under reduced pressure and the residue is precipitated from methylene chloride by the addition of DIPE. The title compound is obtained after lyophilisation from dioxane/tert-butanol. FAB-MS: (M+H)$^+$=830, $t_{Ref}$(I)=19.6 min, $R_f$(B)=0.32.

a) Z-(L)-Glu(O-tert-butyl)-[Phe$^{NN}$(p-F)Phe]←((L)-Glu(O-tert-butyl))-Z

Analogously to Example 37, the title compound is obtained from 100 mg (0.24 mmol) of H-[Phe$^{NN}$(p-F)Phe]-H.3HCl, 245 mg (0.73 mmol) of Z-(L)-glutamic acid tert-butyl ester, 321 mg (0.73 mmol) of BOP, 98 mg (0.73 mmol) of HOBt and 4.8 ml of 0.3M NMM in DMF after chromatographic purification on silica gel with methylene chloride/ether (1:1). $t_{Ref}$(I)=30.2 min, $R_f$(H)=0.17.

b) H-[Phe$^{NN}$(p-F)Phe]-H.3HCl

Analogously to Example 2a), the title compound is obtained from 1.77 g (3.51 mmol) of Boc-[Phe$^{NN}$(p-F)Phe]-Boc after lyophilisation. FAB-MS: (M+H)$^+$=304, $R_f$(K)=0.19.

c) Boc-[Phe$^{NN}$(p-F)Phe]-Boc

Analogously to Example 1, the title compound is obtained starting from 2.0 g (7.60 mmol) of (2R)-[1'(S)-Boc-amino-2'-phenylethyl]oxirane and 2.17 g (9.04 mmol) of tert-butyl-3-(4-fluorophenyl-methyl)-carbazate from Example 16f) after chromatographic purification on silica gel with hexane/ethyl acetate (2:1). FAB-MS: (M+H)$^+$=504, $t_{Ref}$(I)=26.2 min, $R_f$(F)=0.26.

EXAMPLE 43

N-(2-Pyridylmethyl)-N-methylaminocarbonyl-(L)-Val-[Phe$^{NN}$(p-F)-Phe]←(N-(N-(2-pyridylmethyl)-N-methylaminocarbonyl)-(L)-Val)

Analogously to Example 37, the title compound is obtained from 70 mg (0.17 mmol) of H-[Phe$^{NN}$(p-F)Phe]-

H.3HCl from Example 42b), 135 mg (0.51 mmol) of N-(N-(2-pyridyl-methyl)-N-methylaminocarbonyl)-(L)-valine (preparation as described in EP 0 402 646 A1 of 19th Dec. 1990), 225 mg (0.51 mmol) of BOP, 69 mg (0.51 mmol) of HOBt and 3.4 ml of 0.3M NMM in DMF after chromatography on silica gel with methylene chloride/methanol (15:1) and lyophilisation of the product-containing fractions from dioxane. FAB-MS: $(M+H)^+=798$, $t_{Ref}(IV)=35$ min, $R_f(U)=0.21$.

EXAMPLE 44

N-(3-(Tetrazol-1-yl)-propionyl)-Val-[Phe$^{NN}$(p-F)Phe]←(N-(3-(tetrazol-1-yl)-propionyl)-Val)

Analogously to Example 37, the title compound is obtained from 100 mg (0.24 mmol) of H-[Phe$^{NN}$)p-F)Phe]-H.3HCl (from Example 42b), 146 mg (0.61 mmol) of N-(3-(tetrazol-1-yl)-propionyl)-(L)-valine, 268 mg (0.61 mmol) of BOP, 82 mg (0.61 mmol) of HOBt and 4 ml of 0.3M NMM in DMF after precipitation from methylene chloride by the addition of DIPE and lyophilisation from dioxane (4 diastereoisomers differentiable by HPLC). FAB-MS: $(M+H)^{30}=750$, $t_{Ref}(III)=30.8; 31.4; 32.4$ and $32.8$ min, $R_f(K)=0.5$.

EXAMPLE 44a

N-(3-(Tetrazol-1-yl)-propionyl)-(L)-valine

Analogously to Example 9b, starting from 4 g (16.4 mmol) of (L)-valine-benzyl ester.HCl, 2.1 g (14.9 mmol) of 3-(tetrazol-1-yl)-propionic acid (preparation: U.S. Pat. No. 4,794,109 A of 27th Dec. 1988), 2.4 ml of cyanophosphonic acid diethyl ester and 4.4 ml of triethylamine in DMF, N-(3-(tetrazol-1-yl)-propionyl)-(L)-valine-benzyl ester is obtained after chromatographic purification on silica gel with methylene chloride/methanol (30:1). 2.66 g (8.03 mmol) thereof are hydrogenated in methanol/water (9:1) in the presence of 530 mg of 10% palladium on carbon, at 1 atm hydrogen pressure, to yield the title compound after precipitation from methanol/DIPE. $^1$H-NMR (200 MHz, CD$_3$OD): 0.9 (d, J=7 Hz, 6H), 2.1 (m, 1H), 2.95 (m, 2H), 4.29 (d, J=6 Hz, 1H), 4.78 (m, 2H), 9.15 (s, 1H).

EXAMPLE 45

Z-(L)-Val-[Phe$^{NN}$(p-F)Phe]←((L)-Val)-Z

Analogously to Example 37, the title compound is obtained from 100 mg (0.24 mmol) of H-[Phe$^{NN}$(p-F)Phe]-H.3HCl (from Example 42b), 182 mg (0.38 mmol) of Z-(L)-valine, 321 mg (0.73 mmol) of BOP, 98 mg (0.73 mmol) of HOBt and 4.8 ml of 0.3M NMM in DMF after precipitation from methylene chloride by the addition of DIPE and lyophilisation from dioxane. FAB-MS: $(M+H)^+=770$, $t_{Ref}(I)=26.3$ min, $R_{f(H)}=0.25$.

EXAMPLE 46

Acetyl-Val-[Phe$^{NN}$(p-F)Phe]←(N-acetyl-Val)

Analogously to Example 37, the title compound is obtained from 80 mg (0.19 mmol) of H-[Phe$^{NN}$(p-F)Phe]-H.3HCl from Example 42b), 124 mg (0.78 mmol) of N-acetyl-(L)-valine, 344 mg (0.78 mmol) of BOP, 105 mg (0.76 mmol) of HOBt and 4.5 ml of 0.3M NMM in DMF after reprecipitation twice from methylene chloride/methanol by the addition of DIPE and lyophilisation from dioxane/tert-butanol. FAB-MS: $(M+H)^+=586$, $t^{Ref}(I)=15.8$ min, $R_f(E)=0.32$.

EXAMPLE 47

Acetyl-Val-[Phe$^{NN}$(p-CN)Phe]←(N-acetyl-Val)

Analogously to Example 37, the title compound is obtained in the form of a mixture of 2 diastereoisomers differentiable by HPLC from 80 mg (0.19 mmol) of H-[Phe$^{NN}$(p-CN)Phe]-H.3HCl, 124 mg (0.78 mmol) of N-acetyl-(L)-valine, 344 mg (0.78 mmol) of BOP, 105 mg (0.78 mmol) of HOBt and 4.5 ml of 0.3M NMM in DMF after precipitation from methylene chloride/methanol by the addition of DIPE and lyophilisation from dioxane. FAB-MS: $(M+H)^+=593$, $t_{Ref}(I)=14.4$ and $14.6$ min, $R_f(D)=0.39$.

a) H-[Phe$^{NN}$(p-CN)Phe]-H.3HCl

Analogously to Example 2a), the title compound is obtained from 2.69 g (5.27 mmol) of Boc-[Phe$^{NN}$(p-CN)Phe]-Boc after lyophilisation. FAB-MS: $(M+H)^+=311$, $R_f(K)=0.16$.

b) Boc-[Phe$^{NN}$(p-CN)Phe]-Boc

Analogously to Example 1, the title compound is obtained from 2.0 g (7.60 mmol) of (2R)-[1'(S)-Boc-amino-2'-phenylethyl]oxirane and 1.87 g (7.6 mmol) of tert-butyl-3-(4-cyanophenyl-methyl)-carbazate after crystallisation from methanol/DIPE. FAB-MS: $(M+H)^+=511$, $t_{Ref}(I)=25$ min, $R_f(Y)=0.19$.

c) tert-Butyl-3-(4-cyanophenyl-methyl)-carbazate

Analogously to Example 4b), 10 g (76.3 mmol) of 4-cyanobenzaldehyde and 10 g (76.3 mmol) of tert-butylcarbazate in ethanol are reacted to yield 4-cyanophenylcarbaldehyde-tert-butoxycarbonylhydrazone. 11.1 g thereof are hydrogenated in 150 ml of THF in the presence of 2 g of 10% palladium on carbon at 2 atm hydrogen pressure to yield the title compound. $^1$H-NMR (200 MHz, CDCl$_3$): 7.65 (d, J=8 Hz, 2H), 7.45 (d, J=8 Hz, 2H), 6.08 (s, br, 1H), 4.3 (s, br, 1H), 4.02 (s, 2H), 1.45 (s, 9H).

EXAMPLE 48

Z-(L)-Val-[Phe$^{NN}$(p-CN)Phe]←((L)-Val)-Z

Analogously to Example 37, the title compound is obtained from 70 mg (0.17 mmol) of H-[Phe$^{NN}$(p-CN)Phe]-H.3HCl (from Example 47a)), 125 mg (0.5 mmol) of Z-(L)-valine, 221 mg (0.5 mmol) of BOP, 68 mg (0.5 mmol) of HOBt and 3.33 ml of 0.3M NMM in DMF after precipitation from methylene chloride by the addition of hexane and lyophilisation from dioxane. FAB-MS: $(M+H)^+=777$, $t_{Ref}(I)=25.3$ min, $R_f(D)=0.69$.

EXAMPLE 49

Z-(L)-Ile-[Phe$^{NN}$Leu]←((L)-Ile)-Z

Analogously to Example 37, the title compound is obtained from 70 mg (0.19 mmol) of H-[Phe$^{NN}$Leu]-H.3HCl (from Example 13a)), 154 mg (0.58 mmol) of Z-(L)-isoleucine, 257 mg (0.58 mmol) of BOP, 79 mg (0.58 mmol) of HOBt and 3.88 ml of 0.3M NMM in DMF after chromatography on silica gel with methylene chloride/ether (3:1) and precipitation of the product-containing fractions from methylene chloride/DIPE and lyophilisation from dioxane. FAB-MS: $(M+H)^+=746$, $t_{Ref}(I)=28.2$ min, $R_f(H)=0.39$.

EXAMPLE 50

Isobutoxycarbonyl-(L)-Val-[Phe$^{NN}$Leu]←(N-isobutoxycarbonyl-(L)-Val)

Analogously to Example 37, the title compound is obtained from 70 mg (0.19 mmol) of H-[Phe$^{NN}$Leu]-H.3HCl (from Example 13a)), 130 mg (0.58 mmol) of N-(isobutoxycarbonyl)-(L)-valine, 256 mg (0.58 mmol) of BOP, 78 mg (0.58 mmol) of HOBt and 3.9 ml of 0.3M NMM in DMF after chromatography on silica gel with methylene chloride/ether (1:1) and lyophilisation of the product-containing fractions from dioxane. FAB-MS: (M+H)⁺=650, $t_{Ref}(I)$=26.4 min, $R_f(H)$=0.38.

a) N-(Isobutoxycarbonyl)-(L)-valine 11.2 ml (85.3 mmol) of isobutyl chloroformate are added to a solution of 10 g (85.3 mmol) of (L)-valine in 100 ml of 2N sodium hydroxide solution and the solution is stirred at RT for 18 h. The reaction solution is washed with methylene chloride, acidified with 4N hydrochloric acid and extracted with methylene chloride. The organic extracts are washed with brine and filtered through cotton wadding to yield the title compound in the form of a colourless resin after concentration by evaporation. ¹H-NMR (200 MHz, CD₃OD): 0.95 (m, 12H), 1.9 (m, 1H), 2.15 (m, 1H), 3.85 (d, J=7 Hz, 2H), 4.05 (d broad, 1H).

EXAMPLE 51

N-(3-(Tetrazol-1-yl)-propionyl)-(L)-Val-[Phe$^{NN}$Leu] ←(N-3-(tetrazol-1-yl)-propionyl-(L)-Val)

Analogously to Example 37, the title compound is obtained from 150 mg (0.42 mmol) of H-[Phe$^{NN}$Leu]-H.3HCl (from Example 13a)), 251 mg (1.04 mmol) of N-(3-(tetrazol-1-yl-propionyl)-(L)-valine from Example 44a, 460 mg (1.04 mmol) of BOP, 140 mg (1.04 mmol) of HOBt and 6.9 ml of 0.3M N-methylmorpholine in DMF after precipitation from methylene chloride/DIPE and lyophilisation from dioxane/tert-butanol/water. FAB-MS: (M+H)⁺=689, $t_{Ref}(I)$=14.7 min, $R_f(K)$=0.36.

EXAMPLE 52

Acetyl-Val-[Phe$^{NN}$Leu]←-(N-acetyl-Val)

Analogously to Example 37, the title compound is obtained from 70 mg (0.19 mmol) of H-[Phe$^{NN}$Leu]-H.3HCl (from Example 13a)), 184 mg (1.16 mmol) of N-acetyl-(L)-valine, 512 mg (1.16 mmol) of BOP, 156 mg (1.16 mmol) of HOBt and 7.8 ml of 0.3M NMM in DMF after precipitation from methylene chloride/methanol by the addition of DIPE and lyophilisation from dioxane/tert-butanol/water (2 diastereoisomers differentiable according to HPLC). FAB-MS: (M+H)⁺=534, $t_{Ref}(I)$=14.7 and 15.1 min, $R_f(D)$=0.35.

EXAMPLE 53

Boc-(L)-Val-[Phe$^{NN}$Leu]←((L)-Val)-Boc

Analogously to Example 7, the title compound is obtained from 300 mg (0.83 mmol) of H-[Phe$^{NN}$Leu]-H.3HCl (from Example 13a)), 722 mg (3.33 mmol) of Boc-(L)-valine, 1.262 g (3.33 mmol) of HBTU and 0.927 ml (6.66 mmol) of triethylamine in DMF after chromatographic purification on silica gel with methylene chloride/ether (1:1), precipitation of the product-containing fractions and lyophilisation from dioxane. FAB-MS: (M+H)⁺=650, $t_{Ref}(I)$=26.3 min, $R_f(H)$=0.64.

EXAMPLE 54

H-(L)-Val-[Phe$^{NN}$Leu]←((L)-Val)-H.3HCl

Analogously to Example 5, the title compound is obtained from 396 mg (0.61 mmol) of Boc-(L)-Val-[Phe$^{NN}$Leu]←((L)-Val)-Boc from Example 53 and 10 ml 4N hydrogen chloride in dioxane after lyophilisation of the reaction solution. FAB-MS: (M+H)⁺=450, $t_{Ref}(II)$=24.1 min, $R_f(K)$=0.25.

EXAMPLE 55

N-Thiomorpholinocarbonyl-(L)-Val-[Phe$^{NN}$Leu←(N-thiomorpholinocarbonyl(L)-Val)

Analogously to Example 6, the title compound is obtained in the form of an amorphous solid starting from 100 mg (0.16 mmol) of H-(L)-Val-[Phe$^{NN}$Leu]←(L)-Val-H.3HCl, 78.5 mg (0.47 mmol) of (4-thiomorpholinylcarbonyl) chloride from Example 6a and 0.172 ml of triethylamine in DMF after chromatographic purification on silica gel with methylene chloride/methanol (95:5), precipitation of the product-containing fractions from methylene chloride/hexane and lyophilisation from dioxane. FAB-MS: (M+H)⁺=708, $t_{Ref}(I)$=21.4 min, $R_f(E)$=0.45.

EXAMPLE 56

2(R,S)-Tetrahydrofuryl-methoxycarbonyl-(L)-Val-[Cha$^{NN}$Leu]←(N-2(R,S)-tetrahydrofuryl-methoxycarbonyl-(L)-Val)

Analogously to Example 37, the title compound is obtained from 80 mg (0.22 mmol) of H-[Cha$^{NN}$Leu]-H.3HCl, 160 mg (0.65 mmol) of N-(2(R,S)-tetrahydrofuryl-methoxycarbonyl)-(L)-valine, 289 mg (0.65 mmol) of BOP, 88 mg (0.65 mmol) of HOBt and 4.35 ml of 0.3M NMM in DMF after chromatographic purification on silica gel with ethyl acetate and lyophilisation of the product-containing fractions from dioxane. FAB-MS: (M+H)⁺=712, $t_{Ref}(I)$=22.4 min, $R_f(E)$=0.21.

a) H-[Cha$^{NN}$Leu]-H.3HCl

Analogously to Example 5, 100 mg (83%) of the title compound are obtained from 150 mg (0.33 mmol) of Boc-[Cha$^{NN}$Leu]-Boc and 10 ml of 4N hydrogen chloride in dioxane after lyophilisation of the reaction solution. $R_f(K)$=0.26.

b) Boc-[Cha$^{NN}$Leu]-Boc

A solution of 200 mg (0.24 mmol) of Boc-[Phe$^{NN}$Leu]-Boc (Example 12) in 15 ml of methanol is hydrogenated for 4 h at 1 atm hydrogen pressure in the presence of 10 mg of Nishimura-catalyst (Rh(III)- and Pt(IV)-oxide monohydrate, Degussa). The catalyst is removed by filtration, the solvent is fully concentrated by evaporation and the title compound is obtained after crystallisation from methylene chloride/hexane. $t_{Ref}(I)$=26.7 min, $R_f(V)$=0.21.

c) N-(2(R,S)-Tetrahydrofuryl-methoxycarbonyl)-(L)-valine

Analogously to Example 50a, the title compound is obtained in the form of a mixture of 2 diastereoisomers from 7 g (60 mmol) of (L)-valine and 9.8 g (60 mmol) of 2(R,S)-tetrahydrofurylmethyl-chloroformate (Heterocycles 27, 1155 (1988)) in 100 ml of 2N sodium hydroxide solution and 30 ml of dioxane. $t_{Ref}(II)$=23.5 and 23.8 min.

EXAMPLE 57

Z-Val-[Phe$^{NN}$Leu]←(N-(3-(tetrazol-1-yl)-propionyl)-Val)

Analogously to Example 37, the title compound is obtained (in the form of 2 diastereoisomers differentiable by HPLC) from 100 mg (0.21 mmol) of Z-(L)-Val-[Phe$^{NN}$Leu]-H, 75 mg (0.31 mmol) of N-(3-(tetrazol-1-yl)-propionyl)-(L)-valine from Example 44a, 137 mg (0.31 mmol) of BOP, 42 mg (0.31 mmol) of HOBt and 2 ml of 0.3M NMM in DMF after precipitation from methylene chloride/hexane and lyophilisation from dioxane/tert-butanol. FAB-MS: (M+H)⁺=708, $t_{Ref}$(I)=21.1 and 21.1 min, $R_f$(D)=0.45.

a) Z-(L)-Val-[Phe$^{NN}$Leu]-H

A solution of 250 mg (0.43 mmol) of Z-(L)-Val-[Phe$^{NN}$Leu]-Boc in 5 ml of formic acid is stirred for 7.5 h at RT. After that time no more starting material can be detected by HPLC analysis ($t_{Ref}$(I)=27.5 min), and the reaction solution is concentrated by evaporation. The residue is dissolved in chloroform and washed with saturated sodium hydrogen carbonate solution. The chloroform phase is filtered through cotton wadding and yields the crude title compound after removal of the solvent by evaporation. $t_{Ref}$(I)=16.7 min, $R_f$(K)=0.21.

b) Z-(L)-Val-[Phe$^{NN}$Leu]-Boc

Analogously to Example 37, the title compound is obtained from 230 mg (0.653 mmol) of H-[Phe$^{NN}$Leu]-Boc, 247 mg (0.98 mmol) of Z-(L)-valine, 434 mg (0.98 mmol) of BOP, 133 mg (0.98 mmol) of HOBt and 6.5 ml of 0.3M NMM in DMF after precipitation from methylene chloride/methanol by the addition of DIPE. FAB-MS: (M+H)⁺=585, $t_{Ref}$(I)=27.5 min, $R_f$(C)=0.71.

c) H-[Phe$^{NN}$Leu]-Boc

Analogously to Example 17a), the title compound is obtained starting from 1.27 g (2.84 mmol) of N-trifluoroacetyl-[Phe$^{NN}$Leu]-Boc and 24 ml of 1N aqueous sodium carbonate solution in 90 ml of methanol by precipitation from methylene chloride by the addition of DIPE. $t_{Ref}$(I)=14.9 min, $R_f$(K)=0.38.

d) N-Trifluoroacetyl-[Phe$^{NN}$Leu]-Boc

Analogously to Example 16, the title compound is obtained starting from 3 g (11.57 mmol) of 2(R)-[1'(S)-(trifluoroacetylamino)-2'-phenylethyl]-oxirane from Example 16d) and 2.3 g (12.15 mmol) of tert-butyl-3-isobutyl-carbazate (preparation: J. Chem. Soc. Perkin I, 1712 (1975)) after chromatographic purification on silica gel with methylene chloride/ether (20:1). $t_{Ref}$(I)=24.7 min, $R_f$(W)=0.36.

EXAMPLE 58

Acetyl-Val-[Phe$^{NN}$Leu]←(N-(2(R,S)-carbamoyl-3-phenyl-propionyl)-Val)

Analogously to Example 37, the title compound is obtained (in the form of 2 diastereoisomers differentiable by HPLC) from 140 mg (0.3 mmol) of acetyl-(L)-Val-[Phe$^{NN}$Leu]-H.2HCl, 132 mg (0.45 mmol) of N-(2(R,S)-carbamoyl-3-phenyl-propionyl)-(L)-valine (preparation: Synth., Struct., Funct., Proc. Am. Pept. Symp., 7$^{th}$, 85, (1981)), 199 mg (0.45 mmol) of BOP, 61 mg (0.45 mmol) of HOBt and 3.5 ml of 0.3M NMM in DMF after precipitation from methylene chloride/DIPE and lyophilisation from dioxane. FAB-MS: (M+H)⁺=667, $t_{Ref}$(I)=17.9 and 18.4 min, $R_f$(D)=0.33.

a) Acetyl-Val-[Phe$^{NN}$Leu]1H.2HCl

Analogously to Example 2a), the title compound is obtained starting from 230 mg (0.46 mmol) of acetyl-(L)-Val-[Phe$^{NN}$Leu]-Boc after lyophilisation. $t_{Ref}$(I)=10.5 min, $R_f$(D)=0.38.

b) Acetyl-Val-[Phe$^{NN}$Leu]-Boc

Analogously to Example 37, the title compound is obtained from 250 mg (0.71 mmol) of H-[Phe$^{NN}$Leu]-Boc from Example 57c), 170 mg (1.07 mmol) of N-acetyl-(L)-valine, 471 mg (1.07 mmol) of BOP, 144 mg (1.07 mmol) of HOBt and 7.1 ml of 0.3M NMM in DMF after precipitation from methylene chloride by the addition of DIPE and lyophilisation from dioxane. FAB-MS: (M+H)⁺=493, $t_{Ref}$(I)=20.5 min, $R_f$(D)=0.59.

EXAMPLE 59

N-Morpholinocarbonyl-(L)-Val-[Phe$^{NN}$Leu]←(N-(3-(tetrazol-1-yl)-propionyl)-Val)

Analogously to Example 37, the title compound is obtained (in the form of 2 diastereoisomers differentiable by HPLC) from 100 mg (0.19 mmol) of N-morpholinocarbonyl-(L)-Val-[Phe$^{NN}$Leu]-H.2HCl, 67 mg (0.38 mmol) of N-(3-(tetrazol-1-yl)-propionyl)-(L)-valine from Example 44a, 124 mg (0.28 mmol) of BOP, 38 mg (0.28 mmol) of HOBt and 2.1 ml of 0.3M NMM in DMF after precipitation from methylene chloride by the addition of DIPE and lyophilisation from dioxane. FAB-MS: (M+H)⁺=687, $t_{Ref}$(I)=15.2 and 15.4 min, $R_f$(D)=0.25.

a) N-Morpholinocarbonyl-(L)-Val-[Phe$^{NN}$Leu]-H.2HCl

Analogously to Example 2a), the title compound is obtained starting from 279 mg (0.49 mmol) of N-morpholinocarbonyl-(L)-Val-[Phe$^{NN}$Leu]-Boc after lyophilisation. FAB-MS: (M+H)⁺=464, $t_{Ref}$(II)=30.3 min, $R_f$(D)=0.46.

b) N-Morpholinocarbonyl-(L)-Val-[Phe$^{NN}$Leu]-Boc

Analogously to Example 37, the title compound is obtained from 250 mg (0.71 mmol) of H-[Phe$^{NN}$Leu]-Boc (from Example 57c)), 265 mg (1.07 mmol) of N-morpholinocarbonyl-(L)-valine from Example 7a), 471 mg (1.07 mmol) of BOP, 144 mg (1.07 mmol) of HOBt and 7.1 ml of 0.3M NMM in DMF after precipitation from methylene chloride/hexane and lyophilisation from dioxane. FAB-MS: (M+H)⁺=564, $t_{Ref}$(I)=21.5 min, $R_f$(K)=0.69.

EXAMPLE 60

N-Trifluoroacetyl-[Phe$^{NN}$Leu]←(N-(2(R,S)-carbamoyl-3-phenyl-propionyl)-(L)-Val)

Analogously to Example 37, the title compound is obtained (in the form of 2 diastereoisomers differentiable by HPLC) from 136 mg (0.32 mmol) of N-trifluoroacetyl-[Phe$^{NN}$Leu]-H.2HCl, 142 mg (0.49 mmol) of N-(2(R,S)-carbamoyl-3-phenyl-propionyl)-(L)-valine (preparation: Synth., Struct., Funct., Proc. Am. Pept. Symp., 7$^{th}$, 85, (1981)), 215 mg (0.49 mmol) of BOP, 66 mg (0.49 mmol) of HOBt and 3.5 ml of 0.3M NMM in DMF after chromatographic purification on silica gel with chloroform/methanol (15:1), precipitation of the product-containing fractions from methylene chloride/DIPE and lyophilisation from dioxane/tert-butanol. FAB-MS: (M+H)⁺=622, $t_{Ref}$(I)=21.6 and 22.0 min, $R_f$(K)=0.26.

a) N-Trifluoroacetyl-[Phe$^{NN}$Leu]-H.2HCl

Analogously to Example 2a), the title compound is obtained starting from 300 mg (0.67 mmol) of N-trifluoroacetyl-[Phe$^{NN}$Leu]-Boc from Example 57d) after lyophilisation. $R_f$(W)<0.1.

EXAMPLE 61

Z-(L)-Val-[Phe$^{NN}$Nle]←(N-(2(R,S)-(N-(2-morpholinoethyl)-carbamoyl)-3-methyl)-butyryl)

Analogously to Example 37, the title compound is obtained (in the form of 2 diastereoisomers differentiable by HPLC) from 100 mg (0.17 mmol) of Z-(L)-Val-[Phe$^{NN}$Nle]-H.2HCl, 69 mg (0.27 mmol) of 2(R,S)-(N-(2-morpholinoethyl)-carbamoyl)-3-methylbutyric acid (isopropylmalonic acid N-(2-morpholinoethyl)monoamide), 119 mg (0.27 mmol) of BOP, 36 mg (0.27 mmol) of HOBt and 2.1 ml of 0.3M NMM in DMF after precipitation from methylene chloride/DIPE and lyophilisation from dioxane. FAB-MS: (M+H)⁺=725, $t_{Ref}$(I)=17.2 and 17.6 min, $R_f$(D)=0.56.

189 a) Z-(L)-Val-[Phe$^{NN}$Nle]-H.2HCl

Analogously to Example 2a), the title compound is obtained starting from 310 mg (0.53 mmol) of Z-(L)-Val-[Phe$^{NN}$Nle]-Boc after lyophilisation. $t_{Ref}(I)$=16.4 min, $R_f(U)$=0.25.

b) Z-(L)-Val-[Phe$^{NN}$Nle]-Boc

Analogously to Example 37, the title compound is obtained from 250 mg (0.71 mmol) of H-[Phe$^{NN}$Nle]-Boc, 268 mg (1.07 mmol) of Z-(L)-valine, 472 mg (1.07 mmol) of BOP, 144 mg (1.07 mmol) of HOBt and 7.1 ml of 0.3M NMM in DMF after chromatographic purification on silica gel with methylene chloride/methanol (40:1) and precipitation of the product-containing fractions from methylene chloride/DIPE. $t_{Ref}(I)$=25.6 min, $R_f(X)$=0.17.

c) H-[Phe$^{NN}$Nle]-Boc

Analogously to Example 17a), the title compound is obtained starting from 830 mg (1.85 mmol) of N-trifluoroacetyl-[Phe$^{NN}$Nle]-Boc after precipitation from methylene chloride/DIPE. $t_{Ref}(I)$=15.4 min, $R_f(K)$=0.54.

d) N-Trifluoroacetyl-[Phe$^{NN}$Nle]-Boc

Analogously to Example 16, the title compound is obtained starting from 1 g (3.86 mmol) of 2(R)-[1'-(S)-(trifluoroacetylamino)-2'-phenylethyl]-oxirane from Example 16d) and 720 mg (3.86 mmol) of tert-butyl-3-butyl-carbazate after chromatographic purification on silica gel with methylene chloride/ether (20:1). $t_{Ref}(I)$=25.3 min, $R_f(Q)$=0.43.

e) tert-Butyl-3-butyl-carbazate

Analogously to Example 4b), the corresponding tert-butoxycarbonyl-hydrazone (25 g, 99%) is obtained from 18.0 g (136.2 mmol) of tert-butyl-carbazate and 12.3 ml (136.2 mmol) of n-butanal in the form of a crude product, which is hydrogenated as described in Example 4a) in the presence of 10 g of 5% platinum on carbon at 4 atm hydrogen pressure. Chromatographic purification of the crude product on silica gel with hexane/ethyl acetate (1:1) yields the title compound. $R_f(N)$=0.44, $^1$H-NMR (200 MHz, CD$_3$OD), 0.92 (t, J=7 Hz, 3H), 1.43 (s, 9H), 1.30 to 1.50 (m, 4H), 2.75 (t, J=7 Hz, 2H).

f) 2(R,S)-(N-(2-Morpholinoethyl)-carbamoyl)-3-methylbutyric acid

Analogously to Example 9b) there is obtained from 7 g (43.7 mmol) of racemic isopropylmalonic acid monomethyl ester (Chem. Ber. 119, 1196 (1986)), 6.3 ml (48.1 mmol) of aminoethyl-morpholine, 6.6 ml (43.7 mmol) of cyanophosphonic acid diethyl ester and 12.8 ml (91.8 mmol) of triethylamine in DMF, 2(R,S)-(N-(2-morpholinoethyl)-carbamoyl)-3-methyl-butyric acid methyl ester (isopropylmalonic acid N-morpholinoethylamide methyl ester). This is stirred for 5 h in a mixture of 28 ml of 2N sodium hydroxide solution and 28 ml of dioxane at RT, acidified with 2N hydrochloric acid and fully concentrated by evaporation. The residue is digested with ethanol, filtered off, and concentration by evaporation of the filtrate yields the title compound. $^1$H-NMR (200 MHz, CD$_3$OD): 0.95 and 1.00 (2 d, J=7H, 6H), 2.25 (m, 4H), 2.70 (m, 6H), 2.75 (d, J=8 Hz, 1H), 3.45 (m, 2H), 3.75 (m, 4H).

EXAMPLE 62

Z-(L)-Val-[Phe$^{NN}$Nle]←(N-(3-(tetrazol-1-yl)-propionyl)-Val)

Analogously to Example 37, the title compound is obtained (in the form of 2 diastereoisomers differentiable by HPLC) from 100 mg (0.18 mmol) of Z-(L)-Val-[Phe$^{NN}$Nle]-H.2HCl (from Example 61a)), 65 mg (0.27 mmol) of N-(3-(tetrazol-1-yl)-propionyl)-(L)-valine from Example 44a, 119 mg (0.27 mmol) of BOP, 36 mg (0.27 mmol) of HOBt and 2.1 ml of 0.3M N-methylmorpholine in DMF after precipitation from methylene chloride/DIPE and lyophilisation from dioxane/tert-butanol. FAB-MS: (M+H)$^+$= 708, $t_{Ref}(I)$=20.3 and 20.6 min, $R_f(D)$=0.43.

EXAMPLE 63

Z-(L)-Val-[Phe$^{NN}$Nle]←(N-(2(R,S)-(N-(2-pyridylmethyl)-carbamoyl)-3-methyl)-butyryl) (dibenzenesulfonate)

Analogously to Example 37, the title compound is obtained in the form of the free amine from 95 mg (0.17 mmol) of Z-(L)-Val-[Phe$^{NN}$Nle]-H.2HCl from Example 61a), 60 mg (0.26 mmol) of (R,S)-isopropylmalonic acid N-(2-picolyl)-monoamide, 113 mg (0.26 mmol) of BOP, 35 mg (0.26 mmol) of HOBt and 2.0 ml of 0.3M NMM in DMF after chromatographic purification on silica gel with methylene chloride/methanol (15:1). The free amine is dissolved in methylene chloride, 2 equivalents of benzenesulfonic acid are added, and precipitation is effected by the addition of DIPE. Lyophilisation from tert-butanol yields the dibenzenesulfonate salt (in the form of 2 diastereoisomers differentiable by HPLC). FAB-MS: (M+H)$^+$=703, $t_{Ref}(.)$=17.7 and 18.0 min, $R_f(D)$=0.54.

a) Isopropylmalonic acid N-(2-picolyl)monoamide 10.6 ml (103 mmol) of N-methylmorpholine are added to a solution of 15 g (93.6 mmol) of isopropylmalonic acid monomethyl ester (preparation: Chem. Ber. 119, 1196 (1986)) in 150 ml of THF and subsequently 13.5 ml (103 mmol) of isobutyl chloroformate are added dropwise thereto. After 30 min 15.3 ml (150 mmol) of 2-picolylamine are added and the resulting suspension is stirred for 2 h. The reaction mixture is diluted with 1N sodium hydroxide solution and water and washed with methylene chloride, and the organic phase is filtered through cotton wadding and concentrated by evaporation. Crystallisation of the residue yields isopropylmalonic acid N-(2-picolylamide) methyl ester, which is hydrolysed in 2N sodium hydroxide solution and dioxane as described in Example 61f) to yield the title compound. $t_{Ref}(II)$=16.0 min.

EXAMPLE 64

Z-(L)-Val-[Phe$^{NN}$(p-F)Phe]←(N-(3-(tetrazol-1-yl)-propionyl)-(L)-Val) (benzenesulfonate)

Analogously to Example 37, the title compound is obtained in the form of the free amine from 100 mg (0.16 mmol) of Z-(L)-Val-[Phe$^{NN}$(p-F)Phe]-H from Example 22a), 59 mg (0.25 mmol) of N-(3-(tetrazol-1-yl)-propionyl)-(L)-valine from Example 44a, 109 mg (0.25 mmol) of BOP, 33 mg (0.25 mmol) of HOBt and 1.19 ml of 0.3M N-methylmorpholine in DMF after precipitation from methylene chloride/DIPE. The free amine is dissolved in methylene chloride/methanol, 1 equivalent of benzenesulfonic acid is added, and precipitation is effected by adding hexane. Lyophilisation from tert-butanol yields the title compound in the form of the benzenesulfonate salt. FAB-MS: (M+H)$^+$= 760, $t_{Ref}(I)$=21.6 min, $R_f(B)$=0.49.

EXAMPLE 65

Methylsulfonyl-[Phe$^{NN}$Phe]←(N-phenylacetyl-(L)-Val)

132 mg (0.28 mmol) of methylsulfonyl-[Phe$^{NN}$Phe]-H.2HCl is reacted analogously to Example 7 with 197 mg (0.84 mmol) of N-phenylacetyl-(L)-valine (preparation: Mem. Tokyo Univ. Agric. 20, 51 (1978)), 317 mg (0.84 mmol) of HBTU and 0.23 ml (1.67 mmol) of triethylamine in DMF to yield the title compound after precipitation from methanol by the addition of ether. FAB-MS: (M+H)$^+$=581, $t_{Ref}$(I)=20.2 min, $R_f$(B)=0.64.

a) Methylsulfonyl-[Phe$^{NN}$Phe]-H.2HCl

Analogously to Example 2a), the title compound is obtained starting from 130 mg (0.28 mmol) of methylsulfonyl-[Phe$^{NN}$Phe]-Boc after lyophilisation. FAB-MS: (M+H)$^+$=364, $t_{Ref}$(II)=28.5 min, $R_f$(K)=0.56.

b) Methylsulfonyl-[Phe$^{NN}$Phe]-Boc

Analogously to Example 16a), the title compound is obtained as a diastereoisomeric mixture in a ratio of 4:1 starting from 1.1 g (4.56 mmol) of 2(R)-[1'(S)-(methylsulfonylamino)-2'-phenylethyl]oxirane and 1.11 g (5.02 mmol) of tert-butyl-3-benzyl-carbazate (preparation: J. Chem. Soc. Perkin I, 1712 (1975)). By crystallisation from methylene chloride/hexane the ratio in favour of the 2S-diastereoisomer is improved to 10:1. FAB-MS: (M+H)$^+$ =464, $t_{Ref}$(I)=21.3 min, $R_f$(N)=0.26.

c) 2(R)-[1'(S)-(Methylsulfonylamino)-2'-phenylethyl] oxirane 2.36 g (13.6 mmol) of methansulfonic acid anhydride and 1.88 ml (13.6 mmol) of triethylamine are added at 0° C. to a solution of 1 g (6.8 mmol) of 1-phenyl-3-buten-2(S)-amine from Example 16b) in 10 ml methylene chloride and the mixture is stirred for 1 h. The reaction mixture is washed with water and saturated sodium hydrogen carbonate solution and the organic phase is filtered through cotton wadding and concentrated by evaporation to yield 2(S)-methylsulfonylamino-1-phenyl-3-butene. 1 g (4.4 mmol) of that crude product is dissolved in 30 ml of methylene chloride, 3.05 g (17.7 mmol) of 4-chloroperbenzoic acid are added at RT and stirring is carried out for 18 h. The reaction solution is washed 5 times with 10% aqueous sodium sulfite solution, filtered through cotton wadding and fully concentrated by evaporation. According to $^1$H-NMR the crude product contains both the (2R)- and the (2S)-epimer in a ratio of 4:1. $^1$H-NMR (200 MHz, CD$_3$OD): 2.30 and 2.52 (2 s, together 3H), 2.6 to 3.2 (m, 5H), 3.55 (m, 1H) 7.32 (m, 5H).

EXAMPLE 66

Methoxycarbonyl-(L)-Val-[Phe$^{NN}$Leu]←(N-methoxycarbonyl-(L)-Val)

Analogously to Example 37, the title compound is obtained from 200 mg (0.55 mmol) of H-[Phe$^{NN}$Leu]-H.3HCl (from Example 13a)), 291 mg (1.66 mmol) of N-methoxycarbonyl-(L)-valine (preparation: Chem. Lett. 705, (1980)), 735 mg (1.66 mmol) of BOP, 225 mg (1.66 mmol) of HOBt and 11 ml of 0.3M NMM in DMF after precipitation from methylene chloride/DIPE and lyophilisation from dioxane. FAB-MS: (M+H)$^+$=566, $t_{Ref}$(I)=18.6 min, $R_f$(U)=0.33.

EXAMPLE 67

Methoxycarbonyl-(L)-Val-[Phe$^{NN}$(p-F)Phe]←(N-methoxycarbonyl-(L)-Val)

Analogously to Example 37, the title compound is obtained from 200 mg (0.48 mmol) of H-[Phe$^{NN}$(p-F)Phe] -H.3HCl (from Example 42b)), 255 mg (1.45 mmol) of N-methoxycarbonyl-(L)-valine (preparation: Chem. Lett. 705, (1980)), 643 mg (1.45 mmol) of BOP, 196 mg (1.45 mmol) of HOBt and 9.7 ml of 0.3M NMM in DMF after precipitation from methylene chloride/DIPE and lyophilisation from dioxane. FAB-MS: (M+H)$^+$=618, $t_{Ref}$(I)=19.5 min, $R_f$(U)=0.22.

EXAMPLE 68

Methoxycarbonyl-(L)-Val-[Phe$^{NN}$(p-CN)Phe]←(N-methoxycarbonyl-(L)-Val)

Analogously to Example 37, the title compound is obtained from 200 mg (0.48 mmol) of H-[Phe$^{NN}$(p-CN)Phe] -H.3HCl (from Example 47a)), 250 mg (1.43 mmol) of N-methoxycarbonyl-(L)-valine (preparation: Chem. Lett. 705, (1980)), 631 mg (1.43 mmol) of BOP, 193 mg (1.43 mmol) of HOBt and 9.5 ml of 0.3M NMM in DMF after chromatographic purification on silica gel with methylene chloride/methanol (15:1) and lyophilisation of the product-containing fractions from dioxane. FAB-MS: (M+H)$^+$=625, $t_{Ref}$(I)=18 min, $R_f$(U)=0.31.

EXAMPLE 69

Z-(L)-Val-[(p-F)Phe$^{NN}$(p-F)Phe]←(N-(2(R,S)-(N-(2-morpholinoethyl)-carbamoyl)-3-methyl)-butyryl)

Analogously to Example 18, 23.0 mg (0.089 mmol) of 2(R,S)-(N-(2-morpholinoethyl)-carbamoyl)-3-methylbutyric acid (Example 61f)) and 45 mg (0.081 mmol) of Z-(L)-Val-[(p-F)Phe$^{NN}$(p-F)Phe]-H (Example 32) are reacted with 33.8 mg (0.089 mmol) of HBTU in 0.76 ml of 0.25M NMM/CH$_3$CN to yield the title compound which is reprecipitated with DMF/DIPE: TLC $R_f$(P)=0.42; FAB-MS (M+H)$^+$=795.

EXAMPLE 70

Z-(L)-Val-[(p-F)Phe$^{NN}$(p-F)Phe]←(N-(2(R,S)-(N-(2-pyridylmethyl)-carbamoyl)-3-methyl)-butyryl)

Analogously to Example 18, 21.0 mg (0.089 mmol) of rac. isopropylmalonic acid N-(2-picolyl)amide (Example 63a)) and 45 mg (0.081 mmol) of Z-(L)-Val-[(p-F)Phe$^{NN}$(p-F)Phe]-H (Example 32) are reacted with 33.8 mg (0.089 mmol) of HBTU in 0.76 ml of 0.25M NMM/CH$_3$CN to yield the title compound which is reprecipitated with DMF/DIPE: TLC $R_f$(P)=0.52; FAB-MS (M+H)$^+$=773.

EXAMPLE 71

The following compounds can be prepared analogously to one of the afore-mentioned processes:

A) Z-(L)-Val-[(p-F)Phe$^{NN}$(p-F)Phe]←((L)-Val)←(N-morpholinocarbonyl-Gly);

B) N-Morpholinocarbonyl-(L)-Val-[(p-F)Phe$^{NN}$(p-F)Phe] ←((L)-Val)←(N-morpholinocarbonyl-Gly)

C) N-(Quinoline-2-carbonyl)-(L)-Asn-[Phe$^{NN}$(p-F)Phe] ←((L)-Val)-Z

D) N-(Morpholinosulphonyl)-(L)-Val-[Phe$^{NN}$Leu]←(N (morpholinosulphonyl)-(L)-Val)

E) N-(Quinoline-2-carbonyl)-(L)-Asn-[Phe$^{NN}$Cha]←((L) -Val)-Z (=1-[2(S)-hydroxy-3(S)-(N-(quinoline-2-carbonyl)-(L)-asparagyl)amino-4-phenyl-butyl]-1-[cyclohexylmethyl]-2-[N-(benzyloxycarbonyl)-(L)-valyl]-hydrazine)

Under a nitrogen atmosphere, 27 mg (0.107 mmol) of Z-valine in 0.59 ml of a 0.3M solution of NMM in DMF are activated with 47 mg (0.107 mmol) of BOP and 14 mg (0.107 mmol) of HOBT and, after 15 min, 50 mg (0.089 mmol) of 1-[2(S)-hydroxy-3(S)-(N-(quinoline-2-carbonyl)-

(L)-asparagyl)amino-4-phenyl-butyl]-1-[cyclohexylmethyl]-hydrazine are added. The mixture is stirred for 18 h at RT and concentrated by evaporation under HV. The residue is dissolved in methylene chloride and washed with saturated NaHCO₃ solution, water and brine, the aqueous phases are extracted twice with methylene chloride, and the organic phases are dried with Na₂SO₄ and concentrated by evaporation. Column chromatography (SiO₂, ethyl acetate/ethanol 100:3) yields the pure title compound: TLC R$_f$(D')=0.21; t$_{Ref}$(V)=16.7 min; FAB-MS (M+H)⁺=794.

The starting material is prepared as follows:

a) 1-[2(S)-Hydroxy-3(S)-(N-(quinoline-2-carbonyl)-(L)-asparagyl)amino-4-phenyl-butyl]-1-[cyclohexylmethyl]-hydrazine Analogously to Example 98 (see below), 921 mg (1.39 mmol) of 1-[2(S)-hydroxy-3(S)-(N-(quinoline-2-carbonyl)-(L)-asparagyl) amino-4-phenyl-butyl]-1-[cyclohexylmethyl]- 2-[tert-butoxy-carbonyl]-hydrazine (Example 100 A), see below) in 37 ml of formic acid are reacted to form the title compound and used directly in the next step.

F) N-(Quinoline-2-carbonyl)-(L)-Asn-[Phe$^{NN}$(p-F)Phe] ←(N-(methoxycarbonyl)-(L)-Val)

EXAMPLE 72

1-[2(S)-Acetoxy-3(S)-(N-(2-methoxyethoxycarbonyl)-()-valyl)amino-4-phenyl-butyl]-1l-[cyclohexylmethyl]-2-[N-(2-methoxyethoxycarbonyl)-(L)-valyl]-hydrazine Under a nitrogen atmosphere, 200 mg (0.29 mmol) of N-(2-methoxy-ethoxycarbonyl)-(L)-Val-[Phe$^{NN}$Cha]←(N-(2-methoxy-ethoxycarbonyl)-(L)-Val) in 4 ml of THF and 60 μl (0.43 mmol) of triethylamine are acetylated with 40 μl (0.43 mmol) of acetic anhydride for 3 h at RT in the presence of 0.5 mg (0.003 mmol) of DMAP. The reaction mixture is partitioned between 3 portions of methylene chloride, water, saturated NaHCO₃ solution and brine. The title compound is obtained from the organic phases after drying with Na₂SO₄, concentrating by evaporation and column chromatography (SiO₂, methylene chloride/methanol 30:1): TLC R$_f$(Z)0.17 ; t$_{Ref}$(I)=22.5 min; FAB-MS (M+H)⁺=736.

The starting materials are prepared as follows:

a) N-(2-Methoxy-ethoxycarbonyl)-(L)-Val-[Phe$^{NN}$Cha]←(N-(2-methoxy-ethoxycarbonyl)-(L)-Val)

Analogously to Example 2, 820 mg (3.74 mmol) of N-(2-methoxy-ethoxycarbonyl)-(L)-valine are activated with 1.65 g (3.74 mmol) of BOP and 505 mg (3.74 mmol) of HOBT in 25 ml of a 0.3M solution of NMM in DMF and, after 10 min, reacted with 500 mg (1.25 mmol) of H-[Phe$^{NN}$Cha]-H (hydrochloride salt) (see Example 10a) for 18 h. The reaction mixture is concentrated by evaporation under HV, and the residue is dissolved in CHCl₃ and washed with 10% citric acid solution, saturated NaHCO₃ solution and brine. The aqueous phases are extracted with 2 portions of CHCl₃, and the organic phases are dried with Na₂SO₄ and concentrated by evaporation. Column chromatography (SiO₂, CHCl₃/MeOH 30:1) and precipitation with hexane from a CH₂Cl₂ solution yields the title compound: TLC R$_f$(T)=0.37; t$_{Ref}$(I)=21.5 min; FAB-MS (M+H)⁺=694.

b) Chloroformic acid (2-methoxy-ethyl) ester

Under a nitrogen atmosphere, 13.3 ml (168 mmol) of 2-methoxy-ethanol are added dropwise at from 0 to 5° C. to 100 ml (202 mmol) of a 20% solution of phosgene in toluene, and the mixture is stirred for 90 min at 0° C. and for 18 h at RT to complete the reaction. The reaction mixture is extracted with water, and the organic phase is filtered through cotton wadding and concentrated by evaporation: IR (CH₂Cl₂): inter alia 3055 w, 2995 w, 2935 w, 2895 w, 2825 w, 1775 s, 1167 s, 1127 s; ¹H-NMR (200 MHz, CDCl₃): 3.38 (s, 3H), 3.64 and 4.44 (2t, J=5 Hz, each 2H).

c) N-(2-Methoxy-ethoxycarbonyl)-(L)-valine

A solution of 3.06 g (22.1 mmol) of chloroformic acid (2-methoxy-ethyl) ester in 18 ml of dioxane is added to 2.59 g (22.1 mmol) of L-valine in 26.4 ml of 2N NaOH and the mixture is then stirred for 18 h at RT. The reaction mixture is extracted with chloroform, and the inorganic phase is acidified with 4N HCl and extracted again with chloroform. The chloroform phase last obtained is dried and concentrated by evaporation to yield the title compound: ¹H-NMR (200 MHz, CDCl₃): 0.92 and 0.99 (2 d, J=7 Hz, 6H), 2.2 (m, 1H), 3.38 (s, 3H), 3.59 and 4.24 (2m, each 2H), 4.3 (m, 1H), 5.4 (d, J=9 Hz, HN), 8.5 (sb, 1H).

EXAMPLE 73

1-[2(S)-Acetoxy-3(S)-(N-(methoxycarbonyl)-(L)-valyl)amino-4-phenyl-butyl]-1-[cyclohexylmethyl]-2-[N-(methoxycarbonyl)-(L)-valyl]-hydrazine Analogously to Example 72, 200 mg (0.33 mmol) of N-(methoxycarbonyl)-(L)-Val-[Phe$^{NN}$Cha]←(N-(methoxycarbonyl)-(L)-Val) in 4 ml of THF and 68 μl (0.50 mmol) of triethylamine are reacted with 46 μl (0.50 mmol) of acetic anhydride in the presence of 1.2 mg (0.01 mmol) of DMAP. Precipitation with DIPE from a concentrated solution of the crude product in methanol yields the pure title compound: TLC R$_f$(A')=0.42; t$_{Ref}$(I)=22.6 min; FAB-MS (M+H)⁺=648.

The starting material is prepared as follows:

a) N-(Methoxycarbonyl)-(L)-Val-[Phe$^{NN}$Cha]←(N-(methoxycarbonyl)-(L)-Val) (=1-[2(S)-hydroxy-3(S)-(N-(methoxycarbonyl)-(L)-valyl)-amino-4-phenyl-butyl]-1-[cyclohexylmethyl]-2-[N-(methoxycarbonyl)-(L)-valyl]-hydrazine)

Analogously to Example 2, 1.47 g (8.4 mmol) of N-(methoxycarbonyl)-(L)-valine are activated with 3.71 g (8.4 mmol) of BOP and 1.13 g (8.4 mmol) of HOBT in 54 ml of a 0.3M solution of NMM in DMF and, after 15 min, reacted with 1.12 g (2.8 mmol) of H-[Phe$^{NN}$Cha]-H (hydrochloride salt) (see Example 10a) for 18 h. The reaction mixture is concentrated by evaporation using a RE at 50° C. (→brown residue), and the residue is dissolved in methylene chloride and washed twice with saturated NaHCO₃ solution and brine. The aqueous phases are extracted with 2 portions of methylene chloride and the organic phases are dried with Na₂SO₄ and concentrated by evaporation. Filtration through silica gel (methylene chloride/methanol 15:1) and precipitation twice with DIPE from a concentrated methylene chloride solution yields the title compound: TLC R$_f$(U)=0.33; t$_{Ref}$(I)=21.5 min; FAB-MS (M+H)⁺=606.

The starting material is prepared as follows:

b) N-(Methoxycarbonyl)-(L)-valine 5.67 g (60 mmol) of chloroformic acid methyl ester are added to 7.0 g (60 mmol) of L-valine in 100 ml of 2N NaOH and 30 ml of dioxane (→exothermic reaction) and the mixture is then stirred for 18 h at RT. The reaction mixture is extracted with methylene chloride and the aqueous phase is acidified with 27 ml of 4N HCl and extracted again with methylene chloride. Drying and concentration by evaporation of the latter methylene chloride phase yields the title compound: t$_{Ref}$(I)=7.2 min; ¹H-NMR (200 MHz, CD₃OD): 0.96 (t, J=7 Hz, 6H), 2.16 (m, 1H), 3.67 (s, 3H), 4.06 (m, 1H), 7.07 (d, J=8 Hz, HN$_{partially\ exchanged}$).

EXAMPLE 74

1-[2(S)-(2-Pyridylcarbonyl)oxy-3(S)-(N-(methoxycarbonyl)-(L)-valyl)amino-4-phenyl-butyl]-1-[cyclohexylmethyl]-2-[N-(methoxycarbonyl)-(L)-valyl]-hydrazine Under a nitrogen atmosphere, 56 µl (0.4 mmol) of 1-chloro-N,N,2-trimethyl-1-propenamine (B. Haveaux, A., Dekoker, M. Rens, A. R. Sidani, J. Toye, L. Ghosez, M. Murakami, M. Yoshioka, and W. Nagata, Organic Syntheses 59, 26 (1980)) are added at 0° C. to 81 mg (0.66 mmol) of 2-picolinic acid in 4 ml of methylene chloride. After 45 min at RT, 1.3 ml of pyridine, 100 mg (0.165 mmol) of N-(methoxycarbonyl)-(L)-Val-[Phe$^{NN}$Cha]←(N-(methoxycarbonyl)-(L)-Val) (Example 73a) and a spatula tip of DMAP are added and the mixture is stirred for 18 h at RT. The dark reaction mixture is partitioned between 3 portions of methylene chloride, 2 portions of saturated NaHCO$_3$ solution, water and brine. Column chromatography (SiO$_2$, ethyl acetate) of the concentration residue of the methylene chloride phase dried with Na$_2$SO$_4$ yields the pure title compound: TLC: R$_f$(O)=0.23; t$_{Ref}$(I)=22.5 min; FAB-MS (M+H)$^+$=711.

EXAMPLE 75

The following are prepared in accordance with one of the afore-mentioned processes:

a) 1-[2(S)-propionyloxy-3(S)-(N-(methoxycarbonyl)-(L)-valyl)amino-4-phenyl-butyl]-1-[cyclohexylmethyl]-2-[N-(methoxycarbonyl)-(L)-valyl]-hydrazine b) 1-[2(S)-butyryloxy-3(S)-(N-(methoxycarbonyl)-(L)-valyl)amino-4-phenyl-butyl]-1-[cyclohexylmethyl]-2-[N-(methoxycarbonyl)-(L)-valyl]-hydrazine;

c) 1-[2(S)-pentanoyloxy-3(S)-(N-(methoxycarbonyl)-(L)-valyl)amino-4-phenyl-butyl]-1-[cyclohexylmethyl]-2-[N-(methoxycarbonyl)-(L)-valyl]-hydrazine;

d) 1-[2(S)-octanoyloxy-3(S)-(N-(methoxycarbonyl)-(L)-valyl)amino-4-phenyl-butyl]-1-[cyclohexylmethyl]-2-[N-(methoxycarbonyl)-(L)-valyl]-hydrazine;

e) 1-[2(S)-decanoyloxy-3(S)-(N-(methoxycarbonyl)-(L)-valyl)amino-4-phenyl-butyl]-1-[cyclohexylmethyl]-2-[N-(methoxycarbonyl)-(L)-valyl]-hydrazine;

f) 1-[2(S)-dodecanoyloxy-3(S)-(N-(methoxycarbonyl)-(L)-valyl)amino-4-phenyl-butyl]-1-[cyclohexylmethyl]-2-[N-(methoxycarbonyl)-(L)-valyl]-hydrazine;

g) 1-[2(S)-pivaloyloxy-3(S)-(N-(methoxycarbonyl)-(L)-valyl)amino-4-phenyl-butyl]-1-[cyclohexylmethyl]-2-[N-(methoxycarbonyl)-(L)-valyl]-hydrazine;

h) 1-[2(S)-(2-furylcarbonyl)oxy-3(S)-(N-(methoxycarbonyl)-(L)-valyl)amino-4-phenyl-butyl]-1-[cyclohexylmethyl]-2-[N-(methoxycarbonyl)-(L)-valyl]-hydrazine;

i) 1-[2(S)-(4-imidazolylcarbonyl)oxy-3(S)-(N-(methoxycarbonyl)-(L)-valyl)amino-4-phenyl-butyl]-1-[cyclohexylmethyl]-2-[N-(methoxycarbonyl)-(L)-valyl]-hydrazine;

j) 1-[2(S)-(4-imidazolylacetyl)oxy-3(S)-(N-(methoxycarbonyl)-(L)-valyl)amino-4-phenyl-butyl]-1-[cyclohexylmethyl]-2-[N-(methoxycarbonyl)-(L)-valyl]-hydrazine;

k) 1-[2(S)-(3-(4-imidazolyl)-propionyl)oxy-3(S)-(N-(methoxycarbonyl)-(L)-valyl)amino-4-phenyl-butyl]-1-[cyclohexylmethyl]-2-[N-(methoxycarbonyl)-(L)-valyl]-hydrazine;

l) 1-[2(S)-benzoyloxy-3(S)-(N-(methoxycarbonyl)-(L)-valyl)amino-4-phenyl-butyl]-1-[cyclohexylmethyl]-2-[N-(methoxycarbonyl)-(L)-valyl]-hydrazine;

m) 1-[2(S)-(2-pyridylacetyl)oxy-3(S)-(N-(methoxycarbonyl)-(L)-valyl)amino-4-phenyl-butyl]-1-[cyclohexylmethyl]-2-[N-(methoxycarbonyl)-(L)-valyl]-hydrazine;

n) 1-[2(S)-(3-(pyridin-2-yl)-propionyl)oxy-3(S)-(N-(methoxycarbonyl)-(L)-valyl)amino-4-phenylbutyl)]-1-[cyclohexylmethyl]-2-[N-(methoxycarbonyl)-(L)-valyl]-hydrazine;

o) 1-[2(S)-(quinolin-2-ylcarbonyl)oxy-3(S)-(N-(methoxycarbonyl)-(L)-valyl)amino-4-phenyl-butyl]-1-[cyclohexylmethyl]-2-[N-(methoxycarbonyl)-(L)-valyl]-hydrazine;

p) 1-[2(S)-(aminoacetyl)oxy-3(S)-(N-(methoxycarbonyl)-(L)-valyl)amino-4-phenyl-butyl]-1-[cyclohexylmethyl]-2-[N-(methoxycarbonyl)-(L)-valyl]-hydrazine;

q) 1-[2(S)-(N-methylaminoacetyl)oxy-3(S)-(N-(methoxycarbonyl)-(L)-valyl)amino-4-phenyl-butyl]-1-[cyclohexylmethyl]-2-[N-(methoxycarbonyl)-(L)-valyl]-hydrazine;

r) 1-[2(S)-(N,N-dimethylaminoacetyl)oxy-3(S)-(N-(methoxycarbonyl)-(L)-valyl)amino-4-phenyl-butyl]-1-[cyclohexylmethyl]-2-[N-(methoxycarbonyl)-(L)-valyl]-hydrazine;

s) 1-[2(S)-(N-benzyloxycarbonyl-N-methylaminoacetyl)oxy-3(S)-(N-(methoxycarbonyl)-(L)-valyl)amino-4-phenyl-butyl]-1-[cyclohexylmethyl]-2-[N-(methoxycarbonyl)-(L)-valyl]-hydrazine;

t) 1-[2(S)-prolyloxy-3(S)-(N-(methoxycarbonyl)-(L)-valyl)amino-4-phenyl-butyl]-1-[cyclohexylmethyl]-2-[N-(methoxycarbonyl)-(L)-valyl]-hydrazine;

u) 1-[2(S)-(4-morpholinomethylbenzoyl)oxy-3(S)-(N-(methoxycarbonyl)-(L)-valyl)-amino-4-phenyl-butyl]-1-[cyclohexylmethyl]-2-[N-(methoxycarbonyl)-(L)-valyl]-hydrazine;

v) 1-[2(S)-(4-chloromethylbenzoyl)oxy-3(S)-(N-(methoxycarbonyl)-(L)-valyl)amino-4-phenyl-butyl]-1-[cyclohexylmethyl]-2-[N-(methoxycarbonyl)-(L)-valyl]-hydrazine;

w) 1-[2(S)-(3-carboxypropionyl)oxy-3(S)-(N-(methoxycarbonyl)-(L)-valyl)amino-4-phenyl-butyl]-1-[cyclohexylmethyl]-2-[N-(methoxycarbonyl)-(L)-valyl]-hydrazine.

EXAMPLE 76

From the title compounds of Examples 1 to 70, there are prepared in accordance with one of the above-mentioned processes the monoacetylated derivatives that contain a 2(S)-acetoxy group instead of the free 2(S)-hydroxy group in the relevant central divalent radical derivatised from butan-2(S)-ol and designated -[Phe$^{NN}$Phe], -[Phe$^{NN}$Cha], -[Phe$^{NN}$Leu], -[Phe$^{NN}$Nle], -[Phe$^{NN}$(p-F)Phe], -[(p-F)Phe$^{NN}$(p-F)Phe], -[Phe$^{NN}$(p-CN)Phe] or -[Cha$^{NN}$Leu].

EXAMPLE 77

The following compounds are prepared in accordance with one of the above-mentioned processes (the starting materials are indicated in square brackets ([]) (e.g. the respective Example of which the title compound is used as starting material)):

a) 1-[2(S)-(2-furylcarbonyl)oxy-3(S)-(N-(benzyloxycarbonyl)-(L)-valyl)-amino-4-phenylbutyl)]-1-[benzyl]-2-[N-(benzyloxycarbonyl)-(L)-valyl]-hydrazine [from the title compound of Example 2 and furan-2-carboxylic acid chloride];

b) 1-[2(S)-pivaloyloxy-3(S)-(N-(benzyloxycarbonyl)-(L)-valyl)-amino-4-phenyl-butyl]-1-[cyclohexylmethyl]-2-

[N-(benzyloxycarbonyl)-(L)-valyl]-hydrazine [from the title compound of Example 11 and pivalic acid anhydride];

c) 1-[2(S)-(N-methylaminoacetyl)oxy-3(S)-(N-(morpholinocarbonyl)-(L)-valyl)-amino-4-phenyl-butyl]-1-[p-fluorophenylmethyl]-2-[N-(benzyloxycarbonyl)-(L)-valyl]-hydrazine [from the title compound of Example 18 and N-benzyloxycarbonyl-N-methlaminoacetic acid with subsequent hydrogenolysis of the resulting 2(S)-(N-benzyloxycarbonyl-N-methylaminoacetyl compound catalysed by Pd/C];

d) 1-[2(S)-(N-benzyloxycarbonyl-N-methylaminoacetyl) oxy-3(S)-(N-(benzyloxycarbonyl)-(L)-valyl)-amino-4-phenyl-butyl]-1-[p-fluorophenylmethyl]-2-[N-(N-(morpholinocarbonyl)-glycyl)-(L)-valyl]-hydrazine [from the title compound of Example 24 and N-benzyloxycarbonyl-N-methylaminoacetic acid chloride];

e) 1-[2(S)-(N,N-dimethylaminoacetyl)oxy-3(S)-(N-(quinolin-2-ylcarbonyl)-(L)-aspartoyl)-amino-4-phenyl-butyl]-1-[p-fluorophenylmethyl]-2-[tert-butoxycarbonyl]-hydrazine [from the title compound of Example 27 and dimethylaminoacetic acid chloride];

f) 1-[2(S)-(2-pyridylcarbonyl)oxy-3(S)-(N-(benzyloxycarbonyl)-(L)-aspartoyl)-amino-4-phenyl-butyl]-1-[p-fluorophenylmethyl]-2-[N-(benzyloxycarbonyl)-(L)-valyl]-hydrazine [from the title compound of Example 28 and 2-pyridinecarboxylic acid chloride);

g) 1-[2(S)-(4-(morpholinomethyl)benzoyl)oxy-3(S)-(N-(benzyloxycarbonyl)-(L)-valyl)-amino-4-(p-fluorophenyl)-butyl]-1-[p-fluorophenylmethyl]-2-[tert-butoxycarbonyl]-hydrazine [from the title compound of Example 31 and 4-morpholinomethylbenzoic acid by way of the acid chloride in the presence of N,N,2-trimethyl-1-chloropropen-(1)-amine];

h) 1-[2(S)-benzoyloxy-3(S)-(N-(benzyloxycarbonyl)-(L)-valyl)-amino-4-(p-fluorophenyl)-butyl]-1-[p-fluorophenylmethyl]-2-[N-(N-(2-pyridylmethyl)-N-methylaminocarbonyl)-(L)-valyl]-hydrazine [from the title compound of Example 33 and benzoyl chloride];

i) 1-[2(S)-(4-chloromethylbenzoyl)oxy-3(S)-(N-(benzyloxycarbonyl)-(L)-valyl)-amino-4-(p-fluorophenyl)-butyl]-1-[p-fluorophenylmethyl]-2-[N-(2(R,S)-carbamoyl-3-phenylpropionyl)-(L)-valyl]-hydrazine [from the title compound of Example 34 and 4-chloromethylbenzoic acid in the presence of N,N,2-trimethyl-1-chloropropen-(1)-amine];

j) 1-[2(S)-(imidazol-4-ylacetyl)oxy-3(S)-(N-acetyl-valyl)-amino-4-phenyl-butyl]-1-[benzyl]-2-[N-acetyl-valyl]-hydrazine [from the title compound of Example 35 and 1-tritylimidazolyl-4-acetic acid (prepared from trityl chloride and 4-imidazolylacetic acid in the presence of pyridine) in the presence of N,N,2-trimethyl-1-chloropropen-(1)-amine by way of the trityl-protected intermediate with subsequent acidolytic removal of the trityl protecting group, e.g. using trifluoroacetic acid];

k) 1-[2(S)-(2-pyridylacetyl)oxy-3(S)-(N-(quinolin-2-ylcarbonyl)-valyl)-amino-4-phenyl-butyl]-1-[benzyl]-2-[N-quinolin-2-yl-carbonyl-valyl]-hydrazine [from the title compound of Example 37 and 2-pyridineacetic acid in the presence of N,N,2-trimethyl-1-chloropropen-(1)-amine];

l) 1-[2(S)-(3-pyridylacetyl)oxy-3(S)-(N-acetyl-(L)-valyl)-amino-4-phenyl-butyl]-1-[cyclohexylmethyl]-2-[N-acetyl-(L)-valyl]-hydrazine [from the title compound of Example 38 and 3-pyridineacetic acid in the presence of N,N,2-trimethyl-1-chloropropen-(1)-amine];

m) 1-[2(S)-(4-pyridylacetyl)oxy-3(S)-(N-(3-pyridylacetyl)-(L)-valyl)-amino-4-phenyl-butyl]-1-[cyclohexylmethyl]-2-[N-(3-pyridylacetyl)-(L)-valyl]-hydrazine [from the title compound of Example 39 and 4-pyridineacetic acid in the presence of N,N,2-trimethyl-1-chloropropen-(1)-amine];

n) 1-[2(S)-(quinolin-2-ylcarbonyl)oxy-3(S)-(N-(N-(2-pyridylmethyl)-N-methylamino-carbonyl)-(L)-valyl)-amino-4-phenyl-butyl]-1-[p-fluorophenylmethyl]-2-[N-(N-(2-pyridylmethyl)-N-methylaminocarbonyl)-(L)-valyl]-hydrazine [from the title compound of Example 43 and quinoline-2-carboxylic acid in the presence of N,N,2-trimethyl-1-chloropropen-(1)-amine];

o) 1-[2(S)-(2-pyrrolidinylcarbonyl)oxy-3(S)-(N-(benzyloxycarbonyl)-(L)-valyl)-amino-4-phenyl-butyl]-1-[p-fluorophenylmethyl]-2-[N-(benzyloxycarbonyl)-(L)-valyl]-hydrazine [from the title compound of Example 45 and proline in the presence of N,N,2-trimethyl-1-chloropropen-(1)-amine];

p) 1-[2(S)-propionyloxy-3(S)-(N-(benzyloxycarbonyl)-(L)-valyl)-amino-4-phenyl-butyl]-1-[p-cyanophenylmethyl]-2-[N-(benzyloxycarbonyl)-(L)-valyl]-hydrazine [from the title compound of Example 48 and propanoic acid anhydride];

q) 1-[2(S)-butyryloxy-3(S)-(N-(benzyloxycarbonyl)-(L)-isoleucyl)-amino-4-phenyl-butyl]-1-[isobutyl]-2-[N-(benzyloxycarbonyl)-(L)-isoleucyl]-hydrazine [from the title compound of Example 49 and butyric acid anhydride];

r) 1-[2(S)-pentanoyloxy-3(S)-(N-(isobutoxycarbonyl)-(L)-valyl)-amino-4-phenyl-butyl]-1-[isobutyl]-2-[N-(isobutoxycarbonyl)-(L)-valyl]-hydrazine [from the title compound of Example 50 and pentanoic acid chloride];

s) 1-[2(S)-decanoyloxy-3(S)-(N-acetyl-valyl)-amino-4-phenyl-butyl]-1-[isobutyl]-2-[N-acetyl-valyl]-hydrazine [from the title compound of Example 52 and decanoic acid in the presence of N,N,2-trimethyl-1-chloropropen-(1)-amine];

t) 1-[2(S)-dodecanoyloxy-3(S)-N-valyl-amino-4-phenyl-butyl]-1-[isobutyl]-2-[N-valyl]-hydrazine [from the title compound of Example 54, protected at the two free valylamino groups by benzyloxycarbonyl, in the presence of N,N,2-trimethyl-1-chloropropen-(1)-amine with subsequent hydrogenolytic removal of the benzyloxycarbonyl protecting groups from the obtainable intermediate];

u) 1-[2(S)-(3-carboxypropionyl)oxy-3(S)-(N-(thiomorpholinocarbonyl)-(L)-valyl)-amino-4-phenyl-butyl]-1-[isobutyl]-2-[N-(thiomorpholinocarbonyl)-(L)-valyl]-hydrazine [prepared from the title compound of Example 55 and succinic acid anhydride in the presence of pyridine];

v) 1-[2(S)-(4-imidazolylacetyl)oxy-3(S)-(N-(benzyloxycarbonyl)-(L)-valyl)amino- 4-phenyl-butyl]-1-[isobutyl]-2-[N-(3-(tetrazol-1-yl)propionyl)-(L)-valyl]-hydrazine [prepared from the title compound of Example 57 and 1-trityl-4-imidazolylacetic acid analogously to Example 77j];

w) 1-[2(S)-(furan-2-ylcarbonyl)oxy-3(S)-(N-acetyl-(L)-valyl)amino-4-phenyl-butyl]-1-[isobutyl]-2-[N-(2(R,S)-carbamoyl-3-phenyl-propionyl)-(L)-valyl]-hydrazine [prepared from the title compound of Example 58 and furan-2-carboxylic acid chloride];

x) 1-[2(S)-pivaloyloxy-3(S)-(N-(benzyloxycarbonyl)-(L)-valyl)amino-4phenyl-butyl]-1-[n-butyl]-2-[2(R,S)-(N-(2-morpholinoethyl)carbamoyl)-3-methylbutyryl]-hydrazine [prepared from the title compound of Example 61 and pivalic acid anhydride];

y) 1-[2(S)-(N-benzyloxycarbonyl-N-methylaminoacetyl) oxy-3(S)-(N-(benzyloxycarbonyl)-(L)-valyl)amino-4-phenylbutyl]-1-[n-butyl]-2-[N-(3-(tetrazol-1-yl)-propionyl)valyl]-hydrazine [from the title compound of Example 62 analogously to Example 77d];

z) 1-[2(S)-(N-methylaminoacetyl)oxy-3(S)-(N-(benzyloxycarbonyl)-(L)-valyl)amino-4-phenyl-butyl]-1-[n-butyl]-2-[N-(2(R,S)-(N-(2-pyridylmethyl)-carbamoyl)-3-methyl)butyryl]-hydrazine [from the title compound of Example 63 by way of the 2(S)-N-benzyloxycarbonyl-N-methylaminoacetoxy analogue by hydrogenolysis in accordance with Example 77c].

EXAMPLE 78

The following compounds are prepared in accordance with one of the above-mentioned processes (the starting materials are given in square brackets ([ ]) (e.g. the respective Example of which the title compound is used as starting material)):

a) 1-[2(S)-(N,N-dimethylaminoacetyl)oxy-3(S)-((N-benzyloxycarbonyl)-(L)-valyl)-amino-4-phenyl-butyl]-1-[p-fluorophenylmethyl]-2-[N-(3-(tetrazol-1-yl)-propionyl)valyl]-hydrazine [from the title compound of Example 64 and dimethylaminoacetic acid chloride];

b) 1-[2(S)-(pyridin-2-ylcarbonyl)oxy-3(S)-(N-methoxycarbonyl)-(L)-valyl)-amino-4-phenyl-butyl]-1-[isobutyl]-2-[N-(methoxycarbonyl)-(L)-valyl]-hydrazine [from the title compound of Example 66 and 2-pyridinecarboxylic acid chloride].

c) 1-[2(S)-(4-morpholinomethylbenzoyl)oxy-3(S)-(N-methoxycarbonyl)-(L)-valyl)-amino-4-phenyl-butyl]-1-[p-fluorophenylmethyl]-2-[N-(methoxycarbonyl)-(L)-valyl]-hydrazine [from the title compound of Example 67 and 4-morpholinomethyl benzoic acid (by way of the acid chloride in the presence of N,N,2-trimethyl-1-chloropropen-(1)-amine)];

d) 1-[2(S)-benzoyloxy-3(S)-(N-methoxycarbonyl)-(L)-valyl)-amino-4-phenyl-butyl]-1-[p-cyanophenylmethyl]-2-[N-(methoxycarbonyl)-(L)-valyl]-hydrazine [from the title compound of Example 68 and benzoic acid anhydride].

EXAMPLE 79

1-[2(S)-Hydroxy-3(S)-(N-allyloxycarbonyl-(L)-valyl)amino-4-phenylbutyl]-1-[cyclohexylmethyl]-2-[N-allyloxycarbonyl-(L)-valyl]-hydrazine Analogously to Example 2, the title compound is obtained from 500 mg (1.25 mmol) of H-[Phe$^{NN}$Cha]-H.3HCl from Example 10a, 753 mg (3.74 mmol) of N-allyloxycarbonyl-(L)-valine, 1.65 g (3.74 mmol) of BOP, 505 mg (3.74 mmol) of HOBt and 24.7 ml of 0.3M N-methylmorpholine in DMF after precipitation twice from methylene chloride by the addition of DIPE and lyophilisation from dioxane. FAB-MS: (M+H)$^+$=658, t$_{Ref}$(I)=25.5 min, R$_f$(H)=0.44.

The starting compound is prepared in the following manner:

a) Allyloxycarbonyl-(L)-valine

The title compound is obtained in the form of a colourless oil analogously to Example 1c) starting from 10 g (85.3 mmol) of (L)-valine and 10.3 g (85.3 mmol) of allyl chloroformate. $^1$H-NMR (200 MHz, CDCl$_3$): 6.05–5.8 (m, 1H), 5.35 (s, broad, 1H), 5.20 (m, 2H), 4.60 (d, broad, J=6 Hz, 2H), 4.33 (m, 1H), 2.25 (m, 1H), 1.00 (d, J=7 Hz, 3H), 0.93 (d, J=7 Hz, 3H).

EXAMPLE 80

1-[2(S)-Hydroxy-3(S)-(N-ethoxycarbonyl-(L)-valyl) amino-4-phenylbutyl]-1-cyclohexylmethyl]-2-[N-ethoxycarbonyl-(L)-valyl]-hydrazine Analogously to Example 2, the title compound is obtained from 500 mg (1.25 mmol) of H-[Phe$^{NN}$Cha]-H.3 HCl from Example 10a, 708 mg (3.74 mmol) of N-ethoxycarbonyl-(L)-valine, 1.65 g (3.74 mmol) of BOP, 505 mg (3.74 mmol) of HOBt and 24.7 ml of 0.3M N-methylmorpholine in DMF after chromatographic purification (SiO$_2$, methylene chloride/diethyl ether (1:1)), precipitation from methylene chloride by the addition of DIPE and lyophilisation from dioxane. FAB-MS: (M+H)$^+$=634, t$_{Ref}$(I)=24.2 min., R$_f$(H)= 0.3.

The starting compound is prepared in the following manner:

a) N-Ethoxycarbonyl-(L)-valine

Analogously to Example 1c, the title compound is obtained in the form of a colourless oil starting from 10 g (85.3 mmol) of (L)-valine and 9.3 g (85.3 mmol) of ethyl chloroformate. $^1$H-NMR (200 MHz, CDCl$_3$): 5.15 (d, broad, 1H), 4.32 (m, 1H), 4.15 (q, J=7 Hz, 2H), 2.25 (m, 1H), 1.25 (t, J=7 Hz, 3H) 0.98 (d, J=7 Hz, 3H), 0.92 (d, J=7 Hz, 3H).

EXAMPLE 81

1-[2(S)-Hydroxy-3(S)-(N-trifluoroacetyl-(L)-valyl) amino-4-phenylbutyl]-1-[cyclohexylmethyl]-2-[N-trifluoroacetyl-(L)-valyl]-hydrazine Analogously to Example 2, the title compound is obtained from 500 mg (1.25 mmol) of H-[Phe$^{NN}$Cha]-H.3HCl from Example 10a, 798 mg (3.74 mmol) of N-trifluoroacetyl-(L) -valine, 1.65 g (3.74 mmol) of BOP, 505 mg (3.74 mmol) of HOBt and 24.7 ml of 0.3M N-methylmorpholine in DMF after chromatographic purification (SiO$_2$, methylene chloride/diethyl ether (1:1)), precipitation from methylene chloride by the addition of hexane and lyophilisation from dioxane. FAB-MS: (M+H)$^+$=682, t$_{Ref}$(I)=26.1 min. R$_f$(H)= 0.65.

The starting compound is prepared in the following manner:

a) N-Trifluoroacetyl-(L)-valine

At 0°, 6 ml (42.8 mmol) of trifluoroacetic anhydride are added dropwise to a solution of 8.16 g (38.9 mmol) of (L)-valine-tert-butyl ester and 17.3 ml (124.5 mmol) of triethylamine in 100 ml of methylene chloride and the reaction mixture is stirred overnight at RT. After washing with 10% citric acid and saturated sodium chloride solution, the organic phase is concentrated by evaporation and yields N-trifluoroacetyl-(L)-valine tert-butyl ester in the form of a yellow oil, which is dissolved in 40 ml of a (1:1) mixture of methylene chloride and TFA and stirred for 5 h at RT. Concentration by evaporation of the reaction solution and digestion of the residue with hexane yields the title compound in the form of a white solid. $^1$H-NMR (200 MHz, CD$_3$OD): 4.32 (d, J=6 Hz, 1H), 2.23 (m, 1H), 0.98 (d, J=7 Hz, 3H), 0.96 (d, J=7 Hz, 3H).

EXAMPLE 82

1-[2(S)-Hydroxy-3(S)-(N-(2-(2-methoxyethoxy) ethoxy)carbonyl-(L)-valyl)-amino-4-phenylbutyl]-1-[cyclohexylmethyl]-2-[N-(2-(2-methoxyethoxy) ethoxy)carbonyl-(L)-valyl]-hydrazine Analogously to Example 2, the title compound is obtained from 500 mg (1.25 mmol) of H-[Phe$^{NN}$Cha]-H.3 HCl from Example 10a, 985 mg (3.74 mmol) of N-methoxyethoxy-ethoxycarbonyl-(L)-valine, 1.65 g (3.74 mmol) of BOP, 505 mg (3.74 mmol) of HOBt and 24.7 ml of 0.3M N-methylmorpholine in DMF after chromatographic purification (SiO$_2$, chloroform/methanol (30:1)), precipitation from methylene chloride by the addition of hexane and lyophilisation from dioxane. FAB-MS: (M+H)$^+$=782, t$_{Ref}$(I) =21.2 min, R$_f$(T)=0.26.

The starting compound is prepared in the following manner:

a) N-(2-(2-Methoxyethoxy)-ethoxy)carbonyl-(L)-valine 19.8 ml (168 mmol) of diethylene glycol monomethyl ether are added dropwise at 0° to 100 ml of a 20% solution of phosgene in toluene and the mixture is stirred overnight at RT. Excess phosgene is expelled with nitrogen and the reaction solution is washed with water and concentrated by evaporation. Analogously to Example 1c, 10 g (85.4 mmol) of (L)-valine are added to the crude 2-(2-methoxyethoxy) ethylchloroformate (15.6 g, 85.4 mmol) yielding the title compound in the form of a colourless resin. $^1$H-NMR (200 MHz, CD$_3$OD): 4.18 (m, 2H), 4.05 d, J=6 Hz, 1H), 3.72–3.40 (m, 8H), 3.35 (s, 3H), 2.18 (m, 1H), 0.95 (t, J=7H, 6H).

EXAMPLE 83

1-[2(S)-Hydroxy-3(S)-(N-(2-methoxyethoxy)acetyl-(L)-valyl)amino-4-phenylbutyl]-1-[cyclohexylmethyl]-2-[N-(2-methoxyethoxy)acetyl-(L)-valyl]-hydrazine Analogously to Example 2, the title compound is obtained from 500 mg (1.25 mmol) of H-[Phe$^{NN}$Cha]-H-3 HCl from Example 10a, 873 mg (3.74 mmol) of N-(2)-methoxyethoxyacetyl-(L)-valine, 1.65 g (3.74 mmol) of BOP, 505 mg (3.74 mmol) of HOBt and 24.7 ml of 0.3M N-methylmorpholine in DMF after chromatographic purification (SiO$_2$, chloroform/methanol (30:1)), precipitation from methylene chloride by the addition of hexane and lyophilisation from dioxane. FAB-MS: (M+H)$^+$=722, t$_{Ref}$(I) =21.3 min, R$_f$(T)=0.23.

The starting compound is prepared in the following manner:

a) N-(2-Methoxyethoxy)-acetyl-(L)-valine

At 0°, 6.4 ml (45.7 mmol) of triethylamine are added to a solution of 5 g (23.9 mmol) of (L)-valine tert-butyl ester, 2.91 g (21.7 mmol) of 2-(methoxyethoxy)-acetic acid and 3.55 g (21.7 mmol) of cyanophosphonic acid diethyl ester in 30 ml of DMF and the mixture is then stirred overnight at RT. The reaction mixture is diluted with methylene chloride, washed in succession with 10% citric acid, saturated sodium hydrogen carbonate solution and saturated sodium chloride solution and, after concentration by evaporation of the organic phase, yields 5.1 g of N-methoxyethoxyacetyl-(L)-valine tert-butyl ester, which is stirred for 1 h at RT in 22 ml of a (1:1) mixture of methylene chloride and TFA. Concentration by evaporation of the reaction solution yields the title compound in the form of a colourless oil. $^1$H-NMR (200 MHz, CDCl$_3$): 10.0 (s, broad, 1H), 7.62 d, broad, 1H), 4.55 (m, 1H), 4.10 (s, 2H), 3.70 (m, 2H), 3.58 (m, 2H), 3.40 (s, 3H), 2.28 (m, 1H), 0.98 (d, J=7 Hz, 3H), 0.95 (d, J=7 Hz, 3H).

EXAMPLE 84

The following compounds are obtained analogously to the Examples and processes described hereinbefore and hereinafter:

A) 1-[2(S)-hydroxy-3(S)-(N-acetyl-(L)-valyl)amino-4-phenylbutyl]-1-[thien-2-ylmethyl]-2-[N-acetyl-(L)-valyl]-hydrazine;

B) 1-[2(S)-hydroxy-3(S)-(N-methoxycarbonyl-(L)-valyl) amino-4-phenylbutyl]-1-[thien-2-ylmethyl]-2-[N-methoxycarbonyl-(L)-valyl]-hydrazine;

C) 1-[2(S)-hydroxy-3(S)-(N-ethoxycarbonyl-(L)-valyl) amino-4-phenylbutyl]-1-[thien-2-ylmethyl]-2-[N-ethoxycarbonyl-(L)-valyl]-hydrazine;

D) 1-[2(S)-hydroxy-3(S)-(N-(N,N-dimethylaminocarbonyl)-(L)-valyl)amino-4-phenylbutyl]-1-[thien-2-ylmethyl]-2-[N-(N,N-dimethylaminocarbonyl)-(L)-valyl]-hydrazine;

E) 1-[2(S)-hydroxy-3(S)-(N-(N-(2-methoxyethyl) aminocarbonyl)-(L)-valyl)amino-4-phenylbutyl]-1-[thien-2-ylmethyl]-2-[N-(N-(2-methoxyethyl) aminocarbonyl)-(L)-valyl]-hydrazine;

F) 1-[2(S)-hydroxy-3(S)-(N-(N-(2-(morpholin-4-yl)ethyl) aminocarbonyl)-(L)-valyl)-amino-4-phenylbutyl]-1-[thien-2-ylmethyl]-2-[N-(N-(2-(morpholin-4-yl)ethyl) aminocarbonyl)-(L)-valyl]-hydrazine;

G) 1-[2(S)-hydroxy-3(S)-(N-(N-(2-(morpholin-4-yl)ethyl)-N-methyl-aminocarbonyl)-(L)-valyl)amino-4-phenylbutyl]-1-[thien-2-ylmethyl]-2-[N-(N-(2-(morpholin-4-yl)ethyl)-N-methylaminocarbonyl)-(L)-valyl]-hydrazine.

EXAMPLE 85

The following compounds are obtained analogously to the Examples and processes described hereinbefore and hereinafter:

A) 1-[2(S)-hydroxy-3(S)-(N-acetyl-(L)-valyl)amino-4-phenylbutyl]-1-[2,3,5,6-tetrahydropyran-4-ylmethyl]-2-[N-acetyl-(L)-valyl]-hydrazine;

B) 1-[2(S)-hydroxy-3(S)-(N-methoxycarbonyl-(L)-valyl) amino-4-phenylbutyl]-1-[2,3,5,6-tetrahydropyran-4-ylmethyl]-2-[N-methoxycarbonyl-(L)-valyl]-hydrazine;

C) 1-[2(S)-hydroxy-3(S)-(N-ethoxycarbonyl-(L)-valyl) amino-4-phenylbutyl]-1-[2,3,5,6-tetrahydropyran-4-ylmethyl]-2-[N-ethoxycarbonyl-(L)-valyl]-hydrazine;

D) 1-[2(S)-hydroxy-3(S)-(N-(N,N-dimethylaminocarbonyl)-(L)-valyl)amino-4-phenylbutyl]-1-[2,3,5,6-tetrahydropyran-4-ylmethyl]-2-[N-(N,N-dimethylaminocarbonyl)-(L)-valyl]-hydrazine;

E) 1-[2(S)-hydroxy-3(S)-(N-(N-(2-methoxyethyl) aminocarbonyl)-(L)-valyl)amino-4-phenylbutyl]-1-[2,3,5,6-tetrahydropyran-4-ylmethyl]-2-[N-(N-(2-methoxyethyl)aminocarbonyl)-(L)-valyl]-hydrazine;

F) 1-[2(S)-hydroxy-3(S)-(N-(N-(2-(morpholin-4-yl)ethyl) aminocarbonyl)-(L)-valyl)-amino- 4-phenylbutyl]-1-[2,3,5,6-tetrahydropyran-4-ylmethyl]-2-[N-(N-(2-(morpholin-4-yl)ethyl)aminocarbonyl)-(L)-valyl]-hydrazine;

G) 1-[2(S)-hydroxy-3(S)-(N-(N-(2-(morpholin-4-yl)ethyl)-N-methylaminocarbonyl)-(L)-valyl)amino-4-phenylbutyl]-1-[2,3,5,6-tetrahydropyran-4-ylmethyl]-2-[N-(N-(2-(morpholin-4-yl)ethyl)-N-methylaminocarbonyl)-(L)-valyl]-hydrazine.

EXAMPLE 86

The following compounds are obtained analogously to the Examples and processes described hereinbefore and hereinafter:

A) 1-[2(S)-Hydroxy-3(S)-(N-acetyl-(L)-valyl)amino-4-phenylbutyl]-1-[4-hydroxyphenylmethyl]-2-[N-acetyl-(L)-valyl]-hydrazine;

Analogously to Example 37, the title compound is obtained from 200 mg (0.48 mmol) of 1-[2(S)-hydroxy-3(S)-amino-4-phenylbutyl]-1-[4-hydroxyphenylmethyl]-hydrazine.3HCl, 175 mg (1.07 mmol) of N-methoxycarbonyl-(L)-valine from Example 73b, 473 mg (1.07 mmol) of BOP, 145 mg (1.07 mmol) of HOBt and 8.4 ml of 0.3M N-methylmorpholine in DMF after chromatographic purification (SiO$_2$, methylene chloride/diethyl ether/methanol (10:1:1)), precipitation from methylene chloride by the addition of DIPE and lyophilisation from dioxane. FAB-MS: (M+H)$^+$=616, t$_{Ref}$(V)=11.6 min., R$_f$(K')=0.56.

The starting compounds are prepared in the following manner:

a) 1-[2(S)-Hydroxy-3(S)-amino-4-phenylbutyl]-1-[4-hydroxyphenylmethyl]-hydrazine.3HCl Analogously to Example 2a, the title compound is obtained from 470 mg (0.94 mmol) of 1-[2(S)-hydroxy-3(S)-tert-butoxycarbonylamino-4-phenylbutyl]-1-[4-hydroxyphenylmethyl]-2-[tert-butoxycarbonyl]-hydrazine after complete concentration by evaporation and digestion of the residue with methylene chloride. $^1$H-NMR (200 MHz, CD$_3$OD): 7.42–7.15 (m, 7H), 6.92 (d, J=8 Hz, 2H), 4.1–3.85 (m, 3H), 3.55 (m, 1H), 3.1 (m, 2H), 2.8 (m, 2H).

b) 1-[2(S)-Hydroxy-3(S)-tert-butoxycarbonylamino-4-phenylbutyl]-1-[4-hydroxyphenyl-methyl]-2-[tert-butoxycarbonyl]-hydrazine Analogously to Example 1, the title compound is obtained from 26.2 g (23.6 mmol) of (2R,3S)-1-[3-Boc-amino-2-phenylethyl]oxirane and 5.63 g (23.6 mmol) of tert-butyl-3-(4-hydroxyphenyl-methyl)-carbazate after crystallisation from ethyl acetate/DIPE.

$^1$H-NMR (200 MHz, CD$_3$OD): 7.28–7.10 (m, 7H), 6.70 (d, J=8 Hz, 2H), 4.7 (m, 4H), 2.95–2.45 (m, 4H), 1.31 (s, 9H), 1.28 (s, 9H), t$_{Ref}$(V)=15.0 min.

c) tert-Butyl-3-(4-hydroxyphenyl-methyl)-carbazate

Analogously to Example 4a, 14 g (106 mmol) of 4-hydroxybenzaldehyde and 14 g (117 mmol) of tert-butylcarbazate in 125 ml of ethanol are reacted to form 4-hydroxybenzaldehyde-tert-butoxycarbonylhydrazone. (19.8 g, 80%). 9.73 g thereof are hydrogenated in 200 ml of THF in the presence of 0.6 g of 5% palladium on carbon at 1 atm hydrogen pressure to yield the title compound, which is crystallised from hot methanol. $^1$H-NMR (200 MHz, CD$_3$OD): 7.18 (d, J=8 Hz, 2H), 6.73 (d, J=8 Hz, 2H), 3.80 (s, 2H), 1.45 (s, 9H).

B) 1-[2(S)-Hydroxy-3(S)-(N-methoxycarbonyl-(L)-valyl)amino-4-phenylbutyl]-1-[4-hydroxyphenylmethyl]-2-[N-methoxycarbonyl-(L)-valyl]-hydrazine C) 1-[2(S)-Hydroxy-3(S)-(N-ethoxycarbonyl-(L)-valyl)amino-4-phenylbutyl]-1-[4-hydroxyphenylmethyl]-2-[N-ethoxycarbonyl-(L)-valyl]-hydrazine A solution of 2.0 g (4.86 mmol) of 1-[2(S)-hydroxy-3(S)-amino-4-phenylbutyl]-1-[4-methoxyphenylmethyl]-hydrazine.3HCl (Example 86A) a)), 2.54 g (13.8 mmol) of N-ethoxycarbonyl-(L)-valine from Example 9a and 2.13 ml (13.8 mmol) of cyanophosphonic acid diethyl ester in 45 ml of DMF is cooled to 0° and 4.0 ml (29.2 mmol) of triethylamine are added. The reaction mixture is stirred for 6 h at RT under a nitrogen atmosphere and fully concentrated by evaporation in vacuo. The residue is dissolved in methylene chloride, washed with saturated sodium carbonate solution, 10% aqueous citric acid and saturated sodium chloride solution, filtered through cotton wadding and concentrated by evaporation. Chromatographic purification (SiO$_2$, methylene chloride/diethyl ether/methanol (10:10:1)) and precipitation twice from methanol/methylene chloride by the addition of DIPE yields the title compound. FAB-MS: (M+H)$^+$=644, t$_{Ref}$(V)=12.8 min, R$_f$(B)=0.41.

D) 1-[2(S)-Hydroxy-3(S)-(N-(N,N-dimethylaminocarbonyl)-(L)-valyl)amino-4-phenylbutyl]-1-[4-hydroxyphenylmethyl]-2-[N-(N,N-dimethylaminocarbonyl)-(L)-valyl]-hydrazine.

E) 1-[2(S)-Hydroxy-3(S)-(N-(N-(2-methoxyethyl)aminocarbonyl)-(L)-valyl)amino-4-phenylbutyl]-1-[4-hydroxyphenylmethyl]-2-[N-(N-(2-methoxyethyl)aminocarbonyl)-(L)-valyl]-hydrazine.

F) 1-[2(S)-Hydroxy-3(S)-(N-(N-(2-(morpholin-4-yl)ethyl)aminocarbonyl)-(L)-valyl)-amino- 4-phenylbutyl]-1-[4-hydroxyphenylmethyl]-2-[N-(N-(2-(morpholin-4-yl)ethyl)-aminocarbonyl)-(L)-valyl]-hydrazine.

G) 1-[2(S)-Hydroxy-3(S)-(N-(N-(2-(morpholin-4-yl)ethyl)-N-methyl-aminocarbonyl)-(L)-valyl)amino-4-phenylbutyl]-1-[4-hydroxyphenylmethyl]-2-[N-(N-(2-(morpholin-4-yl)ethyl)-N-methylaminocarbonyl)-(L)-valyl]-hydrazine.

EXAMPLE 87

The following compounds are obtained analogously to the Examples and processes described hereinbefore and hereinafter:

A) 1-[2(S)-Hydroxy-3(S)-(N-acetyl-(L)-valyl)amino-4-phenylbutyl]-1-[4-methoxyphenylmethyl]-2-[N-acetyl-(L)-valyl]-hydrazine:

Analogously to Example 37, the title compound is obtained from 200 mg (0.47 mmol) of 1-[2(S)-hydroxy-3(S)-amino-4-phenylbutyl]-1-[4-methoxyphenylmethyl]-hydrazine.3HCl, 225 mg (1.41 mmol) of N-acetyl-(L)-valine, 624 mg (1.41 mmol) of BOP, 191 mg (1.41 mmol) of HOBt and 9.4 ml of 0.3M N-methylmorpholine in DMF after chromatographic purification (SiO$_2$, methylene chloride/methanol (12:1)) and lyophilisation from dioxane/water/tert-butanol. FAB-MS: (M+H)$^+$=598, t$_{Ref}$(V)=11.2 min, R$_f$(T)=0.25.

The starting materials are prepared in the following manner:

a) 1-[2(S)-Hydroxy-3(S)-amino-4-phenylbutyl]-1-[4-methoxyphenylmethyl]-hydrazine-3HCl Analogously to Example 2a, the title compound is obtained from 2.65 g (5.14 mmol) of 1-[2(S)-hydroxy-3(S)-tert-butoxycarbonylamino-4-phenylbutyl]-1-[4-methoxyphenylmethyl]-2-[tert-butoxycarbonyl]-hydrazine after lyophilisation. $^1$H-NMR (200 MHz, CD$_3$OD): 7.42–7.15 (m, 7H), 6.92 (d, J=8 Hz, 2H), 4.1–3.8 (m, 3H), 3.75 (s, 3H), 3.55 (m, 1H), 3.1 (m, br, 2H), 2.75 (m, br, 2H).

b) 1-[2(S)-Hydroxy-3(S)-tert-butoxycarbonylamino-4-phenylbutyl]-1-[4-methoxyphenylmethyl]-2-[tert-butoxycarbonyl]-hydrazine Analogously to Example 1, the title compound is obtained from 3.13 g (11.9 mmol) of (2R,3S)-1-[3-Boc-amino-2-phenylethyl]oxirane and 3.0 g (11.9 mmol) of tert-butyl-3-(4-methoxyphenyl-methyl)-carbazate from Example 100 C) b) (see below) after crystallisation from methanol/DIPE. $^1$H-NMR (200 MHz, CD$_3$OD): 7.3–7.1 (m, 7H), 6.85 (d, J=8 Hz, 2H), 3.78 (s, 3H), 3.65 (m, 4H), 2.9–2.5 (m, 4H), 1.25 (s, 9H), 1.20 (s, 9H), t$_{Ref}$(V)=16.6 min.

B) 1-[2(S)-Hydroxy-3(S)-(N-methoxycarbonyl-(L)-valyl)amino-4-phenylbutyl]-1-[4-methoxyphenylmethyl]-2-[N-methoxycarbonyl-(L)-valyl]-hydrazine:

Analogously to Example 37, the title compound is obtained from 200 mg (0.47 mmol) of the title compound of Example 87A) a), 247 mg (1.41 mmol) of N-methoxycarbonyl-(L)-valine from Example 73b, 624 mg (1.41 mmol) of BOP, 191 mg (1.41 mmol) of HOBt and 9.4 ml of 0.3M N-methylmorpholine in DMF after chromatographic purification (SiO$_2$, methylene chloride/methanol (19:1)) and lyophilisation from dioxane. FAB-MS: (M+H)$^+$=630, t$_{Ref}$(V)=13.5 min. R$_f$(A')=0.27.

C) 1-[2(S)-Hydroxy-3(S)-(N-ethoxycarbonyl-(L)-valyl) amino-4-phenylbutyl]-1-[4-methoxyphenylmethyl]-2-[N-methoxycarbonyl-(L)-valyl]-hydrazine:

Analogously to Example 37, the title compound is obtained from 200 mg (0.47 mmol) of the title compound of Example 87A) a), 267 mg (1.41 mmol) of N-ethoxycarbonyl-(L)-valine from Example 80a, 624 mg (1.41 mmol) of BOP, 191 mg (1.41 mmol) of HOBt and 9.4 ml of 0.3M N-methylmorpholine in DMF after chromatographic purification (SiO$_2$, methylene chloride/methanol (12:1)), precipitation from methylene chloride by the addition of DIPE and lyophilisation from dioxane. FAB-MS: (M+H)$^+$=658, t$_{Ref}$(V)=15.0 min. R$_f$(I')=0.55.

D) 1-[2(S)-Hydroxy-3(S)-(N-(N,N-dimethylaminocarbonyl)-(L)-valyl)amino-4-phenylbutyl]-1-[4-methoxyphenylmethyl]-2-[N-(N,N-dimethylaminocarbonyl)-(L)-valyl]-hydrazine.

E) 1-[2(S)-Hydroxy-3(S)-(N-(N-(2-methoxyethyl) aminocarbonyl)-(L)-valyl)amino-4-phenylbutyl]-1-[4-methoxyphenylmethyl]-2-[N-(N-(2-methoxyethyl) aminocarbonyl)-(L)-valyl]-hydrazine.

F) 1-[2(S)-Hydroxy-3(S)-(N-(N-(2-(morpholin-4-yl)ethyl) aminocarbonyl)-(L)-valyl)-amino-4-phenylbutyl]-1-[4-methoxyphenylmethyl]-2-[N-(N-(2-(morpholin-4-yl) ethyl)-aminocarbonyl)-(L)-valyl]-hydrazine.

G) 1-[2(S)-Hydroxy-3(S)-(N-(N-(2-(morpholin-4-yl)ethyl)-N-methyl-aminocarbonyl)-(L)-valyl)amino-4-phenylbutyl]-1-[4-methoxyphenylmethyl]-2-[N-(N-(2-(morpholin-4-yl)ethyl)-N-methylaminocarbonyl)-(L)-valyl]-hydrazine.

EXAMPLE 88

The following compounds are obtained analogously to the Examples and processes described hereinbefore and hereinafter:

A) 1-[2(S)-hydroxy-3(S)-(N-acetyl-(L)-valyl)amino-4-phenylbutyl]-1-[4-benzyloxyphenylmethyl]-2-[N-acetyl-(L)-valyl]-hydrazine;

B) 1-[2(S)-hydroxy-3(S)-(N-methoxycarbonyl-(L)-valyl) amino-4-phenylbutyl]-1-[4-benzyloxyphenylmethyl]-2-[N-methoxycarbonyl-(L)-valyl]-hydrazine;

C) 1-[2(S)-hydroxy-3(S)-(N-ethoxycarbonyl-(L)-valyl) amino-4-phenylbutyl]-1-[4-benzyloxyphenylmethyl]-2-[N-ethoxycarbonyl-(L)-valyl]-hydrazine;

D) 1-[2(S)-hydroxy-3(S)-(N-(N,N-dimethylaminocarbonyl)-(L)-valyl)amino-4-phenylbutyl]-1-[4-benzyloxyphenylmethyl]-2-[N-(N,N-dimethylaminocarbonyl)-(L)-valyl]-hydrazine;

E) 1-[2(S)-hydroxy-3(S)-(N-(N-(2-methoxyethyl) aminocarbonyl)-(L)-valyl)amino-4-phenylbutyl]-1-[4-benzyloxyphenylmethyl]-2-[N-(N-(2-methoxyethyl) aminocarbonyl)-(L)-valyl]-hydrazine;

F) 1-[2(S)-hydroxy-3(S)-(N-(N-(2-(morpholin-4-yl)ethyl) aminocarbonyl)-(L)-valyl)amino-4-phenylbutyl]-1-[4-benzyloxyphenylmethyl]-2-[N-(N-(2-(morpholin-4-yl) ethyl)aminocarbonyl)-(L)-valyl]-hydrazine;

G) 1-[2(S)-hydroxy-3(S)-(N-(N-(2-(morpholin-4-yl)ethyl)-N-methyl-aminocarbonyl)-(L)-valyl)amino-4-phenylbutyl]-1-[4-benzyloxyphenylmethyl]-2-[N-(N-(2-(morpholin-4-yl)ethyl)-N-methylaminocarbonyl)-(L)-valyl]-hydrazine.

EXAMPLE 89

The following compounds are obtained analogously to the Examples and processes described hereinbefore and hereinafter:

A) 1-[2(S)-hydroxy-3(S)-(N-acetyl-(L)-valyl)amino-4-phenylbutyl]-1-[4-(3,4-dimethoxybenzyl) oxyphenylmethyl]-2-[N-acetyl-(L)-valyl]-hydrazine;

B) 1-[2(S)-hydroxy-3(S)-(N-methoxycarbonyl-(L)-valyl) amino-4-phenylbutyl]-1-[4-(3,4-dimethoxybenzyl) oxyphenylmethyl]-2-[N-methoxycarbonyl-(L)-valyl]-hydrazine;

C) 1-[2(S)-hydroxy-3(S)-(N-ethoxycarbonyl-(L)-valyl) amino-4-phenylbutyl]-1-[4-(3,4-dimethoxybenzyl) oxyphenylmethyl]-2-[N-ethoxycarbonyl-(L)-valyl]-hydrazine;

D) 1-[2(S)-hydroxy-3(S)-(N-(N,N-dimethylaminocarbonyl)-(L)-valyl)amino-4-phenylbutyl]-1-[4-(3,4-dimethoxybenzyl)oxyphenylmethyl]-2-[N-(N,N-dimethylaminocarbonyl)-(L)-valyl]-hydrazine;

E) 1-[2(S)-hydroxy-3(S)-(N-(N-(2-methoxyethyl) aminocarbonyl)-(L)-valyl)amino-4-phenylbutyl]-1-[4-(3,4-dimethoxybenzyl)oxyphenylmethyl]-2-[N-(N-(2-methoxyethyl)aminocarbonyl)-(L)-valyl]-hydrazine;

F) 1-[2(S)-hydroxy-3(S)-(N-(N-(2-(morpholin-4-yl)ethyl) aminocarbonyl)-(L)-valyl)amino-4-phenylbutyl]-1-[4-(3,4-dimethoxybenzyl)oxyphenylmethyl]-2-[N-(N-(2-(morpholin-4-yl)ethyl)aminocarbonyl)-(L)-valyl]-hydrazine;

G) 1-[2(S)-hydroxy-3(S)-(N-(N-(2-(morpholin-4-yl)ethyl)-N-methylaminocarbonyl)-(L)-valyl)amino-4-phenylbutyl]-1-[4-(3,4-dimethoxybenzyl) oxyphenylmethyl]-2-[N-(N-(2-(morpholin-4-yl)ethyl)-N-methylaminocarbonyl)-(L)-valyl]-hydrazine.

EXAMPLE 90

The following compounds are obtained analogously to the Examples and processes described hereinbefore and hereinafter:

A) 1-[2(S)-hydroxy-3(S)-(N-acetyl-(L)-valyl)amino-4-phenylbutyl]-1-[4-isobutoxyphenylmethyl]-2-[N-acetyl-(L)-valyl]-hydrazine;

B) 1-[2(S)-hydroxy-3(S)-(N-methoxycarbonyl-(L)-valyl) amino-4-phenylbutyl]-1-[4-isobutoxyphenylmethyl]-2-[N-methoxycarbonyl-(L)-valyl]-hydrazine;

C) 1-[2(S)-hydroxy-3(S)-(N-ethoxycarbonyl-(L)-valyl) amino-4-phenylbutyl]-1-[4-isobutoxyphenylmethyl]-2-[N-ethoxycarbonyl-(L)-valyl]-hydrazine;

D) 1-[2(S)-hydroxy-3(S)-(N-(N,N-dimethylaminocarbonyl)-(L)-valyl)amino-4-phenylbutyl]-1-[4-isobutoxyphenylmethyl]-2-[N-(N,N-dimethylaminocarbonyl)-(L)-valyl]-hydrazine;

E) 1-[2(S)-hydroxy-3(S)-(N-(N-(2-methoxyethyl) aminocarbonyl)-(L)-valyl)amino-4-phenylbutyl]-1-[4-isobutoxyphenylmethyl]-2-[N-(N-(2-methoxyethyl) aminocarbonyl)-(L)-valyl]-hydrazine;

F) 1-[2(S)-hydroxy-3(S)-(N-(N-(2-(morpholin-4-yl)ethyl) aminocarbonyl)-(L)-valyl)amino-4-phenylbutyl]-1-[4- isobutoxyphenylmethyl]-2-[N-(N-(2-(morpholin-4-yl) ethyl)-aminocarbonyl)-(L)-valyl]-hydrazine;

G) 1-[2(S)-hydroxy-3(S)-(N-(N-(2-(morpholin-4-yl)ethyl)-N-methylaminocarbonyl)-(L)-valyl)amino-4-phenylbutyl]-1-[4-isobutoxyphenylmethyl]-2-[N-(N-(2-(morpholin-4-yl)-ethyl)-N-methylaminocarbonyl)-(L)-valyl]-hydrazine.

EXAMPLE 91

The following compounds are obtained analogously to the Examples and processes described hereinbefore and hereinafter:

A) 1-[2(S)-hydroxy-3(S)-(N-acetyl-(L)-valyl)amino-4-phenylbutyl]-1-[4-(2-methoxyethoxy)phenylmethyl]-2-[N-acetyl-(L)-valyl]-hydrazine;

B) 1-[2(S)-hydroxy-3(S)-(N-methoxycarbonyl-(L)-valyl)amino-4-phenylbutyl]-1-[4-(2-methoxyethoxy)phenylmethyl]-2-[N-methoxycarbonyl-(L)-valyl]-hydrazine;

C) 1-[2(S)-hydroxy-3(S)-(N-ethoxycarbonyl-(L)-valyl)amino-4-phenylbutyl]-1-[4-(2-methoxyethoxy)phenylmethyl]-2-[N-ethoxycarbonyl-(L)-valyl]-hydrazine;

D) 1-[2(S)-hydroxy-3(S)-(N-(N,N-dimethylaminocarbonyl)-(L)-valyl)amino-4-phenylbutyl]-1-[4-(2-methoxyethoxy)phenylmethyl]-2-[N-(N,N-dimethylaminocarbonyl)-(L)-valyl]-hydrazine;

E) 1-[2(S)-hydroxy-3(S)-(N-(N-(2-methoxyethyl)aminocarbonyl)-(L)-valyl)amino-4-phenylbutyl]-1-[4-(2-methoxyethoxy)phenylmethyl]-2-[N-(N-(2-methoxyethyl)aminocarbonyl)-(L)-valyl]-hydrazine;

F) 1-[2(S)-hydroxy-3(S)-(N-(N-(2-(morpholin-4-yl)ethyl)aminocarbonyl)-(L)-valyl)-amino-4-phenylbutyl]-1-[4-(2-methoxyethoxy)phenylmethyl]-2-[N-(N-(2-(morpholin-4-yl)ethyl)aminocarbonyl)-(L)-valyl]-hydrazine;

G) 1-[2(S)-hydroxy-3(S)-(N-(N-(2-(morpholin-4-yl)ethyl)-N-methylaminocarbonyl)-(L)-valyl)amino-4-phenylbutyl]-1-[4-(2-methoxyethoxy)phenylmethyl]-2-[N-(N-(2-(morpholin-4-yl)ethyl)-N-methylaminocarbonyl)-(L)-valyl]-hydrazine.

EXAMPLE 92

The following compounds are obtained analogously to the Examples and processes described hereinbefore and hereinafter:

A) 1-[2(S)-hydroxy-3(S)-(N-acetyl-(L)-valyl)amino-4-phenylbutyl]-1-[methylene-3,4-dioxyphenylmethyl]-2-[N-acetyl-(L)-valyl]-hydrazine;

B) 1-[2(S)-hydroxy-3(S)-(N-methoxycarbonyl-(L)-valyl)amino-4-phenylbutyl]-1-[methylene-3,4-dioxyphenylmethyl]-2-[N-methoxycarbonyl-(L)-valyl]-hydrazine;

C) 1-[2(S)-hydroxy-3(S)-(N-ethoxycarbonyl-(L)-valyl)amino-4-phenylbutyl]-1-[methylene-3,4-dioxyphenylmethyl]-2-[N-ethoxycarbonyl-(L)-valyl]-hydrazine;

D) 1-[2(S)-hydroxy-3(S)-(N-(N,N-dimethylaminocarbonyl)-(L)-valyl)amino-4-phenylbutyl]-1-[methylene-3,4-dioxyphenylmethyl]-2-[N-(N,N-dimethylaminocarbonyl)-(L)-valyl]-hydrazine;

E) 1-[2(S)-hydroxy-3(S)-(N-(N-(2-methoxyethyl)aminocarbonyl)-(L)-valyl)amino-4-phenylbutyl]-1-[methylene-3,4-dioxyphenylmethyl]-2-[N-(N-(2-methoxyethyl)aminocarbonyl)-(L)-valyl]-hydrazine;

F) 1-[2(S)-hydroxy-3(S)-(N-(N-(2-(morpholin-4-yl)ethyl)aminocarbonyl)-(L)-valyl)amino-4-phenylbutyl]-1-[methylene-3,4-dioxyphenylmethyl]-2-[N-(N-(2-(morpholin-4-yl)ethyl)aminocarbonyl)-(L)-valyl]-hydrazine;

G) 1-[2(S)-hydroxy-3(S)-(N-(N-(2-(morpholin-4-yl)ethyl)-N-methylaminocarbonyl)-(L)-valyl)amino-4-phenylbutyl]-1-[methylene-3,4-dioxyphenylmethyl]-2-[N-(N-(2-(morpholin-4-yl)ethyl)-N-methylaminocarbonyl)-(L)-valyl]-hydrazine;

H) 1-[2(S)-hydroxy-3(S)-(N-acetyl-(L)-valyl)amino-4-phenylbutyl]-1-[3,4-dimethoxyphenylmethyl]-2-[N-acetyl-(L)-valyl]-hydrazine;

I) 1-[2(S)-hydroxy-3(S)-(N-methoxycarbonyl-(L)-valyl)amino-4-phenylbutyl]-1-[3,4-dimethoxyphenylmethyl]-2-[N-methoxycarbonyl-(L)-valyl]-hydrazine;

J) 1-[2(S)-hydroxy-3(S)-(N-ethoxycarbonyl-(L)-valyl)amino-4-phenylbutyl]-1-[3,4-dimethoxyphenylmethyl]-2-[N-ethoxycarbonyl-(L)-valyl]-hydrazine;

K) 1-[2(S)-hydroxy-3(S)-(N-(N,N-dimethylaminocarbonyl)-(L)-valyl)amino-4-phenylbutyl]-1-[3,4-dimethoxyphenylmethyl]-2-[N-(N,N-dimethylaminocarbonyl)-(L)-valyl]-hydrazine;

L) 1-[2(S)-hydroxy-3(S)-(N-(N-(2-methoxyethyl)aminocarbonyl)-(L)-valyl)amino-4-phenylbutyl]-1-[3,4-dimethoxyphenylmethyl]-2-[N-(N-(2-methoxyethyl)aminocarbonyl)-(L)-valyl]-hydrazine;

M) 1-[2(S)-hydroxy-3(S)-(N-(N-(2-(morpholin-4-yl)ethyl)aminocarbonyl)-(L)-valyl)-amino-4-phenylbutyl]-1-[3,4-dimethoxyphenylmethyl]-2-[N-(N-(2-(morpholin-4-yl)ethyl)aminocarbonyl)-(L)-valyl]-hydrazine;

N) 1-[2(S)-hydroxy-3(S)-(N-(N-(2-(morpholin-4-yl)ethyl)-N-methylaminocarbonyl)-(L)-valyl)amino-4-phenylbutyl]-1-[3,4-dimethoxyphenylmethyl]-2-[N-(N-(2-(morpholin-4-yl)ethyl)-N-methylaminocarbonyl)-(L)-valyl]-hydrazine.

EXAMPLE 93

The following compounds are obtained analogously to the Examples and processes described hereinbefore and hereinafter:

A) 1-[2(S)-Hydroxy-3(S)-(N-acetyl-(L)-valyl)amino-4-phenylbutyl]-1-[4-biphenylylmethyl]-2-[N-acetyl-(L)-valyl]-hydrazine Preparation analogously as described in Example 93B) with acetyl-(L)-valine instead of the methoxycarbonyl-(L)-valine. After purification by column chromatography on silica gel (eluent: 15:1 dichloromethane:methanol), the title compound is obtained: FAB MS (M+H)$^+$=644. R$_f$(15:1 dichloromethane:methanol)=0.40.

B) 1-[$^2$(S)-Hydroxy-3(S)-(N-methoxycarbonyl-(L)-valyl)amino-4-phenylbutyl]-1-[4-biphenylylmethyl]-2-[N-methoxycarbonyl-(L)-valyl]-hydrazine 82.9 ml (594.6 mmol) of triethylamine are added to a stirred and cooled (0 ° C.) suspension of 48.4 g (276.1 mmol) of methoxycarbonyl-(L)-valine, 101.8 g (530.9 mmol) of dimethyl-3-[3-dimethylamino)propyl] carbodiimide hydrochloride and 43 g (318.5 mmol) of 1-hydroxybenzotriazole hydrate in 1 l of DMF. After 30 min, 50 g (106.2 mmol) of 1-(4-biphenylyl)-5(S)-2,5-diamino-4 (S)-hydroxy-6-phenyl-2-azahexane hydrochloride are added in one portion. After 10 min, the cooling bath is removed and the mixture is allowed to stir at room temperature for 16 h. The solvent is evaporated under reduced pressure, and the residue is dissolved in 500 ml of dichloromethane. This solution is subsequently washed with 1 l of 10% aqueous citric acid, 1 l of saturated NaHCO$_3$ solution and 1 l of brine. The aqueous layers are re-extracted three times with 500 ml of dichloromethane. The combined organic layers are filtered through a pad of cotton wool and evaporated under reduced pressure. The residue is crystallized by dissolving it in 100 ml of dichloromethane and adding diisopropylether. Crystallisation is completed upon cooling to 5° C. for 16 h. Filtration of the solid and drying at 60° C. gives the title compound as a white, amorphous solid which is homogenous by thin layer chromatography (15:1 dichloromethane:methanol):

m.p. 214°–216° C., $^1$H-NMR (CD$_3$OD) δ=7.58–7.15 (m, 14H), 4.13 (t, br, 1H), 4.0 and 3.90 (AB-system, J=8, 2H), 3.81 (d, J=4, 1H), 3.75 /d, br, 1H), 3.63–3.60 (m, 1H), 3.6 (s, 3H), 3.60 (s, 3H), 2.96–2.80 (m, 3H), 2.65 (dd, J=8, 1, 1H), 1.83 (sept, J=7, 1H), 1.64 (sept, J=7, 1H), 0.76 (apparent t, J=7, 6H), 0.63 (d, J=7, 3H), 0.61 (J=7, 3H); FAB-MS (M+H)$^+$=676.

The starting material is prepared as follows:

a) N$^1$-(4-Biphenylylcarbaldehyde)-N$^2$-(tert-butoxycarbonyl)-hydrazone 75.8 g (0.416 mol) of biphenylyl-4-carbaldehyde (Fluka, Buchs, Schweiz) are added at ambient temperature to a solution of 50 g (0.378 mol) of N-(tert-butoxycarbonyl)-hydrazine (tert-butylcarbazate) in 750 ml of absolute ethanol. Upon completion of the addition, the mixture is heated to reflux during 16 h. Then about 200 ml of solvent are removed by distillation, and the remainder is diluted with 500 ml of water. Spontaneous crystallisation of the product is completed by cooling the mixture to 0° C. The resulting solid is separated by filtration, washed with 1 l of water and dried at 60° C. to give the title compound:

m.p. 188°–189° C., $^1$H-NMR (CH$_3$OD): δ=7.92 (s, 1H), 7.78 and 7.65 (AB-system, J=8, 4H), 7.63 (m, 2H), 7.5–7.3 (m, 3H), 1.52 (s, 9H).

b) N$^1$-(tert-Butoxycarbonyl)-N$^2$-(4-biphenylylmethyl)-hydrazine

A suspension of 9.4 g 5% Pd on carbon is added to a solution of 94.4 g (0.318 mol) of N$^1$-(4-biphenylylcarbaldehyde)-N$^2$-(tert-butoxycarbonyl)-hydrazone in 2.5 l of methanol, and the mixture is hydrogenated during 2 h at room temperature using hydrogen at atmospheric pressure. After uptake of the theoretically required amount of hydrogen the catalyst is filtered off, and the filtrate is concentrated under reduced pressure. The resulting solid is suspended in 1 l of hexane to give the title compound as a solid which is separated by filtration. The mother liquors are allowed to stand for several days in order to obtain a further amount of the title compound.

Physical properties of the title compound: m.p. 84°–85° C., $^1$H-NMR (CD$_3$OD) δ=7.55 (m, 4H), 7.50–7.38 (m, 5H), 3.95 (s, 2H), 1.45, (s, 9H).

c) 1-[2(S)-hydroxy-3(S)-(tert-butoxycarbonylamino)-4-phenylbutyl]-1-[4-biphenylylmethyl]-2-[tert-butoxycarbonyl)hydrazine A solution of 58.7 g (197 mmol) of N$^1$-(tert-butoxycarbonyl)-N$^2$-(4-biphenylylmethyl)hydrazine and 51.8 g (197 mmol) of N-(tert-butoxycarbonyl)-2(S)-amino-1-phenyl-3(R)-3,4-epoxybutane (=(2R,3S)-1-[3-Boc-amino-2-phenylethyl]-oxirane) in 700 ml of absolute methanol is heated to reflux temperature during 16 h. The mixture is then cooled to 0° C. and diluted with 1.5 l of water. The solid is filtered and dried at 70° C. for 6 h to give the title compound:

$^1$H-NMR (CD$_3$OD) δ=7.55 (m, 5H), 7.45–7.18 (m, 9H), 3.95 (br, 1H), 3.88 (br, 1H), 3.70 (m, 2H), 2.90–2.55 (m, 4H), 1.33 (s, 9H), 1.28 (s, 9H); R$_f$(30:1 dichloromethane:methanol)=0.75.

d) 1-(4-Biphenylyl)-5(S)-2,5-diamino-4(S)-hydroxy-6-phenyl-2-azahexane hydrochloride A solution of 95.19 g (169.5 mmol) of 1-[2(S)-hydroxy-3(S)-(tert-butoxycarbonylamino)-4-phenylbutyl]-1-[4-biphenylylmethyl]-2-[tert-butoxycarbonyl)hydrazine in 300 ml of 4N HCl in dioxane is stirred at room temperature. Thin layer chromatography (5:1 chloroform:methanol) indicates completion of the reaction after 3 h at ambient temperature. The mixture is evaporated under reduced pressure, and the residue is suspended in 300 ml dioxane and evaporated to dryness to give the title compound as an amorphous white solid:

$^1$H-NMR (CD$_3$OD) δ=7.70–7.15 (m, 15H), 4.22–3.92 (m, 3H), 3.55 (apparent q, 1H), 3.10 (m, 2H), 2.75 (apparent d, J=4, 2H); R$_f$(5:1 dichloromethane:methanol)=0.27.

C) 1-[2(S)-Hydroxy-3(S)-(N-ethoxycarbonyl-(L)-valyl)amino-4-phenylbutyl]-1-[4-biphenylylmethyl]-2-[N-ethoxycarbonyl-(L)-valyl]-hydrazine Preparation analogously as described in Example 93B) with ethoxycarbonyl-(L)-valine (Example 80a)) instead of the methoxycarbonyl-(L)-valine. After purification by column chromatography on silica gel (eluent: 30:1 dichloromethane:methanol), the title compound is obtained:

$^1$H-NMR (CD$_3$OD) δ=7.6–7.1 (m, 14H), 4.18–3.95 (m, 6H), 3.9 (d, J=8, 1H), 3.77 (d, J=4, 1H), 3.72 (d, br, 1H), 3.69 (2 s, 2×CH$_3$), 3.65 (d, J=4, 1H), 2.95–2.75 (m, 3H), 2.65 (dd, J=8, 1, 1H), 1.84 (sept, J=7, 1H), 1.66 (sept, J=7, 1H), 1.22 (m, 6H), 0.75 (apparent t, J=7, 6H), 0.62 (d, J=7, 3H), 0.60 (d, J=7, 3H); FAB MS (M+H)$^+$=644, R$_f$(15:1 dichloromethane:methanol)=0.53.

D) 1-[2(S)-hydroxy-3(S)-(N-(N,N-dimethylaminocarbonyl)-(L)-valyl)amino-4-phenylbutyl]-1-[4-biphenylylmethyl]-2-[N-(N,N-dimethylaminocarbonyl)-(L)-valyl]-hydrazine;

E) 1-[2(S)-hydroxy-3(S)-(N-(N-(2-methoxyethyl)aminocarbonyl)-(L)-valyl)amino-4-phenylbutyl]-1-[4-biphenylylmethyl]-2-[N-(N-(2-methoxyethyl)aminocarbonyl)-(L)-valyl]-hydrazine;

F) 1-[2(S)-hydroxy-3(S)-(N-(N-(2-(morpholin-4-yl)ethyl)aminocarbonyl)-(L)-valyl)-amino-4-phenylbutyl]-1-[4-biphenylylmethyl]-2-[N-(N-(2-(morpholin-4-yl)ethyl)aminocarbonyl)-(L)-valyl]-hydrazine;

G) 1-[2(S)-hydroxy-3(S)-(N-(N-(2-(morpholin-4-yl)ethyl)-N-methylaminocarbonyl)-(L)-valyl)amino-4-phenylbutyl]-1-[4-biphenylylmethyl]-2-[N-(N-(2-(morpholin-4-yl)ethyl)-N-methylaminocarbonyl)-(L)-valyl]-hydrazine.

EXAMPLE 94

1-[2(S)-Hydroxy-3(S)-(N-(methoxycarbonyl)-(L)-valyl)amino-4-cyclohexyl-butyl]-1-[cyclohexylmethyl]-2-[N-methoxycarbonyl-(L)-valyl]-hydrazine In the presence of 20 mg of Nishimura catalyst (Rh(III)- and Pt(VI)-oxide monohydrate, Degussa) 100 mg (0.165 mmol) of 1-[2(S)-hydroxy-3(S)-(N-(methoxycarbonyl)-(L)-valyl)amino-4-phenyl-butyl]-1-[cyclohexylmethyl]-2-[N-methoxycarbonyl-(L)-valyl]-hydrazine (Example 73a) in the form of a solution in 8 ml of methanol are hydrogenated under low pressure at RT. Removal of the catalyst by filtration through ®Celite and concentration of the filtrate by evaporation yields the title compound: FAB-MS (M+H)$^+$=612.

EXAMPLE 95

1-[2(S)-Hydroxy-3(S)-(N-(n-propoxycarbonyl)-(L)-valyl)amino-4-phenylbutyl]-1-[cyclohexylmethyl]-2-[N-(n-propyl)oxycarbonyl-(L)-valyl]-hydrazine Hydrogenation under low pressure at RT of a solution of 100 mg (0.152 mmol) of 1-[2(S)-hydroxy-3(S)-(N-(allyloxycarbonyl)-(L)-valyl)amino-4-phenyl-butyl]-1-[cyclohexylmethyl]-2-[N-allyloxycarbonyl-(L)-valyl]-hydrazine (Example 79) in 4 ml of methanol using 50 mg of 5% Pd/C as catalyst, followed by filtration through ®Celite (siliceous earth; Fluka, Switzerland), concentration of the filtrate by evaporation and digestion from DIPE, yields the pure title compound: FAB-MS $(M+H)^+=662$.

EXAMPLE 96

1-[2(R)-Hydroxy-3(S)-(N-(methoxycarbonyl)-(L)-valyl)amino-4-phenylbutyl]-1-[cyclohexylmethyl]-2-[N-methoxycarbonyl-(L)-valyl]-hydrazine Under a protective gas atmosphere, 33 mg (0.186 mmol) of N-methoxycarbonyl-(L)-valine (Example 73b) are activated with 82 mg (0.186 mmol) of BOP and 25 mg (0.186 mmol) of HOBT in 1.24 ml of a 0.3M solution of NMM in DMF and, after 15 min, reacted with 25 mg (0.062 mmol) of 1-[2(R)-hydroxy-3(S)-amino-4-phenyl-butyl]-1-[cyclohexylmethyl]-hydrazine (in the form of the hydrochloride salt) for 18 h. The reaction mixture is concentrated by evaporation under HV and the residue is partitioned between 3 portions of methylene chloride, 2 portions of saturated NaHCO$_3$ solution and brine. Column chromatography (Si$_2$, methylene chloride/methanol 99:1→15:1) and precipitation with DIPE from a concentrated solution in DMF yields the pure title compound: $t_{Ref}(V)$=14.7 min; FAB-MS $(M+H)^+=606$.

The starting material is prepared as follows:

a) 2(R)-[1'(S)-(Trifluoroacetylamino)-2'-phenylethyl]-oxirane (Alternative to Example 16d)

54.28 g (314 mmol) of m-chloroperbenzoic acid are added to a solution of 14.5 g (60 mmol) of N-trifluoroacetyl-1-phenyl-3-buten-2(S)-amine (Example 16c) in 600 ml of chloroform and the mixture is stirred for 16 h at RT to complete the reaction. The reaction mixture is washed twice with 10% sodium sulfite solution, twice with saturated sodium carbonate solution, with water and finally with brine. The aqueous phases are extracted a further twice with methylene chloride, and the combined organic phases are dried with sodium sulfate and concentrated by evaporation. Column chromatography (SiO$_2$, hexane/ethyl acetate 2:1) yields the title compound in the form of a 6:1 mixture of the (2R)- and (2S)-epimers: TLC R$_f$(F)=0.41, TLC R$_f$(N)=0.6; $t_{Ref}(V)$=12.6 min; $^1$H-NMR (200 MHz, CDCl$_3$): inter alia 4.08 (m, 1/7H, H—C(2(S))), 4.47 (m, 6/7H, H—C(2(R))).

b) 1-[2(S)-Hydroxy-3(S)-(trifluoroacetylamino)-4-phenyl-butyl]-1-[cyclohexylmethyl]-2-[tert-butoxycarbonyl]-hydrazine and 1-[2(R)-hydroxy-3(S)-(trifluoroacetylamino)-4-phenyl-butyl]-1-[cyclohexylmethyl]-2-[tert-butoxycarbonyl]-hydrazine Under a nitrogen atmosphere, 2.5 g (9.65 mmol) of 2(R)-[1'(S)-(trifluoroacetylamino)-2'-phenylethyl]-oxirane (contains 14% of the (2S)-epimer) and 2.2 g (9.65 mmol) of tert-butyl-3-cyclohexylmethyl-carbazate (Example 4a) dissolved in 31 ml of methanol are reacted for 18 h at 75° C. The reaction mixture is concentrated by evaporation and the residue is chromatographed (SiO$_2$, toluene/ethyl acetate 10:1). The (2S)-epimer is eluted first as the main product, followed by the (2R)-epimer: (2S)-epimer TLC R$_f$(I)=0.7; $t_{Ref}(V)$=18.5 min; Anal: calc. C 59.12%, H 7.44%, N 8.62%; found C 59.10%, H 7.09%, N 8.81%. (2R)-epimer TLC R$_f$(I)=0.6; $t_{Ref}(V)$=18.5 min; FAB-MS $(M+H)^+=488$.

c) 1-[2(R)-Hydroxy-3(S)-amino-4-phenyl-butyl]-1-[cyclohexylmethyl]-2-[tert-butoxycarbonyl]-hydrazine Under a nitrogen atmosphere, 326 mg (0.669 mmol) of 1-[2(R)-hydroxy-3(S)-(trifluoroacetylamino)-4-phenyl-butyl]-1-[cyclohexylmethyl]-2-[tert-butoxycarbonyl]-hydrazine dissolved in 52 ml of MeOH are heated to 70° C., 17 ml of 1M aqueous K$_2$CO$_3$ solution are added dropwise and the mixture is stirred for 16 h at 70° C. The reaction mixture is concentrated by evaporation and the residue is partitioned between 3 portions of methylene chloride, 2 portions of water and brine. Concentration by evaporation of the organic phases which have been dried with Na$_2$SO$_4$ yields the title compound, which is used directly in the next step: $^1$H-NMR (200 MHz, CD$_3$OD): 1.42 (s, 9 H, Boc), 0.8–2.1 (m, 11 H, cyclohexyl), 2.4–3.0 (m, 6H), 3.1 (m, 1H), 3.54 (m, 1H), 7.28 (m, 5H).

d) 1-[2(R)-Hydroxy-3(S)-amino-4-phenyl-butyl]-1-[cyclohexylmethyl]-hydrazine (hydrochloride salt):

Under a nitrogen atmosphere, 2 ml of 4N HCl/dioxane are added to a solution of 80 mg (0.204 mmol) of 1-[2(R)-hydroxy-3(S)-amino-4-phenyl-butyl]-1-[cyclohexylmethyl]-2-[tert-butoxycarbonyl]-hydrazine in 2 ml of dioxane and the mixture is stirred for 7 h at RT and then lyophilised. The crude product is used directly in the above reaction.

EXAMPLE 97

1-[2(R)-Hydroxy-3(R)-(N-(methoxycarbonyl)-(L)-valyl)amino-4-phenylbutyl]-1-[cyclohexylmethyl]-2-[ N-methoxycarbonyl-(L)-valyl]-hydrazine Under a nitrogen atmosphere, 315 mg (1.80 mmol) of N-methoxycarbonyl-(L)-valine (Example 73b) are activated with 795 mg (1.80 mmol) of BOP and 267 mg (1.80 mmol) of HOBT in 12 ml of a 0.3M solution of NMM in DMF and, after 15 min, reacted for 48 h with 240 mg (0.60 mmol) of 1-[2(R)-hydroxy-3(R)-amino-4-phenyl-butyl]-1-[cyclohexylmethyl]-hydrazine (in the form of the hydrochloride salt) (can be prepared analogously to 1-[2(S)-hydroxy-3(S)-amino-4-phenyl-butyl]-1-[cyclohexylmethyl]-hydrazine hydrochloride salt (Example 10a, =H-[Phe$^{NN}$Cha]-H.3HCl) from (D)-N-Boc-phenylalanine). The reaction mixture is concentrated by evaporation under HV and the residue is partitioned between 3 portions of methylene chloride, 2 portions of saturated NaHCO$_3$ solution and brine. Column chromatography (SiO$_2$, methylene chloride/methanol 19:1) and digestion with methylene chloride/DIPE yields the pure title compound: TLC R$_f$(B')=0.60; $t_{Ref}(V)$= 14.7 min; FAB-MS $(M+H)^+=606$.

EXAMPLE 98

1-[2(S)-Hydroxy-3(S)-(benzyloxycarbonylamino)-4-phenyl-butyl]-1-[phenylmethyl]-2-[ N-methoxycarbonyl-(L)-valyl]-hydrazine Under a nitrogen atmosphere, 0.28 mmol of 1-[2(S)-hydroxy-3(S)-(benzyloxycarbonylamino)-4-phenyl-butyl]-1-[phenylmethyl]-hydrazine and 54.3 mg (0.31 mmol) of N-methoxycarbonyl-(L)-valine (Example 73b) are dissolved in 3.36 ml of 0.25M NMM/CH$_3$CN, 117.6 mg (0.31 mmol) of HBTU are added and the mixture is stirred for 3 h at RT. During that time the pure title compound separates from the initially clear solution in the form of a precipitate, which is filtered off and washed with 3 ml of CH$_3$CN/DIPE 1:2: TLC R_f(I)=0.22; t_Ret(V)=15.4 min; FAB-MS (M+H)⁺=577. Further product can be recovered by concentrating the filtrate by evaporation, partitioning the residue between 3 portions of ethyl acetate, 2 portions of saturated NaHCO$_3$ solution, water and brine, drying the organic phases with Na$_2$SO$_4$, concentrating by evaporation and digesting from DIPE. T he starting material is prepared as follows:

a) 1-[2(S)-Hydroxy-3(S)-(benzyloxycarbonylamino)-4-phenyl-butyl]-1-[phenylmethyl]-2-[tert-butoxycarbonyl]-hydrazine Under a nitrogen atmosphere, 220 mg (0.57 mmol) of 1-[2(S)-hydroxy-3(S)-amino-4-phenyl-butyl]-1-[phenylmethyl]-2-[tert-butoxycarbonyl]-hydrazine (=H-[Phe^NN Phe]-Boc, Example 30b) in 15 ml of dioxane/water 1:1 and 408 mg (2.9 mmol) of K$_2$CO$_3$ are reacted with 120 mg (0.69 mmol) of chloroformic acid benzyl ester for 16 h at RT. KHSO$_4$ solution is added, the mixture is extracted with 3 portions of ethyl acetate, and the organic phases are washed with water and brine, dried with Na$_2$SO$_4$ and concentrated by evaporation. Digestion from hexane yields the pure title compound: TLC R_f(I)=0.52; t_Ret(V)=17.1 min; FAB-MS (M+H)⁺=520.

b) 1-[2(S)-Hydroxy-3(S)-(benzyloxycarbonylamino)-4-phenyl-butyl]-1-[phenylmethyl]hydrazine 148 mg (0.28 mmol) of 1-[2(S)-hydroxy-3(S)-(benzyloxycarbonylamino)-4-phenylbutyl]-1-[(phenylmethyl]-2-[tert-butoxycarbonyl]-hydrazine dissolved in 7 ml of formic acid are stirred overnight at RT. The reaction mixture is concentrated by evaporation under HV, the residue is partitioned between 3 portions of ethyl acetate, 2 portions of NaHCO$_3$ solution and brine, and the organic phases are dried with Na$_2$SO$_4$ and concentrated by evaporation: TLC R_f(I)=0.50; t_Ret(V)=11.8 min.

EXAMPLE 99

1-[2(S)-Hydroxy-3(S)-(N-(methoxycarbonyl)-(L)-valyl)amino-4-cyclohexyl-butyl]-1-[phenylmethyl]-2-[N-methoxycarbonyl)-L-valyl]-hydrazine Analogously to Example 87B, 91.7 mg (0.52 mmol) of N-methoxycarbonyl-(L)-valine (Example 73b) are activated with 232 mg (0.52 mmol) of BOP and 70.7 mg (0.53 mmol) of HOBT in 3.5 ml of a 0.3M solution of NMM in DMF and reacted with 70 mg (0.174 mmol) of 1-[2(S)-hydroxy-3(S)-amino-4-cyclohexyl-butyl]-1-[phenylmethyl]hydrazine (in the form of the hydrochloride salt) for 18 h. The reaction mixture is concentrated by evaporation under HV, and the residue is partitioned between 3 portions of methylene chloride, 2 portions of saturated NaHCO$_3$ solution and brine. Precipitation with DIPE from a concentrated solution in DMF yields the pure title compound: TLC R_f(G')=0.61; t_Ret(V)=14.7 min; FAB-MS (M+H)⁺=606.

The starting material is prepared as follows:

a) N-3(S)-(Boc-amino)-2(R,S)-hydroxy-4-cyclohexyl-1-trimethylsilyl-butane

Using 2.94 g of Nishimura catalyst (Rh(III)- and Pt(VI)-oxide monohydrate, Degussa, Germany) 25 g (81.3 mmol) of N-3(S)-(Boc-amino)-2(R,S)-hydroxy-4-phenyl-1-trimethylsilyl-butane (for preparation see EP-532 466-A2, page 42) in 882 ml of methanol are hydrogenated under low pressure at RT. Removal of the catalyst by filtration through ®Celite and concentration by evaporation of the filtrate yields the title compound: TLC R_f(I)=0.7; FAB-MS (M+H)⁺=344.

b) 1-Cyclohexyl-3-buten-2(S)-amine 42.2 ml (336 mmol) of an approximately 48% solution of boron trifluoride in ether are added at 5° C. to a solution of 23.1 g (67.2 mmol) of 3(S)-(Boc-amino)-2(R,S)-hydroxy-4-cyclohexyl-1-trimethylsilyl-butane in 460 ml of methylene chloride. The reaction mixture is then stirred for 6 h at RT and 3M sodium carbonate solution is added. The aqueous phase is removed and extracted twice with methylene chloride. The organic extracts are washed with brine, dried over sodium sulfate and concentrated by evaporation. The title product is further used without additional purification.

c) N-Boc-1-cyclohexyl-3-buten-2(S)-amine 15.2 g (69.5 mmol) of Boc-anhydride are added at RT to 8.2 g (53.5 mmol) of 1-cyclohexyl-3-buten-2(S)-amine in the form of a solution in 110 ml of methylene chloride. The mixture is stirred for 17 h at RT and then extracted twice with 10% citric acid, water and brine. The aqueous phases are washed a further twice with methylene chloride, dried with sodium sulfate and concentrated by evaporation. Column chromatography (SiO$_2$, hexane/ethyl acetate 4:1) yields the title compound: TLC R_f(I)=0.8.

d) 2(R)-[1'(S)-(Boc-amino)-2'-cyclohexylethyl]-oxirane 8.5 g (172 mmol) of m-chloroperbenzoic acid are added to a solution of 2.5 g (9.86 mmol) of N-Boc-1-cyclohexyl-3-buten-2(S)-amine in 65 ml of chloroform and the mixture is stirred for 18 h at RT to complete the reaction. The reaction mixture is washed with 10% sodium sulfite solution, saturated sodium carbonate solution, water and brine. The aqueous phases are extracted a further twice with methylene chloride, and the combined organic phases are dried with sodium sulfate and concentrated by evaporation. Column chromatography (SiO$_2$, hexane/ethyl acetate 5:1) finally yields the pure title compound: TLC R_f(L)=0.22.

e) 1-[2(S)-Hydroxy-3(S)-(tert-butoxycarbonylamino)-4-cyclohexyl-butyl]-1-[phenylmethyl]-2-[tert-butoxycarbonyl]-hydrazine Under a nitrogen atmosphere, 200 mg (0.745 mmol) of 2(R)-[1'(S)-(Boc-amino)-2'-cyclohexylethyl]-oxirane and 165 mg (0.745 mmol) of tert-butyl-3-benzyl-carbazate (J. Chem. Soc., Perkin I, 1712 (1975)) in 6 ml of methanol are stirred for 2 days at 75° C. Concentration of the reaction mixture by evaporation and precipitation with hexane from a concentrated solution in methylene chloride yields the title compound: TLC R_f(I)=0.54.

f) 1-[2(S)-Hydroxy-3(S)-amino-4-cyclohexyl-butyl]-1-[phenylmethyl]-hydrazine (hydrochloride salt)

0.5 ml of 4N HCl/dioxane are added, with the exclusion of moisture, to a solution of 90 mg (0.183 mmol) of 1-[2(S)-hydroxy-3(S)-(tert-butoxycarbonylamino)-4-cyclohexylbutyl]-1-[phenylmethyl]-2-[tert-butoxycarbonyl]-hydrazine in 0.5 ml of dioxane. After 5 h at RT the reaction mixture is lyophilised and the lyophilisate is directly further used.

EXAMPLE 100

A) 1-[2(S)-Hydroxy-3(S)-(N-(quinoline-2-carbonyl)-(L)-asparaginyl)amino-4-phenyl-butyl]-1-[cyclohexylmethyl]-2-[tert-butoxycarbonyl]-hydrazine At 5° C., 940 mg (3.27 mmol) of quinoline-2-carbonyl-(L)-asparagine (in the form of the hydrochloride salt) are dissolved in 35 ml of THF, and 736 mg (3.57 mmol) of DCC are added. After 10 min. 482 mg (3.57 mmol) of HOBT, 0.82 ml (7.44 mmol) of NMM and 1.165 g (2.98 mmol) of 1-[2(S)-hydroxy-3(S)-amino-4-phenyl-butyl]-1-[cyclohexylmethyl]-2-[tert-butoxycarbonyl]-hydrazine are added and the mixture is stirred at RT for 18 h. The reaction mixture is filtered and the filtrate is concentrated by evaporation. The residue is partitioned between 3 portions of ethyl acetate, saturated NaHCO$_3$ solution, water and brine, and the organic phases, which have been dried with Na$_2$SO$_4$, are concentrated by evaporation and subjected to column chromatography (SiO2, ethyl acetate) to yield the title compound: TLC $R_f(O)$=0.16; $t_{Ret}(V)$=16.5 min; FAB-MS (M+H)$^+$=661.

The starting compound is prepared in the following manner:

a) Quinoline-2-carbonyl-(L)-asparagine tert-butyl ester

Analogously to Example 100, 5.45 g (31.4 mmol) of quinaldic acid in 161 ml of THF are reacted with 7.08 g (34.3 mmol) of DCC, 4.63 g (34.3 mmol) of HOBT and 5.38 g (28.6 mmol) of (L)-asparagine tert-butyl ester (Bachem, Bubendorf/Switzerland). Filtration, extraction and column chromatography (SiO$_2$, ethyl acetate/hexane 3:1) yields the pure title compound: TLC $R_f(C')$=0.15; $t_{Ret}(V)$=12.2 min; FAB-MS (M+H)$^+$=344.

b) Quinoline-2-carbonyl-(L)-asparagine (hydrochloride salt)

Under a nitrogen atmosphere, 4.0 g (11.6 mmol) of quinoline-2-carbonyl-(L)-asparagine tert-butyl ester are dissolved in 40 ml of dioxane, and 40 ml of 4N HCl/dioxane are added. On stirring for 17 h at RT, the product is precipitated in the form of a solid. Filtration and washing with DIPE yields the pure title compound: $^1$H-NMR (200 MHz, CD$_3$OD): 3.02 (d, J=6 Hz, 2H), 5.09 (t, J=6 Hz, 1H), 7.92 (m, 1H), 8.12 (m, 1H), 8.26 (m, 1H), 8.4 (m, 2H), 9.03 (m, 1H).

c) 1-[2(S)-Hydroxy-3(S)-amino-4-phenyl-butyl]-1-[cyclohexylmethyl]-2-[tert-butoxycarbonyl]-hydrazine Under a nitrogen atmosphere, 2.0 g (4.10 mmol) of 1-[2(S)-hydroxy-3(S)-(trifluoroacetylamino)-4-phenyl-butyl]-1-[cyclohexylmethyl]-2-[tert-butoxycarbonyl]-hydrazine (Example 96b) dissolved in 316 ml of MeOH are heated to 70° C., 103 ml of 1M aqueous K$_2$CO$_3$ solution are added dropwise, and the mixture is stirred for 18 h at 70° C. The reaction mixture is concentrated by evaporation under HV and the residue is partitioned between 3 portions of methylene chloride, 2 portions of water and brine. Concentration by evaporation of the organic phases, which have been dried with Na$_2$SO$_4$, yields the title compound: $^1$H-NMR (200 MHz, CD$_3$OD): 1.42 (s, 9 H, Boc), 0.8–2.1 (m, 11H, cyclohexyl), 2.35–3.0 (m, 7H), 3.51 (m, 1H), 7.25 (m, 5H).

B) 1-[2(S)-Hydroxy-3(S)-(N-(quinoline-2-carbonyl)-(L)-asparaginyl)amino-4-phenyl-butyl]1-[phenylmethyl]-2-[tert-butoxycarbonyl]-hydrazine At 0° C., 3.84 g (13.4 mmol) of quinoline-2-carbonyl-(L)-asparagine (hydrochloride salt) (Example 100A) b)) are added to 4.69 g (12.2 mmol) of 1-[2(S)-hydroxy-3(S)-amino-4-phenyl-butyl]-1-[phenylmethyl]-2-[tert-butoxycarbonyl]-hydrazine in 250 ml of THF, 2.18 g (13.4 mmol) of HOBT, 2.76 g (13.4 mmol) of DCC and 2.14 ml (19.5 mmol) of NMM are added to the suspension which is then stirred for 30 min at 0° C. and for 17 h at RT. The reaction mixture is filtered and the filtrate is concentrated by evaporation to a residual volume of approximately 50 ml. The fine suspension is taken up in methylene chloride and washed with NaHCO$_3$ solution and brine, and the aqueous phases are extracted with 2 portions of methylene chloride. Filtration of the combined organic phases through cotton wadding, concentration by evaporation and precipitation from a concentrated solution in methanol/methylene chloride with DIPE and finally hexane yields the pure title compound: TLC $R_f(P)$=0.41; $t_{Ret}(V)$=14.8 min; FAB-MS (M+H)$^+$=655.

The starting material is prepared as follows:

a) 1-[2(S)-Hydroxy-3(S)-(trifluoroacetylamino)-4-phenyl-butyl]-1-[phenylmethyl]-2-[tert-butoxycarbonyl]-hydrazine: (improved version for Example 30a))

Under a nitrogen atmosphere, 20.49 g (79 mmol) of 2(R)-[1'(S)-(trifluoroacetylamino)-2'-phenylethyl]-oxirane (Example 96a) and 17.56 g (79 mmol) of tert-butyl-3-benzylcarbazate (J. Chem., Perkin I, 1712 (1975)) in 300 ml of ethanol are heated at 80° C. for 20 h. Cooling and partial concentration by evaporation until crystallisation commences, filtration and washing with a small amount of ethanol yields the pure title compound: $t_{Ret}(V)$=16.1 min; FAB-MS (M+H)$^+$=482; $^1$H-NMR (200 MHz, CD$_3$OD): 1.30 (s, 9H), 2.70 (m, 2H), 2.83–3.08 (m, 2H), 3.76 (m, 1H), 3.85 (s, 2H), 4.21 (m, 1H 7.2–7.4 (m, 10H).

b) 1-[2(S)-Hydroxy-3(S)-amino-4-phenyl-butyl]-1-[phenylmethyl]-2-[tert-butoxycarbonyl]-hydrazine: (improved version for Example 30b))

Under a nitrogen atmosphere, 6.0 g (12.5 mmol) of 1-[2(S)-hydroxy-3(S)-(trifluoroacetylamino)-4-phenyl-butyl]-1-[phenylmethyl]-2-[tert-butoxycarbonyl]-hydrazine dissolved in 420 ml of MeOH are heated to 80° C., 125 ml of 1M aqueous K$_2$CO$_3$ solution are added dropwise (15 min) and the mixture is stirred for 18 h at 80° C. The reaction mixture is concentrated by evaporation and the residue is partitioned between 3 portions of methylene chloride, water and brine. Concentration by evaporation of the organic phases, which have been filtered through cotton wadding, yields the title compound: $t_{Ret}(V)$=11.5 min; $^1$H-NMR (200 MHz, CD$_3$OD): 1.29 (s, 9H), 2.5–3.05 (m, 5H), 3.56 (m, 1H), 3.8–3.95 (AB, 2H), 7.1–7.4 (m, 10H).

C): 1-[2(S)-Hydroxy-3(S)-(N-(quinoline-2-carbonyl)-(L)-asparaginyl)amino-4-phenylbutyl]-1-[p-(methoxyphenyl) methyl]-2-[tert-butoxycarbonyl]-hydrazine Analogously to Example 100B), 7.00 g (16.8 mmol) of 1-[2(S)-hydroxy-3(S)-amino-4-phenyl-butyl]-1-[p-(methoxy-phenyl)methyl]-2-[tert-butoxycarbonyl]-hydrazine in 420 ml of THF are reacted with 5.3 g (18.5 mmol) of quinoline-2-carbonyl-(L)-asparagine (hydrochloride salt) (Example 100A) b)), 3.0 g (18.5 mmol) of HOBT, 3.8 g (18.5 mmol) of DCC and 5 ml of NMM. The reaction mixture is filtered, the filtrate is concentrated by evaporation, and the evaporation residue is taken up in ethyl acetate and washed twice in each case with NaHCO$_3$ solution and brine. The aqueous phases are extracted with 2 portions of ethyl acetate and the organic phases are dried with Na$_2$SO$_4$ and concentrated by evaporation. Column chromatography (SiO$_2$, ethyl acetate) yields the pure title compound: TLC $R_f(O)$=0.59; $t_{Ret}(V)$=14.5 min; FAB-MS (M+H)$^+$=685.

The starting material is prepared as follows:

a) p-(Methoxyphenyl)-carbaldehyde tert-butoxycarbonylhydrazone

Under protective gas, 65 ml (534 mmol) of freshly distilled anisaldehyde are dissolved in 850 ml of ethanol, 70.6 g (534 mmol) of tert-butylcarbazate are added and the mixture is heated for 3 h at 80° C. Concentration of the reaction mixture by evaporation yields the title compound: $^1$H-NMR (200 MHz, CD$_3$OD): 1.53 (s, 9H), 3.82 (s, 3H), 6.94 and 7.64 (2 d, J=9 Hz, each 2H), 7.86 (s, 1H).

b) tert-Butyl-3-(p-methoxyphenyl-methyl)-carbazate 130 g (520 mmol) of p-(methoxyphenyl)-carbaldehyde tert-butoxycarbonylhydrazone are hydrogenated in 1.3 l of THF in the presence of 11.5 g of 5% Pd/C. Removal of the catalyst by filtration through ®Celite and concentration by evaporation of the filtrate yields the title compound: TLC $R_f(F)$=0.3; $t_{Ret}(V)$=8.9 min; $^1$H-NMR (200 MHz, CD$_3$OD): 1.44 (s, 9H), 3.77 (s, 3H), 3.83 (s, 2H), 6.87 and 7.26 (2 d, J=8 Hz, each 2H).

c) 1-[2(S)-Hydroxy-3(S)-(trifluoroacetylamino)-4-phenyl-butyl]-1-[p-(methoxyphenyl)methyl]-2-[tert-butoxycarbonyl]-hydrazine Under protective gas, 15 g (57.9 mmol) of 2(R)-[1'(S)-(trifluoroacetylamino)-2'-phenylethyl]-oxirane (Example 96a) and 14.6 g (57.9 mmol) of tert-butyl-3-(p-methoxyphenylmethyl)-carbazate in 220 ml of ethanol are heated for 18 h at 80° C. Cooling, concentration by evaporation and digestion in DIPE yields the title compound: TLC $R_f(F)$=0.42; $t_{Ret}(V)$=15.8 min.

d) 1-[2(S)-Hydroxy-3(S)-amino-4-phenyl-butyl]-1-[p-(methoxyphenyl)methyl]-2-[tert-butoxycarbonyl]-hydrazine Analogously to Example 100B) b), 19.7 g (38.4 mmol) of 1-[2(S)-hydroxy-3(S)-(trifluoroacetylamino)-4-phenyl-butyl]-1-[p-(methoxy-phenyl)methyl]-2-[tert-butoxycarbonyl]-hydrazine in 1 l of methanol are hydrolysed with 384 ml of 1M $K_2CO_3$ solution to yield the title compound: TLC $R_f(G')$=0.4.

EXAMPLE 101

1-[2(S)-Hydroxy-3(S)-(N-(quinoline-2-carbonyl)-(L)-asparaginyl)amino-4-phenyl-butyl]-1-[cyclohexylmethyl]-2-[N-methoxycarbonyl-(L)-valyl]-hydrazine Under a nitrogen atmosphere, 100 mg (0.178 mmol) of 1-[2(S)-hydroxy-3(S)-(N-(quinoline-2-carbonyl)-(L)-asparaginyl)amino-4-phenyl-butyl]-1-[cyclohexylmethyl] hydrazine (Example 71e) i)) and 34 mg (0.196 mmol) of N-methoxycarbonyl-(L)-valine (Example 73b) are dissolved in 1.75 ml of a 0.3M solution of NMM in DMF, 74 mg (0.196 mmol) of HBTU are added and the mixture is stirred at RT. Since, after 3 days, there is still unreacted hydrazine present, a further 0.3 equivalents in each case of N-methoxycarbonyl-(L)-valine and HBTU in 0.48 ml of 0.3M NMM/DMF is added. After 18 h the reaction mixture is concentrated by evaporation under HV, the residue is dissolved in methylene chloride and washed with saturated $NaHCO_3$ solution, water and brine, the aqueous phases are extracted twice with methylene chloride, and the organic phases are dried with $Na_2SO_4$ and concentrated by evaporation. Column chromatography ($SiO_2$, methylene chloride/methanol 15:1) and digestion from DIPE yields the title compound: TLC $R_f(A')$=0.17; $t_{Ret}(V)$=14.6 min; FAB-MS $(M+H)^+$=718.

EXAMPLE 102

1-[2(S)-Hydroxy-3(S)-(N-(quinoline-2-carbonyl)-(L)-asparaginyl)amino-4-phenyl-butyl]-1-[cyclohexylmethyl]-2-[3,3-dimethylbutylyl]-hydrazine Under a protective gas atmosphere, 100 mg (0.178 mmol) of 1-[2(S)-hydroxy-3(S)-(N-(quinoline-2-carbonyl)-(L)-asparaginyl)amino-4-phenyl-butyl]-1-[cyclohexylmethyl] hydrazine (Example 71E) i)) and 25 µl (0.196 mmol) of 3,3-dimethylbutyric acid are dissolved in 1.75 ml of a 0.3M solution of NMM in DMF, 74 mg (0.196 mmol) of HBTU are added and the mixture is stirred at RT. Since, after 18 h, there is still unreacted hydrazine present, a further 0.3 equivalents in each case of 3,3-dimethylbutyric acid and HBTU in 0.5 ml of 0.3N NMM/DMF is added. Working up analogously to Example 101, column chromatography ($SiO_2$, ethyl acetate/ethanol 20:1) and digestion from DIPE yields the title compound: TLC $R_f(E')$=0.23; $t_{Ret}(V)$=15.6 min; FAB-MS $(M+H)^+$=659.

EXAMPLE 103

1-[2(S)-Hydroxy-3(S)-(N-(quinoline-2-carbonyl)-(L)-asparaginyl)amino-4-phenyl-butyl]-1-[cyclohexylmethyl]-2-[tert-butylaminocarbonyl]-hydrazine Under a protective gas atmosphere, 100 mg (0.178 mmol) of 1-[2(S)-hydroxy-3(S)-(N-(quinoline-2-carbonyl)-(L)-asparaginyl)amino-4-phenyl-butyl]-1-[cyclohexylmethyl] hydrazine (Example 71E) i)) are dissolved in 0.7 ml of THF and reacted with 19 µl (0.169 mmol) of tert-butyl-isocyanate for 17 h at RT. The reaction mixture is concentrated by evaporation, the residue is dissolved in ethyl acetate and washed with 5% citric acid solution, water and brine, and the inorganic phases are extracted twice with ethyl acetate, dried with $Na_2SO_4$ and concentrated by evaporation. Column chromatography ($SiO_2$, ethyl acetate/ethanol 10:1) yields the title compound: TLC $R_f(F')$=0.16; $t_{Ret}(V)$=15.3 min; FAB-MS $(M+H)^+$=660.

EXAMPLE 104

1-[2(S)-Hydroxy-3(S)-(N-(quinoline-2-carbonyl)-(L)-asparaginyl)amino-4-phenyl-butyl]-1-[cyclohexylmethyl]-2-[benzylaminocarbonyl]-hydrazine Analogously to Example 103, 100 mg (0.178 mmol) of 1-[2(S)-hydroxy-3(S)-(N-(quinoline-2-carbonyl)-(L)-asparaginyl)amino-4-phenyl-butyl]-1-[cyclohexylmethyl] hydrazine (Example 71E) i) in 0.7 ml of THF are reacted with 21 µl (0.169 mmol) of benzyl isocyanate. Column chromatography ($SiO_2$, methylene chloride/methanol 15:1) and digestion from DIPE yields the title compound: TLC $R_f(A')$=0.12; $t_{Ret}(V)$=15.5 min; FAB-MS $(M+H)^+$=694.

EXAMPLE 105

1-[2(S)-Butyryloxy-3(S)-(N-(methoxycarbonyl)-(L)-valyl)amino-4-phenylbutyl]-1-[cyclohexylmethyl]-2-[N-methoxycarbonyl-(L)-valyl]-hydrazine 50 µ(0.495 mmol) of butyric acid chloride and 2 mg (0.017 mmol) of DMAP are added to an ice-cooled mixture of 200 mg (0.33 mmol) of 1-[2(S)-hydroxy-3(S)-(N-(methoxy-carbonyl)-(L)-valyl)amino-4-phenyl-butyl]-1-[cyclohexylmethyl]-2-[N-methoxycarbonyl-(L)-valyl]-hydrazine (Example 73a) in 2.6 ml of dioxane and 0.4 ml of pyridine. After 18 h at RT, according to HPLC there is still 1-[2(S)-hydroxy-3(S)-(N-(methoxycarbonyl)-(L)-valyl) amino-4-phenyl-butyl]-1-[cyclohexylmethyl]-2-[N-methoxycarbonyl-(L)-valyl]-hydrazine present in the reaction mixture, and therefore a further 0.75 equivalents of butyric acid chloride and a few granules of DMAP are added. After a further 18 h, a 3rd portion of 1.5 equivalents of butyric acid chloride is added and the mixture is further stirred for one night at RT (→HPLC: fully reacted). The reaction mixture is diluted with ethyl acetate and washed with 2 portions of saturated $NaHCO_3$ solution, water and brine, the aqueous phases are extracted twice with ethyl acetate, and the organic phases are dried with $Na_2SO_4$ and concentrated by evaporation. Digestion of the oily residue from hexane in an ultrasound bath yields the pure title compound: TLC $R_f(O)$=0.67; $t_{Ret}(V)$=17.2 min; FAB-MS $(M+H)^+$=676.

EXAMPLE 106

1-[2(S)-Palmitoyloxy-3(S)-(N-(methoxycarbonyl)-(L)-valyl)amino-4-phenyl-butyl]-1-[cyclohexylmethyl]-2-[N-methoxycarbonyl-(L)-valyl]-hydrazine Analogously to Example 105, 200 mg (0.33 mmol) of 1-[2(S)-hydroxy-3(S)-(N-(methoxy-carbonyl)-(L)-valyl) amino-4-phenyl-butyl]-1-[cyclohexylmethyl]-2-[N-methoxycarbonyl-(L)-valyl]-hydrazine (Example 73a) in 2.6 ml of dioxane and 0.4 ml of pyridine are reacted with 0.15 ml (0.495 mmol) of palmitic acid chloride and 2 mg (0.017 mmol) of DMAP. To complete the reaction a further 0.3 ml of palmitic acid chloride and a small amount of DMAP are added and the mixture is stirred. Extraction and column chromatography (SiO$_2$, ethyl acetate/hexane 3:2) yields the pure title compound: TLC R$_f$(H')=0.47; t$_{Ret}$(V)= 25.2 min; FAB-MS (M+H)$^+$=844.

EXAMPLE 107

1-[2(S)-(Methoxy-acetoxy)-3(S)-(N-(methoxycarbonyl)-(L)-valyl)amino-4-phenyl-butyl]-1-[cyclohexylmethyl]-2-[N-methoxycarbonyl-(L)-valyl]-hydrazine Analogously to Example 105, 200 mg (0.33 mmol) of 1-[2(S)-hydroxy-3(S)-(N-(methoxycarbonyl)-(L)-valyl) amino-4-phenyl-butyl]-1-[cyclohexylmethyl]-2-[N-methoxycarbonyl-(L)-valyl]-hydrazine (Example 73a) in 2.6 ml of dioxane and 0.4 ml of pyridine are reacted with 50 μl (0.495 mmol) of methoxyacetic acid chloride and 2 mg (0.017 mmol) of DMAP. To complete the reaction a further 0.5 equivalents of methoxyacetic acid chloride and a few granules of DMAP are added and the mixture is stirred. Extraction and digestion from DIPE/hexane in an ultrasound bath yields the pure title compound: TLC R$_f$(O)=0.48; t$_{Ret}$(V)=15.6 min; FAB-MS (M+H)$^+$=678.

EXAMPLE 108

1-[2(S)-(2-Pyridyl-carbonyl)oxy-3(S)-(tert-butoxycarbonyl)amino-4-phenyl-butyl]-1-[cyclohexylmethyl]-2-[tert-butoxycarbonyl]-hydrazine At 0° C. under a nitrogen atmosphere, 500 mg (4.07 mmol) of picolinic acid (Fluka; Buchs/Switzerland) in 25 ml of methylene chloride are converted into the acid chloride with 0.57 ml (4.07 mmol) of 1-chloro-N,N,2-trimethyl-1-propenamine [B. Haveaux, A. Dekoker, M. Rens, A. R. Sidani, J. Toye, L. Ghosez, M. Murakami, M. Yoshioka, and W. Nagata, Organic Syntheses 59, 26 (1980)]. After 45 min, 10 ml of THF, 8.3 ml of pyridine, 10 mg of DMAP and 1.00 g (2.03 mmol) of 1-[2(S)-hydroxy-3(S)-(tert-butoxycarbonyl)amino-4-phenyl-butyl]-1-[cyclohexylmethyl]-2-(tert-butoxycarbonyl)-hydrazine (=Boc-[Phe$^{NN}$Cha]-Boc, Example 4) are added and the mixture is stirred for 16 h at RT. Since according to HPLC there is still 1-[2(S)-hydroxy-3(S)-(tert-butoxycarbonyl) amino-4-phenyl-butyl]-1-[cyclohexylmethyl]-2-[tert-butoxycarbonyl]-hydrazine present in the reaction mixture, a further 2 equivalents of picolinic acid chloride (prepared as described above) dissolved in 20 ml of methylene chloride are added. After 18 h at RT the mixture is diluted with methylene chloride and washed twice with saturated NaHCO$_3$ solution, water and brine, and the organic phases are extracted with 2 portions of methylene chloride, dried with Na$_2$SO$_4$ and concentrated by evaporation. The brown residue is dissolved in methylene chloride/ethyl acetate, 10 g of silica gel are added and the mixture is concentrated by evaporation. The resulting powder is applied to a silica gel column (hexane/ethyl acetate 1:1). Elution with hexane/ethyl acetate 1:1 yields the title compound: TLC R$_f$(N)= 0.17; t$_{Ret}$(V)=19.9 min; $^1$H-NMR (200 MHz, CD$_3$OD): 0.6–1.85 (m, 11H, cyclohexyl), 1.36 and 1.40 (2 s, 18H, 2 Boc), 2.4–3.1 (m, 6H), 4.28 (m, 1H), 5.28 (m, 2H), 7.1–7.3 (m, 5H), 7.72 (m, 1H), 8.08 (m, 1H), 8.28 (d, J=7 Hz, 1H), 8.75 (d, J=5 Hz, 1H).

a) 1-[2(S)-Hydroxy-3(S)-(N-(methoxycarbonyl)-(L)-valyl) amino-4-phenyl-butyl]-1-[cyclohexylmethyl]-2-[pyridin-2-yl-carbonyl]-hydrazine i. Under a nitrogen atmosphere, 200 mg (0.335 mmol) of 1-[2(S)-(pyridin-2-yl-carbonyl)-oxy-3(S)-(tert-butoxycarbonyl)amino-4-phenyl-butyl]-1-[cyclohexylmethyl]-2-[tert-butoxycarbonyl]-hydrazine are dissolved in 200 ml of formic acid and the solution is stirred for 16 h at RT and then concentrated by evaporation under HV. The residue is partitioned between 3 portions of methylene chloride, saturated NaHCO$_3$ solution and brine and the organic phases are dried with Na$_2$SO$_4$ and concentrated by evaporation (t$_{Ret}$(V)=11.9 min).

ii. The above residue is dissolved in 5.3 ml of 0.25M NMM in acetonitrile, and 134 mg (0.763 mmol) of N-(methoxycarbonyl)-(L)-valine (Example 73b) and 313 mg (0.826 mmol) of HBTU are added. On stirring for 18 h at RT the title compound separates out in the form of a precipitate and can then be filtered off and washed with a small amount of acetonitrile. t$_{Ret}$(V)=15.9 min; FAB-MS (M+H)$^+$=554, $^1$H-NMR (500 MHz, DMSO-d$_6$): 0.64 and 0.70 (2s, J=7 Hz, (H$_3$C)$_2$C), 0.81 (m, 2 H$_{ax}$—C$_6$H$_{11}$), 1.08 (m, 3 H$_{ax}$—C$_6$H$_{11}$), 1.30 (m, H$_{1-az}$—C$_6$H$_{11}$), 1.57 (m, 3 H$_{eq}$—C$_6$H$_{11}$), 1.74 (m, 1 H$_{eq}$—C$_6$H$_{11}$), 1.79 (octet, J=7 Hz, HC(CH$_3$)$_2$), 1.88 (m, 1 H$_{eq}$—C$_6$H$_{11}$), 2.47–2.60 (m, H—C$_1$, HCH—C$_6$H$_{11}$), 2.66–2.84 (m, H—C$_1$, HCH—C$_6$H$_{11}$, H$_2$C-phenyl), 3.44 (m, HC$_2$), 3.50 (s, H$_3$C—O), 3.73 (m, HC$_α$-Val), 3.94 (m, HC$_3$), 4.94 (s, HO), 6.97 (d, J=9 Hz, HN-Val), 7.05 (m, HC$_{phenyl}$), 7.12 (m, 4 HC$_{phenyl}$), 7.51 (d, J=9 Hz, HN—C$_3$), 7.61 (m, H$_5$-Py), 8.00 (m, H$_3$-Py, H$_4$Py), 8.61 (d, J=5 Hz, H$_6$-Py, 9.70 (s, HN—N).

EXAMPLE 109

1-[2(S)-Hydroxy-3(S)-(N-(quinoline-2-carbonyl)-(L)-asparaginyl)amino-4-phenyl-butyl]-1-[benzyl]-2-[N-methoxycarbonyl)-(L)-valyl]-hydrazine Analogously to Example 111, 157.4 mg (0.898 mmol) of N-(methoxycarbonyl)-(L)-valine (Example 73b) and 453 mg (0.817 mmol) of 1-[2(S)-hydroxy-3(S)-(N-(quinoline-2-carbonyl)-(L)-asparaginyl)amino-4-phenyl-butyl]-1-[phenylmethyl]-hydrazine in 8 ml of 0.3M NMM/DMF are reacted with 340 mg (0.898 mmol) of HBTU. Column chromatography (SiO$_2$, methylene chloride→methylene chloride/methanol 50:1→25:1) yields the title compound: TLC R$_f$(J')=0.16; t$_{Ret}$(V)=13.6 min; FAB-MS (M+H)$^+$=712.

EXAMPLE 110

1-[2(S)-Hydroxy-3(S)-(N-(quinoline-2-carbonyl)-(L)-asparaginyl)amino-4-phenyl-butyl]-1-[benzyl]-2-[N-ethoxycarbonyl)-(L)-valyl]-hydrazine Under protective gas, 36 mg (0.189 mmol) of N-(ethoxycarbonyl)-(L)-valine (Example 80a), 35 mg (0.259 mmol) of HOBT and 38 mg (0.198 mmol) of EDC are dissolved in 0.7 ml of 0.3M NMM/DMF and the solution is stirred for 10 min at RT. 100 mg (0.180 mmol) of 1-[2(S)-hydroxy-3(S)-(N-(quinoline-2-carbonyl)-(L)-asparaginyl)amino-4-phenyl-butyl]-1-[phenylmethyl]-hydrazine (Example 111a) are added and the mixture is then stirred for 18 h at RT. The reaction mixture is concentrated by evaporation under HV, and the residue is taken up in ethyl acetate and washed with 2 portions of 10% citric acid solution, water, saturated NaHCO$_3$ solution and brine. The aqueous phases are extracted with ethyl acetate and the combined organic phases are dried with Na$_2$SO$_4$ and concentrated by evaporation. Column chromatography (SiO$_2$, methylene chloride/methanol 12:1) yields the title compound: TLC $R_f(I')$=0.25; $t_{Ret}(V)$=14.3 min.

EXAMPLE 111

1-[2(S)-Hydroxy-3(S)-(N-(quinoline-2-carbonyl)-(L)
-asparaginyl)amino-4-phenyl-butyl]-1-[benzyl]-2-
[N-benzyloxycarbonyl)-(L)-valyl]-hydrazine Under a nitrogen atmosphere, 50 mg (0.198 mmol) of Z-(L)-valine and 100 mg (0.18 mmol) of 1-[2(S)-hydroxy-3(S)-(N-(quinoline-2-carbonyl)-(L)-asparaginyl)amino-4-phenyl-butyl]-1-[phenylmethyl]-hydrazine are dissolved in 1.8 ml of a 0.3M solution of NMM in DMF, 75.1 mg (0.198 mmol) of HBTU are added and the mixture is stirred for 18 h at RT. The reaction mixture is concentrated by evaporation under HV, and the residue is taken up in ethyl acetate and washed with 2 portions of 10% citric acid solution, water, saturated NaHCO$_3$ solution and brine. The aqueous phases are extracted a further twice with ethyl acetate and the combined organic phases are dried with Na$_2$SO$_4$ and concentrated by evaporation. Column chromatography (SiO$_2$, methylene chloride/methanol 19:1) yields the title compound: TLC $R_f(J')$=0.27; $t_{Ret}(V)$=15.7 min; FAB-MS (M+H)$^+$=788.

The starting material is prepared as follows:

a) 1-[2(S)-Hydroxy-3(S)-(N-(quinoline-2-carbonyl)-(L)-asparaginyl)amino-4-phenylbutyl]-1-[phenylmethyl]-hydrazine 1.0 g (1.53 mmol) of 1-[2(S)-hydroxy-3(S)-(N-(quinoline-2-carbonyl)-(L)-asparaginyl)amino-4-phenyl-butyl]-1-[phenylmethyl]-2-[tert-butoxycarbonyl]-hydrazine (Example 100 B) is dissolved in 10 ml of formic acid under protective gas and stirred for 16 h at RT. The formic acid is removed by evaporation under HV, the residue is partitioned between 3 portions of ethyl acetate, saturated NaHCO$_3$ solution and brine, and the organic phases are dried with Na$_2$SO$_4$ and concentrated by evaporation to yield the title compound: $t_{Ret}(V)$=10.7 min.

EXAMPLE 112

1-[2(S)-Hydroxy-3(S)-(N-(quinoline-2-carbonyl)-(L)
-asparaginyl)amino-4-phenyl-butyl]-1-[benzyl]-2-
[N-allyloxycarbonyl)-(L)-valyl]-hydrazine is
prepared in accordance with one of the processes
mentioned hereinbefore or hereinafter.

EXAMPLE 113

1-[2(S)-Hydroxy-3(S)-(N-(quinoline-2-carbonyl)-(L)
-asparaginyl)amino-4-phenyl-butyl]-1-[4-
methoxyphenylmethyl]-2-[N-methoxycarbonyl)-(L)-
valyl]-hydrazine is prepared in accordance with one
of the processes mentioned hereinbefore or
hereinafter.

EXAMPLE 114

1-[2(S)-Hydroxy-3(S)-(N-(quinoline-2-carbonyl)-(L)
-asparaginyl)amino-4-phenyl-butyl]-1-[p-
(methoxyphenyl)methyl]-2-[N-(benzyloxycarbonyl)-
(L)-valyl]hydrazine Under a nitrogen atmosphere, 330 mg (1.32 mmol) of Z-(L)-valine and 700 mg (1.197 mmol) of 1-[2(S)-hydroxy-3(S)-(N-(quinoline-2-carbonyl)-(L)-asparaginyl)amino-4-phenyl-butyl]-1-[p-(methoxyphenyl)methyl]-hydrazine (Example 120B) a)) are dissolved in 11.6 ml of a 0.3M solution of NMM in DMF, 0.50 g (1.32 mmol) of HBTU is added and the mixture is stirred for 18 h at RT. The reaction mixture is concentrated by evaporation under HV and the residue is taken up in ethyl acetate and washed with saturated NaHCO$_3$ solution, water and brine. The aqueous phases are extracted a further twice with ethyl acetate and the combined organic phases are dried with Na$_2$SO$_4$ and concentrated by evaporation. Column chromatography (SiO$_2$, ethyl acetate) yields the title compound after crystallisation from DIPE. TLC $R_f(G')$=0.50; $t_{Ret}(V)$=15.4 min.

EXAMPLE 115

1-[2(S)-Hydroxy-3(S)-(N-(quinoline-2-carbonyl)-(L)
-asparaginyl)amino-4-phenyl-butyl]-1-[4-
methoxyphenylmethyl]-2-[N-allyloxycarbonyl)-(L)-
valyl]-hydrazine is prepared in accordance with one
of the processes mentioned hereinbefore or
hereinafter.

EXAMPLE 116

1-[2(S)-Hydroxy-3(S)-(N-(quinoline-2-carbonyl)-(L)
-asparaginyl)amino-4-(4-methoxyphenyl)-butyl]-1-
[benzyl]-2-[N-methoxycarbonyl)-(L)-valyl]-
hydrazine is prepared in accordance with one of the
processes mentioned hereinbefore or hereinafter.

EXAMPLE 117

1-[2(S)-Hydroxy-3(S)-(N-(quinoline-2-carbonyl)-(L)
-asparaginyl)amino-4-(4-methoxyphenyl)-butyl]-1-
[benzyl]-2-[N-benzyloxycarbonyl)-(L)-valyl]-
hydrazine is prepared in accordance with one of the
processes mentioned hereinbefore or hereinafter.

EXAMPLE 118

1-[2(S)-Hydroxy-3(S)-(N-(quinoline-2-carbonyl)-(L)
-asparaginyl)amino-4-(4-benzyloxyphenyl)-butyl]-1-
[benzyl]-2-[N-methoxycarbonyl)-(L)-valyl]-
hydrazine is prepared in accordance with one of the
processes mentioned hereinbefore or hereinafter.

EXAMPLE 119

1-[2(S)-Hydroxy-3(S)-(N-(quinoline-2-carbonyl)-(L)
-asparaginyl)amino-4-(4-benzyloxyphenyl)-butyl]-1-
[benzyl]-2-[N-allyloxycarbonyl)-(L)-valyl]-
hydrazine is prepared in accordance with one of the
processes mentioned hereinbefore or hereinafter.

EXAMPLE 120

1-[2(S)-Hydroxy-3(S)-(N-(guinoline-2-carbonyl)-(L)
-asparaginyl)amino-4-phenyl-butyl]-1-[p-
(methoxyphenyl)methyl]-2-[N-(ethoxycarbonyl)-(L)
-valyl]-hydrazine Analogously to Example 110, 71.2 mg (0.376 mmol) of N-(ethoxycarbonyl)-(L)-valine (Example 80a), 66 mg (0.487 mmol) of HOBT, 72.1 mg (0.376 mmol) of EDC and 200 mg (0.34 mmol) of 1-[2(S)-hydroxy-3(S)-(N-(quinoline-2-carbonyl)-(L)-asparaginyl)amino-4-phenyl-butyl]-1-[p-(methoxyphenyl)methyl]-hydrazine are reacted in 1.33 ml of 0.3M NMM/DMF. Column chromatography (SiO$_2$, methylene chloride→methylene chloride/methanol 50:1→20:1) yields the title compound: $t_{Ret}(V)$=13.9 min.

The starting material is prepared as follows:

a) 1-[2(S)-Hydroxy-3(S)-(N-(quinoline-2-carbonyl)-(L)-asparaginyl)amino-4-phenylbutyl]-1-[p-(methoxyphenyl)methyl]-hydrazine Analogously to Example 111a), 4.6 g (6.71 mmol) of 1-[2(S)-hydroxy-3(S)-(N-(quinoline-2-carbonyl)-(L)-asparaginyl)amino-4-phenyl-butyl]-1-[p-(methoxyphenyl)methyl]-2-[tert-butoxycarbonyl]-hydrazine (Example 100C) are reacted in 168 ml of formic acid to form the title compound: $t_{Ref}(V)$=10.8 min.

EXAMPLE 121

1-[2(S)-Hydroxy-3(S)-(N-(quinoline-2-carbonyl)-(L)-asparaginyl)amino-4-phenyl-butyl]-1-[4-methoxyphenylmethyl]-2-[N-allyloxycarbonyl)-(L)-valyl]-hydrazine is prepared in accordance with one of the processes mentioned hereinbefore or hereinafter.

EXAMPLE 122

1-[2(S)-hydroxy-3(S)-(N-(quinoline-2-carbonyl)-(L)-asparaginyl)amino-4-phenyl-butyl]-1-[4-benzyloxyphenylmethyl]-2-[N-methoxycarbonyl)-(L)-valyl]-hydrazine is prepared in accordance with one of the processes mentioned hereinbefore or hereinafter.

EXAMPLE 123

1-[2(S)-Hydroxy-3(S)-(N-(quinoline-2-carbonyl)-(L)-asparaginyl)amino-4-phenyl-butyl]-1-[4-benzyloxyphenylmethyl]-2-[N-allyloxycarbonyl)-(L)-valyl]-hydrazine is prepared in accordance with one of the processes mentioned hereinbefore or hereinafter.

EXAMPLE 124

The following are prepared analogously to one of the processes mentioned herein before:

A) 1-[2(S)-hydroxy-3(S)-(N-methoxycarbonyl-(L)-valyl) amino-4-cyclohexyl-butyl]-1-[4-methoxyphenylmethyl]-2-[N-methoxycarbonyl)-(L)-valyl]-hydrazine;

B) 1-[2(S)-hydroxy-3(S)-(N-methoxycarbonyl-(L)-valyl) amino-4-cyclohexyl-butyl]-1-[4-isobutoxyphenylmethyl]-2-[N-methoxycarbonyl)-(L)-valyl]-hydrazine;

C) 1-[2(S)-hydroxy-3(S)-(N-methoxycarbonyl-(L)-valyl) amino-4-cyclohexyl-butyl]-1-[4-ethoxyphenylmethyl]-2-[N-methoxycarbonyl)-(L)-valyl]-hydrazine;

D) 1-[2(S)-hydroxy-3(S)-(N-methoxycarbonyl-(L)-valyl) amino-4-cyclohexyl-butyl]-1-[4-benzyloxyphenylmethyl]-2-[N-methoxycarbonyl)-(L)-valyl]-hydrazine.

EXAMPLE 125

1-[2(S)-Hydroxy-3(S)-(N-methoxycarbonyl-(L)-valyl)amino-4-phenylbutyl]-1-[cyclohexylmethyl]-2-[2-pyridylcarbonyl]-hydrazine is prepared analogously to one of the processes mentioned hereinbefore

EXAMPLE 126

1-[2(S)-Hydroxy-3(S)-(N-(quinoline-2-carbonyl)-(L)-asparaginyl)amino- 4-phenyl-butyl]-1-[phenylmethyl]-2-[N-(methoxy-ethoxy-ethoxycarbonyl)-(L)-valyl]-hydrazine Analogously to Example 111, 52 mg (0.198 mmol) of N-(2-(2-methoxy-ethoxy)-ethoxy)carbonyl-(L)-valine (Example 82a)) and 100 mg (0.180 mmol) of 1-[2(S)-hydroxy-3(S)-(N-(quinoline-2-carbonyl)-(L)-asparaginyl) amino-4-phenyl-butyl]-1-[phenylmethyl]-hydrazine in 1.8 ml of 0.3M NMM/DMF are reacted with 75.1 mg (0.198 mmol) of HBTU. The evaporation residue is taken up in methylene chloride and washed with 2 portions of 10% citric acid solution, water, saturated NaHCO₃ solution and brine. The aqueous phases are extracted a further twice with methylene chloride and the combined organic phases are dried with Na₂SO₄ and concentrated by evaporation. Column chromatography (SiO₂, methylene chloride/methanol 19:1) yields the title compound: TLC $R_f(J)$=0.08; $t_{Ref}(V)$= 13.5 min; FAB-MS (M+H)⁺+800.

EXAMPLE 127

1-[2(S)-(2-Pyridyl-carbonyl)oxy-3(S)-(N-(quinoline-2-carbonyl)-(L)-asparaginyl)amino-4-phenyl-butyl]-1-[phenylmethyl]-2-[N-(methoxycarbonyl)-(L)-valyl]-hydrazine Analogously to Example 108, 51 mg (0.416 mmol) of 2-picolinic acid in 0.8 ml of methylene chloride are converted with 59 μl (0.416 mmol) of 1-chloro-N,N,2-trimethyl-1-propenamine into the acid chloride. After the addition of 0.5 ml of dioxane and 0.4 ml of pyridine to the latter, the mixture is reacted with 148 mg (0.208 mmol) of 1-[2(S)-hydroxy-3(S)-(N-(quinoline-2-carbonyl)-(L)-asparaginyl)amino-4-phenyl-butyl]-1-[phenylmethyl]-2-[N-(methoxycarbonyl)-(L)-valyl]-hydrazine (Example 109) in 5 ml of dioxane in the presence of 0.5 mg of DMAP. Since, after 18 h, not all of the educt has been acylated according to HPLC, further acid chloride is added. Column chromatography (SiO₂, methylene chloride→methylene chloride/methanol 15:1) yields the title compound: FAB-MS (M+H)⁺+817.

EXAMPLE 128

1-[2(S)-Butyroxy-3(S)-(N-(quinoline-2-carbonyl)-(L)-asparaginyl)amino-4-phenyl-butyl]-1-[phenylmethyl]2-[N-(methoxycarbonyl)-(L)-valyl]-hydrazine Under a nitrogen atmosphere, a small amount of DMAP and 0.2 ml of butyric acid chloride are added to a solution of 121 mg (0.17 mmol) of 1-[2(S)-hydroxy-3(S)-(N-(quinoline-2-carbonyl)-(L)-asparaginyl)amino-4-phenyl-butyl]-1-[phenylmethyl]-2-[N-(methoxycarbonyl)-(L)-valyl]-hydrazine (Example 109) in 3.5 ml of dioxane, 2 ml of methylene chloride and 0.4 ml of pyridine. Dilution of the reaction mixture with methylene chloride, washing with 2 portions of saturated NaHCO₃ solution, water and brine, extraction of the aqueous phases with 2 portions of methylene chloride, drying of the organic phases with Na₂SO₄, concentration by evaporation and column chromatography (SiO₂, methylene chloride/methanol 50:1→19:1) yields the title compound: TLC $R_f(I)$=0.5; $t_{Ref}(V)$=15.6 min.

EXAMPLE 129

1-[2(S)-(2-Pyridyl-carbonyl)oxy-3(S)-(N-(guinoline-2-carbonyl)-(L)-asparaginyl)amino-4-phenyl-butyl]-1-[p-(methoxyphenyl)methyl]-2-[N-(benzyloxycarbonyl)-(L)-valyl]-hydrazine Analogously to Example 108, 72.7 mg (0.591 mmol) of 2-picolinic acid in 2 ml of methylene chloride are converted with 87 μl (0.614 mmol) of 1-chloro-N,N,2-trimethyl-1-

225 propenamine into the acid chloride. After the addition of 1.36 ml of pyridine to the latter, the mixture is reacted with 100 mg (0.118 mmol) of 1-[2(S)-hydroxy-3(S)-(N-(quinoline-2-carbonyl)-(L)-asparaginyl)amino-4-phenyl-butyl]-1-[p-(methoxyphenyl)-methyl]-2-[N-(benzyloxycarbonyl)-(L)-valyl]-hydrazine (Example 114)) in the presence of 1 mg of DMAP. Further acid chloride is added in portions until according to HPLC all of the educt has been acylated to the title compound.

EXAMPLE 130

1-[2(S)-(Methoxy-acetoxy)-3(S)-(N-(quinoline-2-carbonyl)-L)-asparaginyl)amino-4-phenyl-butyl]-1-[p-(methoxyphenyl)methyl]-2-[N-(benzyloxycarbonyl)-(L)-valyl]-hydrazine Analogously to Example 105, 100 mg (0.118 mmol) of 1-[2(S)-hydroxy-3(S)-(N-(quinoline-2-carbonyl)-(L)-asparaginyl)amino-4-phenyl-butyl]-1-[p-(methoxyphenyl)-methyl]-2-[N-(benzyloxycarbonyl)-(L)-valyl]-hydrazine (Example 114)) in 2.4 ml of dioxane and 0.14 ml of pyridine are acylated in the presence of 0.7 mg of DMAP with 38.5 µl (0.35 mmol) of methoxyacetic acid chloride to form the title compound: $t_{Rel}(V)=17.8$ min.

EXAMPLE 131

Gelatine solution

A sterile-filtered aqueous solution, with 20% cyclodextrins as solubilisers, of one of the compounds of formula I or I-A mentioned in the preceding Examples as active ingredient, is so mixed under aseptic conditions, with heating, with a sterile gelatine solution containing phenol as preservative, that 1.0 ml of solution has the following composition:

| | |
|---|---|
| active ingredient | 3 mg |
| gelatine | 150.0 mg |
| phenol | 4.7 mg |
| dist. water with 20% cyclodextrins as solubilisers | 1.0 ml |

EXAMPLE 132

Sterile dry substance for injection 5 mg of one of the compounds of formula I or I-A mentioned in the preceding Examples as active ingredient are dissolved in 1 ml of an aqueous solution with 20 mg of mannitol and 20% cyclodextrins as solubilisers. The solution is sterile-filtered and introduced under aseptic conditions into a 2 ml ampoule, deep-frozen and lyophilised. Before use, the lyophilisate is dissolved in 1 ml of distilled water or 1 ml of a physiological saline solution. The solution is administered intramuscularly or intravenously. This formulation can also be introduced into a twin-chambered injection ampoule.

EXAMPLE 133

Nasal spray 500 mg of finely ground (<5.0 µm) powder of one of the compounds of formula I or I-A mentioned in the preceding Examples is suspended as active ingredient in a mixture of 3.5 ml of Myglyol 812® and 0.08 g of benzyl alcohol. The suspension is introduced into a container having a metering valve. 5.0 g of Freon 12® are introduced under pressure into the container through the valve. The "Freon" is dissolved in the Myglyol/benzyl alcohol mixture by shaking. The spray container contains approximately 100 single doses which can be administered individually.

226

EXAMPLE 134

Film-coated tablets

The following ingredients are used for the preparation of 10 000 tablets each containing 100 mg of active ingredient:

| | |
|---|---|
| active ingredient | 1000 g |
| corn starch | 680 g |
| colloidal silica | 200 g |
| magnesium stearate | 20 g |
| stearic acid | 50 g |
| sodium carboxymethyl starch | 250 g |
| water | quantum satis |

A mixture of one of the compounds of formula I or I-A mentioned in the preceding Examples as active ingredient, 50 g of corn starch and the colloidal silica is processed with a starch paste, made from 250 g of corn starch and 2.2 kg of demineralised water, to form a moist mass. This is forced through a sieve having a mesh size of 3 mm and dried at 45° for 30 min in a fluidised bed drier. The dry granules are pressed through a sieve having a mesh size of 1 mm, mixed, with a pre-sieved mixture (1 mm sieve) of 330 g of corn starch, the magnesium stearate, the stearic acid and the sodium carboxymethyl starch, and compressed to form slightly biconvex tablets.

What is claimed is:

1. A compound of formula I

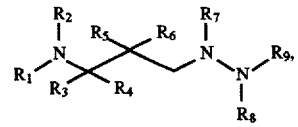

wherein $R_1$ and $R_9$ are each independently of the other hydrogen, lower alkoxycarbonyl, 2-halo-lower alkoxycarbonyl, aryloxycarbonyl wherein aryl has from 6 to 14 carbon atoms, aryl-lower alkoxycarbonyl wherein aryl has from 6 to 14 carbon atoms, 2-tri-lower alkylsilyl-lower alkoxycarbonyl, 2-triarylsilyl-lower alkoxycarbonyl wherein aryl is phenyl or 1- or 2-naphthyl, the radical, bonded via the carboxy group, of an amino acid selected from glycine, alanine, valine, norvaline, leucine, isoleucine, norleucine, serine, homoserine, threonine, methionine, cysteine, proline, trans-3- and trans-4-hydroxyproline, phenylalanine, tyrosine, 4-aminophenylalanine, 4-chlorophenylalanine, 4-carboxyphenylalanine, b-phenylserine, phenylglycine, a-naphthylalanine, cyclohexylalanine, cyclohexylglycine, tryptophan, indoline-2-carboxylic acid, 1,2,3,4-tetrahydroisoquinoline-3-carboxylic acid, aspartic acid, asparagine, aminomalonic acid, aminomalonic acid monoamide, glutamic acid, glutamine, histidine, arginine, lysine, d-hydroxylysine, ornithine, a,g-diaminobutyric acid and a,b-diaminopropionic acid in the D-, L- or (D,L)-form, and wherein the a-amino group may be unsubstituted or mono- or di-N-alkylated by lower alkyl, by amino-lower alkyl or by phenyl- or naphthylamino-lower alkyl, or may be N-acylated by lower alkanoyl; by aryl-lower alkanoyl wherein aryl is selected from phenyl, indenyl, indanyl, naphthyl, anthryl, phenanthryl, acenaphthyl and fluorenyl and may be unsubstituted or mono- to tri-substituted by lower alkyl, halo-lower alkyl, phenyl, 1- or 2-naphthyl, hydroxy, lower alkoxy, carbamoyl-lower alkoxy, N-lower alkylcarbamoyl-lower alkoxy or N,N-di-lower alkylcarbamoyl-lower alkoxy, amino, mono- or di-lower alkylamino, lower alkanoylamino, halogen, carboxy, lower alkoxycarbonyl, phenyl-, naphthyl- or fluorenyl-lower alkoxycarbonyl, lower alkanoyl, sulfo, lower alkylsulfonyl, phosphono, hydroxy-lower alkoxyphosphoryl or di-lower alkoxyphosphoryl, carbamoyl, mono- or di-lower alkylcarbamoyl, sulfamoyl, mono- or di-lower alkylaminosulfonyl, nitro and/or by cyano, wherein phenyl may be present up to three times, and wherein lower alkanoyl may be unsubstituted or substituted by lower alkyl, hydroxy, lower alkoxy, lower alkanoyloxy, acetoacetoxy, amino- or benzyloxy-carbonylamino-lower alkanoyloxy, aryl-lower alkanoyloxy wherein aryl has from 6 to 10 carbon atoms, lower alkoxycarbonyloxy, mono- or di-lower alkylaminocarbonyloxy, aryloxycarbonyloxy wherein aryl has from 6 to 10 carbon atoms, aryl-lower alkoxycarbonyloxy wherein aryl has from 6 to 14 carbon atoms, sulfonyloxy, lower alkylsulfonyloxy, phenylsulfonyloxy, 2- or 4-toluenesulfonyloxy or 1- or 2-naphthylsulfonyloxy, carboxy, esterified carboxy selected from lower alkoxycarbonyl, aryloxycarbonyl wherein aryl has from 6 to 10 carbon atoms, aryl-lower alkoxycarbonyl wherein aryl has from 6 to 12 carbon atoms, lower alkanoyl, lower alkylsulfonyl, hydroxy-lower alkoxyphosphoryl and di-lower alkoxyphosphoryl, carbamoyl, carbamoyl substituted by one or two radicals selected from lower alkyl, carboxy-lower alkyl, lower alkoxycarbonyl-lower alkyl, di-lower alkylamino-lower alkyl, aminocarboxy-lower alkyl, hydroxy-lower alkyl and di-lower alkoxy-lower alkyl sulfamoyl, phosphono, oxo and/or by cyano and is branched or unbranched; by heterocyclyl-lower alkanoyl selected from morpholinyl-, thiomorpholinyl- and S,S-dioxothiomorpholinyl lower alkanoyl (including -carbonyl), the mentioned heterocyclyl radicals being unsubstituted or substituted by lower alkyl, phenyl, 1- or 2-naphthyl, phenyl-lower alkyl, hydroxy-lower alkyl, lower alkoxy-lower alkyl, phenoxy- or naphthyloxy-lower alkyl, phenyl-lower alkoxy- or naphthyl-lower alkoxy-lower alkyl, lower alkanoyloxy-lower alkyl, phenyl- or naphthyl-lower alkanoyloxy-lower alkyl, lower alkoxycarbonyloxy-lower alkyl, phenyl-, naphthyl- or fluorenyl-lower alkoxycarbonyloxy-lower alkyl, amino-lower alkyl, carboxy-lower alkyl, hydroxy, lower alkoxy, phenyl- or naphthyl-lower alkoxy, amino, lower alkylamino, di-lower alkylamino, carboxy, lower alkoxycarbonyl, phenyl- or naphthyl-lower alkoxycarbonyl, halogen, lower alkanoyl, lower alkylsulfonyl, phosphono, hydroxy-lower alkoxyphosphoryl, dialkoxyphosphoryl, carbamoyl, mono- or di-lower alkylcarbamoyl, hydroxy- or carboxy-lower alkylcarbamoyl, sulfamoyl, nitro, oxo and/or by cyano; by carboxy-lower alkanoyl; by lower alkoxycarbonyl-lower alkanoyl; by hydroxy-lower alkoxy-lower alkanoyl; by amino-lower alkanoyl; or by benzyloxy-carbonylamino-lower alkanoyl wherein the amino group is not bonded in the a- or b-position; by carbamoyl; by phenyl-lower alkylaminocarbonyl; by N-di-lower alkylamino-lower alkyl-N-lower alkylaminocarbonyl; by N-dihydroxy-lower alkyl-N-lower alkylaminocarbonyl; by sulfonyl; by lower alkylsulfonyl; by arylsulfonyl wherein aryl has from 6 to 10 carbon atoms and is unsubstituted or substituted by lower alkyl or by lower alkoxy; by sulfamoyl;

a carboxy group of the side chain is present in free form or in esterified form as a lower alkyl ester group, as an aryl ester group or as an aryl-lower alkyl ester group, wherein aryl is phenyl, 4-nitrophenyl, naphthyl or biphenylyl, or in amidated form as a carbamoyl, lower alkylcarbamoyl, di-lower alkylaminocarbamoyl, mono- or di-(hydroxy-lower alkyl)-carbamoyl or mono- or di-(carboxy-lower alkyl)-carbamoyl group, an amino group of the side chain is present in free form or in alkylated form as mono- or di-lower alkylamino or in acylated form as lower alkanoylamino, as amino-lower alkanoylamino, as aryl-lower alkanoylamino wherein aryl has from 6 to 14 carbon atoms and is unsubstituted or substituted by lower alkyl, hydroxy, lower alkoxy, carboxy, carbamoyl or by sulfamoyl, as a lower alkoxycarbonylamino group, an arylmethoxycarbonylamino group wherein aryl has from 6 to 14 carbon atoms, morpholinocarbonyl, thiomorpholinocarbonyl or as S,S-dioxothiomorpholinocarbonyl and/or a hydroxy group of the side chain is present in free form or in etherified or esterified form as a lower alkoxy, aryl-lower alkoxy, lower alkanoyloxy or lower alkoxycarbonyloxy group,
lower alkylsulfonyl, (2- or 3-morpholinyl)-, (2- or 3-thiomorpholinyl)- or (S,S-dioxothiomorpholin-2- or -3-yl)-, (2- or 3-indolinyl)-, methylsulfonyl, phenyl- or 1- or 2-naphthyl-sulfonyl that is unsubstituted or mono- or di-substituted by lower alkyl, lower alkoxysulfonyl, or
benzyloxysulfonyl or 1- or 2-naphthyloxysulfonyl, with the result that not more than one of the radicals $R_1$ and $R_9$ may be hydrogen, and $R_2$ and $R_8$ are each independently of the other hydrogen or the same radicals as $R_1$ and $R_9$, $R_3$ is cycloalkyl-lower alkyl wherein cycloalkyl has from 3 to 7 carbon atoms and is unsubstituted or mono- to tri-substituted by lower alkyl, halo-lower alkyl, hydroxy, lower alkoxy, carbamoyl-lower alkoxy, N-lower alkylcarbamoyl-lower alkoxy or N,N-di-lower alkylcarbamoyl-lower alkoxy, amino, mono- or di-lower alkylamino, halogen, carboxy, lower alkoxycarbonyl, phenyl-, naphthyl- or fluorenyl-lower alkoxycarbonyl, lower alkanoyl, lower alkylsulfonyl, phosphono, hydroxy-lower alkoxyphosphoryl or di-lower alkoxyphosphoryl, carbamoyl, mono- or di-lower alkylaminocarbamoyl, sulfamoyl, mono- or di-lower alkylsulfamoyl, nitro and/or by cyano and is bonded to lower alkyl, or aryl-lower alkyl wherein aryl is selected from phenyl, indenyl, indanyl, naphthyl, anthryl, phenanthryl, acenaphthyl and fluorenyl, which may be unsubstituted or mono- to tri-substituted by lower alkyl, halo-lower alkyl, phenyl, 1- or 2-naphthyl, hydroxy, lower alkoxy, carbamoyl-lower alkoxy, N-lower alkylcarbamoyl-lower alkoxy or N,N-di-lower alkylcarbamoyl-lower alkoxy, amino, mono- or di-lower alkylamino, lower alkanoylamino, halogen, carboxy, lower alkoxycarbonyl, phenyl-, naphthyl- or fluorenyl-lower alkoxycarbonyl, lower alkanoyl, sulfo, lower alkylsulfonyl, phosphono, hydroxy-lower alkoxyphosphoryl or di-lower alkoxyphosphoryl, carbamoyl, mono- or di-lower alkylcarbamoyl, sulfamoyl, mono- or di-lower alkylsulfamoyl, nitro and/or by cyano, wherein phenyl may be present up to three times, and wherein lower alkyl is unsubstituted or substituted by lower alkyl, heterocyclyl selected from pyrrolyl, furyl, thienyl, imidazolyl, pyrazolyl, oxazolyl, thiazolyl, pyridyl, pyrazinyl, pyrimidinyl, indolyl, quinolyl, isoquinolyl, quinoxalinyl, b-carbolinyl and a benzo-fused, cyclopenta-, cyclohexa- or cyclohepta-fused derivative of those radicals, which may also be fully or partially saturated, hydroxy, lower alkoxy, lower alkanoyloxy, acetoacetoxy, amino- or benzyloxycarbonylamino-lower alkanoyloxy, aryl-lower alkanoyloxy wherein aryl has from 6 to 10 carbon atoms, lower alkoxycarbonyloxy, mono- or di-lower alkylaminocarbonyloxy, aryloxycarbonyloxy wherein aryl has from 6 to 10 carbon atoms, aryl-lower alkoxycarbonyloxy wherein aryl has from 6 to 12 carbon atoms, sulfonyloxy, lower alkylsulfonyloxy, phenylsulfonyloxy, 2- or 4-toluenesulfonyloxy or 1- or 2-naphthylsulfonyloxy, amino, mono- or di-lower alkylamino, N-lower alkoxy-N-lower alkylamino, mono- or di-(phenyl- or naphthyl-lower alkyl)-amino, lower alkanoylamino, carboxy, esterified carboxy selected from lower alkoxycarbonyl, aryloxycarbonyl wherein aryl has from 6 to 10 carbon atoms, aryl-lower alkoxycarbonyl wherein aryl has from 6 to 12 carbon atoms, lower alkanoyl, lower alkylsulfonyl, hydroxy-lower alkoxyphosphoryl and di-lower alkoxyphosphoryl, carbamoyl, carbamoyl substituted by one or two radicals selected from lower alkyl, from carboxy-lower alkyl or lower alkoxycarbonyl-lower alkyl, from di-lower alkylamino-lower alkyl, from aminocarboxy-lower alkyl, from hydroxy-lower alkyl and from di-lower alkoxy-lower alkyl, or carbamoyl substituted by one radical selected from ethylene, trimethylene, tetramethylene and pentamethylene in which a carbon atom may have been replaced by nitrogen, oxygen, sulfur or by sulfur mono- or di-substituted by oxygen and which may be unsaturated, and also sulfamoyl, phosphono, benzofuranyl, oxo and/or by cyano and is unbranched or branched, $R_4$ is hydrogen, $R_5$ is hydroxy and $R_6$ is hydrogen, or $R_5$ and $R_5$ together are oxo and $R_7$ is lower alkyl, cycloalkyl-lower alkyl wherein cycloalkyl has from 3 to 7 carbon atoms and is unsubstituted or mono- to tri-substituted by lower alkyl, halo-lower alkyl, hydroxy, lower alkoxy, carbamoyl-lower alkoxy, N-lower alkylcarbamoyl-lower alkoxy or N,N-di-lower alkylcarbamoyl-lower alkoxy, amino, mono- or di-lower alkylamino, halogen, carboxy, lower alkoxycarbonyl, phenyl-, naphthyl- or fluorenyl-lower alkoxycarbonyl, lower alkanoyl, lower alkylsulfonyl, phosphono, hydroxy-lower alkoxyphosphoryl or di-lower alkoxyphosphoryl, carbamoyl, mono- or di-lower alkylaminocarbamoyl, sulfamoyl, mono- or di-lower alkylsulfamoyl, nitro and/or by cyano and is bonded to lower alkyl, bicycloalkyl-lower alkyl wherein bicycloalkyl contains from 5 to 10 carbon atoms, tricycloalkyl-lower alkyl wherein tricycloalkyl contains from 8 to 10 carbon atoms, aryl-lower alkyl wherein aryl is selected from phenyl, indenyl, indanyl, naphthyl, anthryl, phenanthryl, acenaphthyl and fluorenyl, which may be unsubstituted or mono- to tri-substituted by lower alkyl, halo-lower alkyl, phenyl, 1- or 2-naphthyl, hydroxy, lower alkoxy, carbamoyl-lower alkoxy, N-lower alkylcarbamoyl-lower alkoxy, N,N-di-lower alkylcarbamoyl-lower alkoxy, amino, mono- or di-lower alkylamino, lower alkanoylamino, halogen, carboxy, lower alkoxycarbonyl, benzyl-, naphthyl- or fluorenyl-lower alkoxycarbonyl, lower alkanoyl, sulfo, lower alkylsulfonyl, phosphono, hydroxy-lower alkoxyphosphoryl, di-lower alkoxyphosphoryl, carbamoyl, mono- or di-lower alkylcarbamoyl, sulfamoyl, mono- or di-lower alkylsulfamoyl, nitro and/or by cyano, wherein phenyl may be present up to three times, and wherein lower alkyl is unsubstituted or substituted by lower alkyl, heterocyclyl selected from pyrrolyl, furyl, thienyl, imidazolyl, pyrazolyl, oxazolyl, thiazolyl, pyridyl, pyrazinyl, pyrimidinyl, indolyl, quinolyl, isoquinolyl, quinoxalinyl, 1-carbolinyl and a benzo-fused, cyclopenta-, cyclohexa- or cyclohepta-fused derivative of those radicals, which may also be fully or partially saturated, hydroxy, lower alkoxy, lower alkanoyloxy, acetoacetoxy, amino- or benzyloxycarbonylamino-lower alkanoyloxy, aryl-lower alkanoyloxy wherein aryl has from 6 to 10 carbon atoms, lower alkoxycarbonyloxy, mono- or di-lower alkylaminocarbonyloxy, aryloxycarbonyloxy wherein aryl has from 6 to 10 carbon atoms, aryl-lower alkoxycarbonyloxy wherein aryl has from 6 to 12 carbon atoms, sulfonyloxy, lower alkylsulfonyloxy, phenylsulfonyloxy, 2- or 4-toluenesulfonyloxy, 1- or 2-naphthylsulfonyloxy, amino, mono- or di-lower alkylamino, N-lower alkoxy-N-lower alkylamino, mono- or di-(phenyl- or naphthyl-lower alkyl)amino, lower alkanoylamino, carboxy, esterified carboxy selected from lower alkoxycarbonyl, aryloxycarbonyl wherein aryl has from 6 to 10 carbon atoms, aryl-lower alkoxycarbonyl wherein aryl has from 6 to 12 carbon atoms, lower alkanoyl, lower alkylsulfonyl, hydroxy-lower alkoxyphosphoryl and di-lower alkoxyphosphoryl, carbamoyl, carbamoyl substituted by one or two radicals selected from lower alkyl, from carboxy-lower alkyl, from lower alkoxycarbonyl-lower alkyl, from di-lower alkylamino-lower alkyl, from aminocarboxy-lower alkyl, from hydroxy-lower alkyl and from di-lower alkoxy-lower alkyl, or carbamoyl substituted by one radical selected from ethylene, trimethylene, tetramethylene and pentamethylene in which a carbon atom may have been replaced by nitrogen, oxygen, sulfur or by sulfur mono- or di-substituted by oxygen and which may be unsaturated, and also sulfamoyl, phosphono, benzofuranyl, oxo (which is not bonded to the carbon atom that is linked to the nitrogen atom bonding the radical $R_7$) and/or by cyano and is unbranched or branched, heterocyclyl-lower alkyl wherein heterocyclyl is selected from pyrrolyl, furyl, thienyl, imidazolyl, pyrazolyl, oxazolyl, thiazolyl, pyridyl, pyrazinyl, pyrimidinyl, indolyl, quinolyl, isoquinolyl, quinoxalinyl, β-carbolinyl and a benzo-fused, cyclopenta-, cyclohexa- or cyclohepta-fused derivative of those radicals, which may also be fully or partially saturated,
hydroxy-lower alkyl,
lower alkoxy-lower alkyl,
phenoxy-lower alkyl or nitrophenoxy-lower alkyl,
naphthyloxy-lower alkyl,
lower alkanoyloxy-lower alkyl,
acetoacetoxy-lower alkyl,
arylmercapto-lower alkyl wherein aryl has from 6 to 10 carbon atoms,
amino-lower alkyl,
mono- or di-lower alkylamino-lower alkyl,
phenyl- or naphthyl-amino-lower alkyl,
lower alkanoylamino-lower alkyl,
piperazinylcarbonyl-lower alkyl substituted at the nitrogen atom by lower alkyl,
lower alkoxycarbonylamino-lower alkyl,
phenyl-lower alkoxycarbonylamino-lower alkyl,
aminocarbonylamino-lower alkyl,
N-phenyl-lower alkyl-N-lower alkylaminocarbonylamino-lower alkyl,
halo-lower alkyl,
carboxy-lower alkyl,
lower alkoxycarbonyl-lower alkyl,
2-halo-lower alkoxycarbonyl-lower alkyl,
phenyl- or naphthyl-lower alkoxycarbonyl-lower alkyl,
heterocyclyl-lower alkoxycarbonyl-lower alkyl wherein heterocyclyl is selected from pyrrolyl, furyl, thienyl, imidazolyl, pyrazolyl, oxazolyl, thiazolyl, pyridyl, pyrazinyl, pyrimidinyl, indolyl, quinolyl, isoquinolyl, quinoxalinyl, β-carbolinyl and a benzo-fused, cyclopenta-, cyclohexa- or cyclohepta-fused derivative of those radicals, it also being possible for the mentioned radicals to be fully or partially saturated,
lower alkylsulfonyl-lower alkyl,
arylsulfonyl-lower alkyl wherein aryl has from 6 to 10 carbon atoms,
carbamoyl-lower alkyl,
lower alkylcarbamoyl-lower alkyl,
di-lower alkylcarbamoyl-lower alkyl,
hydroxy-lower alkylcarbamoyl- or di(hydroxy-lower alkyl)carbamoyl-lower alkyl,
N-lower alkoxy-lower alkoxy-lower alkylcarbamoyl-lower alkyl,
carboxy-lower alkylcarbamoyl- or di(carboxy-lower alkyl)carbamoyl-lower alkyl,
carbamoyl-lower alkyl substituted at the nitrogen atom by one radical selected from ethylene, trimethylene, tetramethylene and pentamethylene wherein a carbon atom may have been replaced by nitrogen, oxygen, sulfur or by sulfur mono- or di-substituted by oxygen, it also being possible for the radical so formed to be fully or partially unsaturated,
N-lower alkyl-N-heterocyclyl-lower alkylcarbamoyl-lower alkyl wherein heterocyclyl is selected from pyrrolyl, furyl, thienyl, imidazolyl, pyrazolyl, oxazolyl, thiazolyl, pyridyl, pyrazinyl, pyrimidinyl, indolyl, quinolyl, isoquinolyl, quinoxalinyl, β-carbolinyl and a benzo-fused, cyclopenta-, cyclohexa- or cyclohepta-fused derivative of those radicals, which may also be fully or partially saturated,
sulfamoyl-lower alkyl,
N-(phenyl- or naphthyl-lower alkyl)sulfamoyl-lower alkyl,
sulfamoyl-lower alkyl substituted at the nitrogen atom by one radical selected from ethylene, trimethylene, tetramethylene and pentamethylene wherein a carbon atom may have been replaced by nitrogen, lower alkyl-substituted nitrogen, oxygen, sulfur or by sulfur mono- or di-substituted by oxygen, it also being possible for the radical so formed to be fully or partially unsaturated,
oxo-lower alkyl (wherein oxo is not bonded to the carbon atom that is linked to the nitrogen atom that carries $R_7$),
cyano-lower alkyl,
hydroxy-carboxy-lower alkyl,
a-naphthyloxy-carboxy-lower alkyl,
hydroxy-lower alkoxycarbonyl-lower alkyl,
a-naphthyloxy-lower alkoxycarbonyl-lower alkyl,
lower alkylcarbonyl-halo-lower alkyl,
a-naphthyloxyethoxycarbonyl-lower alkyl,
a-naphthyloxy-benzyloxycarbonyl-lower alkyl,
esterified hydroxy-lower alkoxycarbonyl-lower alkyl wherein the hydroxy group is esterified by lower alkanoyl, cycloalkyl-lower alkanoyl wherein cycloalkyl has from 3 to 7 carbon atoms, bicycloalkyl-lower alkanoyl wherein bicycloalkyl has from 5 to 10 carbon atoms, tricycloalkyl-lower alkanoyl wherein tricycloalkyl has from 8 to 10 carbon atoms, aryl-lower alkanoyl wherein aryl has from 6 to 14 carbon atoms and may be unsubstituted or mono- to tri-substituted by lower alkyl, hydroxy, lower alkoxy, carbamoyl-lower alkoxy, N-lower alkylcarbamoyl-lower alkoxy or N,N-di-lower alkylcarbamoyl-lower alkoxy, amino, mono- or di-lower alkylamino, halogen, carboxy, lower alkoxycarbonyl, phenyl-, naphthyl- or fluorenyl-lower alkoxycarbonyl, lower alkanoyl, lower alkylsulfonyl, phosphono, hydroxy-lower alkoxyphosphoryl, di-lower alkoxyphosphoryl, carbamoyl, sulfamoyl, nitro and/or by cyano, lower alkoxycarbonyl, 2-halo-lower alkoxycarbonyl or by phenyl- or fluorenyl-lower alkoxycarbonyl,
dihydroxy-carboxy-lower alkyl,
dihydroxy-lower alkoxycarbonyl-lower alkyl,
dihydroxy-lower alkoxycarbonyl-lower alkyl esterified by lower alkanoyl, lower alkoxycarbonyl, phenyl- or fluorenyl-lower alkoxycarbonyl, lower alkylsulfonyl or by toluenesulfonyl,
a-naphthyloxy-di-lower alkylamino-lower alkyl,
a-naphthyloxy-carbamoyl-lower alkyl,
a-naphthyloxy-oxo-lower alkyl (wherein oxo is not bonded to the carbon atom that is linked to the nitrogen atom that carries $R_7$), or
a-naphthyloxy-cyano-lower alkyl,
or a salt thereof where salt-forming groups are present.

2. A compound of formula I according to claim 1, wherein $R_1$ and $R_9$ are each independently of the other hydrogen; lower alkanoyl; aryl-lower alkanoyl wherein aryl is phenyl, indenyl, indanyl, naphthyl, anthryl, phenanthryl, acenaphthyl or fluorenyl and may be unsubstituted or mono- to tri-substituted by lower alkyl, halo-lower alkyl, phenyl, 1- or 2-naphthyl, hydroxy, lower alkoxy, carbamoyl-lower alkoxy, N-lower alkylcarbamoyl-lower alkoxy, N,N-di-lower alkylcarbamoyl-lower alkoxy, amino, mono- or di-lower alkylamino, lower alkanoylamino, halogen, carboxy, lower alkoxycarbonyl, phenyl-, naphthyl- or fluorenyl-lower alkoxycarbonyl, lower alkanoyl, sulfo, lower alkylsulfonyl, phosphono, hydroxy-lower alkoxyphosphoryl, di-lower alkoxyphosphoryl, carbamoyl, mono- or di-lower alkylcarbamoyl, sulfamoyl, mono- or di-lower alkylaminosulfonyl, nitro and/or by cyano, wherein phenyl may be present up to three times, and wherein lower alkanoyl is unsubstituted or substituted by carbamoyl or by carbamoyl substituted at the nitrogen atom by one or two radicals selected from lower alkyl, carboxy-lower alkyl, lower alkoxycarbonyl-lower alkyl, di-lower alkylamino-lower alkyl, amino-carboxy-lower alkyl, hydroxy-lower alkyl and di-lower alkoxy-lower alkyl; heterocyclyl-lower alkanoyl wherein lower alkanoyl is unsubstituted and wherein heterocyclyl is selected from morpholinyl, thiomorpholinyl and S,S-dioxo-thiomorpholinyl, the mentioned heterocyclyl radicals being unsubstituted or substituted by lower alkyl, phenyl, 1- or 2-naphthyl, phenyl-lower alkyl, hydroxy-lower alkyl, lower alkoxy-lower alkyl, phenoxy- or naphthoxy-lower alkyl, phenyl-lower alkoxy- or naphthyl-lower alkoxy-lower alkyl, lower alkanoyloxy-lower alkyl, phenyl- or naphthyl-lower alkanoyloxy-lower alkyl, lower alkoxycarbonyloxy-lower alkyl, phenyl-, naphthyl- or fluorenyl-lower alkoxycarbonyloxy-lower alkyl, amino-lower alkyl, carboxy-lower alkyl, hydroxy, lower alkoxy, phenyl- or naphthyl-lower alkoxy, amino, lower alkylamino, di-lower alkylamino, carboxy, lower alkoxycarbonyl, phenyl- or naphthyl-lower alkoxycarbonyl, halogen, lower alkanoyl, lower alkylsulfonyl, phosphono, hydroxy-lower alkoxyphosphoryl or dialkoxyphosphoryl, carbamoyl, mono- or di-lower alkylcarbamoyl, hydroxy- or carboxy-lower alkylcarbamoyl, sulfamoyl, nitro, oxo and/or by cyano; amino-lower alkanoyl substituted at the amino nitrogen atom by heterocyclyl-lower alkanoyl wherein heterocyclyl-lower alkanoyl is as defined for heterocyclyl-lower alkanoyl $R_1$ and R,; halo-lower alkanoyl containing up to three halogen atoms; (N-heterocyclyl-lower alkylcarbamoyl)-lower alkanoyl wherein heterocyclyl is selected from morpholine and from thiomorpholine; lower alkoxycarbonyl; aryl-lower alkoxycarbonyl wherein aryl is phenyl, biphenylyl, 1- or 2-naphthyl, fluorenyl, or phenyl mono- or poly-substituted by lower alkyl, hydroxy, lower alkoxy, halogen and/or by nitro; heterocyclyl-lower alkoxycarbonyl wherein heterocyclyl is selected from morpholine or thiomorpholine and is unsubstituted or substituted by lower alkyl; lower alkylsulfonyl; morpholinosulfonyl, thiomorpholinosulfonyl; N-heterocyclyl-lower alkyl-N-lower alkylcarbamoyl wherein heterocyclyl is selected from morpholinyl, thiomorpholinyl and S,S-dioxothiomorpholinyl the mentioned radicals being unsubstituted or substituted by lower alkyl, phenyl, 1- or 2-naphthyl, phenyl-lower alkyl, hydroxy-lower alkyl, lower alkoxy-lower alkyl, phenoxy- or naphthoxy-lower alkyl, phenyl-lower alkoxy- or naphthyl-lower alkoxy-lower alkyl, lower alkanoyloxy-lower alkyl, phenyl- or naphthyl-lower alkanoyloxy-lower alkyl, lower alkoxycarbonyloxy-lower alkyl, phenyl-, naphthyl- or fluorenyl-lower alkoxycarbonyloxy-lower alkyl, amino-lower alkyl, carboxy-lower alkyl, hydroxy, lower alkoxy, phenyl- or naphthyl-lower alkoxy, amino, lower alkylamino, di-lower alkylamino, carboxy, lower alkoxycarbonyl, phenyl- or naphthyl-lower alkoxycarbonyl, halogen, lower alkanoyl, lower alkylsulfonyl, phosphono, hydroxy-lower alkoxyphosphoryl or dialkoxyphosphoryl, carbamoyl, mono- or di-lower alkylcarbamoyl, hydroxy- or carboxy-lower alkylcarbamoyl, sulfamoyl, nitro, oxo and/or by cyano; or an acyl radical of an amino acid the amino function of which is free or has been acylated by one of the other radicals mentioned hitherto for $R_1$ and $R_9$, the amino acids being selected from glycine, alanine, valine, norvaline, leucine, isoleucine, norleucine, serine, homoserine, threonine, methionine, cysteine, proline, trans-3- and trans-4-hydroxyproline, phenylalanine, tyrosine, 4-aminophenylalanine, 4-chlorophenylalanine, 4-carboxyphenylalanine, β-phenylserine, phenylglycine, a-naphthylalanine, cyclohexylalanine, cyclohexylglycine, tryptophan, indoline-2-carboxylic acid, 1,2,3,4-tetrahydroisoquinoline- 3-carboxylic acid, aspartic acid, asparagine, aminomalonic acid, aminomalonic acid monoamide, glutamic acid, glutamine, histidine, arginine, lysine, d-hydroxylysine, ornithine, 3-aminopropanoic acid, a,g-diaminobutyric acid and a,β-diaminopropionic acid, wherein each of the mentioned amino acid residues (with the exception of glycine) is in the D-, L- or (D,L)-form; with the proviso that not more than one of the radicals $R_1$ and $R_9$ is hydrogen, $R_2$, $R_4$, $R_6$ and $R_8$ are hydrogen, $R_3$ is lower alkyl; cycloalkyl-lower alkyl wherein cycloalkyl has from 3 to 7 carbon atoms and may be unsubstituted or mono- to tri-substituted by lower alkyl, halo-lower alkyl, hydroxy, lower alkoxy, carbamoyl-lower alkoxy, N-lower alkylcarbamoyl-lower alkoxy, N,N-di-lower alkylcarbamoyl-lower alkoxy, amino, mono- or di-lower alkylamino, halogen, carboxy, lower alkoxycarbonyl, phenyl-, naphthyl- or fluorenyl-lower alkoxycarbonyl, lower alkanoyl, lower alkylsulfonyl, phosphono, hydroxy-lower alkoxyphosphoryl or di-lower alkoxyphosphoryl, carbamoyl, mono- or di-lower alkylaminocarbamoyl, sulfamoyl, mono- or di-lower alkylsulfamoyl, nitro and/or by cyano; or is aryl-lower alkyl wherein aryl is phenyl, indenyl, indanyl, naphthyl, anthryl, phenanthryl, acenaphthyl or fluorenyl and is unsubstituted or mono- to tri-substituted by lower alkyl, isopropyl, halo-lower alkyl, phenyl, 1- or 2-naphthyl, hydroxy, lower alkoxy, carbamoyl-lower alkoxy, N-lower alkylcarbamoyl-lower alkoxy, N,N-di-lower alkylcarbamoyl-lower alkoxy, amino, mono- or di-lower alkylamino, lower alkanoylamino, halogen, carboxy, lower alkoxycarbonyl, benzyl-, naphthyl- or fluorenyl-lower alkoxycarbonyl, lower alkanoyl, sulfo, lower alkylsulfonyl, phosphono, hydroxy-lower alkoxyphosphoryl, di-lower alkoxyphosphoryl, carbamoyl, mono- or di-lower alkylcarbamoyl, sulfamoyl, mono- or di-lower alkylsulfamoyl, nitro and/or by cyano, wherein phenyl may be present up to three times, $R_5$ is hydroxy, and $R_7$ is unsubstituted lower alkyl; or cycloalkyl-lower alkyl as last described for cycloalkyl-lower alkyl $R_3$; or aryl-lower alkyl as last described for aryl-lower alkyl $R_3$;

or a salt thereof where at least one salt-forming group is present.

3. A compound of formula I according to claim 2, wherein $R_1$ and $R_9$ are each independently of the other hydrogen, lower alkanoyl, phenyl-lower alkanoyl, phenyl-lower alkanoyl wherein the lower alkanoyl radical is substituted by carbamoyl; morpholino-lower alkanoyl, thiomorpholino-lower alkanoyl, amino-lower alkanoyl substituted at the amino nitrogen atom by N-morpholino- or N-thiomorpholino-carbonyl; halo-lower alkanoyl containing up to three halogen atoms, 2-(N-morpholino-lower alkylcarbamoyl)-lower alkanoyl, lower alkoxycarbonyl, phenyl-lower alkoxycarbonyl, benzyloxycarbonyl, lower alkylsulfonyl, morpholinosulfonyl, thiomorpholinosulfonyl, or an acyl radical of an amino acid selected from glycine, alanine, valine, leucine, isoleucine, glutamic acid and asparagine in the (D)-, (L)- or (D,L)-form, wherein the α-amino group is unsubstituted or acylated by one of the other radicals $R_1$ or $R_9$ mentioned hitherto, with the proviso that not more than one of the radicals $R_1$ and $R_9$ is hydrogen, $R_2$, $R_4$, $R_6$ and $R_8$ are hydrogen, $R_3$ is lower alkyl; cyclohexyl-lower alkyl; or phenyl-lower alkyl that is unsubstituted or substituted by halogen, lower alkoxy or by cyano;

$R_5$ is hydroxy, and $R_7$ is lower alkyl; cyclohexyl-lower alkyl; or phenyl-lower alkyl that is unsubstituted or substituted by halogen, lower alkoxy or by cyano; as last defined for $R_3$, or a salt thereof where salt-forming groups are present.

4. The compound of formula I according to claim 1 wherein $R_1$ and $R_9$ are each the monovalent residue of the amino acid (L)-valine bonded via the carboxy group and acylated by benzyloxycarbonyl at the amino nitrogen atom, $R_2$ and $R_8$ are hydrogen, $R_3$ is benzyl, $R_4$ is hydrogen, $R_5$ is hydroxy, $R_6$ is hydrogen and $R_7$ is benzyl, and the asymmetric carbon atoms carrying the radicals $R_3$ and $R_5$ are in the S-configuration, or a pharmacologically acceptable salt of that compound.

5. The compound of formula I according to claim 1 wherein $R_1$ and $R_9$ are each the monovalent residue of the amino acid (L)-valine bonded via the carboxy group and acylated by 4-thiomorpholinocarbonyl at the amino nitrogen atom, $R_2$ and $R_8$ are hydrogen, $R_3$ is benzyl, $R_4$ is hydrogen, $R_5$ is hydroxy, $R_6$ is hydrogen and $R_7$ is isobutyl, and the asymmetric carbon atoms carrying the radicals $R_3$ and $R_5$ are in the S-configuration, or a pharmacologically acceptable salt of that compound.

6. A compound of formula I according to claim 1 wherein $R_1$ is lower alkoxycarbonyl, phenyl-lower alkoxycarbonyl, the monovalent radical, bonded via the carboxy group, of an aliphatic amino acid selected from valine, alanine, leucine and isoleucine, or the radical, bondend via the carboxy group, of an aliphatic amino acid as defined above that is acylated at the amino nitrogen atom by one of the radicals phenyl-lower alkanoyl, morpholinyl-lower alkanoyl, thiomorpholinyl-lower alkanoyl, S,S-dioxothiomorpholinyl-lower alkanoyl, lower alkoxycarbonyl and phenyl-lower alkoxycarbonyl, all the mentioned radicals being in the D-, D,L- or L- form, $R_2$ is hydrogen, $R_3$ is phenyl-lower alkyl, $R_4$ is hydrogen, $R_5$ is hydroxy, $R_6$ is hydrogen, $R_7$ is lower alkyl, cyclohexyl-lower alkyl or phenyl-lower alkyl, $R_8$ is hydrogen and $R_9$ is one of the radicals mentioned for $R_1$ and the asymmetric carbon atoms carrying the radicals $R_3$ and $R_5$ are in the S-configuration, or a pharmaceutically acceptable salt of such a compound.

7. A pharmaceutical composition suitable for administration to a warm-blooded animal for the treatment of a disease responsive to the inhibition of a retroviral protease, comprising a compound of formula I, or a salt thereof, according to claim 1 in an amount effective for the inhibition of a retroviral protease, together with a pharmaceutically acceptable carrier.

8. A compound of formula I-A

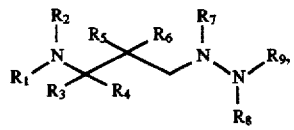

wherein $R_1$ and $R_9$ are each independently of the other hydrogen; lower alkanoyl; aryl-lower alkanoyl wherein aryl has from 6 to 14 carbon atoms and may be unsubstituted or mono- to tri-substituted by lower alkyl, halo-lower alkyl, phenyl, 1- or 2-naphthyl, hydroxy, lower alkoxy, carbamoyl-lower alkoxy, N-lower alkylcarbamoyl-lower alkoxy, N,N-di-lower alkylcarbamoyl-lower alkoxy, amino, mono- or di-lower alkylamino, lower alkanoylamino, halogen, carboxy, lower alkoxycarbonyl, phenyl-, naphthyl- or fluorenyl-lower alkoxycarbonyl, lower alkanoyl, sulfo, lower alkylsulfonyl, phosphono, hydroxy-lower alkoxyphosphoryl or di-lower alkoxyphosphoryl, carbamoyl, mono- or di-lower alkylcarbamoyl, sulfamoyl, mono- or di-lower alkylaminosulfonyl, nitro and/or by cyano, and wherein lower alkanoyl is unsubstituted or substituted by carbamoyl or by carbamoyl substituted at the nitrogen atom by one or two radicals selected from lower alkyl, carboxy-lower alkyl, lower alkoxycarbonyl-lower alkyl, di-lower alkylamino-lower alkyl, hydroxy-lower alkyl and di-lower alkoxy-lower alkyl; heterocyclyl-lower alkanoyl wherein heterocyclyl is morpholinyl, thiomorpholinyl or S,S-dioxothiomorpholinyl, which is bonded via a ring carbon atom or a ring nitrogen atom; (lower alkoxy-lower alkoxy)-lower alkanoyl; amino-lower alkanoyl substituted at the amino nitrogen atom by heterocyclyl-lower alkanoyl, wherein heterocyclyl-lower alkanoyl is independently as defined above for heterocyclyl-lower alkanoyl $R_1$ or $R_9$; halo-lower alkanoyl containing up to three halogen atoms; (N-heterocyclyl-lower alkylcarbamoyl)-lower alkanoyl wherein heterocyclyl is selected from morpholinyl and from thiomorpholinyl; lower alkoxycarbonyl; aryl-lower alkoxycarbonyl wherein aryl is phenyl, biphenylyl, 1- or 2-naphthyl, fluorenyl, or phenyl that is mono- or poly-substituted by lower alkyl, hydroxy, lower alkoxy, halogen and/or by nitro; heterocyclyl-lower alkoxycarbonyl wherein heterocyclyl is selected from morpholinyl and from thiomorpholinyl and is unsubstituted or substituted by lower alkyl; lower alkenyloxycarbonyl wherein the lower alkenyl radical is bonded to the oxygen atom via a saturated carbon atom; lower alkoxy-lower alkoxy-carbonyl; (lower alkoxy-lower alkoxy)-lower alkoxy-carbonyl; lower alkanesulfonyl; heterocyclylsulfonyl wherein heterocyclyl is selected from morpholinyl and from thiomorpholinyl and may be unsubstituted or substituted by lower alkyl; carbamoyl; N-heterocyclyl-lower alkyl-N-lower alkylcarbamoyl wherein heterocyclyl is independently one of the radicals mentioned above in the definition of heterocyclyl-lower alkanoyl $R_1$ or $R_9$ or an acyl radical, bonded via the carbonyl group of the 1-carboxy function, of an amino acid the amino function of which is free or acylated by one of the other radicals mentioned hitherto for $R_1$ and $R_9$, the amino acid residues being selected from the residues, bonded via the carbonyl of their 1-carboxy group, of the amino acids glycine, alanine, valine, norvaline, leucine, isoleucine, norleucine, serine, homoserine, threonine, methionine, cysteine, proline, trans-3- and trans-4-hydroxyproline, phenylalanine, tyrosine, 4-aminophenylalanine, 4-chlorophenylalanine, 4-carboxyphenylalanine, b-phenylserine, phenylglycine, a-naphthylalanine, cyclohexylalanine, cyclohexylglycine, tryptophan, indoline-2-carboxylic acid, 1,2,3,4-tetrahydroisoquinoline-3-carboxylic acid, aspartic acid, asparagine, aminomalonic acid, aminomalonic acid monoamide, glutamic acid, glutamine, histidine, arginine, lysine, d-hydroxylysine, ornithine, 3-aminopropanoic acid, a,g-diaminobutyric acid and a,b-diaminopropionic acid, it being possible for each of the mentioned amino acids (with the exception of glycine) to be in the D-, L- or (D,L)-form and the a-amino group being unsubstituted or N-acylated by one of the radicals mentioned above for $R_1$ and $R_9$ with the exception of one of the mentioned acyl radicals of an amino acid;

with the proviso that not more than one of the two radicals $R_1$ and $R_9$ may be hydrogen, $R_2$, $R_4$, $R_6$ and $R_8$ are hydrogen, $R_3$ is lower alkyl; $C_3$–$C_7$cycloalkyl-lower alkyl wherein $C_3$–$C_7$cycloalkyl is unsubstituted or mono- to tri-substituted by lower alkyl, halo-lower alkyl, hydroxy, lower alkoxy, amino, mono- or di-lower alkylamino, halogen, nitro and/or by cyano; or is aryl-lower alkyl wherein aryl is independently as defined in aryl-lower alkanoyl $R_1$ or $R_9$;

$R_5$ is lower alkanoyloxy, octanoyloxy, nonanoyloxy, decanoyloxy, undecanoyloxy, dodecanoyloxy, hydroxy-lower alkanoyloxy, lower alkoxy-lower alkanoyloxy, lower alkanoyloxy-lower alkanoyloxy, halo-lower alkanoyloxy, carboxy-lower alkanoyloxy, lower alkoxycarbonyl-lower alkanoyloxy, carbamoyl-lower alkanoyloxy, lower alkylcarbamoyl-lower alkanoyloxy, di-lower alkylcarbamoyl-lower alkanoyloxy, hydroxy-carboxy-lower alkanoyloxy, hydroxy-lower alkoxycarbonyl-lower alkanoyloxy, dihydroxy-carboxy-lower alkanoyloxy, dihydroxy-lower alkoxycarbonyl-lower alkanoyloxy, pyrrolylcarbonyloxy, furyl-lower alkanoyloxy, thienylcarbonyloxy, imidazolyl-lower alkanoyloxy, pyridyl-lower alkanoyloxy, indolylcarbonyloxy, quinolyl-lower alkanoyloxy, pyrrolidinylcarbonyloxy, piperidinylcarbonyloxy, morpholinocarbonyloxy, thiomorpholinocarbonyloxy, morpholinoacetoxy, thio-morpholinoacetoxy or 4-lower alkyl-1-piperazinoacetoxy, lower alkenoyloxy, lower alkynoyloxy, $C_3$–$C_8$cycloalkylcarbonyloxy, $C_3$–$C_8$cycloalkylacetoxy, phenyl-lower alkanoyloxy unsubstituted, mono- or poly-substituted in the phenyl radical by lower alkyl, halo-lower alkyl, halogen, hydroxy, lower alkoxy, piperidinomethyl, piperazin-1-ylmethyl, 4-lower alkylpiperazin-1-ylmethyl, 4-lower alkanoyl-piperazin-1-ylmethyl, morpholino-lower alkyl, thiomorpholinomethyl, cyano and/or by nitro, or is the residue, bonded via a carbonyloxy group containing the carbonyl from the carboxy group of the amino acid in question, of an amino acid selected from glycine, alanine, 2-aminobutyric acid, 3-aminobutyric acid, 4-aminobutyric acid, 3-aminopentanoic acid, 4-aminopentanoic acid, 5-aminopentanoic acid, 3-aminohexanoic acid, 4-aminohexanoic acid, 5-aminohexanoic acid, valine, norvaline, leucine, isoleucine, norleucine, serine, homoserine, threonine, methionine, cysteine, proline, phenylalanine, tyrosine, cyclohexylalanine, tryptophan, aspartic acid, asparagine, glutamic acid, glutamine, histidine, arginine, lysine, ornithine, 3-aminopropanoic acid, a,g-diaminobutyric acid and a,b-diaminopropionic acid, it being possible for each of the mentioned amino acids to be in the D-, L- or (D,L)-form (except in cases where there is no asymmetric carbon atom), and wherein an amino group is unsubstituted or is mono- or di-N-alkylated by lower alkyl, by pyridyl-lower alkyl and/or by phenyl-lower alkyl, and/or is N-acylated by lower alkanoyl, by phenyl-lower alkanoyl, by lower alkoxycarbonyl or by phenyl-lower alkoxycarbonyl;

and $R_7$ is independently of $R_3$ one of the radicals defined for $R_3$.

or a salt thereof where at least one salt-forming group is present.

9. A compound of formula I-A according to claim 8 wherein $R_1$ and $R_9$ are each independently of the other hydrogen, lower alkanoyl, phenyl-lower alkanoyl, phenyl-lower alkanoyl wherein the lower alkanoyl radical is substituted by carbamoyl, morpholino-lower alkanoyl, thiomorpholino-lower alkanoyl, amino-lower alkanoyl substituted at the amino nitrogen atom N-morpholino- or N-thiomorpholino-carbonyl, halo-lower alkanoyl containing up to three halogen atoms, 2-(N-morpholino-lower alkylcarbamoyl)-lower alkanoyl, lower alkoxycarbonyl, phenyl-lower alkoxycarbonyl, lower alkenyloxycarbonyl, lower alkoxy-lower alkoxycarbonyl, (lower alkoxy-lower alkoxy)-lower alkoxycarbonyl, lower alkanesulfonyl, morpholinosulfonyl, thiomorpholinosulfonyl, or an acyl radical, bonded via the carbonyl of its carboxy group, of an amino acid selected from glycine, alanine, valine, leucine, isoleucine, glutamic acid and asparagine in the (D)-, (L)- or (D,L)-form (with the exception of glycine), wherein the a-amino group is unsubstituted or acylated by one of the other radicals $R_1$ or $R_9$ mentioned hitherto with the exception of an acyl radical of an amino acid; with the proviso that not more than one of the radicals $R_1$ and $R_9$ is hydrogen, $R_2$, $R_4$, $R_6$ and $R_8$ are hydrogen, $R_3$ is lower alkyl, cyclohexyl-lower alkyl or phenyl-lower alkyl that is unsubstituted or substituted by halogen, lower alkoxy or by cyano, $R_5$ is lower alkanoyloxy, octanoyloxy, decanoyloxy, dodecanoyloxy, carboxy-lower alkanoyloxy, furyl-lower alkanoyloxy, imidazolyl-lower alkanoyloxy, pyridyl-lower alkanoyloxy, quinolyl-lower alkanoyloxy, aminoacetoxy, N-lower alkylaminoacetoxy, N,N-di-lower alkylaminoacetoxy, N-lower alkyl-N-phenyl-lower alkoxycarbonylaminoacetoxy, phenyl-lower alkanoyloxy, 4-morpholino-lower alkylbenzoyloxy, 4-halomethylbenzoyloxy, histidyloxy or prolyloxy and $R_7$ has the same definitions as $R_3$, or a pharmaceutically acceptable salt thereof where at least one salt-forming group is present.

10. A compound of the formula I-A according to claim 8 wherein $R_1$ is lower alkoxycarbonyl, halo-lower alkoxycarbonyl, phenyl-lower alkoxycarbonyl, the monovalent residue, bonded via carbonyl, of an aliphatic amino acid selected from valine, alanine, leucine and isoleucine or the residue, bonded via carbonyl, of an aliphatic amino acid as defined above acylated at the amino nitrogen atom by one of the radicals phenyl-lower alkanoyl, morpholinyl-lower alkanoyl, thiomorpholinyl-lower alkanoyl, lower alkoxycarbonyl and phenyl-lower alkoxycarbonyl, all the mentioned amino acids being in the D-, D,L- or L-form, $R_2$ is hydrogen, $R_3$ is phenyl-lower alkyl, 4-fluorophenyl-lower alkyl or cyclohexyl-lower alkyl, $R_4$ is hydrogen, $R_5$ is lower alkanoyloxy, octanoyloxy, decanoyloxy, dodecanoyloxy, carboxy-lower alkanoyloxy, furyl-lower alkanoyloxy, imidazolyl-lower alkanoyloxy, pyridyl-lower alkanoyloxy, quinolyl-lower alkanoyloxy, aminoacetoxy, N-lower alkylaminoacetoxy, N,N-di-lower alkylaminoacetoxy, N-lower alkyl-N-phenyl-lower alkoxycarbonylaminoacetoxy, phenyl-lower alkanoyloxy, 4-morpholinomethylbenzoyloxy, 4-halomethylbenzoyloxy, histidyloxy or prolyloxy, $R_6$ is hydrogen, $R_7$ is lower alkyl, cyclohexyl-lower alkyl, phenyl-lower alkyl, 4-cyanophenyl-lower alkyl or 4-fluorophenyl-lower alkyl, $R_8$ is hydrogen, $R_9$, is one of the radicals mentioned for $R_1$, and the asymmetric carbon atoms carrying the radicals $R_3$ and $R_5$ are in the S-configuration, or a pharmaceutically acceptable salt thereof.

11. A compound of formula I-A according to claim 8 wherein $R_1$ and $R_9$ are N-methoxycarbonylvalyl, $R_2$, $R_4$, $R_6$ and $R_8$ are hydrogen, $R_3$ is benzyl or cyclohexylmethyl, $R_5$ is lower alkanoyloxy or pyridylcarbonyloxy and $R_7$ is cyclohexylmethyl or benzyl, or a pharmaceutically acceptable salt thereof.

12. An isomer of a compound of formula I-A according to claim 11, wherein the carbon atom carrying $R_3$ and the carbon atom carrying $R_5$ are in the (S)-configuration and the radicals are as defined in claim 11, or a pharmaceutically acceptable salt thereof.

13. A compound according to claim 8 selected from
1-[2(S)-acetoxy-3(S)-(N-(2-methoxyethoxycarbonyl)-(L)-valyl)amino-4-phenyl-butyl]-1-[cyclohexylmethyl]-2-[N-(2-methoxyethoxycarbonyl)-(L)-valyl]hydrazine,
1-[2(S)-acetoxy-3(S)-(N-(methoxycarbonyl)-(L)-valyl) amino-4-phenyl-butyl]-1-[cyclohexylmethyl]-2-[N-(methoxycarbonyl)-(L)-valyl]hydrazine,
1-[2(S)-(2-pyridylcarbonyl)oxy-3(S)-(N-(methoxycarbonyl)-(L)-valyl)amino-4-phenylbutyl]-1-[cyclohexylmethyl]-2-[N-(methoxycarbonyl)-(L)-valyl]hydrazine and
1-[2(S)-butyryloxy-3(S)-(N-(methoxy-carbonyl)-(L)-valyl) amino-4-phenyl-butyl]-1-[cyclohexylmethyl]-2-[N-methoxy-carbonyl-(L)-valyl]hydrazine, or a pharmaceutically acceptable salt thereof.

14. A compound according to claim 8 selected from
1-[2(S)-propionyloxy-3(S)-(N-methoxycarbonyl)-(L)-valyl) amino-4-phenyl-butyl]-1-[cyclohexylmethyl]-2-[N-(methoxycarbonyl)-(L)-valyl]hydrazine;
1-[2(S)-pentanoyloxy-3(S)-(N-(methoxycarbonyl)-(L)-valyl)amino-4-phenyl-butyl]-1-[cyclohexylmethyl]-2-[N-(methoxycarbonyl)-(L)-valyl]hydrazine;
1-[2(S)-octanoyloxy-3(S)-(N-(methoxycarbonyl)-(L)-valyl) amino-4-phenyl-butyl]-1-[cyclohexylmethyl]-2-[N-(methoxycarbonyl)-(L)-valyl]hydrazine;
1-[2(S)-decanoyloxy-3(S)-(N-(methoxycarbonyl)-(L)-valyl)amino-4-phenyl-butyl]-1-[cyclohexylmethyl]-2-[N-(methoxycarbonyl)-(L)-valyl]hydrazine;
1-[2(S)-dodecanoyloxy-3(S)-(N-(methoxycarbonyl)-(L)-valyl)amino-4-phenyl-butyl]-1-[cyclohexylmethyl]-2-[N-(methoxycarbonyl)-(L)-valyl]hydrazine;
1-[2(S)-pivaloyloxy-3(S)-(N-(methoxycarbonyl)-(L)-valyl) amino-4-phenyl-butyl]-1-[cyclohexylmethyl]-2-[N-(methoxycarbonyl)-(L)-valyl]hydrazine;
1-[2(S)-benzoyloxy-3(S)-(N-(methoxycarbonyl)-(L)-valyl) amino-4-phenyl-butyl]-1-[cyclohexylmethyl]-2-[N-(methoxycarbonyl)-(L)-valyl]hydrazine;
1-[2(S)-(3-(pyridin-2-yl)-propionyl)oxy-3(S)-(N-(methoxycarbonyl)-(L)-valyl)amino-4-phenylbutyl)]-1-[cyclohexylmethyl]-2-[N-(methoxycarbonyl)-(L)-valyl] hydrazine;
1-[2(S)-(aminoacetyl)oxy-3(S)-(N-(methoxycarbonyl)-(L)-valyl)amino-4-phenyl-butyl]-1-[cyclohexylmethyl]-2-[N-(methoxycarbonyl)-(L)-valyl]hydrazine;
1-[2(S)-(N-methylaminoacetyl)oxy-3(S)-(N-(methoxycarbonyl)-(L)-valyl)amino-4-phenyl-butyl]-1-[cyclohexylmethyl]-2-[N-(methoxycarbonyl)-(L)-valyl] hydrazine;
1-[2(S)-(N,N-dimethylaminoacetyl)oxy-3(S)-(N-(methoxycarbonyl)-(L)-valyl)amino-4-phenylbutyl]-1-[cyclohexylmethyl]-2-[N-(methoxycarbonyl)-(L)-valyl] hydrazine;
1-[2(S)-(N-benzyloxycarbonyl-N-methyl-aminoacetyl)oxy-3(S)-(N-(methoxycarbonyl)-(L)-valyl)amino-4-phenyl-butyl]-1-[cyclohexylmethyl]-2-[N-(methoxycarbonyl)-(L)-valyl]hydrazine;
1-[2(S)-prolyloxy-3(S)-(N-(methoxycarbonyl)-(L)-valyl) amino-4-phenyl-butyl-1-[cyclohexylmethyl]-2-[N-(methoxycarbonyl)-(L)-valyl]hydrazine;
1-[2(S)-(4-morpholinomethylbenzoyl)oxy-3(S)-(N-(methoxycarbonyl)-(L)-valyl)amino-4-phenyl-butyl]-1-[cyclohexylmethyl]-2-(N-(methoxycarbonyl)-(L)-valyl] hydrazine;
1-[2(S)-(4-chloromethylbenzoyl)oxy-3(S)-(N-(methoxycarbonyl)-(L)-valyl)amino-4-phenylbutyl]-1-[cyclohexylmethyl]-2-[N-(methoxycarbonyl)-(L)-valyl] hydrazine; and
1-[2(S)-(3-carboxypropionyl)oxy-3(S)-(N-(methoxycarbonyl)-(L)-valyl)amino-4-phenylbutyl]-1-[cyclohexylmethyl]-2-[N-(methoxycarbonyl)-(L)-valyl] hydrazine, or a pharmaceutically acceptable salt thereof.

15. 1-[2(S)-Hydroxy-3(S)-(N-methoxycarbonyl-(L)-valyl)amino-4-phenylbutyl]-1-[4-biphenylylmethyl]-2-[N-methoxycarbonyl-(L)-valyl]-hydrazine according to claim 1, or a pharmaceutically acceptable salt thereof.

16. A pharmaceutical composition suitable for administration to a warm-blooded animal for the treatment of a disease responsive to the inhibition of a retroviral protease, comprising a compound of formula I-A, or a salt thereof, according to claim 8 in an amount effective for the inhibition of a retroviral protease, together with a pharmaceutically acceptable carrier.

17. A compound of formula I of claim 2 selected from the group comprising,
1-[2(S)-hydroxy-3(S)-(N-(methoxycarbonyl)-(L)-valyl)-amino-4 phenyl-butyl]-1-[cyclohexylmethyl]-2-[N-(methoxycarbonyl)-(L)-valyl]hydrazine,
1-[2(S)-hydroxy-3(S)-(N-(methoxycarbonyl)-(L)-valyl)-amino-4 phenyl-butyl]-1-[thienyl-2-ylmethyl]-2-[N-(methoxycarbonyl)-(L)-valyl]hydrazine,
1-[2(S)-hydroxy-3(S)-(N-(methoxycarbonyl)-(L)-valyl)-amino-4 phenyl-butyl]-1-[4-methoxyphenylmethyl]-2-[N-(methoxycarbonyl)-(L)-valyl]hydrazine,
1-[2(S)-hydroxy-3(S)-(N-acetyl-(L)-valyl)-amino-4-phenyl-butyl-1-[4-biphenylylmethyl]-2-[N-acetyl-(L)-valyl]hydrazine, and
1-[2-(S)-hydroxy-3-(S)-(N-ethoxycarbonyl-(L)-valyl)-amino-4-phenyl-butyl-1-[4-biphenylmethyl]-2-[N-ethoxycarbonyl-(L)-valyl]hydrazine,
or a pharmaceutically acceptable salt thereof, if a salt forming group is present.

18. A compound of formula I-A of claim 8 named
1-[2(S)-(methoxy-acetoxy)-3(S)-(N-(methoxycarbonyl)-(L)-valyl-amino-4-phenylbutyl]-1-[cyclohexylmethyl]-2-[N-(methoxycarbonyl)-(L)-valyl]hydrazine,
or a pharmaceutically acceptable salt thereof if a salt forming group is present.

* * * * *